US007329529B2

(12) United States Patent
Kapeller-Libermann

(10) Patent No.: US 7,329,529 B2
(45) Date of Patent: Feb. 12, 2008

(54) UBIQUTIN PROTEASES

(75) Inventor: Rosana Kapeller-Libermann, Chestnut Hill, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 909 days.

(21) Appl. No.: 10/165,231

(22) Filed: Jun. 6, 2002

(65) Prior Publication Data
US 2007/0292845 A1 Dec. 20, 2007

Related U.S. Application Data

(60) Continuation-in-part of application No. 09/390,038, filed on Sep. 3, 1999, now abandoned, and a continuation-in-part of application No. 09/796,089, filed on Feb. 28, 2001, now abandoned, which is a continuation-in-part of application No. 09/464,039, filed as application No. PCT/US00/33873 on Dec. 15, 2000, now Pat. No. 7,094,565, and a continuation-in-part of application No. 09/972,525, filed on Oct. 5, 2001, now abandoned, which is a division of application No. 09/408,865, filed on Sep. 30, 1999, now Pat. No. 6,329,171, and a continuation-in-part of application No. 09/963,908, filed on Sep. 26, 2001, now Pat. No. 6,797,502, which is a division of application No. 09/434,613, filed on Nov. 5, 1999, now Pat. No. 6,337,187, and a continuation-in-part of application No. 09/461,076, filed on Dec. 14, 1999, now abandoned, and a continuation-in-part of application No. 09/802,127, filed on Feb. 26, 2001, now abandoned.

(60) Provisional application No. 60/185,611, filed on Feb. 29, 2000.

(51) Int. Cl.
*C12N 9/64* (2006.01)
*G01N 33/53* (2006.01)
*G01N 33/00* (2006.01)
*C12Q 1/37* (2006.01)
*C07K 14/00* (2006.01)
*C12P 21/06* (2006.01)
*C12N 15/00* (2006.01)
*C12N 5/10* (2006.01)
*C12N 1/20* (2006.01)
*C07H 21/04* (2006.01)

(52) U.S. Cl. .................. 435/226; 435/23; 435/69.1; 435/320.1; 435/325; 435/252.3; 435/7.1; 530/350; 536/23.2; 536/23.5; 436/86

(58) Field of Classification Search ............... 435/226, 435/69.1, 23, 320.1, 325, 252.3, 7.1; 530/350; 536/23.2, 23.5; 436/86
See application file for complete search history.

(56) References Cited

U.S. PATENT DOCUMENTS

| 6,908,748 | B2 | 6/2005 | Ota et al. |
|---|---|---|---|
| 2003/0017480 | A1 | 1/2003 | Ota et al. |
| 2003/0082776 | A1 | 5/2003 | Ota et al. |
| 2003/0157569 | A1 | 8/2003 | Ota et al. |
| 2005/0164934 | A1 | 7/2005 | Ota et al. |
| 2005/0250144 | A1 | 11/2005 | Ota et al. |

FOREIGN PATENT DOCUMENTS

| WO | WO 00/01817 | 1/2000 |
|---|---|---|
| WO | WO 00/58473 A2 | 10/2000 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Quesada et al., Biochemical and Biophysical Research Communications 314:54-62, 2004.*
Guo et al., PNAS 101(25):9205-9210, 2004.*
BLAST Search in PATENT, NRP, DBEST, and NRN Databases.
Blast Search of 23431 against Dbest, NRN, NRP and Patent Databases.
GenBank Report, Accession No. AC004895, Waterston, R.H., "The Sequence of Homo Sapiens Clone," Unpublished, Waterston, R. H., Direct Submission, Submitted May 29, 1999.
Zhu et al, DUB-2 is a Member of a Novel Family of Cytokine-Inducible Deubiquitinating Enzymes, *J. Biol Chem,* Jan. 1997, pp. 51-57, vol. 272(1), published Medical Abstract.
Jensen et al., BAP1: A Novel Ubiquitin Hydrolase Which Binds to the BRCA1 RING Finger and Enhances BRCA1-Mediated Cell Growth Suppression, Oncogen, Mar. 5, 1998, pp. 1097-1112, vol. 16(9), Published Medical Abstract.
Lucero et al., Catabolite Inactivation of the Yeast Maltose Transporter Requires Ubiquitin-ligase npi 1/rsp5 and Ubiquitin-Hydrolase npi2/doa4, FEMS Microbiology Letters, Feb. 15, 1997, pp. 273-277, vol. 147(2), Published Medical Abstract.

(Continued)

*Primary Examiner*—Delia M. Ramirez

(57) ABSTRACT

The invention provides isolated nucleic acids molecules that encode novel ubiquitin protease polypeptides. The invention also provides antisense nucleic acid molecules, recombinant expression vectors containing the ubiquitin protease nucleic acid molecules of the invention, host cells into which the expression vectors have been introduced, and nonhuman transgenic animals in which a ubiquitin protease sequence of the invention has been introduced or disrupted. The invention still further provides isolated ubiquitin protease proteins, fusion proteins, antigenic peptides and antibodies. Diagnostic methods utilizing compositions of the invention are also provided.

8 Claims, 88 Drawing Sheets

OTHER PUBLICATIONS

Swanson et al., a Ubiquitin C-Terminal Hydrolase Gene on the Proximal Short Arm of the X Chromosome: Implications for X-Linked Retinal Disorders, Human Molecular Genetics, Apr. 1996, pp. 533-538, vol. 5(4), Published Medical Abstract.

Zhu et al. (1997), "*DUB-2* Is a Member of a Novel Family of Cytokine-inducible Deubiquitinating Enzymes," *The Journal of Biological Chemistry 272*(1):51-57, Division of Pediatric Oncology and Division of Cellular and Molecular Biology.

Jensen et al. (1998), "BAP1: A Novel Ubiquitin Hydrolase Which Binds to the BRCA1 RING Finger and Enhances BRCA1-Mediated Cell Growth Suppression," *Oncogene 16*:1097-1112, The Wistar Institute.

Lucero et al. (1997), "Catabolite Inactivation of the Yeast Maltose Transporter Requires Ubiquitin-Ligase npi1/rsp5 and Ubiquitin-Hydrolase npi2/doa4," *FEMS Microbiology Letters 147*:273-277, Federation of European Microbiological Societies.

Swanson et al. (1996), "A Ubiquitin C-terminal Hydrolase Gene on the Proximal Short Arm of the X Chromosome: Implications for X-Linked Retinal Disorders," *Human Molecular Genetics 5*(4):533-538, Howard Hughes Medical Institute.

D'Andrea et al. (1998) "Deubiquitinating Enzymes: A New Class of Biological Regulators" *Critical Reviews in Biochemistry and Molecular Biology 33*(5):337-352. (XP-000943127).

EMBL Database Accession No. AK001671. (XP-002159104).

Nagase et al. (2000) "Prediction of the Coding Sequences of Unidentified Human Genes, XVII. The Complete Sequences of 100 New cDNA Clones from Brain Which Code for Large Proteins in vitro" *DNA Research 7*:143-150. (XP-000943428).

PCT Notification of Transmittal of the International Search Report or the Declaration mailed Feb. 8, 2001, International Application No. PCT/US00/26915, International Filing Date Sep. 29, 2000.

GenBank Report, Accession No. AC004895, Waterston, R. H., "The Sequence of Homo Sapiens Clone," Unpublished, Waterson, R. H., Direct Submission, Submitted May 29, 1999.

Zhu et al., "DUB-2 Is a Member of a Novel Family Cytokine-Inducible Deubiquitinating Enzymes," *The Journal of Biological Chemistry*, vol. 272, No. 1 (1997), pp. 51-57.

Jensen et al., "BAP1: A Novel Ubiquitin Hydrolase Which Binds to the BRCA1 RING Finger and Enhances BRCA1-Mediated Cell Growth Suppression," *Oncogene*, vol. 16, No. 9 (1998) pp. 1097-1112, The Wistar Institute.

Lucero et al., "Catabolite Inactivation of the Yeast Maltose Transporter Requires Ubiquitin-Ligase npl1/rsp5 and Ubiquitin-Hydrolase npi2/doa4," *FEMS Microbiology Letters*, vol. 147, No. 2 (1997) pp. 273-277, Federation of European Microbiological Societies.

Swanson et al., "A Ubiquitin C-Terminal Hydrolase Gene on the Proximal Short Arm of the X Chromosome: Implications for X-Linked Retinal Disorders," *Human Molecular Genetics*, vol. 5, No. 4 (1996) pp. 533-538, Howard Hughes Medical Institute.

D'Andrea et al., "Deubiquitinating Enzymes: A New Class of Biological Regulators," *Critical Reviews in Biochemistry and Molecular Biology*, vol. 33, No. 5 (1998) pp. 337-352 (XP-000943127).

EMBL Database Accession No. AK001671, Isogal, T., "*Homo sapiens* cDNA FLJ10809 lis, clone NT2RP4000927, weakly similar to Ubiquitin Carboxyl-Terminal Hydrolase DUB-1 (EC 3.1.2.15)," submitted Feb. 16, 2000 (XP-002159104).

Nagase et al., "Prediction of the Coding Sequences of Unidentified Human Genes, XVII, The Complete Sequences of 100 New cDNA Clones from Brain Which Code for Large Proteins in vitro," *DNA Research*, vol. 7 (2000) pp. 143-150 (XP-000943428).

PCT Notification of Transmittal of the International Search Report of the Declaration mailed Feb. 8, 2001, International Application No. PCT/US00/26915, International Filing Date Sep. 29, 2000.

Henchoz, S., et al., "The Dose of a Putative Ubiquitin-Specific Protease Affects Position-Effect Variegation in *Drosophila melanogaster*," *Molecular and Cellular Biology*, vol. 16, No. 10 (1996) pp. 5717-5725.

Hershko, A., et al., "The Ubiquitin System," *Annual Review of Biochemistry*, vol. 67 (Jul. 1998) pp. 425-479.

Wall, R. J., et al., "Transgenic Dairy Cattle: Genetic Engineering on a Large Scale," *Journal of Dairy Science*, vol. 80 (1997) pp. 2213-2224.

Hammer, R. E., et al., "Genetic Engineering of Mammalian Embryos," *Journal of Animal Science*, vol. 63 (1986) pp. 269-278.

Verma, I. M., et al., "Gene Therapy—Promises, Problems and Prospects," *Nature*, vol. 389 (Sep. 18, 1997) pp. 239-242.

Anderson, W. F., "Human Gene Therapy," *Nature*, vol. 392, 6679 Supplement (Apr. 30, 1998) pp. 25-30.

* cited by examiner

CLUSTAL W (1.74) multiple sequence alignment

```
Fbh23552      MLSRCRSRLLHVLGLSFLLQTRRPILLCSPRLMKPLVVFVLGGPGAGKGTQCARIVEKYG
Q29561        ------------------------------MRPKVVFVLGGPGAGKGTQCARIVEKYG
                                            *:* ***********************

Fbh23552      YTHLSAGELLRDERKNPDSQYGELIEKYIKEGKIVPVEITISLLKREMDQTMAANAQKNK
Q29561        YTHLSAGELLRDERKNPDSQYGELIEKYIKDGKIVPVEITISLLRREMDQTMAANAQKNK
              ******************************:*************:**************

Fbh23552      FLIDGFPRNQDNLQGWNKTMDGKADVSFVLFFDCNNEICIERCLERGKSSGRSDDNRESL
Q29561        FLIDGFPRNQDNLQGWNKTMDGKADVSFVLFFDCNNEICIERCLERGKSSGRSDDNRESL
              ************************************************************

Fbh23552      EKRIQTYLQSTKPIIDLYEEMGKVKKIDASKSVDEVFDEVVQIPDKEG
Q29561        EKRIQTYLQSTKPIIDLYEEMGKVKKIDASKSVDEVFDEVVKIFDKEG
              ****************************************:*:****
```

FIG. 1.

Input file 23552cons; Output File 23552prot
Sequence length 1434

CGTGGGCGGACGCGTGGGTGCGTGTGTGGCCTTTTTTATTTGAGAGAGCAAGAGGCGCCNCGGACGCCTGGGCAGCCAC

GGCGGCGGGGCCGCGGTGGGCGCCGGCTCAGCCCGCCCCTTTCTCCCGCCGCCTCCCCGCCCCGCCCCGCGCCGCGCCG

```
                                          M   L   S   R   C   R   S   R   L     9
GCCGCTGTCAGCTCCCTCAGCGTCCGGCCGAGGCGCGGTGT ATG CTG AGC CGC TGC CGC AGC CGG CTG    27

L   H   V   L   G   L   S   F   L   L   Q   T   R   R   P   I   L   L   C   S   29
 CTC CAC GTC CTG GGC CTT AGC TTC CTG CTG CAG ACC CGC CGG CCG ATT CTC CTC  TGC TCT  87

P   R   L   M   K   P   L   V   V   F   V   L   G   G   P   G   A   G   K   G   49
 CCA CGT CTC ATG AAG CCG CTG GTC GTG TTC GTC CTC GGC GGC CCC GGC GCC GGC AAG GGG  147

T   Q   C   A   R   I   V   E   K   Y   G   Y   T   H   L   S   A   G   E   L   69
 ACC CAG TGC GCC CGC ATC GTC GAG AAA TAT GGC TAC ACA CAC CTT TCT GCA GGA GAG CTG  207

L   R   D   E   R   K   N   P   D   S   Q   Y   G   E   L   I   E   K   Y   I   89
 CTT CGT GAT GAA AGG AAG AAC CCA GAT TCA CAG TAT GGT GAA CTT ATT GAA AAG TAC ATT  267

K   E   G   K   I   V   P   V   E   I   T   I   S   L   L   K   R   E   M   D   109
 AAA GAA GGA AAG ATT GTA CCA GTT GAG ATA ACC ATC AGT TTA TTA AAG AGG GAA ATG GAT  327

Q   T   M   A   A   N   A   Q   K   N   K   F   L   I   D   G   F   P   R   N   129
 CAG ACA ATG GCT GCC AAT GCT CAG AAG AAT AAA TTC TTG ATT GAT GGG TTT CCA AGA AAT  387

Q   D   N   L   Q   G   W   N   K   T   M   D   G   K   A   D   V   S   F   V   149
 CAA GAC AAC CTT CAA GGA TGG AAC AAG ACC ATG GAT GGG AAG GCA GAT GTA TCT TTC GTT  447

L   F   F   D   C   N   N   E   I   C   I   E   R   C   L   E   R   G   K   S   169
 CTC TTT TTT GAC TGT AAT AAT GAG ATT TGT ATT GAA CGA TGT CTT GAG AGG GGA AAG AGT  507

S   G   R   S   D   D   N   R   E   S   L   E   K   R   I   Q   T   Y   L   Q   189
 AGT GGT AGG AGT GAT GAC AAC AGA GAG AGC TTG GAA AAG AGA ATT CAG ACC TAC CTT CAG  567

S   T   K   P   I   I   D   L   Y   E   E   M   G   K                           203
 TCA ACA AAG CCA ATT ATT GAC TTA TAT GAA GAA ATG GGG AAA                          609
```

GTCAAGAAAATAGATGCTTCTAAATCTGTTGATGAAGTTTTTGATGAAGTTGTGCAGATTTTTGACAAGGAAGGCTAAT

TCTAAACCTGAAAGCATCCTTGAAATCATGCTTGAATATTGCTTTGATAGCTGCTATCATGACCCCTTTTTAAGGCAAT

TCTAATCTTTCATAACTACATCTCAATTAGTGGCTGGAAAGTACATGGTAAAACAAAGTAAATTTTTTTATGTTCTTTT

TTTTGGTCACAGGAGTAGACAGTGAATTCAGGTTTAACTTCACCTTAGTTATGGTGCTCACCAAACGAAGGGTATCAGC

TATTTTTTTTTAAATTCAAAAAGAATATCCCTTTTATAGTTTGTGCCTTCTGTGAGCAAAACTTTTTAGTACGCGTATA

TATCCCTCTAGTAATCACAACATTTTAGGATTTAGGGATCCCGCTTCCTCTTTTTCTTGCAAGTTTTAAATTTCCAACC

TTAAGTGAATTTGTGGACCAAATTTCAAAGGAACTTTTTGTGTAGTCAGTTCTTGCACATGTGTTTGGTAAACAAACTC

AAAATGGATTCTTAGGAGCATTTAAGTGGTTATTAAATACTGACCATTTGCTGTAAAAAGATGAAAAAACTTA

FIG. 2.

>Fbh23552
MLSRCRSRLLHVLGLSFLLQTRRPILLCSPRLMKPLVVFVLGGPGAGKGTQCARIVEKYG
YTHLSAGELLRDERKNPDSQYGELIEKYIKEGKIVPVETTISLLKREMDQTMAANAQKNK
FLIDGFPRNQDNLQGWNKTMDGKADVSFVLFFDCNNEICIERCLERGKSSGRSDDNRESL
EKRIQTYLQSTKPIIDLYEEMGKVKKIDASKSVDEVFDEVVQIFDKEG

>PS00001|PDOC00001|ASN_GLYCOSYLATION N-glycosylation site.

Query:   137        NKTM       140

>PS00005|PDOC00005|PKC_PHOSPHO_SITE Protein kinase C phosphorylation site.

Query:   21         TRR        23
Query:   29         SPR        31
Query:   170        SGR        172
Query:   190        STK        192

>PS00006|PDOC00006|CK2_PHOSPHO_SITE Casein kinase II phosphorylation site.

Query:   65         SAGE       68
Query:   212        SVDE       215

>PS00007|PDOC00007|TYR_PHOSPHO_SITE Tyrosine kinase phosphorylation site.

Query:   54         RIVEKYGY        61
Query:   74         RKNPDSQY        81

>PS00008|PDOC00008|MYRISTYL N-myristoylation site.

Query:   42         GGPGAG     47
Query:   49         GTQCAR     54

>PS00113|PDOC00104|ADENYLATE_KINASE Adenylate kinase signature.

Query:   121        FLIDGFPRNQDN    132

FIG. 5.

```
Query:  Fbh23552

Scores for sequence family classification (score includes all domains):
Model              Description                              Score      E-value   N
--------           -----------                              -----      -------  ---
adenylatekinase    PF00406 Adenylate kinase                 203.0      4.7e-57   1

Parsed for domains:
Model              Domain    seq-f  seq-t     hmm-f  hmm-t      score   E-value
--------           ------    -----  -----     -----  -----      -----   -------
adenylatekinase    1/1         40    203  ..      1    190 []    203.0   4.7e-57

Alignments of top-scoring domains:
adenylatekinase: domain 1 of 1, from 40 to 203: score 203.0, E = 4.7e-57
                    *->LlGpPGaGKGTQAerIvkkygipHLSTGDlLRaevks.gTelGkeaK
                       +lG+PGaGKGTQ++rIv+kyg++HLS+G lLR+e k++ +++G+++
      Fbh23552    40    VLGGPGAGKGTQCARIVEKYGYTHLSAGELLRDERKNpDSQYGELIE  86 eyMDkGeLVPDEvviglvkerLeqnv..dakknGFLLDGFPRTvpQAeaL
                    +y+++G++VP E++i l+k +++q +   +a+kn+FL+DGFPR+ ++ + +
      Fbh23552    87    KYIKEGKIVPVEITISLLKREMDQTMaaNAQKNKFLIDGFPRNQDNLQGW 136 eemLeeagikldaVieldVpdevLveRltgRrihptSGRsYHleFnPPKv
                    + + + + ++ +V+++d++ e+ +eR ++R   +++SGR
      Fbh23552   137    NKTM-DGKADVSFVLFFDCNNEICIERCLER--GKSSGR----------- 172 eGkDDVtGepllqrRaDDneEtvkkRLetYhkqTePvIdyYkkkGk<-*
                         +  DDn E+++kR +tY + T+P+Id Y++ Gk
      Fbh23552   173    -------------S--DDNRESLEKRIQTYLQSTKPIIDLYEEMGK     203
```

FIG. 6.

Input file Fbh21620fl.seq; Output file 21620.trans
Sequence length 1909

TACTTAGACTCAGCCGGCTTTTCCACGCTTTGCCTGACCCTGCTTTGCTCAACTGTACGTCTTGTTTCGTTTTCTGTTC

TGCGCCGTTACAGATCCAAGCTCTGAAAAACCAGAAAGTTAACTGGTAAGTTTAGTCTTTTTGTCTTTTATTTCAGGTC

CCGGATCCGGTGATCCAAATCTAAGAACTGCTCCTCAGTGAGTGTTGCCTTTACTTCTAGGCCTGTACGGAAGTGTTAC

TTCTGCTCTAAAAGCTGCGGAATTCTAATACGACTCACTATAGGGAGTCGACCCACGCGTCCGGGGTCTAGGCGCGGAT

CGGACCCAAGCAGGTCGGCGGCGGCGGCAGGAGAGCGGCCGGGCGTCAGCTCCTCGACCCCCGTGTCGGGCTAGTCCAG

```
                                        M   A   R   P   G   M   E   R   W   R   D   R   L    13
CGAGGCGGACGGGCGGCGTGGGCCC ATG GCC AGG CCC GGC ATG GAG CGG TGG CGC GAC CGG CTG    39
         A   L   V   T   G   A   S   G   G   I   G   A   A   V   A   R   A   L   V   Q    33
        GCG CTG GTG ACG GGG GCC TCG GGG GGC ATC GGC GCG GCC GTG GCC CGG GCC CTG GTC CAG    99
         Q   G   L   K   V   V   G   C   A   R   T   V   G   N   I   E   E   L   A   A    53
        CAG GGA CTG AAG GTG GTG GGC TGC GCC CGC ACT GTG GGC AAC ATC GAG GAG CTG GCT GCT   159
         E   C   K   S   A   G   Y   P   G   T   L   I   P   Y   R   C   D   L   S   N    73
        GAA TGT AAG AGT GCA GGC TAC CCC GGG ACT TTG ATC CCC TAC AGA TGT GAC CTA TCA AAT   219
         E   E   D   I   L   S   M   F   S   A   I   R   S   Q   H   S   G   V   D   I    93
        GAA GAG GAC ATC CTC TCC ATG TTC TCA GCT ATC CGT TCT CAG CAC AGC GGT GTA GAC ATC   279
         C   I   N   N   A   G   L   A   R   P   D   T   L   L   S   G   S   T   S   G   113
        TGC ATC AAC AAT GCT GGC TTG GCC CGG CCT GAC ACC CTG CTC TCA GGC AGC ACC AGT GGT   339
         W   K   D   M   F   N   V   N   V   L   A   L   S   I   C   T   R   E   A   Y   133
        TGG AAG GAC ATG TTC AAT GTG AAC GTG CTG GCC CTC AGC ATC TGC ACA CGG GAA GCC TAC   399
         Q   S   M   K   E   R   N   V   D   D   G   H   I   I   N   I   N   S   M   S   153
        CAG TCC ATG AAG GAG CGG AAT GTG GAC GAT GGG CAC ATC ATT AAC ATC AAT AGC ATG TCT   459
         G   H   R   V   L   P   L   S   V   T   H   F   Y   S   A   T   K   Y   A   V   173
        GGC CAC CGA GTG TTA CCC CTG TCT GTG ACC CAC TTC TAT AGT GCC ACC AAG TAT GCC GTC   519
         T   A   L   T   E   G   L   R   Q   E   L   R   E   A   Q   T   H   I   R   A   193
        ACT GCG CTG ACA GAG GGA CTG AGG CAA GAG CTT CGG GAG GCC CAG ACC CAC ATC CGA GCC   579
         T   C   I   S   P   G   V   V   E   T   Q   F   A   F   K   L   H   D   K   D   213
        ACG TGC ATC TCT CCA GGT GTG GTG GAG ACA CAA TTC GCC TTC AAA CTC CAC GAC AAG GAC   639
         P   E   K   A   A   A   T   Y   E   Q   M   K   C   L   K   P   E   D   V   A   233
        CCT GAG AAG GCA GCT GCC ACC TAT GAG CAA ATG AAG TGT CTC AAA CCC GAG GAT GTG GCC   699
         E   A   V   I   Y   V   L   S   T   P   A   H   I   Q   I   G   D   I   Q   M   253
        GAG GCT GTT ATC TAC GTC CTC AGC ACT CCC GCA CAC ATC CAG ATT GGA GAC ATC CAG ATG   759
         R   P   T   E   Q   V   T   *                                                   261
        AGG CCC ACG GAG CAG GTG ACC TAG                                                   783
```

TGACTGTGGGAGCTCCTCCTTCCCTCCCCACCCTTCATGGCTTGCCTCCTGCCTCTGGATTTTAGGTGTTGATTTCTGG

ATCACGGGATACCACTTCCTGTCCACACCCCGACCAGGGGCTAGAAAATTTGTTTGAGATTTTTATATCATCTTGTCAA

ATTGCTTCAGTTGTAAATGTGAAAAATGGGCTGGGGAAAGGAGGTGGTGTCCCTAATTGTTTTACTTGTTAACTTGTTC

FIG. 7A.

```
TTGTGCCCCTGGGCACTTGGCCTTTGTCTGCTCTCAGTGTCTTCCCTTTGACATGGGAAAGGAGTTGTGGCCAAAATCC
CCATCTTCTTGCACCTCAACGTCTGTGGCTYANGGGCTGGGGTGGCAGAGGGAGGCCTTCACCTTATATCTGTGTTGTT
ATCCAGGGCTCCAGACTTCCTCCTCTGCCTGCCCCACTGCACCCTCTCCCCCTTATCTATCTCCTTCTCGGCTCCCCAG
CCCAGTCTTGGCTTCTTGTCCCCTCCTGGGGTCATCCCTCCACTCTGACTCTGACTATGGCAGCAGAACACCAGGGCCT
GGCCCAGTGGATTTCATGGTGATCATTAAAAAAGAAAAATCGCAACCAAAAAAAAAAAAAAAGGGCGGGCCGCTAGAC
TAGTYTAGAGAAAAAACCTCCCACACCTCCCCYBDAMMYTKACGCCGNACGCNANGGGGGCAATCAAGGACGCT
```

FIG. 7B.

Back to orfanal.cpi

Analysis of 21620 (260 aa)

Signal Peptide Predictions for 21620

| Method | Predict | Score | Mat@ |
|---|---|---|---|
| SignalP (eukaryote) | NO | | |

Note: amino-terminal 70aa used for signal peptide prediction

Transmembrane Segments Predicted by MEMSAT

| Start | End | Orient | Score |
|---|---|---|---|
| 13 | 32 | ins–>out | 1.3 |

Prosite Pattern Matches for 21620

>PS00005/PDOC00005/PKC_PHOSPHO_SITE Protein kinase C phosphorylation site.

Query: 135    SMK    137

>PS00006/PDOC00006/CK2_PHOSPHO_SITE Casein kinase II phosphorylation site.

Query: 72    SNEE    75
Query: 89    SGVD    92

Analysis of 21620

Query: 135    SMKE    138

>PS00008/PDOC00008/MYRISTYL N-myristoylation site.

Query: 18     GASGGI    23
Query: 24     GAAVAR    29
Query: 40     GCARTV    45
Query: 90     GVDICI    95
Query: 109    GSTSGW    114
Query: 199    GVVETQ    204

>PS00061/PDOC00060/ADH_SHORT Short-chain alcohol dehydrogenase family signature.

Query: 166    YSATKYAVTAL    176

FIG. 10.

Input file Fbh33756.seq; Output File 33756.trans
Sequence length 1153

CCGCGCCCCGCCCTCGCAGCCCANNTNCGGACGCGGGCCCAGCCGCGCCTGCGCTTCCGCTCGCCTGTGGCTGCAANNA

GCGCGCTCTTCCTCGGAGCTACCCAGGCGGCTGGTGTAGCAGCAAGCTCCGCGCCGACCCCTGACGCCTGACGCCTGTC

CCCGGCCCGGCATGAGCCGCTACCTGCTGCCGCTGTCGGCGCTGGGCACGGTAGCAGGCGCTCGCCGTGCTGCTCAAGA

```
                                    M   E   K   C   E   A   A   A   K   D   I   R   G    13
GGCAACATCATCCTGGCCTGCCGAGAC        ATG GAG AAG TGT GAG GCG GCA GCA AAG GAC ATC CGC GGG  39
 E   T   L   N   H   H   V   N   A   R   H   L   D   L   A   S   L   K   S   I    33
GAG ACC CTC AAT CAC CAT GTC AAC GCC CGG CAC CTG GAC TTG GCT TCC CTC AAG TCT ATC    99
 R   E   F   A   A   K   I   I   E   E   E   E   R   V   D   I   L   I   N   N    53
CGA GAG TTT GCA GCA AAG ATC ATT GAA GAG GAG GAG CGA GTG GAC ATT CTA ATC AAC AAC   159
 A   G   V   M   R   C   P   H   W   T   T   E   D   G   F   E   M   Q   F   G    73
GCG GGT GTG ATG CGG TGC CCC CAC TGG ACC ACC GAG GAC GGC TTC GAG ATG CAG TTT GGC   219
 V   N   H   L   G   H   F   L   L   T   N   L   L   L   D   K   L   K   A   S    93
GTT AAC CAC CTG GGT CAC TTT CTC TTG ACA AAC TTG CTG CTG GAC AAG CTG AAA GCC TCA   279
 A   P   S   R   I   I   N   L   S   S   L   A   H   V   A   G   H   I   D   F   113
GCC CCT TCG CGG ATC ATC AAC CTC TCG TCC CTG GCC CAT GTT GCT GGG CAC ATA GAC TTT   339
 D   D   L   N   W   Q   T   R   K   Y   N   T   K   A   A   Y   C   Q   S   K   133
GAC GAC TTG AAC TGG CAG ACG AGG AAG TAT AAC ACC AAA GCC GCC TAC TGC CAG AGC AAG   399
 L   A   I   V   L   F   T   K   E   L   S   R   R   L   Q   G   S   G   V   T   153
CTC GCC ATC GTC CTC TTC ACC AAG GAG TTG AGC CGG CGG CTG CAA GGC TCT GGT GTG ACT   459
 V   N   A   L   H   P   G   V   A   R   T   E   L   G   R   H   T   G   I   H   173
GTC AAC GCC CTG CAC CCC GGC GTG GCC AGG ACA GAG CTG GGC AGA CAC ACG GGC ATC CAT   519
 G   S   T   F   S   S   T   T   L   G   P   I   F   W   L   L   V   K   S   P   193
GGC TCC ACC TTC TCC AGC ACC ACA CTC GGG CCC ATC TTC TGG CTG CTG GTC AAG AGC CCC   579
 E   L   A   A   Q   P   S   T   Y   L   A   V   A   E   E   L   A   D   V   S   213
GAG CTG GCC GCC CAG CCC AGC ACA TAC CTG GCC GTG GCG GAG GAA CTG GCG GAT GTT TCC   639
 G   K   Y   F   D   G   L   K   Q   K   A   P   A   P   E   A   E   D   E   E   233
GGA AAG TAC TTC GAT GGA CTC AAA CAG AAG GCC CCG GCC CCC GAG GCT GAG GAT GAG GAG   699
 V   A   R   R   L   W   A   E   S   A   R   L   V   G   L   E   A   P   S   V   253
GTG GCC CGG AGG CTT TGG GCT GAA AGT GCC CGC CTG GTG GGC TTA GAG GCT CCC TCT GTG   759
 R   E   Q   P   L   P   R   *                                                    261
AGG GAG CAG CCC CTC CCC AGA TAA                                                   783
```

CCTCTGGAGCAGATTTGAAAGCCAGGATGGCGCCTCCAGACCGAGGACAGCTGTCCGCCATGCCCGCAGCTTCCTGGCA

CTACCTGAGCCGGGAGACCCAGGACTG

FIG. 13.

Back to orfanal.cgi

Analysis of 33756 (260 aa)

Signal Peptide Predictions for 33756

| Method | Predict | Score | Mat@ |
|---|---|---|---|
| SignalP (eukaryote) | NO | | |

Note: amino-terminal 70aa used for signal peptide prediction

No TM domains predicted by MEMSAT for 33756

Prosite Pattern Matches for 33756

>PS00001/PDOC00001/ASN_GLYCOSYLATION N-glycosylation site.

Query: 100    NLSS    103

>PS00005/PDOC00005/PKC_PHOSPHO_SITE Protein kinase C phosphorylation site.

Query: 29     SLK     31
Query: 32     SIR     34
Query: 120    TRK     122
Query: 144    SRR     146
Query: 213    SGK     215
Query: 242    SAR     244
Query: 252    SVR     254

>PS00006/PDOC00006/CK2_PHOSPHO_SITE Casein kinase II phosphorylation site.

Query: 32     SIRE    35
Query: 63     TTED    66
Query: 252    SVRE    255

>PS00008/PDOC00008/MYRISTYL N-myristoylation site.

Query: 149    GSGVTV  154
Query: 160    GVARTE  165
Query: 171    GIHGST  176

FIG. 16.

Input file Fbh21676.seq; Output File 21676.trans
Sequence length 1699

GCNTGTGGGTCCCTTCTTNAAATTGGGTCCCCCCGTTTTAGGTAAGTTTAAAAGCTCAAGGTTCAAAGACNGGNCCTTT

TGTCGGGGGCTCCTGAAGCCTACTAGATCANCGGCTCTCAGCTTTTTTTTTTGGGGGNCCCCCCCCTTTGGGAACCCC

CNTGGCTTTGCTTCAAACTTCTAAGGTCTTTTGTTTCGTTTTCTGTTCCTGCGCCGTTACAGATCCAAGYTCTGAAAAA

CCAGAAAGTTAACTGGTAAGTTTAGTCTTTTTGTCTTTTATTTCAGGTCCCGGATCCGGTGGTGGTGCAAATCAAAGAA

CTGCTCCTCAGTGGATGTTGCCTTTACTTCTAGGCCTGTACGAAGTGTTACTTCTGCTCTAAAAGCTGCGGAATTCTAA

TACGACTCACTATAGGGAGTCGACCCACGCGTCCGCGGACGCGTGGGCGGACGCGTGGGCGGAGTACCCAGGCGGCTG

|  |  |  |  |  |  |  |  |  |  |  |  |  |  |  | M | S | R | Y | 4 |
| GTGTGCAGCAAGCTCCGCGCCGACTCCGGACGCCTGACGCCTGACGCCTGTCCCCGGCCCGGC | ATG | AGC | CGC | TAC | 12 |

| L | L | P | L | S | A | L | G | T | V | A | G | A | A | V | L | L | K | D | Y | 24 |
| CTG | CTG | CCG | CTG | TCG | GCG | CTG | GGC | ACG | GTA | GCA | GGC | GCC | GCC | GTG | CTG | CTC | AAG | GAC | TAT | 72 |

| V | T | G | G | A | C | P | S | K | A | T | I | P | G | K | T | V | I | V | T | 44 |
| GTC | ACC | GGT | GGG | GCT | TGC | CCC | AGC | AAG | GCC | ACC | ATC | CCT | GGG | AAG | ACG | GTC | ATC | GTG | ACG | 132 |

| G | A | N | T | G | I | G | K | Q | T | A | L | E | L | A | R | R | G | G | N | 64 |
| GGC | GCC | AAC | ACA | GGC | ATC | GGG | AAG | CAG | ACC | GCC | TTG | GAA | CTG | GCC | AGG | AGA | GGA | GGC | AAC | 192 |

| I | I | L | A | C | R | D | M | E | K | C | E | A | A | A | K | D | I | R | G | 84 |
| ATC | ATC | CTG | GCC | TGC | CGA | GAC | ATG | GAG | AAG | TGT | GAG | GCG | GCA | GCA | AAG | GAC | ATC | CGC | GGG | 252 |

| E | T | L | N | H | H | V | N | A | R | H | L | D | L | A | S | L | K | S | I | 104 |
| GAG | ACC | CTC | AAT | CAC | CAT | GTC | AAC | GCC | CGG | CAC | CTG | GAC | TTG | GCT | TCC | CTC | AAG | TCT | ATC | 312 |

| R | E | F | A | A | K | I | I | E | E | E | R | V | D | I | L | I | N | N | 124 |
| CGA | GAG | TTT | GCA | GCA | AAG | ATC | ATT | GAA | GAG | GAG | GAG | CGA | GTG | GAC | ATT | CTA | ATC | AAC | AAC | 372 |

| A | G | V | M | R | C | P | H | W | T | T | E | D | G | F | E | M | Q | F | G | 144 |
| GCG | GGT | GTG | ATG | CGG | TGC | CCC | CAC | TGG | ACC | ACC | GAG | GAC | GGC | TTC | GAG | ATG | CAG | TTT | GGC | 432 |

| V | N | H | L | G | H | F | L | L | T | N | L | L | L | D | K | L | K | A | S | 164 |
| GTT | AAC | CAC | CTG | GGT | CAC | TTT | CTC | TTG | ACA | AAC | TTG | CTG | CTG | GAC | AAG | CTG | AAA | GCC | TCA | 492 |

| A | P | S | R | I | I | N | L | S | S | L | A | H | V | A | G | H | I | D | F | 184 |
| GCC | CCT | TCG | CGG | ATC | ATC | AAC | CTC | TCG | TCC | CTG | GCC | CAT | GTT | GCT | GGG | CAC | ATA | GAC | TTT | 552 |

| D | D | L | N | W | Q | T | R | K | Y | N | T | K | A | A | Y | C | Q | S | K | 204 |
| GAC | GAC | TTG | AAC | TGG | CAG | ACG | AGG | AAG | TAT | AAC | ACC | AAA | GCC | GCC | TAC | TGC | CAG | AGC | AAG | 612 |

| L | A | I | V | L | F | T | K | E | L | S | R | R | L | Q | G | S | G | V | T | 224 |
| CTC | GCC | ATC | GTC | CTC | TTC | ACC | AAG | GAG | CTG | AGC | CGG | CGG | CTG | CAA | GGC | TCT | GGT | GTG | ACT | 672 |

| V | N | A | L | H | P | G | V | A | R | T | E | L | G | R | H | T | G | I | H | 244 |
| GTC | AAC | GCC | CTG | CAC | CCC | GGC | GTG | GCC | AGG | ACA | GAG | CTG | GGC | AGA | CAC | ACG | GGC | ATC | CAT | 732 |

| G | S | T | F | S | S | T | T | L | G | P | I | F | W | L | L | V | K | S | P | 264 |
| GGC | TCC | ACC | TTC | TCC | AGC | ACC | ACA | CTC | GGG | CCC | ATC | TTC | TGG | CTG | CTG | GTC | AAG | AGC | CCC | 792 |

| E | L | V | A | Q | P | S | T | Y | L | A | V | A | E | E | L | A | D | V | S | 284 |
| GAG | CTG | GTC | GCC | CAG | CCC | AGC | ACA | TAC | CTG | GCC | GTG | GCG | GAG | GAA | CTG | GCG | GAT | GTT | TCC | 852 |

| G | K | Y | F | D | G | L | K | Q | K | A | P | A | P | E | A | E | D | E | E | 304 |

FIG. 17A.

```
GGA AAG TAC TTC GAT GGA CTC AAA CAG AAG GCC CCG GCC CCC GAG GCT GAG GAT GAG GAG   912
 V   A   R   R   L   W   A   E   S   A   R   L   V   G   L   E   A   P   S   V   324
GTG GCC CGG AGG CTT TGG GCT GAA AGT GCC CGC CTG GTG GGC TTA GAG GCT CCC TCT GTG   972
 R   E   Q   P   L   P   R   *                                                    332
AGG GAG CAG CCC CTC CCC AGA TAA                                                   996
```

CCTCTGGAGCAGATTTGAAAGCCAGGATGGCGCCTCCAGACCGAGGACAGCTGTCCGCCATGCCCGCAGCTTCCTGGCA

CTACCTGAGCCGGGAGACCCAGGACTGGCGGCCGCTAGACTAGTCTAGAGAAAAAACCTCCCACACCTCCCCCTGAACC

TGAAACAT

FIG. 17B.

Back to orfanal.cgi

Analysis of 21676 (331 aa)

Signal Peptide Predictions for 21676

| Method | Predict | Score | Mat@ |
|---|---|---|---|
| SignalP (eukaryote) | YES | | 17 |

Note: amino-terminal 70aa used for signal peptide prediction.

Transmembrane Segments Predicted by MEMSAT

| Start | End | Orient | Score |
|---|---|---|---|
| 8 | 25 | out→ins | 0.2 |
| 242 | 261 | ins→out | 1.5 |

Transmembrane segments for presumed mature peptide

| Start | End | Orient | Score |
|---|---|---|---|
| 226 | 245 | out→ins | 2.1 |

Prosite Pattern Matches for 21676

>PS00001/PDOC00001/ASN_GLYCOSYLATION N-glycosylation site.

Query: 171    NLSS    174

>PS00005/PDOC00005/PKC_PHOSPHO_SITE Protein kinase C phosphorylation site.

Query: 100    SLK    102
Query: 103    SIR    105
Query: 191    TRK    193
Query: 215    SRR    217
Query: 284    SGK    286
Query: 313    SAR    315
Query: 323    SVR    325

>PS00006/PDOC00006/CK2_PHOSPHO_SITE Casein kinase II phosphorylation site.

Query: 54     TALE   57
Query: 103    SIRE   106
Query: 134    TTED   137
Query: 323    SVRE   326

>PS00008/PDOC00008/MYRISTYL N-myristoylation site.

Query: 12     GTVAGA   17
Query: 28     GACPSK   33
Query: 45     GANTGI   50
Query: 220    GSGVTV   225
Query: 231    GVARTE   236
Query: 242    GIHGST   247

FIG. 20.

Input file Fbh21612f11.seq; Output file 21612.trans
Sequence length 2535

AGGCAGAAGTATGCAAAGCATGCATCTCAAATTAGTCAGCAAACCATAGTCCCGGCCCCTAACTCCGCCCATCCCGCCC

CTAACTCCGNCCCAGTTCCGGCCCATTCTCCGCCCCATGGCTGACTAATTTTTTTTATTTATGCAGAGCCGAGGCCGCC

TCGGCCTCTGAGCTATTCCAGAAGTAGTGAGGAGGCTTTTTTGGAGGCCTAGGCTTTTGCAAAAAGCTCCTCGATCGAG

GGGCTCGCATCTCTCCTTCACGCGCCCGCCGCCCTACCTGAGGCCGCCATCCACGCCGGTTGAGTCGCGTTCTGCCGCC

TCCCGCCTGTGGTGCCTCCTGAACTGCGTCCGCCGTCTAGGTAAGTTTAAAGCTCAGGTCGAGACCGGGCCTTTGTCCG

GCGCTCCCTTGGAGCCTACCTAGACTCAGCCGGCTCTCCACGCTTTGCCTGACCCTGCTTGCTCAACTCTACGTCTTTG

TTTCAGTTTTCTGTTCTGCGCCGTTACAGATCCAAGCTCTGAAAAACCAGAAAGTTAACTGGTAAGTTTAGTCTTTTTG

TCTTTTATTTCAGGTCCCGGATCCGGTGGTGGTGCAAATCAAAGAACTGCTCCTCAGTGGATGTTGCCTTTACTTCTAG

GCCTGTACGGAAGTGTTACTTCTGCTCTAAAAGCTGCGGAATTCTAATACGACTCACTATAGGGWGTCGACCCACGCGT

```
                                                           M   L   P   N   T   G   R    7
CCGCTCGCCGCCGCCGCTGTCGCCGCCACCTCCTCTGATCTACGAAAGTC ATG TTA CCC AAC ACC GGG AGG   21
 L   A   G   C   T   V   F   I   T   G   A   S   R   G   I   G   K   A   I   A   27
CTG GCA GGA TGT ACA GTT TTT ATC ACA GGT GCA AGC CGT GGC ATT GGC AAA GCT ATT GCA   81
 L   K   A   A   K   D   G   A   N   I   V   I   A   A   K   T   A   Q   P   H    47
TTG AAA GCA GCA AAG GAT GGA GCA AAT ATT GTT ATT GCT GCA AAG ACC GCC CAG CCA CAT  141
 P   K   L   L   G   T   I   Y   T   A   A   E   E   I   E   A   V   G   G   K    67
CCA AAA CTT CTA GGC ACA ATC TAT ACT GCT GCT GAA GAA ATT GAA GCA GTT GGA GGA AAG  201
 A   L   P   C   I   V   D   V   R   D   E   Q   Q   I   S   A   A   V   E   K    87
GCC TTG CCA TGT ATT GTT GAT GTG AGA GAT GAA CAG CAG ATC AGT GCT GCA GTG GAG AAA  261
 A   I   K   K   F   G   G   I   D   I   L   V   N   N   A   S   A   I   S   L   107
GCC ATC AAG AAA TTT GGA GGA ATT GAT ATT CTG GTA AAT AAT GCC AGT GCC ATT AGT TTG  321
 T   N   T   L   D   T   P   T   K   R   L   D   L   M   M   N   V   N   T   R   127
ACC AAT ACA TTG GAC ACA CCT ACC AAG AGA TTG GAT CTG ATG ATG AAC GTG AAC ACC AGA  381
 G   T   Y   L   A   S   K   A   C   I   P   Y   L   K   K   S   K   V   A   H   147
GGC ACC TAC CTT GCA TCT AAA GCA TGT ATT CCT TAT TTG AAA AAG AGC AAA GTT GCT CAT  441
 I   L   N   I   S   P   P   L   N   L   N   P   V   W   F   K   Q   H   C   A   167
ATC CTC AAT ATC AGT CCA CCA CTG AAC CTA AAT CCA GTT TGG TTC AAA CAG CAC TGT GCT  501
 Y   T   I   A   K   Y   G   M   S   M   Y   V   L   G   M   A   E   E   F   K   187
TAT ACC ATT GCT AAG TAT GGT ATG TCT ATG TAT GTG CTT GGA ATG GCA GAA GAA TTT AAA  561
 G   E   I   A   V   N   A   L   W   P   K   T   A   I   H   T   A   A   M   D   207
GGT GAA ATT GCA GTC AAT GCA TTA TGG CCT AAA ACA GCC ATA CAC ACT GCT GCT ATG GAT  621
 M   L   G   G   P   G   I   E   S   Q   C   R   K   V   D   I   I   A   D   A   227
ATG CTG GGA GGA CCT GGT ATC GAA AGC CAG TGT AGA AAA GTT GAT ATC ATT GCA GAT GCA  681
 A   Y   S   I   F   Q   K   P   K   S   F   T   G   N   F   V   I   D   E   N   247
GCA TAT TCC ATT TTC CAA AAG CCA AAA AGT TTT ACT GGC AAC TTT GTC ATT GAT GAA AAT  741
 I   L   K   E   E   G   I   E   N   F   D   V   Y   A   I   K   P   G   H   P   267
```

FIG. 21A.

```
ATC TTA AAA GAA GAA GGA ATA GAA AAT TTT GAC GTT TAT GCA ATT AAA CCA GGT CAT CCT  801
 L   Q   P   D   F   F   L   D   E   Y   P   E   A   V   S   K   K   V   E   S   287
TTG CAA CCA GAT TTC TTC TTA GAT GAA TAC CCA GAA GCA GTT AGC AAG AAA GTG GAA TCA  861
 T   G   A   V   P   E   F   K   E   E   K   L   Q   L   Q   P   K   P   R   S   307
ACT GGT GCT GTT CCA GAA TTC AAA GAA GAG AAA CTG CAG CTG CAA CCA AAA CCA CGT TCT  921
 G   A   V   E   E   T   F   R   I   V   K   D   S   L   S   D   D   V   V   K   377
GGA GCT GTG GAA GAA ACA TTT AGA ATT GTT AAG GAC TCT CTC AGT GAT GAT GTT GTT AAA  981
 A   T   Q   A   I   Y   L   F   E   L   S   G   E   D   G   G   T   W   F   L   347
GCC ACT CAA GCA ATC TAT CTG TTT GAA CTC TCC GGT GAA GAT GGT GGC ACG TGG TTT CTT 1041
 D   L   K   S   K   G   G   N   V   G   Y   G   E   P   S   D   Q   A   D   V   367
GAT CTG AAA AGC AAG GGT GGG AAT GTC GGA TAT GGA GAG CCT TCT GAT CAG GCA GAT GTG 1101
 V   M   S   M   T   T   D   D   F   V   K   M   F   S   G   K   L   K   P   T   387
GTG ATG AGT ATG ACT ACT GAT GAC TTT GTA AAA ATG TTT TCA GGG AAA CTA AAA CCA ACA 1161
 M   A   F   M   S   G   K   L   K   I   K   G   N   M   A   L   A   I   K   L   407
ATG GCA TTC ATG TCA GGG AAA TTG AAG ATT AAA GGT AAC ATG GCC CTA GCA ATC AAA TTG 1221
 E   K   L   M   N   Q   M   N   A   R   L   *                                   419
GAG AAG CTA ATG AAT CAG ATG AAT GCC AGA CTG TGA                                 1257
```

AGGAAAATATAAAAAAAAAGTCGACTGCTATGCTCAAAAAGTAAAAAAAGCTCAACAGTTAAAATCTAATGTTTGTTTT

CTTTCCTGTTATATTATAAGGATATGCACGTTTGTTCTGGAAAAGATAGAATTTGTCTCTAAAAGACTTGAAATTGTAA

TTAAAATGGCAAGCTAATCAAACATAAGCTTCATTAAGTGGGATTCTAAGACAGTCTGTGTTTTTATATTTCAAGGGTT

TAACCCTTTGAGCCTTACATCTCATTCACTGTCTTTCTCCAAGAAAAGTATTTTGGGCGGACAGTCAGATCAAGCAGTA

AAATTAGCTCTTTCAAATCTTCTTGTCATGTAAAATGAAGCTAGTCTGTTTTAAAATTTTTAGTTTTGGATTGTATACT

AATGAAAATCTTAATGATGTTTTKRWTTTTTATATACYTAWTTTWAARRAAAWYYTWWWWWRKWCMTTTTTWMCAAAAAW

TWTTAAAAAWKRRWWWKWRYTSKGSGMGRASWMWAWRWRAMMC

FIG. 21B.

Prosite Pattern Matches for 21612

>PS00001/PDOC00001/ASN_GLYCOSYLATION N-glycosylation site.

Query: 101    NASA    104

>PS00005/PDOC00005/PKC_PHOSPHO_SITE Protein kinase C phosphorylation site.

Query: 5      TGR     7
Query: 115    TKR     117
Query: 282    SKK     284
Query: 313    TFR     315
Query: 381    SGK     383
Query: 392    SGK     394

>PS00006/PDOC00006/CK2_PHOSPHO_SITE Casein kinase II phosphorylation site.

Query: 56     TAAE    59
Query: 320    SLSD    323
Query: 338    SGED    341
Query: 372    TTDD    375

>PS00008/PDOC00008/MYRISTYL N-myristoylation site.

Query: 17     GASRGI  22
Query: 52     GTIYTA  57
Query: 128    GTYLAS  133
Query: 353    GGNVGY  358

>PS00342/PDOC00299/MICROBODIES_CTER Microbodies C-terminal targeting signal.

Query: 416    ARL     418

FIG. 24.

> Fbh21615a - Import - complete

```
1     ATGCAAAAGC CGAGNCCGCC TCGGCCTCTA AGCTATTCCA GAAGTAGTAA GAAGGCTTTT
61    TTGAAGGCCT AGGCTTTTGC AAAAAGCTCC TCGATCGAGG GGCTCGCATC TCTCCTTCAC
121   GGGGCCGCCG CCCTACCTGA GGCCGCCATC CACGCCGGTT GAGTCGCGTT CTGCCGCCTC
181   CCGCCTGTGG TGCCTCCTGA ACTGCGTCCG CCGTYTAGGT AAGTTTAAAG CTCAGGTCGA
241   GACCGGGCCT TTGTCCGGCG CTCCCTTGGA GCCTACCTAG ACTCAGCCGG CTCTCCACGC
301   TTTGCCTGAC CCTGCTTGCT CAACTCTACG TCTTTGTTTC GTTTTCTGTT CTGCGCCGTT
361   ACAGATCCAA GCTCTGAAAA ACCAGAAAGT TAACTGGTAA GTTTAGTCTT TTTGTCTTTT
421   ATTTCAGGTC CCGGATCCGG TGGTGGTGCA AATCAAAGAA CTGCTCCTCA GTGGATGTTG
481   CCTTTACTTC TAGGCCTGTA CGGAAGTGTT ACTTCTGCTC TAAAAGCTGC GGAATTCTAA
541   TACGACTCAC TATAGGGAGT CGACCCACGC GTCCGCAAAC CGAGTTCTGG AGAACGCCAT
601   CAGCTCGCTG CTTAAAATTA AACCACAGGT TCCATTATGG GTCGACTTGA TGGGAAAGTC
661   ATCATCCTGA CGGCCGCTGC TCAGGGGATT GGCCAAGCAG CTGCCTTAGC TTTTGCAAGA
721   GAAGGTGCCA AAGTCATAGC CACAGACATT AATGAGTCCA AACTTCAGGA ACTGGAAAAG
781   TACCCGGGTA TTCAAACTCG TGTCCTTGAT GTCACAAAGA GAAACAAAT TGATCAGTTT
841   GCCAATGAAG TTGAGAGACT TGATGTTCTC TTTAATGTTG CTGGTTTTGT CCATCATGGA
901   ACTGTCCTGG ATTGTGAGGA GAAAGACTGG GACTTCTCGA TGAATCTCAA TGTGCGCAGC
961   ATGTACCTGA TGATCAAGGC ATTCCTTCCT AAAATGCTTG CTCAGAAATC TGGCAATATT
1021  ATCAACATGT CTTCTGTGGC TTCCAGCGTC AAAGGAGTTG TGAACAGATG TGTGTACAGC
1081  ACAACCAAGG CAGCCGTGAT TGGCCTCACA AAATCTGTGG CTGCAGATTT CATCCAGCAG
1141  GGCATCAGGT GCAACTGTGT GTGCCCAGGA ACAGTTGATA CGCCATCTCT ACAAGAAAGA
1201  ATACAAGCCA GAGGAAATCC TGAAGAGGCA CGGAATGATT TCCTGAAGAG ACAAAAGACG
1261  GGAAGATTCG CAACTGCAGA AGAAATAGCC ATGCTCTGCG TGTATTTGGC TTCTGATGAA
1321  TCTGCTTATG TAACTGGTAA CCCTGTCATC ATTGATGGAG CTGGAGCTT GTGATTTTAG
1381  GATCTCCATG GTGGGAAGGA AGGCAGGCCC TTCCTATCCA CAGTGAACCT GGTTACGAAG
1441  AAAACTCACC AATCATCTCC TTCCTGTTAA TCACATGTTA ATGAAAATAA GCTCTTTTTA
1501  ATGATGTCAC TGTTTGCAAG AGTCTGATTC TTTAAGTATA TTAATCTCTT GTAATCTCT
1561  TCTGAAATCA TTGTAAAGAA ATAAAAATAT TGAACTCAAA AAAAAAAAAA AAAAAAGGGC
1621  GGCCGCTAGA CTAGTCTAGA GAAAAAACCT CCCACACCTC CCCCTGAACC TGAAACATAA
1681  AATGAATGCM ATTGTTGKTG GTAACTTGTT ATTGCA
```

FIG. 25A.

> Fbh21615a - Import - complete

```
                                  MGRDDGKV IILTAAAQGI GQAAALAFAR
EGAKVIATDI NESKLQELEK YPGIQTRVLD VTKKKQIDQF ANEVERLDVL FNVAGFVHHG
TVLDCEEKDW DFSMNLNVRS MYLMIKAFLP KMLAQKSGNI INMSSVASSV KGVVNRCVYS
TTKAAVIGLT KSVAADFIQQ GIRCNCVCPG TVDTPSLQER IQARGNPEEA RNDFLKRQKT
GRFATAEEIA MLCVYLASDE SAYVTGNPVI IDGGWSL*
```

FIG. 25B.

Prosite Pattern Matches for 21615

>PS00001/PDOC00001/ASN_GLYCOSYLATION N-glycosylation site.

Query: 39      NESK      42
Query: 130     NMSS      133

>PS00005/PDOC00005/PKC_PHOSPHO_SITE Protein kinase C phosphorylation site.

Query: 60      TKK       62
Query: 137     SVK       139

Query: 149     TTK       151
Query: 208     TGR       210

>PS00006/PDOC00006/CK2_PHOSPHO_SITE Casein kinase II phosphorylation site.

Query: 89      TVLD      92
Query: 184     SLQE      187
Query: 213     TAEE      216

>PS00007/PDOC00007/TYR_PHOSPHO_SITE Tyrosine kinase phosphorylation site.

Query: 42      KLQELEKY       49

>PS00008/PDOC00008/MYRISTYL N-myristoylation site.

Query: 17      GIGQAA    22
Query: 126     GNIINM    131
Query: 156     GLTKSV    161
Query: 169     GIRCNC    174

>PS00061/PDOC00060/ADH_SHORT Short-chain alcohol dehydrogenase family signature.

Query: 147     YSTTKAAVIGL    157

FIG. 28.

Input file Fbb23484FL2.seq; Output File 23484.trans
Sequence length 3941

CACGCGTCCGGGCGCCGGAGGCCCGGATGGTGCGCGTGCTGGGCCGCGGGCCGAAGGAGTCGCCAGGGCTGCGTAGGCT

TGTGGCGCGCCCGCGGAGAGGCCGGGGCTCTGACGCCCGCTCTGCGGCTTCGGTGTTTGAACAGGCCACAGTCCAGGAG

CGCTTACATTCAGGAGCTCCGCGTAGCACCTGCCCAACCAAACTCAGCCCTCCGTTAAGATCCTGGTTCCATGCCGCAG

|  |  |  |  |  |  |  |  |  | M | P | I | V | D | K | L | K | E | 9 |
|--|--|--|--|--|--|--|--|--|--|--|--|--|--|--|--|--|--|--|
| TAGGACAGCAGGCCCAAGTCTGCACATCCCAGTGATGCACC | | | | | | | | | ATG | CCA | ATA | GTG | GAT | AAG | TTG | AAG | GAG | 27 |

| A | L | K | P | G | R | K | D | S | A | D | D | G | E | L | G | K | L | L | A | 29 |
|--|--|--|--|--|--|--|--|--|--|--|--|--|--|--|--|--|--|--|--|--|
| GCC | CTG | AAA | CCC | GGC | CGC | AAG | GAC | TCG | GCT | GAT | GAT | GGA | GAA | CTG | GGG | AAG | CTT | CTT | GCC | 87 |

| S | S | A | K | K | V | L | L | Q | K | I | E | F | E | P | A | S | K | S | F | 49 |
| TCC | TCT | GCC | AAG | AAG | GTC | CTT | TTA | CAG | AAA | ATC | GAG | TTC | GAG | CCA | GCC | AGC | AAG | AGC | TTC | 147 |

| S | Y | Q | L | E | A | L | K | S | K | Y | V | L | L | N | P | K | T | E | G | 69 |
| TCC | TAC | CAG | CTG | GAG | GCC | TTA | AAG | AGC | AAA | TAT | GTG | TTG | CTC | AAC | CCC | AAA | ACA | GAG | GGA | 207 |

| A | S | R | H | K | S | G | D | D | P | P | A | R | R | Q | G | S | E | H | T | 89 |
| GCT | AGT | CGC | CAC | AAG | AGT | GGA | GAT | GAC | CCA | CCG | GCC | AGG | AGA | CAG | GGC | AGT | GAG | CAC | ACG | 267 |

| Y | E | S | C | G | D | G | V | P | A | P | Q | K | V | L | F | P | T | E | R | 109 |
| TAT | GAG | AGC | TGT | GGT | GAC | GGA | GTC | CCA | GCC | CCG | CAG | AAA | GTG | CTT | TTC | CCC | ACG | GAG | CGA | 327 |

| L | S | L | R | W | E | R | V | F | R | V | G | A | G | L | H | N | L | G | N | 129 |
| CTG | TCT | CTG | AGG | TGG | GAG | CGG | GTC | TTC | CGC | GTG | GGC | GCA | GGA | CTC | CAC | AAC | CTT | GGC | AAC | 387 |

| T | C | F | L | N | A | T | I | Q | C | L | T | Y | T | P | P | L | A | N | Y | 149 |
| ACC | TGC | TTT | CTC | AAT | GCC | ACC | ATC | CAG | TGC | TTG | ACC | TAC | ACA | CCA | CCT | CTA | GCC | AAC | TAC | 447 |

| L | L | S | K | E | H | A | R | S | C | H | Q | G | S | F | C | M | L | C | V | 169 |
| CTG | CTC | TCC | AAG | GAG | CAT | GCT | CGC | AGC | TGC | CAC | CAG | GGA | AGC | TTC | TGC | ATG | CTG | TGT | GTC | 507 |

| M | Q | N | H | I | V | Q | A | F | A | N | S | G | N | A | I | K | P | V | S | 189 |
| ATG | CAG | AAC | CAC | ATT | GTC | CAG | GCC | TTC | GCC | AAC | AGC | GGC | AAC | GCC | ATC | AAG | CCC | GTC | TCC | 567 |

| F | I | R | D | L | K | K | I | A | R | H | F | R | F | G | N | Q | E | D | A | 209 |
| TTC | ATC | CGA | GAC | CTG | AAA | AAG | ATC | GCC | CGA | CAC | TTC | CGC | TTT | GGG | AAC | CAG | GAG | GAC | GCG | 627 |

| H | E | F | L | R | Y | T | I | D | A | M | Q | K | A | C | L | N | G | C | A | 229 |
| CAT | GAG | TTC | CTG | CGG | TAC | ACC | ATC | GAC | GCC | ATG | CAG | AAA | GCC | TGC | CTG | AAT | GGC | TGT | GCC | 687 |

| K | L | D | R | Q | T | Q | A | T | T | L | V | H | Q | I | F | G | G | Y | L | 249 |
| AAG | TTG | GAT | CGT | CAA | ACG | CAG | GCT | ACT | ACC | TTG | GTC | CAT | CAA | ATT | TTT | GGA | GGG | TAT | CTC | 747 |

| R | S | R | V | K | C | S | V | C | K | S | V | S | D | T | Y | D | P | Y | L | 269 |
| AGA | TCA | CGC | GTG | AAG | TGC | TCC | GTG | TGC | AAG | AGC | GTC | TCG | GAC | ACC | TAC | GAC | CCC | TAC | TTG | 807 |

FIG. 33A.

```
  D   V   A   L   E   I   R   Q   A   A   N   I   V   R   A   L   E   L   F   V   289
GAC GTC GCG CTG GAG ATC CGG CAA GCT GCG AAT ATT GTG CGT GCT CTG GAA CTT TTT GTG  867
  K   A   D   V   L   S   G   E   N   A   Y   M   C   A   K   C   K   K   K   V   309
AAA GCA GAT GTC CTG AGT GGA GAG AAT GCC TAC ATG TGT GCT AAA TGC AAG AAG AAG GTT  927
  P   A   S   K   R   F   T   I   H   R   T   S   N   V   L   T   L   S   L   K   329
CCA GCC AGC AAG CGC TTC ACC ATC CAC AGA ACA TCC AAC GTC TTA ACC CTT TCC CTC AAG  987
  R   F   A   N   F   S   G   G   K   I   T   K   D   V   G   Y   P   E   F   L   349
CGC TTT GCC AAC TTC AGC GGG GGG AAG ATC ACC AAG GAT GTA GGC TAT CCG GAA TTC CTC 1047
  N   I   R   P   Y   M   S   Q   N   N   G   D   P   V   M   Y   G   L   Y   A   369
AAC ATA CGT CCG TAT ATG TCC CAG AAT AAT GGT GAT CCT GTC ATG TAT GGA CTC TAT GCT 1107
  V   L   V   H   S   G   Y   S   C   H   A   G   H   Y   Y   C   Y   V   K   A   389
GTC CTG GTG CAC TCG GGC TAC AGC TGC CAT GCC GGG CAC TAT TAC TGC TAC GTG AAG GCA 1167
  S   N   G   Q   W   Y   Q   M   N   D   S   L   V   H   S   S   N   V   K   V   409
AGC AAT GGA CAG TGG TAC CAG ATG AAT GAT TCC TTG GTC CAT TCC AGC AAC GTC AAG GTG 1227
  V   L   N   Q   Q   A   Y   V   L   F   Y   L   R   I   P   G   S   K   K   S   429
GTT CTG AAC CAG CAG GCC TAC GTG CTG TTC TAT CTG CGA ATT CCA GGC TCT AAG AAA AGT 1287
  P   E   G   L   I   S   R   T   G   S   S   S   L   P   G   R   P   S   V   I   449
CCC GAG GGC CTC ATC TCC AGG ACA GGC TCC TCC TCC CTT CCC GGC CGC CCG AGT GTG ATT 1347
  P   D   H   S   K   K   N   I   G   N   G   I   I   S   S   P   L   T   G   K   469
CCA GAT CAC TCC AAG AAG AAC ATC GGC AAT GGG ATT ATT TCC TCC CCA CTG ACT GGA AAG 1407
  R   Q   D   S   G   T   M   K   K   P   H   T   T   E   E   I   G   V   P   I   489
CGA CAA GAC TCT GGG ACG ATG AAG AAG CCG CAC ACC ACT GAA GAG ATT GGT GTG CCC ATA 1467
  S   R   N   G   S   T   L   G   L   K   S   Q   N   G   C   I   P   P   K   L   509
TCC AGG AAT GGC TCC ACC CTG GGC CTG AAG TCC CAG AAC GGC TGC ATT CCT CCA AAG CTG 1527
  P   S   G   S   P   S   P   K   L   S   Q   T   P   T   H   M   P   T   I   L   529
CCC TCG GGG TCC CCT TCC CCC AAA CTC TCC CAG ACA CCC ACA CAC ATG CCA ACC ATC CTA 1587
  D   D   P   G   K   K   V   K   K   P   A   P   P   Q   H   F   S   P   R   T   549
GAC GAC CCT GGA AAG AAG GTG AAG AAG CCA GCT CCT CCA CAG CAC TTT TCC CCC AGA ACT 1647
  A   Q   G   L   P   G   T   S   N   S   N   S   S   R   S   G   S   Q   R   Q   569
GCT CAG GGG CTG CCT GGG ACC AGC AAC TCG AAT AGC AGC AGA TCT GGG AGC CAA AGG CAG 1707
  G   S   W   D   S   R   D   V   V   L   S   T   P   K   L   L   A   T   A   589
GGC TCC TGG GAC AGC AGG GAT GTT GTC CTC TCT ACC TCA CCT AAG CTC CTG GCT ACA GCC 1767
  T   A   N   G   H   G   L   K   G   N   D   E   S   A   G   L   D   R   R   G   609
ACT GCC AAC GGG CAT GGG CTG AAG GGG AAC GAC GAG AGC GCT GGC CTC GAC AGG AGG GGC 1827
  S   S   S   S   P   E   H   S   A   S   S   D   S   T   K   A   P   Q   T   629
TCC AGC AGC TCC AGC CCA GAG CAC TCG GCC AGC AGC GAC TCC ACC AAG GCC CCC CAG ACC 1887
```

FIG. 33B.

```
      P   R   S   G   A   A   H   L   C   D   S   Q   E   T   N   C   S   T   A   G   649
     CCC AGG AGT GGA GCG GCC CAT CTC TGC GAT TCT CAG GAA ACG AAC TGT TCC ACC GCT GGC 1947
      H   S   K   T   P   P   S   G   A   D   S   K   T   V   K   L   K   S   P   V   669
     CAC TCC AAA ACG CCG CCA AGT GGA GCA GAT TCT AAG ACG GTG AAG CTG AAG TCC CCT GTC 2007
      L   S   N   T   T   T   E   P   A   S   T   M   S   P   P   P   A   K   K   L   689
     CTG AGC AAC ACC ACC ACT GAG CCT GCA AGC ACC ATG TCT CCT CCA CCA GCC AAA AAA CTG 2067
      A   L   S   A   K   K   A   S   T   L   W   R   A   T   G   N   D   L   R   P   709
     GCC CTT TCT GCC AAG AAG GCC AGC ACC CTG TGG AGG GCG ACC GGC AAT GAC CTC CGT CCA 2127
      P   P   P   S   P   S   S   D   L   T   H   P   M   K   T   S   H   P   V   V   729
     CCT CCC CCC TCA CCA TCC TCC GAC CTC ACC CAC CCC ATG AAA ACC TCT CAC CCC GTC GTT 2187
      A   S   T   W   P   V   H   R   A   R   A   V   S   P   A   P   Q   S   S   S   749
     GCC TCC ACT TGG CCC GTC CAT AGA GCC AGG GCT GTG TCA CCT GCT CCC CAA TCA TCC AGC 2247
      R   L   Q   P   P   F   S   P   H   P   T   L   L   S   S   T   P   K   P   P   769
     CGC CTG CAA CCC CCC TTC AGC CCC CAC CCC ACA TTG CTG TCC AGT ACC CCC AAG CCC CCA 2307
      G   T   S   E   P   R   S   C   S   S   I   S   T   A   L   P   Q   V   N   E   789
     GGG ACG TCA GAA CCA CGG AGC TGC TCC TCC ATC TCG ACG GCG CTG CCT CAG GTC AAC GAG 2367
      D   L   V   S   L   P   H   Q   L   P   E   A   S   E   P   P   Q   S   P   S   809
     GAC CTT GTG TCT CTT CCA CAC CAG TTG CCA GAG GCC AGT GAG CCC CCC CAG AGC CCC TCT 2427
      E   K   R   K   K   T   F   V   G   E   P   Q   R   L   G   S   E   T   R   L   829
     GAG AAG AGG AAA AAG ACC TTT GTG GGA GAG CCG CAG AGG CTG GGC TCA GAG ACG CGC CTC 2487
      P   Q   H   I   R   E   A   T   A   A   P   H   G   K   R   K   R   K   K   K   849
     CCA CAG CAC ATC AGG GAG GCC ACT GCG GCT CCC CAC GGG AAG AGG AAG AGG AAG AAG AAG 2547
      K   R   P   E   D   T   A   A   S   A   L   Q   E   G   Q   T   Q   R   Q   P   869
     AAG CGC CCG GAG GAC ACA GCT GCC AGC GCC CTG CAG GAG GGG CAG ACA CAG AGA CAG CCT 2607
      G   S   P   M   Y   R   R   E   G   Q   A   Q   L   P   A   V   R   R   Q   E   889
     GGG AGC CCC ATG TAC AGG AGG GAG GGC CAG GCA CAG CTG CCC GCT GTC AGA CGG CAG GAA 2667
      D   G   T   Q   P   Q   V   N   G   Q   Q   V   G   C   V   T   D   G   H   H   909
     GAT GGC ACA CAG CCA CAG GTG AAT GGC CAG CAG GTG GGA TGT GTT ACG GAC GGC CAC CAC 2727
      A   S   S   R   K   R   R   R   K   G   A   E   G   L   G   E   E   G   G   L   929
     GCG AGC AGC AGG AAG CGG AGG AGG AAA GGA GCA GAA GGT CTT GGT GAA GAA GGC GGC CTG 2787
      H   Q   D   P   L   R   H   S   C   S   P   M   G   D   G   D   P   E   A   M   949
     CAC CAG GAC CCA CTT CGG CAC AGC TGC TCT CCC ATG GGT GAT GGT GAT CCA GAG GCC ATG 2847
      E   E   S   P   R   K   K   K   K   K   R   K   Q   E   T   Q   R   A   V   969
     GAA GAG TCT CCA AGG AAA AAG AAA AAG AAA AAA AGA AAG CAG GAG ACA CAG CGG GCA GTA 2907
      E   E   D   G   H   L   K   C   P   R   S   A   K   P   Q   D   A   V   V   P   989
     GAA GAG GAT GGG CAT CTC AAA TGC CCA AGG AGT GCC AAG CCC CAA GAT GCT GTT GTC CCC 2967
```

FIG. 33C.

```
    E   S   S   S   C   A   P   S   A   N   G   W   C   P   G   D   R   M   G   L   1009
   GAG TCC AGC AGC TGC GCA CCA TCC GCG AAT GGC TGG TGT CCT GGG GAC CGC ATG GGG CTG 3027
    S   Q   A   P   P   V   S   W   N   G   E   R   E   S   D   V   V   Q   E   L   1029
   AGC CAG GCC CCT CCT GTG TCT TGG AAT GGA GAG CGG GAG TCT GAT GTG GTC CAG GAA CTG 3087
    L   K   Y   S   S   D   K   A   Y   G   R   K   V   L   T   W   D   G   K   M   1049
   CTC AAA TAC TCA TCT GAT AAA GCT TAC GGG AGA AAA GTT CTG ACC TGG GAT GGC AAG ATG 3147
    S   A   V   S   Q   D   A   I   E   D   S   R   Q   A   R   T   E   T   V   V   1069
   TCG GCG GTC AGT CAG GAT GCT ATT GAA GAC AGC AGA CAG GCC CGG ACT GAG ACC GTG GTT 3207
    D   D   W   D   E   E   F   D   R   G   K   E   K   K   I   K   K   F   K   R   1089
   GAT GAC TGG GAC GAA GAG TTT GAC CGA GGG AAG GAA AAG AAA ATT AAA AAA TTT AAG AGA 3267
    E   K   R   R   N   F   N   A   F   Q   K   L   Q   T   R   R   N   F   W   S   1109
   GAG AAG AGG AGA AAC TTC AAC GCC TTC CAG AAA CTT CAG ACT CGA CGG AAC TTC TGG TCT 3327
    V   T   H   P   A   K   A   A   S   L   S   Y   R   R   *                       1124
   GTG ACT CAC CCA GCA AAG GCT GCC AGC CTC AGC TAT CGC CGC TGA                     3372
```

CTGTGCCCCTGTGGAAGGAGATGATCAAGCGGTGCTGATTCACGAGAGTGGAAGCCTCCAGAGCTTGGGGCTTTCTGGC

TGCTCTTCATTGACCTGTGTGTTCCCAGCACACGAACAGCGCCCCTAACGGAGATTTGTTCAGCGACTGAATATACACC

TGTAAACGAGTAGCATGTATACATTGATTTTGATTACAAATGGTTCTGTATTATATACCACCGTTCTGACTGCTTTTTT

CACTTATAGCTTGGAAATTGTCTTCTGTTGGTAATACAGAAATCTGTTTCAGTC

FIG. 33D.

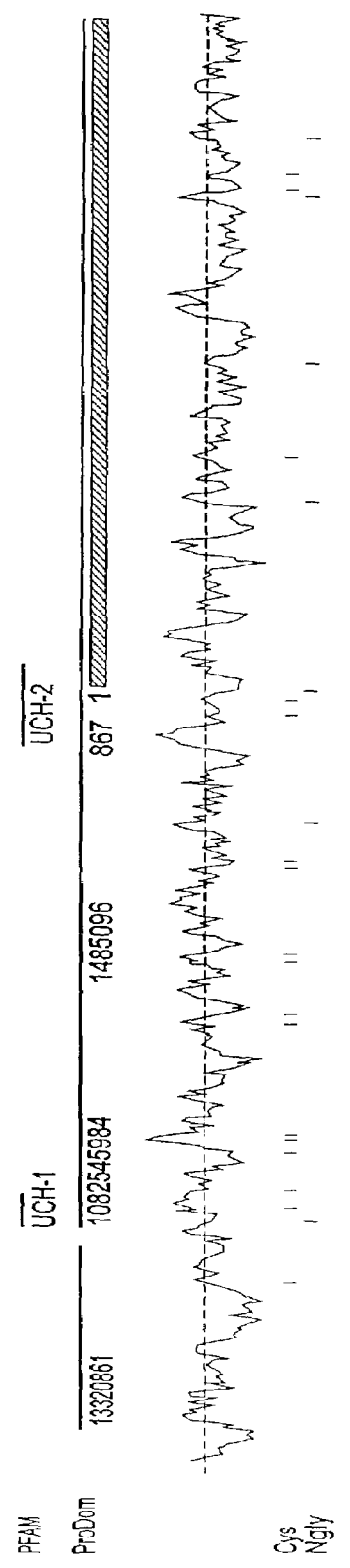

FIG. 35.

>23484
MPIVDKLKEALKPGRKDSADDGELGKLLASSAKKVLLQKIEFEPASKSFYQLEALKSKY
VLLNPKTEGASRHKSGDDPARRQSEHTYESCGDGVPAPQKVLFPTERLSLRWERVFRV
GAGLHNLGNTCFLNATIQCLFYPPLANYLLSKEHARSCHQGSFCMLCMQNHIVQAFAN
SGNAIKPVSFIRDLKKIARHFRFGNQEDAHEFLRYTIDAMQKACLNGCAKLDRQTQATTL
VHQTFGGYLRSPVKCSVCKSVSDTYDPYLDXALEIRQAANIVRALELFVKADVLSGENAY
MCAKCKKKVPASKFTIHRTSNVLTLSLKRFANFSGGKITKDVGYPEFLNIRPYMSQNNG
DPVKYGLYAVLVHSGYSCHAGHYYCYVKASNGQWYQMNDSLYHSSNVKVVLNQQAYLFY
LRIPGSKKSPEGLISRTGSSSLPQRPSVIPDHSKKNIGNGIISSPLTGKRQDSGTMKKPH
TEEIGVPISRNGSTLGLKSQNGCIPPKLPSGSPSPKLSQTPTHMPTILDPPGKKVKKPA
PPQHFSPRTAQGLPGTSNNSRSGSGRQGSWDSRDVVLSTSPKLLATATANGHLKGND
ESAGLDRRGSSSSSPEHSASSDSTKAPQTPRSGAAHLCDSQEINCSTAGHSKTPPSGADS
KTVKLKSPVLSNTTTEPASTMSPPPAAKKLALSAKKASTLWRATGNDLRPPPPSPSSDLTH
PMKTSHPVVASTWPVHRARAYSPAPQSSSRLQPPFSPHPTLLSSTPKPPGTSEPRSCSSI
STALPQWNEDLVSLPHQLPEASEPPQSPSEKRKKTFVGEPQRLGSETRLPQHIREATAAP
HGKRKKKKRPEDIAASALQEGQTQRQPGSPMYRREGAAQLPAVRRQEDGTQRQVNGQQ
VGCVTDGHHASSRKRRRKGAEGLGEEGGLHQDPLRHSCSPMGDGDPEAMEESPRKKKKKKK
RKQETQRAVEEDGHLKCPRSAKPQDAVVPESSSCAPSANGWCPGDRMGLSGAPPYSWNGE
RESDVVQELLKYSSBKAYGRKVLTWDGKMSAVSQDAIEDSRQARTETVVDDWDEEFDRGK
EKKIKKFKREKRRNFNAFQKLQTRRNFWSYTHPAKAASLSYRR

Prosite Pattern Matches for 23484

Prosite version: Release 12.2 of February 1995

>PS00001|PDOC00001|ASN_GLYCOSYLATION N-glycosylation site.

| Query: | 134 | NATI | 137 |
|---|---|---|---|
| Query: | 333 | NFSG | 336 |
| Query: | 398 | NDSL | 401 |
| Query: | 492 | NGST | 495 |
| Query: | 560 | NSSR | 563 |

FIG. 36A.

Query: 644    NCST    647
Query: 672    NTTT    675

>PS00004|PDOC00004|CAMP_PHOSPHO_SITE cAMP- and cGMP-dependent protein kinase phosphorylation site.

Query: 15     RKDS    18
Query: 313    KRFT    316
Query: 607    RRGS    610
Query: 694    KKAS    697
Query: 812    RKKT    815

>PS00005|PDOC00005|PKC_PHOSPHO_SITE Protein kinase C phosphorylation site.

Query: 31     SAK     33
Query: 107    TER     109
Query: 111    SLR     113
Query: 312    SKR     314
Query: 327    SLK     329
Query: 426    SKK     428
Query: 453    SKK     455
Query: 467    TGK     469
Query: 475    TMK     477
Query: 515    SPK     517
Query: 546    SPR     548
Query: 561    SSR     563
Query: 566    SQR     568
Query: 582    SPK     584
Query: 623    STK     625
Query: 629    TPR     631
Query: 662    TVK     664

FIG. 36B.

| Query: | 692 | SAK | 694 |
| Query: | 748 | SSR | 750 |
| Query: | 765 | TPK | 767 |
| Query: | 809 | SEK | 811 |
| Query: | 865 | TQR | 867 |
| Query: | 911 | SSR | 913 |
| Query: | 952 | SPR | 954 |
| Query: | 965 | TQR | 967 |
| Query: | 980 | SAK | 982 |
| Query: | 1034 | SDK | 1036 |
| Query: | 1103 | TRR | 1105 |
| Query: | 1120 | SYR | 1122 |

>PS00006|PDOC00006|CK2_PHOSPHO_SITE Casein kinase II phosphorylation site.

| Query: | 18 | SADD | 21 |
| Query: | 75 | SGDD | 78 |
| Query: | 92 | SCGD | 95 |
| Query: | 260 | SVSD | 263 |
| Query: | 481 | TTEE | 484 |
| Query: | 527 | TILD | 530 |
| Query: | 613 | SSPE | 616 |
| Query: | 656 | SGAD | 659 |
| Query: | 673 | TTTE | 676 |
| Query: | 703 | TGND | 706 |
| Query: | 807 | SPSE | 810 |
| Query: | 1067 | TVVD | 1070 |

FIG. 36C.

>PS00007|PDOC00007|TYR_PHOSPHO_SITE Tyrosine kinase phosphorylation site.

| Query: | 83 | RQGSEHTY | 90 |
|---|---|---|---|
| Query: | 338 | KITKDVGY | 345 |
| Query: | 1031 | KYSSDKAY | 1038 |

>PS00008|PDOC00008|MYRISTYL N-myristoylation site.

| Query: | 85 | GSEHTY | 90 |
|---|---|---|---|
| Query: | 336 | GGKITK | 341 |
| Query: | 486 | GVPISR | 491 |
| Query: | 493 | GSTLGL | 498 |
| Query: | 552 | GLPGTS | 557 |
| Query: | 570 | GSWDSR | 575 |
| Query: | 595 | GLKGND | 600 |
| Query: | 609 | GSSSSS | 614 |
| Query: | 898 | GQQVGC | 903 |

>PS00009|PDOC00009|AMIDATION Amidation site.

| Query: | 13 | PGRK | 16 |
|---|---|---|---|
| Query: | 467 | TGKR | 470 |
| Query: | 532 | PGKK | 535 |
| Query: | 841 | HGKR | 844 |
| Query: | 1038 | YGRK | 1041 |

>PS00290|PDOC00262|IG_MHC Immunoglobulins and major histocompatibility complex proteins signature.

Query:   376    YSCHAGH    382

>PS00973|PDOC00750|UCH_2_2 Ubiquitin carboxyl-terminal hydrolases family 2 signature 2.

Query:   365    YGLYAVLVHSGYSCHAGHY    383

FIG. 36D.

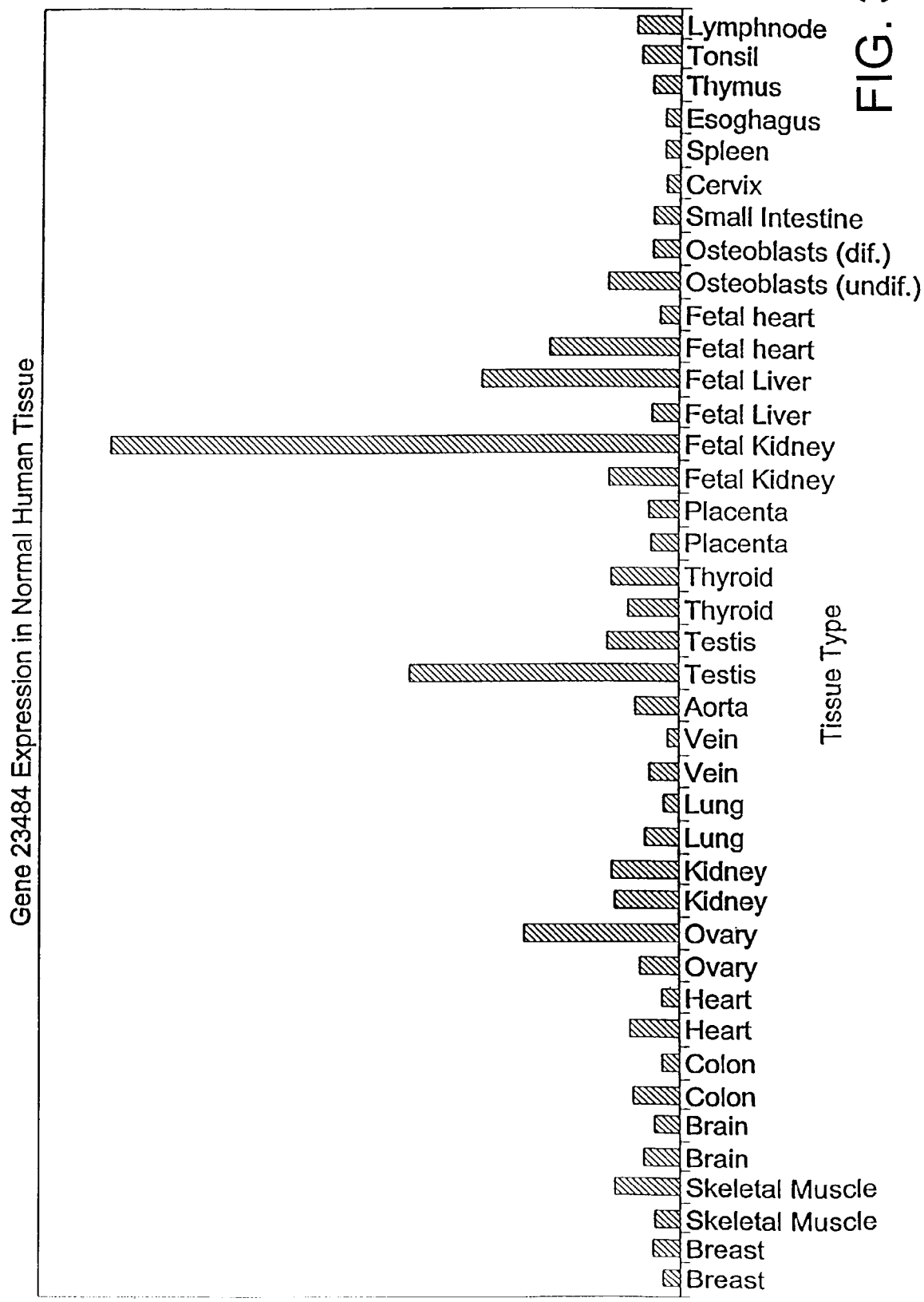

Input file Fbh18991FL.seq; Output File 18891.trans
Sequence length 1964

CACGCGTCCGGCTGGGCTGGGCGCCGGAGCCGGGAGCGGCGCGGGTAGGAGCCCGGCGGCAGGTCCCAGCCCGGGGCTA

GAGACCGAGGGCCGGGGTCCGGGCCCGGCGGCGGGACCCAGGCGGTTGAGGCTGGTCAGGAGTCAGCCAGCCTGAAAGA

```
               M   D   L   D   V   V   N   M   F   V   I   A   G   G   T   L   A   I    18
        GCAGG ATG GAT CTT GAT GTG GTT AAC ATG TTT GTG ATT GCG GGC GGC ACG CTG GCC ATC    54
       P   I   L   A   F   V   A   S   F   L   L   W   P   S   A   L   I   R   I   Y    38
     CCA ATC CTG GCA TTT GTG GCT TCA TTT CTT CTG TGG CCT TCA GCA CTG ATA AGA ATC TAT   114
       Y   W   Y   W   R   R   T   L   G   M   Q   V   R   Y   V   H   H   E   D   Y    58
     TAT TGG TAC TGG CGG AGG ACA TTG GGC ATG CAA GTC CGC TAT GTT CAC CAT GAA GAC TAT   174
       Q   F   C   Y   S   F   R   G   R   P   G   H   K   P   S   I   L   M   L   H    78
     CAG TTC TGT TAT TCC TTC CGG GGC AGG CCT GGG CAC AAA CCC TCC ATC CTC ATG CTC CAC   234
       G   F   S   A   H   K   D   M   W   L   S   V   V   K   F   L   P   K   N   L    98
     GGA TTC TCT GCC CAC AAG GAT ATG TGG CTC AGT GTG GTC AAG TTC CTT CCA AAG AAC CTG   294
       H   L   V   C   V   D   M   P   G   H   E   G   T   T   R   S   S   L   D   D   118
     CAC TTG GTC TGC GTG GAC ATG CCA GGA CAT GAG GGC ACC ACC CGC TCC TCC CTG GAT GAC   354
       L   S   I   D   G   Q   V   K   R   I   H   Q   F   V   E   C   L   K   L   N   138
     CTG TCC ATA GAT GGG CAA GTT AAG AGG ATA CAC CAG TTT GTA GAA TGC CTG AAG CTG AAC   414
       K   K   P   F   H   L   V   G   T   S   M   G   G   Q   V   A   G   V   Y   A   158
     AAA AAA CCT TTC CAC CTG GTA GGC ACC TCC ATG GGT GGC CAG GTG GCT GGG GTG TAT GCT   474
       A   Y   Y   P   S   D   V   S   S   L   C   L   V   C   P   A   G   L   Q   Y   178
     GCT TAC TAC CCA TCG GAT GTC TCC AGC CTG TGT CTC GTG TGT CCT GCT GGC CTG CAG TAC   534
       S   T   D   N   Q   F   V   Q   R   L   K   E   L   Q   G   S   A   A   V   E   198
     TCA ACT GAC AAT CAA TTT GTA CAA CGG CTC AAA GAA CTG CAG GGC TCT GCC GCC GTG GAG   594
       K   I   P   L   I   P   S   T   P   E   E   M   S   E   M   L   Q   L   C   S   218
     AAG ATT CCC TTG ATC CCG TCT ACC CCA GAA GAG ATG AGT GAA ATG CTT CAG CTC TGC TCC   654
       Y   V   R   F   K   V   P   Q   Q   I   L   Q   G   L   V   D   V   R   I   P   238
     TAT GTC CGC TTC AAG GTG CCC CAG CAG ATC CTG CAA GGC CTT GTC GAT GTC CGC ATC CCT   714
       H   N   N   F   Y   R   K   L   F   L   E   I   V   S   E   K   S   R   Y   S   258
     CAT AAC AAC TTC TAC CGA AAG TTG TTT TTG GAA ATC GTC AGT GAG AAG TCC AGA TAC TCT   774
       L   H   Q   N   M   D   K   I   K   V   P   T   Q   I   I   W   G   K   Q   D   278
     CTC CAT CAG AAC ATG GAC AAG ATC AAG GTT CCG ACG CAG ATC ATC TGG GGG AAA CAA GAC   834
       Q   V   L   D   V   S   G   A   D   M   L   A   K   S   I   A   N   C   Q   V   298
     CAG GTG CTG GAT GTG TCT GGG GCA GAC ATG TTG GCC AAG TCA ATT GCC AAC TGC CAG GTG   894
       E   L   L   E   N   C   G   H   S   V   V   M   E   R   P   R   K   T   A   K   318
     GAG CTT CTG GAA AAC TGT GGG CAC TCA GTA GTG ATG GAA AGA CCC AGG AAG ACA GCC AAG   954
       L   I   I   D   F   L   A   S   V   H   N   T   D   N   N   K   K   L   D   *   338
     CTC ATA ATC GAC TTT TTA GCT TCT GTG CAC AAC ACA GAC AAC AAC AAG AAG CTG GAC TGA 1014
```

GGCCCCGACTGCAGCCTGCATTCTGCACACAGCATCTGCTCCCATCCCCCAAGTCTGACGCAGCCACCACTCTCAGGGA

TCCTGCCCCAAATGCGGTCGGAGCGCCAGTGACCCTGAGGAAGCCCGTCCCTTATCCCTGGTATCCACGGTTCCCCAGA

GCTTTGGGGACCACGCGAAAACCTCCAAGATATTTTTCACAAAATAGAAACTCATATGGAACAAAATAAGAAACCCCAG

FIG. 39A.

```
CCATGAAATCTACCATGAAGTCTTCAAGTTCATGTCACTGAGAAGCTTGTGCAAAGCAGCCACCTTGGACCATAATTAA
ATCAAGGACATTTTCTTTGAGACATTCCTTATAGTTGGAGACTCAAGATATTTTTGTTGCATCAGGTGTATTCCCTTGC
ATGGGCAGTGGCTTTTATAGGAGCATTAGTCCTCATTCGCTGAACCCTGTTGTTTAGGTCTAATTTAAGTTTTACATAG
AGACCCATGTATGACTGCAGCCCATTGGCTGCAAGACCAGGGAGGAAAGTGGCAAGCTGTAGAAAATGTTTACACGCAT
GGAGGGGCATTGCTCTAGCCCTCAGAGCGTCCGGAGCAGCAGGGTACATGGGTGGGAGGTTCATTCAGCACCCACCAGT
CAGGTATGTTCTGAGTGAACCCACAGCAGTCGCAGAATGAGCACCTGGCAGGGTGGGTTTCCTAGGAATAATTTATTAT
TTTTAAAAATAGGCCTAATAAAGCAATAATGTTCTAGAAAAAAAAAAAAAAAAAAAAAAAAAAAAAAAAAAAAAAAAAA
```

FIG. 39B.

Prosite Pattern Matches for 18891

Prosite version: Release 12.2 of February 1995

>PS00005/PDOC00005/PKC_PHOSPHO_SITE Protein kinase C phosphorylation site.

| Query: | 63 | SFR | 65 |
| Query: | 111 | TTR | 113 |

| Query: | 252 | SEK | 254 |
| Query: | 316 | TAK | 318 |

>PS00006/PDOC00006/CK2-PHOSPHO_SITE Casein kinase II phosphorylation site.

| Query: | 114 | SSLD | 117 |
| Query: | 205 | STPE | 208 |
| Query: | 284 | SGAD | 287 |

>PS00008/PDOC00008/MYTRISTYL N-myristoylation site.

| Query: | 13 | GGTLAI | 18 |
| Query: | 110 | GTTRSS | 115 |
| Query: | 146 | GTSMGG | 151 |
| Query: | 155 | GVYAAY | 160 |
| Query: | 175 | GLQYST | 180 |

FIG. 42.

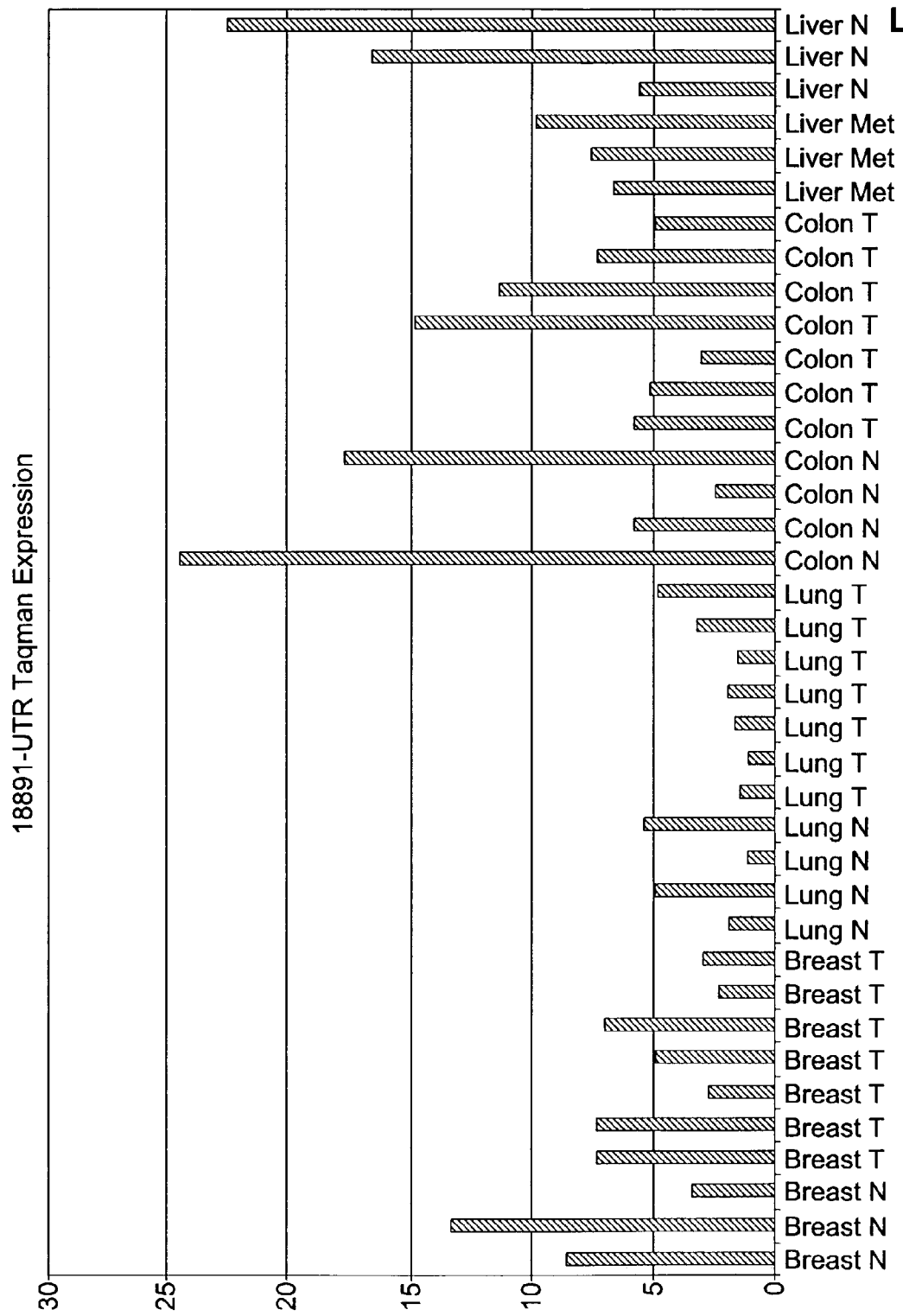

```
Input file Fbh25678FL.seq; Output File 25678.trans
Sequence length 4011
          10        20        30        40        50        60        70   M   R        2
CACGCGTCCGCCCGGCCCCCGCCCGCGCACGGCGGGCGCCCTGTGAGCGGCCCCGATGTGGCAGGAGGCG ATG CGG          6    72
  R   R   R   Y   L   R   D   R   S   E   E   A   A   G   G   G   D   G   L   P        22
CGC CGC CGC TAC CTG CGG GAC CGC TCC GAG GAG GCG GCG GGC GGC GGA GAC GGG CTG CCG         66   132
  R   S   R   D   W   L   Y   E   S   Y   Y   C   M   S   Q   Q   H   P   L   I        42
CGG TCC CGG GAC TGG CTC TAC GAG TCC TAC TAC TGC ATG AGC CAG CAG CAC CCG CTC ATC        126   192
  V   F   L   L   L   I   V   M   G   S   C   L   A   L   L   A   V   F   F   A        62
GTC TTC CTG CTG CTC ATC GTC ATG GGC TCC TGC CTC GCC CTG CTC GCC GTC TTC TTC GCG        186   252
  L   G   L   E   V   E   D   H   V   A   F   L   I   T   V   P   T   A   L   A        82
CTC GGG CTG GAA GTT GAA GAC CAT GTG GCG TTT CTA ATA ACA GTT CCA ACT GCC CTG GCG        246   312
  I   F   F   A   I   F   I   L   V   C   I   E   S   V   F   K   K   L   L   R       102
ATT TTC TTT GCG ATA TTT ATC CTG GTC TGC ATC GAG TCT GTG TTT AAG AAG CTG CTG CGC        306   372
  L   F   S   L   V   I   W   I   C   L   V   A   M   G   Y   L   F   M   C   F       122
CTC TTC TCG TTG GTG ATA TGG ATA TGC CTT GTT GCC ATG GGA TAC CTG TTC ATG TGT TTT        366   432
  G   G   T   V   S   P   W   D   Q   V   S   F   F   L   F   I   I   F   V   V       142
GGA GGC ACC GTC TCT CCC TGG GAC CAG GTA TCG TTC TTC CTC TTC ATC ATC TTC GTG GTG        426   492
  Y   T   M   L   P   F   N   M   R   D   A   I   I   A   S   V   L   T   S   S       162
TAC ACC ATG CTG CCC TTC AAC ATG CGA GAC GCC ATC ATT GCC AGC GTC CTC ACC TCC TCC        486   552
  S   H   T   I   V   L   S   V   C   L   S   A   T   P   G   G   K   E   H   L       182
TCC CAC ACC ATC GTG CTT AGC GTC TGC CTG TCT GCA ACA CCG GGA GGC AAG GAG CAC CTG        546   612
  V   W   Q   I   L   A   N   V   I   I   F   I   C   G   N   L   A   G   A   Y       202
GTC TGG CAG ATC CTG GCC AAT GTG ATC ATT TTC ATC TGT GGG AAC CTG GCG GGA GCC TAC        606   672
  H   K   H   L   M   E   L   A   L   Q   Q   T   Y   Q   D   T   C   N   C   I       222
CAT AAG CAC CTC ATG GAA CTC GCT CTT CAG CAA ACA TAT CAG GAC ACC TGT AAT TGC ATC        666   732
  K   S   R   I   K   L   E   F   E   K   R   Q   Q   E   R   L   L   L   S   L       242
AAG TCG CGG ATC AAG TTG GAA TTT GAA AAA CGT CAA CAG GAG CGG CTT CTG CTC TCC CTG        726   792
  L   P   A   H   I   A   M   E   M   K   A   E   I   I   Q   R   L   Q   G   P       262
CTG CCG GCC CAC ATC GCC ATG GAG ATG AAA GCG GAG ATC ATC CAG AGG CTG CAG GGC CCC        786   852
  K   A   G   Q   M   E   N   T   N   N   F   H   N   L   Y   V   K   R   H   T       282
AAG GCG GGC CAG ATG GAG AAC ACA AAT AAC TTC CAC AAC CTG TAT GTG AAG CGG CAT ACA        846   912
  N   V   S   I   L   Y   A   D   I   V   G   F   T   R   L   A   S   D   C   S       302
AAC GTG AGC ATC TTA TAC GCT GAC ATC GTT GGC TTT ACC CGG CTG GCA AGT GAC TGC TCC        906   972
  P   G   E   L   V   H   M   L   N   E   L   F   G   K   F   D   Q   I   A   K       322
CCG GGA GAA CTA GTC CAC ATG CTG AAT GAG CTC TTT GGA AAG TTT GAT CAA ATT GCA AAG        966  1032
  E   N   E   C   M   R   I   K   I   L   G   D   C   Y   Y   C   V   S   G   L       342
GAG AAT GAA TGC ATG AGA ATT AAA ATT TTA GGA GAC TGC TAC TAC TGT GTA TCT GGA CTC       1026  1092
  P   I   S   L   P   N   H   A   K   N   C   V   K   M   G   L   D   M   C   E       362
CCT ATA TCT CTC CCT AAC CAT GCC AAG AAC TGT GTG AAA ATG GGG CTG GAC ATG TGT GAA       1086  1152
  A   I   K   K   V   R   D   A   T   G   V   D   I   N   M   R   V   G   V   H       382
```

FIG. 46A.

```
GCC ATA AAG AAA GTG AGG GAT GCT ACT GGA GTT GAT ATC AAC ATG CGC GTG GGC GTG CAT 1146 1212
 S   G   N   V   L   C   G   V   I   G   L   Q   K   W   Q   Y   D   V   W   S   402
TCT GGG AAT GTC CTG TGT GGC GTG ATT GGT CTG CAG AAG TGG CAA TAT GAT GTG TGG TCA 1206 1272
 H   D   V   T   L   A   N   H   M   E   A   G   G   V   P   G   R   V   H   I   422
CAT GAT GTG ACC TTG GCC AAC CAC ATG GAA GCT GGA GGG GTC CCT GGA CGT GTT CAC ATT 1266 1332
 S   S   V   T   L   E   H   L   N   G   A   Y   K   V   E   E   G   D   G   D   442
TCT TCT GTC ACC CTG GAG CAC TTG AAT GGC GCT TAT AAA GTG GAG GAG GGA GAT GGT GAC 1326 1392
 I   R   D   P   Y   L   K   Q   H   L   V   K   T   Y   F   V   I   N   P   K   462
ATT AGG GAC CCA TAT TTA AAA CAG CAC CTG GTG AAA ACC TAC TTT GTG ATC AAC CCC AAG 1386 1452
 G   E   R   R   S   P   Q   H   L   F   R   P   R   H   T   L   D   G   A   K   482
GGA GAA CGA CGG AGC CCC CAG CAT CTC TTC AGA CCT CGC CAC ACC CTT GAT GGA GCC AAA 1446 1512
 M   R   A   S   V   R   M   T   R   Y   L   E   S   W   G   A   A   K   P   F   502
ATG AGG GCC TCG GTC CGC ATG ACC CGG TAC TTG GAG TCC TGG GGG GCA GCC AAG CCC TTT 1506 1572
 A   H   L   H   H   R   D   S   M   T   T   E   N   G   K   I   S   T   T   D   522
GCA CAC CTA CAT CAC AGG GAC AGC ATG ACC ACA GAG AAC GGC AAG ATC AGC ACC ACG GAT 1566 1632
 V   P   M   G   Q   H   N   F   Q   N   R   T   L   R   T   K   S   Q   K   K   542
GTA CCC ATG GGT CAG CAT AAT TTT CAA AAT CGC ACC TTA AGA ACC AAG TCA CAA AAG AAG 1626 1692
 R   F   E   E   E   L   N   E   R   M   I   Q   A   I   D   G   I   N   A   Q   562
AGA TTT GAA GAA GAA TTG AAT GAA AGG ATG ATT CAA GCA ATT GAT GGG ATT AAT GCA CAG 1686 1752
 K   Q   W   L   K   S   E   D   I   Q   R   I   S   L   L   F   Y   N   K   V   582
AAG CAA TGG CTC AAG TCT GAA GAC ATT CAG AGA ATC TCA CTG CTT TTC TAT AAC AAA GTA 1746 1812
 L   E   K   E   Y   R   A   T   L   P   A   F   K   Y   Y   V   T   C   A   602
CTA GAA AAA GAG TAC CGG GCC ACG GCA CTG CCA GCG TTC AAG TAT TAT GTG ACT TGT GCC 1806 1872
 C   L   I   F   F   C   I   F   I   V   Q   I   L   V   L   P   K   T   S   V   622
TGT CTC ATA TTC TTC TGC ATC TTC ATT GTG CAG ATT CTC GTG CTG CCA AAA ACG TCT GTC 1866 1932
 L   G   I   S   F   G   A   A   F   L   L   L   A   F   I   L   F   V   C   F   642
CTG GGC ATC TCC TTT GGG GCT GCG TTT CTC TTG CTG GCC TTC ATC CTC TTC GTC TGC TTT 1926 1992
 A   G   Q   L   L   Q   C   S   K   K   A   S   P   L   L   M   W   L   L   K   662
GCT GGA CAG CTT CTG CAA TGC AGC AAA AAA GCC TCT CCC CTG CTC ATG TGG CTT TTG AAG 1986 2052
 S   S   G   I   I   A   N   R   P   W   P   R   I   S   L   T   I   I   T   T   682
TCC TCG GGC ATC ATT GCC AAC CGC CCC TGG CCA CGG ATC TCT CTC ACG ATC ATC ACC ACA 2046 2112
 A   I   I   L   M   M   A   V   F   N   M   F   F   L   S   D   S   E   E   T   702
GCC ATC ATA TTA ATG ATG GCC GTG TTC AAC ATG TTT TTC CTG AGT GAC TCA GAG GAA ACA 2106 2172
 I   P   P   T   A   N   T   T   N   T   S   F   S   A   S   N   N   Q   V   A   722
ATC CCT CCA ACT GCC AAC ACA ACA AAC ACA AGC TTT TCA GCC TCA AAT AAT CAG GTG GCG 2166 2232
 I   L   R   A   Q   N   L   F   F   L   P   Y   F   I   Y   S   C   I   L   G   742
ATT CTG CGT GCG CAG AAT TTA TTT TTC CTC CCG TAC TTT ATC TAC AGC TGC ATT CTG GGA 2226 2292
 L   I   S   C   S   V   F   L   R   V   N   Y   E   L   K   M   L   I   M   M   762
CTG ATA TCC TGT TCC GTG TTC CTG CGG GTA AAC TAT GAG CTG AAG ATG TTG ATC ATG ATG 2286 2352
 V   A   L   V   G   Y   N   T   I   L   L   H   T   H   A   H   V   L   G   D   782
GTG GCC TTG GTG GGC TAC AAC ACC ATC CTA CTC CAC ACC CAC GCC CAC GTC CTG GGC GAC 2346 2412
```

FIG. 46B.

```
  Y   S   Q   V   L   F   E   R   P   G   I   W   K   D   L   K   T   M   G   S    802
TAC AGC CAG GTC TTA TTT GAG AGA CCA GGC ATT TGG AAA GAC CTG AAG ACC ATG GGC TCT 2406 2472
  V   S   L   S   I   F   F   I   T   L   L   V   L   G   R   Q   N   E   Y   Y    822
GTG TCT CTC TCT ATA TTC TTC ATC ACA CTG CTT GTT CTG GGT AGA CAG AAT GAA TAT TAC 2466 2532
  C   R   L   D   F   L   W   K   N   K   F   K   K   E   R   E   E   I   E   T    842
TGT AGG TTA GAC TTC TTA TGG AAG AAC AAA TTC AAA AAA GAG CGG GAG GAG ATA GAG ACC 2526 2592
  M   E   N   L   N   R   V   L   L   E   N   V   L   P   A   H   V   A   E   H    862
ATG GAG AAC CTG AAC CGC GTG CTG CTG GAG AAC GTG CTT CCC GCG CAC GTG GCT GAG CAC 2586 2652
  F   L   A   R   S   L   K   N   E   E   L   Y   H   Q   S   Y   D   C   V   C    882
TTC CTG GCC AGG AGC CTG AAG AAT GAG GAG CTA TAC CAC CAG TCC TAT GAC TGC GTC TGC 2646 2712
  V   M   F   A   S   I   P   D   F   K   E   F   Y   T   E   S   D   V   N   K    902
GTC ATG TTT GCC TCC ATT CCG GAT TTC AAA GAA TTT TAT ACA GAA TCC-GAC GTG AAC AAG 2706 2772
  E   G   L   E   C   L   R   L   L   N   E   I   I   A   D   F   D   D   L   L    922
GAG GGC TTG GAA TGC CTT CGG CTC CTG AAC GAG ATC ATC GCT GAC TTT GAT GAT CTT CTT 2766 2832
  S   K   P   K   F   S   G   V   E   K   I   K   T   I   G   S   T   Y   M   A    922
TCC AAG CCA AAA TTC AGT GGA GTT GAA AAG ATT AAG ACC ATT GGC AGC ACA TAC ATG GCA 2766 2832
  A   T   G   L   S   A   V   P   S   Q   E   H   S   Q   E   P   E   R   Q   Y    962
GCA ACA GGT CTG AGC GCT GTG CCC AGC CAG GAG CAC TCC CAG GAG CCC GAG CGG CAG TAC 2886 2952
  M   H   I   G   T   M   V   E   F   A   F   A   L   V   G   K   L   D   A   I    982
ATG CAC ATT GGC ACC ATG GTG GAG TTT GCT TTT GCC CTG GTA GGG AAG CTG GAT GCC ATC 2946 3012
  N   K   H   S   F   N   D   F   K   L   R   V   G   I   N   H   G   P   V   I   1002
AAC AAG CAC TCC TTC AAC GAC TTC AAA TTG CGA GTG GGT ATT AAC CAT GGA CCT GTG ATA 3006 3072
  A   G   V   I   G   A   Q   K   P   Q   Y   D   I   W   G   N   T   V   N   V   1022
GCT GGT GTG ATT GGA GCT CAG AAG CCA CAA TAT GAT ATC TGG GGC AAC ACT GTC AAT GTG 3066 3132
  A   S   R   M   D   S   T   G   V   L   D   K   I   Q   V   T   E   E   T   S   1042
GCC AGT AGG ATG GAC AGC ACC GGA GTC CTG GAC AAA ATA CAG GTT ACC GAG GAG ACG AGC 3126 3192
  L   V   L   Q   T   L   G   Y   T   C   T   C   R   G   I   I   N   V   K   G   1062
CTC GTC CTG CAG ACC CTC GGA TAC ACG TGC ACC TGT CGA GGA ATA ATC AAC GTG AAA GGA 3186 3252
  K   G   D   L   K   T   Y   F   V   N   T   E   M   S   R   S   L   S   Q   S   1082
AAG GGG GAC CTG AAG ACG TAC TTT GTA AAC ACA GAA ATG TCA AGG TCC CTT TCC CAG AGC 3246 3312
  N   V   A   S   *                                                                1087
AAC GTG GCA TCC TGA                                                                3261 3324
```

AGAGTCACCTTCATTTTGGCAAGAAGACTGTATTTTCAGGAAGGTATCACACACTTTCTGACTGCAACTTCTGTCCCTT

GTTTTTGATGTGCGTGCTGTCTGTCCTATGGAGCCTCTGCAGACTCGTTCTCGTGACCCAGTGGCATACCGTTTGGTGT

CTGATGTGTGCCCAGATCGTTCTGCCACTTGCACTGTGCTTGCTCCTAAGCAAAAGGGAAAAGGAGCGCGCGTGATAGA

AGAAAAGCACTGGGAGAACTAACAGAGGAGAAAGGTGAAACACACACACATTCTTAAGGCAATAAAACTAGGGGGTGTA

TATTATCTTCTGGGGCATGTTCTTTTCTGGAAAATATGGTAGCTCGCCAACCGCATCTGCTCATCTGATATTCAAACAC

ACAGTATTCGTGAATAAGTTGATTCTGTCCCCACGTGGACTCTGTGCTCACCCATTGTCTCATTGCCAGTGGTGTCCA

FIG. 46C.

AGGGCCCCCGTTGGGACCCACGGCTCTCGTCCCTCTGCTCCGTGTGTCTCATGCCAGCAGCACGTCGCCATCCGTCACC

AGAATTAGTCCTCACAGCCTAGGACCAGTTTTGTATCAAACTCGTCTGATGTTTTGATGCCATTTGTCTTTTGTAAAGT

TAATTCATTAAAAGTTTTTATGTACTTTGAAAAAAAAAAAAAAAAGAGCG

FIG. 46D.

Signal Peptide Predictions for 25678

| Method | Predict | Score | Mat@ |
|---|---|---|---|
| SignalP (eukaryote) | MAYBE | | 70 |

Note: amino-terminal 70aa used for signal peptide prediction

Transmembrane Segments Predicted by MEMSAT

| Start | End | Orient | Score |
|---|---|---|---|
| 46 | 68 | ins->out | 7.0 |
| 76 | 98 | out->ins | 6.6 |
| 108 | 129 | ins->out | 5.1 |
| 137 | 153 | out->ins | 3.7 |
| 160 | 179 | ins->out | 1.8 |
| 187 | 207 | out->ins | 3.2 |
| 602 | 622 | ins->out | 5.9 |
| 630 | 652 | out->ins | 4.7 |
| 680 | 701 | ins->out | 5.0 |
| 734 | 755 | out->ins | 5.0 |
| 763 | 779 | ins->out | 2.6 |
| 805 | 821 | out->ins | 4.0 |
| 938 | 954 | ins->out | 0.4 |

Transmembrane segments for presumed mature peptide

| Start | End | Orient | Score |
|---|---|---|---|
| 7 | 29 | out->ins | 6.6 |
| 39 | 60 | ins->out | 5.1 |
| 68 | 84 | out->ins | 3.7 |
| 91 | 110 | ins->out | 1.8 |
| 118 | 138 | out->ins | 3.2 |
| 533 | 553 | ins->out | 5.9 |
| 561 | 583 | out->ins | 4.7 |
| 611 | 632 | ins->out | 5.0 |
| 665 | 686 | out->ins | 5.0 |
| 694 | 710 | ins->out | 2.6 |
| 736 | 752 | out->ins | 4.0 |
| 869 | 885 | ins->out | 0.4 |

Prosite Pattern Matches for 25678

)PS00001/PDOC00001/ASN_GLYCOSYLATION N-glycosylation site.

Query: 288 NVSI 291
Query: 537 NRTL 540
Query: 713 NTTN 716

)PS00004/PDOC00004/CAMP_PHOSPHO_SITE cAMP- and cGMP-dependent protein kinase phosphorylation site.

Query: 284 KRHT 287
Query: 656 KKAS 659

)PS00005/PDOC00005/PKC_PHOSPHO_SITE Protein kinase C phosphorylation site.
Query: 491 SVR 493

FIG. 49A.

```
Query: 539    TLR    541
Query: 544    SQK    546
Query: 655    SKK    657
Query: 872    SLK    874
Query: 1058   TCR    1060
```

>PS00006/PDOC00006/CK2_PHOSPHO_SITE Casein kinase II phosphorylation site.

```
Query: 132    SPWD    135
Query: 219    TYQD    222
Query: 307    SPGE    310
Query: 376    TGVD    379
Query: 524    STTD    527
Query: 702    SDSE    705
Query: 892    SIPD    895
Query: 901    TESD    904
Query: 933    SGVE    936
Query: 972    TMVE    975
Query: 991    SFND    994
Query: 1029   SRMD    1032
```

>PS00007/PDOC00007/TYR_PHOSPHO_SITE Tyrosine kinase phosphorylation site.

```
Query: 28     RSRDWLY    34
Query: 335    KILGDCYY   342
Query: 586    KVLEKEY    592
Query: 1066   KGKGDLKTY  1074
```

>PS00008/PDOC00008/MYRISTYL N-myristoylation site.

```
Query: 21     GGGDGL    26
Query: 56     GSCLAL    61
Query: 201    GNLAGA    206
Query: 270    GQMENT    275
Query: 346    GLPISL    351
Query: 362    GLDMCE    367
Query: 377    GVDINM    382
Query: 385    GVHSGN    390
Query: 419    GGVPGR    424
Query: 629    GISFGA    634
Query: 670    GIIANR    675
Query: 747    GLISCS    752
Query: 1009   GVIGAQ    1014
Query: 1022   GNTVNV    1027
```

>PS00013/PDOC00013/PROKAR_LIPOPROTEIN Prokaryotic membrane lipoprotein lipid attachment site.
```
       ## Non-eukaryotic pattern
       RU    Additional rules:
       RU    (1) The cysteine must be between positions 15 and 35 of the sequence in
       RU    consideration.
       RU    (2) There must be at least one charged residue (Lys or Arg) in the first
       RU    seven residues of the sequence.

Query: 48     VFLLLIVMGSC    58
Query: 741    IYSCILGLISC    751
```

>PS00453/PDOC00425/GUANYLATE_CYCLASES Guanylate cyclases signature.

FIG. 49B.

Query: 394   GVIGLQKWQYDVWSHDVTLANHME     417
Query: 1009  GVIGAQKPQYDIWGNTVNVASRMD     1032

FIG. 49C.

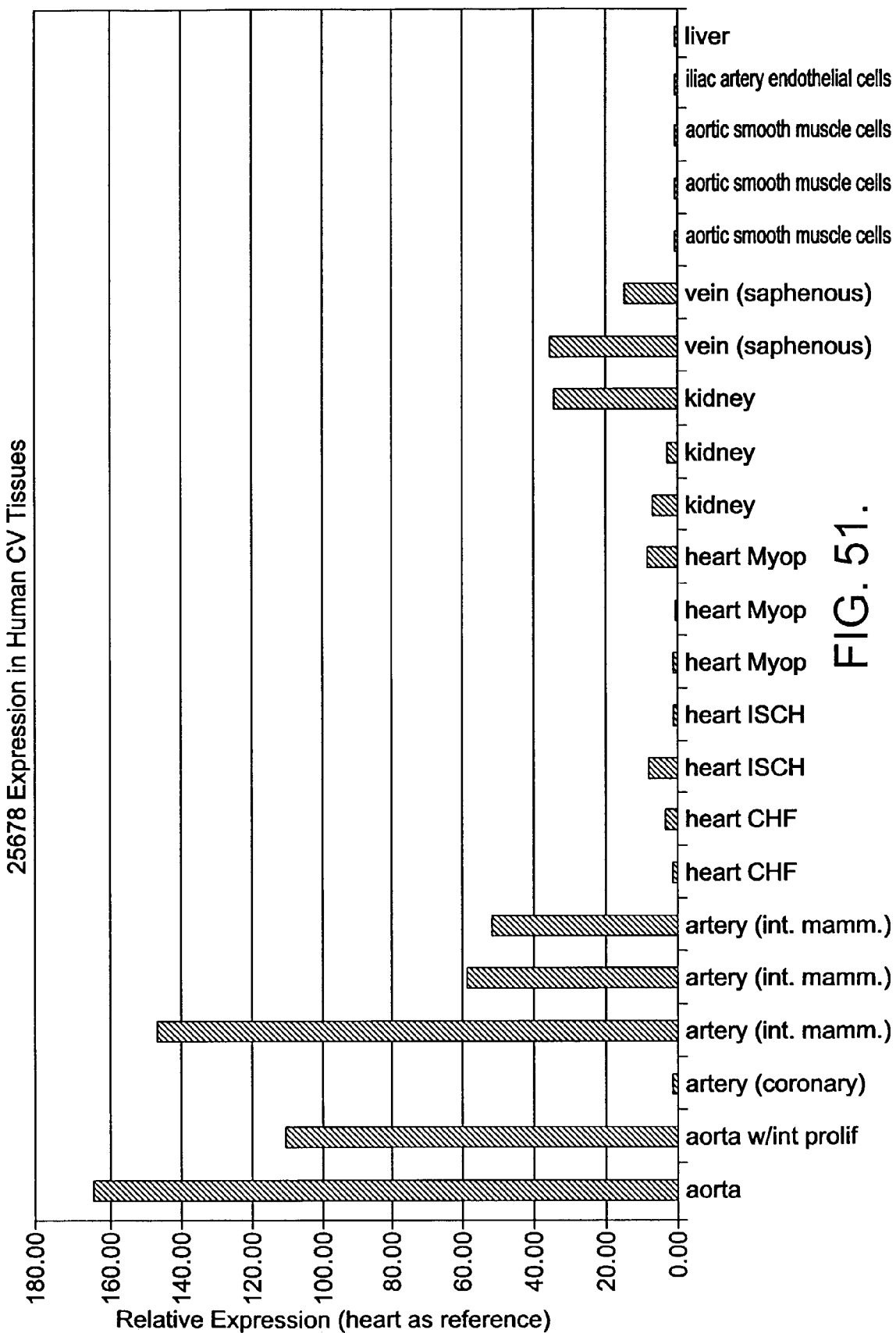

```
                                                        M   G   G   C   I     5
TCACTATAGGGAGTCGACCCACGCGTCCGATGCAGCCTTGATAATCATCCGATTCCAGA ATG GGT GGC TGC ATT  15
 P   F   L   K   A   A   R   A   L   C   P   R   I   M   P   P   L   L   L    25
CCT TTT CTG AAG GCA GCA AGG GCA CTG TGC CCC AGA ATC ATG CCC CCT TTG CTG TTG TTG  75
 S   A   F   I   F   L   V   S   V   L   G   G   A   P   G   H   N   P   D   R   45
TCC GCC TTC ATT TTT TTA GTG AGT GTC TTG GGA GGA GCC CCA GGA CAC AAC CCC GAC CGC 135
 R   T   K   M   V   S   I   H   S   L   S   E   L   E   R   L   K   L   Q   E   65
AGG ACG AAG ATG GTA TCG ATA CAC AGC CTC TCT GAG CTG GAG CGT CTG AAG CTG CAA GAG 195
 T   A   Y   H   E   L   V   A   R   H   F   L   S   E   F   K   P   D   R   A   85
ACT GCT TAC CAC GAA CTC GTG GCC AGA CAT TTC CTC TCC GAA TTC AAA CCT GAC AGA GCT 255
 L   P   I   D   R   P   N   T   L   D   K   W   F   L   I   L   R   G   Q   Q  105
CTG CCT ATT GAC CGT CCG AAC ACC TTG GAT AAG TGG TTT CTG ATT TTG AGA GGA CAG CAG 315
 R   A   V   S   H   K   T   F   G   I   S   L   E   E   V   L   V   N   E   F  125
AGG GCT GTA TCA CAC AAG ACA TTT GGC ATT AGC CTG GAA GAG GTC CTG GTG AAC GAG TTT 375
 T   R   R   K   H   L   E   L   T   A   T   M   Q   V   E   E   A   T   G   Q  145
ACC CGC CGC AAG CAT CTT GAA CTG ACA GCC ACG ATG CAG GTT GAA GAA GCC ACC GGT CAG 435
 A   A   G   R   R   R   G   N   V   V   R   R   V   F   G   R   I   R   R   F  165
GCT GCG GGC CGT CGT CGG GGA AAC GTG GTG CGA AGG GTG TTT GGC CGC ATC CGG CGC TTT 495
 F   S   R   R   R   N   E   P   T   L   P   R   E   F   T   R   R   G   R   R  185
TTC AGT CGC AGG CGG AAT GAG CCC ACC TTG CCC CGG GAG TTC ACT CGC CGT GGG CGT CGA 555
 G   A   V   S   V   D   S   L   A   E   L   E   D   G   A   L   L   L   Q   T  205
GGT GCA GTG TCT GTG GAT AGT CTG GCT GAG CTG GAA GAC GGA GCC CTG CTG CTG CAG ACC 615
 L   Q   L   S   K   I   S   F   P   I   G   Q   R   L   L   G   S   K   R   K  225
CTG CAG CTT TCA AAA ATT TCC TTT CCA ATT GGC CAA CGA CTT CTG GGA TCC AAA AGG AAG 675
 M   S   L   N   P   I   A   K   Q   I   P   Q   V   V   E   A   C   C   Q   F  245
ATG AGT CTC AAT CCG ATT GCG AAA CAA ATC CCC CAG GTT GTT GAG GCT TGC TGC CAA TTC 735
 I   E   K   H   G   L   S   A   V   G   I   F   T   L   E   Y   S   V   Q   R  265
ATT GAA AAA CAT GGC TTA AGC GCA GTG GGG ATT TTT ACC CTT GAA TAC TCC GTG CAG CGA 795
 V   R   Q   L   R   E   E   F   D   Q   G   L   D   V   V   L   D   D   N   Q  285
GTG CGT CAG CTC CGT GAA GAA TTT GAT CAA GGT CTG GAT GTA GTG CTG GAT GAC AAT CAG 855
 N   V   H   D   V   A   A   L   L   K   E   F   F   R   D   M   K   D   S   L  305
AAT GTG CAT GAT GTG GCT GCA CTC CTC AAG GAG TTT TTC CGT GAC ATG AAG GAT TCT CTG 915
 L   P   D   D   L   Y   M   S   F   L   L   T   A   L   K   P   Q   D   Q      325
CTG CCA GAT GAT CTG TAC ATG TCA TTC CTC CTG ACA GCA ACT TTA AAG CCC CAG GAT CAG 975
 L   S   A   L   Q   L   L   V   Y   L   M   P   P   C   H   S   D   T   L   E  345
CTT TCT GCC CTG CAG TTG CTG GTC TAC CTG ATG CCA CCC TGC CAC AGT GAT ACC CTG GAG 1035
 R   L   L   K   A   L   H   K   I   T   E   N   C   E   D   S   I   G   I   D  365
CGT CTG CTG AAG GCC CTG CAT AAA ATC ACT GAG AAC TGC GAG GAC TCA ATT GGC ATT GAT 1095
 G   Q   L   V   P   G   N   R   M   T   S   T   N   L   A   L   V   F   G   S  385
```

FIG. 52A.

```
        G   Q   L   V   P   G   N   R   M   T   S   T   N   L   A   L   V   F   G   S      1155
        A   L   L   K   K   G   K   F   G   K   R   E   S   R   K   T   K   L   G   I    405
        GCT CTC CTG AAA AAA GGA AAG TTT GGC AAG AGA GAG TCC AGG AAA ACA AAG CTG GGG ATT    1215
        D   H   Y   V   A   S   V   N   V   V   R   A   M   I   D   N   W   D   V   L    425
        GAT CAC TAT GTT GCT TCT GTC AAT GTG GTC CGT GCC ATG ATT GAT AAC TGG GAT GTC CTC    1275
        F   Q   V   P   P   H   I   Q   R   Q   V   A   K   R   V   W   K   S   S   P    445
        TTC CAG GTG CCT CCC CAT ATT CAG AGG CAG GTT GCT AAG CGC GTG TGG AAG TCC AGC CCG    1335
        E   A   L   D   F   I   R   R   R   N   L   R   K   I   Q   S   A   R   I   K    465
        GAA GCA CTT GAT TTT ATC AGA CGC AGG AAC TTG AGG AAG ATC CAG AGT GCA CGC ATA AAG    1395
        M   E   E   D   A   L   L   S   D   P   V   E   T   S   A   E   A   R   A   A    485
        ATG GAA GAG GAT GCA CTA CTT TCT GAT CCA GTG GAA ACC TCT GCT GAA GCC CGG GCT GCT    1455
        V   L   A   Q   S   K   P   S   D   E   G   S   S   E   E   P   A   V   P   S    505
        GTC CTT GCT CAA AGC AAG CCT TCT GAT GAA GGT TCC TCT GAG GAG CCA GCT GTG CCT TCC    1515
        G   T   A   R   S   H   D   D   E   E   G   A   G   N   P   P   I   P   E   Q    525
        GGC ACT GCC CGT TCC CAT GAC GAT GAG GAA GGA GCG GGT AAC CCT CCC ATT CCG GAG CAA    1575
        D   R   P   L   L   R   V   P   R   E   K   E   A   K   T   G   V   S   Y   F    545
        GAC CGC CCA TTG CTC CGT GTG CCC CGG GAG AAG GAG GCC AAA ACT GGC GTC AGC TAC TTC    1635
        F   P   *                                                                          548
        TTT CCT TAG                                                                        1644
```

ATGTTTTTCCTTCTATAAGGTGCCAGACAGGGGAAAAGGGTGGGGGTACATCTGGGATGTCACAGGAAACATTAAGGAG
AGAGTTGAAGGTAAAGATCTGAAGGTAAGAAGGAGTTCCACCTGATGCTCGGGTCAGGATGAGAATTCCAAACACACTG
CCAGCCCCTTCACTGGGGATGCTTGGKCTCTTCTGCTGGTAAAAGCAGAGATGTTTTCTGTGTCATGCCCAAGCTCCCC
GGTGCTACCTTGCCTTTCTCTTTTACCCCTGATCTTGGCTTTCTCTCTCTCTCTGCAGACTTTCCTTTAATTGATGTGA
CATTTGTGGTAAACACCTTTCCCAGGGAACCTCACAAATCTTGAGATGCTTTCCCTTCCCCAAATGGGATTGCATGATT
TCCCTGACTTTCCTACCCTCCTCCAGAGAGCTCAGTTGGAAAGGCCCTCAAGAGGCATGCTAGAACGTTAGGTCAGCCT
ACTGACAGCTGACAAACAATTAATGCGAAATCATGTCACACCAACCCATAGCCGTGTCCACGCAGCAACTCCACCACCT
TAGGATTTCCCCCTCCAAATTATTCAGACCAATGGCTTGCCAAATGGCCTCTCCCAAAATTCTGTACAGTTTTGCTCAG
GTCACGCCAACAGGGAAACCTCAAGTGTAGGTCTAATTAGTGTTTCTGGGATCCAAAGTTAGAGGAAAATTTAGATTTT
ATTGCCTGGATCTGCTTTAAAGACAATTGGTGTTTACACCCTCTTGTCAGCAAAACAGCTAGTTAGGTAAGGACATATA
GTTCCAAGTAGGTAAAGTCACTTGATTACAAATGTTCTTAACTATCGTCTCTGTAATTCCTTTATACAGGACAGTACAA
AATTGTGGGACATGCTCTGGTAACACACAGATATGGGTTGCATATGATCCAGAATTACAGCTGATATTATGGATGACAA
CTGCTAAGGTCCATAAAATGAAGACTGTATTGTATTGAGGGATAGAAATTGATCATTTAATGGGTAACAACTGCTGAGC
TCAAAGATTTGTGATTGTTAAAACTTCTCTGGCATTTAATCATTAATAAACATCTGTATTGTGCCACCAGCATAAAAAA
AAAAAAAAAAAAAAAAAAAAAAAAAAAAAAAAAAAAAGG

Prosite Pattern Matches for 26651

>PS00004|PDOC00004|CAMP_PHOSPHO_SITE cAMP-and cGMP-dependent protein kinase phosphorylation site.

Query: 224   RKMS   227
Query: 395   KRES   398

>PS00005|PDOC00005|PKC_PHOSPHO_SITE Protein kinase C phosphorylation site.

Query: 109   SHK   111
Query: 126   TRR   128
Query: 167   SRR   169
Query: 180   TRR   182
Query: 222   SKR   224
Query: 319   TLK   321
Query: 398   SRK   400
Query: 461   SAR   463
Query: 507   TAR   509

>PS00006|PDOC00006|CK2_PHOSPHO_SITE Casein kinase II phosphorylation site.

Query:  54   SLSE   57
Query: 116   SLEE   119
Query: 192   SLAE   195
Query: 443   SSPE   446
Query: 478   TSAE   481
Query: 497   SSEE   500
Query: 510   SHDD   513

>PS00007|PDOC00007|TYR_PHOSPHO_SITE Tyrosine kinase phosphorylation site.

Query:  62   KLQETAY   68

>PS00008|PDOC00008|MYRISTYL N-myristoylation site.

Query:  36   GGAPGH   41
Query: 103   GQQRAV   108
Query: 144   GQAAGR   149
Query: 371   GNRMTS   376
Query: 506   GTARSH   511

>PS00009|PDOC00009|AMIDATION Amidation site.

Query: 147   AGRR   150
Query: 182   RGRR   185
Query: 393   FGKR   396

```
Protein Family/Domain Matches, HMMer
Searching for complete domain in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
HMM file:            /prod/ddm/seqanal/PFAM/pfam4.4/Pfam
Sequence file:       /tmp/orfanal.14638.aa Query:    26651

Scores for sequence family classification (score includes all domains):
Model       Description                         Score     E-value    N
RhoGAP      RhoGAP domain                       94.0      3e-24      1
Dockerin_1  Dockerin domain type I              6.8       2.2        1

Parsed for domains:
Model       Domain  seq-f  seq-t   hmm-f   hmm-t     score   E-value Dockerin_1  1/1     278    298 ..  1       22  ()    6.8     2.2
RhoGAP      1/1     236    397 ..  1       170 ()    94.0    3e-24

RhoGAP: domain 1 of 1, from 236 to 397: score 94.0, E=3e-24
                *->PiivekcveyIeklYPLaerGlqeEGIYRvsGsasrvkeLreafdkd
                   P +ve+c +Iek        +Gl +Gl+ + s  rv++Lre+fd++
         26651 236 PQVVEACCQFIEK------HGLSAVGIFTLEYSVQRVRQLREEFDQG   276 gapdslelsekewfDvhvvagILKlYLReLPePLipydlyeefiraakeq
                 d + + ++   +vh va ILK ++R+ ++L+p+dly f+   a
         26651 277 --LDVVLDDNQ---NVHDVAALLKEFFRDMKDSLLPDDLYMSFLLTAT--   319 iedpderlralkellsSkLPrahynTLryLlthLnrvaei.....yie..
                +p +l+al+ l++ + P++h +TL+ Ll+ L++++e  +++ +i+++
         26651 320 -LKPQDQLSALQLLVY-LMPPCHSDTLERLLKALHKITENcedsiGIDgq  367 nsavNkMnarNLAivFgPtLlrppdkesndK-*
                 + N+M+   NLA+vFg+ Ll       + +
         26651 368 LVPGNRMTSTNLALVFGSALLKKGKFGKRE       397
```

FIG. 56A.

```
//
Searching for complete domains in SMART
hmmpfam - search a single seq against HMM database
HMMER 2.1.2 (Dec 1998)
Copyright (C) 1992-1998 Washington University School of Medicine
HMMER is freely distributed under the GNU General Public License (GPL).
HMM file:        /ddm/robison/smart/smart/smart/smart.all.hmms
Sequence file:   /tmp/orfanal.14638.aa
  Query:    26651
Scores for sequence family classification (score includes all domains):

Model     Description                                    Score    E-value    N
-----     -----------                                    -----    -------    -
RhoGAP_3                                                 171.4    1.5e-47    1

Parsed for domains:
Model     Domain   seq-f   seq-t    hmm-f    hmm-t    score    E-value
-----     ------   -----   -----    -----    -----    -----    -------
RhoGAP_3   1/1      233     423 ..     1      193 ()   171.4    1.5e-47
Alignments of top-scoring domains:
RhoGAP_3: domain 1 of 1, from 233 to 423: score 171.4, E = 1.5e-47
```

```
                    *->spiPiivekCieylekrGldteGIYRvsGsksrvkeLreafdsged
                       ++iP++ve C++++ek+Gl  +GI+ ++ s+ rv++Lre+fd+g d
        26651  233    KQIPQVVEACCQFIEKHGLSAVGIFTLEYSVQRVRQLREEFDQGLDv    279 dldsldesiteesedleeydvhdvAglLKlyLReLPePLltfelyeefie
                    +              ++++++vhdvA lLK ++R++ ++Ll+++ly f+
        26651  280  V---------------LDDNQNVHDVAALLKEFFRDMKDSLLPDDLYMSFLL   316 aaklyqieatsrkqseksedeeerlralrellslLPpanratLryLl.HL
                    a                     ++ +l al++l++l Pp++ ++L++Ll+ L
        26651  317  TAT---------------LKPQDQLSALQLLVYLMPPCHSDTLERLLkAL   351 nrVA..........ehsevNkMtarNLAivFgPtLlrpp..........
                    +++ ++ +++ + +++   + N+Mt+ NLA+vFg  Ll   +  +++++++
        26651  352  HKITencedsigidgQLVPGNRMTSTNLALVFGSALLKKGkfgkresrkt   401

...ltdiknqnkvvetlienad<-*
                    + ++ ++       +vv +i+n+d
        26651  402  klgIDHYVASVNVVRAMIDNWD        423

```
GAGGAAGCCAGGCGGGGTGCAGACGGCTGCTGATTCTGGGGCTGGTCAGGAAACCAAGGAGACCCCCCCCCCCACC
```

| | | | | | | | | | | | | | | | | | | | | |
|---|---|---|---|---|---|---|---|---|---|---|---|---|---|---|---|---|---|---|---|---|
| | M | D | P | P | S | P | S | R | T | S | Q | T | Q | P | T | A | T | S | P | L | 20 |
| | ATG | GAC | CCA | CCG | TCG | CCA | AGC | CGG | ACC | TCC | CAA | ACC | CAG | CCC | ACA | GCC | ACC | TCT | CCG | CTG | 60 |
| | T | S | Y | R | W | H | T | G | G | G | G | E | K | A | A | G | G | F | R | W | 40 |
| | ACT | TCC | TAC | CGC | TGG | CAC | ACA | GGG | GGC | GGT | GGG | GAG | AAG | GCG | GCT | GGA | GGG | TTC | CGC | TGG | 120 |
| | G | R | F | A | G | W | G | R | A | L | S | H | Q | E | P | M | V | S | T | Q | 60 |
| | GGC | CGC | TTT | GCT | GGC | TGG | GGC | AGG | GCC | CTG | AGC | CAC | CAG | GAG | CCC | ATG | GTC | AGC | ACC | CAG | 180 |
| | P | A | P | R | S | I | F | R | R | V | L | S | A | P | P | K | E | S | R | T | 80 |
| | CCA | GCC | CCT | CGC | TCG | ATA | TTC | CGT | CGG | GTC | CTA | TCT | GCG | CCT | CCC | AAG | GAG | TCA | CGG | ACC | 240 |
| | S | R | L | R | L | S | K | A | L | W | G | R | H | K | N | P | P | P | E | P | 100 |
| | AGT | CGC | CTT | CGA | CTC | TCC | AAG | GCC | CTC | TGG | GGG | AGG | CAT | AAG | AAC | CCA | CCG | CCG | GAG | CCA | 300 |
| | D | P | E | P | E | Q | E | A | P | E | L | E | P | E | P | E | L | E | P | P | 120 |
| | GAC | CCG | GAG | CCG | GAG | CAG | GAG | GCC | CCA | GAG | CTG | GAG | CCG | GAG | CCA | GAG | CTG | GAG | CCC | CCT | 360 |
| | T | P | Q | I | P | E | A | P | T | P | N | V | P | V | W | D | I | G | G | F | 140 |
| | ACC | CCA | CAG | ATC | CCT | GAG | GCC | CCC | ACA | CCC | AAC | GTG | CCT | GTC | TGG | GAC | ATT | GGG | GGC | TTC | 420 |
| | T | L | L | D | G | K | L | V | L | L | G | G | E | E | G | P | R | R | P | | 160 |
| | ACC | CTG | CTT | GAT | GGG | AAG | CTG | GTG | CTG | CTT | GGA | GGA | GAG | GAG | GAG | GGT | CCT | CGA | AGG | CCC | 480 |
| | R | V | G | S | A | S | S | E | G | S | I | H | V | A | M | G | N | F | R | D | 180 |
| | CGG | GTG | GGA | AGT | GCT | AGC | TCC | GAG | GGC | AGC | ATC | CAC | GTG | GCC | ATG | GGG | AAC | TTC | AGG | GAT | 540 |
| | P | D | R | M | P | G | K | T | E | P | E | T | A | G | P | N | Q | V | H | N | 200 |
| | CCA | GAT | CGG | ATG | CCT | GGA | AAA | ACA | GAA | CCG | GAG | ACT | GCT | GGT | CCC | AAC | CAG | GTC | CAC | AAC | 600 |
| | V | R | G | L | L | K | R | L | K | E | K | K | A | R | P | P | S | A | L | | 220 |
| | GTT | CGG | GGG | TTG | CTC | AAG | AGG | CTG | AAA | GAG | AAG | AAA | AAG | GCC | AGA | CCC | CCC | AGT | GCT | CTG | 660 |
| | G | S | R | E | S | L | A | T | L | S | E | L | D | L | G | A | E | R | D | V | 240 |
| | GGC | TCT | AGG | GAG | TCG | CTG | GCC | ACA | CTC | TCT | GAA | CTG | GAC | CTG | GGT | GCC | GAG | CGG | GAT | GTG | 720 |
| | R | I | W | P | L | H | P | S | L | L | G | E | P | H | C | F | Q | V | T | W | 260 |
| | CGG | ATC | TGG | CCA | CTG | CAC | CCC | AGC | CTC | CTG | GGG | GAG | CCC | CAC | TGC | TTT | CAG | GTA | ACC | TGG | 780 |
| | T | G | G | S | R | C | F | S | C | R | S | A | A | E | R | D | R | W | I | E | 280 |
| | ACG | GGT | GGA | AGC | CGC | TGC | TTC | TCT | TGT | CGC | TCG | GCC | GCT | GAG | AGA | GAC | CGC | TGG | ATC | GAG | 840 |
| | D | L | R | R | Q | F | Q | P | T | Q | D | N | V | E | R | E | E | T | W | L | 300 |
| | GAC | CTT | CGT | CGC | CAA | TTC | CAG | CCC | ACC | CAG | GAC | AAC | GTG | GAG | CGG | GAA | GAG | ACA | TGG | CTG | 900 |
| | S | V | W | V | H | E | A | K | G | L | P | R | A | A | A | G | A | P | G | V | 320 |
| | AGC | GTG | TGG | GTG | CAC | GAA | GCG | AAG | GGG | CTT | CCC | CGA | GCA | GCG | GCG | GGG | GCA | CCC | GGC | GTG | 960 |
| | R | A | E | L | W | L | D | G | A | L | L | A | R | T | A | P | R | A | G | P | 340 |
| | CGC | GCC | GAG | CTG | TGG | CTG | GAT | GGC | GCG | CTG | CTG | GCA | CGC | ACG | GCG | CCT | CGG | GCC | GGC | CCA | 1020 |
| | G | Q | L | F | W | A | E | R | F | H | F | E | A | L | P | P | A | R | R | L | 360 |
| | GGC | CAG | CTC | TTC | TGG | GCC | GAG | CGC | TTC | CAC | TTC | GAG | GCG | CTG | CCA | CCG | GCA | CGT | CGC | CTG | 1080 |
| | S | L | R | L | R | G | L | G | P | G | S | A | V | L | G | R | V | A | L | A | 380 |

FIG. 57A.

```
           L   E   E   L   D   A   P   R   A   P   A   A   G   L   E   R   V   F   P   L        400
TCG CTG CGG CTG CGC GGC TTG GGC CCG GGA AGC GCG GTG CTG GGC CGC GTG GCC CTG GCG            1140
           L   G   A   P   A   G   A   A   L   R   A   R   I   R   A   R   R   L   R   V        420
CTG GAG GAG CTG GAC GCC CCA CGC GCG CCT GCC GCC GGT CTG GAG CGC TGG TTC CCG CTG            1200
           L   P   S   E   R   Y   K   E   L   A   E   F   L   T   F   H   Y   A   R   L        440
CTC GGG GCG CCG GCG GGC GCA GCG CTG CGG GCG CGG ATT CGG GCG CGT CGC CTG CGC GTG            1260
           C   G   A   L   E   P   A   L   P   A   Q   A   K   E   E   L   A   A   A   M        460
CTG CCG TCC GAG CGC TAC AAG GAG CTG GCG GAG TTC CTC ACC TTC CAC TAT GCG CGC CTC            1320
           V   R   V   L   R   A   T   G   R   A   Q   A   L   V   T   D   L   G   T   A        480
TGC GGG GCC CTG GAG CCC GCG CTG CCT GCG CAG GCC AAG GAG GAG CTG GCG GCA GCC ATG            1380
           E   L   A   R   C   G   G   R   E   A   L   L   F   R   E   N   T   L   A   T        500
GTG CGC GTG CTG CGG GCC ACC GGC CGG GCG CAG GCG CTG GTG ACT GAC CTG GGC ACT GCG            1440
           K   A   I   D   E   Y   M   K   L   V   A   Q   D   Y   L   Q   E   T   L   G        520
GAG CTG GCG CGC TGT GGA GGC CGT GAG GCG CTG CTG TTC CGG GAA AAC ACA TTG GCC ACC            1500
           Q   V   V   R   R   L   C   A   S   T   E   D   C   E   V   D   P   S   K   C        540
AAG GCT ATC GAT GAG TAC ATG AAG CTC GTG GCA CAG GAT TAC CTC CAG GAG ACC CTG GGA            1560
           P   A   S   E   L   P   E   H   Q   A   R   L   R   N   S   C   E   E   V   F        560
CAG GTT GTG CGG CGT CTC TGT GCT TCT ACT GAG GAC TGT GAA GTG GAC CCC AGC AAA TGT            1620
           E   T   I   I   H   S   Y   D   W   F   P   A   E   L   G   I   V   F   S   S        580
CCA GCC TCG GAG CTG CCA GAG CAC CAG GCC AGA CTT CGG AAC AGC TGC GAG GAG GTC TTC            1680
           W   R   E   A   C   K   E   R   G   S   E   V   L   G   P   R   L   V   C   A        600
GAA ACC ATT ATC CAT TCC TAC GAC TGG TTC CCT GCG GAG CTG GGC ATC GTG TTC TCA AGC            1740
           S   L   F   L   R   L   L   C   P   A   I   L   A   P   S   L   F   G   L   A        620
TGG CGA GAA GCA TGT AAA GAA CGT GGC TCT GAG GTG CTG GGC CCC CGA CTG GTG TGC GCC            1800
           P   D   H   P   A   P   G   P   A   R   T   L   T   L   I   A   K   V   I   Q        640
TCC CTC TTC CTG CGG CTC CTG TGC CCT GCC ATC CTG GCA CCC AGC CTC TTT GGT TTG GCA            1860
           N   L   A   N   R   A   P   F   G   E   K   E   A   Y   M   G   F   M   N   S        660
CCA GAC CAT CCA GCA CCC GGC CCA GCC CGC ACC CTC ACA CTG ATT GCC AAG GTC ATC CAG            1920
           F   L   E   E   H   G   P   A   M   Q   C   F   L   D   Q   V   A   M   V   D        680
AAC CTC GCC AAC CGT GCC CCG TTC GGT GAG AAG GAG GCC TAC ATG GGC TTC ATG AAT AGC            1980
           V   D   A   A   P   S   G   Y   Q   G   S   G   D   L   A   L   Q   L   A   V        700
TTC CTG GAG GAA CAT GGA CCA GCC ATG CAA TGC TTC CTG GAC CAG GTA GCC ATG GTG GAT            2040
           L   H   A   Q   L   C   T   I   F   A   E   L   D   Q   T   T   R   D   T   L        720
GTG GAT GCT GCC CCC AGT GGT TAC CAG GGC AGT GGT GAT CTG GCC CTC CAG TTA GCT GTC            2100
           E   P   L   P   T   I   L   R   A   I   E   E   G   Q   P   V   L   V   S   V        740
CTG CAT GCC CAG CTC TGT ACA ATT TTT GCT GAG CTT GAC CAG ACA ACC CGA GAC ACC CTG            2160
           P   M   R   L   P   L   P   P   A   Q   V   H   S   S   L   S   A   G   E   K        760
GAA CAA CTG CCC ACC ATC CTG CGA GCC ATT GAG GAG GGC CAG CCT GTG CTT GTG TCA GTG            2220
           P   G   F   L   A   P   R   D   L   P   K   H   T   P   L   I   S   K   S   Q        780
CCA ATG CGT CTC CCA CTG CCC CCG GCC CAG GTC CAC TCC AGC CTC TCC GCA GGG GAG AAG            2280
CCC GGC TTC CTG GCC CCC CGG GAC CTC CCC AAG CAC ACC CCT CTC ATC TCC AAG AGC CAG            2340
```

FIG. 57B.

```
  S   L   R   S   V   R   R   S   E   S   W   A   R   P   R   P   D   E   E   R    800
TCT CTG CGC AGC GTT CGC CGC TCA GAG AGT TGG GCC CGG CCA CGG CCG GAC GAA GAG CGG   2400
  P   L   R   R   P   R   P   V   Q   R   T   Q   S   V   P   V   R   R   P   A    820
CCC CTG CGG CGG CCC CGG CCG GTG CAG CGC ACG CAG AGT GTC CCG GTC CGG CGT CCT GCC   2460
  R   R   R   Q   S   A   G   P   W   P   R   P   K   G   S   L   S   M   G   P    840
CGC CGC CGC CAA TCT GCG GGG CCC TGG CCG CGA CCC AAA GGC TCC CTG AGC ATG GGA CCA   2520
  A   P   R   A   R   P   W   T   R   D   S   A   S   L   P   R   K   P   S   V    860
GCG CCC CGC GCC CGG CCT TGG ACC CGG GAC TCC GCC TCG CTG CCT CGG AAG CCG TCG GTA   2580
  P   W   Q   R   Q   M   D   Q   P   Q   D   R   N   Q   A   L   G   T   H   R    880
CCC TGG CAG CGC CAA ATG GAC CAG CCG CAA GAC CGA AAC CAG GCA CTG GGC ACG CAC CGA   2640
  P   V   N   K   L   A   E   L   Q   C   E   V   A   A   L   R   E   E   Q   K    900
CCT GTG AAC AAG TTG GCA GAG CTG CAG TGC GAG GTG GCC GCT CTG CGT GAG GAG CAG AAA   2700
  V   L   S   R   L   V   E   S   L   S   T   Q   I   R   A   L   T   E   Q   Q    920
GTG CTG TCC CGC CTC GTG GAG TCG CTG AGC ACC CAA ATC CGG GCC TTG ACG GAG CAG CAG   2760
  E   Q   L   R   G   Q   L   Q   D   L   D   S   R   L   R   A   G   S   S   E    940
GAG CAG CTG CGG GGC CAG CTG CAG GAT CTG GAC TCC AGG CTC CGT GCT GGG AGC TCA GAG   2820
  F   D   S   E   H   N   L   T   S   N   E   G   H   S   L   K   N   L   E   H    960
TTT GAT TCA GAG CAC AAC CTA ACA AGC AAT GAA GGG CAC AGT CTG AAA AAC CTG GAG CAC   2880
  R   L   N   E   M   E   R   T   Q   A   Q   L   R   D   A   V   Q   S   L   Q    980
CGC CTA AAT GAG ATG GAG AGA ACT CAG GCT CAG CTG AGG GAT GCT GTC CAG AGC CTG CAG   2940
  L   S   P   R   T   R   G   S   W   S   Q   P   Q   P   L   K   A   P   C   L   1000
CTT TCT CCA AGG ACG CGG GGG TCT TGG AGT CAA CCC CAG CCC CTC AAA GCA CCC TGC CTC   3000
  N   G   D   T   T   *                                                            1006
AAT GGA GAC ACC ACC TGA                                                           3018
```

GCTGCCCATCCTGCCTCATCACACGTGGTCTGGGAGCAGAGAGATAGCCATCTTAGGGGGGGTGTCTGACTTTGCCTTA

GCCCTACTTGGCCTACAGTGGGGAGTGGAGCTGCTGGTCCCAACCACTCTGGCAGTATGAAGTTGCCCAGTAAAATCTT

GATTTCAGTGAAAAAAAAAAAAAAAAGGGCGGRCCGCTAGACTWAGTCTAGAGAAAAAACCTCCCACACCTCCCCCTGA

ACCTRAAACATHCCAMMACCTCCCCCTSAWSMWSMWRMAWMAWARAAWKSAAWGCAATG

>PS00001|PDOC00001|ASN_GLYCOSYLATION N-glycosylation site.
Query: 946  NLTS  949

>PS00004|PSOC00004|CAMP_PHOSPHO_SITE cAMP-and cGMP-dependent protein kinase phosphorylation site.
Query: 358  RRLS  361
Query: 822  RRQS  825
Query: 856  RKPS  859

>PS00005|PDOC00005|PKC_PHOSPHO_SITE Protein kinase C phosphorylation site.
Query: 22   SYR  24
Query: 80   TSR  82
Query: 268  SCR  270
Query: 361  SLR  363
Query: 423  SER  425
Query: 467  TGR  469
Query: 580  SWR  582
Query: 715  TTR  717
Query: 781  SLR  783
Query: 784  SVR  786
Query: 878  THR  880
Query: 954  SLK  956
Query: 982  SPR  984

>PS0006|PDOC00006|CK2_PHOSPHO_SITE Casein kinase II phosphorylation site.
Query: 51   SHQE  54
Query: 141  TLLD  144
Query: 188  TEPE  191
Query: 228  TLSE  231
Query: 271  SAAE  274
Query: 529  STED  532
Query: 555  SCEE  558
Query: 580  SWRE  583
Query: 660  SFLE  663
Query: 715  TTRD  718
Query: 756  SAGE  759
Query: 939  SEFD  942
Query: 948  TSNE  951

>PS00008|PDOC00008|MYRISTYL N-myristoylation site.
Query: 30   GGEKAA  35
Query: 163  GSASSE  168
Query: 221  GSRESL  226
Query: 262  GGSRCF  267
Query: 309  GLPRAA  314
Query: 328  GALLAR  333
Query: 366  GLGPGS  371
Query: 402  GAPAGA  407
Query: 486  GGREAL  491
Query: 575  GIVFSS  580

>PS00029|PDOC00029|LEUCINE_ZIPPER Leucine zipper pattern.
Query: 360  LSLRLRGLGPGSAVLGRVALAL  381

Analysis of 26138

Query: 22    SYR    24
Query: 80    TSR    82
Query: 268   SCR    270
Query: 361   SLR    363
Query: 423   SER    425
Query: 467   TGR    469
Query: 580   SWR    582
Query: 715   TTR    717
Query: 781   SLR    783
Query: 784   SVR    786
Query: 878   THR    880
Query: 954   SLK    956
Query: 982   SPR    984

>PS00006|PDOC00006|CK2_PHOSPHO_SITE Casein kinase II phosphorylation site.
Query: 51    SHQE   54
Query: 141   TLLQ   144
Query: 188   TEPE   191
Query: 228   TLSE   231
Query: 271   SAAE   274
Query: 529   STED   532
Query: 555   SCEE   558
Query: 580   SWRE   583
Query: 660   SFLE   663
Query: 715   TTRD   718
Query: 756   SAGE   759
Query: 939   SEFD   942
Query: 948   TSNE   951

>PS00008|PDOC00008|MYRISTYL N-myristoylation site.
Query: 30    GGEKAA   35
Query: 163   GSASSE   168
Query: 221   GSRESL   226
Query: 262   GGSRCF   267
Query: 309   GLPRAA   314
Query: 328   GALLAR   333
Query: 366   GLGPGS   371
Query: 402   GAPAGA   407
Query: 486   GGREAL   491
Query: 575   GIVFSS   580

>PS00029|PDOC00029|LEUCINE_ZIPPER Leucine zipper pattern.
Query: 360   LSLRLRGLGPGSAVLGRVALAL   381

FIG. 60B.

```
Protein Family/Domain Matches, HMMer
Searching for complete domain in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
HMM file:         /prod/ddm/seqanal/PFAM/pfam4.4/Pfam
Sequence file:    /prod/ddm/wspace/orfanal/oa-script.8746.seq Query:    26138

Scores for sequence family classification (score includes all domains):
Model     Description                                    Score     E-value   N
RasGAP    GTPase-activator protein for Ras-like GTPase   109.8     5.1e-29   1

Parsed for domains:
Model     Domain   seq-f   seq-t   hmm-f   hmm-t      score    E-value RasGAP    1/1      473     645 ..    1      231 ()    109.8    5.1e-29

RasGAP: domain 1 of 1, from 473 to 645: score 109.8, E = 5.1e-29
                *->LvktllqkEIeSkaddpttlfRgNslaskmleqyfRrarGneYLrkt
                   Lv+ l + E+   +    lfR N+la+k++++y++++ ++ YL+ t
       26138 473 LVTDLGTAELARCGGREALLFRENTLATKAIDEYMKLV-AQDYLQET    518

LrpvLkelieskdVqHLscEiDPlkvykklVNqgelstsEldydlTnEev
                 L +v+++ +s +    cE+DP+k
       26138 519 LGQVVRRLCASTE----DCEVDPSKC------------------------    540

IdeeekseaieenlrnLlkytekllealtsSsdefPpeLryIckclrqsa
                 + se  e +++L++  e+++e I+ S d fP eL  ++   r++
       26138 541 ----PASEL-PEHQARLRNSCEEVFETIIHSYDWFPAELGIVFSSWREAC    585 cekFPdnatVKEKKENKKSVVSqRFeqvilsavGgfvFLRFinPAIvsPd
                 e   +                            ++v  +FLR+ +PAI++P
       26138 586 KERGSEV-------------------LGPRLVCASLFLRLLCPAILAPS    615 lfnIidkspsaqaTTDqrRtLtliAKviQslANg<-*
                 lf++  + p +     +RtLtliAKviQ+lAN
       26138 616 LFGLAPDHPAPGP----ARTLTLIAKVIQNLANR         645
```

```
//
Searching for complete domains in SMART
hmmpfam - search a single seq against HMM database
HMMER 2.1.1 (Dec 1998)
Copyright (C) 1992-1998 Washington University School of Medicine
HMMER is freely distributed under the GNU General Public License (GPL).
HMM file:         /ddm/robison/smart/smart/smart.all.hmms
Sequence file:    /prod/ddm/wspace/orfanal/oa-script.8746.seq Query:    26138

Scores for sequence family classification (score includes all domains):
Model       Description                                    Score    E-value    N
RasGAP_2                                                   276.4    3.8e-79    1

Parsed for domains:
Model       Domain    seq-f    seq-t    hmm-f    hmm-t    score    E-value    N RasGAP      1/1       401      723 ..    1        390 ()   276.4    3.8e-79    1

Alignments of top-scoring domains:

RasGAP_2: domain 1 of 1, from 401 to 723: score 276.4, E = 3.8e-79
                *->lkqgelgslrlktvyttdfilpseaYeeLleLllesvdvepltasla
                   l    lr +++ + +++lpse Y+eL e+l+++++       l+
       26138 401 LGAPAGAALRARIRARRLRVLPSERYKELAEFLTFHYA------RLC      441 saleevcsvldkdelAtkLvrlFlrrgrgkpfLraLidkEvertddpvnt
                 ale++++   k+elA ++vr+++ +gr++ ++++L +E++r+ +   +
       26138 442 GALEPALPAQAKEELAAAMVRVLRATGRAQALVTDLGTAELARCGGREAL    491 lFRgNsLatKsmevymklvGnqYLhttLkpvLkkiveekkescEvDPsKl
                 lFR+N+LatK++++ymklv++++YL++tL+ v+++++++ + cEvDpsK+
       26138 492 LFRENTLATKAIDEYMKLVAQDYLQETLGQVVRRLCASTE-DCEVDPSKC    540 evndviSfgdpvegedletnlenLlqyverlfdalinSsdrlPyglRdic
                 + ++l ++++++L++ +e++f+ Ii S+d +P +L ++
       26138 541 -----------PASELPEHQARLRNSCEEVFETIIHSYDWFPAELGIVF     578 kqLrqaaekrFpsatqdvrykaVssFvFLRFfcPAIlSPklFnLvdehpd
                 +++r+a+ +r ++         ++V ++FLR++cPAIl P+lF+L ++hp
       26138 579 SSWREACKERGSEV---LGPRLVCASLFLRLLCPAILAPSLFGLAPDHPA    625 pttrRtLtLiAKvlQnLANlseskskIfgsKEpwmeplfkndflkqhkdr
                 p +RtLtLiAKv+QnLAN +      fg KE +m ++   n fl++h   +
       26138 626 PGPARTLTLIAKVIQNLANRAP-----FGEKEAYMGFM--NSFLEEHGPA    668 vkdFLdelssvdepsesLvdkveelptkskPVstisgrelsllHslllen
                 + FLd+ + vd       + +++                       + +
       26138 669 MQCFLDQVAMVD-------VDAAPSG------------------YQGSG    692 gdalkrkknnnrDHKAlgedpldkllfklryfrltthkltngk<-*
                 +al +                + +l++ +++++++tt+  +
       26138 693 DLALQLAVL------------HAQLCTIFAELDQTTRDTLEPL           723
```

Analysis of 26138 (1005 aa)

PSORT Prediction of Protein Localization

MITDISC: discrimination of mitochondrial targeting seq
    R content:        2        Hyd Moment (75):  9.38
    Hyd Moment (95): 1.43     G content:          4
    D/E content:     2        S/T content:       11
    Score: -3.90

Gavel: prediction of cleavage sites for mitochondrial preseq
    R-2 motif at 102 GRH|KN NUDISC: discrimination of nuclear localization signals
    pat4: RRPR (4) at 158
    pat4: RRPR (4) at 803
    pat7: PRRPRVG (5) at 157
    pat7: PLRRPRP (4) at 801
    pat7: PARRRQS (5) at 819
    bipartite: none
    content of basic residues: 13.2%
    NLS Score: 1.23

Final Results (k = 9/23):
    43.5 %: nuclear
    26.1 %: mitochondrial
     8.7 %: cytoplasmic
     4.3 %: plasma membrane
     4.3 %: vesicles of secretory system
     4.3 %: extracellular, including cell wall
     4.3 %: peroxisomal prediction for 26128 is nuc (k=23)

FIG. 62A.

| Start | End | Feature | Sequence |
|---|---|---|---|
| 142 | 143 | Dileucine motif in the tail | LL |
| 149 | 150 | Dileucine motif in the tail | LL |
| 204 | 205 | Dileucine motif in the tail | LL |
| 249 | 250 | Dileucine motif in the tail | LL |
| 330 | 331 | Dileucine motif in the tail | LL |
| 360 | 381 | Leucine zipper pattern (PS00029) | LSLRLRGLGP...AVLGRVALAL |
| 400 | 401 | Dileucine motif in the tail | LL |
| 491 | 492 | Dileucine motif in the tail | LL |
| 881 | 981 | coiled coil | VNKLAELQCE...RDAVQSLQLS |
| 888 | 909 | Leucine zipper pattern (PS00029) | LQCEVAALRE...KVLSRLVESL |

FIG. 62B.

Mapping Panel: Genebridge 4 Human RH
Chromosome: hu19
Syntenic Chromosome:
Flanking Markers: WI-6344 (15.3 cR)WI-1413 (40 cR)
Forward primer: AGCCTGCAGCTTTCTCCAAGG
Reverse primer: CTCCACTCCCCACTGTAGGC
Nearby Mutations/Loci: Human- ATHS, ATHEROSCLEROSIS SUSCEPTIBILITY; ATCAY, CEREBELLAR ATAXIA, CAYMAN TYPE; FEB2, FEBRIL CONVULSIONS, FAMILIAL,2; HHC2, HYPOCALCIURIC HYPERCALCEMIA, FAMILIAL, TYPE II; MDRV, MUSCULAR DYSTROPHY, AUTOSOMAL DOMINANT, WITH RIMMED VACUOLES; THYROID CARCINOMA, NONMEDULLARY, WITH CELL OXYPHILIA; EXT3, EXOSTOSES, MULTIPLE, TYPE III; Mouse- Nearby Known Genes: CD97, NDUFB7, PRKCL1, NOTCH3, ERBAL2, CYP4F2

FIG. 63.

FROM FIG. 64A.

UBIQUTIN PROTEASES

CROSS-REFERENCE TO RELATED APPLICATIONS

This application is a continuation-in-part of Ser. No. 09/390,038, filed Sep. 3, 1999, now abandoned; and a continuation-in-part of Ser. No. 09/796,089, filed Feb. 28, 2001, now abandoned, which is a continuation-in-part of Ser. No. 09/464,039, filed Dec. 15, 1999, now U.S. Pat. No. 7,094,565, and claims the benefit of 371 PCT/US00/33873, filed Dec. 15, 2000; and a continuation-in-part of Ser. No. 09/972,525, filed Oct. 5, 2001, now abandoned, which is a divisional of Ser. No. 09/408,865, filed Sep. 30, 1999, now U.S. Pat. No. 6,329,171; and a continuation-in-part of Ser. No. 09/963,908, filed Sep. 26, 2001, now U.S. Pat. No. 6,797,502, which is a divisional of Ser. No. 09/434,613, filed Nov. 5, 1999, now U.S. Pat. No. 6,337,187; and a continuation-in-part of Ser. No. 09/461,076, filed Dec. 14, 1999, now abandoned; and a continuation-in-part of Ser. No. 09/802,127, filed Feb. 26, 2001, now abandoned, which claims the benefit of U.S. Provisional 60/185,611, filed Feb. 29, 2000, now expired; all of which are hereby incorporated in their entirety by reference herein.

FIELD OF THE INVENTION

The invention relates to novel nucleic acid sequences and polypeptides. Also provided are vectors, host cells, and recombinant methods for making and using the novel molecules.

TABLE OF CONTENTS

Chapter 1  23552, A Novel Adenylate Kinase
    i)   SEQ ID NOS: 1-4
    ii)  FIGS. 1-6
    iii) Continuation-In-Part of 09/390,038, filed Sep. 3, 1999
Chapter 2  21612, 21615, 21620, 21676, 33756, Novel Human Alcohol Dehydrogenases
    i)   SEQ ID NOS: 5-14
    ii)  FIGS. 7A-32
    iii) Continuation-In-Part of 09/796,089, filed Feb. 28, 2001, which is a continuation-in-part of 09/464,039, filed Dec. 15, 1999, and claims the benefit of 371 PCT/US00/33873, filed Dec. 15, 2000
Chapter 3  23484, A Novel Human Ubiquitin Protease
    i)   SEQ ID NOS: 15-16
    ii)  FIGS. 33A-38
    iii) Continuation-In-Part of 09/972,525, filed Oct. 5, 2001, which is a divisional of 09/408,865, filed Sep. 30, 1999, now U.S. Pat. No. 6,329,171
Chapter 4  18891, A Novel Human Lipase
    i)   SEQ ID NOS: 17-18
    ii)  FIGS. 39A-45
    iii) Continuation-In-Part of 09/963,908, filed Sep. 26, 2001, which is a divisional of 09/434,613, filed Nov. 5, 1999, now U.S. Pat. No. 6,337,187
Chapter 5  25678, A Novel Human Adenylate Cyclase
    i)   SEQ ID NOS: 19-20
    ii)  FIGS. 46A-51
    iii) Continuation-In-Part of 09/461,076, filed Dec. 14, 1999
Chapter 6  Novel Human GTPase Activators
    i)   SEQ ID NOS: 21-30
    ii)  FIGS. 52A-64B
    iii) Continuation-In-Part of 09/802,127, filed Feb. 26, 2001, which claims the benefit of U.S. Provisional 60/185,611, filed Feb. 29, 2000

BRIEF DESCRIPTION OF THE DRAWINGS

FIG. 1 shows the amino acid sequence alignment for the protein (h23552; SEQ ID NO:2) encoded by human 23552 (SEQ ID NO:1) with the porcine UMP-CMP kinase (SP Accession Number Q29561; SEQ ID NO:3). The sequence alignment was generated using the Clustal method. The two sequences share approximately 97.4% identity over a 196 amino acid overlap as determined by pairwise alignment. Asterisks indicate identical residues.

FIG. 2 shows the 23552 nucleotide sequence (SEQ ID NO:1) and amino acids 1 to 609 of the amino acid sequence set forth in SEQ ID NO:2.

FIG. 5 shows an analysis of the 23552 open reading frame for amino acids corresponding to specific functional sites. These sites are relevant with regard to providing fragments of the 23552 nucleic acid or peptide as disclosed herein. The 23552 amino acid sequence contains an N-glycosylation site from amino acids 137 to 140 of SEQ ID NO:2; protein kinase C phosphorylation sites at amino acids 21-23, 29-31, 170-172, 190-192 of SEQ ID NO:2; casein kinase II phosphorylation sites at amino acids 65-68 and 212-215 of SEQ ID NO:2; tyrosine kinase phosphorylation sites at amino acids 54-61 and 74-81 of SEQ ID NO:2; N-myristoylation sites at amino acids 42-47 and 49-54 of SEQ ID NO:2; and an adenylate kinase signature at amino acids 121-132 of SEQ ID NO:2.

FIG. 6 shows a comparison of the 23552 protein against the prosite database of protein patterns, specifically showing a high score against an adenylate kinase consensus sequence set forth in SEQ ID NO:4.

FIGS. 7A-7B show the nucleotide sequence (SEQ ID NO:6) and the deduced amino acid sequence (SEQ ID NO:5) of the novel 21620 ADH.

FIG. 10 shows an analysis of the 21620 ADH open reading frame for amino acids (SEQ ID NO:5) corresponding to specific functional sites. A putative protein kinase C phosphorylation site is found from about amino acid 135 to about amino acid 137. Putative casein kinase II phosphorylation sites are found from about amino acid 72 to about amino acid 75, from about amino acid 89 to about amino acid 92, and from about amino acid 135 to about amino acid 138. Putative N-myristoylation sites are found from about amino acid 18 to about amino acid 23, from about amino acid 24 to about amino acid 29, from about amino acid 40 to about amino acid 45, from about amino acid 90 to about amino acid 95, from about amino acid 109 to about amino acid 114, and from about amino acid 199 to about amino acid 204. In addition, amino acids corresponding to the short-chain alcohol dehydrogenase family signature are found in the sequence at about amino acids 166 to 176.

FIG. 13 shows the nucleotide sequence (SEQ ID NO:8) and the deduced amino acid sequence (SEQ ID NO:7) of the novel 33756 ADH.

FIG. 16 shows an analysis of the 33756 ADH open reading frame (SEQ ID NO:7) for amino acids corresponding to specific functional sites. A putative N-glycosylation site is found from about amino acid 100 to about amino acid 103. Putative protein kinase C phosphorylation sites are found from about amino acid 29 to about amino acid 31, from about amino acid 32 to about amino acid 34, from about amino acid 120 to about amino acid 122, from about amino acid 144 to about amino acid 146, from about amino acid 213 to about amino acid 215, from about amino acid 242 to about amino acid 244, and from about amino acid 252 to about amino acid 254. Putative casein kinase II phosphorylation sites are found from about amino acid 32 to about amino acid 35, from about amino 63 to about amino acid 66, and from about amino acid 252 to about amino acid 255. Putative N-myristoylation sites are found from about amino acid 149 to about amino acid 154, from about amino acid 160 to about amino acid 165, and from about amino acid 171 to about amino acid 176.

FIGS. 17A-17B show the nucleotide sequence (SEQ ID NO:9) and the deduced amino acid sequence (SEQ ID NO:10) of the novel 21676 ADH.

FIG. 20 shows an analysis of the 21676 ADH open reading frame (SEQ ID NO:9) for amino acids corresponding to specific functional sites. A putative N-glycosylation site is found from about amino acid 171 to about amino acid 174. A putative protein kinase C phosphorylation sites are found from about amino acid 100 to about amino acid 102, from about amino acid 103 to about amino acid 105, from about amino acid 191 to about amino acid 193, from about amino acid 215 to about amino acid 217, from about amino acid 284 to about amino acid 286, from about amino acid 313 to about amino acid 315, and from about amino acid 323 to about amino acid 325. A putative casein kinase II phosphorylation sites are found from about amino acid 54 to about amino acid 57, from about amino 103 to about amino acid 106, from about amino acid 134 to about amino acid 137, and from about amino acid 323 to about amino acid 326. Putative N-myristoylation sites are found from about amino acid 12 to about amino acid 17, from about amino acid 28 to about amino acid 33, from about amino acid 45 to about amino acid 50, from about amino acid 220 to about amino acid 225, from about amino acid 231 to about amino acid 236, and from about amino acid 242 to about amino acid 247.

FIGS. 21A-21B show the nucleotide sequence (SEQ ID NO:12) and the deduced amino acid sequence (SEQ ID NO:11) of the novel 21612 ADH.

FIG. 24 shows an analysis of the 21612 ADH open reading frame (SEQ ID NO:11) for amino acids corresponding to specific functional sites. A putative N-glycosylation site is found from about amino acid 101 to about amino acid 104. A putative protein kinase C phosphorylation sites are found from about amino acid 5 to about amino acid 7, from about amino acid 115 to about amino acid 117, from about amino acid 282 to about amino acid 284, from about amino acid 313 to about amino acid 315, from about amino acid 381 to about amino acid 383, and from about amino acid 392 to about amino acid 394. A putative casein kinase II phosphorylation sites are found from about amino acid 56 to about amino acid 59, from about amino acid 320 to about amino acid 323, from about amino acid 338 to about amino acid 341, and from about amino acid 372 to about amino acid 375. A putative N-myristoylation sites are found from about amino acid 17 to about amino acid 22, from about amino acid 52 to about amino acid 57, from about amino acid 128 to about amino acid 133, and from about amino acid 353 to about amino acid 358. In addition, a microbodies C-terminal targeting signal is found from about amino acid 416 to about amino acid 418.

FIGS. 25A-25B show the nucleotide sequence (SEQ ID NO:14) and the deduced amino acid sequence (SEQ ID NO:13) of the novel 21615 ADH.

FIG. 28 shows an analysis of the 21615 ADH open reading frame (SEQ ID NO: 13) for amino acids corresponding to specific functional sites. Putative N-glycosylation sites are found from about amino acid 39 to about amino acid 42 and from about amino acid 130 to about 133. Putative protein kinase C phosphorylation site are found from about amino acid 60 to about amino acid 62, from about amino acid 137 to about amino acid 139, from about amino acid 149 to about amino acid 151, and from about amino acid 208 to about amino acid 210. Putative casein kinase II phosphorylation sites are found from about amino acid 89 to about amino acid 92, from about amino 184 to about amino acid 187, from about amino acid 213 to about amino acid 216. A putative tyrosine kinase site is found from about amino acid 42 to about amino acid 49. Putative N-myristoylation sites are found from about amino acid 17 to about amino acid 22, from about amino acid 126 to about amino acid 131, from about amino acid 156 to about amino acid 161, and from about amino acid 169 to about amino acid 174. In addition, a short-chain alcohol dehydrogenase family signature is found from about amino acid 147 to about amino acid 157.

FIGS. 33A-33D show the nucleotide sequence (SEQ ID NO:16) and the deduced amino acid sequence (SEQ ID NO:15) of the novel ubiquitin protease. The underlined amino acids designate the conserved cysteine region and conserved histidine region. These regions are conserved among thiol protease members of the UBP and UCH protein families.

FIG. 35 shows a hydrophobicity plot of the ubiquitin protease (SEQ ID NO:15).

FIGS. 36A-36D show an analysis of the ubiquitin protease open reading frame for amino acids corresponding to specific functional sites of SEQ ID NO:15. Glycosylation sites are found from about amino acid 134 to 137, with the modified amino acid at position 134; about amino acid 333 to 336, with the modified amino acid at position 333; from about amino acid 398 to 401 with the modified amino acid at position 398, from about 492 to 495 with the modified amino acid at position 492, from about 560 to 563 with the modified amino acid at position 560, from about 644 to 647 with the modified amino acid at position 644, and from about 672 to 675 with the modified amino acid at position 672. Cyclic AMP and cyclic GMP-dependent protein kinase phosphorylation sites are found from about amino acid 15 to 18 with the modified amino acid at position 18, from about amino acid 313 to 316 with the modified amino acid at position 316, from about 607 to 610 with the modified amino acid at position 610; from about amino acid 694 to 697 with the modified amino acid at position 697; from about amino acid 812 to 815 with the modified amino acid at position 815. Protein kinase C phosphorylation sites are found from about amino acid 31 to 33, with the modified amino acid at position 31; from about amino acid 107 to 109, with the modified amino acid at position 107; from about amino acid 111 to 113, with the modified amino acid at position 111; from about amino acid 312 to 314, with the modified amino acid at position 312; from about amino acid 327 to 329, with the modified amino acid at position 327; from about amino acid 426 to 428, with the modified amino acid at position 426; from about amino acid 453 to 455, with the modified amino acid at position 453; from about amino acid 467 to 469, with the modified amino acid at position 467; from about amino acid 475 to 477, with the modified amino acid at position 475; from about amino acid 515 to 517, with the modified amino acid at position 515; from about amino acid 546 to 548, with the modified amino acid at position 546; from about amino acid 561 to 563, with the modified amino acid at position 561; from about amino acid 556 to 568, with the modified amino acid at position 566; from about amino acid 582 to 584, with the modified amino acid at position 582; from about amino acid 623 to 625, with the modified amino acid at position 623; from about amino acid 629 to 631, with the modified amino acid at position 629; from about amino acid 662 to 664, with the modified amino acid at position 662; from about 692 to 694, with the modified amino acid at position 692; from about amino acid 748 to 750, with the modified amino acid at position 748; from about amino acid 765 to 767, with the modified amino acid at position 765; from about amino acid 809 to 811, with the modified amino acid at position 809; from about amino acid 865 to 867, with the modified amino acid at position 865; from about amino acid 911 to 913, with the modified amino acid at position 911; from about amino acid 952 to 954, with the modified amino acid at position 952; from about amino acid 965 to 967, with the modified amino acid at position 965; from about amino acid 980 to 982, with the modified amino acid at position 980; from about amino acid 1034 to 1036, with the modified amino acid at position 1034; from about amino acid 1103 to 1105, with the modified amino acid at position 1103; and from about amino acid 1120 to 1122, with the modified amino acid at 1120. Casein kinase II phosphorylation sites are found from about amino acid 18 to 21; from amino acid 75 to 78; from amino acid 92 to 95; from amino acid 260 to 263; from amino acid 481 to 484; from amino acid 527 to 530; from amino acid 613 to 616; from amino acid 656 to 659; from amino acid 673 to 676; from amino acid 703 to 706; from amino acid 807 to 810; and from amino acid 1067 to 1070. Tyrosine kinase phosphorylation sites are found from about amino acid 83 to 90, with the modified amino acid at position 90; from about amino acid 338 to 345, with the modified amino acid at position 345; and from about amino acid 1031 to 1038, with the modified amino acid at position 1038. N-myristoylation sites are found from about amino acid from about 85 to 90, with the modified amino acid at position 85; from about amino acid 336 to 341, with the modified amino acid at position 336; from about amino acid 486 to 491, with the modified amino acid at position 486, from about amino acid 493 to 498, with the modified amino acid at position 493, from about amino acid 552 to 557, with the modified amino acid at position 552; from amino acid 570 to 575, with the modified amino acid at position 570; from amino acid 595 to 600, with the modified amino acid at position 595; from amino acid 609 to 614, with the modified amino acid at position 609; and from amino acid 898 to 903, with the modified amino acid at position 898. Amidation sites are found from about amino acid 13 to 16, from about amino acid 467 to 470, from about amino acid 532 to 535; from about amino acid 841 to 844; and from about amino acids 1038 to 1041. In addition, an amino acid signature corresponding to the MHC immunoglobulins and major histocompatibility complex proteins is found from amino acids 376 to 382. The amino acids corresponding to the UCH family 2 signature are found at amino acids 365-383.

FIG. 38 shows expression of the protease in various tissues and cell types in culture. The expression data was derived from RT-PCR of various cDNA libraries.

FIGS. 39A-39B show the nucleotide sequence (SEQ ID NO:18) and the deduced amino acid sequence (SEQ ID NO:17) of the novel lipase.

FIG. 42 shows an analysis of the lipase open reading frame for amino acids corresponding to specific functional sites of SEQ ID NO:17. Protein kinase C phosphorylation sites are found from about amino acid 63 to 65; from about amino acid 111 to 113; from about amino acid 252 to 254; from about amino acid 316 to 318. Casein kinase II phosphorylation sites are found from about amino acid 114 to 117; from amino acid 205 to 208; from amino acid 284 to 287. N-myristoylation sites are found from about amino acid from about 13 to 18, with the modified amino acid at position 13; from about amino acid 110 to 115, with the modified amino acid at position 110; from about amino acid 146 to 151, with the modified amino acid at position 146, from about amino acid 155 to 160, with the modified amino acid at position 155, from about amino acid 175 to 180, with the modified amino acid at position 175.

FIG. 45 shows expression of the lipase mRNA in normal and malignant breast, lung, liver and colon tissues. The liver metastases are derived from malignant colonic tissue. The expression data was derived from RT-PCR designed to amplify the untranslated region of the lipase.

FIGS. 46A-46D show the adenylate cyclase nucleotide sequence (SEQ ID NO:20) and the deduced amino acid sequence (SEQ ID NO:19).

FIGS. 49A-49C show an analysis of the adenylate cyclase open reading frame for amino acids corresponding to specific functional sites of SEQ ID NO:19. Glycosylation sites are shown in the figure with the actual modified residue being the first amino acid. Protein kinase C phosphorylation sites are shown in the figure with the actual modified residue being the first amino acid. Casein kinase II phosphorylation sites are shown in the figure with the actual modified residue being the first amino acid. Tyrosine kinase phosphorylation sites are shown in the figure with the actual modified residue being the last amino acid. N-myristoylation sites are shown in the figure, with the actual modified residue being the first amino acid. In addition, amino acids corresponding to the guanylate cyclase signature are found at amino acids 394-417 and 1009-1032.

FIG. 51 shows expression of the 25678 adenylate cyclase in various cardiovascular tissues. Int. Mamm: internal mammary artery; CHF: congestive heart failure; ISCH: ischemic heart; myop: myopathic heart.

FIGS. 52A-52B show the 26651 nucleotide sequence (SEQ ID NO:21) and the deduced amino acid sequence (SEQ ID NO:22). The coding sequence for 26651 is set forth in SEQ ID NO:23.

FIG. 55 shows an analysis of the 26651 open reading frame (SEQ ID NO:22) for amino acids corresponding to predicted functional sites. For the cAMP- and cGMP-dependent protein kinase phosphorylation site, the actual modified residue is the last amino acid (pattern matches at amino acids 224-227 and 395-398 of SEQ ID NO:22). For the protein kinase C phosphorylation sites, the actual modified residue is the first amino acid. For the casein kinase II phosphorylation sites, the actual modified residue is the first amino acid (pattern matches at amino acids 54-57, 116-119, 192-195, 443-446, 478-481, 497-500, and 510-513 of SEQ ID NO:22). For the tyrosine kinase phosphorylation site, the actual modified residue is the last amino acid (pattern match at amino acids 62-68 of SEQ ID NO:22). N-myristoylation site pattern matches at amino acids 36-41, 103-108, 144-149, 371-376 and 506-511 of SEQ ID NO:22), and an amidation site pattern matches at amino acids 147-150, 182-185, and 393-396 of SEQ ID NO:22).

FIGS. 56A-56B depict an alignment of the rho-GAP domain of human 26651 with a consensus amino acid sequence derived from a hidden Markov model. The upper sequence is the consensus amino acid sequence (SEQ ID NO:27), while the lower amino acid sequence corresponds to amino acids 236 to 397 of SEQ ID NO:22. The top half of the figure was obtained by searching for complete domains using PFAM. In the lower portion of the figure, a portion of human 26651 (amino acids 233 to 423 of SEQ ID NO:22) is aligned with a consensus rho-GAP_3 domain (SEQ ID NO:28). The lower half of the figure was obtained by searching for complete domains in SMART.

FIGS. 57A-57C show the 26138 nucleotide sequence (SEQ ID NO:24) and the deduced 26138 amino acid sequence (SEQ ID NO:25). The coding sequence for 26138 is set forth in SEQ ID NO:26.

FIGS. 60A-60B show an analysis of the 26138 open reading frame (SEQ ID NO:25) for amino acids corresponding to predicted functional sites. For the N-glycosylation site, the actual modified residue is the first amino acid (pattern match at amino acids 946-949 of SEQ ID NO:25). For the N-myristoylation, the actual modified residue is the first amino acid. For the cAMP- and cGMP-dependent protein kinase phosphorylation site, the actual modified residue is the first amino acid (pattern matches at amino acids 358-361, 822-825, and 856-859 of SEQ ID NO:25). For the protein kinase C phosphorylation sites, the actual modified residue is the first amino acid. For the casein kinase II phosphorylation sites, the actual modified residue is the first amino acid (pattern matches at amino acids 51-54, 141-144, 188-191, 228-231, 271-274, 529-532, 555-558, 580-583, 660-663, 715-718, 756-759, 939-942, 948-951 of SEQ ID NO:25). In addition there is a Ras GTPase activating protein signature. N-myristoylation site pattern matches are shown at amino acids 30-35, 163-168, 221-226, 309-314, 328-333, 366-371, 402-407, 486-491, 575-580 of SEQ ID NO:25. Leucine zipper pattern match is shown at amino acids 360-381 of SEQ ID NO:25.

FIGS. 61A-61B depict an alignment of the ras-GAP domain of human 26138 with a consensus amino acid sequence derived from a hidden Markov model. The upper sequence is the consensus amino acid sequence (SEQ ID NO:29), while the lower amino acid sequence corresponds to amino acids 473 to 645 of SEQ ID NO:25. The top half of the figure shows the results of a search for complete domains using PFAM for the 26138 protein. In the lower portion of the figure, a portion of human 26138 (amino acids 401 to 723 of SEQ ID NO:25) is aligned with a consensus ras-GAP_2 domain (SEQ ID NO:30). The lower half of the figure was obtained by searching for complete domains in SMART.

FIGS. 62A-62B show a PSORT prediction of protein localization for the 26138 GAP protein (SEQ ID NO:25). Gavel prediction of cleavage sites for mitochondrial preseg is shown at sequence GRH|KN, which corresponds to amino acids 91-95 of SEQ ID NO:25. NUDISC: discrimination of nuclear localization signals shown at amino acids 158-161, 803-806, 157-163, 801-807, and 819-825 of SEQ ID NO:25. In FIG. 62B, leucine zipper patterns are shown at amino acids 360-381, and 888-909 of SEQ ID NO:25, and a coiled coil feature is shown at amino aids 881-981 of SEQ ID NO:25.

FIG. 63 shows chromosome mapping information for the 26138 GAP gene.

CHAPTER 1

23552, a Novel Adenylate Kinase

BACKGROUND OF THE INVENTION

Figure 3:
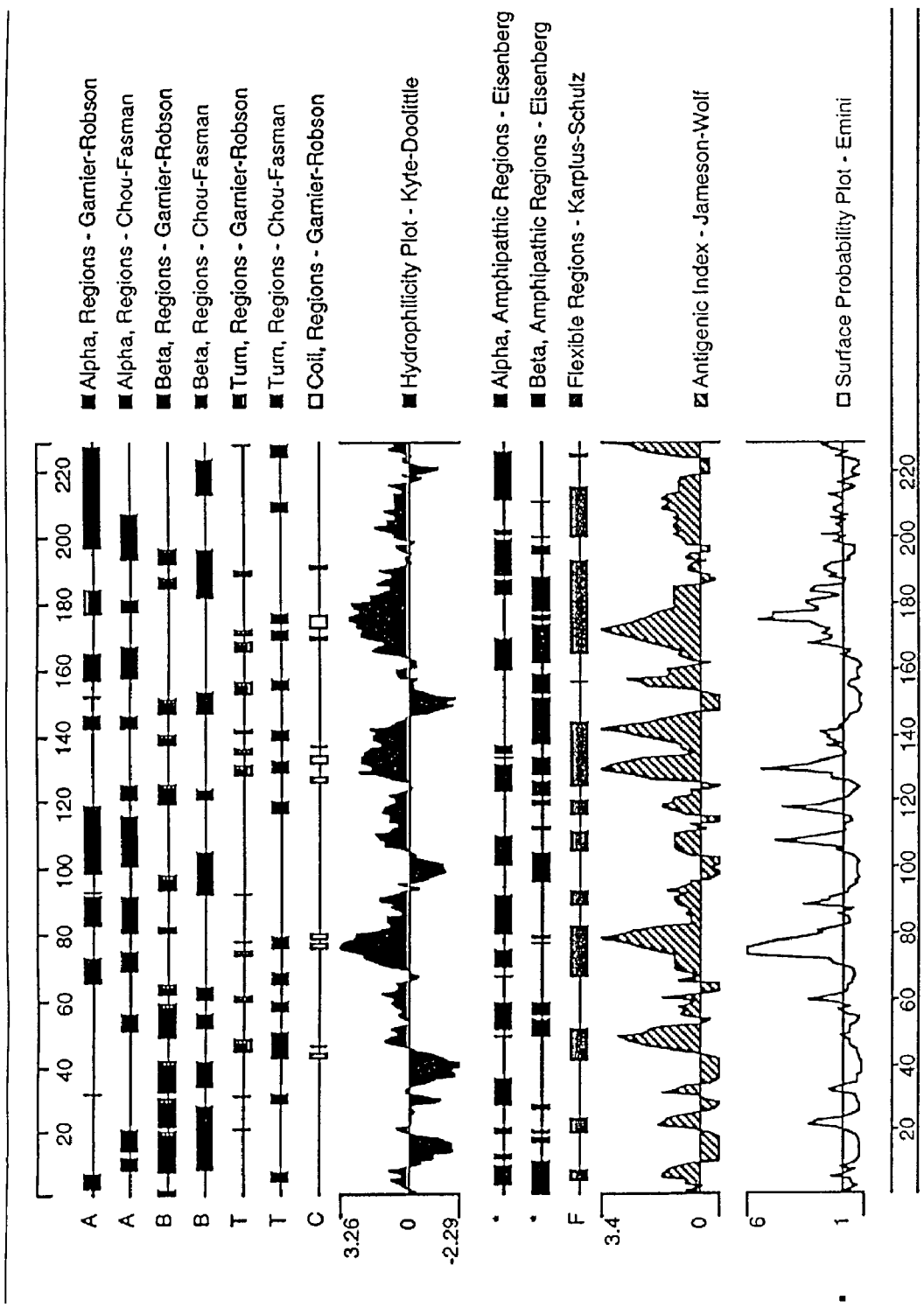
FIG. 3 shows an analysis of the 23552 amino acid sequence: αβ turn and coil regions; hydrophilicity; amphipathic regions; flexible regions; antigenic index; and surface probability plot.
Figure 4:
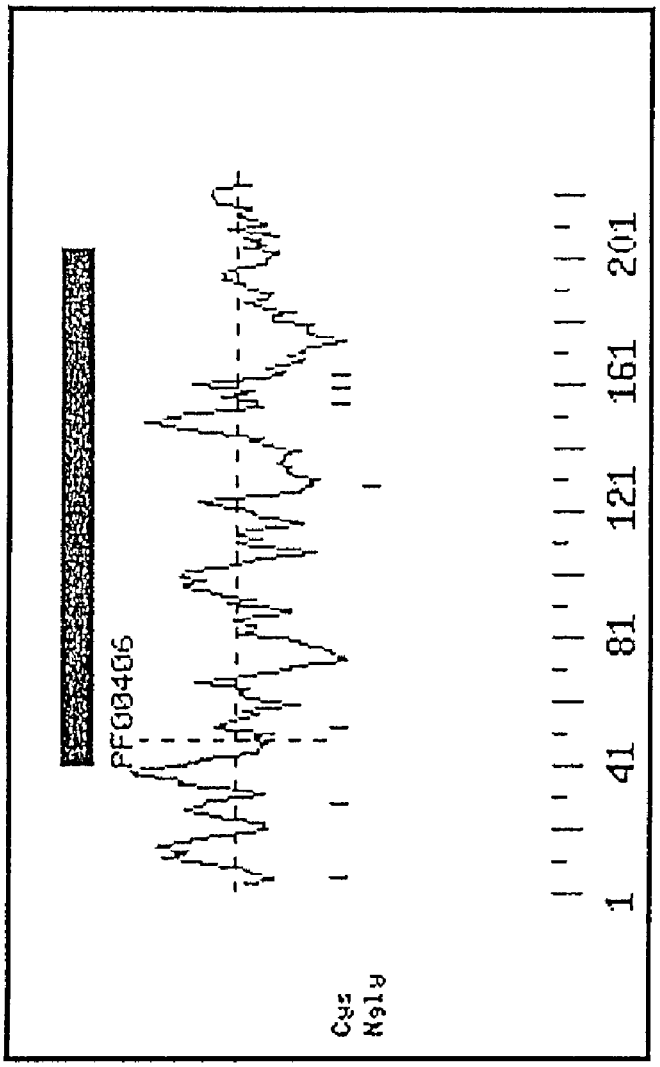
FIG. 4 shows a 23552 receptor hydrophobicity plot and the 23552 amino acid sequence (SEQ ID NO:2).
Figure 8:
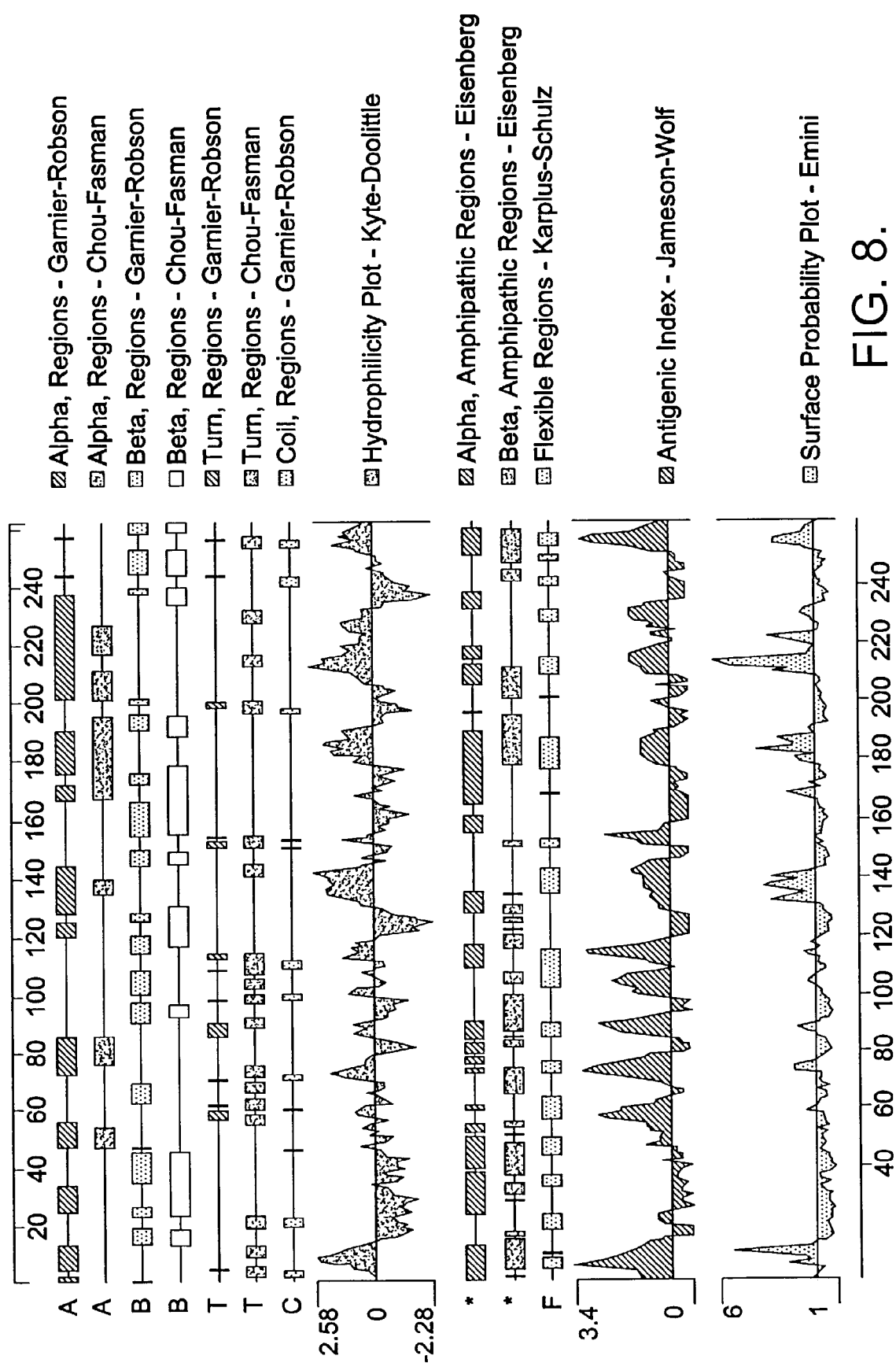
FIG. 8 shows an analysis of the 21620 ADH amino acid sequence: αβturn and coil regions; hydrophilicity; amphipathic regions; flexible regions; antigenic index; and surface probability plot.
Figure 9:
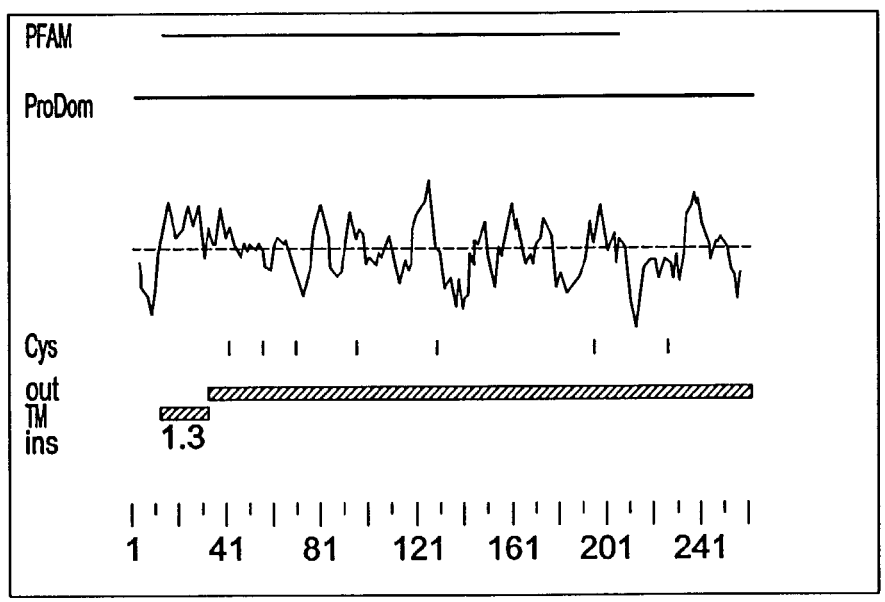
FIG. 9 shows a hydrophobicity plot of the 21620 ADH amino acid sequence (SEQ ID NO:5). Also shown is the predicted transmembrane segment from about amino acid 13 to about amino acid 32. In addition, a graphical representation of the functional domain of ADH short chain is also shown.

Adenylate kinases play a key role in the regulation of energy balance within cells, particularly maintenance of the ratio of ATP with its diphosphate (ADP) and monophosphate forms (AMP). ATP serves as the primary source of energy for biochemical reactions in cells and is also a key precursor in DNA and RNA synthesis during cellular growth and replication. The energy associated with the terminal phosphate bonds of ATP may be transferred to other nucleotides using a nucleoside monophosphate kinase such as adenlyate kinase. In this manner, the terminal energy-rich phosphate bonds of ATP may be transferred to the appropriate nucleotides for use in a variety of biosynthetic and energy-requiring processes, such as biosynthesis of macromolecules, active ion transport, muscle contraction, thermogenesis, etc. A number of these energy-requiring biosynthetic reactions hydrolyze ATP into AMP plus pyrophosphate. Reutilization of the resulting AMP requires conversion back into the triphosphate form following conversion to ADP. Various nucleotide monophosphate kinases carry out the first step of phosphorylating AMP to its diphosphate form at the expense of ATP. In the case of adenylate kinase, this reversible reaction is given as AMP+ATP⇌2 ADP.

Adenylate kinases also play a role in regulating the flow of carbon between net accumulation of glucose via the gluconeogenesis pathway and its subsequent catabolism via the glycolytic pathway by way of their control over the ratio of AMP to ATP. AMP is a positive allosteric effector of the enzyme 6-phophofructo-1-kinase, which shifts, and a negative allosteric effector for the enzyme fructose-1,6-bisphosphatase. When the first of these enzymes is activated, carbon flow is shifted in the direction of glycolysis; when the second of these enzymes is activated, carbon flow shifts in the direction of gluconeogenesis. Thus, increases in the ratio of AMP to ATP shift carbon flow toward glycolysis, while decreases in the ratio of AMP to ATP shift carbon flow toward glucose formation.

These enzymes have been studied in a number of mammals, including rat, porcine, chicken, bovine, rabbit, and humans. Evidence from biochemical studies suggests that human tissues have five adenylate kinase isozymes, AK1-AK5. Thus far the cDNAs of human AK1, AK2, AK4, and AK5 have been cloned. Adenylate kinase isoforms in humans are sequence related and also related to UMP/CMP kinases from several species. See Rompay et al. (1999) *Eur. J. Biochem.* 261:509-516, and the references cited therein.

The adenylate kinase isozymes AK1 (or myokinase), which is a cytosolic enzyme present in brain, skeletal muscle, and erythrocytes, and AK2, which is associated with the mitochondrial membrane in liver, spleen, heart, and kidney, both utilize ATP as their nucleoside triphosphate donor substrate. AK3 (or GTP:AMP phosphotransferase) is located in the mitochondrial matrix, primarily in heart and liver cells, and uses MgGTP instead of MgATP. AK4 and AK5 are both localized in brain tissue.

Several regions of AK family enzymes are well conserved, including the nucleoside triphosphate binding glycine-rich region, the nucleoside monophosphate binding site, and the lid domain that closes over the substrate upon binding (see Schulz (1987) *Cold Spring Harbor Symp. Quant. Biol.* 52:429-439).

These enzymes assist with maintenance of energy production and utilization within cells, particularly in cells having high rates of growth and metabolic activity such as in heart, skeletal muscle, and liver. In fact, adenylate kinase deficiency has been linked to hemolytic anemia and neurological disorders such as neurofibromatosis (Xu et al. (1992) *Genomics* 13:537-542. In addition, targeting regulation of ATP synthesis has been the basis of antiproliferative drugs for treatment of viral infections and cancer.

Adenylate kinases are also useful for activating nucleoside analogues used as pharmaceuticals, especially for cancer and viral infection. Most of these analogues must be phosphorylated to the triphosphate form in order to be pharmaceutically active. The first phosphorylation step in the activation of nucleoside analogs is catalyzed by deoxyribonucleoside kinases. Phosphorylation to the di- and triphosphates are then required.

Accordingly, adenylate kinases are a major target for drug action and development. Thus, it is valuable to the field of pharmaceutical development to identify and characterize previously unknown adenylate kinases. The present invention advances the state of the art by providing a previously unidentified human adenylate kinase.

SUMMARY OF THE INVENTION

Isolated nucleic acid molecules corresponding to adenylate kinase nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2 or the nucleotide sequences encoding the DNA sequence deposited in a bacterial host with the Patent Depository of the American Type Culture Collection (ATCC) as Patent Deposit Number PTA-1850. Further provided are adenylate kinase polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The adenylate kinase molecules of the present invention are useful for modulating cellular growth and/or cellular metabolic pathways particularly for regulating one or more proteins involved in growth and metabolism. Accordingly, in one aspect, this invention provides isolated nucleic acid molecules encoding adenylate kinase proteins or biologically active portions thereof, as well as nucleic acid fragments suitable as primers or hybridization probes for the detection of adenylate kinase-encoding nucleic acids.

Another aspect of this invention features isolated or recombinant adenylate kinase proteins and polypeptides. Preferred adenylate kinase proteins and polypeptides possess at least one biological activity possessed by naturally occurring adenylate kinase proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the adenylate kinase polypeptides and fragments are provided. Such antibodies are useful in detecting the adenylate kinase polypeptides as well as in regulating the T-cell immune response and cellular activity, particularly growth and proliferation.

In another aspect, the present invention provides a method for detecting the presence of adenylate kinase activity or expression in a biological sample by contacting the biological sample with an agent capable of detecting an indicator of adenylate kinase activity such that the presence of adenylate kinase activity is detected in the biological sample.

In yet another aspect, the invention provides a method for modulating adenylate kinase activity comprising contacting a cell with an agent that modulates (inhibits or stimulates) adenylate kinase activity or expression such that adenylate kinase activity or expression in the cell is modulated. In one embodiment, the agent is an antibody that specifically binds to adenylate kinase protein. In another embodiment, the agent modulates expression of adenylate kinase protein by modulating transcription of an adenylate kinase gene, splicing of an adenylate kinase mRNA, or translation of an adenylate kinase mRNA. In yet another embodiment, the agent is a nucleic acid molecule having a nucleotide sequence that is antisense to the coding strand of the adenylate kinase mRNA or the adenylate kinase gene.

In one embodiment, the methods of the present invention are used to treat a subject having a disorder characterized by aberrant adenylate kinase protein activity or nucleic acid expression by administering an agent that is an adenylate kinase modulator to the subject. In one embodiment, the adenylate kinase modulator is an adenylate kinase protein. In another embodiment, the adenylate kinase modulator is an adenylate kinase nucleic acid molecule. In other embodiments, the adenylate kinase modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding an adenylate kinase protein; (2) misregulation of a gene encoding an adenylate kinase protein; and (3) aberrant post-translational modification of an adenylate kinase protein, wherein a wild-type form of the gene encodes a protein with an adenylate kinase activity.

In another aspect, the invention provides a method for identifying a compound that binds to or modulates the activity of an adenylate kinase protein. In general, such methods entail measuring a biological activity of an adenylate kinase protein in the presence and absence of a test compound and identifying those compounds that alter the activity of the adenylate kinase protein.

The invention also features methods for identifying a compound that modulates the expression of adenylate kinase genes by measuring the expression of the adenylate kinase sequences in the presence and absence of the compound.

Other features and advantages of the invention will be apparent from the following detailed description and claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is based, at least in part, on the identification of novel molecules, referred to herein as adenylate kinase nucleic acid and polypeptide molecules, which play a role in, or function in, numerous biochemical pathways associated with cellular growth and/or cellular metabolic activity. These growth and metabolic pathways are described in Lodish et al. (1995) *Molecular Cell Biology* (Scientific American Books Inc., New York, N.Y.) and Devlin (1997) *Textbook of Biochemistry with Clinical Correlations* (Wiley-Liss, Inc., New York, N.Y.), the contents of which are incorporated herein by reference. In one embodiment, the adenylate kinase molecules modulate the activity of one or more proteins involved in cellular growth or differentiation, e.g., cardiac, epithelial, or neuronal cell growth or differentiation. In another embodiment, the adenylate kinase molecules of the present invention are capable of modulating the phosphorylation state of a nucleoside mono-, di-, or triphosphate molecule or the phosphorylation state of one or more proteins involved in cellular growth or differentiation, e.g., cardiac, epithelial, or neuronal cell growth or differentiation, as described in, for example, Lodish et al. (1995) and Devlin (1997), supra. In addition, the substrates of the adenylate kinases of the present invention are targets of drugs described in Goodman and Gilman (1996), *The Pharmacological Basis of Therapeutics* ($9^{th}$ ed.) Hartman & Limbard Editors, the contents of which are incorporated herein by reference. Particularly, the adenylate kinases of the invention may modulate phosphorylation activity in tissues and cells including lymph node, spleen, thymus, brain, lung, skeletal muscle, fetal liver, tonsil, colon, heart, liver, immune cells, including T cells, Th1 and Th2 cells, leukocytes, blood marrow, etc. In one embodiment, the adenylate kinase sequences of the invention are used to manipulate the nucleoside mono-, di-, and triphosphate pool to alter cellular metabolic pathways, such as glycolysis and gluconeogenesis.

Adenylate kinases play an important role in the regulation of energy balance within cells and in energy-requiring biochemical processes associated with cellular growth and development. Inhibition or over-stimulation of the activity of adenylate kinases affects the cellular equilibrium between nucleoside mono-, di-, and triphosphates, particularly AMP, ADP, and ATP, all of which are integrally involved in energy-requiring biochemical processes associated with cellular growth and development. Disruption or modulation of this equilibrium can lead to perturbed cellular growth, which can in turn lead to cellular growth related-disorders. As used herein, a "cellular growth-related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma. Disorders associated with the following cells or tissues are also encompassed: lymph node, spleen, thymus, brain, lung, skeletal muscle, fetal liver, tonsil, colon, heart, liver, immune cells, including T cells, Th1 and Th2 cells, leukocytes, blood marrow, etc. The compositions are also useful for the treatment of liver fibrosis and other liver-related disorders.

Furthermore, adenylate kinase activity increases in cerebrospinal fluid at the acute onset of ischemic brain damage and is correlated with the severity of the lesion (Buttner et al. (1986) *J. Neurol.* 233:297-303). Adenyl kinase activity also increases in cerebrous spinal fluid in some brain tumors (Ronquist et al. (1977) *Lancet i:* 1284-1286). Further, adenyl kinase may be expressed in damaged tissue and therefore is a useful target to measure tissue damage. Finally, deletions at 1p31 locus in many tumors is associated with hemolytic anemia (Matsuura et al. (1989) *J. Biol. Chem.* 264:10148-10155 and Mitelman et al. (1997) *Nature Genet.* 15:417-474). Accordingly, the compositions are also useful for treatment and diagnosis related to these disorders.

The disclosed invention relates to methods and compositions for the modulation, diagnosis, and treatment of immune, inflammatory, respiratory, and hematological disorders.

Immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

Respiratory disorders include, but are not limited to, apnea, asthma, particularly bronchial asthma, berillium disease, bronchiectasis, bronchitis, bronchopneumonia, cystic fibrosis, diphtheria, dyspnea, emphysema, chronic obstructive pulmonary disease, allergic bronchopulmonary aspergillosis, pneumonia, acute pulmonary edema, pertussis, pharyngitis, atelectasis, Wegener's granulomatosis, Legionnaires disease, pleurisy, rheumatic fever, and sinusitis.

Hematologic disorders include but are not limited to anemias including sickle cell and hemolytic anemia, hemophilias including types A and B, leukemias, thalassemias, spherocytosis, Von Willebrand disease, chronic granulomatous disease, glucose-6-phosphate dehydrogenase deficiency, thrombosis, clotting factor abnormalities and deficiencies including factor VM and IX deficiencies, hemarthrosis, hematemesis, hematomas, hematuria, hemochromatosis, hemoglobinuria, hemolytic-uremic syndrome, thrombocytopenias including HIV-associated thrombocytopenia, hemorrhagic telangiectasia, idiopathic thrombocytopenic purpura, thrombotic microangiopathy, hemosiderosis.

Liver disorders include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, including, but not limited to, infectious hepatitis, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; other forms of hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including hepatocellular carcinoma, primary carcinoma of the liver and metastatic tumors.

Preferred disorders include, but are not limited to hepatitis, and especially viral hepatitis and hepatocellular carcinoma.

The disclosed invention also relates to methods and compositions for the modulation, diagnosis, and treatment of disorders involving the brain, heart, lung, colon, and spleen.

Disorders involving the brain include, but are limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyclitis and acute necrotizing hemorrhagic encephalomyclitis, and other diseases with demyclination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart include, but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders of the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving the skeletal muscle include tumors such as rhabdomyosarcoma.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

In normal bone marrow, the myelocytic series (polymorphoneuclear cells) make up approximately 60% of the cellular elements, and the erythrocytic series, 20-30%. Lymphocytes, monocytes, reticular cells, plasma cells and megakaryocytes together constitute 10-20%. Lymphocytes make up 5-15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2-8) of *Immunology, Immunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angioimmunoblastic T-cell lymphoma, angiocentric lymphoma (NK/T-cell lymphoma[4a]), intestinal T-cell lymphoma, adult T-cell leukemia/lymphoma, and anaplastic large cell lymphoma.

Specifically, the present invention provides isolated nucleic acid molecules comprising nucleotide sequences encoding the adenylate kinase polypeptide whose amino acid sequence is given in SEQ ID NO:2, or a variant or fragment of the polypeptides. A nucleotide sequence encoding an adenylate kinase polypeptide of the invention, more particularly the polypeptide of SEQ ID NO:2, is set forth in SEQ ID NO:1.

A novel human gene, termed clone h23552 is provided. This sequence, and complements thereof, are referred to as "adenylate kinase" indicating that the gene sequences share sequence similarity to adenylate kinase genes.

The novel h23552 adenylate kinase gene encodes an approximately 1.43 Kb mRNA transcript having the corresponding cDNA set forth in SEQ ID NO:1. This transcript has a 634 nucleotide open reading frame (nucleotides 200-883 of SEQ ID NO:1), which encodes a 228 amino acid protein (SEQ ID NO:2). An analysis of the full-length h23552 polypeptide predicts that the N-terminal 47 amino acids may represent a region comprising a signal peptide. Prosite program analysis was used to predict various sites within the h23552 protein. An N-glycosylation site was predicted at aa 137-140. Protein kinase C phosphorylation sites were predicted at aa 21-23, 29-31, 170-172, and 190-192. Casein kinase II phosphorylation sites were predicted at aa 65-68 and 212-215. Tyrosine kinase phosphorylation sites were predicted at aa 54-61 and 74-81. N-myristoylation sites were predicted at aa 42-47 and 49-54. An adenylate kinase signature sequence was predicted at aa 121-132.

The h23552 adenylate kinase protein possesses an adenylate kinase domain sequence, from aa 40-203, as predicted by HMMer, Version 2. This region of the protein comprises the three functional subdomains common to nucleoside monophosphate kinases: the nucleoside triphosphate binding glycine-rich region, the nucleoside monophosphate binding site, and the lid domain that closes over the substrate upon binding (see Schulz (1987) *Cold Spring Harbor Symp. Quant. Biol.* 52:429-439).

The h23552 protein displays closest similarity to the porcine UMP-CMP kinase (SP Accession Number Q29561; SEQ ID NO:3), approximately 97.4% identity when aa 33-228 are aligned over the full-length sequence for the porcine kinase (see FIG. 1) The N-terminal region of the h23552 protein (aa 1-32) is novel. Alignment of the h23552 protein with the porcine UMP-CMP kinase indicates that the glycine-rich region corresponding to the binding site of the nucleoside triphosphate donor resides at approximately amino acid residues 42-50 of the h23552 protein. The region corresponding to the nucleoside monophosphate binding site resides at approximately amino acid residues 65-95; and the region corresponding to the lid domain resides at approximately amino acid residues 166-175. The similarity of the novel h23552 protein to the porcine UMP-CMP kinase indicates the h23552 adenylate kinase is a member of the subclass of nucleoside monophosphate kinases referred to as "short enzymes". Members of this subclass, which are characterized by their short-length lid domain, include adenylate kinase 1 (AK1, identified in rabbit, bovine, human, pig, and chicken), adenylate kinase 5 (AK5 identified in human), and UMP-CMP kinases (identified in porcine, *Dictyostelium discoideum, Saccharomyces cereviseae*). See Rompay et al. (1999) *Eur. J. Biochem.* 261:509-516 and Fukami-Kobayashi et al. (1996) *FEBS Lett.* 385:214-220.

A plasmid containing the h23552 cDNA insert was deposited with the Patent Depository of the American Type Culture Collection (ATCC), 10801 University Boulevard, Manassas, Va., on May 29, 2000, and assigned Patent Deposit Number PTA 1850. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

The adenylate kinase sequences of the invention are members of a family of molecules having conserved functional features. The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homologue of that protein of human origin, as well as a second, distinct protein of human origin and a murine homologue of that protein. Members of a family may also have common functional characteristics.

Preferred adenylate kinase polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to adenylate kinase nucleic acid molecules of the invention. BLAST protein searches can be performed with the XBLAST program, score=50, wordlength=3 to obtain amino acid sequences homologous to adenylate kinase protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to adenylate kinase nucleic acid molecules of the invention. BLAST protein searches can be performed with the XBLAST program, score=50, wordlength=3 to obtain amino acid sequences homologous to adenylate kinase protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See www.ncbi.nlm.nih.gov.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.,* 10:3-5; and FASTA described in Pearson and Lipman (1988) *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see bioweb.pasteur.fr/docs/man/man/fasta.1.html#sect2, the contents of which are incorporated herein by reference.

The percent identity between two sequences can be determined using techniques similar to those described above, with or without allowing gaps. In calculating percent identity, typically exact matches are counted.

Accordingly, another embodiment of the invention features isolated adenylate kinase proteins and polypeptides having an adenylate kinase protein activity. As used interchangeably herein, a "adenylate kinase protein activity", "biological activity of an adenylate kinase protein", or "functional activity of an adenylate kinase protein" refers to an activity exerted by an adenylate kinase protein, polypeptide, or nucleic acid molecule on an adenylate kinase responsive cell as determined in vivo, or in vitro, according to standard assay techniques. An adenylate kinase activity can be a direct activity, such as an association with or an enzymatic activity on a second protein, or an indirect activity, such as a cellular activity mediated by interaction of the adenylate kinase protein with a second protein. In a preferred embodiment, an adenylate kinase activity includes at least one or more of the following activities: (1) modulating (stimulating and/or enhancing or inhibiting) cellular proliferation, differentiation, and/or function, particularly in cells in which the sequences are expressed, for example, cells of the lymph node, spleen, thymus, brain, lung, skeletal muscle, fetal liver, tonsil, colon, heart, liver, and immune cells, including Th1,Th2, T cells, natural killer T cells, lymphocytes, leukocytes, blood marrow, etc.); (2) modulating a target cell's energy balance, particularly the ratio between AMP and ATP; (3) modulating the glycolytic pathway; (4) modulating the gluconeogenesis pathway; (4) modulating cell growth; (5) modulating the entry of cells into mitosis; (6) modulating cellular differentiation; (7) modulating cell death; and (8) modulating an immune response.

An "isolated" or "purified" adenylate kinase nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated adenylate kinase nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An adenylate kinase protein that is substantially free of cellular material includes preparations of adenylate kinase protein having less than about 30%, 20%, 10%, or 5% (by dry weight) of non-adenylate kinase protein (also referred to herein as a "contaminating protein"). When the adenylate kinase protein or biologically active portion thereof is recombinantly produced, preferably, culture medium represents less than about 30%, 20%, 10%, or 5% of the volume of the protein preparation. When adenylate kinase protein is produced by chemical synthesis, preferably the protein preparations have less than about 30%, 20%, 10%, or 5% (by dry weight) of chemical precursors or non-adenylate kinase chemicals.

Various aspects of the invention are described in further detail in the following subsections.

I. Isolated Nucleic Acid Molecules

One aspect of the invention pertains to isolated nucleic acid molecules comprising nucleotide sequences encoding adenylate kinase proteins and polypeptides or biologically active portions thereof, as well as nucleic acid molecules sufficient for use as hybridization probes to identify adenylate kinase-encoding nucleic acids (e.g., adenylate kinase mRNA) and fragments for use as PCR primers for the amplification or mutation of adenylate kinase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the adenylate kinase proteins of the present invention include sequences set forth in SEQ ID NO:1, the nucleotide sequence of the cDNA insert of the plasmid deposited with the ATCC as Patent Deposit Number PTA-1850 (the "cDNA of Patent Deposit Number PTA-1850"), and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the adenylate kinase protein encoded by these nucleotide sequences is set forth in SEQ ID NO:2.

Nucleic acid molecules that are fragments of these adenylate kinase nucleotide sequences are also encompassed by the present invention. By "fragment" is intended a portion of the nucleotide sequence encoding an adenylate kinase protein. A fragment of an adenylate kinase nucleotide sequence may encode a biologically active portion of an adenylate kinase protein, or it may be a fragment that can be used as a hybridization probe or PCR primer using methods disclosed below. A biologically active portion of an adenylate kinase protein can be prepared by isolating a portion of one of the adenylate kinase nucleotide sequences of the invention, expressing the encoded portion of the adenylate kinase protein (e.g., by recombinant expression in vitro), and assessing the activity of the encoded portion of the adenylate kinase protein. Nucleic acid molecules that are fragments of an adenylate kinase nucleotide sequence comprise at least 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400 nucleotides, or up to the number of nucleotides present in a full-length adenylate kinase nucleotide sequence disclosed herein (for example, 1434 nucleotides for SEQ ID NO:1) depending upon the intended use.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

For example, when considering the full-length, 1434 nucleotide transcript set forth in SEQ ID NO:1, the nucleotide sequence from about nucleotide (nt) 1 to about nt 200 encompasses isolated fragments greater than about 13, 15, or 20 nucleotides; the nucleotide sequence from about nt 200 to about nt 1034 encompasses isolated fragments greater than about 102, 105, or 110 nucleotides; the nucleotide sequence from about nt 1034 to about nt 1434 encompasses isolated fragments greater than about 24, 25, or 28 nucleotides. The nucleotide sequence corresponding to the open reading frame (nt 200-883 of SEQ ID NO:1) encompasses isolated fragments greater than about 102, 105, or 110 nucleotides.

A fragment of an adenylate kinase nucleotide sequence that encodes a biologically active portion of an adenylate kinase protein of the invention will encode at least 15, 25, 30, 50, 75, 100, 125, 150, 175, 200, or 225 contiguous amino acids, or up to the total number of amino acids present in a full-length adenylate kinase protein of the invention (for example, 228 amino acids for SEQ ID NO:2). Fragments of an adenylate kinase nucleotide sequence that are useful as hybridization probes for PCR primers generally need not encode a biologically active portion of an adenylate kinase protein.

Nucleic acid molecules that are variants of the adenylate kinase nucleotide sequences disclosed herein are also encompassed by the present invention. "Variants" of the adenylate kinase nucleotide sequences include those sequences that encode the adenylate kinase proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the adenylate kinase proteins disclosed in the present invention as discussed below. Generally, nucleotide sequence variants of the invention will have at least 45%, 55%, 65%, 75%, 85%, 95%, or 98% identity to a particular nucleotide sequence disclosed herein. A variant adenylate kinase nucleotide sequence will encode an adenylate kinase protein that has an amino acid sequence having at least 45%, 55%, 65%, 75%, 85%, 95%, or 98% identity to the amino acid sequence of an adenylate kinase protein disclosed herein.

In addition to the adenylate kinase nucleotide sequences shown in SEQ ID NOs:1 and 3, and the nucleotide sequence of the cDNA of Patent Deposit Number PTA-1850, it will be appreciated by those skilled in the art that DNA sequence polymorphisms that lead to changes in the amino acid sequences of adenylate kinase proteins may exist within a population (e.g., the human population). Such genetic polymorphism in an adenylate kinase gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding an adenylate kinase protein, preferably a mammalian adenylate kinase protein. As used herein, the phrase "allelic variant" refers to a nucleotide sequence that occurs at an adenylate kinase locus or to a polypeptide encoded by the nucleotide sequence. Such natural allelic variations can typically result in 1-5% variance in the nucleotide sequence of the adenylate kinase gene. Any and all such nucleotide variations and resulting amino acid polymorphisms or variations in an adenylate kinase sequence that are the result of natural allelic variation and that do not alter the functional activity of adenylate kinase proteins are intended to be within the scope of the invention.

Moreover, nucleic acid molecules encoding adenylate kinase proteins from other species (adenylate kinase homologues), which have a nucleotide sequence differing from that of the adenylate kinase sequences disclosed herein, are intended to be within the scope of the invention. For example, nucleic acid molecules corresponding to natural allelic variants and homologues of the human adenylate kinase cDNA of the invention can be isolated based on their identity to the human adenylate kinase nucleic acid disclosed herein using the human cDNA, or a portion thereof, as a hybridization probe according to standard hybridization techniques under stringent hybridization conditions as disclosed below.

In addition to naturally-occurring allelic variants of the adenylate kinase sequences that may exist in the population, the skilled artisan will further appreciate that changes can be introduced by mutation into the nucleotide sequences of the invention thereby leading to changes in the amino acid sequence of the encoded adenylate kinase proteins, without altering the biological activity of the adenylate kinase proteins. Thus, an isolated nucleic acid molecule encoding an adenylate kinase protein having a sequence that differs from that of SEQ ID NO:2 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of an adenylate kinase protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the adenylate kinase domain sequence of SEQ ID NO:2 (amino acid residues 40-203), where such residues are essential for protein activity.

Alternatively, variant adenylate kinase nucleotide sequences can be made by introducing mutations randomly along all or part of an adenylate kinase coding sequence, such as by saturation mutagenesis, and the resultant mutants can be screened for adenylate kinase biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The adenylate kinase nucleotide sequences of the invention, and fragments and variants thereof, can be used as probes and/or primers to identify and/or clone adenylate kinase homologues in other cell types, e.g., from other tissues, as well as adenylate kinase homologues from other mammals. Such probes can be used to detect transcripts or genomic sequences encoding the same or identical proteins. These probes can be used as part of a diagnostic test kit for identifying cells or tissues that misexpress an adenylate kinase protein, such as by measuring levels of an adenylate kinase-encoding nucleic acid in a sample of cells from a subject, e.g., detecting adenylate kinase mRNA levels or determining whether a genomic adenylate kinase gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Adenylate kinase nucleotide sequences isolated based on their sequence identity to the adenylate kinase nucleotide sequences set forth herein or to fragments and variants thereof are encompassed by the present invention.

In a hybridization method, all or part of a known adenylate kinase nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known adenylate kinase nucleotide sequence disclosed herein. Degenerate primers designed on the basis of conserved nucleotides or amino acid residues in a known adenylate kinase nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of an adenylate kinase nucleotide sequence of the invention or a fragment or variant thereof. Preparation of Probes for Hybridization is Generally Known in the Art and is Disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified adenylate kinase nucleic acid molecule hybridizes under stringent conditions to a probe that is a nucleic acid molecule comprising one of the adenylate kinase nucleotide sequences of the invention or a fragment thereof. In another embodiment, the previously unknown adenylate kinase nucleic acid molecule is at least 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the adenylate kinase nucleotide sequences disclosed herein or a fragment thereof.

Accordingly, in another embodiment, an isolated previously unknown adenylate kinase nucleic acid molecule of the invention is at least 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:1, the cDNA of Patent Deposit Number PTA-1850, or a complement, fragment, or variant thereof.

As used herein, the term "hybridizes under stringent conditions" is intended to describe conditions for hybridization and washing under which nucleotide sequences having at least 60%, 65%, 70%, preferably 75% identity to each other typically remain hybridized to each other. Such stringent conditions are known to those skilled in the art and can be found in *Current Protocols in Molecular Biology* (John Wiley & Sons, New York (1989)), 6.3.1-6.3.6. A preferred, non-limiting example of stringent hybridization conditions is hybridization in 6× sodium chloride/sodium citrate (SSC) at about 45° C., followed by one or more washes in 0.2×SSC, 0.1% SDS at 50-65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to an adenylate kinase sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the adenylate kinase nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the adenylate kinase nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire adenylate kinase coding strand, or to only a portion thereof, e.g., all or part of the protein coding region (or open reading frame). An antisense nucleic acid molecule can be antisense to a noncoding region of the coding strand of a nucleotide sequence encoding an adenylate kinase protein. The noncoding regions are the 5' and 3' sequences that flank the coding region and are not translated into amino acids.

Given the coding-strand sequence encoding an adenylate kinase protein disclosed herein (e.g., SEQ ID NO:1), antisense nucleic acids of the invention can be designed according to the rules of Watson and Crick base pairing. The antisense nucleic acid molecule can be complementary to the entire coding region of adenylate kinase mRNA, but more preferably is an oligonucleotide that is antisense to only a portion of the coding or noncoding region of adenylate kinase mRNA. For example, the antisense oligonucleotide can be complementary to the region surrounding the translation start site of adenylate kinase mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an adenylate kinase protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585-591)) can be used to catalytically cleave adenylate kinase mRNA transcripts to thereby inhibit translation of adenylate kinase mRNA. A ribozyme having specificity for an adenylate kinase-encoding nucleic acid can be designed based upon the nucleotide sequence of an adenylate kinase cDNA disclosed herein (e.g., SEQ ID NO:1). See, e.g., Cech et al., U.S. Pat. No. 4,987,071; and Cech et al., U.S. Pat. No. 5,116,742. Alternatively, adenylate kinase mRNA can be used to select a catalytic RNA having a specific ribonuclease activity from a pool of RNA molecules. See, e.g., Bartel and Szostak (1993) *Science* 261:1411-1418.

The invention also encompasses nucleic acid molecules that form triple helical structures. For example, adenylate kinase gene expression can be inhibited by targeting nucleotide sequences complementary to the regulatory region of the adenylate kinase protein (e.g., the adenylate kinase promoter and/or enhancers) to form triple helical structures that prevent transcription of the adenylate kinase gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of an adenylate kinase molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of an adenylate kinase molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357-63; Mag et al. (1989) *Nucleic Acids Res.* 17:5973; and Peterson et al. (1975) *Bioorganic Med. Chem. Lett.* 5:1119.

II. Isolated Adenylate Kinase Proteins and Anti-adenylate Kinase Antibodies

Adenylate kinase proteins are also encompassed within the present invention. By "adenylate kinase protein" is intended a protein having the amino acid sequence set forth in SEQ ID NO:2, as well as fragments, biologically active portions, and variants thereof.

"Fragments" or "biologically active portions" include polypeptide fragments suitable for use as immunogens to raise anti-adenylate kinase antibodies. Fragments include peptides comprising amino acid sequences sufficiently identical to or derived from the amino acid sequence of an adenylate kinase protein of the invention and exhibiting at least one activity of an adenylate kinase protein, but which include fewer amino acids than the full-length (SEQ ID NO:2) adenylate kinase protein disclosed herein. Typically, biologically active portions comprise a domain or motif with at least one activity of the adenylate kinase protein. A biologically active portion of an adenylate kinase protein can be a polypeptide that is, for example, 10, 25, 50, 100 or more amino acids in length. Such biologically active portions can be prepared by recombinant techniques and evaluated for one or more of the functional activities of a native adenylate kinase protein. As used here, a fragment comprises at least 5 contiguous amino acids of SEQ ID NO:2. The invention encompasses other fragments, however, such as any fragment in the protein greater than 6, 7, 8, or 9 amino acids, depending upon the intended use.

By "variants" is intended proteins or polypeptides having an amino acid sequence that is at least about 45%, 55%, 65%, preferably about 75%, 85%, 95%, or 98% identical to the amino acid sequence of SEQ ID NO:2. Variants also include polypeptides encoded by the cDNA insert of the plasmid deposited with ATCC as Patent Deposit Number PTA-1850, or polypeptides encoded by a nucleic acid molecule that hybridizes to the nucleic acid molecule of SEQ ID NO:1, or a complement thereof, under stringent conditions. Such variants generally retain the functional activity of the adenylate kinase proteins of the invention. Variants include polypeptides that differ in amino acid sequence due to natural allelic variation or mutagenesis.

The invention also provides adenylate kinase chimeric or fusion proteins. As used herein, an adenylate kinase "chimeric protein" or "fusion protein" comprises an adenylate kinase polypeptide operably linked to a non-adenylate kinase polypeptide. A "adenylate kinase polypeptide" refers to a polypeptide having an amino acid sequence corresponding to an adenylate kinase protein, whereas a "non-adenylate kinase polypeptide" refers to a polypeptide having an amino acid sequence corresponding to a protein that is not substantially identical to the adenylate kinase protein, e.g., a protein that is different from the adenylate kinase protein and which is derived from the same or a different organism. Within an adenylate kinase fusion protein, the adenylate kinase polypeptide can correspond to all or a portion of an adenylate kinase protein, preferably at least one biologically active portion of an adenylate kinase protein. Within the fusion protein, the term "operably linked" is intended to indicate that the adenylate kinase polypeptide and the non-adenylate kinase polypeptide are fused in-frame to each other. The non-adenylate kinase polypeptide can be fused to the N-terminus or C-terminus of the adenylate kinase polypeptide.

One useful fusion protein is a GST-adenylate kinase fusion protein in which the adenylate kinase sequences are fused to the C-terminus of the GST sequences. Such fusion proteins can facilitate the purification of recombinant adenylate kinase proteins.

In yet another embodiment, the fusion protein is an adenylate kinase-immunoglobulin fusion protein in which all or part of an adenylate kinase protein is fused to sequences derived from a member of the immunoglobulin protein family. The adenylate kinase-immunoglobulin fusion proteins of the invention can be incorporated into pharmaceutical compositions and administered to a subject to inhibit an interaction between an adenylate kinase ligand and an adenylate kinase protein on the surface of a cell, thereby suppressing adenylate kinase-mediated signal transduction in vivo. The adenylate kinase-immunoglobulin fusion proteins can be used to affect the bioavailability of an adenylate kinase cognate ligand. Inhibition of the adenylate kinase ligand/adenylate kinase interaction may be useful therapeutically, both for treating proliferative and differentiative disorders and for modulating (e.g., promoting or inhibiting) cell survival. Moreover, the adenylate kinase-immunoglobulin fusion proteins of the invention can be used as immunogens to produce anti-adenylate kinase antibodies in a subject, to purify adenylate kinase ligands, and in screening assays to identify molecules that inhibit the interaction of an adenylate kinase protein with an adenylate kinase ligand.

Preferably, an adenylate kinase chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, an adenylate kinase-encoding nucleic acid can be cloned into a commercially available expression vector such that it is linked in-frame to an existing fusion moiety.

Variants of the adenylate kinase proteins can function as either adenylate kinase agonists (mimetics) or as adenylate kinase antagonists. Variants of the adenylate kinase protein can be generated by mutagenesis, e.g., discrete point mutation or truncation of the adenylate kinase protein. An agonist of the adenylate kinase protein can retain substantially the same, or a subset, of the biological activities of the naturally occurring form of the adenylate kinase protein. An antagonist of the adenylate kinase protein can inhibit one or more of the activities of the naturally occurring form of the adenylate kinase protein by, for example, competitively binding to a downstream or upstream member of a cellular signaling cascade that includes the adenylate kinase protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the adenylate kinase proteins.

Variants of an adenylate kinase protein that function as either adenylate kinase agonists or as adenylate kinase antagonists can be identified by screening combinatorial libraries of mutants, e.g., truncation mutants, of an adenylate kinase protein for adenylate kinase protein agonist or antagonist activity. In one embodiment, a variegated library of adenylate kinase variants is generated by combinatorial mutagenesis at the nucleic acid level and is encoded by a variegated gene library. A variegated library of adenylate kinase variants can be produced by, for example, enzymatically ligating a mixture of synthetic oligonucleotides into gene sequences such that a degenerate set of potential adenylate kinase sequences is expressible as individual polypeptides, or alternatively, as a set of larger fusion proteins (e.g., for phage display) containing the set of adenylate kinase sequences therein. There are a variety of methods that can be used to produce libraries of potential adenylate kinase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential adenylate kinase sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of an adenylate kinase protein coding sequence can be used to generate a variegated population of adenylate kinase fragments for screening and subsequent selection of variants of an adenylate kinase protein. In one embodiment, a library of coding sequence fragments can be generated by treating a double-stranded PCR fragment of an adenylate kinase coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the adenylate kinase protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of adenylate kinase proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify adenylate kinase variants (Arkin and Yourvan (1992) *Proc. Natl. Acad. Sci. USA* 89:7811-7815; Delgrave et al. (1993) *Protein Engineering* 6(3):327-331).

An isolated adenylate kinase polypeptide of the invention can be used as an immunogen to generate antibodies that bind adenylate kinase proteins using standard techniques for polyclonal and monoclonal antibody preparation. The full-length adenylate kinase protein can be used or, alternatively, the invention provides antigenic peptide fragments of adenylate kinase proteins for use as immunogens. The antigenic peptide of an adenylate kinase protein comprises at least 8, preferably 10, 15, 20, or 30 amino acid residues of the amino acid sequence shown in SEQ ID NO:2 and encompasses an epitope of an adenylate kinase protein such that an antibody raised against the peptide forms a specific immune complex with the adenylate kinase protein. Preferred epitopes encompassed by the antigenic peptide are regions of a adenylate kinase protein that are located on the surface of the protein, e.g., hydrophilic regions.

Accordingly, another aspect of the invention pertains to anti-adenylate kinase polyclonal and monoclonal antibodies that bind an adenylate kinase protein. Polyclonal anti-adenylate kinase antibodies can be prepared by immunizing a suitable subject (e.g., rabbit, goat, mouse, or other mammal) with an adenylate kinase immunogen. The anti-adenylate kinase antibody titer in the immunized subject can be monitored over time by standard techniques, such as with an enzyme linked immunosorbent assay (ELISA) using immobilized adenylate kinase protein. At an appropriate time after immunization, e.g., when the anti-adenylate kinase antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.);

Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387-402).

Alternative to preparing monoclonal antibody-secreting hybridomas, a monoclonal anti-adenylate kinase antibody can be identified and isolated by screening a recombinant combinatorial immunoglobulin library (e.g., an antibody phage display library) with an adenylate kinase protein to thereby isolate immunoglobulin library members that bind the adenylate kinase protein. Kits for generating and screening phage display libraries are commercially available (e.g., the Pharmacia *Recombinant Phage Antibody System*, Catalog No. 27-9400-01; and the Stratagene *SurfZAP Θ Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant anti-adenylate kinase antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171, 496, 125,023, and 173,494; U.S. Pat. Nos. 4,816,567 and 5,225,539; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *Bio/Techniques* 4:214; Jones et al. (1986) *Nature* 321:552-525; Verhoeyan et al. (1988) *Science* 239:1534; and Beidler et al. (1988) *J. Immunol.* 141:4053-4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65-93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899-903).

An anti-adenylate kinase antibody (e.g., monoclonal antibody) can be used to isolate adenylate kinase proteins by standard techniques, such as affinity chromatography or immunoprecipitation. An anti-adenylate kinase antibody can facilitate the purification of natural adenylate kinase protein from cells and of recombinantly produced adenylate kinase protein expressed in host cells. Moreover, an anti-adenylate kinase antibody can be used to detect adenylate kinase protein (e.g., in a cellular lysate or cell supernatant) in order to evaluate the abundance and pattern of expression of the adenylate kinase protein. Anti-adenylate kinase antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al. (1985) "Monoclonal Antibodies for Immunotargeting of Drugs in Cancer Therapy," in *Monoclonal Antibodies And Cancer Therapy*, ed. Reisfeld et al. (Alan R. Liss, Inc.), pp. 243-56); Hellstrom et al. (1987) "Antibodies for Drug Delivery," in *Controlled Drug Delivery*, ed. Robinson et al. (2d ed., Marcel Dekker, Inc.), pp. 623-53; Thorpe (1985) "Antibody Carriers of Cytotoxic Agents in Cancer Therapy: A Review", in *Monoclonal Antibodies '84:Biological And Clinical Applications*, ed. Pinchera et al., pp. 475-506; "Analysis, Results, and Future Prospective of the Therapeutic Use of Radiolabeled Antibody in Cancer Therapy," in *Monoclonal Antibodies For Cancer Detection And Therapy*, ed. Baldwin et al. (Academic Press, NY), pp. 303-316; and Thorpe et al. (1982) *Immunol. Rev.* 62:119-58. Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding an adenylate kinase protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., adenylate kinase proteins, mutant forms of adenylate kinase proteins, fusion proteins, etc.).

The recombinant expression vectors of the invention can be designed for expression of adenylate kinase protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31-40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301-315) and pET 11d (Studier et al. (1990) in *Gene Expression Technology: Methods in Enzymology* 185 (Academic Press, San Diego, Calif.), pp. 60-89). Strategies to maximize recombinant protein expression in *E. coli* can be found in Gottesman (1990) in *Gene Expression Technology: Methods in Enzymology* 185 (Academic Press, CA), pp. 119-128 and Wada et al. (1992) *Nucleic Acids Res.* 20:2111-2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow and Summers (1989) *Virology* 170:31-39)); yeast cells (examples of vectors for expression in yeast *S. cereivisiae* include pYepSec1 (Baldari et al. (1987) *EMBO J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Patent Publication No. 264,166). Developmentally-regulated promoters are also encompassed, for example the murine hox promoters (Kessel and Gruss (1990) *Science* 249:374-379), the α-fetoprotein promoter (Campes and Tilghman (1989) *Genes Dev.* 3:537-546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to adenylate kinase mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding an adenylate kinase protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) adenylate kinase protein. Accordingly, the invention further provides methods for producing adenylate kinase protein using the host cells of the invention. In one embodiment, the method comprises culturing the host cell of the invention, into which a recombinant expression vector encoding an adenylate kinase protein has been introduced, in a suitable medium such that adenylate kinase protein is produced. In another embodiment, the method further comprises isolating adenylate kinase protein from the medium or the host cell.

The host cells of the invention can also be used to produce nonhuman transgenic animals. In general, methods for producing transgenic animals include introducing a nucleic acid sequence according to the present invention, the nucleic acid sequence capable of expressing the receptor protein in a transgenic animal, into a cell in culture or in vivo. When introduced in vivo, the nucleic acid is introduced into an intact organism such that one or more cell types and, accordingly, one or more tissue types, express the nucleic acid encoding the receptor protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

For example, in one embodiment, a host cell of the invention is a fertilized oocyte or an embryonic stem cell into which adenylate kinase-coding sequences have been introduced. Such host cells can then be used to create nonhuman transgenic animals in which exogenous adenylate kinase sequences have been introduced into their genome or homologous recombinant animals in which endogenous adenylate kinase sequences have been altered. Such animals are useful for studying the function and/or activity of adenylate kinase genes and proteins and for identifying and/or evaluating modulators of adenylate kinase activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous adenylate kinase gene has been altered by homologous recombination between the endogenous gene and an exogenous DNA molecule introduced into a cell of the animal, e.g., an embryonic cell of the animal, prior to development of the animal.

A transgenic animal of the invention can be created by introducing adenylate kinase-encoding nucleic acid into the male pronuclei of a fertilized oocyte, e.g., by microinjection, retroviral infection, and allowing the oocyte to develop in a pseudopregnant female foster animal. The adenylate kinase cDNA sequence can be introduced as a transgene into the genome of a nonhuman animal. Alternatively, a homologue of the mouse adenylate kinase gene can be isolated based on hybridization and used as a transgene. Intronic sequences and polyadenylation signals can also be included in the transgene to increase the efficiency of expression of the transgene. A tissue-specific regulatory sequence(s) can be operably linked to the adenylate kinase transgene to direct expression of adenylate kinase protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the adenylate kinase transgene in its genome and/or expression of adenylate kinase mRNA in tissues or cells of the animals. A transgenic founder animal can then be used to breed additional animals carrying the transgene. Moreover, transgenic animals carrying a transgene encoding adenylate kinase gene can further be bred to other transgenic animals carrying other transgenes.

To create a homologous recombinant animal, one prepares a vector containing at least a portion of an adenylate kinase gene or a homolog of the gene into which a deletion, addition, or substitution has been introduced to thereby alter, e.g., functionally disrupt, the adenylate kinase gene. In a preferred embodiment, the vector is designed such that, upon homologous recombination, the endogenous adenylate kinase gene is functionally disrupted (i.e., no longer encodes a functional protein; also referred to as a "knock out" vector). Alternatively, the vector can be designed such that, upon homologous recombination, the endogenous adenylate kinase gene is mutated or otherwise altered but still encodes functional protein (e.g., the upstream regulatory region can be altered to thereby alter the expression of the endogenous adenylate kinase protein). In the homologous recombination vector, the altered portion of the adenylate kinase gene is flanked at its 5N and 3N ends by additional nucleic acid of the adenylate kinase gene to allow for homologous recombination to occur between the exogenous adenylate kinase gene carried by the vector and an endogenous adenylate kinase gene in an embryonic stem cell. The additional flanking adenylate kinase nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced adenylate kinase gene has homologously recombined with the endogenous adenylate kinase gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford), pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810-813 and PCT Publication Nos. WO 97/07668 and WO 97/07669.

IV. Pharmaceutical Compositions

The adenylate kinase nucleic acid molecules, adenylate kinase proteins, and anti-adenylate kinase antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents that modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL® (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., an adenylate kinase protein or anti-adenylate kinase antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403-410) and BLAZE (Brutlag et al. (1993) *Comp. Chem.* 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express adenylate kinase protein (e.g., via a recombinant expression vector in a host cell in gene therapy applications), to detect adenylate kinase mRNA (e.g., in a biological sample) or a genetic lesion in an adenylate kinase gene, and to modulate adenylate kinase activity. In addition, the adenylate kinase proteins can be used to screen drugs or compounds that modulate the immune response as well as to treat disorders characterized by insufficient or excessive production of adenylate kinase protein or production of adenylate kinase protein forms that have decreased or aberrant activity compared to adenylate kinase wild type protein. In addition, the anti-adenylate kinase antibodies of the invention can be used to detect and isolate adenylate kinase proteins and modulate adenylate kinase activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to adenylate kinase proteins or have a stimulatory or inhibitory effect on, for example, adenylate kinase expression or adenylate kinase activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. Nos. 5,571,698; 5,403,484; and 5,223, 409), plasmids (Cull et al. (1992) *Proc. Natl. Acad. Sci. USA* 89:1865-1869), or phage (Scott and Smith (1990) *Science* 249:386-390; Devlin (1990) *Science* 249:404-406; Cwirla et al. (1990) *Proc. Natl. Acad. Sci. USA* 87:6378-6382; and Felici (1991) *J. Mol. Biol.* 222:301-310).

Determining the ability of the test compound to bind to the adenylate kinase protein can be accomplished, for example, by coupling the test compound with a radioisotope or enzymatic label such that binding of the test compound to the adenylate kinase protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the adenylate kinase protein to bind to or interact with an adenylate kinase target molecule. By "target molecule" is intended a molecule with which an adenylate kinase protein binds or interacts in nature. In a preferred embodiment, the ability of the adenylate kinase protein to bind to or interact with an adenylate kinase target molecule can be determined by monitoring the activity of the target molecule. For example, the activity of the target molecule can be monitored by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., an adenylate kinase-responsive regulatory element operably linked to a nucleic acid encoding a detectable marker, e.g. luciferase), or detecting a cellular response, for example, cellular differentiation or cell proliferation.

In yet another embodiment, an assay of the present invention is a cell-free assay comprising contacting an adenylate kinase protein or biologically active portion thereof with a test compound and determining the ability of the test compound to bind to the adenylate kinase protein or biologically active portion thereof. Binding of the test compound to the adenylate kinase protein can be determined either directly or indirectly as described above. In a preferred embodiment, the assay includes contacting the adenylate kinase protein or biologically active portion thereof with a known compound that binds adenylate kinase protein to form an assay mixture, contacting the assay mixture with a test compound, and determining the ability of the test compound to preferentially bind to adenylate kinase protein or biologically active portion thereof as compared to the known compound.

In another embodiment, an assay is a cell-free assay comprising contacting adenylate kinase protein or biologically active portion thereof with a test compound and determining the ability of the test compound to modulate (e.g., stimulate or inhibit) the activity of the adenylate kinase protein or biologically active portion thereof. Determining the ability of the test compound to modulate the activity of an adenylate kinase protein can be accomplished, for example, by determining the ability of the adenylate kinase protein to bind to an adenylate kinase target molecule as described above for determining direct binding. In an alternative embodiment, determining the ability of the test compound to modulate the activity of an adenylate kinase protein can be accomplished by determining the ability of the adenylate kinase protein to further modulate an adenylate kinase target molecule. For example, the catalytic/ enzymatic activity of the target molecule on an appropriate substrate can be determined as previously described.

In yet another embodiment, the cell-free assay comprises contacting the adenylate kinase protein or biologically active portion thereof with a known compound that binds an adenylate kinase protein to form an assay mixture, contacting the assay mixture with a test compound, and determining the ability of the test compound to preferentially bind to or modulate the activity of an adenylate kinase target molecule.

In the above-mentioned assays, it may be desirable to immobilize either an adenylate kinase protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix.

For example, glutathione-S-transferase/adenylate kinase fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or adenylate kinase protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of adenylate kinase binding or activity determined using standard techniques.

Other techniques for immobilizing proteins on matrices can also be used in the screening assays of the invention. For example, either adenylate kinase protein or its target molecule can be immobilized utilizing conjugation of biotin and streptavidin. Biotinylated adenylate kinase molecules or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with an adenylate kinase protein or target molecules but which do not interfere with binding of the adenylate kinase protein to its target molecule can be derivatized to the wells of the plate, and unbound target or adenylate kinase protein trapped in the wells by antibody conjugation. Methods for detecting such complexes, in addition to those described above for the GST-immobilized complexes, include immunodetection of complexes using antibodies reactive with the adenylate kinase protein or target molecule, as well as enzyme-linked assays that rely on detecting an enzymatic activity associated with the adenylate kinase protein or target molecule.

In another embodiment, modulators of adenylate kinase expression are identified in a method in which a cell is contacted with a candidate compound and the expression of adenylate kinase mRNA or protein in the cell is determined relative to expression of adenylate kinase mRNA or protein in a cell in the absence of the candidate compound. When expression is greater (statistically significantly greater) in the presence of the candidate compound than in its absence, the candidate compound is identified as a stimulator of adenylate kinase mRNA or protein expression. Alternatively, when expression is less (statistically significantly less) in the presence of the candidate compound than in its absence, the candidate compound is identified as an inhibitor of adenylate kinase mRNA or protein expression. The level of adenylate kinase mRNA or protein expression in the cells can be determined by methods described herein for detecting adenylate kinase mRNA or protein.

In yet another aspect of the invention, the adenylate kinase proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Bio/Techniques* 14:920-924; Iwabuchi et al. (1993) *Oncogene* 8:1693-1696; and PCT Publication No. WO 94/10300), to identify other proteins, which bind to or interact with adenylate kinase protein ("adenylate kinase-binding proteins" or "adenylate kinase-bp") and modulate adenylate kinase activity. Such adenylate kinase-binding proteins are also likely to be involved in the propagation of signals by the adenylate kinase proteins as, for example, upstream or downstream elements of the adenylate kinase pathway.

This invention further pertains to novel agents identified by the above-described screening assays and uses thereof for treatments as described herein. Accordingly the invention is directed to agents that modulate the level or activity of the polypeptide or nucleic acid of the invention, the agents being identified by screening cells, tissues, cell extracts, or tissue extracts with the agents. Agents that alter the level or activity can then be tested further for clinical diagnostic or therapeutic use. Any method of screening that allows expression to be measured, such as those disclosed herein, are relevant to produce the identification of these agents. Thus, the invention is directed to agents identified by the screening processes involving measuring or detecting expression (level or activity) of the polypeptides or nucleic acids of the invention. It is understood that agents affecting the ability of the protein or nucleic acid to interact with a cellular component, as in competition binding, would be construed as affecting expression. Accordingly, screening processes also include assays for agents that themselves bind to the protein or nucleic acid of the invention, such as those disclosed herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial adenylate kinase gene sequences of the invention can be used to map their respective adenylate kinase genes on a chromosome, thereby facilitating the location of gene regions associated with genetic disease. Computer analysis of adenylate kinase sequences can be used to rapidly select PCR primers (preferably 15-25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the adenylate kinase sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919-924). Somatic cell hybrids containing only fragments of human chromosomes can also be produced by using human chromosomes with translocations and deletions.

Other mapping strategies that can similarly be used to map an adenylate kinase sequence to its chromosome include in situ hybridization (described in Fan et al. (1990) *Proc. Natl. Acad. Sci. USA* 87:6223-27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma eta a. (1988) *Human Chromosomes: A Manual of Basic Techniques*(Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783-787.

Moreover, differences in the DNA sequences between individuals affected and unaffected with a disease associated with the adenylate kinase gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The adenylate kinase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the adenylate kinase sequences of the invention can be used to prepare two PCR primers from the 5N and 3N ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The adenylate kinase sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:1 can comfortably provide positive individual identification with a panel of perhaps 10 to 1,000 primers that each yield a noncoding amplified sequence of 100 bases. If a predicted coding sequence, such as that in SEQ ID NO:1, is used, a more appropriate number of primers for positive individual identification would be 500 to 2,000.

3. Use of Partial Adenylate Kinase Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the adenylate kinase sequences or portions thereof, e.g., fragments derived from the noncoding regions of SEQ ID NO:1 having a length of at least 20 or 30 bases.

The adenylate kinase sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such adenylate kinase probes, can be used to identify tissue by species and/or by organ type.

In a similar fashion, these reagents, e.g., adenylate kinase primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting adenylate kinase protein and/or nucleic acid expression as well as adenylate kinase activity, in the context of a biological sample. An exemplary method for detecting the presence or absence of adenylate kinase proteins in a biological sample involves obtaining a biological sample from a test subject and contacting the biological sample with a compound or an agent capable of detecting adenylate kinase protein or nucleic acid (e.g., mRNA, genomic DNA) that encodes adenylate kinase protein such that the presence of adenylate kinase protein is detected in the biological sample. Results obtained with a biological sample from the test subject may be compared to results obtained with a biological sample from a control subject.

A preferred agent for detecting adenylate kinase mRNA or genomic DNA is a labeled nucleic acid probe capable of hybridizing to adenylate kinase mRNA or genomic DNA. The nucleic acid probe can be, for example, a full-length adenylate kinase nucleic acid, such as the nucleic acid of SEQ ID NO:1, or a portion thereof, such as a nucleic acid molecule of at least 15, 30, 50, 100, 250, or 500 nucleotides in length and sufficient to specifically hybridize under stringent conditions to adenylate kinase mRNA or genomic DNA. Other suitable probes for use in the diagnostic assays of the invention are described herein.

A preferred agent for detecting adenylate kinase protein is an antibody capable of binding to adenylate kinase protein, preferably an antibody with a detectable label. Antibodies can be polyclonal, or more preferably, monoclonal. An intact antibody, or a fragment thereof (e.g., Fab or F(abN)$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect adenylate kinase mRNA, protein, or genomic DNA in a biological sample in vitro as well as in vivo. For example, in vitro techniques for detection of adenylate kinase mRNA include Northern hybridizations and in situ hybridizations. In vitro techniques for detection of adenylate kinase protein include enzyme linked immunosorbent assays (ELISAs), Western blots, immunoprecipitations, and immunofluorescence. In vitro techniques for detection of adenylate kinase genomic DNA include Southern hybridizations. Furthermore, in vivo techniques for detection of adenylate kinase protein include introducing into a subject a labeled anti-adenylate kinase antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

The invention also encompasses kits for detecting the presence of adenylate kinase proteins in a biological sample (a test sample). Such kits can be used to determine if a subject is suffering from or is at increased risk of developing a disorder associated with aberrant expression of adenylate kinase protein (e.g., an immunological disorder). For example, the kit can comprise a labeled compound or agent capable of detecting adenylate kinase protein or mRNA in a biological sample and means for determining the amount of an adenylate kinase protein in the sample (e.g., an anti-adenylate kinase antibody or an oligonucleotide probe that binds to DNA encoding an adenylate kinase protein, e.g., SEQ ID NO:1). Kits can also include instructions for observing that the tested subject is suffering from or is at risk of developing a disorder associated with aberrant expression of adenylate kinase sequences if the amount of adenylate kinase protein or mRNA is above or below a normal level.

For antibody-based kits, the kit can comprise, for example: (1) a first antibody (e.g., attached to a solid support) that binds to adenylate kinase protein; and, optionally, (2) a second, different antibody that binds to adenylate kinase protein or the first antibody and is conjugated to a detectable agent. For oligonucleotide-based kits, the kit can comprise, for example: (1) an oligonucleotide, e.g., a detectably labeled oligonucleotide, that hybridizes to an adenylate kinase nucleic acid sequence or (2) a pair of primers useful for amplifying an adenylate kinase nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of adenylate kinase proteins.

2. Prognostic Assays

The methods described herein can furthermore be utilized as diagnostic or prognostic assays to identify subjects having or at risk of developing a disease or disorder associated with adenylate kinase protein, adenylate kinase nucleic acid expression, or adenylate kinase activity. Prognostic assays can be used for prognostic or predictive purposes to thereby prophylactically treat an individual prior to the onset of a disorder characterized by or associated with adenylate kinase protein, adenylate kinase nucleic acid expression, or adenylate kinase activity.

Thus, the present invention provides a method in which a test sample is obtained from a subject, and adenylate kinase protein or nucleic acid (e.g., mRNA, genomic DNA) is detected, wherein the presence of adenylate kinase protein or nucleic acid is diagnostic for a subject having or at risk of developing a disease or disorder associated with aberrant adenylate kinase expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease adenylate kinase activity) to effectively treat a disease or disorder associated with aberrant adenylate kinase expression or activity. In this manner, a test sample is obtained and adenylate kinase protein or nucleic acid is detected. The presence of adenylate kinase protein or nucleic acid is diagnostic for a subject that can be administered the agent to treat a disorder associated with aberrant adenylate kinase expression or activity.

The methods of the invention can also be used to detect genetic lesions or mutations in an adenylate kinase gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding an adenylate kinase-protein, or the misexpression of the adenylate kinase gene. For example, such genetic lesions or mutations can be detected by ascertaining the existence of at least one of: (1) a deletion of one or more nucleotides from an adenylate kinase gene; (2) an addition of one or more nucleotides to an adenylate kinase gene; (3) a substitution of one or more nucleotides of an adenylate kinase gene; (4) a chromosomal rearrangement of an adenylate kinase gene; (5) an alteration in the level of a messenger RNA transcript of an adenylate kinase gene; (6) an aberrant modification of an adenylate kinase gene, such as of the methylation pattern of the genomic DNA; (7) the presence of a non-wild-type splicing pattern of a messenger RNA transcript of an adenylate kinase gene; (8) a non-wild-type level of an adenylate kinase-protein; (9) an allelic loss of an adenylate kinase gene; and (10) an inappropriate post-translational modification of an adenylate kinase-protein. As described herein, there are a large number of assay techniques known in the art that can be used for detecting lesions in an adenylate kinase gene. Any cell type or tissue, preferably peripheral blood leukocytes, in which adenylate kinase proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the adenylate kinase gene (see, e.g., Abravaya et al. (1995) *Nucleic Acids Res.* 23:675-682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an adenylate kinase gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in an adenylate kinase molecule can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Medicine* 2:753-759). In yet another embodiment, any of a variety of sequencing reactions known in the art can be used to directly sequence the adenylate kinase gene and detect mutations by comparing the sequence of the sample adenylate kinase gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the adenylate kinase gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in adenylate kinase cDNAs obtained from samples of cells. See, e.g., Hsu et al. (1994) *Carcinogenesis* 15:1657-1662. According to an exemplary embodiment, a probe based on an adenylate kinase sequence, e.g., a wild-type adenylate kinase sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in adenylate kinase genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125-144; Hayashi (1992) *Genet. Anal. Tech. Appl.* 9:73-79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437-2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell. Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving an adenylate kinase gene.

3. Pharmacogenomics

Agents, or modulators that have a stimulatory or inhibitory effect on adenylate kinase activity (e.g., adenylate kinase gene expression) as identified by a screening assay described herein, can be administered to individuals to treat (prophylactically or therapeutically) disorders associated with aberrant adenylate kinase activity as well as to modulate the phenotype of an immune response. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of adenylate kinase protein, expression of adenylate kinase nucleic acid, or mutation content of adenylate kinase genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of adenylate kinase protein, expression of adenylate kinase nucleic acid, or mutation content of adenylate kinase genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an adenylate kinase modulator, such as a modulator identified by one of the exemplary screening assays described herein.

4. Monitoring of Effects During Clinical Trials

Monitoring the influence of agents (e.g., drugs, compounds) on the expression or activity of adenylate kinase genes (e.g., the ability to modulate aberrant cell proliferation and/or differentiation) can be applied not only in basic drug screening but also in clinical trials. For example, the effectiveness of an agent, as determined by a screening assay as described herein, to increase or decrease adenylate kinase gene expression, protein levels, or protein activity, can be monitored in clinical trials of subjects exhibiting decreased or increased adenylate kinase gene expression, protein levels, or protein activity. In such clinical trials, adenylate kinase expression or activity and preferably that of other genes that have been implicated in for example, a cellular proliferation disorder, can be used as a marker of the immune responsiveness of a particular cell.

For example, and not by way of limitation, genes that are modulated in cells by treatment with an agent (e.g., compound, drug, or small molecule) that modulates adenylate kinase activity (e.g., as identified in a screening assay described herein) can be identified. Thus, to study the effect of agents on cellular proliferation disorders, for example, in a clinical trial, cells can be isolated and RNA prepared and analyzed for the levels of expression of adenylate kinase genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of adenylate kinase genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of an adenylate kinase protein, mRNA, or genomic DNA in the preadministration sample; (3) obtaining one or more post-administration samples from the subject; (4) detecting the level of expression or activity of the adenylate kinase protein, mRNA, or genomic DNA in the postadministration samples; (5) comparing the level of expression or activity of the adenylate kinase protein, mRNA, or genomic DNA in the preadministration sample with the adenylate kinase protein, mRNA, or genomic DNA in the postadministration sample or samples; and (vi) altering the administration of the agent to the subject accordingly to bring about the desired effect, i.e., for example, an increase or a decrease in the expression or activity of an adenylate kinase protein.

C. Methods of Treatment

The present invention provides for both prophylactic and therapeutic methods of treating a subject at risk of (or susceptible to) a disorder or having a disorder associated with aberrant adenylate kinase expression or activity. Additionally, the compositions of the invention find use in the treatment of disorders described herein.

1. Prophylactic Methods

In one aspect, the invention provides a method for preventing in a subject a disease or condition associated with an aberrant adenylate kinase expression or activity by administering to the subject an agent that modulates adenylate kinase expression or at least one adenylate kinase gene activity. Subjects at risk for a disease that is caused, or contributed to, by aberrant adenylate kinase expression or activity can be identified by, for example, any or a combination of diagnostic or prognostic assays as described herein. Administration of a prophylactic agent can occur prior to the manifestation of symptoms characteristic of the adenylate kinase aberrancy, such that a disease or disorder is prevented or, alternatively, delayed in its progression. Depending on the type of adenylate kinase aberrancy, for example, an adenylate kinase agonist or adenylate kinase antagonist agent can be used for treating the subject. The appropriate agent can be determined based on screening assays described herein.

2. Therapeutic Methods

Another aspect of the invention pertains to methods of modulating adenylate kinase expression or activity for therapeutic purposes. The modulatory method of the invention involves contacting a cell with an agent that modulates one or more of the activities of adenylate kinase protein activity associated with the cell. An agent that modulates adenylate kinase protein activity can be an agent as described herein, such as a nucleic acid or a protein, a naturally-occurring cognate ligand of an adenylate kinase protein, a peptide, an adenylate kinase peptidomimetic, or other small molecule. In one embodiment, the agent stimulates one or more of the biological activities of adenylate kinase protein. Examples of such stimulatory agents include active adenylate kinase protein and a nucleic acid molecule encoding an adenylate kinase protein that has been introduced into the cell. In another embodiment, the agent inhibits one or more of the biological activities of adenylate kinase protein. Examples of such inhibitory agents include antisense adenylate kinase nucleic acid molecules and anti-adenylate kinase antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of an adenylate kinase protein or nucleic acid molecule. In one embodiment, the method involves administering an agent (e.g., an agent identified by a screening assay described herein), or a combination of agents, that modulates (e.g., upregulates or downregulates) adenylate kinase expression or activity. In another embodiment, the method involves administering an adenylate kinase protein or nucleic acid molecule as therapy to compensate for reduced or aberrant adenylate kinase expression or activity.

Stimulation of adenylate kinase activity is desirable in situations in which an adenylate kinase protein is abnormally downregulated and/or in which increased adenylate kinase activity is likely to have a beneficial effect. Conversely, inhibition of adenylate kinase activity is desirable in situations in which adenylate kinase activity is abnormally upregulated and/or in which decreased adenylate kinase activity is likely to have a beneficial effect.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

CHAPTER 2

21612, 21615, 21620, 21676, 33756, Novel Human Alcohol Dehydrogenases

BACKGROUND OF THE INVENTION

Alcohol dehydrogenases are ubiquitous enzymes that are and are generally classified as members of either the MDR (medium-chain dehydrogenase/reductase) or SDR (short-chain dehydrogenase/reductase) protein families. Members of the SDR and MDR families appear to have similar activities though they work via different mechanisms and structures. The SDR superfamily comprises isomerases, lyases and oxidoreductases. The enzymes of this family cover a wide range of substrate specificities including steroids, alcohols, and aromatic compounds, however, most family members are known to be $NAD^+$- or $NADP^+$-dependent oxidoreductases. In the combined SDR superfamily, only a single tyrosine residue is strictly conserved and ascribed a critical enzymatic function. Members of the MDR superfamily are often multimeric enzymes associated with 0, 1, or 2 zinc atoms. Substrates of the MDR enzymes are often alcohols and aldehydes. Six different classes of mammalian ADH isoforms are members of the MDR family. In addition to the MDR and SDR families, alcohol dehydrogenases have also been associated with protein families reflecting iron-dependant enzymes, long-chain enzymes, and several types of prokaryotic enzymes with other cofactor requirements.

Most dehydrogenase proteins function as dimers or tetramers and possess at least two domains: the first domain comprising the coenzyme binding site, and the second domain comprising the substrate binding site. This latter domain determines the substrate specificity and contains the amino acids involved in catalysis. ADHs have a variety of substrate specificities, but act primarily on primary or secondary alcohols, hemiacetals, cyclic secondary alcohols, or on the corresponding aldehydes and ketones. The catalytic role of ADH in mammalian ethanol oxidation is well studied. ADH catalyzes the conversion of ethanol to acetaldehyde using $NAD^+$ as a cofactor. Specifically, the coenzyme binds ADH, followed by an interaction with ethanol, the ethanol is subsequently converted to acetaldehyde and the $NAD^+$ is converted to NADH. Members of the mammalian ADH protein family have varying electrophoretic mobilities, Michaelis constants (binding affinities) for ethanol, and sensitivities to pyrazol inhibition. For instance, class I ADHs have low $K_m$ values (less than 5 mM) for ethanol oxidation while class II and class IV ADHs have intermediate $K_m$ values (about 30 mM). Class III ADH enzymes are not saturable with ethanol and virtually function exclusively as glutathione-dependent formaldehyde dehydrogenases. Allelic variation of the mammalian genes have been identified. The kinetic properties of the resultant variants differ significantly owing to single amino acid substitutions in the coenzyme binding domains of the enzymes.

Alcohol dehydrogenases play fundamental roles in degradative, synthetic, and detoxification pathways and have been implicated in a variety of critical developmental processes and pathophysiological disease states. For instance, allelic variations of ADH2 and ADH3 appear to influence the susceptibility to alcoholism and alcoholic liver cirrhosis in Asians (Thomasson et al. (1991) *Am. J. Hum Genet.* 48:677-681, Chao et al. (1994) *Hepatology* 19:360-366, and Higuchi et al. (1995) *Am. J. Psychiatry* 152:1219-1221). Furthermore, first-pass metabolism is the difference between the quantity of ethanol that reaches the systemic circulation by the intravenous route and the quantity that entered by the oral dose. Several lines of evidence now indicate that first-pass metabolism of alcohol in humans may occur in the liver via the activity of members of the mammalian ADH family (Yin et al. (1999) *Enzymology and Molecular Biology of Carbonyl Metabolism* 7, Plenum Publishers, New York).

ADHs are also involved in detoxification pathways. For instance, class III ADH is unsaturable by ethanol and mainly functions as a glutathione-dependant formaldehyde dehydrogenase and is therefore important for the elimination of endogenously formed formaldehyde. ADHs are also involved in the metabolism of nitrobenzaldehyde, a dietary carcinogen. It has been suggested that the lack of σ-ADH in Japanese patients may lead to a decreased detoxification of the dietary carcinogen nitrobenzaldehyde and may possible be linked to the high rate of gastric cancer in Japanese (Baron et al. (1991) *Life Sci* 49:1929-34; Grab et al. (1977) *Cancer Res* 37:4181-90 and Seedcake et al. (1980) *Rev Ed* 9:346-51). ADH is also involved in the activation of 1,2 dimethylhydrazine, an experimentally used procarcinogen.

Retinoic acid is a ligand controlling a nuclear receptor signaling pathway that plays a key role in the regulation of embryonic development, spermatogenesis, and epithelial differentiation (Chambon et al. (1996) *FASEB J.* 10:940-954 and Mangelsdorf et al. (1995) *Cell* 83:841-850). The synthesis of retinoic acid occurs via the oxidation of retinol to retinal followed by the conversion of retinal to retinoic acid. Members of the alcohol dehydrogenase and short-chain dehydrogenase/reductase families catalyze the reversible, rate limiting conversion of retinol to retinal, while the oxidation of retinal to retinoic acid is catalyzed by members of the aldehyde dehydrogenase or P450 enzyme families (Deuster et al. (1996) *Biochemistry* 35:12221-12227). Therefore, members of the ADH family influence the growth and developmental processes mediated by the active metabolite retinoic acid.

ADH metabolism of retinol to retinal is inhibited by ethanol, and this may lead to altered epithelial cell differentiation and malignant cell transformation. Furthermore, it has been suggested that the ability of ethanol to inhibit the oxidation of retinol by ADH underlies the pathology of fetal alcohol syndrome, a birth defect characterized by craniofacial, limb, and brain malformations (Duester et al. (1991) *Alcohol Clin Exp Res* 15:568-572). Retinoic acid also functions to maintain differentiation of epithelial cells and influences spermatogenesis in adult vertebrates (Chambon et al. (1996) *FASEB J.* 10:940-954). Data suggests that retinoic acid signaling in spermatogenesis and keratinocyte differentiation may be significantly disrupted by ethanol through ADH pathways. It has been proposed that inhibition of retinol metabolism by ethanol may be responsible for the testicular atrophy and spermatogenesis commonly seen in male chronic alcoholics. Furthermore, skin diseases such as psoriasis, have been associated with heavy drinking.

ADH may also play a role in colorectal cancers. During colorectal carcinogenesis, ADH activity is significantly decreased in polyps and further decreased in cancer tissue.

(Egerer et al. (1997) *Gastroenterology* 112:A1260). Furthermore, epidemiological studies have demonstrated that alcohol consumption is a risk factor for development of oral, esophageal, colorectal, and upper gastrointestinal cancers (Blot et al. (1992) *Cancer Res* 52:2119s-2123s). The role of ADH in cancers of these various tissues may result from the production of acetaldehyde following oxidation of ethanol by ADH, an alteration in retinol metabolism or through the role of ADH in carcinogen metabolism.

Further functional links between disease and the oxidative/reductive actions of various dehydrogenases are being established. For instance, ERAB is a member of the short-chain dehydrogenase/reductase family. Interactions between and Amyloid β peptide and ERAB have been shown to mediate neurotoxicity and apoptosis in neuronal cell lines (Yan et al. (1997) *Nature* 389:689-693) and thus are being implicated in the pathogenesis of neurodegenerative disorders like Alzheimer's disease (Oppermann et al. (1999) *Enzymology and Molecular Biology of Carbonyl Metabolism* 7, Plenum Publishers, New York and Oppermann et al. (1999) *FEBS Letters* 451:238-242).

Accordingly, ADHs are a major target for drug action and development. Therefore, it is valuable to the field of pharmaceutical development to identify and characterize previously unknown ADHs. The present invention advances the state of the art by providing previously unidentified human alcohol dehydrogenases.

SUMMARY OF THE INVENTION

It is an object of the invention to identify novel alcohol dehydrogenases.

It is a further object of the invention to provide novel alcohol dehydrogenase polypeptides that are useful as reagents or targets in assays applicable to treatment and diagnosis of ADH-mediated or -related disorders.

It is a further object of the invention to provide polynucleotides corresponding to the novel ADH polypeptides that are useful as targets and reagents in ADH assays applicable to treatment and diagnosis of ADH-mediated or -related disorders and useful for producing novel ADH polypeptides by recombinant methods.

A specific object of the invention is to identify compounds that act as agonists and antagonists and modulate the expression of the novel ADHs.

A further specific object of the invention is to provide compounds that modulate expression of the alcohol dehydrogenases for treatment and diagnosis of ADH-related disorders.

The invention is thus based on the identification of novel human alcohol dehydrogenases. The amino acid sequence for ADH 21620, 33756, 21676, 21612, and 21615, are shown in SEQ ID NOS:5, 7, 9, 11, and 13, respectfully. The nucleotide sequence for ADH 21620, 33756, 21676, 21612, and 21615 are shown in SEQ ID NOS:6, 8, 10, 12, and 14, respectfully.

The invention provides isolated ADH polypeptides, including a polypeptide having the amino acid sequence shown in SEQ ID NOS:5, 7, 9, 11, and 13, or the amino acid sequence encoded by the cDNA deposited with American Type Culture Collection (ATCC), 10801 University Boulevard, Manassas, Va. 20110-2209, as Patent Deposit No. PTA-2012 (corresponding to the 33756 nucleotide sequence) on Jun. 9, 2000; Patent Deposit No. PTA-2170 (corresponding to the 21612 nucleotide sequence) on Jun. 27, 2000, Patent Deposit No. PTA-2171 (corresponding to the 21620 nucleotide sequence) on Jun. 27, 2000, as Patent Deposit No. PTA-2812 (corresponding to the 21615 nucleotide sequence) on Dec. 14, 2000, and as Patent Deposit No. PTA-2813 (corresponding to the 21676 nucleotide sequence) on Dec. 14, 2000. ATCC Patent Deposits PTA-2012, PTA-2170, PTA-2171, PTA-2812, and PTA-2813 are referred to collectively herein as "the deposited cDNAs."

The invention also provides isolated ADH nucleic acid molecules having the sequences shown in SEQ ID NOS:6, 8, 10, 12, and 14, or in the deposited cDNAs.

The invention also provides variant polypeptides having an amino acid sequence that is substantially homologous to the amino acid sequences shown in SEQ ID NOS:5, 7, 9, 11, and 13, or encoded by the deposited cDNAs.

The invention also provides variant nucleic acid sequences that are substantially homologous to the nucleotide sequences shown in SEQ ID NOS:6, 8, 10, 12, and 14, or in the deposited cDNAs.

The invention also provides fragments of the polypeptides shown in SEQ ID NOS:5, 7, 9, 11, and 13, and nucleotide sequences shown in SEQ ID NOS:6, 8, 10, 12, and 14, as well as substantially homologous fragments of the polypeptides or nucleic acids.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the ADH nucleic acid molecules and polypeptides, and particularly recombinant vectors and host cells.

The invention also provides methods of making the vectors and host cells and methods for using them to produce the ADH nucleic acid molecules and polypeptides.

The invention also provides antibodies or antigen-binding fragments thereof that selectively bind the ADH polypeptides and fragments.

The invention also provides methods of screening for compounds that modulate expression or activity of the ADH polypeptides or nucleic acid (RNA or DNA).

The invention also provides a process for modulating ADH polypeptide or nucleic acid expression or activity, especially using the screened compounds. Modulation may be used to treat conditions related to aberrant activity or expression of the ADH polypeptides or nucleic acids.

The invention also provides assays for determining the activity of or the presence or absence of the ADH polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Polypeptides

The invention is based on the discovery of novel human alcohol dehydrogenases. Specifically, an expressed sequence tag (EST) was selected based on homology to the alcohol dehydrogenase sequence. This EST was used to design primers based on sequences that it contains and used to identify cDNAS from human cDNA libraries, including primary osteoblasts. Positive clones were sequenced and the overlapping fragments were assembled. Analysis of each of the assembled sequences revealed that the cloned cDNA molecules encode ADHs.

The invention thus relates to novel ADHs having the deduced amino acid sequence shown in FIGS. 7A-B, 13, 17A-B, 21A-B, and 25A-B, or the amino acid sequences shown in SEQ ID NOS:5, 7, 9, 11, and 13, or the amino acid sequences encoded by the deposited cDNAs as Patent Deposit Numbers PTA-2012, PTA-2170, or PTA-2171.

The deposits will be maintained under the terms of the Budapest Treaty on the International Recognition of the Deposit of Microorganisms. The deposits are provided as a convenience to those of skill in the art and is not an admission that a deposit is required under 35 U.S.C. § 112. The deposited sequences, as well as the polypeptides encoded by the sequences, are incorporated herein by reference and controls in the event of any conflict, such as a sequencing error, with description in this application.

"ADH polypeptide" or "ADH protein" refers to the polypeptides in SEQ ID NOS:5, 7, 9, 11, and 13, or the polylpeptides encoded by the deposited cDNAs. The term "ADH protein" or "ADH polypeptide", however, further includes the numerous variants described herein, as well as fragments derived from the full-length ADHs and variants.

Figure 11:
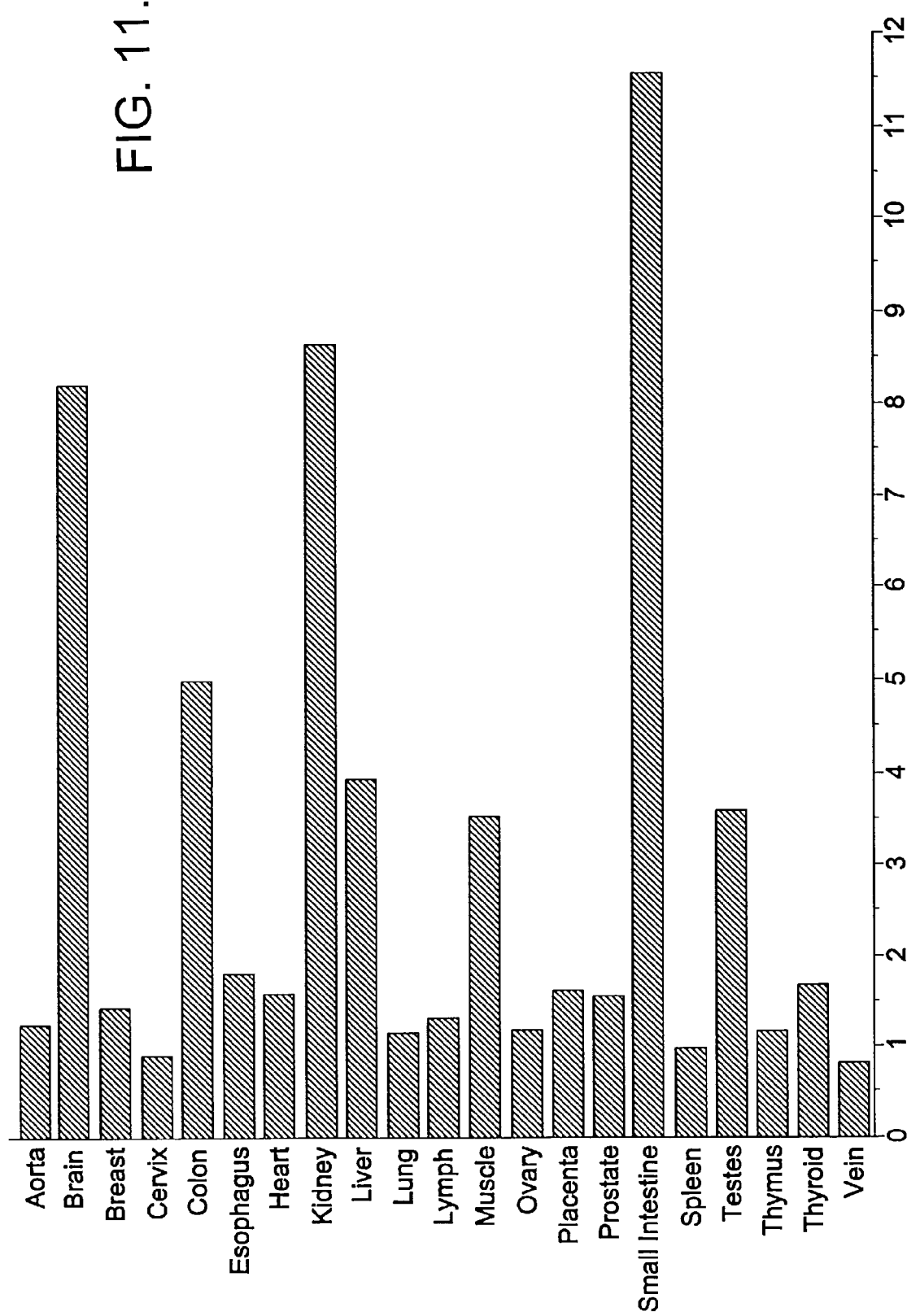
FIG. 11 shows expression of the 21620 ADH mRNA in various tissues. 21620 expression levels were determined by quantitative PCR (Taqman® brand quantitative PCR kit, Applied Biosystems). The quantitative PCR reactions were performed according to the kit manufacturer's instructions.
Figure 12:
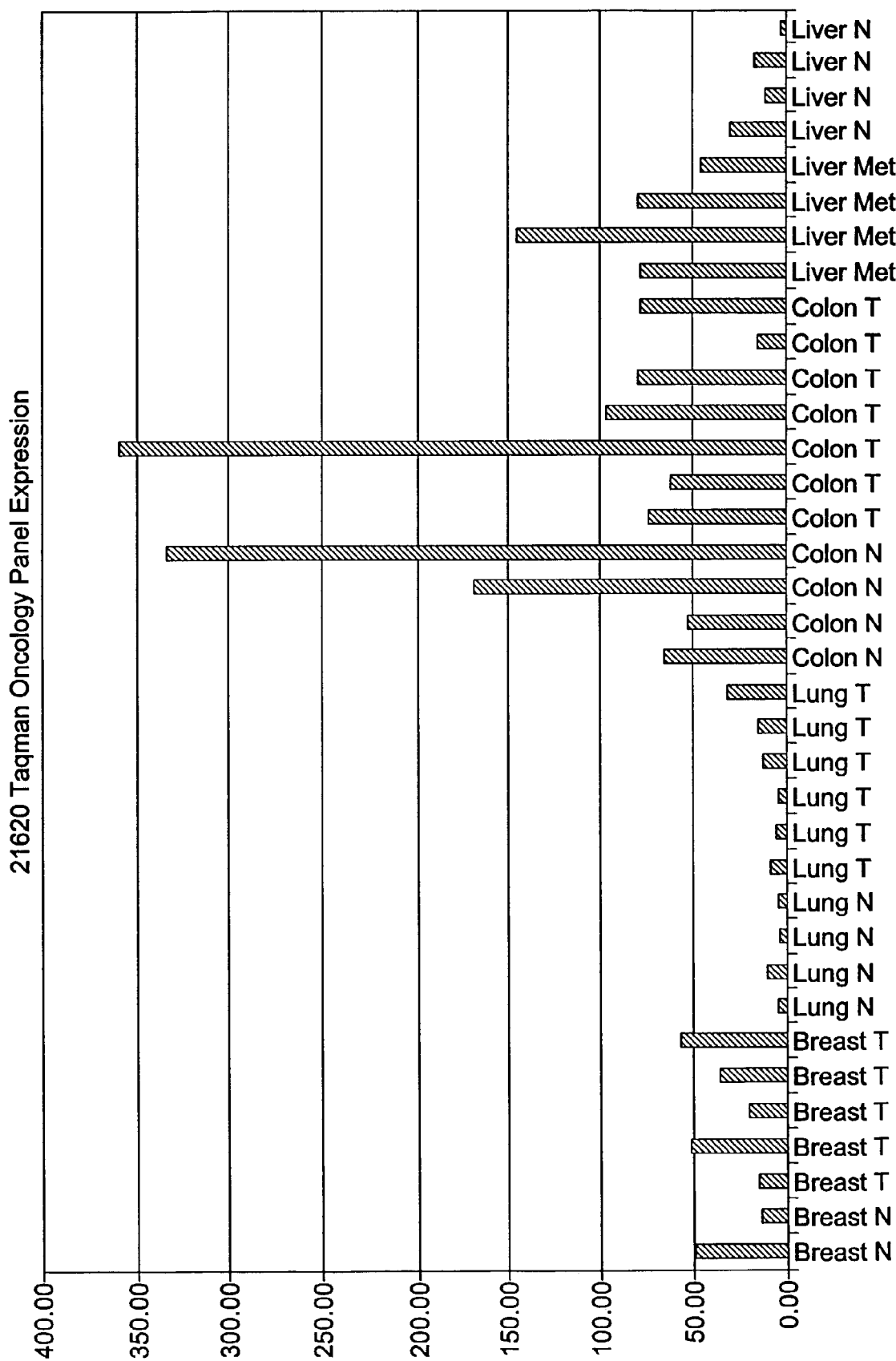
FIG. 12 shows expression of the 21620 ADH mRNA in normal and malignant breast, lung, liver and colon tissues. The liver metastases are derived from malignant colonic tissue. 21620 expression levels were determined by quantitative PCR (Taqman® brand quantitative PCR kit, Applied Biosystems).
Figure 14:
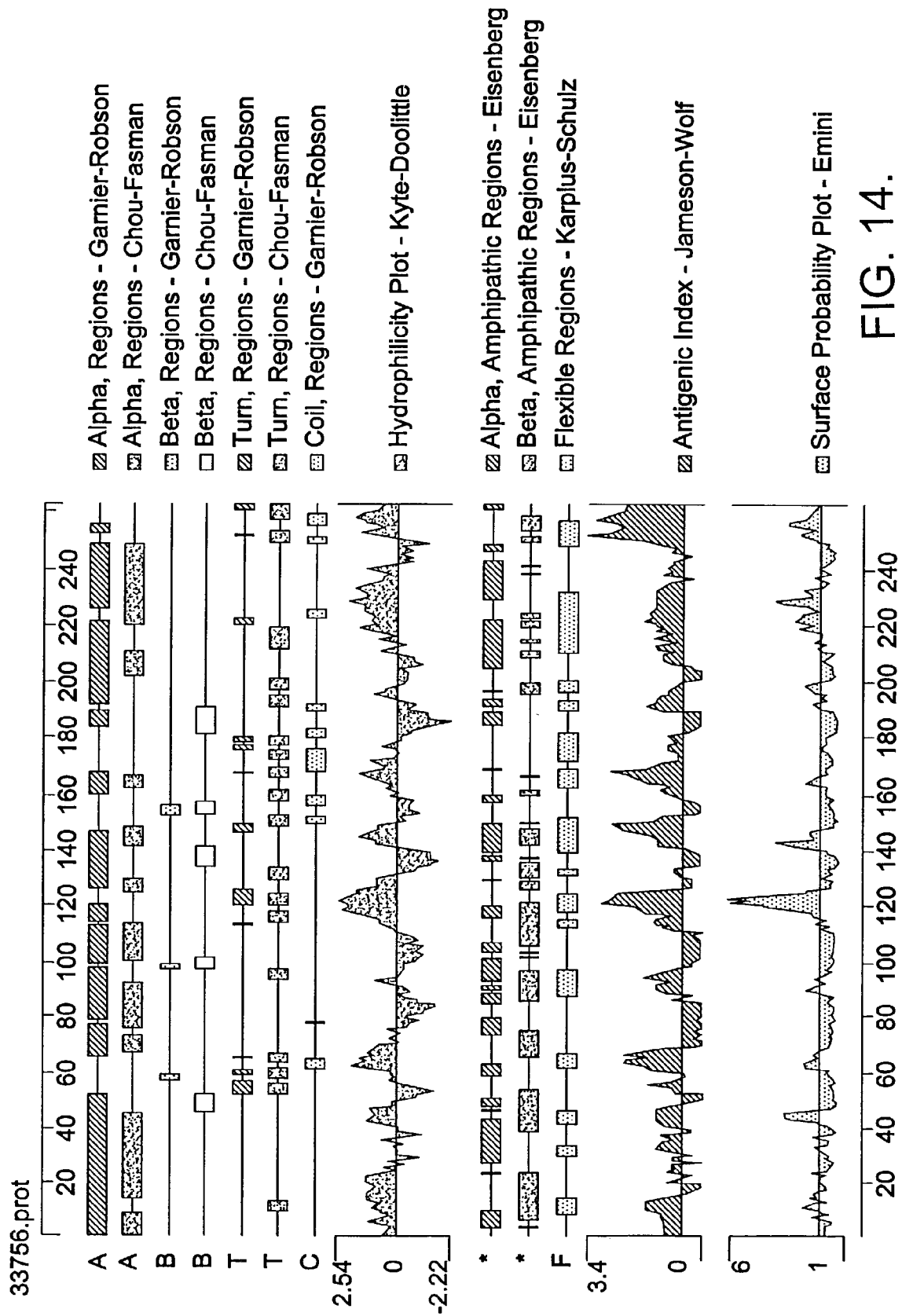
FIG. 14 shows an analysis of the 33756 ADH amino acid sequence: αβturn and coil regions; hydrophilicity; amphipathic regions; flexible regions; antigenic index; and surface probability plot.
Figure 15:
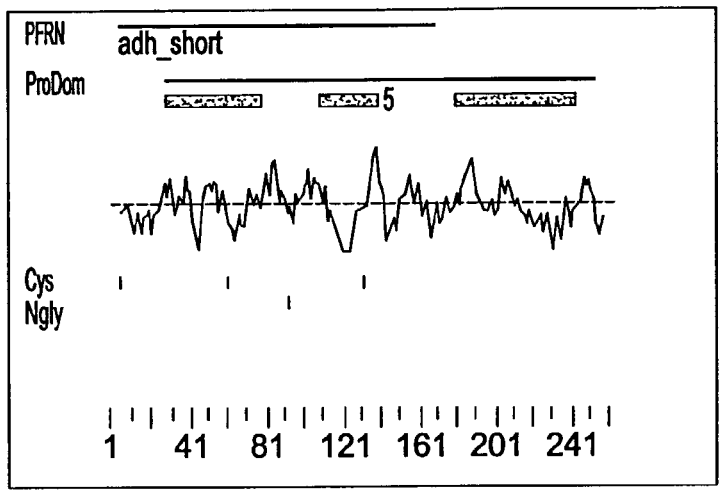
FIG. 15 shows a hydrophobicity plot of the 33756 ADH amino acid sequence (SEQ ID NO:7). Also shown is a graphical representation of the functional domain of ADH short chain.
Figure 18:
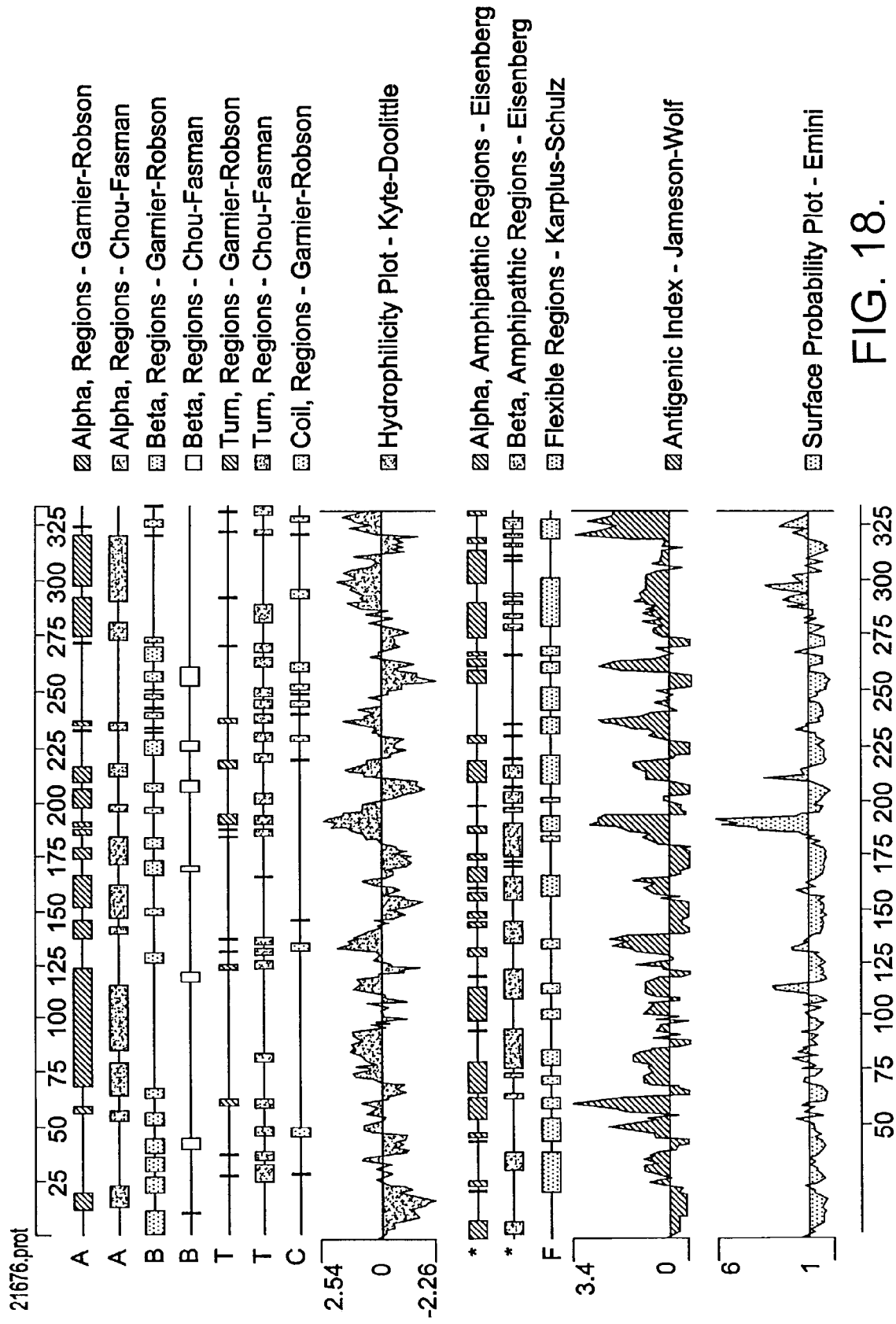
FIG. 18 shows an analysis of the 21676 ADH amino acid sequence: αβturn and coil regions; hydrophilicity; amphipathic regions; flexible regions; antigenic index; and surface probability plot.
Figure 19:
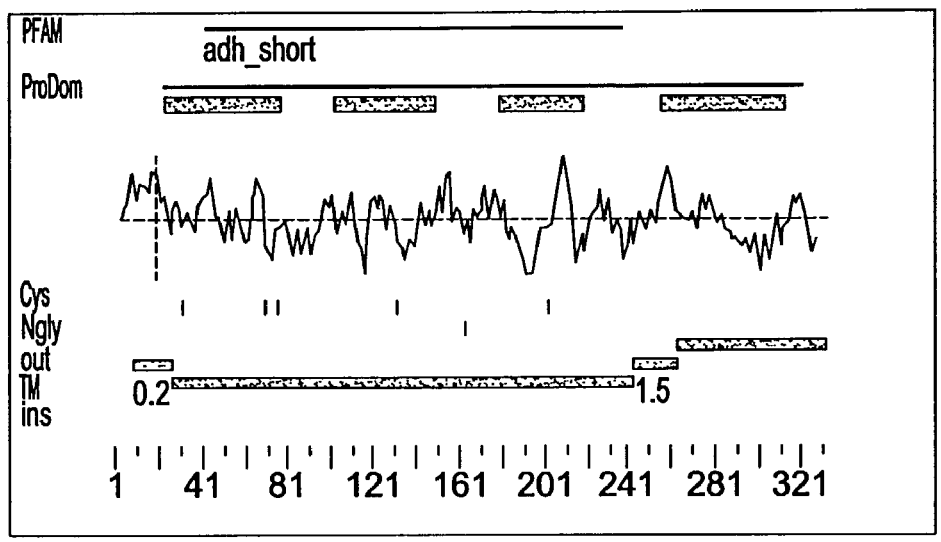
FIG. 19 shows a hydrophobicity plot of the 21676 ADH amino acid sequence (SEQ ID NO:9). Also shown is the predicted amino terminus signal peptide sequence. In addition, two transmembrane segments are predicted for the full-length polypeptide from about amino acid 8 to about amino acid 25 and from about amino acid 242 to about amino acid 261. In the mature form of the polypeptide the transmembrane domain is predicted from about amino acid 226 to about amino acid 245. Also shown is a graphical representation of the functional domain of ADH short chain.
Figure 22:
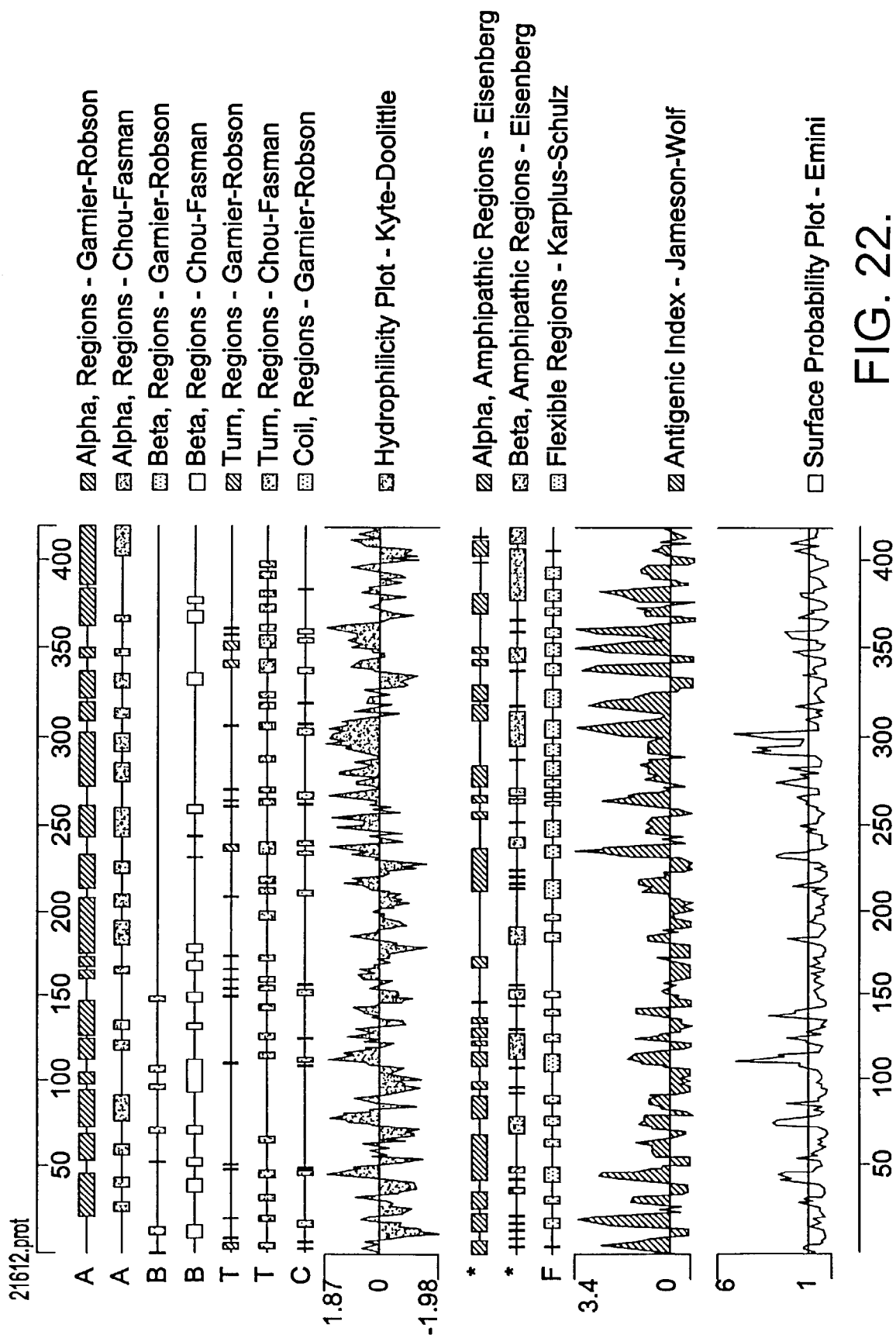
FIG. 22 shows an analysis of the 21612 ADH amino acid sequence: αβturn and coil regions; hydrophilicity; amphipathic regions; flexible regions; antigenic index; and surface probability plot.
Figure 23:
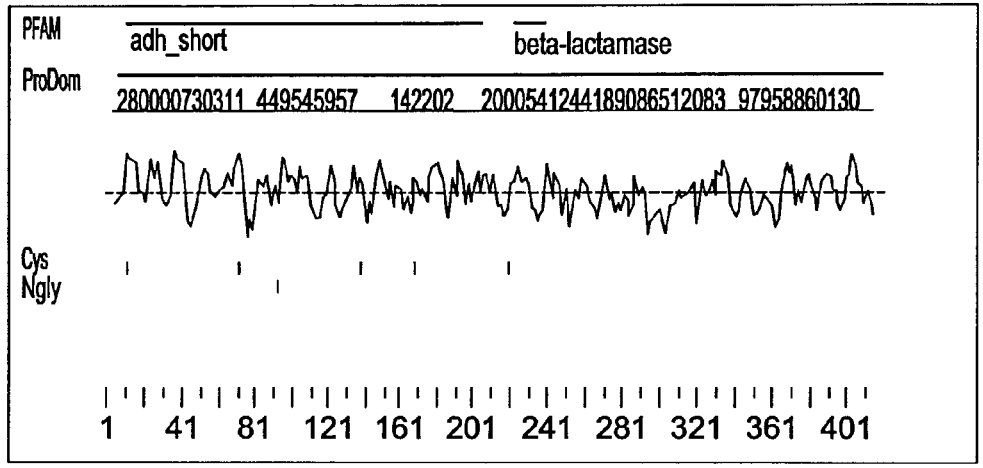
FIG. 23 shows a hydrophobicity plot of the 21612 ADH amino acid sequence (SEQ ID NO:11). Also shown is a graphical representation of the functional domain of ADH short chain.
Figure 26:
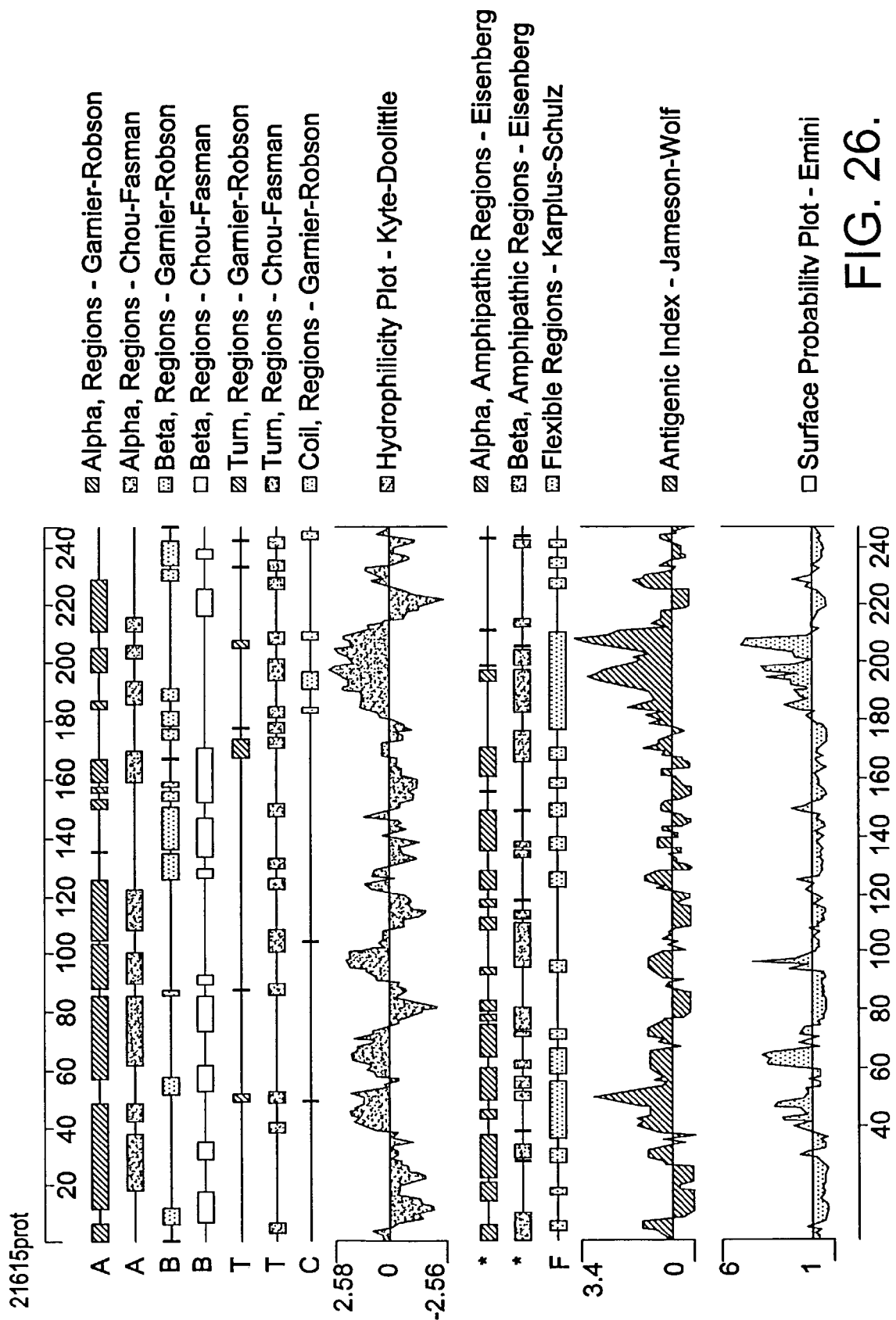
FIG. 26 shows an analysis of the 21615 ADH amino acid sequence: αβturn and coil regions; hydrophilicity; amphipathic regions; flexible regions; antigenic index; and surface probability plot.
Figure 27:
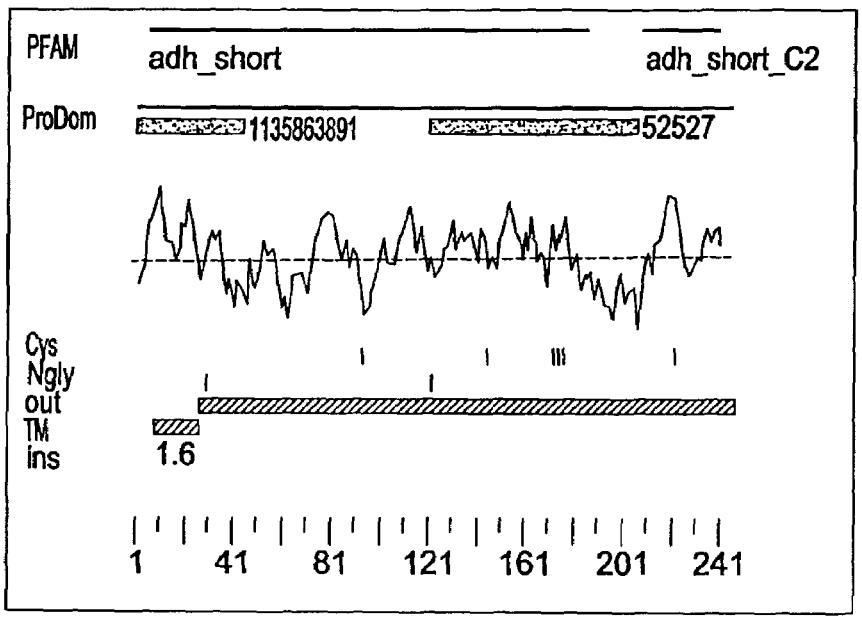
FIG. 27 shows a hydrophobicity plot of the 21615 ADH amino acid sequence (SEQ ID NO:13). Also shown is the predicted transmembrane segment from about amino acid 8 to about amino acid 27. In addition, a graphical representation of the functional domain of ADH short chain is also shown.
Figure 29:
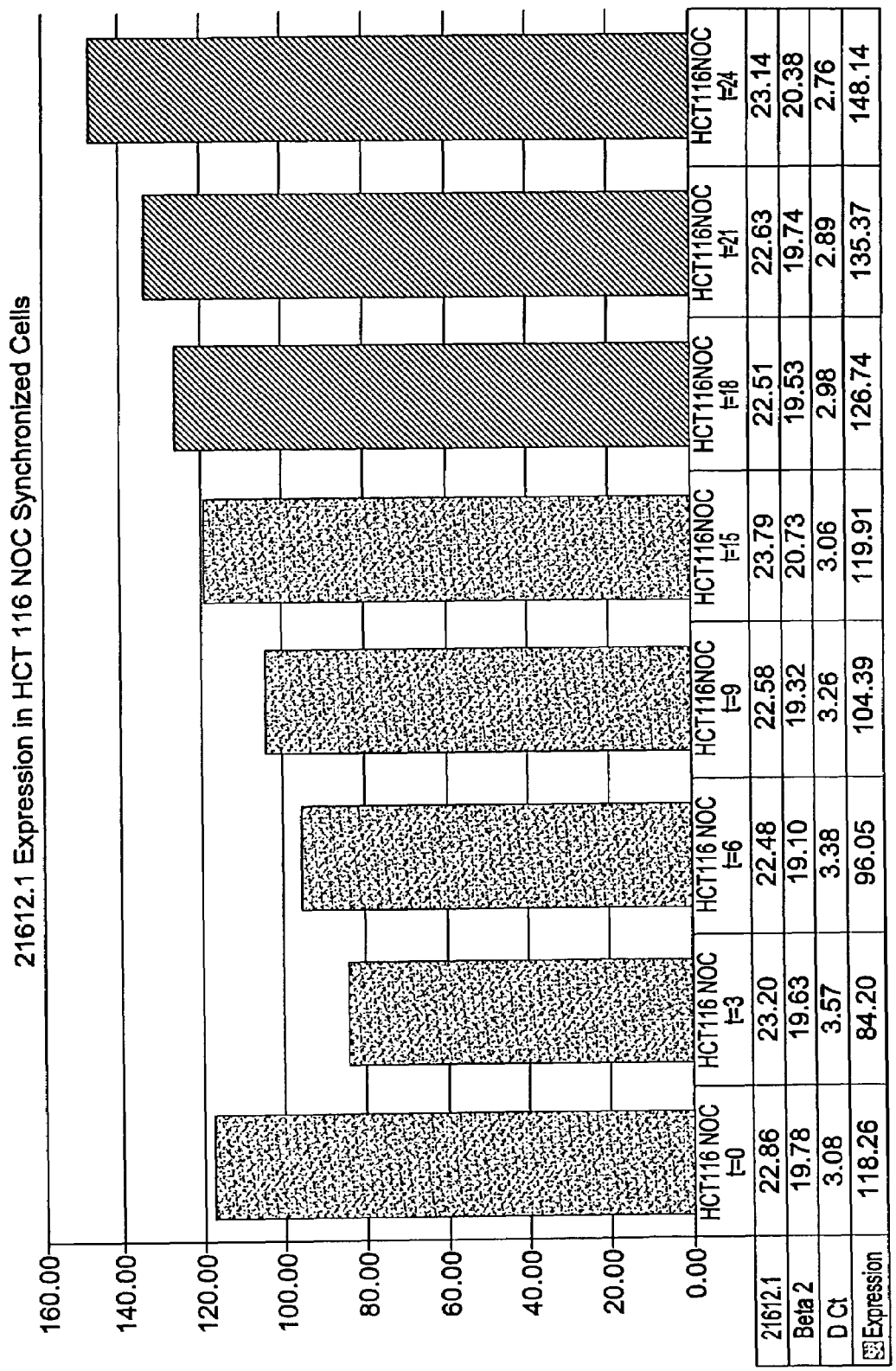
FIG. 29 shows a time course of levels of 21612 mRNA expression in the human colon cancer cell line HCT-116 following synchronization with nocodazole. 21612 mRNA levels rose steadily as the HCT-116 cell re-entered the cell cycle. 21612 expression levels were determined by quantitative PCR (Taqman® brand quantitative PCR kit, Applied Biosystems). The quantitative PCR reactions were performed according to the kit manufacturer's instructions.
Figure 30:
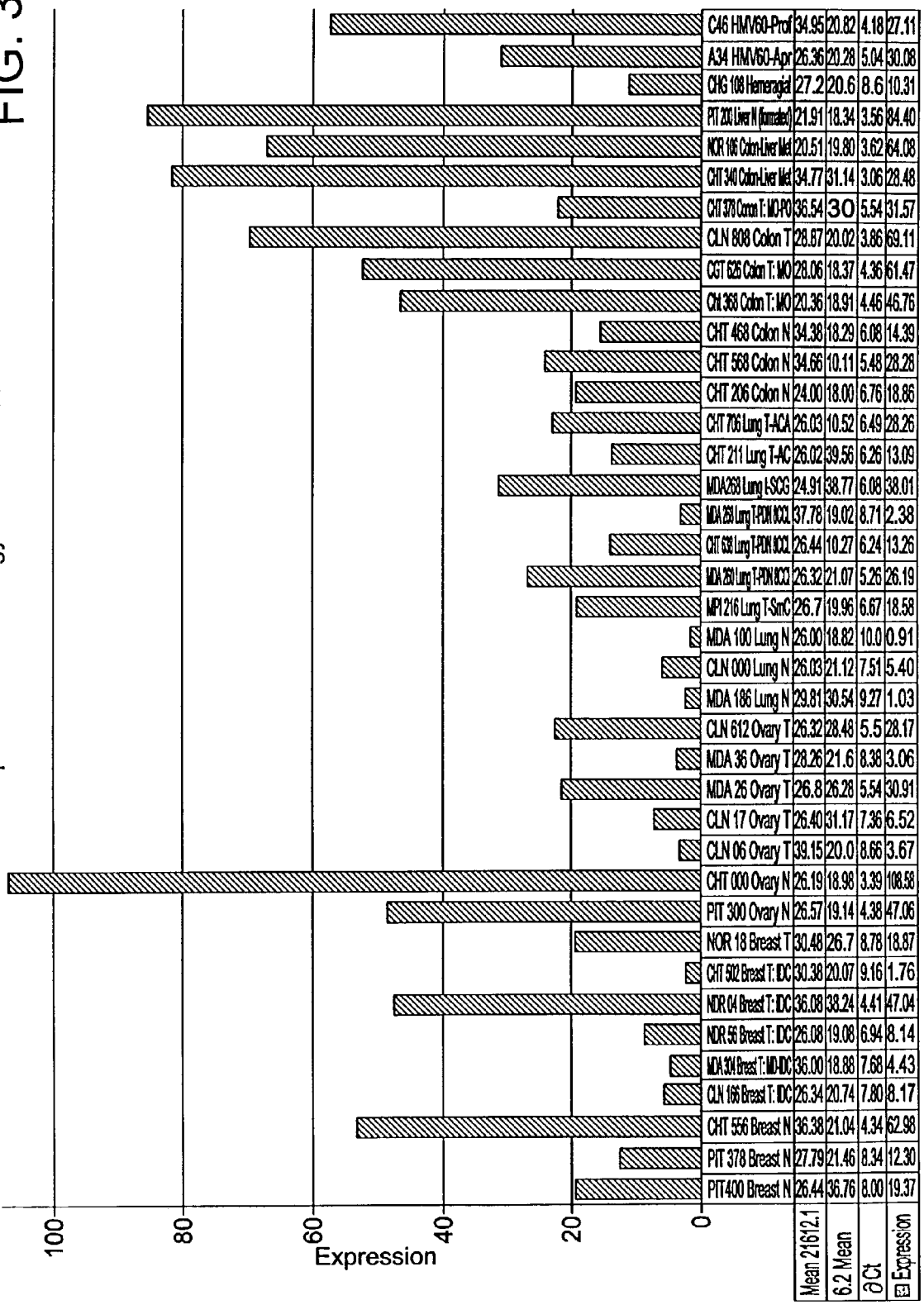
FIG. 30 shows 21612 mRNA expression in a panel of normal and oncological tissues. 21612 expression is shown for 3 normal breast tissue samples (columns 1-3); 6 breast tumor samples (columns 4-9), including invasive ductal carcinomas (columns 4, 6, 7, and 8) and moderately differentiated invasive ductal carcinomas (column 5); 2 normal ovary tissue samples (columns 10 and 11); 5 ovarian cancer samples (columns 12-16); 3 normal lung samples (columns 17-19); 7 lung cancer samples (columns 20-26), including small cell carcinoma (column 20), poorly differentiated non small cell carcinoma of the lung (columns 21-23), adenocarcinoma (column 25 and 26), 3 normal colon samples (columns 27-29); 4 colon cancer samples (columns 30-33), including moderately differentiated (columns 30 and 31) and moderately to partially differentiated tumor (column 33); two colon cancer liver metastases samples (columns 34 and 35); one normal liver sample (column 36); one hemanginoma sample (column 37), and two human pulmonary microvascular endothelial cell samples; one arresting (column 38) and one proliferating (column 39). 21612 expression levels were determined by quantitative PCR (Taqman® brand quantitative PCR kit, Applied Biosystems).
Figure 31:
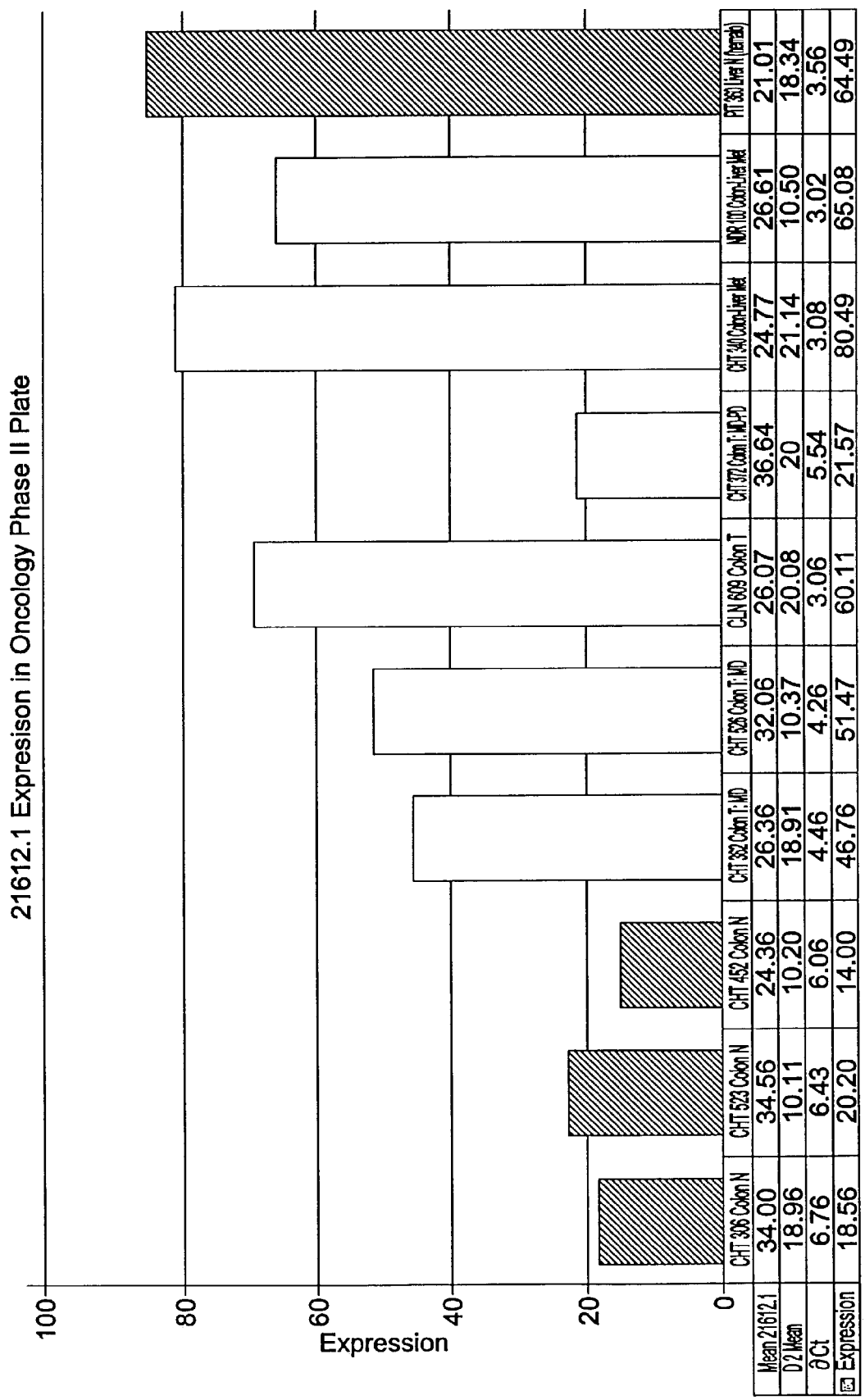
FIG. 31 shows the levels of 21612 mRNA in samples from normal colon (columns 1-3), colon cancer tissue (columns 4-7), colon cancer liver metastases (8 and 9), and normal liver (column 10). 21612 expression levels were determined by quantitative PCR as described above. Note that 21612 mRNA levels were significantly higher in 5 of 6 colon cancer and colon cancer liver metastases samples, in comparison with the expression levels in normal colon samples.
Figure 32:
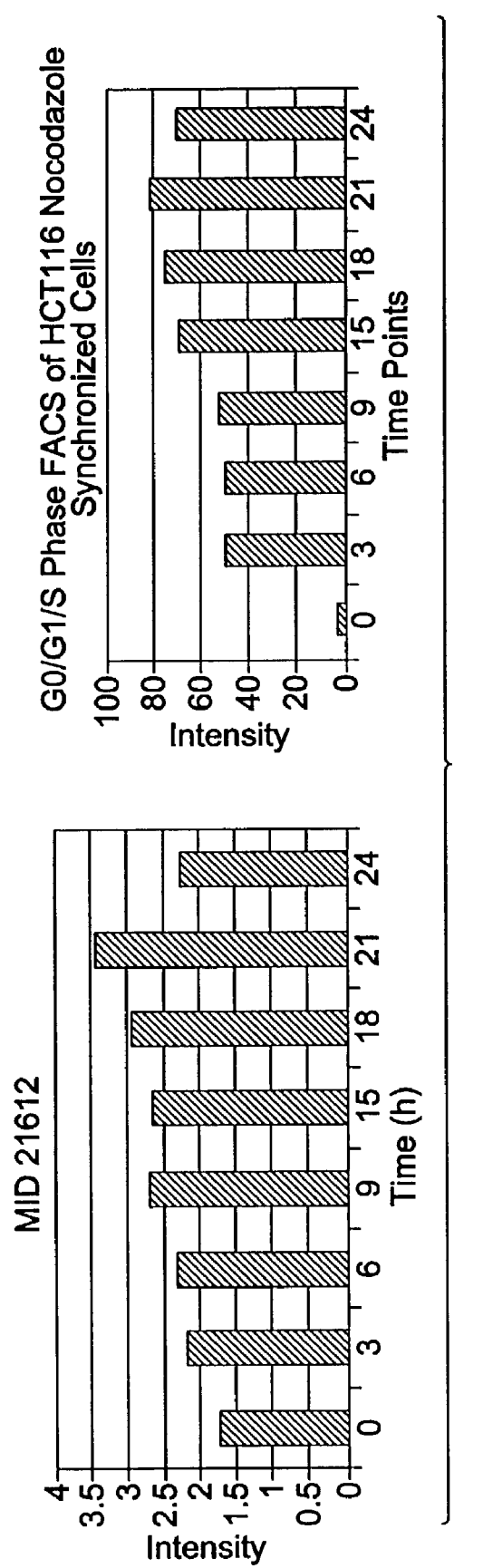
FIG. 32 shows the levels of 21612 mRNA in the human colon cancer cell line HCT116 following cell cycle synchronization with nocodazole. The first panel of this figure shows a time course the level of 21612 mRNA following synchronization. Note the 21612 levels increase for approximately 21 hours following removal of nocodazole. The second panel of this figure shows the time course of 21612 expression in a population of HCT116 cells in the $G_0$, $G_1$, or S phase of the cell cycle. Cell populations containing cells in these phase of the cell cycle were isolated by fluorescence-activated cell sorting. 21612 expression intensity at each time point was determined by microarray hybridization. Note that the levels of 21612 mRNA in $G_0/G_1/S$ phase HCT116 cells increase significantly in the first three hours following withdrawal of nocodazole.

Tissues and/or cells in which the 21620 ADH is found include, but are not limited to those shown in FIGS. 11 and 12. Tissues in which the gene is highly expressed include brain, colon, kidney, and small intestine. Moderate expression occurs in liver, muscle, and testes. Lower positive expression occurs in the aorta, breast, cervix, esophagus, heart, lung, lymph, ovary, placenta, spleen, thymus, thyroid, and vein. The 21620 ADH is also expressed in malignant breast, lung, and colon tissue, and in liver metastases derived from malignant colonic tissue.

The present invention thus provides isolated or purified polypeptides of the 21620 ADH, 33756 ADH, 21676 ADH, 21612 ADH, and 21615 ADH and variants and fragments thereof.

The short-chain alcohol dehydrogenase family signature is found in the 21620 ADH from about amino acid 166 to about amino acid 176 and in the 21615 ADH from about amino acid 147 to about amino acid 157.

Based on a Blast search, highest homology to the 21620 ADH was shown to Antennal-specific Short-chain Dehydrogenase/reductase from *Drosophila melanogaster* (Genbank Acc. No. AF 116553) and to the Oxidoreductase from *Haloferax volcani* (Genbank Acc. No. U95375).

Based on a Blast search, highest homology to the 33756 ADH was shown to CGI-82 from *Homo sapiens* (Genbank Acc. No. AF151840), UBE-1b from *Mus musculus* (Genbank Acc. No. AB030504), UBE-1a from *Mus musculus* (Genbank Acc. No. AB030503).

Based on a Blast search, no significant homology was found to the 21676 ADH.

Based on a Blast search, highest homology to the 21612 ADH was shown to a protein similar to alcohol dehydrogenase from *C. elegans* (Genbank Acc. No. U28739), a protein similar to alcohol dehydrogenase from *C. elegans* (Genbank Acc. No. Z74029), and to the hypothetical protein RV3224 from *Mycobacterium tuberculosis* (Genbank Acc. No. Z95120).

Based on a Blast search, highest homology to the 21615 ADH was shown to a 3-oxoacyl-(acyl carrier protein) reductase from *Thermotoga maritima* (Genbank Acc. No. AAD36790).

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The ADH polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the ADH having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

An ADH polypeptide is also considered to be isolated when it is part of a membrane preparation or is purified and then reconstituted with membrane vesicles or liposomes.

The language "substantially free of chemical precursors or other chemicals" includes preparations of the ADH polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the ADH polypeptides comprise the amino acid sequences shown in SEQ ID NOS:5, 7, 9, 11, and 13. However, the invention also encompasses sequence variants. Variants include a substantially homologous protein encoded by the same genetic locus in an organism, i.e., an allelic variant.

The 21620 ADH has been mapped to human chromosome 17 (17q12-21) with flanking markers WI-3010 (9.7cR) and WI-4251 (17.3cR). Mutations near this locus include, but are not limited to, the following: wilms tumor 4; patella aplasia or hypoplasia; psoriasis susceptibility 2 (psors2); malignant hyperthermia susceptibility 2 (MSH2); pallidopontonigral degeneration (PPND); pseudohypoaldosteronism type II locus B; and gliosis and familial progressive subcortical. In the mouse this locus is associated with the following: susceptibility to lung cancer (Sluc4); pulmonary adenoma resistance (Par1); radiation-induced apoptosis 4 (Rapop4); cocked (co); open eyelids (oe); ovum mutant (Om); rimy (rmy); susceptibility to experimental allergic encephalomyelitis 7 (Eae7); liver weight QTL 4 (Lwq4); alopecia (Al); spleen weight OTL 1 (Swq1); modifier of von willebrand factor (Mvwf); neuron number control (Nncl); recombination induced mutation 3 (rim3); bald-arthritic (Bda); bare skin (Bsk); rex (re); alymphoplasia (aly); cleft lip 1 (clf1); seizure susceptibility 3 (Szs3); uncovered (Uncv). Genes near this locus include CDC18L, RARA, PDE6G, IGFBP4, TCFL4, NAGLU, FZD2, PYY, ERBB2, RABL, SCYAL11, KRT12, NEUROD2, SLC6A4, ACACA, SCYA1, and BRCA1.

The 21612 ADH has been mapped to human chromosome 9 (9q22-33) with flanking markers WI-6207 (5.7 cR) and D9S174 (6.0 cR). Mutations near this locus include, but are not limited to, the following: hypomagnesemia with secondary hypocalcemia (HOMG); hemophagocytic lymphohistiocytosis, familial 1; nephronophthisis (NPHP2), infantile; HSN1, neuropathy, hereditary sensory, type 1; high density lipoprotein deficiency (HDLDT1), tangier type 1; dysautonomia (dys), familial; muscular dystrophy, limb-girdle, type 2H; acrofacial dysostosis 1 (AFD1), nager type; amyotrophic lateral sclerosis 4 (ALS4), juvenile; and multiple self-healing squamous epithelioma (MSSE). In the mouse this locus is associated with the following: vacillans (vc), whirler (wi), ochre (och), Hertwig's anemia (an), b-associated fitness (baf), iris stromal atrophy (isa), lymphoma resistance (lyr), and systemic lupus erythmatosus susceptibility 2 (sle2). Genes near this locus include SCYA5, ZFP37, UGCG, SLC31A2, HXB, HPRP4P, ORM1, TNFSF8, TXN, IKBAKAP, PTPN3, EDG2, CSMF, chondrosarcoma, myxoid extraskeletal, and fused to EWS.

Variants also encompass proteins derived from other genetic loci in an organism, but having substantial homology to the ADHs of SEQ ID NOS:5, 7, 9, 11, and 13. Variants also include proteins substantially homologous to the ADHs but derived from another organism, i.e., an ortholog. Variants also include proteins that are substantially homologous to the ADHs that are produced by chemical synthesis. Variants also include proteins that are substantially homologous to the ADHs that are produced by recombinant methods. It is understood, however, that variants exclude any amino acid sequences disclosed prior to the invention.

As used herein, two proteins (or a region of the proteins) are substantially homologous when the amino acid sequences are at least about 70-75%, typically at least about 80-85%, and most typically at least about 90-95% or more homologous. A substantially homologous amino acid sequence, according to the present invention, will be encoded by a nucleic acid sequence hybridizing to the nucleic acid sequence, or portion thereof, of the sequence shown in SEQ ID NOS:6, 8, 10, 12, and 14 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 502 amino acid residues, at least 165, preferably at least 200, more preferably at least 250, even more preferably at least 300, and even more preferably at least 350, 400, 450, and 500 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the ADH. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306-1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci.* USA 90:5873-5877. Such an algorithm is incorporated into the NBLAST and XBLAST programs (version 2.0) as described in Altschul et al. (1997) *Nucleic Acids Res.* 25:3389-3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444-453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two sequences is determined using the GAP program in the GCG software package (Devereux et al. (1984) *Nucleic Acids Res.* 12(1):387), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3-5; and FASTA described in Pearson et al. (1988) *PNAS* 85:2444-8.

A variant polypeptide can differ in amino acid sequence by one or more substitutions, deletions, insertions, inversions, fusions, and truncations or a combination of any of these.

Variant polypeptides can be fully functional or can lack function in one or more activities. For example, variants of the ADHs can have an altered developmental expression, temporal expression or tissue-preferred expression. ADH variants can also have an altered interaction with cellular components, substrates, coenzymes, metal ions, or ADH subunits. An altered interaction comprising either a higher or lower affinity of the ADH for the various cellular components, substrates, coenzymes, metal ions, or ADH subunits. By "coenzyme" is intended a molecule that is associated with the ADH and is essential for ADH activity. Some coenzymes are covalently linked to their enzyme while others are less tightly bound. A covalently linked coenzyme is referred to as a prosthetic group of the enzyme. By "coenzyme" is also intended the oxidized or reduced product of the coenzyme which is formed following the enzymatic reaction mediated by the ADH polypeptide. For example, in the biological oxidation of an alcohol to an aldehyde, a hydrogen ion is transferred to the coenzyme $NAD^+$ to form the coenzyme product NADH. Coenzymes of ADH include, but are not limited to, $NAD^+$ and $NAD^+$ analogues (Plapp et al. (1986) *Biochemistry* 25:5396-5402 and Yamazaki et al. (1984) *J. Biochem* 95:109-115), $\beta$-$NAD^+$ (Favilla et al. (1980) *Eur. J. Biochem* 104, 223-227 and Creagh et al. (1993) *Biotechnol. Bioeng.* 41:156-161, benzoylpyridine adenine dinucleotide (Samama et al. (1986) *Eur. J. biochem.* 159:375-380), NADH, $NADP^+$, and NADPH. Variants of ADH may also have altered interactions with metal ions including, but not limited to, $Zn^{2+}$, $Co^{2+}$, $Mg^{2+}$, $Fe^{2+}$. See, for example, Yabe et al. (1992) *Biosci. Biotechnol. Biochem.* 56:338-339 and Leblov et al. (1972) *Phytochemistry* 11:1345-1346. Variants of ADH can also have an altered interaction with a substrate. Substrates of ADH include, but are not limited to, primary or secondary alcohols or hemiacetals, and cyclic secondary alcohols. By "substrate" is also intended the products resulting from the oxidation of the above mentioned substrates. Such products include, for example, various aldehydes and ketones. Other substrates include retinol, steroids, and carcinogens such as nitrobenzaldehyde and 1,2-dimethylhydrazine. Variants of ADH can also have an altered subunit interaction that affects the ability of ADH to form an active multimeric structure.

Useful variants of ADH polypeptides further include alterations in catalytic activity. The enzymatic reaction mediated by ADH is reversible and comprises either the oxidation, i.e., removal of electrons, of the above mentioned substrates or their reduction, i.e., addition of electrons. The catalytic reaction further comprises the oxidation or reduction of the coenzyme. Therefore, one embodiment involves a variant that results in binding of the substrate but results in slower oxidation/reduction or no oxidation/reduction of the substrate. Another variation can result in an increased rate of substrate oxidation/reduction. Other useful variation can include an altered binding affinity for a coenzyme or substrate. For example, an increased or decreased binding affinity of a coenzyme can alter the binding affinity of the ADH to the substrate and also alter the rate of substrate oxidation/reduction. Another variation can prevent the ADH monomer from associating with other ADH subunits to form an active multimeric complex.

Another useful variation provides a fusion protein in which one or more domains or subregions are operationally fused to one or more domains or subregions from another ADH. Specifically, a domain or subregion can be introduced that alters the coenzyme or substrate specificities or the rate of the enzymatic reaction.

Fully functional variants typically contain only conservative variations or variations in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the ADH polypeptide. This includes preventing immunogenicity from pharmaceutical formulations by preventing protein aggregation.

Amino acids that are essential for function can be identified by methods known in the art, such as site-directed mutagenesis or alanine-scanning mutagenesis (Cunningham et al. (1985) *Science* 244:1081-1085). The latter procedure introduces single alanine mutations at every residue in the molecule. The resulting mutant molecules are then tested for biological activity, such as the binding affinity for the coenzyme or substrate or determining the catalytic constants for substrate oxidation/reduction. Sites that are critical for coenzyme and substrate binding can also be determined by structural analysis such as crystallization, nuclear magnetic resonance or photoaffinity labeling (Smith et al. (1992) *J. Mol. Biol.* 224:899-904; de Vos et al. (1992) *Science* 255: 306-312).

The assays for ADH enzyme activity are well known in the art and can be found for example, in Oppermann et al. (1999) *FEBS* 451:238-242, Thomasson et al. (1993) *Behavior Genetics* 23:131-136, and Zubey (1988) Macmillan Publishing Company, New York. These assays include, but are not limited to, determination of the Michaelis constants ($K_m$) or the dissociation constant for the ADH/substrate complex. Such analysis of enzyme activity may be performed spectrophotometrically by recording the change in absorbance of $NAD^+$. The catalytic efficiency or $k_{cat}$ can also be measured. $K_{cat}$ is defined as the maximum number of molecules of substrate converted to product per active site per unit of time. The specificity constant ($k_{cat}/K_M$) can also be used to measure the ability of the ADH to discriminate between competing substrates. Similar assays can also be performed to measure ADH/coenzyme interactions. In vivo measurements of ADH activity can be determined by pharmacokinetic studies. In such studies, an ethanol dose in administered and the blood ethanol concentration is monitored over time. The area under the time curve indicates the rate of ethanol elimination from the system. A larger blood alcohol concentration time curve indicates slower ethanol metabolism.

Substantial homology can be to the entire nucleic acid or amino acid sequence or to fragments of these sequences.

The invention thus also includes polypeptide fragments of the ADHs. Fragments can be derived from the amino acid sequences shown in SEQ ID NOS:5, 7, 9, 11, and 13. However, the invention also encompasses fragments of the variants of the ADHs as described herein.

The fragments to which the invention pertains, however, are not to be construed as encompassing fragments that may be disclosed prior to the present invention. Accordingly, a fragment of the 21620 ADH can comprise at least about 9, 15, 20, 25, 30, 35, 40 or more contiguous amino acids. A fragment of the 33756 ADH can comprise at least about 21, 25, 30, 35, 40, 45, 50, or more contiguous amino acids. A fragment of the 21676 ADH can comprise at least about 7, 10, 15, 20, 25, 30, 35 or more contiguous amino acids. A fragment of the 21612 ADH can comprise at least about 14, 20, 25, 30, 35, 40 or more contiguous amino acids. A fragment of the 21615 ADH can comprise at least about 7, 10, 15, 20, 25, 30, 35 or more contiguous amino acids. Fragments can retain one or more of the biological activities of the protein, for example the ability to bind a coenzyme or substrate or the ability catalyze the oxidation/reduction of a substrate. Alternatively, fragments can be used as an immunogen to generate ADH antibodies.

Biologically active fragments (peptides which are, for example, 5, 7, 10, 12, 15, 20, 30, 35, 36, 37, 38, 39, 40, 50, 100 or more amino acids in length) can comprise a domain or motif, e.g., catalytic site, substrate binding site, coenzyme binding site, short-chain alcohol dehydrogenase signature, microbodies C-terminal targeting signals, and sites for glycosylation, protein kinase C phosphorylation, casein kinase II phosphorylation, tyrosine kinase phosphorylation, and N-myristoylation. Further possible fragments include sites important for cellular and subcellular targeting.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the ADH or ADH variants. These epitope-bearing peptides are useful to raise antibodies that bind specifically to an ADH polypeptide or region or fragment. These peptides can contain at least 10, 12, at least 14, or between at least about 15 to about 30 amino acids.

Non-limiting examples of antigenic polypeptides that can be used to generate antibodies include but are not limited to peptides derived from an extracellular site. Regions having a high antigenicity index are shown in FIGS. 8, 14, 18, 22, and 26, for the 21620, 33756, 21676, 21612, and 21615 ADHs, respectfully. However, intracellularly-made antibodies ("intrabodies") are also encompassed, which would recognize intracellular peptide regions.

The epitope-bearing ADH polypeptides may be produced by any conventional means (Houghten, R. A. (1985) *Proc. Natl. Acad. Sci. USA* 82:5131-5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the ADH fragment and an additional region fused to the carboxyl terminus of the fragment.

The invention thus provides chimeric or fusion proteins. These comprise an ADH peptide sequence operatively linked to a heterologous peptide having an amino acid sequence not substantially homologous to the ADH. "Operatively linked" indicates that the ADH peptide and the heterologous peptide are fused in-frame. The heterologous peptide can be fused to the N-terminus or C-terminus of the ADH or can be internally located.

In one embodiment the fusion protein does not affect ADH function per se. For example, the fusion protein can be a GST-fusion protein in which the ADH sequences are fused to the C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant ADH. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52-58 (1995) and Johanson et al. *J. Biol. Chem.* 270:9459-9471). Thus, this invention also encompasses soluble fusion proteins containing an ADH polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). An ADH-encoding nucleic acid can be cloned into such an expression vector such that the fusion moiety is linked in-frame to the ADH.

Another form of fusion protein is one that directly affects ADH functions. Accordingly, an ADH polypeptide is encompassed by the present invention in which one or more of the ADH domains (or parts thereof) has been replaced by homologous domains (or parts thereof) from another ADH or a short-chain dehydrogenase/reductase family member. Accordingly, various permutations are possible. For example, the substrate binding domain, or subregion thereof, can be replaced with the substrate binding domain or subregion from another ADH or a short-chain dehydrogenase/reductase family member. As a further example, the catalytic domain, or coenzyme binding domains or parts thereof, can be replaced with the appropriate domain from another ADH or SDR family member. Thus, chimeric ADHs can be formed in which one or more of the native domains or subregions has been replaced by another.

Additionally, chimeric ADH proteins can be produced in which one or more functional sites is derived from a different ADH or a short-chain dehydrogenase/reductase family member. It is understood however that sites could be derived from the ADH or a short-chain dehydrogenase/reductase family members that occur in the mammalian genome but which have not yet been discovered or characterized. Such sites include but are not limited to the catalytic site, substrate binding site, coenzyme binding site, sites important for targeting to subcellular and cellular locations, sites functional for interaction with ADH subunits, protein kinase A phosphorylation sites, glycosylation sites, and other functional sites disclosed herein.

The isolated ADHs can be purified from cells that naturally express it. Tissues and cells that express high levels of the 21620 ADH include, but are not limited to, brain, colon, kidney, and small intestine. Moderate levels of expression occur in the liver, muscle, and testes. Lower positive expression occurs in the aorta, breast, cervix, esophagus, heart, lung, lymph, ovary, placenta, spleen, thymus, thyroid, and vein. The 21620 ADH is also expressed in malignant breast, lung, and colon tissue, and liver metastases derived from colon. The ADHs of the present invention can also be purified from cells that have been altered to express it (recombinant), or synthesized using known protein synthesis methods.

In one embodiment, the protein is produced by recombinant DNA techniques. For example, a nucleic acid molecule encoding the ADH polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W.H. Freeman and Company, New York (1993). Many detailed reviews are available on this subject, such as by Wold, F., *Posttranslational Covalent Modification of Proteins*, B. C. Johnson, Ed., Academic Press, New York 1-12 (1983); Seifter et al. (1990) *Meth. Enzymol.* 182: 626-646) and Rattan et al. (1992) *Ann. N.Y. Acad. Sci.* 663:48-62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The ADH polypeptides are useful for producing antibodies specific for the ADH, regions, or fragments. Regions having a high antigenicity index score are shown in FIGS. 8,14, 18,22, and 26 for the 21620 ADH, 33756 ADH, 21676 ADH, 21612 ADH, and 21615 ADH, respectfully.

The ADH polypeptides are useful for biological assays related to ADHs. Such assays involve any of the known ADH functions or activities or properties useful for diagnosis and treatment of ADH-related conditions.

The ADH polypeptides are also useful in drug screening assays, in cell-based or cell-free systems. Cell-based systems can be native, i.e., cells that normally express the ADH, as a biopsy or expanded in cell culture. In one embodiment, however, cell-based assays involve recombinant host cells expressing the ADH.

Determining the ability of the test compound to interact with the ADH can also comprise determining the ability of the test compound to preferentially bind to the polypeptide as compared to the ability of a known binding molecule (e.g. a coenzyme or substrate) to bind to the polypeptide.

The polypeptides can be used to identify compounds that modulate ADH activity. Such compounds, for example, can increase or decrease the affinity of the substrate or coenzyme for ADH. Such compound can also increase or decrease the enzymatic activity of the ADH. Additionally, such compounds can also alter the interaction of ADH with a metal ion or alter the ability of the ADH polypeptide to form a multimeric structure. Compounds that modulate ADH activity include, but are not limited to, pyrazole, 4-methylpyrazole, P-hydroxymercuribenzoate, o-Phenanthroline, iodoacetamide, iodoacetate, imidazole, colloidal bismuth subcitrate, cimetidine, ranitidine, and aspirin.

The ADHs of the present invention and appropriate variants and fragments can be used in high-throughput screens to assay candidate compounds for the ability to bind to the ADH. These compounds can be further screened against a functional ADH to determine the effect of the compound on the ADH activity. Compounds can be identified that activate (agonist) or inactivate (antagonist) the ADH to a desired degree. Modulatory methods can be performed in vitro (e.g., by culturing the cell with the agent) or, alternatively, in vivo (e.g., by administering the agent to a subject).

The ADH polypeptides can be used to screen a compound for the ability to stimulate or inhibit interaction between the ADH protein and a target molecule that normally interacts with the ADH protein. The target can be a coenzyme, metal ion, ADH substrate or another ADH subunit of the multimeric ADH enzyme. The assay includes the steps of combining the ADH protein with a candidate compound under conditions that allow the ADH protein or fragment to interact with the target molecule, and to detect the formation of a complex between the ADH protein and the target or to detect the biochemical consequence of the interaction with the ADH and the target, such as the oxidation/reduction of the substrate or coenzyme.

Determining the ability of the ADH to bind to a target molecule can also be accomplished using a technology such as real-time Bimolecular Interaction Analysis (BIA). Sjolander et al. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 97:6378-6382); (Felici (1991) *J. Mol. Biol.* 222:301-310); (Ladner supra).

Candidate compounds include, for example, 1) peptides such as soluble peptides, including Ig-tailed fusion peptides and members of random peptide libraries (see, e.g., Lam et al. (1991) *Nature* 354:82-84; Houghten et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length ADH or fragment that competes for substrate binding or cofactor binding, interferes with the ADH catalyzed reaction, or interferes with ADH subunit interactions. Other candidate compounds include mutant ADHs or appropriate fragments containing mutations that affect ADH function and thus compete for cofactor binding or substrate binding or interfere with the ADH catalyzed reaction or interferes with the ADH subunit interactions. Accordingly, a fragment that competes for substrate or coenzyme binding, for example with a higher affinity, or a fragment that binds substrate but does not catalyze its oxidation/reduction is encompassed by the invention.

The invention provides other end points to identify compounds that modulate (stimulate or inhibit) ADH activity. The assays typically involve an assay of events that result from substrate or coenzyme oxidation/reduction that indicate ADH activity. Thus, the expression of genes that are up- or down-regulated in response to the ADH enzyme can be assayed. In one embodiment, the regulatory region of such genes can be operably linked to a marker that is easily detectable, such as luciferase.

Any of the biological or biochemical functions mediated by the ADH can be used as an endpoint assay. These include all of the biochemical or biological events described herein, in the references cited herein and incorporated by reference, and other ADH functions known to those of ordinary skill in the art.

In the case of ADH, specific end points can include an altered NADH/NAD$^+$ ratio. For instance, ethanol oxidation results in an increased NADH/NAD$^+$ redox potential within the cytosol and mitochondria with subsequent alteration in several tissue metabolites. For example, the increase in cytosolic NADH/NAD$^+$ ratio causes an increase in the lactate/pyruvate ratio mediated via lactate dehydrogenase. Other consequences of ethanol- and acetaldehyde-induced redox changes include, enhanced triglyceride synthesis, inhibition of Krebs cycle activity, lactic acidosis, ketoacidosis, hyperuricaemia and enhanced fibrogenesis. See, for example, Peters et al. (1998) *Novartis Foundation Symposium* 216: 19-34, herein incorporated by reference.

Furthermore, the metabolism of ethanol via ADH results in the production of acetaldehyde, which is removed by the action of acetaldehyde dehydrogenases. Acetaldehyde alters various cellular function including glutathione depletion and inhibition of nuclear repair enzymes. Acetaldehyde can also alter cellular membranes resulting in severe cellular injury (Lieber et al. (1994) *Gastroenterology* 106:1085-105). Acetaldehyde toxicity depends on its net formation and can be increased when ADH activity is low and acetaldehyde dehydrogenase activity is high. Additional end points that can be assayed include biological events that are a consequence of ADH oxidation of retinol to retinal, which include but are not limited to differentiation of epithelium and spermatogenesis.

Binding and/or activating compounds can also be screened by using chimeric ADH proteins in which one or more domains, sites, and the like, as disclosed herein, or parts thereof, can be replaced by their heterologous counterparts derived from other ADHs or of any other short chain dehydrogenase/reductase family member. For example, a substrate binding region or coenzyme binding region can be used that interacts with a different substrate or coenzyme specificity and/or affinity than the native ADH. Accordingly, a different set of oxidized/reduced substrates or coenzymes is available as an end-point assay for activation. Alternatively, a heterologous targeting sequence can replace the native targeting sequence. This will result in different subcellular or cellular localization. As a further alternative, sites that are responsible for developmental, temporal, or tissue specificity can be replace by heterologous sites such that the ADH can be detected under conditions of specific developmental, temporal, or tissue-specific expression.

The ADH polypeptides are also useful in competition binding assays in methods designed to discover compounds that interact with the ADH. Thus, a compound is exposed to an ADH polypeptide under conditions that allow the compound to bind or to otherwise interact with the polypeptide. Soluble ADH polypeptide is also added to the mixture. If the test compound interacts with the soluble ADH polypeptide, it decreases the amount of complex formed or activity from the ADH target. This type of assay is particularly useful in cases in which compounds are sought that interact with specific regions of the ADH. Thus, the soluble polypeptide that competes with the target ADH region is designed to contain peptide sequences corresponding to the region of interest.

Another type of competition-binding assay can be used to discover compounds that interact with specific functional sites. As an example, a substrate, such as ethanol, and a candidate compound can be added to a sample of the ADH. Compounds that interact with the ADH at the same site as the ethanol will reduce the amount of complex formed between the ADH and ethanol. Accordingly, it is possible to discover a compound that specifically prevents interaction between the ADH and ethanol. Another example involves adding a candidate compound to a sample of ADH and a coenzyme, such as NAD$^+$. A compound that competes with NAD$^+$ will reduce the coenzyme interaction with ADH and thereby prevent the subsequent interaction with a substrate or the oxidation of the substrate. Accordingly, compounds can be discovered that directly interact with the ADH and compete with various coenzymes and substrates. Such assays can involve any other component that interacts with the ADH.

To perform cell free drug screening assays, it is desirable to immobilize either the ADH, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/ADH fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of ADH-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of an ADH-binding target component, such as a coenzyme or a substrate, and a candidate compound are incubated in the ADH-presenting wells and the amount of complex trapped in the well can be quantitated. Methods for detecting such complexes, in addition to those described above for the GST-immobilized complexes, include immunodetection of complexes using antibodies reactive with the ADJ target molecule, or which are reactive with ADH and compete with the target molecule; as well as enzyme-linked assays which rely on detecting an enzymatic activity associated with the target molecule.

Modulators of ADH activity identified according to these drug screening assays can be used to treat a subject with a disorder mediated by ADH, by treating cells that express the ADH. These methods of treatment include the steps of administering the modulators of ADH activity in a pharmaceutical composition as described herein, to a subject in need of such treatment.

The ADHs of the present invention are expressed in various cell types. Tissues and/or cells in which the 21620 ADH is found include, but are not limited to those shown in FIGS. 11 and 12. Tissues in which the gene is highly expressed include brain, colon, kidney, and small intestine. Moderate expression occurs in liver, muscle, and testes. Lower positive expression occurs in the aorta, breast, cervix, esophagus, heart, lung, lymph, ovary, placenta, spleen, thymus, thyroid, and vein. The 21620 ADH is also expressed in the malignant breast, lung, and colon tissue, and in colon metastases to liver.

Hence the ADHs of the present invention are relevant to treating disorders involving these tissues. Of particular interest are malignant breast, liver, colon and liver metastases derived from malignant colon tissue.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple mycloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the uterus and endometrium include, but are not limited to, endometrial histology in the menstrual cycle; functional endometrial disorders, such as anovulatory cycle, inadequate luteal phase, oral contraceptives and induced endometrial changes, and menopausal and postmenopausal changes; inflammations, such as chronic endometritis; adenomyosis; endometriosis; endometrial polyps; endometrial hyperplasia; malignant tumors, such as carcinoma of the endometrium; mixed Müllerian and mesenchymal tumors, such as malignant mixed Müllerian tumors; tumors of the myometrium, including leiomyomas, leiomyosarcomas, and endometrial stromal tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myclopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyclinating diseases, including multiple sclerosis, multiple sclerosis variants, acute disseminated encephalomyclitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myelocyiic series (polymorphoneuclear cells) make up approximately 60% of the cellular elements, and the erythrocytic series, 20-30%. Lymphocytes, monocytes, reticular cells, plasma cells and megakaryocytes together constitute 10-20%. Lymphocytes make up 5-15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2-8) of *Immunology, Immunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyangiitis (microscopic polyarteritis, hypersensitivity or leukocytoclastic angiitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus crythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including-Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angioimmunoblastic T-cell lymphoma, angiocentric lymphoma (NK/T-cell lymphoma[4a]), intestinal T-cell lymphoma, adult T-cell leukemia/lymphoma, and anaplastic large cell lymphoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Disorders in which the ADH expression is relevant include, but are not limited to, drug/alcohol interactions, susceptibility to alcoholism, alcohol-induced organ injury such as alcoholic liver cirrhosis, first-pass metabolism of alcohol, fetal alcohol syndrome, and alcohol-related cancers including, but not limited to cancers of the esophagus, oral cavity, upper gastrointestinal tract and colorectum. Furthermore, ADH expression is also relevant to alcohol-induced flushing. Alcohol-induced flushing is characterized by the rapid onset of skin vasodilation of the face, neck and chest regions after consumption of small amounts of alcohol. Tachycardia, headache, nausea, hypotension, and extreme drowsiness are also common symptoms of alcohol-induced flushing. Flush reactions have been correlated with a deficiency or absence of the ADH2 enzyme activity. ADH expression is also relevant in the pathogenesis of male sterility and skin diseases, such as psoriasis. Oxidoreductases have also been implicated in the pathophysiology of neurodegenerative disorders and apoptotic processes related to diseases such as Alzheimer's disease.

Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

A therapeutic agent includes, but is not limited to, small molecules, peptides, antibodies, ribozymes and antisense oligonucleotides.

The ADH polypeptides are thus useful for treating an ADH-associated disorder characterized by aberrant expression or activity of an ADH. In one embodiment, the method involves administering an agent (e.g., an agent identified by a screening assay described herein), or combination of agents that modulates (e.g., upregulates or downregulates) expression or activity of the protein. In another embodiment, the method involves administering the ADH as therapy to compensate for reduced or aberrant expression or activity of the protein.

Methods for treatment include but are not limited to the use of soluble ADH or fragments of the ADH protein that compete for substrate or coenzyme binding, interfere with subunit interaction, or interfere with the reaction mediated by the ADH polypeptide. These ADHs or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer). In another example, the subject has a disorder mediated by an altered $NADH/NAD^+$ redox potential, as described herein.

In yet another aspect of the invention, the proteins of the invention can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO 94/10300), to identify other proteins (captured proteins) which bind to or interact with the proteins of the invention and modulate their activity.

The ADH polypeptides also are useful to provide a target for diagnosing a disease or predisposition to disease mediated by the ADH, including, but not limited to, diseases involving tissues in which the ADHs are expressed as disclosed herein, and particularly in breast, lung, colon, and liver metastases derived from malignant colon tissue. Accordingly, methods are provided for detecting the presence, or levels of, the ADH in a cell, tissue, or organism. The method involves contacting a biological sample with a compound capable of interacting with the ADH such that the interaction can be detected.

One agent for detecting ADH is an antibody capable of selectively binding to ADH. A biological sample includes tissues, cells and biological fluids isolated from a subject, as well as tissues, cells and fluids present within a subject.

The ADH also provides a target for diagnosing active disease, or predisposition to disease, in a patient having a variant ADH. Thus, ADH can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered ADH activity in cell-based or cell-free assay, alteration in substrate or coenzyme binding, altered interaction with ADH subunits, altered rate of substrate oxidation/reduction, altered antibody-binding pattern, altered isoelectric point, direct amino acid sequencing, and any other of the known assay techniques useful for detecting mutations in a protein in general or in an ADH specifically.

In vitro techniques for detection of ADH include enzyme linked immunosorbent assays (ELISAs), Western blots, immunoprecipitations and immunofluorescence. Alternatively, the protein can be detected in vivo in a subject by introducing into the subject a labeled anti-ADH antibody. For example, the antibody can be labeled with a radioactive marker whose presence and location in a subject can be detected by standard imaging techniques. Particularly useful are methods, which detect the allelic variant of the ADH expressed in a subject, and methods, which detect fragments of the ADH in a sample.

The ADH polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10-11):983-985, and Linder, M. W. (1997) *Clin. Chem.* 43(2):254-266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the ADH in which one or more of the ADH functions in one population is different from those in another population. The polypeptides thus allow a target to ascertain a genetic predisposition that can affect treatment modality. Thus, in an ADH-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The ADH polypeptides are also useful for monitoring therapeutic effects during clinical trials and other treatment. Thus, the therapeutic effectiveness of an agent that is designed to increase or decrease gene expression, protein levels or ADH activity can be monitored over the course of treatment using the ADH polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the ADH and its variants and fragments. An antibody is considered to selectively bind, even if it also binds to other proteins that are not substantially homologous with the ADH. These other proteins share homology with a fragment or domain of the ADH. This conservation in specific regions gives rise to antibodies that bind to both proteins by virtue of the homologous sequence. In this case, it would be understood that antibody binding to the ADH is still selective.

To generate antibodies, an isolated ADH polypeptide is used as an immunogen to generate antibodies using standard techniques for polyclonal and monoclonal antibody preparation. Either the full-length protein or antigenic peptide fragment can be used. Regions having a high antigenicity index are shown in FIGS. 8, 14, 18, 22, 26 and 30.

Antibodies are preferably prepared from these regions or from discrete fragments in these regions. However, antibodies can be prepared from any region of the peptide as described herein. A preferred fragment produces an antibody that diminishes or completely prevents substrate or coenzyme binding or prevents the oxidation of substrate. Antibodies can be developed against the entire ADH or domains of the ADH as described herein. Antibodies can also be developed against specific functional sites as disclosed herein.

The antigenic peptide can comprise a contiguous sequence of at least 12, 14, 15, or amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g., Fab or $F(ab')_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

An appropriate immunogenic preparation can be derived from native, recombinantly expressed, or chemically synthesized peptides.

Antibody Uses

The antibodies can be used to isolate an ADH by standard techniques, such as affinity chromatography or immunoprecipitation. The antibodies can facilitate the purification of the natural ADH from cells and recombinantly produced ADH expressed in host cells.

The antibodies are useful to detect the presence of ADH in cells or tissues to determine the pattern of expression of the ADH among various tissues in an organism and over the course of normal development.

The antibodies can be used to detect ADH in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length ADH can be used to identify ADH turnover.

Further, the antibodies can be used to assess ADH expression in disease states such as in active stages of the disease or in an individual with a predisposition toward disease related to ADH function. When a disorder is caused by an inappropriate tissue distribution, developmental expression, or level of expression of the ADH protein, the antibody can be prepared against the normal ADH protein. If a disorder is characterized by a specific mutation in the ADH, antibodies specific for this mutant protein can be used to assay for the presence of the specific mutant ADH. However, intracellularly-made antibodies ("intrabodies") are also encompassed, which would recognize intracellular ADH peptide regions.

The antibodies can also be used to assess normal and aberrant subcellular localization of cells in the various tissues in an organism. Antibodies can be developed against the whole ADH or portions of the ADH.

The diagnostic uses can be applied, not only in genetic testing, but also in monitoring a treatment modality. Accordingly, where treatment is ultimately aimed at correcting ADH expression level or the presence of aberrant ADHs and aberrant tissue distribution or developmental expression, antibodies directed against the ADH or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic ADH can be used to identify individuals that require modified treatment modalities.

The antibodies are also useful as diagnostic tools as an immunological marker for aberrant ADH analyzed by electrophoretic mobility, isoelectric point, tryptic peptide digest, and other physical assays known to those in the art.

The antibodies are also useful for tissue typing. Thus, where a specific ADH has been correlated with expression in a specific tissue, antibodies that are specific for this ADH can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting ADH function, for example, blocking substrate or coenzyme binding or disrupting the oxidation/reduction of substrate.

These uses can also be applied in a therapeutic context in which treatment involves inhibiting ADH function. An antibody can be used, for example, to block coenzyme or substrate binding. Antibodies can be prepared against specific fragments containing sites required for function or against intact ADH associated with a cell.

Completely human antibodies are particularly desirable for therapeutic treatment of human patients. For an overview of this technology for producing human antibodies, see Lonberg et al. (1995) *Int. Rev. Immunol.* 13:65-93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of an ADH protein in a biological sample. The kit can comprise antibodies such as a labeled or labelable antibody and a compound or agent for detecting ADH in a biological sample; means for determining the amount of ADH in the sample; and means for comparing the amount of ADH in the sample with a standard. The compound or agent can be packaged in a suitable container. The kit can further comprise instructions for using the kit to detect ADH.

Polynucleotides

The nucleotide-sequences in SEQ ID NOS:6, 8, 10, 12, and 14, were obtained by sequencing the deposited human cDNA. Accordingly, the sequence of the deposited clones are controlling as to any discrepancies between the two and any reference to the sequences of SEQ ID NOS:6, 8, 10, 12, and 14, includes reference to the sequences of the deposited cDNAs.

The specifically disclosed cDNAs comprise the coding region and 5' and 3' untranslated sequences in SEQ ID NOS:6, 8, 10, 12, and 14.

The invention provides isolated polynucleotides encoding the novel ADHs. The term "ADH polynucleotide" or "ADH nucleic acid" refers to the sequences shown in SEQ ID NOS:6, 8, 10, 12, and 14 or in the deposited cDNAs. The term "ADH polynucleotide" or "ADH nucleic acid" further includes variants and fragments of the ADH polynucleotides.

An "isolated" ADH nucleic acid is one that is separated from other nucleic acid present in the natural source of the ADH nucleic acid. Preferably, an "isolated" nucleic acid is free of sequences which naturally flank the ADH nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the ADH nucleic acid is isolated from flanking sequences such that it can be subjected to the specific manipulations described herein, such as recombinant expression, preparation of probes and primers, and other uses specific to the ADH nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The ADH polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The ADH polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

ADH polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

ADH nucleic acid can comprise the nucleotide sequences shown in SEQ ID NOS:6, 8, 10, 12, and 14, corresponding to human the 21620, 33756, 21676, 21612, and 21615 ADH cDNAs, respectfully.

In one embodiment, the ADH nucleic acid comprises only the coding region.

The invention further provides variant ADH polynucleotides, and fragments thereof, that differ from the nucleotide sequences shown in SEQ ID NOS:6, 8, 10, 12, and 14 due to degeneracy of the genetic code and thus encode the same protein as that encoded by the nucleotide sequences shown in SEQ ID NOS:6, 8, 10, 12, and 14.

The invention also provides ADH nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with nucleic acid molecules of SEQ ID NOS:6, 8, 10, 12, and 14, and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding an ADH that is at least about 60-65%, 65-70%, typically at least about 70-75%, more typically at least about 80-85%, and most typically at least about 90-95% or more homologous to the nucleotide sequence shown in SEQ ID NOS:6, 8, 10, 12, and 14, or a fragment of this sequence. Such nucleic acid molecules can readily be identified as being able to hybridize under stringent conditions, to the nucleotide sequence shown in SEQ ID NOS:6, 8, 10, 12, and 14 or a fragment of the sequence. It is understood that stringent hybridization does not indicate substantial homology where it is due to general homology, such as poly A sequences, or sequences common to all or most proteins, all ADHs, or all short-chain dehydrogenase/reductases. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60-65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1-6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50-65° C. In another non-limiting example, nucleic acid molecules are allowed to hybridize in 6× sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:6, 8, 10, 12, and 14 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NOS:6, 8, 10, 12, and 14 or the complement of SEQ ID NOS: 6, 8, 10, 12, and 14. In one embodiment, the nucleic acid consists of a portion of the nucleotide sequence of SEQ ID NOS: 6, 8, 10, 12, and 14, and the complement of SEQ ID NOS: 6, 8, 10, 12, and 14.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 12, preferably at least about 15, 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

For the 21620 ADH, for example, nucleotide sequences from about 265 to about 300, from about 782 to about 870, from about 1003 to about 1035, and from about 1096 to about 1158 are not disclosed prior to the present invention. The nucleotide sequences from about 1 to about 301 encompasses fragments greater than about 125, 135, 145 or 155 nucleotides; the nucleotide sequences from about 138 to about 1159 encompasses fragments greater than 268, 280, 290, or 300 nucleotides; the nucleotide sequences from about 871 to about 1560 encompasses fragments greater than 265, 275, 285, or 295; and the nucleotide sequences from about 1036 to about 1877 encompasses fragments greater than 266, 275, 285, or 295 nucleotides.

For the 33756ADH, for example, nucleotide sequences from about 66 to about 242 are not disclosed prior to the present invention. The nucleotide sequences from about 1 to about 454 encompass fragments greater than 21, 25, 30, or 35 nucleotides; the nucleotide sequences from about 1 to about 700 encompass fragments greater than 240, 250, 260 or 275 nucleotide; and the nucleotide sequences from about 1 to about 1153 encompass fragments greater than 574, 580, 590 or 600 nucleotides.

For the 21676 ADH, for example, nucleotide sequences from about 1 to about 14, from about 69 to about 94, and from about 206 to about 1699 are not disclosed prior to the present invention. The nucleotide sequences from about 1 to about 206 encompasses fragments greater than 20, 25, 30, 35, 40 or 45 nucleotides.

For the 21612 ADH, for example, nucleotide sequences from about 32 to about 51, from about 679 to about 710, and from about 1525 to about 2535 are not disclosed prior to the present invention. The nucleotide sequences from about 1 to about 678 encompasses fragments greater than 247, 260, 270, or 280 nucleotides and the nucleotide sequences from about 147 to about 2535 encompasses fragments greater than 417, 425, 435, 445 or 455 nucleotides.

For the 21615 ADH, for example, nucleotide sequences from about 538 to about 1615 are not disclosed prior to the present invention. The nucletotide sequence from about nucleotide 1 to about nucleotide 788 encompasses fragments greater than 230, 240, 250 or 260 nucleotides and the nucleotide sequence from about nucleotide 442 to about 1615 encompasses fragments greater than 670, 680, 690 or 700 nucleotides.

Furthermore, the invention provides polynucleotides that comprise a fragment of the full-length ADH polynucleotides. The fragment can be single or double-stranded and can comprise DNA or RNA. The fragment can be derived from either the coding or the non-coding sequence.

In another embodiment an isolated ADH nucleic acid encodes the entire coding region. In another embodiment the isolated ADH nucleic acid encodes a sequence corresponding to the mature protein. For example, the mature form of the 21676 ADH is from about amino acid 16 to the last amino acid. Other fragments include nucleotide sequences encoding the amino acid fragments described herein.

Thus, ADH nucleic acid fragments further include sequences corresponding to the domains described herein, subregions also described, and specific functional sites. ADH nucleic acid fragments also include combinations of the domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains.

However, it is understood that an ADH fragment includes any nucleic acid sequence that does not include the entire gene.

The invention also provides ADH nucleic acid fragments that encode epitope bearing regions of the ADH proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497-1500. Typically, a probe comprises a region of nucleotide sequence that hybridizes under highly stringent conditions to at least about 15, typically about 20-25, and more typically about 40, 50 or 75 consecutive nucleotides of the nucleic acid sequence shown in SEQ ID NOS: 6, 8, 10, 12, and 14 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The ADH polynucleotides are thus useful for probes, primers, and in biological assays.

Where the polynucleotides are used to assess ADH properties or functions, such as in the assays described herein, all or less than all of the entire cDNA can be useful. Assays specifically directed to ADH functions, such as assessing agonist or antagonist activity, encompass the use of known fragments. Further, diagnostic methods for assessing ADH function can also be practiced with any fragment, including those fragments that may have been known prior to the invention. Similarly, in methods involving treatment of ADH dysfunction, all fragments are encompassed including those, which may have been known in the art.

The ADH polynucleotides are useful as a hybridization probe for cDNA and genomic DNA to isolate a full-length cDNA and genomic clones encoding the polypeptides described in SEQ ID NOS:5, 7, 9, 11, and 13, and to isolate cDNA and genomic clones that correspond to variants producing the same polypeptides shown in SEQ ID NOS: 5, 7, 9, 11, and 13 or the other variants described herein. Variants can be isolated from the same tissue and organism from which the polypeptides shown in SEQ ID NOS: 5, 7, 9, 11, and 13, were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the ADH. Accordingly, it could be derived from 5' noncoding regions, the coding region, and 3' noncoding regions.

The nucleic acid probe can be, for example, the full-length cDNA of SEQ ID NOS:6, 8, 10, 12, and 14, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NOS:6, 8, 10, 12, and 14, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357-63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell ADHs in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958-976) or intercalating agents (see, e.g., Zon (1988) *Pharm Res.* 5:539-549).

The ADH polynucleotides are also useful as primers for PCR to amplify any given region of an ADH polynucleotide.

The ADH polynucleotides are also useful for constructing recombinant vectors. Such vectors include expression vectors that express a portion of, or all of, the ADH polypeptides. Vectors also include insertion vectors, used to integrate into another polynucleotide sequence, such as into the cellular genome, to alter in situ expression of ADH genes and gene products. For example, an endogenous ADH coding sequence can be replaced via homologous recombination with all or part of the coding region containing one or more specifically introduced mutations.

The ADH polynucleotides are also useful for expressing antigenic portions of the ADH proteins.

The ADH polynucleotides are also useful as probes for determining the chromosomal positions of the ADH polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783-787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The ADH polynucleotide probes are also useful to determine patterns of the presence of the gene encoding the ADHs and their variants with respect to tissue distribution, for example, whether gene duplication has occurred and whether the duplication occurs in all or only a subset of tissues. The genes can be naturally occurring or can have been introduced into a cell, tissue, or organism exogenously.

The ADH polynucleotides are also useful for designing ribozymes corresponding to all, or a part, of the mRNA produced from genes encoding the polynucleotides described herein.

The ADH polynucleotides are also useful for constructing host cells expressing a part, or all, of the ADH polynucleotides and polypeptides.

The ADH polynucleotides are also useful for constructing transgenic animals expressing all, or a part, of the ADH polynucleotides and polypeptides.

The ADH polynucleotides are also useful for making vectors that express part, or all, of the ADH polypeptides.

The ADH polynucleotides are also useful as hybridization probes for determining the level of ADH nucleic acid expression. Accordingly, the probes can be used to detect the presence of, or to determine levels of, ADH nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the ADH genes.

Alternatively, the probe can be used in an in situ hybridization context to assess the position of extra copies of the ADH genes, as on extrachromosomal elements or as integrated into chromosomes in which the ADH gene is not normally found, for example as a homogeneously staining region.

These uses are relevant for diagnosis of disorders involving an increase or decrease in ADH expression relative to normal, such as a proliferative disorder or a differentiative or developmental disorder.

Tissues and/or cells in which the 21620 ADH is expressed are shown in FIGS. 11 and 12 and are described above herein. As such, the gene is particularly relevant for the treatment of disorders involving these tissues.

Furthermore, disorders in which ADH expression is relevant are disclosed herein above.

Thus, the present invention provides a method for identifying a disease or disorder associated with aberrant expression or activity of ADH nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the ADH, such as by measuring the level of an ADH-encoding nucleic acid in a sample of cells from a subject e.g., mRNA or genomic DNA, or determining if the ADH gene has been mutated.

Nucleic acid expression assays are useful for drug screening to identify compounds that modulate ADH nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the ADH gene. The method typically includes assaying the ability of the compound to modulate the expression of the ADH nucleic acid and thus identifying a compound that can be used to treat a disorder characterized by undesired ADH nucleic acid expression.

The assays can be performed in cell-based and cell-free systems. Cell-based assays include cells naturally expressing the ADH nucleic acid or recombinant cells genetically engineered to express specific nucleic acid sequences.

Alternatively, candidate compounds can be assayed in vivo in patients or in transgenic animals.

The assay for ADH nucleic acid expression can involve direct assay of nucleic acid levels, such as mRNA levels, or on collateral compounds involved in the ADH catalyzed reaction (such as oxidized/reduced products, $NAD^+/NADH$ ratio, or components of the retinoic and signaling pathway). Further, the expression of genes that are up- or down-regulated in response to the ADH signal pathway can also be assayed. In this embodiment the regulatory regions of these genes can be operably linked to a reporter gene such as luciferase.

Thus, modulators of ADH gene expression can be identified in a method wherein a cell is contacted with a candidate compound and the expression of mRNA determined. The level of expression of ADH mRNA in the presence of the candidate compound is compared to the level of expression of ADH mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate ADH nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid. Disorders that the gene is particularly relevant for treating have been disclosed herein above.

Alternatively, a modulator for ADH nucleic acid expression can be a small molecule or drug identified using the screening assays described herein as long as the drug or small molecule inhibits the ADH nucleic acid expression.

The ADH polynucleotides are also useful for monitoring the effectiveness of modulating compounds on the expression or activity of the ADH gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The ADH polynucleotides are also useful in diagnostic assays for qualitative changes in ADH nucleic acid, and particularly in qualitative changes that lead to pathology. The polynucleotides can be used to detect mutations in ADH genes and gene expression products such as mRNA. The polynucleotides can be used as hybridization probes to detect naturally-occurring genetic mutations in the ADH gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the ADH gene associated with a dysfunction provides a diagnostic tool for an active disease or susceptibility to disease when the disease results from overexpression, underexpression, or altered expression of an ADH.

Mutations in the ADH gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *PNAS* 91:360-364), the latter of which can be particularly useful for detecting point mutations in the gene (see Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in an ADH gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant ADH gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286-295), electrophoretic mobility of mutant and wild type nucleic acid is compared (Orita et al. (1989) *PNAS* 86:2766; Cotton et al. (1993) *Mutat. Res.* 285:125-144; and Hayashi et al. (1992) *Genet. Anal. Tech. Appl.* 9:73-79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244-255; Kozal et al. (1996) *Nature Medicine* 2:753-759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The ADH polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the ADH gene that results in altered affinity for a coenzyme could result in an excessive or decreased drug effect with standard concentrations of the coenzyme that activates the ADH. Accordingly, the ADH polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The ADH polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The ADH polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the ADH sequence can be used to provide an alternative technique, which determines the actual DNA sequence of selected fragments in the genome of an individual. Thus, the ADH sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The ADH sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The ADH polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The ADH polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The ADH polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of ADH probes can be used to identify tissue by species and/or by organ type.

In a similar fashion, these primers and probes can be used to screen tissue culture for contamination (i.e. screen for the presence of a mixture of different types of cells in a culture).

Alternatively, the ADH polynucleotides can be used directly to block transcription or translation of ADH gene sequences by means of antisense or ribozyme constructs. Thus, in a disorder characterized by abnormally high or undesirable ADH gene expression, nucleic acids can be directly used for treatment.

The ADH polynucleotides are thus useful as antisense constructs to control ADH gene expression in cells, tissues, and organisms. A DNA antisense polynucleotide is designed to be complementary to a region of the gene involved in transcription, preventing transcription and hence production of ADH protein. An antisense RNA or DNA polynucleotide would hybridize to the mRNA and thus block translation of mRNA into ADH protein.

Examples of antisense molecules useful to inhibit nucleic acid expression include antisense molecules complementary to a fragment of the 5' untranslated region of SEQ ID NOS:6, 8, 10, 12, and 14, which also includes the start codon and antisense molecules which are complementary to a fragment of the 3' untranslated region of SEQ ID NOS:6, 8, 10, 12, and 14.

Alternatively, a class of antisense molecules can be used to inactivate mRNA in order to decrease expression of an ADH nucleic acid. Accordingly, these molecules can treat a disorder characterized by abnormal or undesired ADH nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the ADH protein.

The ADH polynucleotides also provide vectors for gene therapy in patients containing cells that are aberrant in ADH gene expression. Thus, recombinant cells, which include the patient's cells that have been engineered ex vivo and returned to the patient, are introduced into an individual where the cells produce the desired ADH protein to treat the individual.

The invention also encompasses kits for detecting the presence of an ADH nucleic acid in a biological sample. For example, the kit can comprise reagents such as a labeled or labelable nucleic acid or agent capable of detecting ADH nucleic acid in a biological sample; means for determining the amount of ADH nucleic acid in the sample; and means for comparing the amount of ADH nucleic acid in the sample with a standard. The compound or agent can be packaged in a suitable container. The kit can further comprise instructions for using the kit to detect ADH mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention.

Examples of such software includes, but is not limited to, MacPattern (EMBL), BLASTN and BLASTX (NCBIA).

For example, software which implements the BLAST (Altschul et al. (1990) *J. Mol. Biol.* 215:403-410) and BLAZE (Brutlag et al. (1993) *Comp. Chem.* 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the ADH polynucleotides. The term "vector" refers to a vehicle, preferably a nucleic acid molecule that can transport the ADH polynucleotides. When the vector is a nucleic acid molecule, the ADH polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the ADH polynucleotides. Alternatively, the vector may integrate into the host cell genome and produce additional copies of the ADH polynucleotides when the host cell replicates.

The invention provides vectors for the maintenance (cloning vectors) or vectors for expression (expression vectors) of the ADH polynucleotides. The vectors can function in procaryotic or eukaryotic cells or in both (shuttle vectors).

Expression vectors contain cis-acting regulatory regions that are operably linked in the vector to the ADH polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the ADH polynucleotides from the vector. Alternatively, a trans-acting factor may be supplied by the host cell. Finally, a trans-acting factor can be produced from the vector itself.

It is understood, however, that in some embodiments, transcription and/or translation of the ADH polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual 2nd. ed.*, Cold Spring Harbor Laboratory Press, Cold Spring Harbor, N.Y.).

A variety of expression vectors can be used to express an ADH polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual 2nd. ed.*, Cold Spring Harbor Laboratory Press, Cold Spring Harbor, N.Y. X The regulatory sequence may provide constitutive expression in one or more host cells (i.e., tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The ADH polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the ADH polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301-315) and pET 11d (Studier et al. (1990) *Gene Expression Technology: Methods in Enzymology* 185:60-89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119-128). Alternatively, the sequence of the polynucleotide of interest can be altered to provide preferential codon usage for a specific host cell, for example *E. coli*. (Wada et al. (1992) *Nucleic Acids Res.* 20:2111-2118).

The ADH polynucleotides can also be expressed by expression vectors that are operative in yeast. Examples of vectors for expression in yeast e.g., *S. cerevisiae* include pYepSec1 (Baldari et al. (1987) *EMBO J.* 6:229-234), pMFa (Kurjan et al. (1982) *Cell* 30:933-943), pJRY88 (Schultz et al. (1987) *Gene* 54:113-123), and pYES2 (Invitrogen Corporation, San Diego, Calif.).

The ADH polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow et al. (1989) *Virology* 170:31-39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187-195).

The expression vectors listed herein are provided by way of example only of the well-known vectors available to those of ordinary skill in the art that would be useful to express the ADH polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual 2nd, ed., Cold Spring Harbor Laboratory*, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the ADH polynucleotides can be introduced either alone or with other polynucleotides that are not related to the ADH polynucleotides such as those providing trans-acting factors for expression vectors. When more than one vector is introduced into a cell, the vectors can be introduced independently, co-introduced or joined to the ADH polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the ADH polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing ADH proteins or polypeptides that can be further purified to produce desired amounts of ADH protein or fragments. Thus, host cells containing expression vectors are useful for polypeptide production.

Host cells are also useful for conducting cell-based assays involving the ADH or ADH fragments. Thus, a recombinant host cell expressing a native ADH is useful to assay for compounds that stimulate or inhibit ADH function. This includes gene expression at the level of transcription or translation, interactions with coenzymes, substrates or ADH subunits, and catalysis of substrate oxidation/reduction.

Host cells are also useful for identifying ADH mutants in which these functions are affected. If the mutants naturally occur and give rise to a pathology, host cells containing the mutations are useful to assay compounds that have a desired effect on the mutant ADH (for example, stimulating or inhibiting function) which may not be indicated by their effect on the native ADH.

Recombinant host cells are also useful for expressing the chimeric polypeptides described herein to assess compounds that activate or suppress activation by means of a heterologous domain, segment, site, and the like, as disclosed herein.

Further, mutant ADHs can be designed in which one or more of the various functions is engineered to be increased or decreased (e.g., coenzyme, substrate, or ADH subunits) and used to augment or replace ADH proteins in an individual. Thus, host cells can provide a therapeutic benefit by replacing an aberrant ADH or providing an aberrant ADH that provides a therapeutic result. In one embodiment, the cells provide ADHs that are abnormally active.

In another embodiment, the cells provide ADH that are abnormally inactive. These ADHs can compete with endogenous ADHs in the individual.

In another embodiment, cells expressing ADHs that are not catalytically active, are introduced into an individual in order to compete with endogenous ADHs for substrate, coenzymes or ADH subunits. For example, in the case in which excessive amounts of an ADH substrate is part of a treatment modality, it may be necessary to inactivate this molecule at a specific point in treatment. Providing cells that compete for the molecule, but which cannot be affected by ADH activation would be beneficial.

Homologously recombinant host cells can also be produced that allow the in situ alteration of endogenous ADH polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the ADH polynucleotides or sequences proximal or distal to an ADH gene are allowed to integrate into a host cell genome by homologous recombination where expression of the gene can be affected. In one embodiment, regulatory sequences are introduced that either increase or decrease expression of an endogenous sequence. Accordingly, an ADH protein can be produced in a cell not normally producing it. Alternatively, increased expression of ADH protein can be effected in a cell normally producing the protein at a specific level. Further, expression can be decreased or eliminated by introducing a specific regulatory sequence. The regulatory sequence can be heterologous to the ADH protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant ADH proteins. Such mutations could be introduced, for example, into the specific functional regions such as the substrate-binding site.

In one embodiment, the host cell can be a fertilized oocyte or embryonic stem cell that can be used to produce a transgenic animal containing the altered ADH gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous ADH gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of an ADH protein and identifying and evaluating modulators of ADH protein activity.

Other examples of transgenic animals include non-human primates, sheep, dogs, cows, goats, chickens, and amphibians.

In one embodiment, a host cell is a fertilized oocyte or an embryonic stem cell into which ADH polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the ADH nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the ADH protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse*

Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect substrate and coenzyme binding, and oxidation of the substrate may not be evident from in vitro cell-free or cell-based assays. Accordingly, it is useful to provide non-human transgenic animals to assay in vivo ADH function, including substrate and coenzyme interactions and substrate oxidation. Similar methods could be used to determine the effect of specific mutant ADHs and the effect of chimeric ADHs on such enzyme functions. It is also possible to assess the effect of null mutations, that is mutations that substantially or completely eliminate one or more ADH functions.

In general, methods for producing transgenic animals include introducing a nucleic acid sequence according to the present invention, the nucleic acid sequence capable of expressing the ADH protein in a transgenic animal, into a cell in culture or in vivo. When introduced in vivo, the nucleic acid is introduced into an intact organism such that one or more cell types and, accordingly, one or more tissue types, express the nucleic acid encoding the ADH protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The ADH nucleic acid molecules, protein (such as an extracellular loop), modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an ADH protein or anti-ADH antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

CHAPTER 3

23484, a Novel Human Ubiquitin Protease

BACKGROUND OF THE INVENTION

The Ubiquitin System

Several biological processes are controlled by the ubiquitination of cellular protein. Cellular processes that are affected by ubiquitin modification include the regulation of gene expression, regulation of the cell cycle and cell division, cellular housekeeping, cell-specific metabolic pathways, disposal of mutated or post-translationally damaged proteins, the cellular stress response, modification of cell surface receptors, DNA repair, import of proteins into mitochondria, uptake of precursors into neurons, biogenesis of mitochondria, ribosomes, and peroxisomes, apoptosis, and growth factor-mediated signal transduction.

For some protein substrates ubiquitination leads to protein degradation by the 26S proteasomal complex. A wide variety of protein substrates are degraded by the 26S proteasomal complex following ubiquitination of the substrate. Degradation of a protein by the ubiquitin system involves two steps. The first involves the covalent attachment of multiple ubiquitin molecules to the substrate protein. The second involves degradation of the ubiquitinated protein by the 26S proteasome. In some cases, degradation of the ubiquitinated protein can occur by means of the lysosomal pathway.

The 26S proteasome comprises a 20S core catalytic complex which is flanked by two 19S regulatory complexes. The 26S complex recognizes ubiquitinated proteins. Substrate recognition by the 26S proteasome, however, may be mediated by the interaction of specific subunits of the 19S complex with the ubiquitin chain. The ubiquitinated protein is degraded by specific and energy-dependent proteases into free amino acids and free and reutilizable ubiquitin.

The 19S regulatory complex consists of many subunits that can be classified into ATPases and non-ATPases. This complex is thought to act in recognition, unfolding, and translocation of the substrates into the 20S proteasome for proteolysis. The regulatory complex contains isopeptidases capable of deubiquitinating substrates (Spataro et al. (1998) *British Journal of Cancer* 77:448-455).

The ubiquitin proteasome pathway functions to degrade abnormal proteins, short-lived normal proteins, long-lived normal proteins, and proteins of the endoplasmic recticulum. Important regulatory proteins rapidly inactivated by proteolysis include c-JUN, c-FOS, and p53 (Lecker et al. (1999) *Journal of Nutrition* 129:227 S-237S). Conditions that stimulate protein degradation by the ubiquitin proteasome pathway include eating disorders, renal tubular defects, diabetes, uremia, neuromuscular disease, immobilization, burn injuries, sepsis, cancer, cachexia, hyperadrenocortisolism and hyperthyroidism.

Cellular proteins degraded by the ubiquitin system include cell cycle regulators, including mitotic cyclins, G1 cyclins, CDK inhibitors, anaphase inhibitors, transcription factors, tumor suppressors, and oncoproteins such as NF-κB and IκBα, p53, JUN, β-catenin, E2F-1, and membrane proteins such as Step 2p, GH receptor, T-cell receptor, platelet-derived growth factor, lymphocyte homing receptor, MET tyrosine kinase receptor, hepatocyte growth factor-scatter factor, connexin 43, the high affinity IgE receptor, the prolactin receptor, and the EGF receptor (Hershko et al. (1998) *Annual Review of Biochemistry* 67:425-479).

Ubiquitination does not only result in proteolytic degradation. For some protein substrates, ubiquitination is a reversible post-translational modification that can regulate cellular targeting and enzymatic activity. This includes targeting to the vacuole, activation of enzyme activity, such as Ikβ kinase activation, and activation of cytokine receptor-mediated signal transduction (D'Andrea et al. (1998) *Critical Reviews In Biochemistry and Molecular Biology* 33:337-352). The T-cell receptor undergoes ubiquitination in response to receptor engagement. Platelet derived growth factor undergoes multiple ubiquitination following ligand binding. Soluble steel factor has been shown to stimulate rapid polyubiquitination of the c-KIT receptor.

It has been shown that protein degradation accounts for regulation of proteins such as cyclins, cyclin-dependent kinase inhibitors, p53, c-JUN and c-FOS (Spitaro et al. above). The ubiquitin system has also shown to be involved in antigen presentation. The 26S proteasome is responsible for processing MHC-restricted class I antigens (Spitaro et al. above).

The ubiquitin system has been implicated in various diseases. One group includes pathology that results from loss of function, a mutation in an enzyme or substrate that leads to stabilization of the protein and consequent build up of a protein to abnormally high levels. The second involves pathologies that result from a gain of function that produces increased protein degradation.

The ubiquitin system has been implicated in various malignancies. In cervical carcinoma, low levels of p53 have been found. This protein is targeted for degradation by HPV E6-associated protein. Removal of the suppressor by this oncoprotein may be a mechanism utilized by the virus to transform cells. Other results have shown that c-JUN, but not the transforming counterpart, v-JUN, is ubiquitinated and subsequently degraded. Other studies show that low levels of p27, a cell division kinase inhibitor whose degradation is necessary for proper cell cycle progression, is correlated with colorectal, and breast carcinomas. The low level of this enzyme is due to activation of the ubiquitin system.

Human genetic diseases involving aberrant proteolysis have been reviewed (Kato (1999) *Human Mutation* 13:87-98). Cystic fibrosis has been correlated with the ubiquitin system. The cystic fibrosis transmembrane regulator in cystic fibrosis patients is almost completely degraded by the ubiquitin system so that an abnormally low amount of the wild type protein is found on the cell surface. In Angelman's syndrome, one of the enzymes involved in ubiquitination (E3) is affected. In Liddle syndrome, the E3 enzyme is also affected.

The ubiquitin system can also affect the immune and inflammatory response. The persistence of EBNA-1 contributes to some virus related pathologies. A sequence on this protein was found to inhibit degradation by the ubiquitin system. This inhibited processing and subsequent presentation of viral epitopes by MHC protein.

The ubiquitin system has also been implicated in neurodegenerative diseases. Ubiquitin immunohistochemistry has shown enrichment of ubiquitin conjugates in senile plaques, lysosomes, endosomes, and a variety of inclusion bodies and degenerative fibers in many neurodegenerative diseases, such as Alzheimer's, Parkinson's and Lewy body diseases, amyotrophic lateral sclerosis, and Creutzfeld-Jakob disease.

Further, in Huntington disease and spinocerebellar ataxias, the proteins encoded by the affected genes aggregate in ubiquitin- and proteasome-positive intranuclear inclusion bodies.

The ubiquitin system has been associated with muscle wasting (Mitch et al. (1999) *American Journal of Physiology* 276:C1132-C1138 and Lecker et al. above) and muscle-wasting diseases and in such pathological states as fasting, starvation, sepsis, and denervation, all of which result from accelerated ubiquitin-mediated proteolysis (see Ciechanover, *EMBO Journal* 17:7151-7160 (1998)).

The ubiquitin system is also involved in development. The involvement in human brain development is indicated by the fact that a mutation in an E3 enzyme is implicated as the cause of Angelman's syndrome, a disorder characterized by mental retardation, seizures, and abnormal gait (Hershko et al. above).

The ubiquitin system is also associated with apoptosis. Ubiquitin-proteasome-mediated proteolysis is reported to play an important role in apoptosis of nerve growth factor-deprived neurons (Sadoul et al. (1996) *EMBO Journal* 15:3845-3852). One of the first genes shown to be involved in programmed cell death is the polyubiquitin gene that is regulated during metamorphosis of *Manduca sexta*. Radiation-induced apoptosis in human lymphocytes has been shown to be accompanied by increased ubiquitin mRNA and ubiquitinylated nuclear proteins. Further, drugs that interfere with proteasome function, such as lactacystin, prevent radiation-induced cell death of thymocytes (Hershko et al. above).

Deubiquitinating Enzymes

Deubiquitinating enzymes are cysteine proteases that specifically cleave ubiquitin conjugates at the ubiquitin carboxy terminus. These enzymes are responsible for processing linear polyubiquitin chains to generate free ubiquitin from precursor fusion proteins. They also affect pools of free ubiquitin by recycling branched chain ubiquitin. These enzymes also remove ubiquitin from ubiquitin- and poly-ubiquitin-conjugated target protein, thereby regulating localization or activity of the target. Further, these enzymes can remove ubiquitin from a ubiquitinated tagged protein and thereby rescue the protein from degradation by the 26S proteasome. The end result of each of these activities, is to affect the level of free intracellular ubiquitin (D'Andrea et al., above) and the level of specific proteins.

Ubiquitin is synthesized in a variety of functionally-distinct forms. One of these is a linear head-to-tail poly-ubiquitin precursor. Release of the free molecules involves specific enzymatic cleavage between the fused residues. The last ubiquitin moiety in many of these precursors is encoded with an extra C-terminal residue that must be removed to expose the active C-terminal Gly. In general, the recycling enzymes are thiol proteases that recognize the C-terminal domain/residue of ubiquitin. These are divided into two classes. The first is designated ubiquitin C-terminal hydrolase (UCH) and the second is designated ubiquitin-specific protease (UBP; isopeptidases) (Ciechanover, above). These enzymes have been reviewed in detail in D'Andrea, above.

UBPs contain six conserved regions. One surrounds the conserved cysteine, one surrounds the aspartic acid, one surrounds the histidine, and three additional regions of unknown function have been identified. These six domains provide a molecular signature for the UBP family. Short sequences surrounding the cysteine residue and histidine residue are highly conserved among all UBPs. Sequence comparison of several UBP family members reveals that there are various subfamilies. One subfamily, designated DUB, contains enzymes that are transcriptionally induced in response to cytokines. The UBP family contains enzymes whose members have multiple ubiquitin binding sites. Identified members of this family include DUB1, isoT, UBP3, Doa4, Tre2, and FAF (D'Andrea et al. above).

The UCH family is distinct from the UBP family. These enzymes are cysteine proteases but do not contain the six homology domains characteristic of the UBP family. Further, there is only one binding site for ubiquitin. With respect to substrate specificity, the UCH family preferentially cleaves ubiquitin from small molecules, such as peptides and amino acids. Further, the two families share little sequence homology with each other, although the UCH signature can be found in some UBPs.

The deubiquitinating enzymes can promote either degradation or stabilization of a given substrate. One of the best characterized deubiquitinating enzymes is the yeast UBP14p enzyme which has a human homolog designated isopeptidase-T. Isopeptidase-T hydrolyzes free polyubiquitin chains and stimulates degradation of polyubiquitinated protein substrates by the 26S proteasome. In vitro data suggest that the cellular role of isopeptidase-T is to dissemble unanchored polyubiquitin chains. The isopeptidase-T then sequentially degrades these polyubiquitin chains into ubiquitin monomers.

The yeast Doa4 promotes ubiquitin-mediated proteolysis of cellular substrates. The primary function appears to be the hydrolysis of isopeptide-linked ubiquitin chains from peptides that are the by-products of proteasome degradation. The function appears to be the clipping of polymeric ubiquitin from peptide degradation products. In summary, with respect to a degradation function, isopeptidases can produce free ubiquitin monomers from straight chain polyubiquitin, branched chain polyubiquitin, ubiquitin or polyubiquitin attached to substrate proteins, and ubiquitin or polyubiquitin attached to substrate remnants, such as peptides or amino acids.

Deubiquitinating enzymes that promote stabilization of substrates include the FAF protein. Results show that the FAF protein deubiquitinates and rescues a ubiquitin-conjugated target, preventing its degradation by the proteasome. Another deubiquitinating enzyme, designated PA700 isopeptidase, also prevents proteasome degradation. This enzyme has been isolated from the 19S regulatory complex. This enzyme appears to remove one ubiquitin at a time starting from the distal end of a polyubiquitin chain.

The enzymes have been associated with growth control. The mammalian oncoprotein Tre-2 is a member of the UBP superfamily. The transforming isoform of the Tre-2 oncoprotein is a truncated UPB lacking the histidine domain and lacking deubiquitinating activity. The full length Tre-2 protein has deubiquitinating activity but no transforming activity. Accordingly, it has been suggested that this protein acts as a growth suppressor within the cell.

Another UBP that regulates cellular function is designated DUB. DUB-1 was originally shown to be induced by interleukin-3 stimulation. It has been postulated that the DUB protein family is generally responsive to cytokines. It has also been shown that another family member, DUB-2, is induced by interleukin-2. Zhu et al. (1997) *Journal of Biological Chemistry* 272:51-57.

The enzymes may deubiquitinate cell surface growth factor receptors thereby prolonging receptor half life and amplifying growth signals. They may also deubiquitinate proteins involved in signal transduction and deubiquitinate cell cycle regulators such as cyclins or cyclin-CDK inhibitors. See D'Andrea above.

UBPs have also been linked to the chromatin regulatory process, transcriptional silencing. UBP-3 has been reported to complex with SIR-4, a trans-acting factor that is required for establishment and maintenance of silencing. Accordingly, UBP-3 may act as an inhibitor of silencing by either stabilizing an inhibitor or by removing a positive regulator.

The murine UNP protooncogene has been shown to encode a nuclear ubiquitin protease whose overexpression leads to oncogenic transformation in NIH3T3 cells. A cDNA was cloned corresponding to the human homolog of this gene. It was shown to map to a region frequently rearranged in human tumor cells. Further, it was shown that levels of this gene are elevated in small cell tumors and adenocarcinomas of the lung, suggesting a causative role of the gene in the neoplastic process (Gray et al. (1995) *Oncogene* 10:2179-2183).

A novel ubiquitin-specific protease, designated UBP-43, was cloned from a leukemia fusion protein in AML1-ETO Knockin mice. This protease was shown to function in hematopoitic cell differentiation. The overexpression of this gene was shown to block cytokine-induced terminal differentiation of monocytic cells (Liu et al. (1999) *Molecular and Cellular Biology* 19:3029-3038).

In summary, deubiquitinating enzymes are potentially powerful targets for modulating ubiquitination. Modulation of ubiquitination can increase or decrease the proteolysis of specific proteins, particularly key proteins in cellular processes, can increase or decrease levels of general proteolysis, thus affecting the basic metabolic state, and may increase or decrease the pool of free ubiquitin monomers available for ubiquitination.

Accordingly, ubiquitin proteases are a major target for drug action and development. Thus, it is valuable to the field of pharmaceutical development to identify and characterize previously unknown ubiquitin proteases. The present invention advances the state of the art by providing a previously unidentified human deubiquitinating enzyme.

SUMMARY OF THE INVENTION

It is an object of the invention to identify novel ubiquitin proteases.

It is a further object of the invention to provide novel ubiquitin protease polypeptides that are useful as reagents or targets in assays applicable to treatment and diagnosis of ubiquitin-mediated or -related disorders, especially disorders mediated by or related to deubiquitinating enzymes.

It is a further object of the invention to provide polynucleotides corresponding to the novel ubiquitin protease polypeptides that are useful as targets and reagents in assays applicable to treatment and diagnosis of ubiquitin or ubiquitin protease-mediated or -related disorders and useful for producing novel ubiquitin protease polypeptides by recombinant methods.

A specific object of the invention is to identify compounds that act as agonists and antagonists and modulate the expression of the novel ubiquitin protease.

A further specific object of the invention is to provide compounds that modulate expression of the ubiquitin protease for treatment and diagnosis of ubiquitin and ubiquitin protease-related disorders.

The invention is thus based on the identification of a novel human ubiquitin protease. The amino acid sequence is shown in SEQ ID NO:15. The nucleotide sequence is shown in SEQ ID NO:16.

The invention provides isolated ubiquitin protease polypeptides, including a polypeptide having the amino acid sequence shown in SEQ ID NO:15 or the amino acid sequence encoded by the cDNA deposited as ATCC No. PTA-1849 on May 9, 2000 ("the deposited cDNA").

The invention also provides isolated ubiquitin protease nucleic acid molecules having the sequence shown in SEQ ID NO:16 or in the deposited cDNA.

The invention also provides variant polypeptides having an amino acid sequence that is substantially homologous to the amino acid sequence shown in SEQ ID NO:15 or encoded by the deposited cDNA.

The invention also provides variant nucleic acid sequences that are substantially homologous to the nucleotide sequence shown in SEQ ID NO:16 or in the deposited cDNA.

The invention also provides fragments of the polypeptide shown in SEQ ID NO:15 and nucleotide sequence shown in SEQ ID NO:16, as well as substantially homologous fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the ubiquitin protease nucleic acid molecules and polypeptides, and particularly recombinant vectors and host cells.

The invention also provides methods of making the vectors and host cells and methods for using them to produce the ubiquitin protease nucleic acid molecules and polypeptides.

The invention also provides antibodies or antigen-binding fragments thereof that selectively bind the ubiquitin protease polypeptides and fragments.

The invention also provides methods of screening for compounds that modulate expression or activity of the ubiquitin protease polypeptides or nucleic acid (RNA or DNA).

The invention also provides a process for modulating ubiquitin protease polypeptide or nucleic acid expression or activity, especially using the screened compounds. Modulation may be used to treat conditions related to aberrant activity or expression of the ubiquitin protease polypeptides or nucleic acids or of the ubiquitin system. In addition, modulation may be used to treat conditions, such as viral infection, that are affected by the ubiquitin protease.

The invention also provides assays for determining the activity of or the presence or absence of the ubiquitin protease polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Polypeptides

The invention is based on the identification of a novel human ubiquitin protease. Specifically, an expressed sequence tag (EST) was selected based on homology to ubiquitin protease sequences. This EST was used to design primers based on sequences that it contains and used to identify a cDNA from a human prostate library. Positive clones were sequenced and the overlapping fragments were assembled. Analysis of the assembled sequence revealed that the cloned cDNA molecule encodes a ubiquitin protease containing the conserved amino acid residues found in UBP and UCH thiol proteases.

The invention thus relates to a novel ubiquitin protease having the deduced amino acid sequence shown in FIGS. 33A-33D (SEQ ID NO:15) or having the amino acid sequence encoded by the deposited cDNA, ATCC No. PTA-1849 on May 9, 2000.

The deposits will be maintained under the terms of the Budapest Treaty on the International Recognition of the Deposit of Microorganisms. The deposits are provided as a convenience to those of skill in the art and are not an admission that a deposit is required under 35 U.S.C. § 112. The deposited sequences, as well as the polypeptides encoded by the sequences, are incorporated herein by reference and controls in the event of any conflict, such as a sequencing error, with description in this application.

"Ubiquitin protease polypeptide" or "ubiquitin protease protein" refers to the polypeptide in SEQ ID NO:15 or encoded by the deposited cDNA. The term "ubiquitin protease protein" or "ubiquitin protease polypeptide", however, further includes the numerous variants described herein, as well as fragments derived from the full-length ubiquitin proteases and variants.

Figure 37:
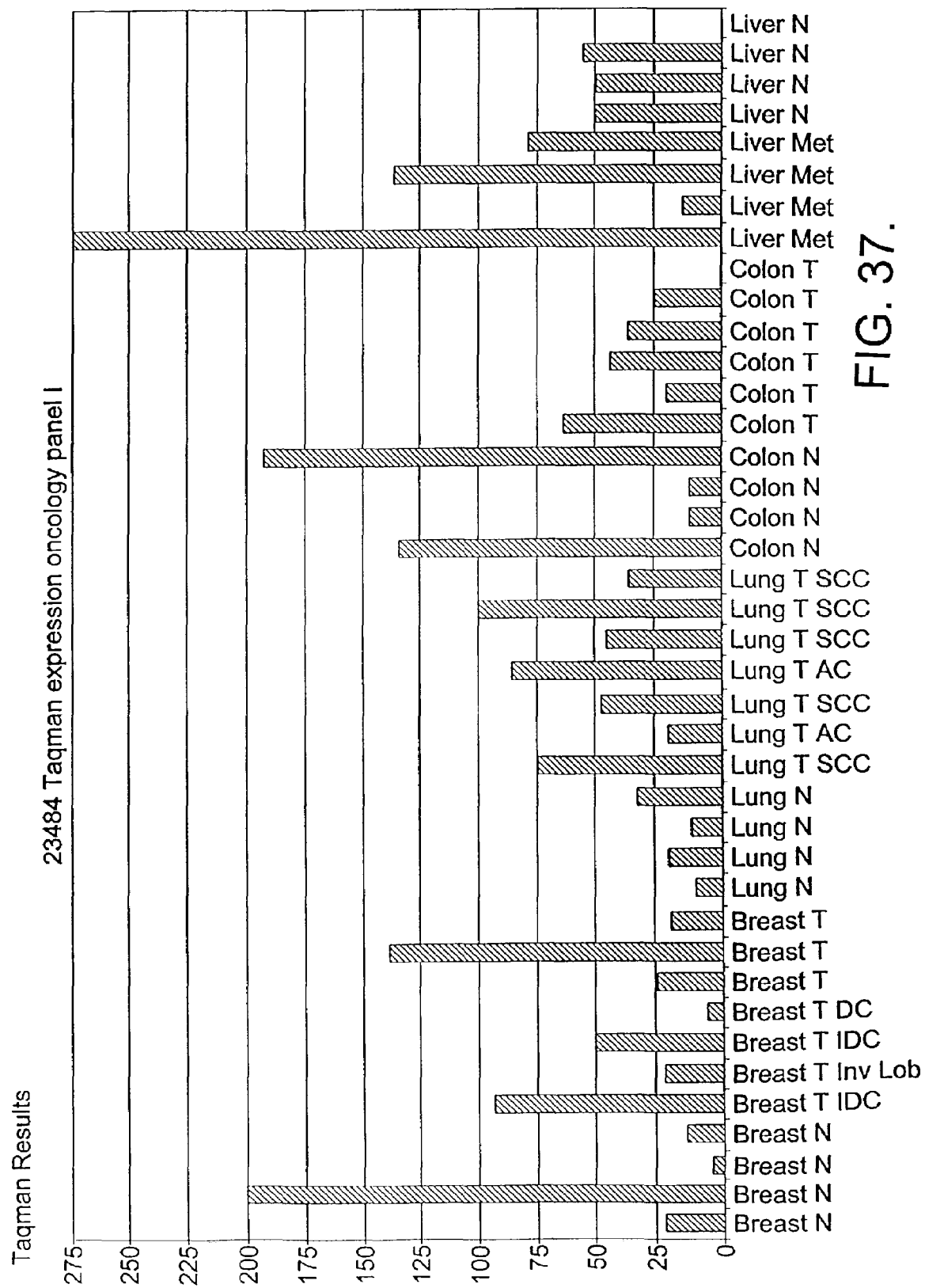
FIG. 37 shows expression of the protease in normal and malignant breast, lung, liver and colon tissues. The liver metastases are derived from malignant colonic tissue.

Tissues and/or cells in which the ubiquitin protease is expressed include, but are not limited to those shown in FIGS. 37 and 38. Tissues in which the gene is highly expressed include fetal kidney, testes, fetal liver, ovary, and fetal heart. Expression is also seen in the kidney, thyroid, undifferentiated osteoblasts and skeletal muscle. The ubiquitin protease is also expressed in normal liver and in normal and malignant breast, lung, and colon tissue and in liver metastases derived from malignant colonic tissues. Hence, the ubiquitin protease is relevant to disorders involving the tissues in which it is expressed, especially in breast, lung, colon, and colon metastases to liver. Expression has been confirmed by Northern blot analysis.

The present invention thus provides an isolated or purified ubiquitin protease polypeptide and variants and fragments thereof.

Based on a BLAST search, highest homology was shown to Ubiquitin Carboxyl-terminal hydrolase (AL031525) from S. pombe.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The ubiquitin protease polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the ubiquitin protease having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

An ubiquitin protease polypeptide is also considered to be isolated when it is part of a membrane preparation or is purified and then reconstituted with membrane vesicles or liposomes.

The language "substantially free of chemical precursors or other chemicals" includes preparations of the ubiquitin protease polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the ubiquitin protease polypeptide comprises the amino acid sequence shown in SEQ ID NO:15. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the ubiquitin protease of SEQ ID NO:15. Variants also include proteins substantially homologous to the ubiquitin protease but derived from another organism, i.e., an ortholog. Variants also include proteins that are substantially homologous to the ubiquitin protease that are produced by chemical synthesis. Variants also include proteins that are substantially homologous to the ubiquitin protease that are produced by recombinant methods. It is understood, however, that variants exclude any amino acid sequences disclosed prior to the invention.

As used herein, two proteins (or a region of the proteins) are substantially homologous when the amino acid sequences are at least about 70-75%, typically at least about 80-85%, and most typically at least about 90-95% or more homologous. A substantially homologous amino acid sequence, according to the present invention, will be encoded by a nucleic acid sequence hybridizing to the nucleic acid sequence, or portion thereof, of the sequence shown in SEQ ID NO:16 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (i.e., 100%=the entire coding sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the ubiquitin protease. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306-1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |

TABLE 1-continued

Conservative Amino Acid Substitutions.

| | |
|---|---|
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci.* USA 90:5873-5877. Such an algorithm is incorporated into the NBLAST and XBLAST programs (version 2.0) as described in Altschul et al. (1997) *Nucleic Acids Res.* 25:3389-3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444-453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3-5; and FASTA described in Pearson et al. (1988) *PNAS* 85:2444-8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of ubiquitin binding, ubiquitin recognition, interaction with ubiquitinated substrate protein, such as binding or proteolysis, subunit interaction, particularly within the proteasome, activation or binding by ATP, developmental expression, temporal expression, tissue-specific expression, interacting with cellular components, such as transcriptional regulatory factors, and particularly trans-acting transcriptional regulatory factors, proteolytic cleavage of peptide bonds in polyubiquitin and peptide bonds between ubiquitin or polyubiquitin and substrate protein, and proteolytic cleavage of peptide bonds between ubiquitin or polyubiquitin and a peptide or amino acid.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the ubiquitin protease polypeptide. This includes preventing immunogenicity from pharmaceutical formulations by preventing protein aggregation.

Useful variations further include alteration of catalytic activity. For example, one embodiment involves a variation at the binding site that results in binding but not hydrolysis, or slower hydrolysis, of the peptide bond. A further useful variation results in an increased rate of hydrolysis of the peptide bond. A further useful variation at the same site can result in higher or lower affinity for substrate. Useful variations also include changes that provide for affinity for a different ubiquitinated substrate protein than that normally recognized. Other useful variations involving altered recognition affect recognition of the type of substrate normally recognized. For example, one variation could result in recognition of ubiquitinated intact substrate but not of substrate remnants, such as ubiquitinated amino acid or peptide that are proteolysis products that result from the hydrolysis of the intact ubiquitinated substrate. Alternatively, the protease could be varied so that one or more of the remnant products is recognized but not the intact protein substrate. Another variation would affect the ability of the protease to rescue a ubiquitinated protein. Thus, protein substrates that are normally rescued from proteolysis would be subject to degradation. Further useful variations affect the ability of the protease to be induced by activators, such as cytokines, including but not limited to, those disclosed herein. Another useful variation would affect the recognition of ubiquitin substrate so that the enzyme could not recognize one or more of a linear polyubiquitin, branched chain polyubiquitin, linear polyubiquitinated substrate, or branched chain polyubiquitin substrate. Specific variations include truncation in which, for example, a HIS domain is deleted, the variation resulting in decrease or loss of deubiquitination activity. Another useful variation includes one that prevents activation by ATP. Another useful variation provides a fusion protein in which one or more domains or subregions are operationally fused to one or more domains or subregions from another UBP or from a UCH. Specifically, a domain or subregion can be introduced that provides a rescue function to an enzyme not normally having this function or for recognition of a specific substrate wherein recognition is not available to the original enzyme. Other variations include those that affect ubiquitin recognition or recognition of a ubiquitinated substrate protein. Further variations could affect specific subunit interaction, particularly in the proteasome. Other variations would affect developmental, temporal, or tissue-specific expression. Other variations would affect the interaction with cellular components, such as transcriptional regulatory factors.

Amino acids that are essential for function can be identified by methods known in the art, such as site-directed mutagenesis or alanine-scanning mutagenesis (Cunningham et al. (1985) *Science* 244:1081-1085). The latter procedure introduces single alanine mutations at every residue in the molecule. The resulting mutant molecules are then tested for biological activity, such as peptide hydrolysis in vitro or ubiquitin-dependent in vitro activity, such as proliferative activity, receptor-mediated signal transduction, and other cellular processes including, but not limited, those disclosed herein that are a function of the ubiquitin system. Sites that are critical for binding or recognition can also be determined by structural analysis such as crystallization, nuclear magnetic resonance or photoaffinity labeling (Smith et al. (1992) *J. Mol. Biol.* 224:899-904; de Vos et al. (1992) *Science* 255:306-312).

The assays for deubiquitinating enzyme activity are well known in the art and can be found, for example, in Zhu et al. (1997) *Journal of Biological Chemistry* 272:51-57, Mitch et al. (1999) *American Journal of Physiology* 276:C1132-C1138, Liu et al. (1999) *Molecular and Cell Biology* 19:3029-3038, and such as those cited in various reviews, for example, Ciechanover et al. (1994) *The FASEB Journal* 8:182-192, Chiechanover (1994) *Biol. Chem. Hoppe-Seyler* 375:565-581, Hershko et al. (1998) *Annual Review of Biochemistry* 67:425-479, Swartz (1999) *Annual Review of Medicine* 50:57-74, Ciechanover (1998) *EMBO Journal* 17:7151-7160, and D'Andrea et al. (1998) *Critical Reviews in Biochemistry and Molecular Biology* 33:337-352. These assays include, but are not limited to, the disappearance of substrate, including decrease in the amount of polyubiquitin or ubiquitinated substrate protein or protein remnant, appearance of intermediate and end products, such as appearance of free ubiquitin monomers, general protein turnover, specific protein turnover, ubiquitin binding, binding to ubiquitinated substrate protein, subunit interaction, interaction with ATP, interaction with cellular components such as trans-acting regulatory factors, stabilization of specific proteins, and the like.

Substantial homology can be to the entire nucleic acid or amino acid sequence or to fragments of these sequences.

The invention thus also includes polypeptide fragments of the ubiquitin protease. Fragments can be derived from the amino acid sequence shown in SEQ ID NO:15. However, the invention also encompasses fragments of the variants of the ubiquitin proteases as described herein.

The fragments to which the invention pertains, however, are not to be construed as encompassing fragments that may be disclosed prior to the present invention.

Accordingly, a fragment can comprise at least about 11, 15, 20, 25, 30, 35, 40, 45, 50 or more contiguous amino acids. Fragments can retain one or more of the biological activities of the protein, for example the ability to bind to ubiquitin or hydrolyze peptide bonds, as well as fragments that can be used as an immunogen to generate ubiquitin protease antibodies.

Biologically active fragments (peptides which are, for example, 5, 7, 10, 12, 15, 20, 30, 35, 36, 37, 38, 39, 40, 50, 100 or more amino acids in length) can comprise a domain or motif, e.g., catalytic site, UCH family 2 signature, signature for the immunoglobulin and major histocompatibility complex proteins, and sites for glycosylation, cAMP and cGMP-dependent protein kinase phosphorylation, protein kinase C phosphorylation, casein kinase II phosphorylation, tyrosine kinase phosphorylation, N-myristoylation, and amidation. Further possible fragments include the catalytic site or domain including conserved amino acid residues found in UBP and UCH thiol proteases. Such regions include, for example, about amino acids 123 to 138 of SEQ ID NO:15 or the UCH2 family 2 signature found from about amino acids 365 to about 383 of SEQ ID NO:15. Additional domains include ubiquitin recognition sites, ubiquitin binding sites, sites important for subunit interaction, and sites important for carrying out the other functions of the protease as described herein.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the ubiquitin protease and variants. These epitope-bearing peptides are useful to raise antibodies that bind specifically to a ubiquitin protease polypeptide or region or fragment. These peptides can contain at least 11, 12, at least 14, or between at least about 15 to about 30 amino acids.

Figure 34:
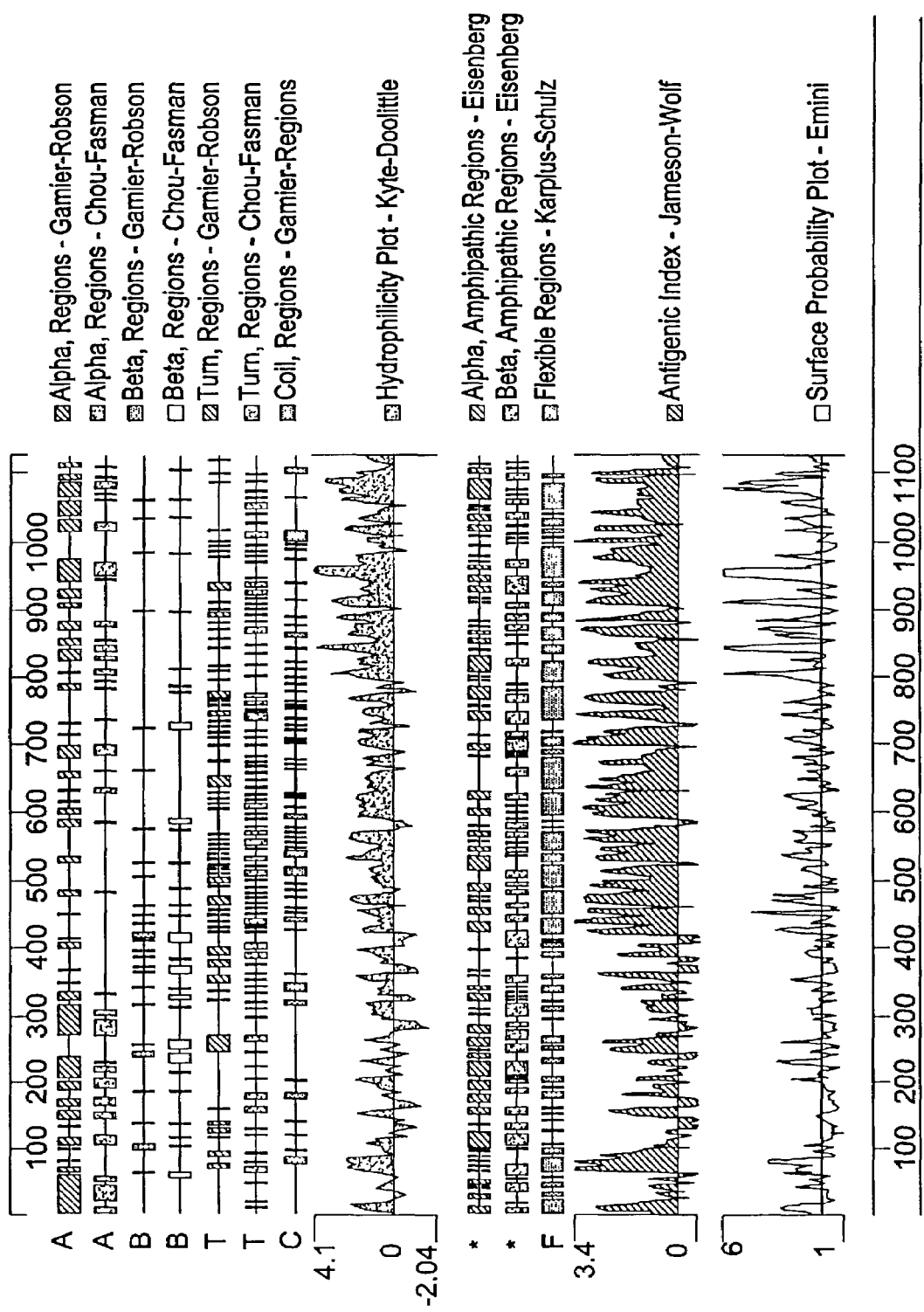
FIG. 34 shows an analysis of the ubiquitin protease amino acid sequence: αβturn and coil regions; hydrophilicity; amphipathic regions; flexible regions; antigenic index; and surface probability plot.

Non-limiting examples of antigenic polypeptides that can be used to generate antibodies include but are not limited to peptides derived from an extracellular site. Regions having a high antigenicity index are shown in FIG. 34. However, intracellularly-made antibodies ("intrabodies") are also encompassed, which would recognize intracellular peptide regions.

The epitope-bearing ubiquitin protease polypeptides may be produced by any conventional means (Houghten, R. A. (1985) *Proc. Natl. Acad. Sci. USA* 82:5131-5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the ubiquitin protease fragment and an additional region fused to the carboxyl terminus of the fragment.

The invention thus provides chimeric or fusion proteins. These comprise a ubiquitin protease peptide sequence operatively linked to a heterologous peptide having an amino acid sequence not substantially homologous to the ubiquitin protease. "Operatively linked" indicates that the ubiquitin protease peptide and the heterologous peptide are fused in-frame. The heterologous peptide can be fused to the N-terminus or C-terminus of the ubiquitin protease or can be internally located.

In one embodiment the fusion protein does not affect ubiquitin protease function per se. For example, the fusion protein can be a GST-fusion protein in which the ubiquitin protease sequences are fused to the C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant ubiquitin protease. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52-58 (1995) and Johanson et al. *J. Biol. Chem.* 270:9459-9471). Thus, this invention also encompasses soluble fusion proteins containing a ubiquitin protease polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). A ubiquitin protease-encoding nucleic acid can be cloned into such an expression vector such that the fusion moiety is linked in-frame to the ubiquitin protease.

Another form of fusion protein is one that directly affects ubiquitin protease functions. Accordingly, a ubiquitin protease polypeptide is encompassed by the present invention in which one or more of the ubiquitin protease domains (or parts thereof) has been replaced by homologous domains (or parts thereof) from another UBP or UCH species. Accordingly, various permutations are possible. One or more functional sites as disclosed herein from the specifically disclosed protease can be replaced by one or more functional sites from a corresponding UBP family member or from a UCH family member. Thus, chimeric ubiquitin proteases can be formed in which one or more of the native domains or subregions has been replaced by another.

Additionally, chimeric ubiquitin protease proteins can be produced in which one or more functional sites is derived from a different ubiquitin protease family. It is understood however that sites could be derived from ubiquitin protease families that occur in the mammalian genome but which have not yet been discovered or characterized. Such sites include but are not limited to any of the functional sites disclosed herein.

The isolated ubiquitin proteases can be purified from any of the cells that naturally express it, such as, fetal kidney, testes, fetal liver, ovary, fetal heart, kidney, thyroid, undifferentiated osteoblasts, skeletal muscle, malignant breast tissue, primary lung tumors and liver metastases derived from colon. Alternatively, the ubiquitin protease may be purified from cells that have been altered to express it (recombinant), or synthesized using known protein synthesis methods.

In one embodiment, the protein is produced by recombinant DNA techniques. For example, a nucleic acid molecule encoding the ubiquitin protease polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W.H. Freeman and Company, New York (1993). Many detailed reviews are available on this subject, such as by Wold, F., *Posttranslational Covalent Modifica-* tion of Proteins, B. C. Johnson, Ed., Academic Press, New York 1-12 (1983); Seifter et al. (1990) *Meth. Enzymol.* 182: 626-646) and Rattan et al. (1992) *Ann. N.Y. Acad. Sci.* 663:48-62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The ubiquitin protease polypeptides are useful for producing antibodies specific for the ubiquitin protease, regions, or fragments. Regions having a high antigenicity index score are shown in FIG. 34.

The ubiquitin protease polypeptides are useful for biological assays related to ubiquitin protease function. Such assays involve any of the known functions or activities or properties useful for diagnosis and treatment of ubiquitin- or ubiquitin protease-related conditions or conditions in which expression of the protease is relevant, such as in viral infections. Potential assays have been disclosed herein and generically include disappearance of substrate, appearance of end product, and general or specific protein turnover.

The ubiquitin protease polypeptides are also useful in drug screening assays, in cell-based or cell-free systems. Cell-based systems can be native, i.e., cells that normally express the ubiquitin protease, as a biopsy or expanded in cell culture. In one embodiment, however, cell-based assays involve recombinant host cells expressing the ubiquitin protease.

Determining the ability of the test compound to interact with the ubiquitin protease can also comprise determining the ability of the test compound to preferentially bind to the polypeptide as compared to the ability of a known binding molecule (e.g., ubiquitin) to bind to the polypeptide.

The polypeptides can be used to identify compounds that modulate ubiquitin protease activity. Such compounds, for example, can increase or decrease affinity for polyubiquitin, either linear or branched chain, ubiquitinated protein substrate, or ubiquitinated protein substrate remnants. Such compounds could also, for example, increase or decrease the rate of binding to these components. Such compounds could also compete with these components for binding to the ubiquitin protease or displace these components bound to the ubiquitin protease. Such compounds could also affect interaction with other components, such as ATP, other subunits, for example, in the 19S complex, and transcriptional regulatory factors. It is understood, therefore, that such compounds can be identified not only by means of ubiquitin, but by means of any of the components that functionally interact with the disclosed protease. This includes, but is not limited to, any of those components disclosed herein.

Both ubiquitin protease and appropriate variants and fragments can be used in high-throughput screens to assay candidate compounds for the ability to bind to the ubiquitin protease. These compounds can be further screened against a functional ubiquitin protease to determine the effect of the compound on the ubiquitin protease activity. Compounds can be identified that activate (agonist) or inactivate (antagonist) the ubiquitin protease to a desired degree. Modulatory methods can be performed in vitro (e.g., by culturing the cell with the agent) or, alternatively, in vivo (e.g., by administering the agent to a subject).

The ubiquitin protease polypeptides can be used to screen a compound for the ability to stimulate or inhibit interaction between the ubiquitin protease protein and a target molecule that normally interacts with the ubiquitin protease protein. The target can be ubiquitin, ubiquitinated substrate, or polyubiquitin or another component of the pathway with which the ubiquitin protease protein normally interacts (for example, ATP). The assay includes the steps of combining the ubiquitin protease protein with a candidate compound under conditions that allow the ubiquitin protease protein or fragment to interact with the target molecule, and to detect the formation of a complex between the ubiquitin protease protein and the target or to detect the biochemical consequence of the interaction with the ubiquitin protease and the target. Any of the associated effects of protease function can be assayed. This includes the production of hydrolysis products, such as free terminal peptide substrate, free terminal amino acid from the hydrolyzed substrate, free ubiquitin, lower molecular weight species of hydrolyzed polyubiquitin, released intact substrate protein resulting from rescue from proteolysis, free polyubiquitin formed from hydrolysis of the polyubiquitin from intact substrate, and substrate remnants, such as amino acids and peptides produced from proteolysis of the substrate protein, and biological endpoints of the pathway.

Determining the ability of the ubiquitin protease to bind to a target molecule can also be accomplished using a technology such as real-time Bimolecular Interaction Analysis (BIA). Sjolander et al. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 97:6378-6382); (Felici (1991) *J. Mol. Biol.* 222:301-310); (Ladner supra).

Candidate compounds include, for example, 1) peptides such as soluble peptides, including Ig-tailed fusion peptides and members of random peptide libraries (see, e.g., Lam et al. (1991) *Nature* 354:82-84; Houghten et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length ubiquitin protease or fragment that competes for substrate binding. Other candidate compounds include mutant ubiquitin proteases or appropriate fragments containing mutations that affect ubiquitin protease function and compete for substrate. Accordingly, a fragment that competes for substrate, for example a fragment with a higher affinity, or a fragment that binds substrate but does not hydrolyze the peptide bond, is encompassed by the invention.

Other candidate compounds include ubiquitinated protein or protein analog that binds to the protease but is not released or released slowly. Other candidate compounds include analogs of the other natural substrates, such as substrate remnants that bind to but are not released or released more slowly. Further candidate compounds include activators of the proteases such as cytokines, including but not limited to, those disclosed herein.

The invention provides other end points to identify compounds that modulate (stimulate or inhibit) ubiquitin protease activity. The assays typically involve an assay of events in the pathway that indicate ubiquitin protease activity. This can include cellular events that result from deubiquitination, such as cell cycle progression, programmed cell death, growth factor-mediated signal transduction, or any of the cellular processes including, but not limited to, those disclosed herein as resulting from deubiquitination. Specific phenotypes include changes in stress response, DNA replication, receptor internalization, cellular transformation or reversal of transformation, and transcriptional silencing.

Assays are based on the multiple cellular functions of deubiquitinating enzymes. These enzymes act at various different levels in the regulation of protein ubiquitination. A deubiquitinating enzyme can degrade a linear polyubiquitin chain into monomeric ubiquitin molecules. Deubiquitinating enzymes, such as isopeptidase-T, can degrade a branched multiubiquitin chain into monomeric ubiquitin molecules. Deubiquitinating enzymes can remove ubiquitin from a ubiquitin-conjugated target protein. The deubiquitinating enzyme, such as FAF or PA700 isopeptidase, can remove polyubiquitin from a ubiquitinated target protein, and thereby rescue the target from degradation by the 26S proteasome. Deubiquitinating enzymes such as Doa-4 can remove polyubiquitin from proteasome degradation products. UCH family members tend to hydrolyze monoubiquitinated substrate (Larsen et al. (1998) *Biochemistry* 10:3358-68). The UCH deubiquitinating enzyme AP-UCH enhances proteolytic activity of Protein Kinase A (PKA) through the ubiquitin-proteosome pathway. Furthermore, BAP1 has been identified as a new member of the UCH family and interacts with BRAC1, thereby enhancing BRCA1 mediated cell growth suppression (Jensen et al. (1998) *Oncogene* 16: 1097-1112). The end result of all of the deubiquitinating enzymes is to regulate the cellular pool of free monomeric ubiquitin. Accordingly, assays can be based on detection of any of the products produced by hydrolysis/deubiquitination.

Further, the expression of genes that are up- or down-regulated by action of the ubiquitin protease can be assayed. In one embodiment, the regulatory region of such genes can be operably linked to a marker that is easily detectable, such as luciferase.

Accordingly, any of the biological or biochemical functions mediated by the ubiquitin protease can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric ubiquitin protease proteins in which one or more domains, sites, and the like, as disclosed herein, or parts thereof, can be replaced by their heterologous counterparts derived from other ubiquitin proteases. For example, a recognition or binding region can be used that interacts with different substrate specificity and/or affinity than the native ubiquitin protease. Accordingly, a different set of pathway components is available as an end-point assay for activation. Further, sites that are responsible for developmental, temporal, or tissue specificity can be replaced by heterologous sites such that the protease can be detected under conditions of specific developmental, temporal, or tissue-specific expression.

The ubiquitin protease polypeptides are also useful in competition binding assays in methods designed to discover compounds that interact with the ubiquitin protease. Thus, a compound is exposed to a ubiquitin protease polypeptide under conditions that allow the compound to bind to or to otherwise interact with the polypeptide. Soluble ubiquitin protease polypeptide is also added to the mixture. If the test compound interacts with the soluble ubiquitin protease polypeptide, it decreases the amount of complex formed or activity from the ubiquitin protease target. This type of assay is particularly useful in cases in which compounds are sought that interact with specific regions of the ubiquitin protease. Thus, the soluble polypeptide that competes with the target ubiquitin protease region is designed to contain peptide sequences corresponding to the region of interest.

Another type of competition-binding assay can be used to discover compounds that interact with specific functional sites. As an example, ubiquitin and a candidate compound can be added to a sample of the ubiquitin protease. Compounds that interact with the ubiquitin protease at the same site as ubiquitin will reduce the amount of complex formed between the ubiquitin protease and ubiquitin. Accordingly, it is possible to discover a compound that specifically prevents interaction between the ubiquitin protease and ubiquitin. Another example involves adding a candidate compound to a sample of ubiquitin protease and polyubiquitin. A compound that competes with polyubiquitin will reduce the amount of hydrolysis or binding of the polyubiquitin to the ubiquitin protease. Accordingly, compounds can be discovered that directly interact with the ubiquitin protease and compete with polyubiquitin. Such assays can involve any other component that interacts with the ubiquitin protease, such as ubiquitinated substrate protein, ubiquitinated substrate remnants, and cellular components with which the protease interacts such as transcriptional regulatory factors.

To perform cell free drug screening assays, it is desirable to immobilize either the ubiquitin protease, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/ubiquitin protease fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of ubiquitin protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a ubiquitin protease-binding target component, such as ubiquitin, polyubiquitin, ubiquitinated substrate protein, ubiquitinated substrate protein remnant, or ubiquitinated remnant amino acid, and a candidate compound are incubated in the ubiquitin protease-presenting wells and the amount of complex trapped in the well can be quantitated. Methods for detecting such complexes, in addition to those described above for the GST-immobilized complexes, include immunodetection of complexes using antibodies reactive with the ubiquitin protease target molecule, or which are reactive with ubiquitin protease and compete with the target molecule; as well as enzyme-linked assays which rely on detecting an enzymatic activity associated with the target molecule.

Modulators of ubiquitin protease activity identified according to these drug screening assays can be used to treat a subject with a disorder mediated or affected by the ubiquitin protease pathway, by treating cells that express the ubiquitin protease or cells in which protease expression is desirable (such as virus-infected cells). Such cells include, for example, fetal kidney, testes, fetal liver, ovary, fetal heart, kidney, thyroid, undifferentiated osteoblasts, skeletal muscle, and malignant breast, lung and colon tissue, as well as liver metastases derived from malignant colonic tissue. These methods of treatment include the steps of administering the modulators of ubiquitin protease activity in a pharmaceutical composition as described herein, to a subject in need of such treatment.

Tissues and/or cells in which the ubiquitin protease is expressed include, but are not limited to those shown in FIGS. 37 and 38. Tissues in which the gene is highly expressed include fetal kidney, testes, fetal liver, ovary, and fetal heart. Expression is also seen in the kidney, thyroid, undifferentiated osteoblasts and skeletal muscle. The ubiquitin protease is also expressed in normal liver and in normal and malignant breast, lung, and colon tissue and in liver metastases derived from malignant colonic tissues. Hence, the ubiquitin protease is relevant to treating disorders involving these tissues, breast, lung, colon carcinoma, and colon metastases to liver.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney and nephronophthisis-uremic medullary cystic disease complex, acquired (dialysis-associated) cystic disease and simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus crythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including, but not limited to, acute tubular necrosis and tubulointerstitial nephritis, including but not limited to, pyelonephritis and urinary tract infection, acute pyelonephritis, chronic pyelonephritis and reflux nephropathy, tubulointerstitial nephritis induced by drugs and toxins, including but not limited to, acute drug-induced interstitial nephritis, analgesic abuse nephropathy, and nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including, including but not limited to, benign nephrosclerosis, malignant hypertension and accelerated nephrosclerosis, renal artery stenosis, and thrombotic microangiopathies, including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Disorders of the breast include, but are not limited to, disorders of development; inflammations, including but not limited to, acute mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors, such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor, choriocarcinoma, teratoma, and mixed tumors, tumors of sex cord-gonadal stroma including, but not limited to, Leydig (interstitial) cell tumors and Sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors, such as rhabdomyosarcoma.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporois, paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, ewing sarcoma, primitive neuroectodermal tumor, giant cell tumor, and metastatic tumors.

The ubiquitin-proteasome pathway has been implicated in the regulation of viral infection. Recent studies have shown that ubiquitination of the herpes simplex virus type I (HSV-1) transactivator protein ICP0 and the hepatitis B virus X protein (HBX) are influenced by the ubiquitin-proteasome pathway during viral infection (Weber et al. (1999) *Virology* 253:288-98 and Hu et al. (1999) *J Virol* 73:7231-40). In addition, inactivation of the ubiquitin-proteasome pathway inhibits Vmw 110, an immediate early protein of HSV-1, from stimulating lytic infection. (Everett et al. (1998) *EMBO J* 17:7161-9). Furthermore, a cellular deubiquitinating enzyme, Herpes-virus associated ubiquitin specific protease, HAUSP, has also been implicated in the regulation of HSV infection (Everett et al. (1997) *EMBO J.* 16:1519-1530). Hence, the ubiquitin protease find use in the treatment of disorders resulting from viral infection.

Transcriptional profiling and Taqman profiling techniques showed that the expression of the ubiquitin protease of the present invention was upregulated in HSV-infected human ganglia cells compared to uninfected ganglia. Furthermore, cell lines that express a hepatitis B virus (HepG2.215) showed higher expression levels of the ubiquitin protease 23484 when compared to the parental HepG2 control cell line. The ubiquitin protease 23484 is therefore an important host gene for HSV and HVB pathogenesis and finds use in the treatment of disorders resulting from herpes simplex virus and hepatitis B infection.

Additional disorders in which the ubiquitin protease expression is relevant include, but are not limited to the following:

Respiratory viral pathogens and their associated disorders include, for example, adenovirus, resulting in upper and lower respiratory tract infections; conjuctivitis and diarrhea; echovirus, resulting in upper respiratory tract infections, pharyngitis and rash; rhinovirus, resulting in upper respiratory tract infections; cosackievirus, resulting in Pleurodynia, herpangia, hand-foot-mouth disease; coronavirus, resulting in upper respiratory tract infections; influenza A and B viruses, resulting in influenza; parainfluenza virus 1-4, resulting in upper and lower respiratory tract infections and croup; respiratory syncytial virus, resulting in bronchiolitis and pneumonia.

Digestive viral pathogens and their associated disorders include, for example, mumps virus, resulting in mumps, pancreatitis, and orchitis; rotavirus, resulting in childhood diarrhea; Norwalk Agent, resulting in gastroenteritis; hepatitis A virus, resulting in acute viral hepatitis; hepatitis B virus, hepatitis D virus and hepatitis C virus, resulting in acute or chronic hepatitis; hepatitis E virus, resulting in enterically transmitted hepatitis.

Systemic viral pathogens associated with disorders involving skin eruptions include, for example, measles virus, resulting in measles (rubeola); rubella virus, resulting in German measles (rubella); parvovirus, resulting in erythema infectiosum and aplastic anemia; varicella-zoster virus, resulting in chicken pox and shingles; herpes simplex virus 1-associated, resulting in cold sores; and herpes simplex virus 2, resulting in genital herpes.

Systemic viral pathogens associated with hematopoietic disorders include, for example, cytomegalovirus, resulting in cytomegalic inclusion disease; Epstein-Barr virus, resulting in mononucleosis; HTLV-1, resulting in adult T-cell leukemia and tropical spastic paraparesis; HTLV-II; and HIV 1 and HIV 2, resulting in AIDS.

Arboviral pathogens associated with hemorrhagic fevers include, for example, dengue virus 1-4, resulting in dengue and hemorrhagic fever; yellow fever virus, resulting in yellow fever; Colorado tick fever virus, resulting in Colorado tick fever; and regional hemorrhagic fever viruses, resulting in Bolivian, Argentinian, Lassa fever.

Viral pathogens associated with warty growths and other hyperplasias include, for example, papillomavirus, resulting in condyloma and cervical carcinoma; and molluscum virus, resulting in molluscum contagiosum.

Viral pathogens associated with central nervous system disorders include, for example, poliovirus, resulting in poliomyelitis; rabiesvirus, associated with rabies; JC virus, associated with progressive multifocal leukoencephalophathy; and arboviral encephalitis viruses, resulting in Eastern, Western, Venezuelan, St. Louis, or California group encephalitis.

Viral pathogens associated with cancer include, for example, human papillomaviruses, implicated in the genesis of several cancers including squamous cell carcinoma of the cervix and anogenital region, oral cancer and laryngeal cancers; Epstein-Barr virus, implicated in pathogenesis of the African form of Burkitt lymphoma, B-cell lymphomas, Hodgkin disease, and nasopharyngeal carcinomas; hepatitis B virus, implicated in liver cancer; human T-cell leukemia virus type 1 (HTLV-1), associated with T-cell leukemia/lymphoma; and the Kaposi sarcoma herpesvirus (KSHV).

The ubiquitin protease polypeptides are thus useful for treating a ubiquitin protease-associated disorder characterized by aberrant expression or activity of a ubiquitin protease. The polypeptides can also be useful for treating a disorder characterized by excessive amounts of polyubiquitin or ubiquitinated substrate/remnant/amino acid. In one embodiment, the method involves administering an agent (e.g., an agent identified by a screening assay described herein), or combination of agents that modulates (e.g., upregulates or downregulates) expression or activity of the protein. In another embodiment, the method involves administering the ubiquitin protease as therapy to compensate for reduced or aberrant expression or activity of the protein.

Methods for treatment include but are not limited to the use of soluble ubiquitin protease or fragments of the ubiquitin protease protein that compete for substrates including those disclosed herein. These ubiquitin proteases or fragments can have a higher affinity for the target so as to provide effective competition.

Stimulation of activity is desirable in situations in which the protein is abnormally downregulated and/or in which increased activity is likely to have a beneficial effect, such as virally-infected cells. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO 94/10300), to identify other proteins (captured proteins) which bind to or interact with the proteins of the invention and modulate their activity.

The ubiquitin protease polypeptides also are useful to provide a target for diagnosing a disease or predisposition to disease mediated by the ubiquitin protease, including, but not limited to, diseases involving tissues in which the ubiquitin proteases are expressed as disclosed herein, such as breast, lung, and liver cancer (colon metastases). Accordingly, methods are provided for detecting the presence, or levels of, the ubiquitin protease in a cell, tissue, or organism. The method involves contacting a biological sample with a compound capable of interacting with the ubiquitin protease such that the interaction can be detected.

The polypeptides are also useful for treating a disorder characterized by reduced amounts of these components. Thus, increasing or decreasing the activity of the protease is beneficial to treatment. The polypeptides are also useful to provide a target for diagnosing a disease characterized by excessive substrate or reduced levels of substrate. Accordingly, where substrate is excessive, use of the protease polypeptides can provide a diagnostic assay. Furthermore, for example, proteases having reduced activity can be used to diagnose conditions in which reduced substrate is responsible for the disorder.

One agent for detecting ubiquitin protease is an antibody capable of selectively binding to ubiquitin protease. A biological sample includes tissues, cells and biological fluids isolated from a subject, as well as tissues, cells and fluids present within a subject.

The ubiquitin protease also provides a target for diagnosing active disease, or predisposition to disease, in a patient having a variant ubiquitin protease. Thus, ubiquitin protease can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered ubiquitin protease activity in cell-based or cell-free assay, alteration in binding to or hydrolysis of polyubiquitin, binding to ubiquitinated substrate protein or hydrolysis of the ubiquitin from the protein, binding to ubiquitinated protein remnant, including peptide or amino acid, and hydrolysis of the ubiquitin from the remnant, general protein turnover, specific protein turnover, antibody-binding pattern, altered isoelectric point, direct amino acid sequencing, and any other of the known assay techniques useful for detecting mutations in a protein in general or in a ubiquitin protease specifically, including assays discussed herein.

In vitro techniques for detection of ubiquitin protease include enzyme linked immunosorbent assays (ELISAs), Western blots, immunoprecipitations and immunofluorescence. Alternatively, the protein can be detected in vivo in a subject by introducing into the subject a labeled anti-ubiquitin protease antibody. For example, the antibody can be labeled with a radioactive marker whose presence and location in a subject can be detected by standard imaging techniques. Particularly useful are methods, which detect the allelic variant of the ubiquitin protease expressed in a subject, and methods, which detect fragments of the ubiquitin protease in a sample.

The ubiquitin protease polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) Clin. Exp. Pharmacol. Physiol. 23(10-11):983-985, and Linder, M. W. (1997) Clin. Chem. 43(2):254-266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the ubiquitin protease in which one or more of the ubiquitin protease functions in one population is different from those in another population. The polypeptides thus allow a target to ascertain a genetic predisposition that can affect treatment modality. Thus, in a ubiquitin-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The ubiquitin protease polypeptides are also useful for monitoring therapeutic effects during clinical trials and other treatment. Thus, the therapeutic effectiveness of an agent that is designed to increase or decrease gene expression, protein levels or ubiquitin protease activity can be monitored over the course of treatment using the ubiquitin protease polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the ubiquitin protease and its variants and fragments. An antibody is considered to selectively bind, even if it also binds to other proteins that are not substantially homologous with the ubiquitin protease. These other proteins share homology with a fragment or domain of the ubiquitin protease. This conservation in specific regions gives rise to antibodies that bind to both proteins by virtue of the homologous sequence. In this case, it would be understood that antibody binding to the ubiquitin protease is still selective.

To generate antibodies, an isolated ubiquitin protease polypeptide is used as an immunogen to generate antibodies using standard techniques for polyclonal and monoclonal antibody preparation. Either the full-length protein or antigenic peptide fragment can be used. Regions having a high antigenicity index are shown in FIG. 34.

Antibodies are preferably prepared from these regions or from discrete fragments in these regions. However, antibodies can be prepared from any region of the peptide as described herein. A preferred fragment produces an antibody that diminishes or completely prevents substrate hydrolysis or binding. Antibodies can be developed against the entire ubiquitin protease or domains of the ubiquitin protease as described herein. Antibodies can also be developed against specific functional sites as disclosed herein.

The antigenic peptide can comprise a contiguous sequence of at least 12, 14, 15, or amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g., Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An appropriate immunogenic preparation can be derived from native, recombinantly expressed, or chemically synthesized peptides.

Antibody Uses

The antibodies can be used to isolate a ubiquitin protease by standard techniques, such as affinity chromatography or immunoprecipitation. The antibodies can facilitate the purification of the natural ubiquitin protease from cells and recombinantly produced ubiquitin protease expressed in host cells.

The antibodies are useful to detect the presence of ubiquitin protease in cells or tissues to determine the pattern of expression of the ubiquitin protease among various tissues in an organism and over the course of normal development.

The antibodies can be used to detect ubiquitin protease in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full-length ubiquitin protease can be used to identify ubiquitin protease turnover.

Further, the antibodies can be used to assess ubiquitin protease expression in disease states such as in active stages of the disease or in an individual with a predisposition toward disease related to ubiquitin or ubiquitin protease function. When a disorder is caused by an inappropriate tissue distribution, developmental expression, or level of expression of the ubiquitin protease protein, the antibody can be prepared against the normal ubiquitin protease protein. If a disorder is characterized by a specific mutation in the ubiquitin protease, antibodies specific for this mutant protein can be used to assay for the presence of the specific mutant ubiquitin protease. However, intracellularly-made antibodies ("intrabodies") are also encompassed, which would recognize intracellular ubiquitin protease peptide regions.

The antibodies can also be used to assess normal and aberrant subcellular localization of cells in the various tissues in an organism. Antibodies can be developed against the whole ubiquitin protease or portions of the ubiquitin protease.

The diagnostic uses can be applied, not only in genetic testing, but also in monitoring a treatment modality. Accordingly, where treatment is ultimately aimed at correcting ubiquitin protease expression level or the presence of aberrant ubiquitin proteases and aberrant tissue distribution or developmental expression, antibodies directed against the ubiquitin protease or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic ubiquitin protease can be used to identify individuals that require modified treatment modalities.

The antibodies are also useful as diagnostic tools as an immunological marker for aberrant ubiquitin protease analyzed by electrophoretic mobility, isoelectric point, tryptic peptide digest, and other physical assays known to those in the art.

The antibodies are also useful for tissue typing. Thus, where a specific ubiquitin protease has been correlated with expression in a specific tissue, antibodies that are specific for this ubiquitin protease can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting ubiquitin protease function, for example, blocking ubiquitin or polyubiquitin binding, or binding to ubiquitinated substrate or substrate remnants.

These uses can also be applied in a therapeutic context in which treatment involves inhibiting ubiquitin protease function. An antibody can be used, for example, to block ubiquitin binding. Antibodies can be prepared against specific fragments containing sites required for function or against intact ubiquitin protease associated with a cell.

Completely human antibodies are particularly desirable for therapeutic treatment of human patients. For an overview of this technology for producing human antibodies, see Lonberg et al. (1995) Int. Rev. Immunol. 13:65-93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a ubiquitin protease protein in a biological sample. The kit can comprise antibodies such as a labeled or labelable antibody and a compound or agent for detecting ubiquitin protease in a biological sample; means for determining the amount of ubiquitin protease in the sample; and means for comparing the amount of ubiquitin protease in the sample with a standard. The compound or agent can be packaged in a suitable container. The kit can further comprise instructions for using the kit to detect ubiquitin protease.

Polynucleotides

The nucleotide sequence in SEQ ID NO:16 was obtained by sequencing the deposited human cDNA. Accordingly, the sequence of the deposited clone is controlling as to any discrepancies between the two and any reference to the sequence of SEQ ID NO:16 includes reference to the sequence of the deposited cDNA.

The specifically disclosed cDNA comprises the coding region and 5' and 3' untranslated sequences in SEQ ID NO:16.

The invention provides isolated polynucleotides encoding the novel ubiquitin protease. The term "ubiquitin protease polynucleotide" or "ubiquitin protease nucleic acid" refers to the sequence shown in SEQ ID NO:16 or in the deposited cDNA. The term "ubiquitin protease polynucleotide" or "ubiquitin protease nucleic acid" further includes variants and fragments of the ubiquitin protease polynucleotide.

An "isolated" ubiquitin protease nucleic acid is one that is separated from other nucleic acid present in the natural source of the ubiquitin protease nucleic acid. Preferably, an "isolated" nucleic acid is free of sequences which naturally flank the ubiquitin protease nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the ubiquitin protease nucleic acid is isolated from flanking sequences such that it can be subjected to the specific manipulations described herein, such as recombinant expression, preparation of probes and primers, and other uses specific to the ubiquitin protease nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The ubiquitin protease polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The ubiquitin protease polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Ubiquitin protease polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

Ubiquitin protease nucleic acid can comprise the nucleotide sequence shown in SEQ ID NO:16, corresponding to human cDNA.

In one embodiment, the ubiquitin protease nucleic acid comprises only the coding region.

The invention further provides variant ubiquitin protease polynucleotides, and fragments thereof, that differ from the nucleotide sequence shown in SEQ ID NO:16 due to degeneracy of the genetic code and thus encode the same protein as that encoded by the nucleotide sequence shown in SEQ ID NO:16.

The invention also provides ubiquitin protease nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecule of SEQ ID NO:16 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a ubiquitin protease that is at least about 60-65%, 65-70%, typically at least about 70-75%, more typically at least about 80-85%, and most typically at least about 90-95% or more homologous to the nucleotide sequence shown in SEQ ID NO:16. Such nucleic acid molecules can readily be identified as being able to hybridize under stringent conditions, to the nucleotide sequence shown in SEQ ID NO:16 or a fragment of the sequence. It is understood that stringent hybridization does not indicate substantial homology where it is due to general homology, such as poly A sequences, or sequences common to all or most proteins or all deubiquitinating enzymes. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60-65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1-6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50-65° C. In another non-limiting example, nucleic acid molecules are allowed to hybridize in 6× sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:15 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:16 or the complement of SEQ ID NO:16. In one embodiment, the nucleic acid consists of a portion of the nucleotide sequence of SEQ ID NO:16 or the complement of SEQ ID NO:16.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 15, preferably at least about 18, 20, 23 or 25 nucleotides, and can be 30, 40, 50, 100, 200, 500 or more nucleotides in length.

For example, nucleotide sequences 1 to about 269, about 761 to about 817, about 994 to about 1554, and about 1735 to about 2314 are not disclosed prior to the invention. The nucleotide sequence from about 269 to 761 encompasses fragments greater than 14, 18, 20, 23 or 25 nucleotides; the nucleotide sequence from about 817 to about 994 encompasses fragments greater than 6, 10, 15, 20, or 25 nucleotides; the nucleotide sequences from about 1154 to 1735 encompasses fragments greater than 13, 18, 20, 23 or 25 nucleotides; and the nucleotide sequence from about 2314 to about 2520 encompasses fragments greater than 33, 40, 45, or 50 nucleotides. Longer fragments, for example, 30 or more nucleotides in length, which encode antigenic proteins or polypeptides described herein are useful.

Furthermore, the invention provides polynucleotides that comprise a fragment of the full-length ubiquitin protease polynucleotides. The fragment can be single or double-stranded standard and can comprise DNA or RNA. The fragment can be derived from either the coding or the non-coding sequence.

In another embodiment an isolated ubiquitin protease nucleic acid encodes the entire coding region. Other fragments include nucleotide sequences encoding the amino acid fragments described herein.

Thus, ubiquitin protease nucleic acid fragments further include sequences corresponding to the domains described herein, subregions also described, and specific functional sites. Ubiquitin protease nucleic acid fragments also include combinations of the domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains.

However, it is understood that a ubiquitin protease fragment includes any nucleic acid sequence that does not include the entire gene.

The invention also provides ubiquitin protease nucleic acid fragments that encode epitope bearing regions of the ubiquitin protease proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497-1500. Typically, a probe comprises a region of nucleotide sequence that hybridizes under highly stringent conditions to at least about 15, typically about 20-25, and more typically about 40, 50 or 75 consecutive nucleotides of the nucleic acid sequence shown in SEQ ID NO:16 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The ubiquitin protease polynucleotides are thus useful for probes, primers, and in biological assays.

Where the polynucleotides are used to assess ubiquitin protease properties or functions, such as in the assays described herein, all or less than all of the entire cDNA can be useful. Assays specifically directed to ubiquitin protease functions, such as assessing agonist or antagonist activity, encompass the use of known fragments. Further, diagnostic methods for assessing ubiquitin protease function can also be practiced with any fragment, including those fragments that may have been known prior to the invention. Similarly, in methods involving treatment of ubiquitin protease dysfunction, all fragments are encompassed including those, which may have been known in the art.

The ubiquitin protease polynucleotides are useful as a hybridization probe for cDNA and genomic DNA to isolate a full-length cDNA and genomic clones encoding the polypeptide described in SEQ ID NO:15 and to isolate cDNA and genomic clones that correspond to variants producing the same polypeptide shown in SEQ ID NO:15 or the other variants described herein. Variants can be isolated from the same tissue and organism from which the polypeptides shown in SEQ ID NO:15 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the ubiquitin protease. Accordingly, it could be derived from 5' noncoding regions, the coding region, and 3' noncoding regions.

The nucleic acid probe can be, for example, the full-length cDNA of SEQ ID NO:16 or a fragment thereof that is sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequence of SEQ ID NO:16, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:1467.0. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357-63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell ubiquitin proteases in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958-976) or intercalating agents (see, e.g., Zon (1988) *Pharm Res.* 5:539-549).

The ubiquitin protease polynucleotides are also useful as primers for PCR to amplify any given region of a ubiquitin protease polynucleotide.

The ubiquitin protease polynucleotides are also useful for constructing recombinant vectors. Such vectors include expression vectors that express a portion of, or all of, the ubiquitin protease polypeptides. Vectors also include insertion vectors, used to integrate into another polynucleotide sequence, such as into the cellular genome, to alter in situ expression of ubiquitin protease genes and gene products. For example, an endogenous ubiquitin protease coding sequence can be replaced via homologous recombination with all or part of the coding region containing one or more specifically introduced mutations.

The ubiquitin protease polynucleotides are also useful for expressing antigenic portions of the ubiquitin protease proteins.

The ubiquitin protease polynucleotides are also useful as probes for determining the chromosomal positions of the ubiquitin protease polynucleotides by means of in situ hybridization methods, such as FISH. (For a review of this technique, see Verma et al. (1988) *Human Chromosomes: A Manual of Basic Techniques*(Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783-787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The ubiquitin protease polynucleotide probes are also useful to determine patterns of the presence of the gene encoding the ubiquitin proteases and their variants with respect to tissue distribution, for example, whether gene duplication has occurred and whether the duplication occurs in all or only a subset of tissues. The genes can be naturally occurring or can have been introduced into a cell, tissue, or organism exogenously.

The ubiquitin protease polynucleotides are also useful for designing ribozymes corresponding to all, or a part, of the mRNA produced from genes encoding the polynucleotides described herein.

The ubiquitin protease polynucleotides are also useful for constructing host cells expressing a part, or all, of the ubiquitin protease polynucleotides and polypeptides.

The ubiquitin protease polynucleotides are also useful for constructing transgenic animals expressing all, or a part, of the ubiquitin protease polynucleotides and polypeptides.

The ubiquitin protease polynucleotides are also useful for making vectors that express part, or all, of the ubiquitin protease polypeptides.

The ubiquitin protease polynucleotides are also useful as hybridization probes for determining the level of ubiquitin protease nucleic acid expression. Accordingly, the probes can be used to detect the presence of, or to determine levels of, ubiquitin protease nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the ubiquitin protease genes.

Alternatively, the probe can be used in an in situ hybridization context to assess the position of extra copies of the ubiquitin protease genes, as on extrachromosomal elements or as integrated into chromosomes in which the ubiquitin protease gene is not normally found, for example as a homogeneously staining region.

These uses are relevant for diagnosis of disorders involving an increase or decrease in ubiquitin protease expression relative to normal, such as a proliferative disorder, a differentiative or developmental disorder, or a hematopoietic disorder.

Tissues and/or cells in which the ubiquitin protease is expressed include, but are not limited to those shown in FIGS. 37 and 38. Tissues in which the gene is highly expressed include fetal kidney, testes, fetal liver, ovary, and fetal heart. Expression is also seen in the kidney, thyroid, undifferentiated osteoblasts and skeletal muscle. The ubiquitin protease is also expressed in normal liver and in normal and malignant breast, lung, and colon tissue and in liver metastases derived from malignant colonic tissues. The ubiquitin proteases are thus specifically involved in breast, lung, and liver cancer.

As such, the gene is particularly relevant for the treatment of disorders involving these tissues. Disorders in which the ubiquitin protease expression is relevant are disclosed herein above.

Furthermore, the ubiquitin protease is useful to treat viral infections and disorders resulting from viral infections. Such disorders are discussed above.

Thus, the present invention provides a method for identifying a disease or disorder associated with aberrant expression or activity of ubiquitin protease nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the ubiquitin protease, such as by measuring the level of a ubiquitin protease-encoding nucleic acid in a sample of cells from a subject e.g., mRNA or genomic DNA, or determining if the ubiquitin protease gene has been mutated.

Nucleic acid expression assays are useful for drug screening to identify compounds that modulate ubiquitin protease nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the ubiquitin protease gene. The method typically includes assaying the ability of the compound to modulate the expression of the ubiquitin protease nucleic acid and thus identifying a compound that can be used to treat a disorder characterized by undesired ubiquitin protease nucleic acid expression.

The assays can be performed in cell-based and cell-free systems. Cell-based assays include cells naturally expressing the ubiquitin protease nucleic acid or recombinant cells genetically engineered to express specific nucleic acid sequences.

Alternatively, candidate compounds can be assayed in vivo in patients or in transgenic animals.

The assay for ubiquitin protease nucleic acid expression can involve direct assay of nucleic acid levels, such as mRNA levels, or on collateral compounds involved in the pathway (such as free ubiquitin pool or protein turnover). Further, the expression of genes that are up- or down-regulated in response to the ubiquitin protease activity can also be assayed. In this embodiment the regulatory regions of these genes can be operably linked to a reporter gene such as luciferase.

Thus, modulators of ubiquitin protease gene expression can be identified in a method wherein a cell is contacted with a candidate compound and the expression of mRNA determined. The level of expression of ubiquitin protease mRNA in the presence of the candidate compound is compared to the level of expression of ubiquitin protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate ubiquitin protease nucleic acid expression. Modulation includes both up-regulation (i.e. activation or agonization) or down-regulation (suppression or antagonization) or effects on nucleic acid activity (e.g., when nucleic acid is mutated or improperly modified). Treatment includes disorders characterized by aberrant expression or activity of the nucleic acid. In addition, disorders that are influenced by the ubiquitin protease may also be treated. Examples of such disorders are disclosed herein.

Alternatively, a modulator for ubiquitin protease nucleic acid expression can be a small molecule or drug identified using the screening assays described herein as long as the drug or small molecule inhibits the ubiquitin protease nucleic acid expression.

The ubiquitin protease polynucleotides are also useful for monitoring the effectiveness of modulating compounds on the expression or activity of the ubiquitin protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The ubiquitin protease polynucleotides are also useful in diagnostic assays for qualitative changes in ubiquitin protease nucleic acid, and particularly in qualitative changes that lead to pathology. The polynucleotides can be used to detect mutations in ubiquitin protease genes and gene expression products such as mRNA. The polynucleotides can be used as hybridization probes to detect naturally-occurring genetic mutations in the ubiquitin protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the ubiquitin protease gene associated with a dysfunction provides a diagnostic tool for an active disease or susceptibility to disease when the disease results from overexpression, underexpression, or altered expression of a ubiquitin protease.

Mutations in the ubiquitin protease gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) PNAS 91:360-364), the latter of which can be particularly useful for detecting point mutations in the gene (see Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a ubiquitin protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant ubiquitin protease gene and a wild-type gene can be determined by direct DNA sequencing. A variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the gene include methods in which protection from cleavage agents is used to detect mismatched bases in RNA/RNA or RNA/DNA duplexes (Myers et al. (1985) Science 230:1242); Cotton et al. (1988) PNAS 85:4397; Saleeba et al. (1992) Meth. Enzymol. 217:286-295), electrophoretic mobility of mutant and wild type nucleic acid is compared (Orita et al. (1989) PNAS 86:2766; Cotton et al. (1993) Mutat. Res. 285:125-144; and Hayashi et al. (1992) Genet. Anal. Tech. Appl. 9:73-79), and movement of mutant or wild-type fragments in polyacrylamide gels containing a gradient of denaturant is assayed using denaturing gradient gel electrophoresis (Myers et al. (1985) Nature 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) Trends Genet. 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) Human Mutation 7:244-255; Kozal et al. (1996) Nature Medicine 2:753-759). For example, genetic mutations can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The ubiquitin protease polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the ubiquitin protease gene that results in altered affinity for ubiquitin could result in an excessive or decreased drug effect with standard concentrations of ubiquitin or analog. Accordingly, the ubiquitin protease polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The ubiquitin protease polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The ubiquitin protease polynucleotides can also be used to identify individuals based on small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the ubiquitin protease sequence can be used to provide an alternative technique, which determines the actual DNA sequence of selected fragments in the genome of an individual. Thus, the ubiquitin protease sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The ubiquitin protease sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The ubiquitin protease polynucleotides can also be used in forensic identification procedures. PCR technology can be used to amplify DNA sequences taken from very small biological samples, such as a single hair follicle, body fluids (e.g., blood, saliva, or semen). The amplified sequence can then be compared to a standard allowing identification of the origin of the sample.

The ubiquitin protease polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The ubiquitin protease polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of ubiquitin protease probes can be used to identify tissue by species and/or by organ type.

In a similar fashion, these primers and probes can be used to screen tissue culture for contamination (i.e., screen for the presence of a mixture of different types of cells in a culture).

Alternatively, the ubiquitin protease polynucleotides can be used directly to block transcription or translation of ubiquitin protease gene sequences by means of antisense or ribozyme constructs. Thus, in a disorder characterized by abnormally high or undesirable ubiquitin protease gene expression, nucleic acids can be directly used for treatment.

The ubiquitin protease polynucleotides are thus useful as antisense constructs to control ubiquitin protease gene expression in cells, tissues, and organisms. A DNA antisense polynucleotide is designed to be complementary to a region of the gene involved in transcription, preventing transcription and hence production of ubiquitin protease protein. An antisense RNA or DNA polynucleotide would hybridize to the mRNA and thus block translation of mRNA into ubiquitin protease protein.

Examples of antisense molecules useful to inhibit nucleic acid expression include antisense molecules complementary to a fragment of the 5' untranslated region of SEQ ID NO:16 which also includes the start codon and antisense molecules which are complementary to a fragment of the 3' untranslated region of SEQ ID NO:16.

Alternatively, a class of antisense molecules can be used to inactivate mRNA in order to decrease expression of ubiquitin protease nucleic acid. Accordingly, these molecules can treat a disorder characterized by abnormal or undesired ubiquitin protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the ubiquitin protease protein.

The ubiquitin protease polynucleotides also provide vectors for gene therapy in patients containing cells that are aberrant in ubiquitin protease gene expression. Thus, recombinant cells, which include the patient's cells that have been engineered ex vivo and returned to the patient, are introduced into an individual where the cells produce the desired ubiquitin protease protein to treat the individual.

The invention also encompasses kits for detecting the presence of a ubiquitin protease nucleic acid in a biological sample. For example, the kit can comprise reagents such as a labeled or labelable nucleic acid or agent capable of detecting ubiquitin protease nucleic acid in a biological sample; means for determining the amount of ubiquitin protease nucleic acid in the sample; and means for comparing the amount of ubiquitin protease nucleic acid in the sample with a standard. The compound or agent can be packaged in a suitable container. The kit can further comprise instructions for using the kit to detect ubiquitin protease mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBIA).

For example, software which implements the BLAST (Altschul et al. (1990) *J. Mol. Biol.* 215:403-410) and BLAZE (Brutlag et al. (1993) *Comp. Chem.* 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the ubiquitin protease polynucleotides. The term "vector" refers to a vehicle, preferably a nucleic acid molecule that can transport the ubiquitin protease polynucleotides. When the vector is a nucleic acid molecule, the ubiquitin protease polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the ubiquitin protease polynucleotides. Alternatively, the vector may integrate into the host cell genome and produce additional copies of the ubiquitin protease polynucleotides when the host cell replicates.

The invention provides vectors for the maintenance (cloning vectors) or vectors for expression (expression vectors) of the ubiquitin protease polynucleotides. The vectors can function in procaryotic or eukaryotic cells or in both (shuttle vectors).

Expression vectors contain cis-acting regulatory regions that are operably linked in the vector to the ubiquitin protease polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the ubiquitin protease polynucleotides from the vector. Alternatively, a trans-acting factor may be supplied by the host cell. Finally, a trans-acting factor can be produced from the vector itself.

It is understood, however, that in some embodiments, transcription and/or translation of the ubiquitin protease polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd. ed., Cold Spring Harbor Laboratory Press, Cold Spring Harbor, N.Y.).

A variety of expression vectors can be used to express a ubiquitin protease polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g., cosmids and phagemids. Appropriate cloning and expression vectors for prokaryotic and eukaryotic hosts are described in Sambrook et al. (1989) *Molecular Cloning: A Laboratory Manual* 2nd. ed., Cold Spring Harbor Laboratory Press, Cold Spring Harbor, N.Y.

The regulatory sequence may provide constitutive expression in one or more host cells (i.e., tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The ubiquitin protease polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the ubiquitin protease polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301-315) and pET 11d (Studier et al. (1990) *Gene Expression Technology: Methods in Enzymology* 185:60-89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119-128). Alternatively, the sequence of the polynucleotide of interest can be altered to provide preferential codon usage for a specific host cell, for example *E. coli*. (Wada et al. (1992) *Nucleic Acids Res.* 20:2111-2118).

The ubiquitin protease polynucleotides can also be expressed by expression vectors that are operative in yeast. Examples of vectors for expression in yeast e.g., *S. cerevisiae* include pYepSec1 (Baldari et al. (1987) *EMBO J.* 6:229-234), pMFa (Kurjan et al. (1982) *Cell* 30:933-943), pJRY88 (Schultz et al. (1987) *Gene* 54:113-123), and pYES2 (Invitrogen Corporation, San Diego, Calif.).

The ubiquitin protease polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow et al. (1989) *Virology* 170:31-39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187-195).

The expression vectors listed herein are provided by way of example only of the well-known vectors available to those of ordinary skill in the art that would be useful to express the ubiquitin protease polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual* 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the ubiquitin protease polynucleotides can be introduced either alone or with other polynucleotides that are not related to the ubiquitin protease polynucleotides such as those providing trans-acting factors for expression vectors. When more than one vector is introduced into a cell, the vectors can be introduced independently, co-introduced or joined to the ubiquitin protease polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the ubiquitin protease polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing ubiquitin protease proteins or polypeptides that can be further purified to produce desired amounts of ubiquitin protease protein or fragments. Thus, host cells containing expression vectors are useful for polypeptide production.

Host cells are also useful for conducting cell-based assays involving the ubiquitin protease or ubiquitin protease fragments. Thus, a recombinant host cell expressing a native ubiquitin protease is useful to assay for compounds that stimulate or inhibit ubiquitin protease function. This includes disappearance of substrate (polyubiquitin, ubiquitinated substrate protein, ubiquitinated substrate remnants), appearance of end product (ubiquitin monomers, polyubiquitin hydrolyzed from substrate or substrate remnant, free substrate that has been rescued by hydrolysis of ubiquitin), general or specific protein turnover, and the various other molecular functions described herein that include, but are not limited to, substrate recognition, substrate binding, subunit association, and interaction with other cellular components. Modulation of gene expression can occur at the level of transcription or translation.

Host cells are also useful for identifying ubiquitin protease mutants in which these functions are affected. If the mutants naturally occur and give rise to a pathology, host cells containing the mutations are useful to assay compounds that have a desired effect on the mutant ubiquitin protease (for example, stimulating or inhibiting function) which may not be indicated by their effect on the native ubiquitin protease.

Recombinant host cells are also useful for expressing the chimeric polypeptides described herein to assess compounds that activate or suppress activation or alter specific function by means of a heterologous domain, segment, site, and the like, as disclosed herein.

Further, mutant ubiquitin proteases can be designed in which one or more of the various functions is engineered to be increased or decreased (e.g., binding to ubiquitin, polyubiquitin, or ubiquitinated protein substrate) and used to augment or replace ubiquitin protease proteins in an individual. Thus, host cells can provide a therapeutic benefit by replacing an aberrant ubiquitin protease or providing an aberrant ubiquitin protease that provides a therapeutic result. In one embodiment, the cells provide ubiquitin proteases that are abnormally active.

In another embodiment, the cells provide ubiquitin proteases that are abnormally inactive. These ubiquitin proteases can compete with endogenous ubiquitin proteases in the individual.

In another embodiment, cells expressing ubiquitin proteases that cannot be activated, are introduced into an individual in order to compete with endogenous ubiquitin proteases for ubiquitin substrates. For example, in the case in which excessive ubiquitin substrate or analog is part of a treatment modality, it may be necessary to inactivate this molecule at a specific point in treatment. Providing cells that compete for the molecule, but which cannot be affected by ubiquitin protease activation would be beneficial.

Homologously recombinant host cells can also be produced that allow the in situ alteration of endogenous ubiquitin protease polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the ubiquitin protease polynucleotides or sequences proximal or distal to a ubiquitin protease gene are allowed to integrate into a host cell genome by homologous recombination where expression of the gene can be affected. In one embodiment, regulatory sequences are introduced that either increase or decrease expression of an endogenous sequence. Accordingly, a ubiquitin protease can be produced in a cell not normally producing it. Alternatively, increased expression of ubiquitin protease can be effected in a cell normally producing the protein at a specific level. Further, expression can be decreased or eliminated by introducing a specific regulatory sequence. The regulatory sequence can be heterologous to the ubiquitin protease protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant ubiquitin protease proteins. Such mutations could be introduced, for example, into the specific functional regions such as the ligand-binding site.

In one embodiment, the host cell can be a fertilized oocyte or embryonic stem cell that can be used to produce a transgenic animal containing the altered ubiquitin protease gene. Alternatively, the host cell can be a stem cell or other early tissue precursor that gives rise to a specific subset of cells and can be used to produce transgenic tissues in an animal. See also Thomas et al., Cell 51:503 (1987) for a description of homologous recombination vectors. The vector is introduced into an embryonic stem cell line (e.g., by electroporation) and cells in which the introduced gene has homologously recombined with the endogenous ubiquitin protease gene is selected (see e.g., Li, E. et al. (1992) Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinion in Biotechnology 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a ubiquitin protease protein and identifying and evaluating modulators of ubiquitin protease protein activity.

Other examples of transgenic animals include non-human primates, sheep, dogs, cows, goats, chickens, and amphibians.

In one embodiment, a host cell is a fertilized oocyte or an embryonic stem cell into which ubiquitin protease polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the ubiquitin protease nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the ubiquitin protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect, for example, binding, activation, and protein turnover, may not be evident from in vitro cell-free or cell-based assays. Accordingly, it is useful to provide non-human transgenic animals to assay in vivo ubiquitin protease function, including substrate interaction, the effect of specific mutant ubiquitin proteases on ubiquitin protease function and substrate interaction, and the effect of chimeric ubiquitin proteases. It is also possible to assess the effect of null mutations, that is mutations that substantially or completely eliminate one or more ubiquitin protease functions.

In general, methods for producing transgenic animals include introducing a nucleic acid sequence according to the present invention, the nucleic acid sequence capable of expressing the receptor protein in a transgenic animal, into a cell in culture or in vivo. When introduced in vivo, the nucleic acid is introduced into an intact organism such that one or more cell types and, accordingly, one or more tissue types, express the nucleic acid encoding the receptor protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The ubiquitin protease nucleic acid molecules, protein modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a ubiquitin protease protein or anti-ubiquitin protease antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the purview of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

CHAPTER 4

18891, a Novel Human Lipase

BACKGROUND OF THE INVENTION

Lipases are indispensable for the bioconversion of lipids within an organism through the catalysis of a variety of reactions that include hydrolysis, alcoholysis, acidolysis, esterfication and aminolysis. In humans, several lipases have been identified which possess lipolytic activities that regulate levels of triglycerides and cholesterol in the body. Enzymes from this superfamily include lipoprotein lipase (LPL), hepatic lipase (HL), and pancreatic lipase (PL). While all three enzymes hydrolyze lipid emulsions and have similar aqueous-lipid interfacial catalytic activities, they each possess unique properties and physiological functions. All three enzymes act preferentially on the sn-1 and sn-3 bonds of triglycerides, to release fatty acids from the glycerol backbone (Dolphin et al. (1992) *Structure and Function of Apolipoproteins*, Rosseneu, M. (ed) CRC Press, Inc, Boca Ratan, 295-362). However, while PL completes the hydrolysis of alimentary triglycerides, the LPL and HL enzymes hydrolyze triglycerides found in circulating lipoproteins.

Due to the insolubility of lipids in water, the plasma transports complex lipids among various tissues as components of lipoproteins. Each lipoprotein contains a neutral lipid core composed of triacylglycerol and/or a cholesterol ester. Surrounding the core is a layer of proteins, phospholipids, and cholesterol. The proteins associated with the lipoprotein comprise a class of proteins referred to as apoproteins (apo). Based on apoprotein composition and density, lipoproteins have been classified into five major types that include chylomicrons, high-density lipoproteins (HDL), intermediate-density lipoproteins (IDL), low-density lipoproteins (LDL), and very-low density lipoproteins (VLDL).

Lipoprotein lipase (LPL) is the major enzyme responsible for the hydrolysis of triglyceride molecules present in circulating lipoproteins. LPL is associated with the luminal side of capillaries and arteries through an interaction with heparin-sulfate chains of proteoglycans and/or by glycerol phosphatidylinostintol. With the help of the activator apo CII, LPL hydrolyzes triglycerides of lipoproteins to produce free fatty acids. Muscle and adipose tissue assimilate these fatty acids. Alternatively, the fatty acids can be bound to albumin and transported to other tissues. As the lipase hydrolyzes the triglycerides of the lipoprotein, the particles become smaller and are often referred to as lipoprotein remnants. Within the plasma compartment, LPL converts chylomicrons to remnants and begins the cascade requirements for conversion of VLDL to LDL.

In its active form, LPL is a glycosylated non-covalent homodimer, with each subunit containing a binding site for heparin and apolipoprotein (apo) CII, an activator protein required for LPL activity. In addition to hydrolysis of triglycerides, LPL can hydrolyze a variety of other substrates, for example, long and short chain glycerides, phospholipids and various synthetic substrates (Olivecrona et al. (1987) *Lipoprotein Lipase* Borensztajn, J. (ed) Evener Publisher, Inc., pages 15-58).

In addition to the lypolytic activity of LPL described above, LPL plays additional roles in lipid metabolism. After sufficient hydrolysis, lipoprotein lipase is released from proteoglycans and travels with the remnants of the chylomicrons or VLDL. In the plasma LPL may then act to sequester the remnant particles on surface proteoglycans. Subsequently LPL can act as a ligand for receptors such as the LDL receptor, LDL-receptor related protein, gp330, or the VLDL receptor. This interaction with the cell surface receptor facilitates the uptake and degradation of plasma lipoproteins by cells (Williams et al. (1992) *J. Biol. Chem.* 267:13284-13292 and Nykjaer et al. (1993) *J. Biol. Chem.* 268:15048-15055).

Furthermore, LPL expressed in macrophages has been implicated in the cellular uptake of lipoprotein lipids and fat soluble vitamins, the degradation of lipid-containing pathogens and cell debris, and the creation of fatty acids for the energy requirements of the cell.

Disruption of LPL activity has also been implicated in other biological functions including, for example, enhanced oxidative stress in blood cells, increased fluidity of the membrane components of these cells and increases the susceptibility of their mitochondrial DNA to structural alterations (Ven Murthy et al. (1996) *Acta Biochimica Polonica* 43:227-40).

Hepatic lipase (HL) has functions in lipid metabolism similar to those of LPL. HL is located on the surface of liver sinusoids through glycosaminoglycan links where it interacts with lipoproteins and hydrolyzes triglycerides into free fatty acids. Unlike LPL, the activity of HL does not require an activator, but its activity may be stimulated by apo E. Thus, the preferred substrates of HL are the triglycerides of apo E-containing lipoproteins, such as chylomicron remnants, IDL, and HDL. Furthermore, the actions of HL on HDL are important in the reverse cholesterol transport process, a mechanism thought to reduce excess accumulation of cholesterol in hepatic tissue.

Like LPL, hepatic lipase has also been implicated in the uptake and degradation of lipoprotein in the hepatic tissue. Evidence suggests that HL may interact with cell surface receptors, such as those described above, and direct hepatic cellular uptake of lipoproteins and lipoprotein remnants. (Chappell et al. (1998) *Progress in Lipid Research* 37: 363-422).

In its active form, HL exists as a monomer comprising both triglyceride lipase activity and phospholipase activity. As with LPL, treatment with heparin, results in the release of HL from the cell surfaces. While glycosylation plays an important role in secretion and affinity of LPL, it does not seem to be crucial for HL activity.

Pancreatic lipase (PL) is synthesized in acinar cells of the exocrine pancreas along with its protein activator, colipase. The pancreatic duct transports glycosylated PL and colipase into the duodenum. PL does not become anchored to membrane surfaces like LPL or HL. Instead, the free monomer of PL interacts with colipase which helps to anchor the PL to the lipid-water interface where the enzyme completes the hydrolysis of alimentary triglycerides.

In summary, lipases play a key role in lipid metabolism by regulating levels of cholesterol and triglycerides and therefore influence major metabolic processes including effects on lipid and lipoprotein concentrations, energy homeostasis, body weight, and body composition-parameters. Each of these metabolic consequences has been associated with common diseases, such as, hypertriglyceridemia, atherosclerosis, obesity and various other disease states described further below.

Accordingly, lipases are a major target for drug action and development. Thus, it is valuable to the field of pharmaceutical development to identify and characterize previously unknown lipases. The present invention advances the state of the art by providing a previously unidentified human lipase enzyme.

SUMMARY OF THE INVENTION

It is an object of the invention to identify novel lipases.

It is a further object of the invention to provide novel lipase polypeptides that are useful as reagents or targets in assays applicable to treatment and diagnosis of lipase-mediated or -related disorders, especially disorders mediated by or related to lipase enzymes.

It is a further object of the invention to provide polynucleotides corresponding to the novel lipase polypeptides that are useful as targets and reagents in assays applicable to treatment and diagnosis of lipase or lipase-mediated or -related disorders and useful for producing novel lipase polypeptides by recombinant methods.

A specific object of the invention is to identify compounds that act as agonists and antagonists and modulate the expression of the novel lipase.

A further specific object of the invention is to provide compounds that modulate expression of the lipase for treatment and diagnosis of lipase and lipase-related disorders.

The invention is thus based on the identification of a novel human lipase. The amino acid sequence is shown in SEQ ID NO:17. The nucleotide sequence is shown in SEQ ID NO:18.

The invention provides isolated lipase polypeptides, including a polypeptide having the amino acid sequence shown in SEQ ID NO:17 or the amino acid sequence encoded by the cDNA deposited as ATCC Patent Deposit No. PTA-1915 on May 24, 2000 ("the deposited cDNA").

The invention also provides isolated lipase nucleic acid molecules having the sequence shown in SEQ ID NO:18 or in the deposited cDNA.

The invention also provides variant polypeptides having an amino acid sequence that is substantially homologous to the amino acid sequence shown in SEQ ID NO:17 or encoded by the deposited cDNA.

The invention also provides variant nucleic acid sequences that are substantially homologous to the nucleotide sequence shown in SEQ ID NO:18 or in the deposited cDNA.

The invention also provides fragments of the polypeptide shown in SEQ ID NO:17 and nucleotide sequence shown in SEQ ID NO:18, as well as substantially homologous fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the lipase nucleic acid molecules and polypeptides, and particularly recombinant vectors and host cells.

The invention also provides methods of making the vectors and host cells and methods for using them to produce the lipase nucleic acid molecules and polypeptides.

The invention also provides antibodies or antigen-binding fragments thereof that selectively bind the lipase polypeptides and fragments.

The invention also provides methods of screening for compounds that modulate expression or activity of the lipase polypeptides or nucleic acid (RNA or DNA).

The invention also provides a process for modulating lipase polypeptide or nucleic acid expression or activity, especially using the screened compounds. Modulation may be used to treat conditions related to aberrant activity or expression of the lipase polypeptides or nucleic acids or aberrant activity resulting in the altered accumulation/degradation of lipids.

The invention also provides assays for determining the activity of or the presence or absence of the lipase polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Polypeptides

The invention is based on the identification of a novel human lipase. Specifically, an expressed sequence tag (EST) was selected based on homology to lipase sequences. This EST was used to design primers based on sequences that it contains and used to identify a cDNA from a brain library. Positive clones were sequenced and the overlapping fragments were assembled. Analysis of the assembled sequence revealed that the cloned cDNA molecule encodes a lipase.

The invention thus relates to a novel lipase having the deduced amino acid sequence shown in FIGS. 39A-39B (SEQ ID NO:17) or having the amino acid sequence encoded by the cDNA insert of the plasmid deposited with American Type Culture Collection (ATCC), 10801 University Boulevard, Manassas, Va. 20110-2209, on May 24, 2000 and assigned Patent Deposit Number PTA-1915.

The deposits will be maintained under the terms of the Budapest Treaty on the International Recognition of the Deposit of Microorganisms. The deposits are provided as a convenience to those of skill in the art and are not an admission that a deposit is required under 35 U.S.C. § 112. The deposited sequences, as well as the polypeptides encoded by the sequences, are incorporated herein by reference and controls in the event of any conflict, such as a sequencing error, with description in this application.

"Lipase polypeptide" or "lipase protein" refers to the polypeptide in SEQ ID NO:17 or encoded by the deposited cDNA. The term "lipase protein" or "lipase polypeptide", however, further includes the numerous variants described herein, as well as fragments derived from the full-length lipase and variants.

Figure 43:
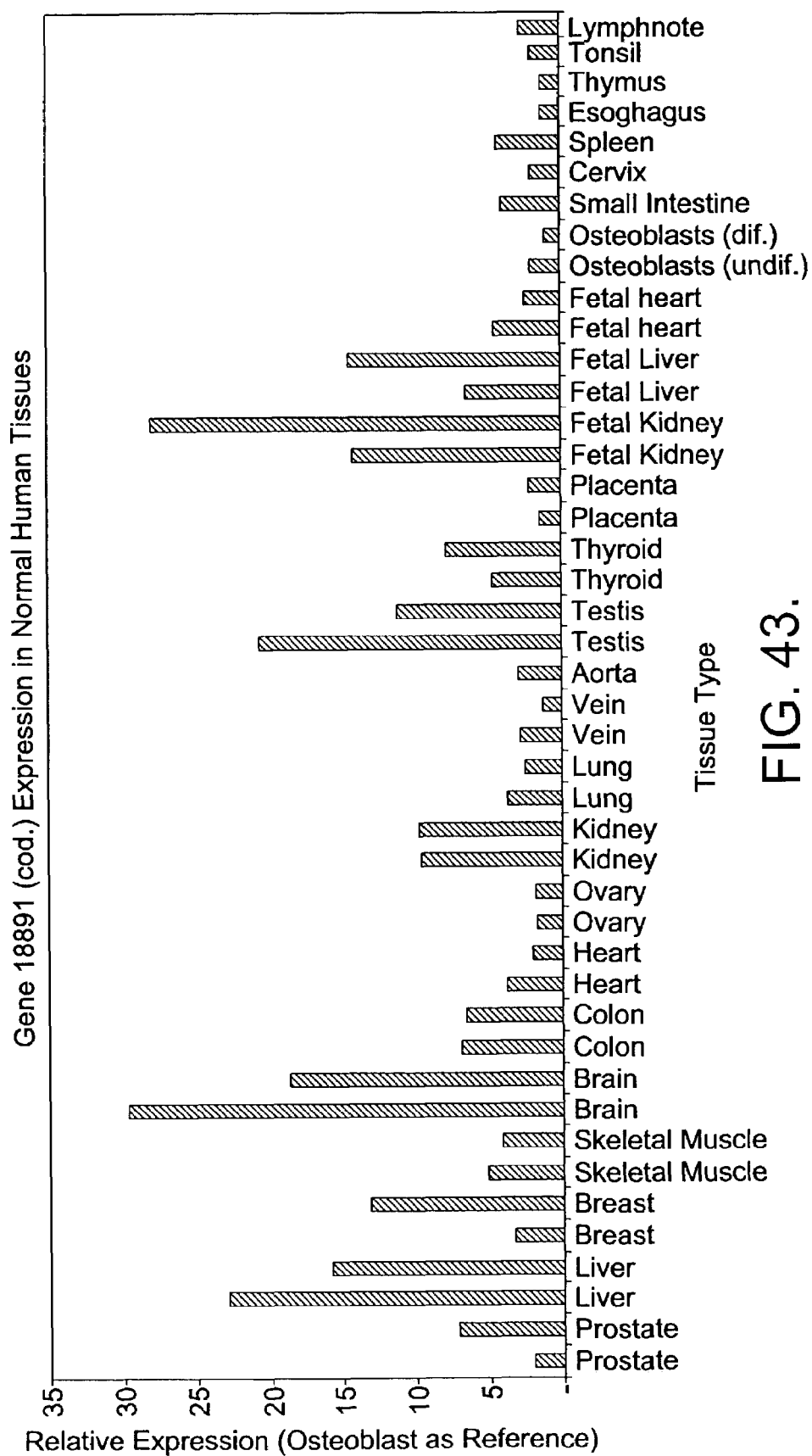
FIG. 43 shows expression of the lipase mRNA in various tissues and cell types in culture. The expression data was derived from RT-PCR of various cDNA libraries. The primers used were designed to amplify coding sequences.
Figure 44:
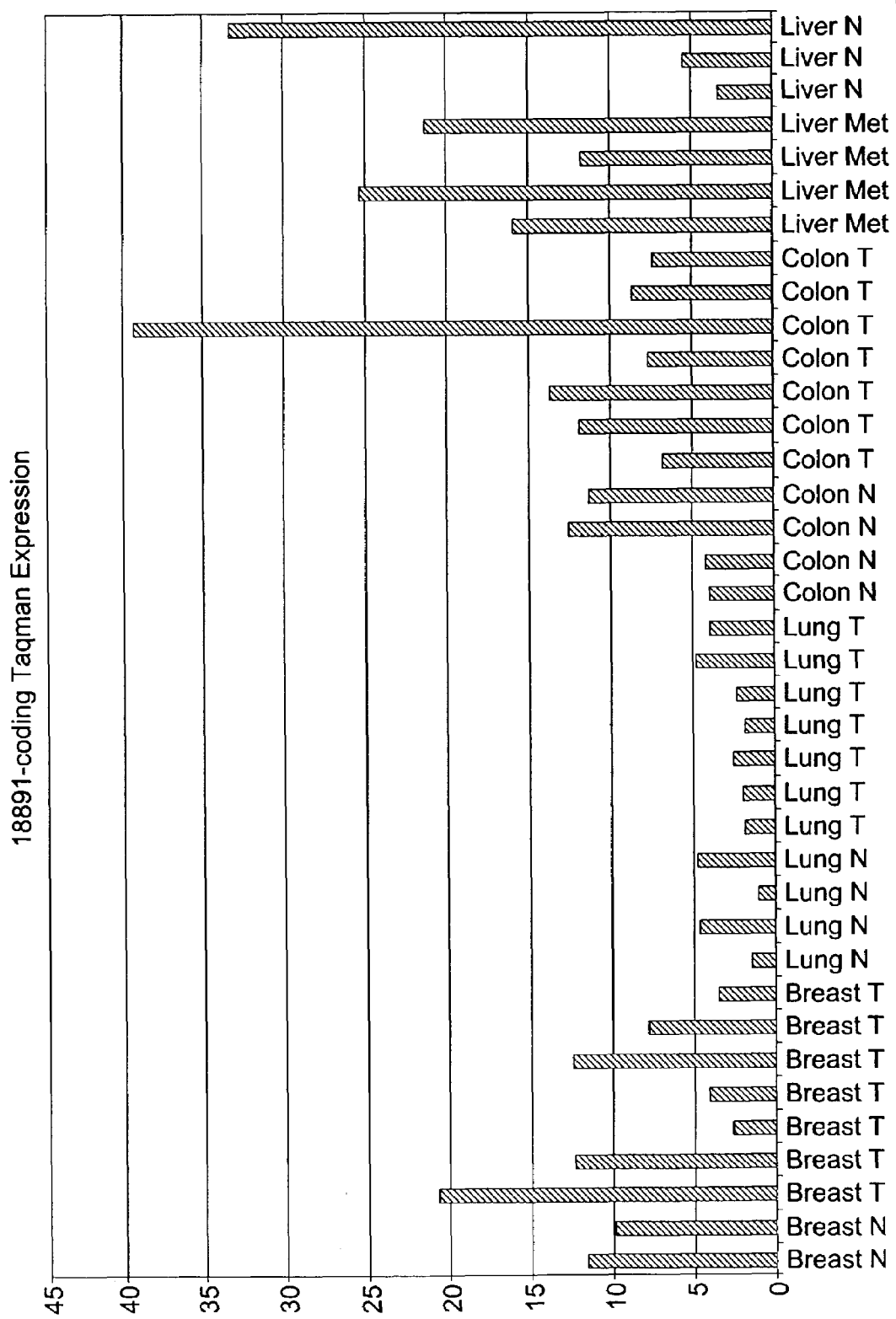
FIG. 44 shows expression of the lipase mRNA in normal and malignant breast, lung, liver and colon tissues. The liver metastases are derived from malignant colonic tissue. The expression data was derived from RT-PCR designed to amplify coding sequences.

Tissues and/or cells in which the lipase is expressed include, but are not limited to those shown in FIGS. 43, 44, and 45. Tissues in which the gene is highly expressed include liver, fetal liver, breast, brain, fetal kidney, and testis. Moderate expression occurs in prostate, skeletal muscle, colon, kidney, and thyroid. Lower positive expression occurs in (heart, fetal heart, small intestine, spleen, lung, ovary, vein, aorta, placenta, osteoblasts, cervix, esophagus, thymus, tonsil, and lymph node. The lipase is also expressed in malignant breast, lung, and colon tissue and in liver metastases derived from malignant colonic tissues. Hence, the lipase is relevant to disorders involving the tissues in which it is expressed.

The present invention thus provides an isolated or purified lipase polypeptide and variants and fragments thereof.

Based on Clustal W sequence alignment, highest homology was shown to lipase 1 precursor (triacylglycerol lipase) from Psychrobacter immobilis (Ace. No. Q02104).

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The lipase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the lipase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A lipase polypeptide is also considered to be isolated when it is part of a membrane preparation or is purified and then reconstituted with membrane vesicles or liposomes.

The language "substantially free of chemical precursors or other chemicals" includes preparations of the lipase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the lipase polypeptide comprises the amino acid sequence shown in SEQ ID NO:17 or the mature form of the polypeptide. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the lipase of SEQ ID NO:17. Variants also include proteins substantially homologous to the lipase but derived from another organism, i.e., an ortholog. Variants also include proteins that are substantially homologous to the lipase that are produced by chemical synthesis. Variants also include proteins that are substantially homologous to the lipase that are produced by recombinant methods. It is understood, however, that variants exclude any amino acid sequences disclosed prior to the invention.

As used herein, two proteins (or a region of the proteins) are substantially homologous when the amino acid sequences are at least about 70-75%, typically at least about 80-85%, and most typically at least about 90-95% or more homologous. A substantially homologous amino acid sequence, according to the present invention, will be encoded by a nucleic acid sequence hybridizing to the nucleic acid sequence, or portion thereof, of the sequence shown in SEQ ID NO:18 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (i.e., 100%=the entire coding sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the lipase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306-1310 (1990).

TABLE 1

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |

TABLE 1-continued

| Conservative Amino Acid Substitutions. | |
|---|---|
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci.* USA 90:5873-5877. Such an algorithm is incorporated into the NBLAST and XBLAST programs (version 2.0) as described in Altschul et al. (1997) *Nucleic Acids Res.* 25:3389-3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444-453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3-5; and FASTA described in Pearson et al. (1988) *PNAS* 85:2444-8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function of the lipase at a variety of biological levels, including, disrupting interactions with the proteoglycans, such as CSPG, HSPG, DSPG, disrupting interaction with cell surface receptors, such as the LDL receptor, LDL-related receptor protein, gp330, or the VLDL receptor, disrupting interactions with heparin, disrupting interactions with apoproteins or lipoproteins, disrupting interactions with activator molecules, such as apo CII or colipase, disrupting triglyceride lipase activity or phospholipase activity, or disrupting homodimer formation. Variant polypeptides having such defects have been identified for LPL and are described in, for example, Murthy et al. (1996) Pharmacol. Ther. 70: 101-135, incorporated herein by reference for teaching these variations.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the lipase polypeptide. This includes preventing immunogenicity from pharmaceutical formulations by preventing protein aggregation.

Useful variations further include alteration of catalytic activity. For example, one embodiment involves a variation at the binding site that results in binding but not hydrolysis, or slower hydrolysis, of the triglyceride or phospholipid. A further useful variation results in an increased rate of hydrolysis of the triglycerides or phospholipids. Additional variations include altered affinity for co-activator proteins, cell surface receptors, proteoglycans, heparin, triglycerides, phospholipids, lipoproteins or apoproteins. A further useful variation at the same site can result in higher or lower affinity for substrates. Useful variations also include changes that result in affinity to a different lipoprotein or lipoprotein remnant than that normally recognized. Other variations could result in altered recognition of apoproteins thereby changing the preferred lipoproteins hydrolyzed by the lipase. Further useful variations affect the ability of the lipase to be induced by various activators, including, but not limited to, those disclosed herein. Specific variations include truncations in which a catalytic domain or substrate binding domain is deleted. This variation results in a decrease or loss of lipid hydrolytic activity or substrate binding. Another useful variation includes one that prevents glycosylation. Further useful variations provide a fusion protein in which one or more domains or subregions are operationally fused to one or more domains or subregions from another lipase. Specifically, a domain or subregion can be introduced that provides a rescue function to an enzyme not normally having this function or for recognition of a specific substrate wherein recognition is not available to the original enzyme. Further variations could affect specific subunit interaction, particularly required for homodimerization or interaction with activator proteins. Other variations would affect developmental, temporal, or tissue-specific expression. Other variations would affect the interaction with cellular components, such as transcriptional regulatory factors.

Amino acids that are essential for function can be identified by methods known in the art, such as site-directed mutagenesis or alanine-scanning mutagenesis (Cunningham et al. (1985) Science 244:1081-1085). The latter procedure introduces single alanine mutations at every residue in the molecule. The resulting mutant molecules are then tested for biological activity, such as the ability to hydrolyze triglycerides or phospholipids in vitro. Alternatively, in vitro activity may be measured by the ability to interact with various molecules, including but not limited to, heparin, proteoglycans, cell surface receptors, lipoproteins, apoproteins or activator proteins. Sites that are critical for binding or recognition can also be determined by structural analysis such as crystallization, nuclear magnetic resonance or photoaffinity labeling (Smith et al. (1992) J. Mol. Biol. 224: 899-904; de Vos et al. (1992) Science 255:306-312).

The assays for lipase enzyme activity are well known in the art and can be found, for example, in Brun et al. (1989) Metabolism 38:1005-1009, Brunzell et al. (1992) Atherosclerosis IX, Stein (eds.) R&L Creative Communications Ltd., Tel Aviv 271-273, Peeva et al. (1992) Int. J. Obes. Relat. Metab. Disord. 16: 737-744, Ma et al. (1991) N. Engl. J. Med. 324: 1761-1766, Ma et al. (1992) J. Biol. Chem. 267: 1918-1923, Connelly et al. (1987) J. Clin. Invest. 80: 1597-1606, Huff et al. (1990) J Lipid Res. 31: 385-396, and Hixson et al. (1990) J. Lipid Res. 31: 545-548. These assays include measurements of triglyceride or lipoprotein concentrations in the blood stream. For lipases associated with proteoglycans, plasma lipolytic activity may be determined following heparin treatment. In this protocol, lipase activity is measured with a synthetic triglyceride substrate using plasma samples obtained following heparin administration. Post-heparin plasma may also be used to measure the lipase mass by immunoassay to determine if a catalytically defective lipase enzyme is released into the plasma. Lipase activity can also be determined in s.c. biopsies of adipose tissue and through the detection of lipase gene mutations. Additional assays include measuring lipase activation by the co-activator molecules.

Substantial homology can be to the entire nucleic acid or amino acid sequence or to fragments of these sequences.

The invention thus also includes polypeptide fragments of the lipase. Fragments can be derived from the amino acid sequence shown in SEQ ID NO:17. However, the invention also encompasses fragments of the variants of the lipase as described herein.

The fragments to which the invention pertains, however, are not to be construed as encompassing fragments that may be disclosed prior to the present invention.

Accordingly, a fragment can comprise at least about 8, 13, 15, 20, 25, 30, 35, 40, 45, 50 or more contiguous amino acids. Fragments can retain one or more of the biological activities of the protein, for example the ability to bind to polyglycan, interact with cell surface receptors, interact with activator molecules, catalyze triglyceride hydrolysis, or retain phospholipase activity. Fragments can be used as an immunogen to generate lipase antibodies.

Biologically active fragments (peptides which are, for example, 5, 7, 10, 12, 15, 20, 30, 35, 36, 37, 38, 39, 40, 50, 100 or more amino acids in length) can comprise a domain or motif, e.g., catalytic sites, signal peptides, transmembrane segments, and sites for protein kinase C phosphorylation, casein kinase II phosphorylation, and N-myristoylation. Additional domains include catalytic domains involved in triglyceride hydrolysis and phospholipase activity, heparin binding sites, cell-surface receptor binding sites, triglyceride binding sites, sites important for homodimerization or activator interaction, and sites important for carrying out the other functions of the lipase as described herein.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the lipase and variants. These epitope-bearing peptides are useful to raise antibodies that bind specifically to a lipase polypeptide or region or fragment. These peptides can contain at least 8, at least 10, 13, 15, or between at least about 16 to about 30 amino acids.

Figure 40:
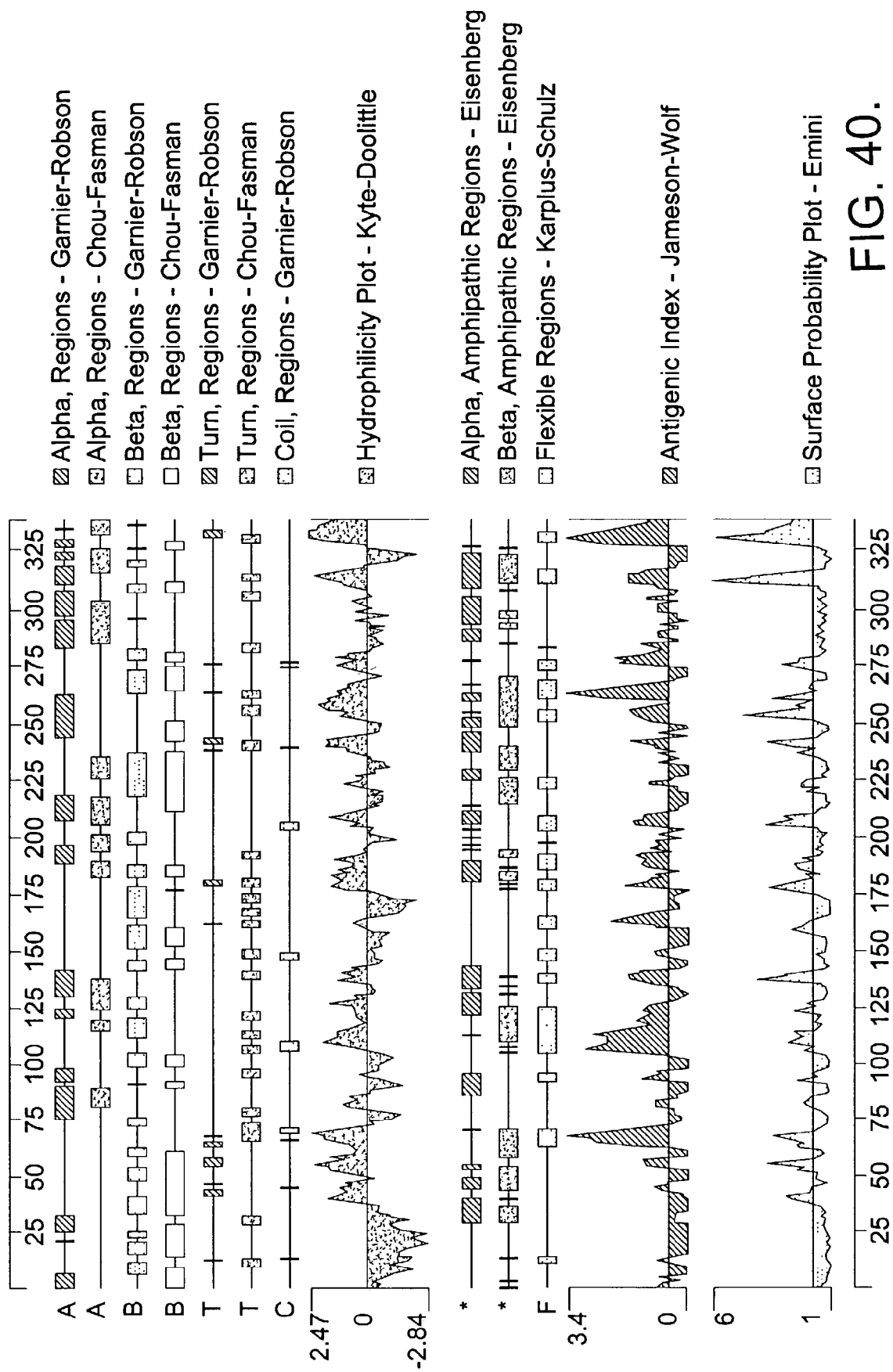
FIG. 40 shows an analysis of the lipase amino acid sequence: αβturn and coil regions; hydrophilicity; amphipathic regions; flexible regions; antigenic index; and surface probability plot.
Figure 41:
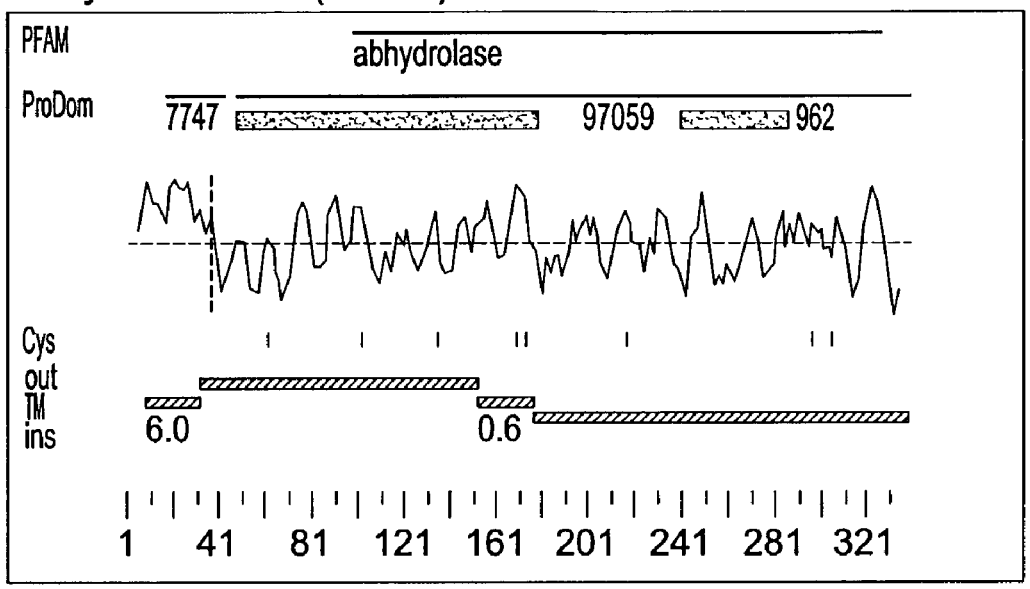
FIG. 41 shows a hydrophobicity plot of the lipase (SEQ ID NO:17). The analysis predicted a 35 amino acid signal peptide sequence at the amino terminus of the protein. Transmembrane segments of both the full length lipase and the mature lipase are also shown.

Non-limiting examples of antigenic polypeptides that can be used to generate antibodies include but are not limited to peptides derived from an extracellular site. Regions having a high antigenicity index are shown in FIG. 40. However, intracellularly-made antibodies ("intrabodies") are also encompassed, which would recognize intracellular peptide regions.

The epitope-bearing lipase polypeptides may be produced by any conventional means (Houghten, R. A. (1985) *Proc. Natl. Acad. Sci. USA* 82:5131-5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the lipase fragment and an additional region fused to the carboxyl terminus of the fragment.

The invention thus provides chimeric or fusion proteins. These comprise a lipase peptide sequence operatively linked to a heterologous peptide having an amino acid sequence not substantially homologous to the lipase. "Operatively linked" indicates that the lipase peptide and the heterologous peptide are fused in-frame. The heterologous peptide can be fused to the N-terminus or C-terminus of the lipase or can be internally located.

In one embodiment the fusion protein does not affect lipase function per se. For example, the fusion protein can be a GST-fusion protein in which the lipase sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of a recombinant lipase protein. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52-58 (1995) and Johanson et al. *J. Biol. Chem.* 270:9459-9471). Thus, this invention also encompasses soluble fusion proteins containing a lipase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fe after the fusion protein has been used for its intended purpose, for example when the fusion protein is to be used as antigen for immunizations. In a particular embodiment, the Fe part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). A lipase-encoding nucleic acid can be cloned into such an expression vector such that the fusion moiety is linked in-frame to the lipase.

Another form of fusion protein is one that directly affects lipase functions. Accordingly, a lipase polypeptide is encompassed by the present invention in which one or more of the lipase domains (or parts thereof) has been replaced by homologous lipase domains (or parts thereof) from another species. Accordingly, various permutations are possible. One or more functional sites as disclosed herein from the specifically disclosed lipase can be replaced by one or more functional sites from a corresponding lipase of another species. Thus, chimeric lipases can be formed in which one or more of the native domains or subregions has been replaced by another. For example, the catalytic domain of the lipase of the present invention may be replaced by the catalytic domain of a different lipase polypeptide. Alternatively, protein domains that mediate the interaction with lipoproteins or domains that mediated the uptake of lipoproteins by cell surface receptors can be used to replace homologous domains of the lipase of the present invention. In doing so the binding affinity to various substrates and/or the rate of catalysis is altered.

Additionally, chimeric lipase proteins can be produced in which one or more functional sites is derived from a different member of the lipase superfamily. It is understood however that sites could be derived from lipase families that occur in the mammalian genome but which have not yet been discovered or characterized. Such sites include but are not limited to any of the functional sites disclosed herein.

The isolated lipase can be purified from any of the cells that naturally express it, including, but not limited to those shown in FIGS. 43, 44, and 45. Tissues in which the gene is highly expressed include liver, fetal liver, breast, brain, fetal kidney, and testis. Moderate expression occurs in prostate, skeletal muscle, colon, kidney, and thyroid. Lower positive expression occurs in heart, fetal heart, small intestine, spleen, lung, ovary, vein, aorta, placenta, osteoblasts, cervix, esophagus, thymus, tonsil, and lymph node. The lipase is also expressed in normal liver and in normal and malignant breast, lung, and colon tissue and in liver metastases derived from malignant colonic tissues. Alternatively, the lipase may be purified from cells that have been altered to express it (recombinant), or synthesized using known protein synthesis methods.

In one embodiment, the protein is produced by recombinant DNA techniques. For example, a nucleic acid molecule encoding the lipase polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd ed., T. E. Creighton, W.H. Freeman and Company, New York (1993). Many detailed reviews are available on this subject, such as by Wold, F., *Posttranslational Covalent Modification of Proteins*, B. C. Johnson, Ed., Academic Press, New York 1-12 (1983); Seifter et al. (1990) *Meth. Enzymol.* 182: 626-646) and Rattan et al. (1992) *Ann. N.Y. Acad. Sci.* 663:48-62).

As is also well known, polypeptides are not always entirely linear. For instance, polypeptides may be branched as a result of lipase, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The lipase polypeptides are useful for producing antibodies specific for the lipase protein, regions, or fragments. Regions having a high antigenicity index score are shown in FIG. 40.

The lipase polypeptides are useful for biological assays related to lipase function. Such assays involve any of the known functions or activities or properties useful for diagnosis and treatment of lipase- or lipase-related conditions or conditions in which expression of the lipase is relevant, such as in hypertriacylglycerolaemia, obesity, atherogenesis, and the various other conditions described herein. Potential assays have been disclosed herein.

The lipase polypeptides are also useful in drug screening assays, in cell-based or cell-free systems. Cell-based systems can be native, i.e., cells that normally express the lipase, as a biopsy or expanded in cell culture. In one embodiment, however, cell-based assays involve recombinant host cells expressing the lipase.

Determining the ability of the test compound to interact with the lipase can also comprise determining the ability of the test compound to preferentially bind to the polypeptide as compared to the ability of a known binding molecule (e.g., an activator (such as colipase, apo CII), cell surface receptor, heparin, proteoglycan, triglyceride, or phospholipid, or lipoprotein) to bind to the polypeptide.

The polypeptides can be used to identify compounds that modulate lipase activity. Modulators of lipase activity comprise agents that influence the enzyme at a variety of biological levels, including, but not limited to agents that disrupt the interaction with the proteoglycans of the cell wall, such as HSPG-degrading enzymes, heparin, chlorate, or APOE; agents that disrupt the interaction with cell surface receptors; agents which disrupt the interaction with activator molecules or homodimer formation; agents that disrupt interaction with lipoproteins; or agents that disrupt triglyceride hydrolysis or phospholipase activity.

The tissue specific regulation of lipase is complex with identical modulators regulating activity differently under various metabolic conditions. While specific modulators of lipase activity have been described above, additional modulators include, but ate not limited to, apoproteins and a non-proteoglycan LPL-binding protein having sequence homology to apo B and apo B (Sivaram et al. (1992) *J. Biol. Chem.* 267:16517-16552; Sivaram et al. (1994) *J. Biol. Chem.* 269:9409-9412). It has also been postulated that the lipolysis-stimulated receptor (LSR) plays a role in LPL activation (Yen et al. (1994) *Biochemistry* 33:1172-1180). Additional modulators of lipase activity include, fasting, feeding, growth hormone, insulin, exercise, estrogen, thyroid hormone, catecholamines, hormones of the adrenergic system, vitamin D derivatives, glucagon, catecholamines, glucocorticoids, and 1,25 dihydroxy-vitamin D. Further modulators comprise inflammatory mediators such as cytokines, interleukins, and interferons.

Modulators associated with an increase activity of lipase activity include, but are not limited to various apoproteins, such as apo CII, and glycosylation. Furthermore, lipase enzymatic activity is stabilized in the presence of lipids or by binding to lipid-water interfaces and detergents, such as deoxycholate. Modulators associated with a decrease in lipase activity include, but are not limited to, increased concentrations of apo CII or apo cm (Shirari et al. (1981) *Biochim. Biophys. Acta* 665:504-510), TNF (Kern et al. (1997) *Journal of Nutrition* 127:1917 S-1922S), fatty acids, high salt concentrations, and Orlistar (La Roche, Basele).

Both transcription and post-transcriptional levels of lipase expression are regulated by various dietary, environmental, and developmental factors and include, for example, hormones, such as insulin, thyroid hormone, and glucocorticoids (Pykalisto et al. (1976) *J. clin. Endocronol. Metab.* 43:591-600; Nillson-Ehle et al. (1980) *Annual Rev Biochem* 49:667-693; and Cryer et al. (1981) *Int. J. Biochem* 13:525-541). Various transcriptional factors such as CEBP, ADD-1, SREBP-1 and PPAR δ also regulate expression of specific lipases. It is understood, therefore, that such compounds can be identified not only by means of direct interaction with the lipase, but by means of any of the components that functionally interact with the disclosed lipase. This includes, but is not limited to, any of those components disclosed herein.

Both lipase and appropriate variants and fragments can be used in high-throughput screens to assay candidate compounds for the ability to bind to the lipase. These compounds can be further screened against a functional lipase to determine the effect of the compound on the lipase activity. Compounds can be identified that activate (agonist) or inactivate (antagonist) the lipase to a desired degree. Modulatory methods can be performed in vitro (e.g., by culturing the cell with the agent) or, alternatively, in vivo (e.g., by administering the agent to a subject).

The lipase polypeptides can be used to screen a compound for the ability to stimulate or inhibit interaction between the lipase protein and a target molecule that normally interacts with the lipase protein. The target can be a lipoprotein, lipoprotein remnant, apoprotein, cell surface receptors, heparin, proteoglycan, triglyceride, phospholipid or another component of the pathway with which the lipase protein normally interacts. The assay includes the steps of combining the lipase protein with a candidate compound under conditions that allow the lipase protein or fragment to interact with the target molecule, and to detect the formation of a complex between the lipase protein and the target or to detect the biochemical consequence of the interaction with the lipase and the target. Any of the associated effects of triglyceride hydrolysis or phospholipase function can be assayed. This includes the production of fatty acids from triglycerides and phospholipids.

Determining the ability of the lipase to bind to a target molecule can also be accomplished using a technology such as real-time Bimolecular Interaction Analysis (BIA). Sjolander et al. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 97:6378-6382); (Felici (1991) *J. Mol. Biol.* 222:301-310); (Ladner supra).

Candidate compounds include, for example, 1) peptides such as soluble peptides, including Ig-tailed fusion peptides and members of random peptide libraries (see, e.g., Lam et al. (1991) *Nature* 354:82-84; Houghten et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length lipase or fragment that competes for substrate binding. Other candidate compounds include mutant lipases or appropriate fragments containing mutations that affect lipase function and compete for substrate. Accordingly, a fragment that competes for substrate, for example with a higher affinity, or a fragment that binds substrate but does not hydrolyze the triglyceride or phospholipid, is encompassed by the invention.

Other candidate compounds include lipase protein or protein analog that binds to the lipid, lipoprotein, proteoglycan, cell surface receptor, or other substrates identified herein but is not released or released slowly. Other candidate compounds include analogs of the other natural substrates, such as substrates that bind to but are not released or released more slowly. Further candidate compounds include activators of the lipases, including but not limited to, those disclosed herein.

The invention provides other end points to identify compounds that modulate (stimulate or inhibit) lipase activity. The assays typically involve an assay of events in the pathway that indicate lipase activity. This can include cellular events that are influenced by lipid metabolism, such as but not limited to, lipid or lipoprotein concentrations. Specific phenotypes include metabolic consequences including effects on energy homeostasis, body weight and body composition-parameters.

Assays are based on the multiple cellular functions of lipase enzymes. As described herein, these enzymes act at various levels in the regulation of lipid metabolism. Accordingly, assays can be based on detection of any of the products produced by the lipase enzyme.

Further, the expression of genes that are up- or down-regulated by action of the lipase can be assayed. In one embodiment, the regulatory region of such genes can be operably linked to a marker that is easily detectable, such as luciferase.

Accordingly, any of the biological or biochemical functions mediated by the lipase can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric lipase proteins in which one or more domains, sites, and the like, as disclosed herein, or parts thereof, can be replaced by their heterologous counterparts derived from other lipase protein. For example, a recognition or binding region can be used that interacts with different substrate specificity and/or affinity than the native lipase. Accordingly, a different set of pathway components is available as an end-point assay for activation. Further, sites that are responsible for developmental, temporal, or tissue specificity can be replaced by heterologous sites such that the lipase can be detected under conditions of specific developmental, temporal, or tissue-specific expression.

The lipase polypeptides are also useful in competition binding assays in methods designed to discover compounds that interact with the lipase. Thus, a compound is exposed to a lipase polypeptide under conditions that allow the compound to bind to or to otherwise interact with the polypeptide. A lipase target, comprising a polypeptide or agent which is known to interact with lipase, is also added to the mixture. If the test compound interacts with the soluble lipase polypeptide, it decreases the amount of complex formed or the activity from the lipase target. This type of assay is particularly useful in cases in which compounds are sought that interact with specific regions of the lipase. Thus, the soluble polypeptide that competes with the target lipase region is designed to contain peptide sequences corresponding to the region of interest.

Another type of competition-binding assay can be used to discover compounds that interact with specific functional sites. As an example, a candidate compound can be added to a sample of the lipase. Compounds that interact with the lipase at the same site as a lipase substrate disclosed herein will reduce the amount of complex formed between the lipase and substrate. Accordingly, it is possible to discover a compound that specifically prevents interaction between the lipase and it various substrates. A compound that competes with lipase catalytic activity will reduce the rate of triglyceride or phospholipid hydrolysis. Alternatively, a compound may also compete at the level of substrate interaction. Accordingly, compounds can be discovered that directly interact with the lipase and interfere with its function. Such assays can involve any other component that interacts with the lipase such as heparin, proteoglycans, lipoproteins, lipoprotein remnants, cell surface receptors, triglycerides, phospholipids, activator proteins, and other compounds described herein.

To perform cell free drug screening assays, it is desirable to immobilize either the lipase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/lipase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of lipase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a lipase-binding target component, such as, activator proteins, cell surface receptors, lipoproteins, apoproteins, triglycerides or phospholipids and a candidate compound are incubated in the lipase-presenting wells and the amount of complex trapped in the well can be quantitated. Methods for detecting such complexes, in addition to those described above for the GST-immobilized complexes, include immunodetection of complexes using antibodies reactive with the lipase target molecule, or which are reactive with lipase and compete with the target molecule; as well as enzyme-linked assays which rely on detecting an enzymatic activity associated with the target molecule.

Modulators of lipase activity identified according to these drug screening assays can be used to treat a subject with a disorder mediated or affected by a lipase, by treating cells that express the lipase or cells in which lipase expression is desirable. These methods of treatment include the steps of administering the modulators of lipase activity in a pharmaceutical composition as described herein, to a subject in need of such treatment.

Tissues and/or cells in which the lipase is expressed include, but are not limited to those shown in FIGS. 43, 44, and 45. Tissues in which the gene is highly expressed include liver, fetal liver, breast, brain, fetal kidney, and testis. Moderate expression occurs in prostate, skeletal muscle, colon, kidney, and thyroid. Lower positive expression occurs in heart, fetal heart, small intestine, spleen, lung, ovary, vein, aorta, placenta, osteoblasts, cervix, esophagus, thymus, tonsil, and lymph node. The lipase is also expressed in malignant breast, lung, and colon tissue and in liver metastases derived from malignant colonic tissues. Hence, the lipase is relevant to disorders involving the tissues in which it is expressed.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyclia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, ewing saracoma, primitive neuroectodermal tumor, giant cell tumor, and metastatic tumors.

In addition, lipases influence a number of processes which affect the biology of both blood vessel walls and the pancreas. Therefore, lipases find use in the treatment of disorders of blood vessels, which include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Lipases play critical roles in lipid metabolism and are associated with various lipid-related pathologies in humans such as, but not limited to, Wolman's disease, hpertension, Type II diabetes, retinopathy and cholesterol ester storage disease. Furthermore, a decrease in LPL activity impairs the catabolism of chylomicrons and VLDL resulting in massive hypertriglyceridemia. Decreased LPL activity has been also associated with many disorders, including for example, chylomicronemia syndrome. This syndrome has multiple clinical symptoms and manifestations review by Murthy et al. (1996) *Pharmacol. Ther.* 70:101-135. Additional disorders resulting from defective LPL activity include, familial lipoprotein lipase deficiency with fasting chylomicronemia (type I hyperlipidemia) (Santamarina et al. (1992) *Curr Opin Lipidology* 3:186), LPL deficiency, familial combined hyperlipidaemia (FCHL) (Babirak et al. (1992) *Arteriosclerosis thromb.* 12:1176; Seed et al. (1994) *Clin Invest* 72: 100), hypertriglyceridemia, pancreatitis and abnormalities in post prandial lipemia. In addition, LPL activity is abnormally regulated in obesity (Kern et al. (1997) *J. Nut.* 127: 1917S-1922S) and is also affected by alcohol and several hormones (Taskinen et al. (1987) *Lipoprotein Lipase*, Borensztajn J. (ed) Evener Chicago). Furthermore, changes in circulating lipoprotein and creation of lipolytic products have been implicated in a number of processes that affect the biology of vessel walls. For example, atherogenesis is associated with increased LPL activity. In addition, autoantibodies against LPL have been reported in patients with idiopathic thrombocytopenic purpura and Grave's disease (Kihara et al. (1989) *N. Engl. J. Med.* 320:1255-1259) and heparin resistance was noted in a case of disseminated lupus erythematosus (Glueck et al. (1969) *Am. J. Med.* 47:318-324). Polymorphisms in LDL gene have also been associated with altered levels of total and HDL cholesterol (Mitchell et al. (1994) *Hum. Biol.* 66:383-397), coronary heart disease (Mattu et al. (1994) *Arterioscler. Thromb.* 14:1090-1097), and insulin resistance (Cole et al. (1993) *Genet. Epidemiol.* 10:177-188).

The hydrolysis of HDL by hepatic lipase regulates cholesterol levels in hepatic tissue. Pathologies associated with cholesterol include, but are not limited to, atherosclerosis, xanthomas, inflammation and necrosis, cholesterolosis and gall stone formation.

The lipase polypeptides are thus useful for treating a lipase-associated disorder characterized by aberrant expression or activity of a lipase. The polypeptides can also be useful for treating a disorder characterized by excessive amounts of lipoproteins, triglycerides or cholesterol. In one embodiment, the method involves administering an agent (e.g., an agent identified by a screening assay described herein), or combination of agents that modulates (e.g., upregulates or downregulates) expression or activity of the protein. In another embodiment, the method involves administering the lipase as therapy to compensate for reduced or aberrant expression or activity of the protein. In another embodiment, the lipase polypeptides are useful for treating breast, lung, colon, and liver cancers.

Methods for treatment include but are not limited to the use of soluble lipase or fragments of the lipase protein that compete for substrates including those disclosed herein. These lipases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant metabolism of lipids resulting in altered lipoprotein concentrations, energy homeostasis, body weight, artherosclerosis, and body weight parameters.

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO 94/10300), to identify other proteins (captured proteins) which bind to or interact with the proteins of the invention and modulate their activity.

The lipase polypeptides also are useful to provide a target for diagnosing a disease or predisposition to disease mediated by the lipase, including, but not limited to, diseases involving tissues in which the lipase are expressed as disclosed herein. Accordingly, methods are provided for detecting the presence, or levels of, the lipase in a cell, tissue, or organism. The method involves contacting a biological sample with a compound capable of interacting with the lipase such that the interaction can be detected.

The polypeptides are also useful for treating a disorder characterized by reduced amounts of these components. Thus, increasing or decreasing the activity of the lipase is beneficial to treatment. The polypeptides are also useful to provide a target for diagnosing a disease characterized by excessive substrate or reduced levels of substrate. Accordingly, where substrate is excessive, use of the lipase polypeptides can provide a diagnostic assay. Furthermore, for example, lipases having reduced activity can be used to diagnose conditions in which reduced substrate is responsible for the disorder.

One agent for detecting lipase is an antibody capable of selectively binding to the lipase polypeptide. A biological sample includes tissues, cells and biological fluids isolated from a subject, as well as tissues, cells and fluids present within a subject.

The lipase also provides a target for diagnosing active disease, or predisposition to disease, in a patient having a variant lipase. Thus, lipase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered lipase activity in cell-based or cell-free assay, alteration in binding to or hydrolysis of lipids, binding to activator proteins, cell surface receptors, apoproteins, lipoproteins, proteoglycans, heparin, or antibody-binding pattern, altered isoelectric point, direct amino acid sequencing, and any other of the known assay techniques useful for detecting mutations in a protein in general or in a lipase specifically, including assays discussed herein.

In vitro techniques for detection of lipase include enzyme linked immunosorbent assays (ELISAs), Western blots, immunoprecipitations and immunofluorescence. Alternatively, the protein can be detected in vivo in a subject by introducing into the subject a labeled anti-lipase antibody. For example, the antibody can be labeled with a radioactive marker whose presence and location in a subject can be detected by standard imaging techniques. Particularly useful are methods, which detect the allelic variant of the lipase expressed in a subject, and methods, which detect fragments of the lipase in a sample.

The lipase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10-11):983-985, and Linder, M. W. (1997) *Clin. Chem.* 43(2):254-266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the lipase in which one or more of the lipase functions in one population is different from those in another population. The polypeptides thus allow a target to ascertain a genetic predisposition that can affect treatment modality. Thus, in a lipase-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The lipase polypeptides are also useful for monitoring therapeutic effects during clinical trials and other treatment. Thus, the therapeutic effectiveness of an agent that is designed to increase or decrease gene expression, protein levels or lipase activity can be monitored over the course of treatment using the lipase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the lipase and its variants and fragments. An antibody is considered to selectively bind, even if it also binds to other proteins that are not substantially homologous with the lipase. These other proteins share homology with a fragment or domain of the lipase polypeptide. This conservation in specific regions gives rise to antibodies that bind to both proteins by virtue of the homologous sequence. In this case, it would be understood that antibody binding to the lipase is still selective.

To generate antibodies, an isolated lipase polypeptide is used as an immunogen to generate antibodies using standard techniques for polyclonal and monoclonal antibody preparation. Either the full-length protein or antigenic peptide fragment can be used. Regions having a high antigenicity index are shown in FIG. 40.

Antibodies are preferably prepared from these regions or from discrete fragments in these regions. However, antibodies can be prepared from any region of the peptide as described herein. A preferred fragment produces an antibody that diminishes or completely prevents substrate hydrolysis or binding. Antibodies can be developed against the entire lipase protein or domains of the lipase as described herein. Antibodies can also be developed against specific functional sites as disclosed herein.

The antigenic peptide can comprise a contiguous sequence of at least 8, 13, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g., Fab or $F(ab')_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

An appropriate immunogenic preparation can be derived from native, recombinantly expressed, or chemically synthesized peptides.

Antibody Uses

The antibodies can be used to isolate a lipase by standard techniques, such as affinity chromatography or immunoprecipitation. The antibodies can facilitate the purification of the natural lipase from cells and recombinantly produced lipase expressed in host cells.

The antibodies are useful to detect the presence of lipase in cells or tissues to determine the pattern of expression of the lipase among various tissues in an organism and over the course of normal development.

The antibodies can be used to detect lipase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length lipase can be used to identify lipase turnover.

Further, the antibodies can be used to assess lipase expression in disease states such as in active stages of the disease or in an individual with a predisposition toward disease related to lipid metabolism. When a disorder is caused by an inappropriate tissue distribution, developmental expression, or level of expression of the lipase protein, the antibody can be prepared against the normal lipase protein. If a disorder is characterized by a specific mutation in the lipase, antibodies specific for this mutant protein can be used to assay for the presence of the specific mutant lipase polypeptides. However, intracellularly-made antibodies ("intrabodies") are also encompassed, which would recognize intracellular lipase-peptide regions.

The antibodies can also be used to assess normal and aberrant subcellular localization of cells in the various tissues in an organism. Antibodies can be developed against the whole lipase or portions of the lipase.

The diagnostic uses can be applied, not only in genetic testing, but also in monitoring a treatment modality. Accordingly, where treatment is ultimately aimed at correcting lipase expression level or the presence of aberrant lipase proteins and aberrant tissue distribution or developmental expression, antibodies directed against the lipase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic lipases can be used to identify individuals that require modified treatment modalities.

The antibodies are also useful as diagnostic tools as an immunological marker for aberrant lipase analyzed by electrophoretic mobility, isoelectric point, tryptic peptide digest, and other physical assays known to those in the art.

The antibodies are also useful for tissue typing. Thus, where a specific lipase has been correlated with expression in a specific tissue, antibodies that are specific for this lipase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting the various lipase functions as described herein.

These uses can also be applied in a therapeutic context in which treatment involves inhibiting lipase function. Antibodies can be prepared against specific fragments containing sites required for function or against intact lipase associated with a cell.

Completely human antibodies are particularly desirable for therapeutic treatment of human patients. For an overview of this technology for producing human antibodies, see Lonberg et al. (1995) *Int. Rev. Immunol.* 13:65-93. For a detailed discussion of this technology for producing human antibodies and human monoclonal antibodies and protocols for producing such antibodies, e.g., U.S. Pat. No. 5,625,126;

U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a lipase protein in a biological sample. The kit can comprise antibodies such as a labeled or labelable antibody and a compound or agent for detecting lipase in a biological sample; means for determining the amount of lipase in the sample; and means for comparing the amount of lipase in the sample with a standard. The compound or agent can be packaged in a suitable container. The kit can further comprise instructions for using the kit to detect lipase.

Polynucleotides

The nucleotide sequence in SEQ ID NO:18 was obtained by sequencing the deposited human cDNA. Accordingly, the sequence of the deposited clone is controlling as to any discrepancies between the two and any reference to the sequence of SEQ ID NO:18 includes reference to the sequence of the deposited cDNA.

The specifically disclosed cDNA comprises the coding region and 5' and 3' untranslated sequences in SEQ ID NO:18.

The invention provides isolated polynucleotides encoding the novel lipase. The term "lipase polynucleotide" or "lipase nucleic acid" refers to the sequence shown in SEQ ID NO:18 or in the deposited cDNA. The term "lipase polynucleotide" or "lipase nucleic acid" further includes variants and fragments of the lipase polynucleotide.

An "isolated" lipase nucleic acid is one that is separated from other nucleic acid present in the natural source of the lipase nucleic acid. Preferably, an "isolated" nucleic acid is free of sequences which naturally flank the lipase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the lipase nucleic acid is isolated from flanking sequences such that it can be subjected to the specific manipulations described herein, such as recombinant expression, preparation of probes and primers, and other uses specific to the lipase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The lipase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The lipase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Lipase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

Lipase nucleic acid can comprise the nucleotide sequence shown in SEQ ID NO:18, corresponding to human cDNA.

In one embodiment, the lipase nucleic acid comprises only the coding region.

The invention further provides variant lipase polynucleotides, and fragments thereof, that differ from the nucleotide sequence shown in SEQ ID NO:18 due to degeneracy of the genetic code and thus encode the same protein as that encoded by the nucleotide sequence shown in SEQ ID NO:18.

The invention also provides lipase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecule of SEQ ID NO:18 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a lipase that is at least about 60-65%, 65-70%, typically at least about 70-75%, more typically at least about 80-85%, and most typically at least about 90-95% or more homologous to the nucleotide sequence shown in SEQ ID NO:18. Such nucleic acid molecules can readily be identified as being able to hybridize under stringent conditions, to the nucleotide sequence shown in SEQ ID NO:18 or a fragment of the sequence. It is understood that stringent hybridization does not indicate substantial homology where it is due to general homology, such as poly A sequences, or sequences common to all or most proteins or all lipase enzymes. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60-65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1-6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50-65° C. In another non-limiting example, nucleic acid molecules are allowed to hybridize in 6× sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:17 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:18 or the complement of SEQ ID NO:18. In one embodiment, the nucleic acid consists of a portion of the nucleotide sequence of SEQ ID NO:18 or the complement of SEQ ID NO:18.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 6, preferably at least about 10, 13, 18, 20, 23 or 25 nucleotides, and can be 30, 40, 50, 100, 200, 500 or more nucleotides in length. Nucleotide sequences from about 1517 to 1964 are not disclosed prior to the invention. Longer fragments, for example, 30 or more nucleotides in length, which encode antigenic proteins or polypeptides described herein are useful.

Furthermore, the invention provides polynucleotides that comprise a fragment of the full-length lipase polynucleotides. The fragment can be single or double-stranded and can comprise DNA or RNA. The fragment can be derived from either the coding or the non-coding sequence.

In another embodiment an isolated lipase nucleic acid encodes the entire coding region. Other fragments include nucleotide sequences encoding the amino acid fragments described herein.

Thus, lipase nucleic acid fragments further include sequences corresponding to the domains described herein, subregions also described, and specific functional sites. Lipase nucleic acid fragments also include combinations of the domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains.

However, it is understood that a lipase fragment includes any nucleic acid sequence that does not include the entire gene.

The invention also provides lipase nucleic acid fragments that encode epitope bearing regions of the lipase proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

The nucleic acid fragments of the invention provide probes or primers in assays such as those described below. "Probes" are oligonucleotides that hybridize in a base-specific manner to a complementary strand of nucleic acid.

Such probes include polypeptide nucleic acids, as described in Nielsen et al. (1991) *Science* 254:1497-1500. Typically, a probe comprises a region of nucleotide sequence that hybridizes under highly stringent conditions to at least about 15, typically about 20-25, and more typically about 40, 50 or 75 consecutive nucleotides of the nucleic acid sequence shown in SEQ ID NO:18 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The lipase polynucleotides are thus useful for probes, primers, and in biological assays.

Where the polynucleotides are used to assess lipase properties or functions, such as in the assays described herein, all or less than all of the entire cDNA can be useful. Assays specifically directed to lipase functions, such as assessing agonist or antagonist activity, encompass the use of known fragments. Further, diagnostic methods for assessing lipase function can also be practiced with any fragment, including those fragments that may have been known prior to the invention. Similarly, in methods involving treatment of lipase dysfunction, all fragments are encompassed including those, which may have been known in the art.

The lipase polynucleotides are useful as a hybridization probe for cDNA and genomic DNA to isolate a full-length cDNA and genomic clones encoding the polypeptide described in SEQ ID NO:17 and to isolate cDNA and genomic clones that correspond to variants producing the same polypeptide shown in SEQ ID NO:17 or the other variants described herein. Variants can be isolated from the same tissue and organism from which the polypeptides shown in SEQ ID NO:17 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the lipase. Accordingly, it could be derived from 5' noncoding regions, the coding region, and 3' noncoding regions.

The nucleic acid probe can be, for example, the full-length cDNA of SEQ ID NO:18 or a fragment thereof that is sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequence of SEQ ID NO:18, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357-63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell lipases in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/0918) or the blood brain barrier (see, e.g., PCT Publication No. WO 89/10134).

In addition, oligonucleotides can be modified with hybridization-triggered cleavage agents (see, e.g., Krol et al. (1988) *Bio-Techniques* 6:958-976) or intercalating agents (see, e.g., Zon (1988) *Pharm Res.* 5:539-549).

The lipase polynucleotides are also useful as primers for PCR to amplify any given region of a lipase polynucleotide.

The lipase polynucleotides are also useful for constructing recombinant vectors. Such vectors include expression vectors that express a portion of, or all of, the lipase polypeptides. Vectors also include insertion vectors, used to integrate into another polynucleotide sequence, such as into the cellular genome, to alter in situ expression of lipase genes and gene products. For example, an endogenous lipase coding sequence can be replaced via homologous recombination with all or part of the coding region containing one or more specifically introduced mutations.

The lipase polynucleotides are also useful for expressing antigenic portions of the lipase proteins.

The lipase polynucleotides are also useful as probes for determining the chromosomal positions of the lipase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783-787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The lipase polynucleotide probes are also useful to determine patterns of the presence of the gene encoding the lipase and their variants with respect to tissue distribution, for example, whether gene duplication has occurred and whether the duplication occurs in all or only a subset of tissues. The genes can be naturally occurring or can have been introduced into a cell, tissue, or organism exogenously.

The lipase polynucleotides are also useful for designing ribozymes corresponding to all, or a part, of the mRNA produced from genes encoding the polynucleotides described herein.

The lipase polynucleotides are also useful for constructing host cells expressing a part, or all, of the lipase polynucleotides and polypeptides.

The lipase polynucleotides are also useful for constructing transgenic animals expressing all, or a part, of the lipase polynucleotides and polypeptides.

The lipase polynucleotides are also useful for making vectors that express part, or all, of the lipase polypeptides.

The lipase polynucleotides are also useful as hybridization probes for determining the level of lipase nucleic acid expression. Accordingly, the probes can be used to detect the presence of, or to determine levels of, lipase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the lipase genes.

Alternatively, the probe can be used in an in situ hybridization context to assess the position of extra copies of the lipase genes, as on extrachromosomal elements or as integrated into chromosomes in which the lipase gene is not normally found, for example as a homogeneously staining region.

These uses are relevant for diagnosis of disorders involving an increase or decrease in lipase expression relative to normal, such as a developmental or a metabolic disorder.

Tissues and/or cells in which the lipase is expressed include, but are not limited to those shown in FIGS. 43, 44, and 45. Such tissues/cells include liver, fetal liver, breast, brain, fetal kidney, and testis. Moderate expression occurs in prostate, skeletal muscle, colon, kidney, and thyroid. Lower positive expression occurs in heart, fetal heart, small intestine, spleen, lung, ovary, vein, aorta, placenta, osteoblasts, cervix, esophagus, thymus, tonsil, and lymph node. The lipase is also expressed in malignant breast, lung, and colon tissue and in liver metastases derived from malignant colonic tissues. Hence, the lipase is relevant to disorders involving the tissues in which it is expressed. As such, the gene is particularly relevant for the treatment of disorders involving breast, lung, liver, and colon cancer. Disorders in which the lipase expression is relevant include, but are not limited to those disclosed herein above.

Thus, the present invention provides a method for identifying a disease or disorder associated with aberrant expression or activity of lipase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the lipase, such as by measuring the level of a lipase-encoding nucleic acid in a sample of cells from a subject e.g., mRNA or genomic DNA, or determining if the lipase gene has been mutated.

Nucleic acid expression assays are useful for drug screening to identify compounds that modulate lipase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the lipase gene. The method typically includes assaying the ability of the compound to modulate the expression of the lipase nucleic acid and thus identifying a compound that can be used to treat a disorder characterized by undesired lipase nucleic acid expression.

The assays can be performed in cell-based and cell-free systems. Cell-based assays include cells naturally expressing the lipase nucleic acid or recombinant cells genetically engineered to express specific nucleic acid sequences.

Alternatively, candidate compounds can be assayed in vivo in patients or in transgenic animals.

The assay for lipase nucleic acid expression can involve direct assay of nucleic acid levels, such as mRNA levels, or on collateral compounds involved in the pathway. Further, the expression of genes that are up- or down-regulated in response to the lipase activity can also be assayed. In this embodiment the regulatory regions of these genes can be operably linked to a reporter gene such as luciferase.

Thus, modulators of lipase gene expression can be identified in a method wherein a cell is contacted with a candidate compound and the expression of mRNA determined. The level of expression of lipase mRNA in the presence of the candidate compound is compared to the level of expression of lipase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate lipase nucleic acid expression. Modulation includes both up-regulation (i.e. activation or agonization) or down-regulation (suppression or antagonization) or effects on nucleic acid activity (e.g. when nucleic acid is mutated or improperly modified). Treatment includes disorders characterized by aberrant expression or activity of the nucleic acid. In addition, disorders that are influenced by the lipase may also be treated. Examples of such disorders are disclosed herein.

Alternatively, a modulator for lipase nucleic acid expression can be a small molecule or drug identified using the screening assays described herein as long as the drug or small molecule inhibits the lipase nucleic acid expression.

The lipase polynucleotides are also useful for monitoring the effectiveness of modulating compounds on the expression or activity of the lipase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The lipase polynucleotides are also useful in diagnostic assays for qualitative changes in lipase nucleic acid, and particularly in qualitative changes that lead to pathology. The polynucleotides can be used to detect mutations in lipase genes and gene expression products such as mRNA. The polynucleotides can be used as hybridization probes to detect naturally-occurring genetic mutations in the lipase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the lipase gene associated with a dysfunction provides a diagnostic tool for an active disease or susceptibility to disease when the disease results from overexpression, underexpression, or altered expression of a lipase.

Mutations in the lipase gene can be detected at the nucleic acid level by a variety of techniques. Genomic DNA can be analyzed directly or can be amplified by using PCR prior to analysis. RNA or cDNA can be used in the same way. In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *PNAS* 91:360-364), the latter of which can be particularly useful for detecting point mutations in the gene (see Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a lipase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant lipase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286-295), electrophoretic mobility of mutant and wild type nucleic acid is compared (Orita et al. (1989) *PNAS* 86:2766; Cotton et al. (1993) *Mutat. Res.* 285:125-144; and Hayashi et al. (1992) *Genet. Anal. Tech. Appl.* 9:73-79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244-255; Kozal et al. (1996) *Nature Medicine* 2:753-759). For example, genetic mutations can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The lipase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). Accordingly, the lipase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The lipase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The lipase polynucleotides can also be used to identify individuals based on small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the lipase sequence can be used to provide an alternative technique, which determines the actual DNA sequence of selected fragments in the genome of an individual. Thus, the lipase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The lipase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The lipase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The lipase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The lipase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of lipase probes can be used to identify tissue by species and/or by organ type.

In a similar fashion, these primers and probes can be used to screen tissue culture for contamination (i.e., screen for the presence of a mixture of different types of cells in a culture).

Alternatively, the lipase polynucleotides can be used directly to block transcription or translation of lipase gene sequences by means of antisense or ribozyme constructs. Thus, in a disorder characterized by abnormally high or undesirable lipase gene expression, nucleic acids can be directly used for treatment.

The lipase polynucleotides are thus useful as antisense constructs to control lipase gene expression in cells, tissues, and organisms. A DNA antisense polynucleotide is designed to be complementary to a region of the gene involved in transcription, preventing transcription and hence production of lipase protein. An antisense RNA or DNA polynucleotide would hybridize to the mRNA and thus block translation of mRNA into lipase protein.

Examples of antisense molecules useful to inhibit nucleic acid expression include antisense molecules complementary to a fragment of the 5' untranslated region of SEQ ID NO:18 which also includes the start codon and antisense molecules which are complementary to a fragment of the 3' untranslated region of SEQ ID NO:18.

Alternatively, a class of antisense molecules can be used to inactivate mRNA in order to decrease expression of lipase nucleic acid. Accordingly, these molecules can treat a disorder characterized by abnormal or undesired lipase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the lipase protein.

The lipase polynucleotides also provide vectors for gene therapy in patients containing cells that are aberrant in lipase gene expression. Thus, recombinant cells, which include the patient's cells that have been engineered ex vivo and returned to the patient, are introduced into an individual where the cells produce the desired lipase protein to treat the individual.

The invention also encompasses kits for detecting the presence of a lipase nucleic acid in a biological sample. For example, the kit can comprise reagents such as a labeled or labelable nucleic acid or agent capable of detecting lipase nucleic acid in a biological sample; means for determining the amount of lipase nucleic acid in the sample; and means for comparing the amount of lipase nucleic acid in the sample with a standard. The compound or agent can be packaged in a suitable container. The kit can further comprise instructions for using the kit to detect lipase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBIA).

For example, software which implements the BLAST (Altschul et al. (1990) *J. Mol. Biol.* 215:403-410) and BLAZE (Brutlag et al. (1993) *Comp. Chem.* 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the lipase polynucleotides. The term "vector" refers to a vehicle, preferably a nucleic acid molecule that can transport the lipase polynucleotides. When the vector is a nucleic acid molecule, the lipase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the lipase polynucleotides. Alternatively, the vector may integrate into the host cell genome and produce additional copies of the lipase polynucleotides when the host cell replicates.

The invention provides vectors for the maintenance (cloning vectors) or vectors for expression (expression vectors) of the lipase polynucleotides. The vectors can function in procaryotic or eukaryotic cells or in both (shuttle vectors).

Expression vectors contain cis-acting regulatory regions that are operably linked in the vector to the lipase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the lipase polynucleotides from the vector. Alternatively, a trans-acting factor may be supplied by the host cell. Finally, a trans-acting factor can be produced from the vector itself.

It is understood, however, that in some embodiments, transcription and/or translation of the lipase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd. ed., Cold Spring Harbor Laboratory Press, Cold Spring Harbor, N.Y.).

A variety of expression vectors can be used to express a lipase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual* 2nd. ed., Cold Spring Harbor Laboratory Press, Cold Spring Harbor, N.Y.

The regulatory sequence may provide constitutive expression in one or more host cells (i.e., tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The lipase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the lipase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301-315) and pET 11d (Studier et al. (1990) *Gene Expression Technology: Methods in Enzymology* 185:60-89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119-128). Alternatively, the sequence of the polynucleotide of interest can be altered to provide preferential codon usage for a specific host cell, for example *E. coli*. (Wada et al. (1992) *Nucleic Acids Res.* 20:2111-2118).

The lipase polynucleotides can also be expressed by expression vectors that are operative in yeast. Examples of vectors for expression in yeast e.g., *S. cerevisiae* include pYepSec1 (Baldari et al. (1987) *EMBO J.* 6:229-234), pMFa (Kurjan et al. (1982) *Cell* 30:933-943), pJRY88 (Schultz et al. (1987) *Gene* 54:113-123), and pYES2 (Invitrogen Corporation, San Diego, Calif.).

The lipase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow et al. (1989) *Virology* 170:31-39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187-195).

The expression vectors listed herein are provided by way of example only of the well-known vectors available to those of ordinary skill in the art that would be useful to express the lipase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual* 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the lipase polynucleotides can be introduced either alone or with other polynucleotides that are not related to the lipase polynucleotides such as those providing trans-acting factors for expression vectors. When more than one vector is introduced into a cell, the vectors can be introduced independently, co-introduced or joined to the lipase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the lipase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing lipase proteins or polypeptides that can be further purified to produce desired amounts of lipase protein or fragments. Thus, host cells containing expression vectors are useful for polypeptide production.

Host cells are also useful for conducting cell-based assays involving the lipase or lipase fragments. Thus, a recombinant host cell expressing a native lipase is useful to assay for compounds that stimulate or inhibit lipase function. This includes disappearance of substrate (triglycerides, phospholipids, lipoproteins), appearance of end product (fatty acids), and the various other molecular functions described herein that include, but are not limited to, substrate recognition, substrate binding, subunit association, and interaction with other cellular components. Modulation of gene expression can occur at the level of transcription or translation.

Host cells are also useful for identifying lipase mutants in which these functions are affected. If the mutants naturally occur and give rise to a pathology, host cells containing the mutations are useful to assay compounds that have a desired effect on the mutant lipase (for example, stimulating or inhibiting function) which may not be indicated by their effect on the native lipase.

Recombinant host cells are also useful for expressing the chimeric polypeptides described herein to assess compounds that activate or suppress activation or alter specific function by means of a heterologous domain, segment, site, and the like, as disclosed herein.

Further, mutant lipase can be designed in which one or more of the various functions is engineered to be increased or decreased, for example, substrate binding activity or the catalytic activity of the lipase, and used to augment or replace lipase proteins in an individual. Thus, host cells can provide a therapeutic benefit by replacing an aberrant lipase or providing an aberrant lipase that provides a therapeutic result. In one embodiment, the cells provide lipase that are abnormally active.

In another embodiment, the cells provide lipase that are abnormally inactive. These lipases can compete with endogenous lipase polypeptides in the individual.

In another embodiment, cells expressing lipase that cannot be activated, are introduced into an individual in order to compete with endogenous lipases for its various substrates. For example, in the case in which excessive lipase or analog is part of a treatment modality, it may be necessary to inactivate this molecule at a specific point in treatment. Providing cells that compete for the molecule, but which cannot be affected by lipase activation would be beneficial.

Homologously recombinant host cells can also be produced that allow the in situ alteration of endogenous lipase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the lipase polynucleotides or sequences proximal or distal to a lipase gene are allowed to integrate into a host cell genome by homologous recombination where expression of the gene can be affected. In one embodiment, regulatory sequences are introduced that either increase or decrease expression of an endogenous sequence. Accordingly, a lipase can be produced in a cell not normally producing it. Alternatively, increased expression of lipase can be effected in a cell normally producing the protein at a specific level. Further, expression can be decreased or eliminated by introducing a specific regulatory sequence. The regulatory sequence can be heterologous to the lipase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant lipase proteins. Such mutations could be introduced, for example, into specific functional regions such as the triglyceride or phospholipid-binding site.

In one embodiment, the host cell can be a fertilized oocyte or embryonic stem cell that can be used to produce a transgenic animal containing the altered lipase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous lipase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a lipase protein and identifying and evaluating modulators of lipase protein activity.

Other examples of transgenic animals include non-human primates, sheep, dogs, cows, goats, chickens, and amphibians.

In one embodiment, a host cell is a fertilized oocyte or an embryonic stem cell into which a lipase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the lipase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the lipase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect, for example, binding, activation, and protein turnover, may not be evident from in vitro cell-free or cell-based assays. Accordingly, it is useful to provide non-human transgenic animals to assay in vivo lipase function, including substrate interaction, the effect of specific mutant on lipase function and substrate interaction, and the effect of chimeric lipases. It is also possible to assess the effect of null mutations, that is mutations that substantially or completely eliminate one or more lipase functions.

In general, methods for producing transgenic animals include introducing a nucleic acid sequence according to the present invention, the nucleic acid sequence capable of expressing the lipase in a transgenic animal, into a cell in culture or in vivo. When introduced in vivo, the nucleic acid is introduced into an intact organism such that one or more cell types and, accordingly, one or more tissue types, express the nucleic acid encoding the lipase. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The lipase nucleic acid molecules, protein modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a lipase protein or anti-lipase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the purview of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

CHAPTER 5

25678, a Novel Human Adenylate Cyclase

BACKGROUND OF THE INVENTION

Adenylate cyclase is a membrane-bound enzyme that acts as an effector protein in a receptor-effector system referred to as the cAMP signal transduction pathway. As such, it plays a key intermediate role in the conversion of extracellular signals, perceived by various receptors following binding of a particular ligand, into intracellular signals that, in turn, generate specific cellular responses.

A variety of hormones, neurotransmitters, and olfactants regulate the synthesis of cAMP by adenylate cyclases. In most tissues, regulation of cAMP synthesis is accomplished through three plasma membrane-associated components: G-protein-coupled receptors (GPCRs), which interact with regulatory hormones and neurotransmitters; heterotrimeric G proteins that either stimulate or inhibit the catalytic subunit of adenylate cyclase in response to interaction of ligands with appropriate GPCRs; and the catalytic entity, adenylate cyclase. Each G protein contains a guanine nucleotide-binding alpha subunit and a complex of tightly associated β- and γ-subunits. When a G protein is activated following binding of a ligand to a GPCR, GDP is released from the α-subunit in exchange for GTP. Binding of the GTP results in conformational changes that yield dissociation of the GTP-bound α-subunit from the β-γ-subunit complex. The resulting macromolecular complexes regulate catalytic activity of adenylate cyclase. Where the receptor is a stimulatory receptor ($R_s$), interaction with a stimulatory G-protein, termed $G_s$, results in activation of the adenylate cyclase catalytic subunit by the GTP-bound form of the $G_s$ α-subunit. In contrast, where the receptor is an inhibitory receptor ($R_i$), interaction with an inhibitory G-protein (one of several known $G_i$s) results in inhibition of the adenylate cyclase catalytic subunit by the GTP-bound form of the $G_i$ α-subunit. In addition, the G-protein β-γ-subunit complex may interact with and influence adenylate cyclase activity independent of or in parallel with the GTP-bound α-subunit, depending upon the adenylate cyclase isoform involved. See Taussig and Gilman (1995) *J. Biol. Chem.* 6:1-4; Hardman et al., eds. (1996) *Goodman and Gilman's Pharmacological Basis of Therapeutics* (McGraw-Hill Company, New York, N.Y.).

When activated, the catalytic subunit of adenylate cyclase converts intracellular ATP into cAMP. This second messenger then activates protein kinases, particularly protein kinase A. Activation of this protein kinase causes the phosphorylation of downstream target proteins involved in a number of metabolic pathways, thus initiating a signal transduction cascade.

The extent to which adenylate cyclase converts ATP to cAMP is highly dependent on the state of phosphorylation of the various components of the hormone-sensitive adenylate cyclase system. For example, stimulatory and inhibitory receptors are desensitized and down-regulated following phosphorylation by various kinases, particularly cAMP-dependent protein kinases, protein kinase C, and other receptor-specific kinases that preferentially use agonist-bound forms of receptors as substrates. In this manner, tight regulation of the cellular cAMP concentration, and hence regulation of the cAMP signal transduction pathway, is achieved (Taussig and Gilman (1995) *J. Biol. Chem.* 270: 1-4).

Adenylate cyclase activation may also occur through increased intracellular calcium concentration, especially in nervous system and cardiovascular tissues. After depolarization, the influx of calcium elicits the activation of calmodulin, an intracellular calcium-binding protein. In the cardiovascular system, this effect gives rise to the contraction of the blood vessels or cardiac myocytes. The activated calmodulin has been shown to bind and activate some isoforms of adenylate cyclase.

Several novel isoforms of mammalian adenylate cyclase have been identified through molecular cloning. Type I adenylate cyclase (CYA1) is primarily localized in brain tissues (see Krupinski et al (1989) *Science* 244:1558-1564; Gilman (1987) *Ann. Rev. Biochem.* 56:615-649, citing Salter et al. (1981) *J. Biol. Chem.* 256:9830-9833; Andreasen et al. (1983) *Biochemistry* 22:2757-2762; and Smigel et al (1986) *J. Biol. Chem.* 261:1976-1982 for bovine CYA1; and Villa-cres et al. (1993) *Genomics* 16:473-478 for human CYA1). The type II adenylate cyclase (CYA2) is localized in brain and lung tissues (see Feinstein et al. (1991) *Proc. Natl. Acad. Sci. USA* 88:10173-10177 for rat CYA2; and Stengel et al. (1992) *Hum. Genet.* 90:126-130 for human CYA2). Type III adenylate cyclase (CYA3) is primarily localized in olfactory neuroepithelium and is thought to mediate olfactory receptor responses (Bakalyar and Reed (1990) *Science* 250:1403-1406; Glatt and Snyder (1993) *Nature* 361:536-538; and Xia (1992) *Neurosci. Lett.* 144:169-173). Type IV adenylate cyclase (CYA4) most resembles type II, but is expressed in a variety of peripheral tissues and in the central nervous system (Gao and Gilman (1991) *Proc. Natl. Acad. Sci. USA* 88:10178-10182, for rat CYA4). Type V adenylate cyclase (CYA5) (Ishikawa et al. (1992) *J. Biol. Chem.* 267:13553-13557; Premont et al. (1992) *Proc. Natl. Acad. Sci. USA* 89:9809-9813; and Glatt and Snyder (1993) *Nature* 361: 536-538; Krupinski et al. (1992) *J. Biol. Chem.* 267:24858-24862) and type VI adenylate cyclase (CYA6) (Premont et al. (1992) *Proc. Natl. Acad. Sci. USA* 89:9808-9813; Yoshimura and Cooper (1992) *Proc. Natl. Acad. Sci. USA* 89:6716-6720; Katsushika et al. (1992) *Proc. Natl. Acad. Sci. USA* 89:8774-8778; and Krupinski et al. (1992) *J. Biol. Chem.* 267:24858-24862) both exhibit a widely distributed expression pattern, with type V having high expression in heart and striatum, and type VI having high expression in heart and brain. Type VII adenylate cyclase (CYA7) is widely distributed, though may be absent from brain tissues (Krupinski et al (1992) *J. Biol. Chem.* 267:24858-24862). Type VIII adenylate cyclase (CYA8) is abundant in brain tissues (Krupinski et al. (1992) *J. Biol. Chem.* 267:24858-24862; and Parma et al. (1991) *Biochem. Biophys. Res. Commun.* 179:455-462). Type IX adenylate cyclase (CYA9) is widely expressed, at high levels in skeletal muscle and brain (Premont et al. (1996) *J. Biol. Chem.* 271:13900-13907).

The different isoforms of adenylate cyclase exhibit unique patterns of regulatory responses (see Sunahara et al. (1996) *Annu. Tev. Pharmacol. Toxicol* 36:461-480). For example, all of these isoforms are activated by the α-subunit of a particular G protein, termed Gs, which couples the stimulatory action of the ligand-bound receptor to activation of adenylate cyclase. The adenylate cyclases designated type I, III, and VIII are also stimulated by $Ca^{2+}$/calmodulin in vitro, while type II, IV, V, VI, VII, and IX are not. Type I is inhibited by G protein β-γ-subunit complex, independently of $G_s$ activation, while Type II is highly stimulated by G protein β-γ-subunit complex when simultaneously activated by Gs alpha subunit. Type III, in contrast, is not affected by G protein β-γ-subunit complex. Type V and type VI are both are inhibited by low levels of $Ca^{2+}$, but appear to be unaffected by G protein β-γ-subunit complex. Type IX is unique in that it is stimulated by $Mg^{2+}$, but is not affected by G protein β-γ-subunit complex.

The genes for these adenylate cyclases all encode proteins having molecular weights of approximately 120,000 and which range from 1064 to 1353 amino acid residues. These proteins are predicted to have a short cytoplasmic amino terminus followed by a first motif consisting of six transmembrane spans and a cytoplasmic (domain $C_1$), and then a second motif, also consisting of six transmembrane spans and a second cytoplasmic domain (domain $C_2$). The two cytoplasmic domains are approximately 40 kDa each and contain a region of homology (designated $C_{1a}$ and $C_{2a}$) with each other and with the catalytic domains of membrane-bound guanylate cyclases. Based on this similarity, these domains are considered to be nucleotide binding domains, and together have been shown to be sufficient to confer enzymatic activity (Tang and Gilman (1995) *Science* 268: 1769-1772).

Alterations in the cAMP signal transduction pathway have been associated with diseases such as asthma, cancer, inflammation, hypertension, atherosclerosis, and heart failure. Antihypertensive drug therapy involves modulation of adenylate cyclase levels (Marcil et al. (1996) *Hypertension* 28:83-90). In addition, studies of heart in human and animal models indicate that adenylate cyclase has a function in cardiomyopathy (Michael et al. (1995) *Hypertension* 25:962-970, Roth et al (1999) *Circulation* 99:3099-3102), ischemia (Sandhu et al. (1996) *Circulation Research* 78:137-147), myocardial infarction (Espinasse et al. (1999) *Cardiovascular Research* 42:87-98) and congestive heart failure (Kawahira et al. (1998) *Circulation* 98:262-267, Panza et al. (1995) *Circulation* 91:1732-1738). The enzyme is also related to some mental disorders. Studies of learning and memory in animal models indicate a likely role for calmodulin-activated adenylate cyclases in conditioning (Abrams and Kandel (1988) *Trends Neurosci.* 11:128-135), learning (Livingstone et al. (1984) *Cell* 37:205-215), and long-term potentiation (Frey et al. (1993) *Science* 260:161-1664). Furthermore, the cAMP signaling pathway plays an important role in cardiovascular physiology. For instance, cAMP activates protein kinase A (PKA). The activated subunits of PKA initiate a series of enzymatic reactions that ultimately activate multiple proteins that regulate both the rate and force of cardiac contraction.

Accordingly, adenylate cyclases are a major target for drug action and development. Accordingly, it is valuable to the field of pharmaceutical development to identify and characterize novel adenylate cyclases and tissues and disorders in which adenylate cyclases are differentially expressed. The present invention advances the state of the art by providing a novel human adenylate cyclase and tissues and disorders in which expression of a human adenylate cyclase is relevant. Accordingly, the invention provides methods directed to expression of the adenylate cyclase.

SUMMARY OF THE INVENTION

It is an object of the invention to identify novel adenylate cyclases and tissues and disorders in which expression of the adenylate cyclase is relevant.

It is a further object of the invention to provide novel adenylate cyclase polypeptides that are useful as reagents or targets in adenylate cyclase assays applicable to treatment and diagnosis of disorders mediated by or related to the adenylate cyclase.

It is a further object of the invention to provide polynucleotides corresponding to the adenylate cyclase polypeptides that are useful as targets or reagents in adenylate cyclase assays applicable to treatment and diagnosis of disorders mediated by or related to the adenylate cyclase and useful for producing novel adenylate cyclase polypeptides by recombinant methods.

A specific object of the invention is to identify compounds that act as agonists and antagonists and modulate the expression of the adenylate cyclase in specific tissues and disorders.

A further specific object of the invention is to provide compounds that modulate expression of the adenylate cyclase for treatment and diagnosis of adenylate cyclase-mediated or related disorders.

The invention is thus based on the identification and expression of a human adenylate cyclase, especially in specific tissues and disorders.

The invention provides methods of screening for compounds that modulate expression or activity of the adenylate cyclase polypeptides or nucleic acid (RNA or DNA) in the specific tissues or disorders.

The invention also provides a process for modulating adenylate cyclase polypeptide or nucleic acid expression or activity, especially using the screened compounds.

Modulation may be used to treat conditions related to aberrant activity or expression of the adenylate cyclase polypeptides or nucleic acids.

The invention also provides assays for determining the activity of or the presence or absence of the adenylate cyclase polypeptides or nucleic acid molecules in specific biological samples, including for disease diagnosis.

The invention also provides assays for determining the presence of a mutation in the polypeptides or nucleic acid molecules, including for disease diagnosis.

The invention provides isolated adenylate cyclase polypeptides, including a polypeptide having the amino acid sequence shown in SEQ ID NO:19 or the amino acid sequence encoded by the cDNA insert of the plasmid deposited as ATCC Patent Deposit PTA-1871 on May 12, 2000 ("the deposited cDNA").

The invention also provides an isolated adenylate cyclase nucleic acid molecule having the sequence shown in SEQ ID NO:20 or encoded by the deposited cDNA.

The invention also provides variant polypeptides having an amino acid sequence that is substantially homologous to the amino acid sequence shown in SEQ ID NO:19 or encoded by the deposited cDNA.

The invention also provides variant nucleic acid sequences that are substantially homologous to the nucleotide sequence shown in SEQ ID NO:20 or in the deposited cDNA.

The invention also provides fragments of the polypeptide shown in SEQ ID NO:19 and nucleotide sequence shown in SEQ ID NO:20, as well as substantially homologous fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells that express the adenylate cyclase and provides methods for expressing the adenylate cyclase nucleic acid molecules and polypeptides in specific cell types and disorders, and particularly recombinant vectors and host cells.

The invention also provides methods of making the vectors and host cells and provides methods for using them to produce adenylate cyclase nucleic acid molecules and polypeptides and to assay expression and cellular effects of expression of the adenylate cyclase nucleic acid molecules and polypeptides in specific cell types and disorders.

The invention also provides antibodies or antigen-binding fragments thereof that selectively bind the adenylate cyclase polypeptides and fragments.

In still a further embodiment, the invention provides a computer readable means containing the nucleotide and/or amino acid sequences of the nucleic acids and polypeptides of the invention.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is based, at least in part, on the identification of novel molecules, referred to herein as adenylate cyclase nucleic acid and polypeptide molecules, which play a key role in regulation of the cyclic AMP (cAMP) signal transduction pathway by virtue of their conversion of intracellular ATP into cAMP. In one embodiment, the adenylate cyclase molecules modulate the activity of one or more proteins involved in cellular metabolism associated with cell maintenance, growth, or differentiation, e.g., cardiac, epithelial, or neuronal cell maintenance, growth, or differentiation. In another embodiment, the adenylate cyclase molecules of the present invention are capable of modulating the phosphorylation state of one or more proteins involved in cellular metabolism associated with cell maintenance, growth, or differentiation, e.g., cardiac, epithelial, or neuronal cell maintenance, growth or differentiation, via their indirect effect on cAMP-dependent protein kinases, particularly protein kinase A, as described in, for example, Devlin (1997) *Textbook of Biochemistry with Clinical Correlations* (Wiley-Liss, Inc., New York, N.Y.). In addition, the receptors which trigger activity of the adenylate cyclases of the present invention are targets of drugs as described in Goodman and Gilman (1996), *The Pharmacological Basis of Therapeutics* ($9^{th}$ ed.) Hartman & Limbard Editors, the contents of which are incorporated herein by reference.

As used herein, a "signaling pathway" refers to the modulation (e.g., stimulation or inhibition) of a cellular function/activity upon the binding of a ligand to a receptor. Examples of such functions include mobilization of intracellular molecules that participate in a signal transduction pathway, e.g., phosphatidylinositol 4,5-bisphosphate ($PIP_2$), inositol 1,4,5-triphosphate ($IP_3$) and adenylate cyclase; polarization of the plasma membrane; production or secretion of molecules; alteration in the structure of a cellular component; cell proliferation, e.g., synthesis of DNA; cell migration; cell differentiation; and cell survival.

The response depends on the type of cell. In some cells, binding of a ligand to the receptor may stimulate an activity such as release of compounds, gating of a channel, cellular adhesion, migration, differentiation, etc., through phosphatidylinositol or cyclic AMP metabolism and turnover while in other cells, binding will produce a different result.

The cAMP turnover pathway is a signaling pathway. As used herein, "cyclic AMP turnover and metabolism" refers to the molecules involved in the turnover and metabolism of cAMP as well as to the activities of these molecules. Cyclic AMP is a second messenger produced in response to ligand-induced stimulation of certain receptors. In the cAMP signaling pathway, binding of a ligand can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

The cGMP turnover pathway is also a signaling pathway. As used herein, "cyclic GMP turnover and metabolism" refers to the molecules involved in the turnover and metabolism of cGMP as well as to the activities of these molecules. Cyclic GMP is a second messenger produced in response to ligand-induced stimulation of certain receptors. In the cGMP signaling pathway, binding of a ligand can lead to the activation of the enzyme guanyl cyclase, which catalyzes the synthesis of cGMP. Synthesized cGMP can in turn activate a cGMP-dependent protein kinase.

Figure 50:
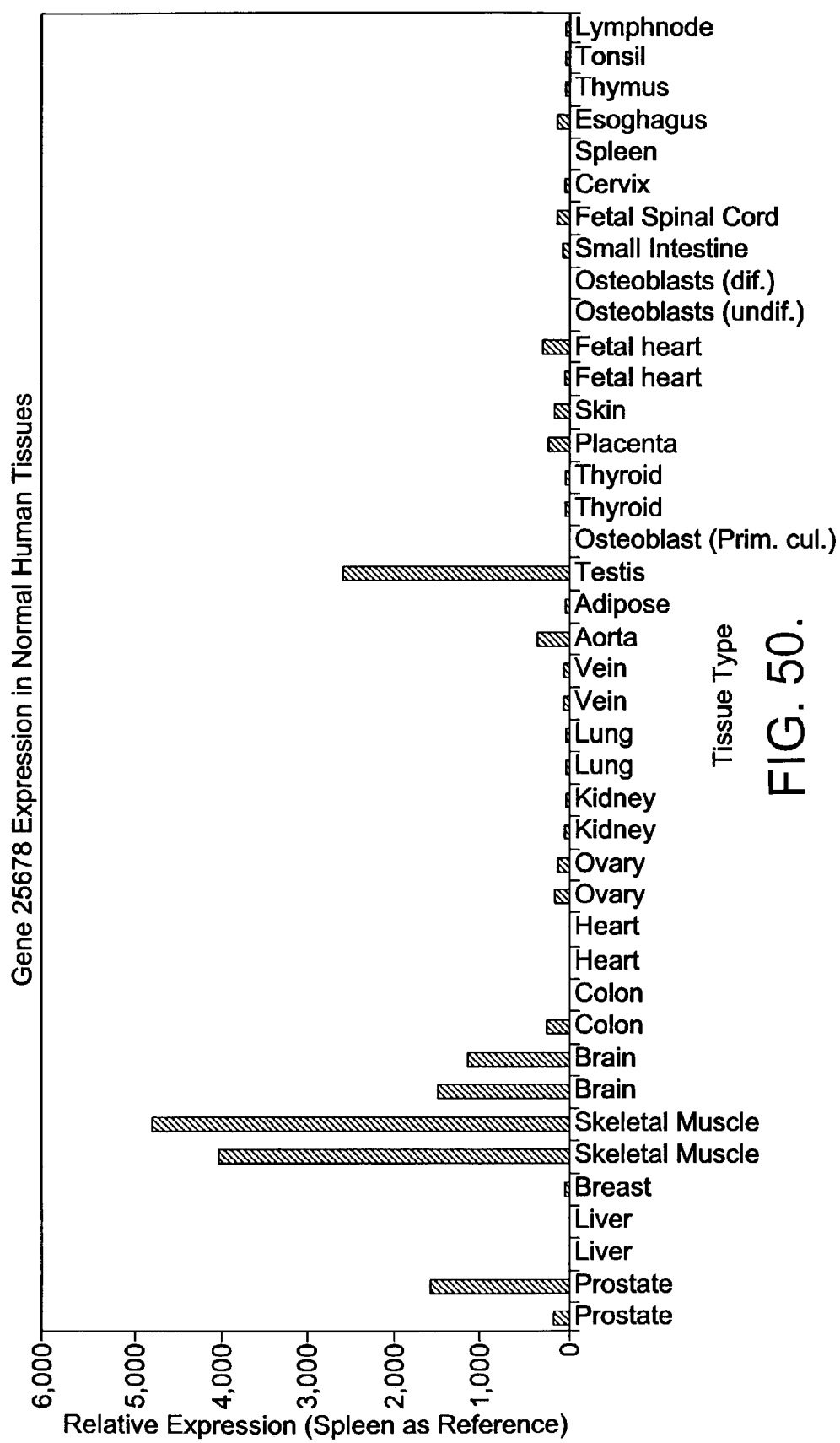
FIG. 50 shows expression of the 25678 adenylate cyclase in various normal human tissues.
Figure 53:
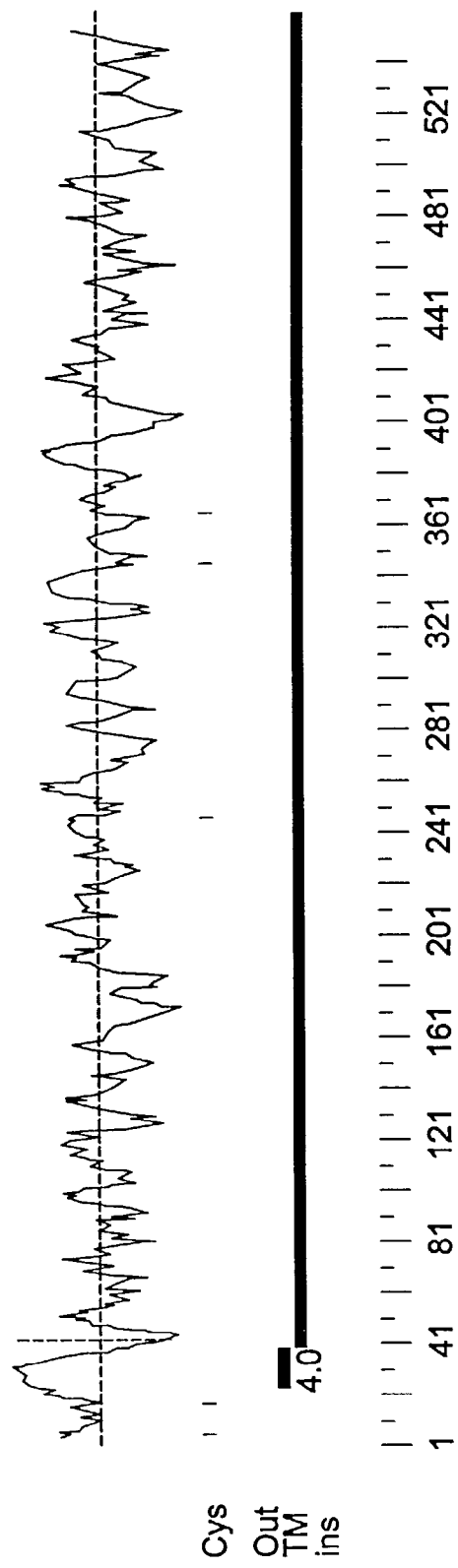
FIG. 53 shows a 26651 protein hydrophobicity plot. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:22) of human 26651 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.

The invention is directed to methods, uses and reagents applicable to methods and uses that are applied to cells, tissues and disorders of these cells and tissues wherein adenylate cyclase expression is relevant. The adenylate cyclase is expressed in a variety of tissues as shown in FIGS. 50 and 51. Accordingly, the methods and uses of the invention as disclosed in greater detail below apply to these tissues, disorders involving these tissues, and particularly to the disorders with which gene expression is associated, as shown in these figures and as disclosed herein. Accordingly, the methods, uses and reagents disclosed in greater detail below especially apply to prostate, skeletal muscle, brain, and testis. In addition, low positive expression is also observed in aorta with lower relative expression in the aorta with intimal proliferations, and internal mammary artery. In addition, using heart as a reference, low positive expression is seen in ischemic and myopathic hearts. Accordingly, the uses, reagents and methods disclosed in detail herein below apply especially to these tissues, cell types, and disorders.

Methods Using the Polypeptides

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3889-3402. When utilizing BLAST and Gapped BLAST programs, the default parameters of the respective programs (e.g., XBLAST and NBLAST) can be used.

Figure 47:
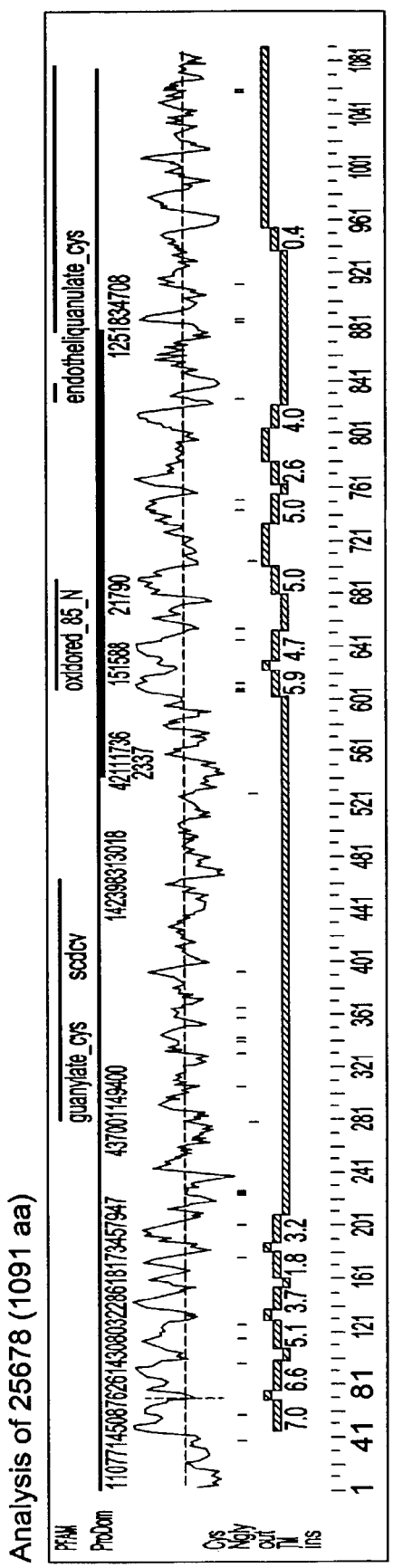
FIG. 47 shows an analysis of the adenylate cyclase amino acid sequence: αβturn and coil regions; hydrophilicity; amphipathic regions; flexible regions; antigenic index; and surface probability plot.

The adenylate cyclase polypeptides are useful for producing antibodies specific for the adenylate cyclase, regions, or fragments. Regions having a high antigenicity index score are shown in FIG. 47.

The invention provides methods using the adenylate cyclase, variants, or fragments, including but not limited to use in the cells, tissues, and disorders as disclosed herein.

The invention provides biological assays related to adenylate cyclases. Such assays involve any of the known functions or activities or properties useful for diagnosis and treatment of cyclic adenylate cyclase-related conditions. These include, but are not limited to, binding and/or activation by G-protein subunits, alpha, beta or gamma, hydrolysis of ATP or GTP and consequent modulation of cAMP and/or cGMP intracellular concentration, ability to be bound by specific antibody, GTP or ATP binding, and protein kinase A phosphorylation, as well as the various other properties and functions disclosed herein and disclosed in the references cited herein.

The invention provides drug screening assays, in cell-based or cell-free systems. Cell-based systems can be native, i.e., cells that normally express the adenylate cyclase, as a biopsy, or expanded in cell culture. In one embodiment, cell-based assays involve recombinant host cells expressing the adenylate cyclase. Accordingly, cells that are useful in this regard include, but are not limited to, those disclosed herein as expressing or differentially expressing the adenylate cyclase, such as those shown in FIGS. 50 and 51. These include, but are not limited to, cells or tissues derived from prostate, skeletal muscle, brain, colon, ovary, aorta, testis, placenta, fetal heart, aorta with intimal proliferations, internal mammary artery, kidney, and saphenous vein. Such cells can naturally express the gene or can be recombinant, containing one or more copies of exogenously-introduced adenylate cyclase sequences or genetically modified to modulate expression of the endogenous adenylate cyclase sequence.

This aspect of the invention particularly relates to cells derived from subjects with disorders involving the tissues in which the adenylate cyclase is expressed or derived from tissues subject to disorders including, but not limited to, those disclosed herein. These disorders may naturally occur, as in populations of human subjects, or may occur in model systems such as in vitro systems or in vivo, such as in non-human transgenic organisms, particularly in non-human transgenic animals.

Such assays can involve the identification of agents that interact with the adenylate cyclase protein. This interaction can be detected by functional assays, such as the ability to be affected by an effector molecule, such as binding and/or activation by G-protein subunits or hydrolysis of ATP and/or GTP to modulate intracellular cAMP/cGMP concentrations. Such interaction can also be measured by ultimate biological effects, such as phosphorylation of protein kinases, for example protein kinase A, and other downstream effectors in the signal transduction pathway, having biological effects on immunity/inflammation or cell proliferation, i.e., any of the effects of modulating the intracellular levels of the second messengers cAMP and cGMP.

Determining the ability of the test compound to interact with the adenylate cyclase can also comprise determining the ability of the test compound to preferentially bind to the polypeptide as compared to the ability of a known binding molecule (e.g., G-protein, calmodulin, GTP or ATP) to bind to the polypeptide.

In yet another aspect of the invention, the invention provides methods to identify proteins that interact with the adenylate cyclase in the tissues and disorders disclosed. The proteins of the invention can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) Biotechniques 14:920-924; Iwabuchi et al. (1993) *Oncogene* 8:1693-1696; and Brent WO 94/10300), to identify other proteins (captured proteins) which bind to or interact with the proteins of the invention and modulate their activity.

The invention provides methods to identify compounds that modulate adenylate cyclase activity. Such compounds, for example, can increase or decrease affinity or rate of binding to GTP or ATP, compete with GTP or ATP for binding to the adenylate cyclase, or displace GTP or ATP bound to the adenylate cyclase. Such compounds can also increase or decrease affinity or rate of binding to calmodulin, compete with calmodulin for binding to the adenyl cyclase, or displace calmodulin bound to the adenyl cyclase. Such compounds can also, for example, increase or decrease the affinity or rate of binding of one or more G-protein subunits, compete with the subunits for binding, or displace the subunits bound to the adenyl cyclase. Both adenylate cyclase and appropriate variants and fragments can be used in high-throughput screens to assay candidate compounds for the ability to bind to the adenylate cyclase. These compounds can be further screened against a functional adenylate cyclase to determine the effect of the compound on the adenylate cyclase activity. Compounds can be identified that activate (agonist) or inactivate (antagonist) the adenylate cyclase to a desired degree. Modulatory methods can be performed in vitro (e.g., by culturing the cell with the agent) or, alternatively, in vivo (e.g., by administering the agent to a subject. The subject can be a human subject, for example, a subject in a clinical trial or undergoing treatment or diagnosis, or a non-human transgenic subject, such as a transgenic animal model for disease.

The invention provides methods to screen a compound for the ability to stimulate or inhibit interaction between the adenylate cyclase protein and a target molecule that normally interacts with the adenylate cyclase protein. The target can be an ATP or GTP, or another component of the signal pathway with which the adenylate cyclase protein normally interacts, including but not limited to, calmodulin, or a G-protein subunit (one or more of alpha, beta, or gamma). The assay includes the steps of combining the adenylate cyclase protein with a candidate compound under conditions that allow the adenylate cyclase protein or fragment to interact with the target molecule, and to detect the formation of a complex between the adenylate cyclase protein and the target, or to detect the biochemical consequence of the interaction with the adenylate cyclase and the target, such as any of the associated effects of signal transduction such as protein kinase A phosphorylation, cAMP or cGMP turnover, and biological endpoints of the pathway.

Determining the ability of the adenylate cyclase to bind to a target molecule can also be accomplished using a technology such as real-time Bimolecular Interaction Analysis (BIA). Sjolander et al. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 97:6378-6382); (Felici (1991) *J. Mol. Biol.* 222:301-310); (Ladner supra).

Candidate compounds include, for example, 1) peptides such as soluble peptides, including Ig-tailed fusion peptides and members of random peptide libraries (see, e.g., Lam et al. (1991) *Nature* 354:82-84; Houghten et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length adenylate cyclase or fragment that competes for GTP or ATP binding. Other candidate compounds include mutant adenylate cyclases or appropriate fragments containing mutations that affect adenylate cyclase function and thus compete for GTP or ATP. Accordingly, a fragment that competes for ATP or GTP, for example with a higher affinity, or a fragment that binds ATP or GTP but does not cyclize it, is encompassed by the invention. Other fragments that are encompassed include, but are not limited to, those that will bind but not be activated by G-protein subunits, or bind but not be activated by calmodulin.

The invention provides other end points to identify compounds that modulate (stimulate or inhibit) adenylate cyclase activity. The assays typically involve an assay of events in the signal transduction pathway that indicate adenylate cyclase activity. Thus, the expression of genes that are up- or down-regulated in response to the adenylate cyclase dependent signal cascade can be assayed. In one embodiment, the regulatory region of such genes can be operably linked to a marker that is easily detectable, such as luciferase.

Any of the biological or biochemical functions mediated by the adenylate cyclase can be used as an endpoint assay. These include all of the biochemical or biochemical/biological events described herein, in the references cited herein, incorporated by reference for these endpoint assay targets, and other functions known to those of ordinary skill in the art.

In the case of the adenylate cyclase, specific end points can include ATP and GTP cyclization and a decrease or increase in intracellular cAMP or cGMP concentrations or in protein kinase A activation.

Assays for adenylate cyclase function include, but are not limited to, those that are well known in the art and available to the person of ordinary skill in the art, for example, G-protein subunit binding and activation of adenyl cyclase such as that disclosed in Taussig et al. (1995), or Sunahara et al., herein above, effect on cAMP- or cGMP-dependent kinases, as described for example in Devlin, herein above, changes in intracellular cAMP and/or cGMP concentration, as described in Sunahara et al., herein above, and stimulation by calmodulin in vitro, as disclosed in Sunahara et al., herein above. Further, nucleotide triphosphate binding domains (e.g., for ATP and GTP) can be assayed according to Tang et al. (1995), herein above. All of these references are incorporated herein by reference for these assays.

Binding and/or activating compounds can also be screened by using chimeric adenylate cyclase proteins in which one or more domains, sites, and the like, as disclosed herein, or parts thereof, can be replaced by their heterologous counterparts derived from other adenylate cyclase isoforms of the same family or from adenylate cyclase isoforms of any other adenylate cyclase family. For example, a catalytic region can be used that interacts with a different cyclic nucleotide specificity and/or affinity than the native adenylate cyclase. Accordingly, a different set of signal transduction components is available as an end-point assay for activation. Alternatively, a heterologous effector protein binding/activation sequence can replace the native sequence. For example, a different G-protein subunit can be bound or interact with the modified adenyl cyclase. Accordingly, the adenyl cyclase is subject to different modulation by different stimulatory or inhibitory G-protein subunits based on inhibitory or stimulatory receptor interaction with the G-protein. As a further alternative, the site of modification by an effector protein, for example phosphorylation by a protein kinase can be replaced with the site from a different effector protein. This could also provide the use of a different signal transduction pathway for endpoint determination. Activation can also be detected by a reporter gene containing an easily detectable coding region operably linked to a transcriptional regulatory sequence that is part of the native signal transduction pathway.

The invention provides competition binding assays designed to discover compounds that interact with the adenylate cyclase. Thus, a compound is exposed to a adenylate cyclase polypeptide under conditions that allow the compound to bind or to otherwise interact with the polypeptide. Soluble adenylate cyclase polypeptide is also added to the mixture. If the test compound interacts with the soluble adenylate cyclase polypeptide, it decreases the amount of complex formed or activity from the adenylate cyclase target. This type of assay is particularly useful in cases in which compounds are sought that interact with specific regions of the adenylate cyclase. Thus, the soluble polypeptide that competes with the target adenylate cyclase region is designed to contain peptide sequences corresponding to the region of interest.

Another type of competition-binding assay can be used to discover compounds that interact with specific functional sites. As an example, calmodulin or one or more G-protein subunits and a candidate compound can be added to a sample of the adenylate cyclase. Compounds that interact with the adenylate cyclase at the same site as these components will reduce the amount of complex formed between the adenylate cyclase and these components. Accordingly, it is possible to discover a compound that specifically prevents interaction between the adenylate cyclase and these components. Another example involves adding a candidate compound to a sample of adenylate cyclase and ATP or GTP. A compound that competes with ATP or GTP will reduce the amount of cyclization or binding of the ATP or GTP to the adenylate cyclase. Accordingly, compounds can be discovered that directly interact with the adenylate cyclase and compete with ATP or GTP. Such assays can involve any other component that interacts with the adenylate cyclase.

To perform cell-free drug screening assays, it is desirable to immobilize either the adenylate cyclase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/adenylate cyclase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of adenylate cyclase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a adenylate cyclase-binding component, such as ATP or G-protein subunit, and a candidate compound are incubated in the adenylate cyclase-presenting wells and the amount of complex trapped in the well can be quantitated. Methods for detecting such complexes, in addition to those described above for the GST-immobilized complexes, include immunodetection of complexes using antibodies reactive with the adenylate cyclase target molecule, or which are reactive with adenylate cyclase and compete with the target molecule; as well as enzyme-linked assays which rely on detecting an enzymatic activity associated with the target molecule.

Modulators of adenylate cyclase level or activity identified according to these assays can be used to test the effects of modulation of expression of the enzyme on the outcome of clinically relevant disorders. This can be accomplished in vitro, in vivo, such as in human clinical trials, and in test models derived from other organisms, such as non-human transgenic subjects. Modulation in such subjects includes, but is not limited to, modulation of the cells, tissues, and disorders particularly disclosed herein. Modulators of adenylate cyclase activity identified according to these drug screening assays can be used to treat a subject with a disorder mediated by the adenylate cyclase pathway, by treating cells that express the adenylate cyclase, such as those disclosed herein, especially in FIGS. 50 and 51, as well as those disorders disclosed in the references cited herein above. In one embodiment, the cells that are treated are derived from prostate, skeletal muscle, brain, testis and aorta, and as such, modulation is particularly relevant to disorders involving these tissues. In another embodiment, modulation is in aortic tissue with intimal proliferations or in ischemic or myopathic heart tissue. Accordingly, disorders in which modulation is particularly relevant can include these tissues. These methods of treatment include the steps of administering the modulators of adenylate cyclase activity in a pharmaceutical composition as described herein, to a subject in need of such treatment.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephalopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the skeletal muscle include tumors such as rhabdomyosarcoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

The invention thus provides methods for treating a disorder characterized by aberrant expression or activity of a adenylate cyclase. In one embodiment, the method involves administering an agent (e.g., an agent identified by a screening assay described herein), or combination of agents that modulates (e.g., upregulates or down-regulates) expression or activity of the protein. In another embodiment, the method involves administering the adenylate cyclase as therapy to compensate for reduced or aberrant expression or activity of the protein.

Methods for treatment include but are not limited to the use of soluble adenylate cyclase or fragments of the adenylate cyclase protein that compete for ATP or GTP or G-protein. These adenylate cyclases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

The invention also provides methods for diagnosing a disease or predisposition to disease mediated by the adenylate cyclase, including, but not limited to, diseases involving tissues in which the adenylate cyclases are expressed, as disclosed herein, and particularly in prostate, skeletal muscle, brain, testes, as well as aorta, aorta with intimal proliferations, internal mammary artery, kidney, and saphenous vein. In addition, as indicated in FIG. 51, positive differential expression occurs in diseased heart tissue from patients with myopathy and ischemia. In view of these results, in one embodiment of the invention, these disorders are treated by modulating the level or activity of the adenylate cyclase gene in diseased hearts. Treatment is therefore especially directed to these tissues and cells thereof. Likewise, in one embodiment, diagnosis is directed to cells and tissues involved in these disorders. As mentioned above, treatment and diagnosis can be in human subjects in which the disease normally occurs and in model systems, both in vitro and in vivo, such as in transgenic animals.

Accordingly, methods are directed to detecting the presence, or levels of, the adenylate cyclase in a cell, tissue, or organism. The methods involve contacting a biological sample with a compound capable of interacting with the adenylate cyclase such that the interaction can be detected.

One agent for detecting adenylate cyclase is an antibody capable of selectively binding to adenylate cyclase. A biological sample includes tissues, cells and biological fluids isolated from a subject, as well as tissues, cells and fluids present within a subject.

The invention also provides methods for diagnosing active disease, or predisposition to disease, in a patient having a variant adenylate cyclase. Thus, adenylate cyclase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered adenylate cyclase activity in cell-based or cell-free assay, alteration in ATP or GTP binding or cyclization, G-protein subunit binding or calmodulin or antibody-binding pattern, altered isoelectric point, direct amino acid sequencing, and any other of the known assay techniques useful for detecting mutations in a protein in general or in a adenylate cyclase specifically.

In vitro techniques for detection of adenylate cyclase include enzyme linked immunosorbent assays (ELISAs), Western blots, immunoprecipitations and immunofluorescence. Alternatively, the protein can be detected in vivo in a subject by introducing into the subject a labeled anti-adenylate cyclase antibody. For example, the antibody can be labeled with a radioactive marker whose presence and location in a subject can be detected by standard imaging techniques. Particularly useful are methods, which detect the allelic variant of the adenylate cyclase expressed in a subject, and methods, which detect fragments of the adenylate cyclase in a sample.

The invention also provides methods of pharmacogenomic analysis including, but not limited to, in the cells, tissues and disorders disclosed herein in which expression of the adenylate cyclase either occurs or shows differential expression. Pharmacogenomics deal with clinically significant hereditary variations in the response to drugs due to altered drug disposition and abnormal action in affected persons. See, e.g., Eichelbaum, M. (1996) Clin. Exp. Pharmacol. Physiol. 23(10-11):983-985, and Linder, M. W. (1997) Clin. Chem. 43(2):254-266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the adenylate cyclase in which one or more of the adenylate cyclase functions in one population is different from those in another population. The polypeptides can be used as a target to ascertain a genetic predisposition that can affect treatment modality. Thus, in a GTP- or ATP-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The invention also provides for monitoring therapeutic effects during clinical trials and other treatment. Thus, the therapeutic effectiveness of an agent that is designed to increase or decrease gene expression, protein levels or adenylate cyclase activity can be monitored over the course of treatment using the adenylate cyclase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Polypeptides

The methods and uses herein disclosed can be based on polypeptide reagents and targets. The invention is thus based on the discovery of a novel human adenylate cyclase. Specifically, an expressed sequence tag (EST) was selected based on homology to adenylate cyclase sequences. This EST was used to design primers based on sequences that it contains and used to identify a cDNA from a fetal testis cDNA library. Positive clones were sequenced and the overlapping fragments were assembled. Analysis of the assembled sequence revealed that the cloned cDNA molecule encodes an adenylate cyclase similar to a rat adenylate cyclase.

The invention thus relates to a novel human adenylate cyclase and to the expression of the adenylate cyclase having the deduced amino acid sequence shown in FIGS. 46A-46D (SEQ ID NO:19) or having the amino acid sequence encoded by the cDNA insert of the plasmid deposited with the ATCC as Patent Deposit Number PTA-1871.

The deposits will be maintained under the terms of the Budapest Treaty on the International Recognition of the Deposit of Microorganisms. The deposits are provided as a convenience to those of skill in the art and are not an admission that a deposit is required under 35 U.S.C. § 112. The deposited sequences as well as the polypeptides encoded by the sequences, are incorporated herein by reference and control in the event of any conflict, such as a sequencing error, with description in this application.

"Adenylate cyclase polypeptide" or "adenylate cyclase protein" refers to the polypeptide in SEQ ID NO:19 or encoded by the deposited cDNA. The term "adenylate cyclase protein" or "adenylate cyclase polypeptide", however, further includes the numerous variants described herein, as well as fragments derived from the full-length adenylate cyclases and variants.

Tissues and/or cells in which the adenylate cyclase is found include, but are not limited to those shown in FIGS. 50 and 51, and particularly in prostate, skeletal muscle, brain, testis and aorta. In addition, the adenylate cyclase is expressed in diseased tissues, including but limited to, heart tissue derived from patients with myopathy or ischemia.

The present invention thus provides an isolated or purified adenylate cyclase polypeptide and variants and fragments thereof.

Based on a BLAST search, high homology was shown to adenyl cyclase from rat, CYA2 Type II (EC 4.6.1.1) (ATP pyrophosphate-lyase), SwissProt Acc. No. P26769, and a rat adenyl cyclase, PATENT Acc. No. R94560.

As used herein, a polypeptide is said to be "isolated" or "purified" when it is substantially free of cellular material, when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The adenylate cyclase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the adenylate cyclase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

An adenylate cyclase polypeptide is also considered to be isolated when it is part of a membrane preparation or is purified and then reconstituted with membrane vesicles or liposomes.

The language "substantially free of chemical precursors or other chemicals" includes preparations of the adenylate cyclase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the adenylate cyclase polypeptide comprises the amino acid sequence shown in SEQ ID NO:19. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the adenylate cyclase of SEQ ID NO:19. Variants also include proteins substantially homologous to the adenylate cyclase but derived from another organism, i.e., an ortholog. Variants also include proteins that are substantially homologous to the adenylate cyclase that are produced by chemical synthesis. Variants also include proteins that are substantially homologous to the adenylate cyclase that are produced by recombinant methods. It is understood, however, that variants exclude any amino acid sequences disclosed prior to the invention.

As used herein, two proteins (or a region of the proteins) are substantially homologous when the amino acid sequences are at least about 70-75%, typically at least about 80-85%, and most typically at least about 90-95% or more homologous. A substantially homologous amino acid sequence, according to the present invention, will be encoded by a nucleic acid sequence hybridizing to the nucleic acid sequence, or portion thereof, of the sequence shown in SEQ ID NO:20 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the adenylate cyclase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306-1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |

TABLE 1-continued

Conservative Amino Acid Substitutions.

| | |
|---|---|
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci. USA* 90:5873-5877. Such an algorithm is incorporated into the NBLAST and XBLAST programs (version 2.0) as described in Altschul et al. (1997) *Nucleic Acids Res.* 25:3389-3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444-453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3-5; and FASTA described in Pearson et al. (1988) *PNAS* 85:2444-8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions corresponding to a catalytic region, regulatory region, targeting region, regions involved in membrane association, regions involved in enzyme activation, for example, by phosphorylation, and regions involved in interaction with components of the cyclic nucleotide-dependent signal transduction pathways, (e.g., ATP, GTP, G-protein, or calmodulin).

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the adenylate cyclase polypeptide. This includes preventing immunogenicity from pharmaceutical formulations by preventing protein aggregation.

Useful variations further include alteration of catalytic activity. For example, one embodiment involves a variation at the binding site that results in binding but not cyclization, or slower cyclization, of ATP or GTP. A further useful variation at the same site can result in altered affinity for ATP or GTP. Useful variation includes one that prevents activation by G-protein. Another useful variation provides a fusion protein in which one or more domains or subregions are operationally fused to one or more domains or subregions from another adenylate cyclase isoform or family.

Amino acids that are essential for function can be identified by methods known in the art, such as site-directed mutagenesis or alanine-scanning mutagenesis (Cunningham et al. (1985) *Science* 244:1081-1085). The latter procedure introduces single alanine mutations at every residue in the molecule. The resulting mutant molecules are then tested for biological activity, such as ATP or GTP cyclization in vitro or cGMP- or cAMP-dependent in vitro activity, such as proliferative activity. Sites that are critical for GTP or ATP or G-protein binding can also be determined by structural analysis such as crystallization, nuclear magnetic resonance or photoaffinity labeling (Smith et al. (1992) *J. Mol. Biol.* 224:899-904; de Vos et al. (1992) *Science* 255:306-312).

Substantial homology can be to the entire nucleic acid or amino acid sequence or to fragments of these sequences.

The invention thus also includes polypeptide fragments of the adenylate cyclase. Fragments can be derived from the amino acid sequence shown in SEQ ID NO:19. However, the invention also encompasses fragments of the variants of the adenylate cyclase as described herein.

The fragments to which the invention pertains, however, are not to be construed as encompassing fragments per se that may have been disclosed prior to the invention (although the methods herein can pertain to known fragments).

Accordingly, a fragment can comprise at least about 10, 15, 20, 25, 30, 35, 40, 45, 50 or more contiguous amino acids. Fragments can retain one or more of the biological activities of the protein, for example the ability to bind to or cyclize GTP or ATP, as well as fragments that can be used as an immunogen to generate adenylate cyclase antibodies.

Biologically active fragments (peptides which are, for example, 5, 7, 10, 12, 15, 20, 30, 35, 36, 37, 38, 39, 40, 50, 100 or more amino acids in length) can comprise a domain or motif, e.g., catalytic site, adenylate cyclase signature, and sites for glycosylation, protein kinase C phosphorylation, casein kinase II phosphorylation, tyrosine kinase phosphorylation, and N-myristoylation. Further possible fragments include the catalytic site, sites important for cellular and subcellular targeting, sites functional for interacting with components of other cGMP or cAMP-dependent signal transduction pathways, and regulatory sites.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the adenylate cyclase and variants. These epitope-bearing peptides are useful to raise antibodies that bind specifically to a adenylate cyclase polypeptide or region or fragment. These peptides can contain at least 10, 12, at least 14, or between at least about 15 to about 30 amino acids.

Figure 48:
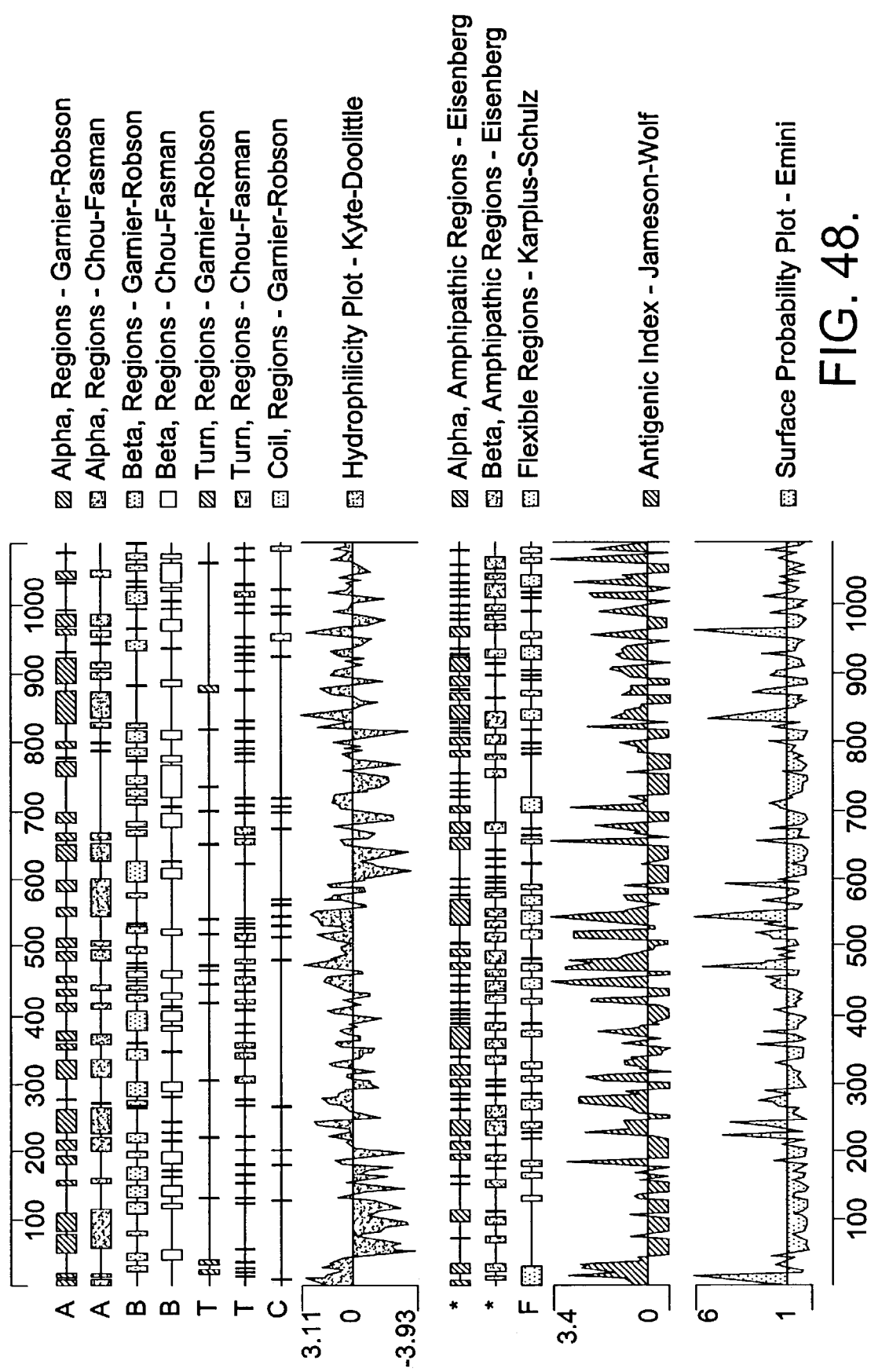
FIG. 48 shows a hydrophobicity plot of the adenylate cyclase.

Non-limiting examples of antigenic polypeptides that can be used to generate antibodies include but are not limited to peptides derived from an extracellular site. Regions having a high antigenicity index are shown in FIG. 48. However, intracellularly-made antibodies ("intrabodies") are also encompassed, which would recognize intracellular peptide regions.

The epitope-bearing adenylate cyclase polypeptides may be produced by any conventional means (Houghten, R. A. (1985) *Proc. Natl. Acad. Sci. USA* 82:5131-5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the adenylate cyclase fragment and an additional region fused to the carboxyl terminus of the fragment.

The invention thus provides chimeric or fusion proteins. These comprise a adenylate cyclase peptide sequence operatively linked to a heterologous peptide having an amino acid sequence not substantially homologous to the adenylate cyclase. "Operatively linked" indicates that the adenylate cyclase peptide and the heterologous peptide are fused in-frame. The heterologous peptide can be fused to the N-terminus or C-terminus of the adenylate cyclase or can be internally located.

In one embodiment the fusion protein does not affect adenylate cyclase function per se. For example, the fusion protein can be a GST-fusion protein in which the adenylate cyclase sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant adenylate cyclase. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52-58 (1995) and Johanson et al. *J. Biol. Chem.* 270:9459-9471). Thus, this invention also encompasses soluble fusion proteins containing a adenylate cyclase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). An adenylate cyclase-encoding nucleic acid can be cloned into such an expression vector such that the fusion moiety is linked in-frame to the adenylate cyclase.

Another form of fusion protein is one that directly affects adenylate cyclase functions. Accordingly, a adenylate cyclase polypeptide is encompassed by the present invention in which one or more of the adenylate cyclase domains (or parts thereof) has been replaced by homologous domains (or parts thereof) from another adenylate cyclase family. Accordingly, various permutations are possible. For example, the aminoterminal regulatory domain, or subregion thereof, can be replaced with the domain or subregion from another isoform or adenylate cyclase family. As a further example, the catalytic domain or parts thereof, can be replaced; the carboxyterminal domain or subregion can be replaced. Thus, chimeric adenylate cyclases can be formed in which one or more of the native domains or subregions has been replaced by another.

Additionally, chimeric adenylate cyclase proteins can be produced in which one or more functional sites is derived from a different isoform, or from another adenylate cyclase family. It is understood, however, that sites could be derived from adenylate cyclase families that occur in the mammalian genome but which have not yet been discovered or characterized. Such sites include but are not limited to a catalytic site, regulatory site, sites important for targeting to subcellular and cellular locations, sites functional for interaction with components of cyclic AMP- and cyclic GMP-dependent signal transduction pathways, phosphorylation sites, glycosylation sites, and other functional sites disclosed herein.

The isolated adenylate cyclase can be purified from cells that naturally express it, such as from those shown in FIGS. 50 and 51 and/or specifically disclosed herein above, among others, especially purified from cells that have been altered to express it (recombinant), or synthesized using known protein synthesis methods.

In one embodiment, the protein is produced by recombinant DNA techniques. For example, a nucleic acid molecule encoding the adenylate cyclase polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1-12 (1983); Seifter et al. (1990) *Meth. Enzymol.* 182: 626-646) and Rattan et al. (1992) *Ann. N.Y. Acad. Sci.* 663:48-62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in E. coli, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Methods Using the Antibodies

Methods for using antibodies as disclosed herein are particularly applicable to the cells, tissues and disorders shown in FIGS. 50 and 51 and as otherwise discussed herein above.

The invention provides methods using antibodies that selectively bind to the adenylate cyclase and its variants and fragments. An antibody is considered to selectively bind, even if it also binds to other proteins that are not substantially homologous with the adenylate cyclase. These other proteins share homology with a fragment or domain of the adenylate cyclase. This conservation in specific regions gives rise to antibodies that bind to both proteins by virtue of the homologous sequence. In this case, it would be understood that antibody binding to the adenylate cyclase is still selective.

The invention provides methods of using antibodies to isolate a adenylate cyclase by standard techniques, such as affinity chromatography or immunoprecipitation. The antibodies can facilitate the purification of the adenylate cyclase from cells naturally expressing it and cells recombinantly producing it.

The antibodies can be used to detect the presence of adenylate cyclase in cells or tissues to determine the pattern of expression of the adenylate cyclase among various tissues in an organism and over the course of normal development.

The antibodies can be used to detect adenylate cyclase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full-length adenylate cyclase can be used to identify adenylate cyclase turnover.

Further, the antibodies can be used to assess adenylate cyclase expression in disease states such as in active stages of the disease or in an individual with a predisposition toward disease related to adenylate cyclase function. When a disorder is caused by an inappropriate tissue distribution, developmental expression, or level of expression of the adenylate cyclase protein, the antibody can be prepared against the normal adenylate cyclase protein. If a disorder is characterized by a specific mutation in the adenylate cyclase, antibodies specific for this mutant protein can be used to assay for the presence of the specific mutant adenylate cyclase. However, intracellularly-made antibodies ("intrabodies") are also encompassed, which would recognize intracellular adenylate cyclase peptide regions.

The antibodies can also be used to assess normal and aberrant subcellular localization in cells in the various tissues in an organism. Antibodies can be developed against the whole adenylate cyclase or portions of the adenylate cyclase.

The diagnostic uses can be applied, not only in genetic testing, but also in monitoring a treatment modality. Accordingly, where treatment is ultimately aimed at correcting adenylate cyclase expression level or the presence of aberrant adenylate cyclases and aberrant tissue distribution or developmental expression, antibodies directed against the adenylate cyclase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic adenylate cyclase can be used to identify individuals that require modified treatment modalities.

Antibodies can also be used in diagnostic procedures as an immunological marker for aberrant adenylate cyclase analyzed by electrophoretic mobility, isoelectric point, tryptic peptide digest, and other physical assays known to those in the art.

The antibodies are also useful for tissue typing. Thus, where the adenylate cyclase is expressed in a specific tissue, antibodies that are specific for this adenylate cyclase can be used to identify the tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting adenylate cyclase function, for example, blocking binding of GTP or ATP, G-protein, or the catalytic site.

These uses can also be applied in a therapeutic context in which treatment involves inhibiting adenylate cyclase function. An antibody can be used, for example, to block ATP or GTP binding. Antibodies can be prepared against specific fragments containing sites required for function or against intact adenylate cyclase.

Completely human antibodies are particularly desirable for therapeutic treatment of human patients. For an overview of this technology for producing human antibodies, see Lonberg et al. 1995) Int. Rev. Immunol. 13:65-93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a adenylate cyclase protein in a biological sample. The kit can comprise antibodies such as a labeled or labelable antibody and a compound or agent for detecting adenylate cyclase in a biological sample; means for determining the amount of adenylate cyclase in the sample; and means for comparing the amount of adenylate cyclase in the sample with a standard.

The compound or agent can be packaged in a suitable container. The kit can further comprise instructions for using the kit to detect adenylate cyclase.

Antibodies

The methods for using antibodies described above are based on the generation of antibodies that specifically bind to the adenylate cyclase or its variants or fragments.

To generate antibodies, an isolated adenylate cyclase polypeptide is used as an immunogen to generate antibodies using standard techniques for polyclonal and monoclonal antibody preparation. Either the full-length protein or antigenic peptide fragment can be used. Regions having a high antigenicity index are shown in FIG. 48.

Antibodies are preferably prepared from these regions or from discrete fragments in these regions. However, antibodies can be prepared from any region of the peptide as described herein. A preferred fragment produces an antibody that diminishes or completely prevents G-protein ATP or GTP binding. Antibodies can be developed against the entire adenylate cyclase or domains of the adenylate cyclase as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g., Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

An appropriate immunogenic preparation can be derived from native, recombinantly expressed, or chemically synthesized peptides.

Methods Using the Polynucleotides

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST protein searches can be performed with the XBLAST program, score=50, wordlength=3 to obtain amino acid sequences homologous to the proteins of the invention. To obtain gapped alignments for comparison purposes, gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

The methods and uses described herein below for the adenylate cyclase polynucleotide are particularly applicable to the cells, tissues, and disorders shown in FIGS. 50 and 51, and specifically discussed herein above.

The nucleic acid fragments useful to practice the invention provide probes or primers in assays, such as those described herein. "Probes" are oligonucleotides that hybridize in a base-specific manner to a complementary strand of nucleic acid. Such probes include polypeptide nucleic acids, as described in Nielsen et al. (1991) *Science* 254:1497-1500. Typically, a probe comprises a region of nucleotide sequence that hybridizes under highly stringent conditions to at least about 15, typically about 20-25, and more typically about 40, 50 or 75 consecutive nucleotides of the nucleic acid sequence shown in SEQ ID NO:20 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The adenylate cyclase polynucleotides can be utilized as probes and primers in biological assays.

Where the polynucleotides are used to assess adenylate cyclase properties or functions, such as in the assays described herein, all or less than all of the entire cDNA can be useful. Assays specifically directed to adenylate cyclase functions, such as assessing agonist or antagonist activity, encompass the use of known fragments. Further, diagnostic methods for assessing adenylate cyclase function can also be practiced with any fragment, including those fragments that may have been known prior to the invention. Similarly, in methods involving treatment of adenylate cyclase dysfunction, all fragments are encompassed including those, which may have been known in the art.

The invention utilizes the adenylate cyclase polynucleotides as a hybridization probe for cDNA and genomic DNA to isolate a full-length cDNA and genomic clones encoding variant polypeptides and to isolate cDNA and genomic clones that correspond to variants producing the same polypeptides shown in SEQ ID NO:19 or the other variants described herein. Variants can be isolated from the same tissue and organism from which the polypeptide shown in SEQ ID NO:19 was isolated, different tissues from the same organism, or from different organisms. This method is useful for isolating variant genes and cDNA that are developmentally controlled and therefore may be expressed in the same tissue or different tissues at different points in the development of an organism. This method is useful for isolating variant genes and cDNA that are expressed in the cells, tissues, and disorders disclosed herein.

The probe can correspond to any sequence along the entire length of the gene encoding the adenylate cyclase. Accordingly, it could be derived from 5' noncoding regions, the coding region, and 3' noncoding regions.

The nucleic acid probe can be, for example, the full-length cDNA of SEQ ID NO:20, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein can also be used to synthesize larger fragments or full-length polynucleotides described herein. For example, a fragment can be hybridized to any portion of an mRNA and a larger or full-length cDNA can be produced.

Fragments can also be used to synthesize antisense molecules of desired length and sequence.

Antisense nucleic acids, useful in treatment and diagnosis, can be designed using the nucleotide sequences of SEQ ID NO:20, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules useful to practice the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357-63, Mag et al. (1989) *Nucleic Acids Res.* 17:5973, and Peterser et al. (1975) *Bioorganic Med. Chem. Lett.* 5:1119.

The nucleic acid molecules and fragments useful to practice the invention can also include other appended groups such as peptides (e.g., for targeting host cell adenylate cyclases in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958-976) or intercalating agents (see, e.g., Zon (1988) *Pharm Res.* 5:539-549).

The adenylate cyclase polynucleotides can also be used as primers for PCR to amplify any given region of a adenylate cyclase polynucleotide.

The adenylate cyclase polynucleotides can also be used to construct recombinant vectors. Such vectors include expression vectors that express a portion of, or all of, the adenylate cyclase polypeptides. Vectors also include insertion vectors, used to integrate into another polynucleotide sequence, such as into the cellular genome, to alter in situ expression of adenylate cyclase genes and gene products. For example, an endogenous adenylate cyclase coding sequence can be replaced via homologous recombination with all or part of the coding region containing one or more specifically introduced mutations.

The adenylate cyclase polynucleotides can also be used to express antigenic portions of the adenylate cyclase protein.

The adenylate cyclase polynucleotides can also be used as probes for determining the chromosomal positions of the adenylate cyclase polynucleotides by means of in situ hybridization methods, such as FISH. (For a review of this technique, see Verma et al. (1988) *Human Chromosomes: A Manual of Basic Techniques*(Pergamon Press, New York), and PCR mapping of somatic cell hybrids. The mapping of the sequence to chromosomes is important in correlating these sequences with genes associated with disease, especially where translocations and/or amplification have occurred.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783-787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The adenylate cyclase polynucleotide probes can also be used to determine patterns of the presence of the gene encoding the adenylate cyclase with respect to tissue distribution, for example, whether gene duplication has occurred and whether the duplication occurs in all or only a subset of cells in a tissue. The genes can be naturally occurring or can have been introduced into a cell, tissue, or organism exogenously.

The adenylate cyclase polynucleotides can also be used to design ribozymes corresponding to all, or a part, of the mRNA produced from genes encoding the polynucleotides described herein, the ribozymes being useful to treat or diagnose a disorder or otherwise modulate expression of the nucleic acid.

The adenylate cyclase polynucleotides can also be used to make vectors that express part, or all, of the adenylate cyclase polypeptides.

The adenylate cyclase polynucleotides can also be used to construct host cells expressing a part, or all, of the adenylate cyclase polynucleotides and polypeptides.

The adenylate cyclase polynucleotides can also be used to construct transgenic animals expressing all, or a part, of the adenylate cyclase polynucleotides and polypeptides.

The adenylate cyclase polynucleotides can also be used as hybridization probes to determine the level of adenylate cyclase nucleic acid expression. Accordingly, the probes can be used to detect the presence of, or to determine levels of, adenylate cyclase nucleic acid in cells, tissues, and in organisms. DNA or RNA level can be determined. Probes can be used to assess gene copy number in a given cell, tissue, or organism. This is particularly relevant in cases in which there has been an amplification of the adenylate cyclase gene.

Alternatively, the probe can be used in an in situ hybridization context to assess the position of extra copies of the adenylate cyclase gene, as on extrachromosomal elements or as integrated into chromosomes in which the adenylate cyclase gene is not normally found, for example, as a homogeneously staining region.

These uses are relevant for diagnosis of disorders involving an increase or decrease in adenylate cyclase expression relative to normal, such as a proliferative disorder, a differentiative or developmental disorder, or a hematopoietic disorder, such as in the cells and tissues shown in FIGS. 50 and 51 and otherwise specifically discussed herein. Thus in one embodiment, disorders include diseases of the heart, such as myopathy and ischemia.

Thus, the present invention provides a method for identifying a disease or disorder associated with aberrant expression or activity of adenylate cyclase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the adenylate cyclase, such as by measuring the level of a adenylate cyclase-encoding nucleic acid in a sample of cells from a subject e.g., mRNA or genomic DNA, or determining if the adenylate cyclase gene has been mutated.

Nucleic acid expression assays are useful for drug screening to identify compounds that modulate adenylate cyclase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gene to a subject) in patients or in transgenic animals.

The invention thus provides a method for identifying a compound that can be used to treat a disorder associated with expression of the adenylate cyclase gene. The method typically includes assaying the ability of the compound to modulate the expression of the adenylate cyclase nucleic acid and thus identifying a compound that can be used to treat a disorder characterized by excessive or deficient adenylate cyclase nucleic acid expression.

The assays can be performed in cell-based and cell-free systems, such as systems using the tissues described herein, in which the gene is expressed or in model systems for the disorders to which the invention pertains. Cell-based assays include cells naturally expressing the adenylate cyclase nucleic acid or recombinant cells genetically engineered to express specific nucleic acid sequences.

Alternatively, candidate compounds can be assayed in vivo in patients or in transgenic animals.

The assay for adenylate cyclase nucleic acid expression can involve direct assay of nucleic acid levels, such as mRNA levels, or on collateral compounds involved in the signal pathway (such as cAMP or cGMP turnover). Further, the expression of genes that are up- or down-regulated in response to the adenylate cyclase signal pathway can also be assayed. In this embodiment the regulatory regions of these genes can be operably linked to a reporter gene such as luciferase.

Thus, modulators of adenylate cyclase gene expression can be identified in a method wherein a cell is contacted with a candidate compound and the expression of mRNA determined. The level of expression of adenylate cyclase mRNA in the presence of the candidate compound is compared to the level of expression of adenylate cyclase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate adenylate cyclase nucleic acid expression. Modulation includes both up-regulation (i.e. activation or agonization) or down-regulation (suppression or antagonization) or effects on nucleic acid activity (e.g., when nucleic acid is mutated or improperly modified). Treatment is of disorders characterized by aberrant expression or activity of the nucleic acid.

The gene is particularly relevant for the treatment of disorders involving the tissues shown in FIGS. 50 and 51, particularly in prostate, skeletal muscle, brain, and testes, as well as tissues and cells involved in myopathy and ischemia.

Alternatively, a modulator for adenylate cyclase nucleic acid expression can be a small molecule or drug identified using the screening assays described herein as long as the drug or small molecule inhibits the adenylate cyclase nucleic acid expression.

The adenylate cyclase polynucleotides are also useful for monitoring the effectiveness of modulating compounds on the expression or activity of the adenylate cyclase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The adenylate cyclase polynucleotides can be used in diagnostic assays for qualitative changes in adenylate cyclase nucleic acid, and particularly in qualitative changes that lead to pathology. The polynucleotides can be used to detect mutations in adenylate cyclase genes and gene expression products such as mRNA. The polynucleotides can be used as hybridization probes to detect naturally-occurring genetic mutations in the adenylate cyclase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the adenylate cyclase gene associated with a dysfunction provides a diagnostic tool for an active disease or susceptibility to disease when the disease results from overexpression, underexpression, or altered expression of a adenylate cyclase.

Mutations in the adenylate cyclase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *PNAS* 91:360-364), the latter of which can be particularly useful for detecting point mutations in the gene (see Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a adenylate cyclase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant adenylate cyclase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286-295), electrophoretic mobility of mutant and wild type nucleic acid is compared (Orita et al. (1989) *PNAS* 86:2766; Cotton et al. (1993) *Mutat. Res.* 285:125-144; and Hayashi et al. (1992) *Genet. Anal. Tech. Appl.* 9:73-79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244-255; Kozal et al. (1996) *Nature Medicine* 2:753-759). For example, genetic mutations can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The adenylate cyclase polynucleotides can also be used for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the adenylate cyclase gene that results in altered affinity for ATP or GTP could result in an excessive or decreased drug effect with standard concentrations of ATP or GTP.

Accordingly, the adenylate cyclase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The adenylate cyclase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The adenylate cyclase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the adenylate cyclase sequence can be used to provide an alternative technique, which determines the actual DNA sequence of selected fragments in the genome of an individual. Thus, the adenylate cyclase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The adenylate cyclase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The adenylate cyclase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The adenylate cyclase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The adenylate cyclase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of adenylate cyclase probes can be used to identify tissue by species and/or by organ type.

In a similar fashion, these primers and probes can be used to screen tissue culture for contamination (i.e., screen for the presence of a mixture of different types of cells in a culture).

Alternatively, the adenylate cyclase polynucleotides can be used directly to block transcription or translation of adenylate cyclase gene sequences by means of antisense or ribozyme constructs. Thus, in a disorder characterized by abnormally high or undesirable adenylate cyclase gene expression, nucleic acids can be directly used for treatment.

The adenylate cyclase polynucleotides are thus useful as antisense constructs to control adenylate cyclase gene expression in cells, tissues, and organisms. A DNA antisense polynucleotide is designed to be complementary to a region of the gene involved in transcription, preventing transcription and hence production of adenylate cyclase protein. An antisense RNA or DNA polynucleotide would hybridize to the mRNA and thus block translation of mRNA into adenylate cyclase protein.

Examples of antisense molecules useful to inhibit nucleic acid expression include antisense molecules complementary to a fragment of the 5' untranslated region of SEQ ID NO:20 which also includes the start codon and antisense molecules which are complementary to a fragment of the 3' untranslated region of SEQ ID NO:20.

Alternatively, a class of antisense molecules can be used to inactivate mRNA in order to decrease expression of adenylate cyclase nucleic acid. Accordingly, these molecules can treat a disorder characterized by abnormal or undesired adenylate cyclase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the adenylate cyclase protein.

The adenylate cyclase polynucleotides also provide vectors for gene therapy in patients containing cells that are aberrant in adenylate cyclase gene expression. Thus, recombinant cells, which include the patient's cells that have been engineered ex vivo and returned to the patient, are introduced into an individual where the cells produce the desired adenylate cyclase protein to treat the individual.

The invention also encompasses kits for detecting the presence of a adenylate cyclase nucleic acid in a biological sample. For example, the kit can comprise reagents such as a labeled or labelable nucleic acid or agent capable of detecting adenylate cyclase nucleic acid in a biological sample; means for determining the amount of adenylate cyclase nucleic acid in the sample; and means for comparing the amount of adenylate cyclase nucleic acid in the sample with a standard. The compound or agent can be packaged in a suitable container. The kit can further comprise instructions for using the kit to detect adenylate cyclase mRNA or DNA.

Polynucleotides

The nucleotide sequence in SEQ ID NO:20 was obtained by sequencing the deposited human cDNA. Accordingly, the sequence of the deposited clone is controlling as to any discrepancies between the two and any reference to the sequence of SEQ ID NO:20 includes reference to the sequence of the deposited cDNA.

The specifically disclosed cDNA comprises the coding region and 5' and 3' untranslated sequences in SEQ ID NO:20.

The invention provides isolated polynucleotides encoding the adenylate cyclase. The term "adenylate cyclase polynucleotide" or "adenylate cyclase nucleic acid" refers to the sequence shown in SEQ ID NO:20 or in the deposited cDNA. The term "adenylate cyclase polynucleotide" or "adenylate cyclase nucleic acid" further includes variants and fragments of the adenylate cyclase polynucleotides.

The methods and uses described herein can be based on the adenylate cyclase polynucleotide as a reagent or as a target.

The invention thus provides methods and uses for the nucleotide sequence in SEQ ID NO:20.

An "isolated" adenylate cyclase nucleic acid is one that is separated from other nucleic acid present in the natural source of the adenylate cyclase nucleic acid. Preferably, an "isolated" nucleic acid is free of sequences which naturally flank the adenylate cyclase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the adenylate cyclase nucleic acid is isolated from flanking sequences such that it can be subjected to the specific manipulations described herein, such as recombinant expression, preparation of probes and primers, and other uses specific to the adenylate cyclase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic-acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The adenylate cyclase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The adenylate cyclase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Adenylate cyclase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

In one embodiment, the adenylate cyclase nucleic acid comprises only the coding region.

The invention further provides variant adenylate cyclase polynucleotides, and fragments thereof, that differ from the nucleotide sequence shown in SEQ ID NO:20 due to degeneracy of the genetic code and thus encode the same protein as that encoded by the nucleotide sequence shown in SEQ ID NO:20.

The invention also provides adenylate cyclase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecule of SEQ ID NO:20 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a adenylate cyclase that is at least about 60-65%, 65-70%, typically at least about 70-75%, more typically at least about 80-85%, and most typically at least about 90-95% or more homologous to the nucleotide sequence shown in SEQ ID NO:20 or a fragment of this sequence. Such nucleic acid molecules can readily be identified as being able to hybridize under stringent conditions, to the nucleotide sequence shown in SEQ ID NO:20 or a fragment of the sequence. It is understood that stringent hybridization does not indicate substantial homology where it is due to general homology, such as poly A sequences, or sequences common to all or most proteins, or all adenylate cyclases. Moreover, variants per se do not include any nucleic acid (or amino acid) sequence disclosed prior to the present invention, although the methods herein can encompass such variants.

As used herein, the term "hybridizes under stringent conditions" is intended to describe conditions for hybridization and washing under which nucleotide sequences encoding a polypeptide at least about 60-65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1-6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50-65° C. In another non-limiting example, nucleic acid molecules are allowed to hybridize in 6× sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:19 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:20 or the complement of SEQ ID NO:20. In one embodiment, the nucleic acid consists of a portion of the nucleotide sequence of SEQ ID NO:20 and the complement of SEQ ID NO:20. The nucleic acid fragments of the invention are at least about 15, preferably at least about 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

Furthermore, the invention provides polynucleotides that comprise a fragment of the full-length adenylate cyclase polynucleotide. The fragment can be single or double-stranded and can comprise DNA or RNA. The fragment can be derived from either the coding or the non-coding sequence.

In another embodiment an isolated adenylate cyclase nucleic acid encodes the entire coding region. In another embodiment the isolated adenylate cyclase nucleic acid encodes a sequence corresponding to the mature protein that may be from about amino acid 6 to the last amino acid. Other fragments include nucleotide sequences encoding the amino acid fragments described herein.

Thus, adenylate cyclase nucleic acid fragments further include sequences corresponding to the domains described herein, subregions also described, and specific functional sites. Adenylate cyclase nucleic acid fragments also include combinations of the domains, segments, and other functional sites described above. A person of ordinary skill in the art would be aware of the many permutations that are possible.

Where the location of the domains or sites have been predicted by computer analysis, one of ordinary skill would appreciate that the amino acid residues constituting these domains can vary depending on the criteria used to define the domains.

However, it is understood that a adenylate cyclase fragment includes any nucleic acid sequence that does not include the entire gene.

The invention also provides adenylate cyclase nucleic acid fragments that encode epitope bearing regions of the adenylate cyclase proteins described herein.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBIA).

For example, software which implements the BLAST (Altschul et al. (1990) *J. Mol. Biol.* 215:403-410) and BLAZE (Brutlag et al. (1993) *Comp. Chem.* 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Methods Using Vectors and Host Cells

The methods using vectors and host cells are particularly relevant where vectors are expressed in the cells, tissues, and disorders shown in FIGS. 50 and 51, and otherwise discussed herein, or where the host cells are those that naturally express the gene, as shown in these figures and which may be the native or a recombinant cell expressing the gene.

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing adenylate cyclase proteins or polypeptides that can be further purified to produce desired amounts of adenylate cyclase protein or fragments. Thus, host cells containing expression vectors are useful for polypeptide production, as well as cells producing significant amounts of the polypeptide, for example, the high-expressers shown in FIG. 51, in other words, testes, prostate, skeletal muscle and brain.

Host cells are also useful for conducting cell-based assays involving the adenylate cyclase or adenylate cyclase fragments. Thus, a recombinant host cell expressing a native adenylate cyclase is useful to assay for compounds that stimulate or inhibit adenylate cyclase function. This includes ATP or GTP binding, gene expression at the level of transcription or translation, G-protein interaction, and components of the signal transduction pathway.

Host cells are also useful for identifying adenylate cyclase mutants in which these functions are affected. If the mutants naturally occur and give rise to a pathology, host cells containing the mutations are useful to assay compounds that have a desired effect on the mutant adenylate cyclase (for example, stimulating or inhibiting function) which may not be indicated by their effect on the native adenylate cyclase.

Recombinant host cells are also useful for expressing the chimeric polypeptides described herein to assess compounds that activate or suppress activation by means of a heterologous domain, segment, site, and the like, as disclosed herein.

Further, mutant adenylate cyclases can be designed in which one or more of the various functions is engineered to be increased or decreased (e.g., ATP binding or G-protein binding) and used to augment or replace adenylate cyclase proteins in an individual. Thus, host cells can provide a therapeutic benefit by replacing an aberrant adenylate cyclase or providing an aberrant adenylate cyclase that provides a therapeutic result. In one embodiment, the cells provide adenylate cyclases that are abnormally active.

In another embodiment, the cells provide a adenylate cyclase that is abnormally inactive. This adenylate cyclase can compete with endogenous adenylate cyclase in the individual.

In another embodiment, cells expressing adenylate cyclases that cannot be activated are introduced into an individual in order to compete with endogenous adenylate cyclase for ATP. For example, in the case in which excessive ATP is part of a treatment modality, it may be necessary to inactivate this molecule at a specific point in treatment. Providing cells that compete for the molecule, but which cannot be affected by adenylate cyclase activation would be beneficial.

Homologously recombinant host cells can also be produced that allow the in situ alteration of endogenous adenylate cyclase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the adenylate cyclase polynucleotides or sequences proximal or distal to a adenylate cyclase gene are allowed to integrate into a host cell genome by homologous recombination where expression of the gene can be affected. In one embodiment, regulatory sequences are introduced that either increase or decrease expression of an endogenous sequence. Accordingly, a adenylate cyclase protein can be produced in a cell not normally producing it. Alternatively, increased expression of adenylate cyclase protein can be effected in a cell normally producing the protein at a specific level. Further, expression can be decreased or eliminated by introducing a specific regulatory sequence. The regulatory sequence can be heterologous to the adenylate cyclase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant adenylate cyclase proteins. Such mutations could be introduced, for example, into the specific functional regions such as the nucleotide triphosphate site.

In one embodiment, the host cell can be a fertilized oocyte or embryonic stem cell that can be used to produce a transgenic animal containing the altered adenylate cyclase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous adenylate cyclase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinions in Biotechnology* 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of an adenylate cyclase protein and identifying and evaluating modulators of adenylate cyclase protein activity.

Other examples of transgenic animals include non-human primates, sheep, dogs, cows, goats, chickens, and amphibians.

In one embodiment, a host cell is a fertilized oocyte or an embryonic stem cell into which adenylate cyclase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the adenylate cyclase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the adenylate cyclase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect cAMP binding, adenylate cyclase activation, and signal transduction, may not be evident from in vitro cell-free or cell-based assays. Accordingly, it is useful to provide non-human transgenic animals to assay in vivo adenylate cyclase function, including ATP interaction, the effect of specific mutant adenylate cyclases on adenylate cyclase function and ATP interaction, and the effect of chimeric adenylate cyclases. It is also possible to assess the effect of null mutations, that is mutations that substantially or completely eliminate one or more adenylate cyclase functions.

In general, methods for producing transgenic animals include introducing a nucleic acid sequence according to the present invention, the nucleic acid sequence capable of expressing the protein in a transgenic animal, into a cell in culture or in vivo. When introduced in vivo, the nucleic acid is introduced into an intact organism such that one or more cell types and, accordingly, one or more tissue types, express the nucleic acid encoding the protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Vectors/Host Cells

The methods using the vectors and host cells discussed above are based on the vectors and host cells including, but not limited to, those described below.

The invention also provides methods using vectors containing the adenylate cyclase polynucleotides. The term "vector" refers to a vehicle, preferably a nucleic acid molecule that can transport the adenylate cyclase polynucleotides. When the vector is a nucleic acid molecule, the adenylate cyclase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the adenylate cyclase polynucleotides. Alternatively, the vector may integrate into the host cell genome and produce additional copies of the adenylate cyclase polynucleotides when the host cell replicates.

The invention provides vectors for the maintenance (cloning vectors) or vectors for expression (expression vectors) of the adenylate cyclase polynucleotides. The vectors can function in procaryotic or eukaryotic cells or in both (shuttle vectors).

Expression vectors contain cis-acting regulatory regions that are operably linked in the vector to the adenylate cyclase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the adenylate cyclase polynucleotides from the vector. Alternatively, a trans-acting factor may be supplied by the host cell. Finally, a trans-acting factor can be produced from the vector itself.

It is understood, however, that in some embodiments, transcription and/or translation of the adenylate cyclase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual 2nd. ed.*, Cold Spring Harbor Laboratory Press, Cold Spring Harbor, N.Y.).

A variety of expression vectors can be used to express a adenylate cyclase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g., cosmids and phagemids. Appropriate cloning and expression vectors for prokaryotic and eukaryotic hosts are described in Sambrook et al. (1989) *Molecular Cloning: A Laboratory Manual 2nd. ed.*, Cold Spring Harbor Laboratory Press, Cold Spring Harbor, N.Y.

The regulatory sequence may provide constitutive expression in one or more host cells (i.e., tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The adenylate cyclase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the adenylate cyclase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301-315) and pET 11d (Studier et al. (1990) *Gene Expression Technology: Methods in Enzymology* 185:60-89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119-128). Alternatively, the sequence of the polynucleotide of interest can be altered to provide preferential codon usage for a specific host cell, for example *E. coli*. (Wada et al. (1992) *Nucleic Acids Res.* 20:2111-2118).

The adenylate cyclase polynucleotides can also be expressed by expression vectors that are operative in yeast. Examples of vectors for expression in yeast e.g., *S. cerevisiae* include pYepSec1 (Baldari et al. (1987) *EMBO J.* 6:229-234), pMFa (Kurjan et al. (1982) *Cell* 30:933-943), pJRY88 (Schultz et al. (1987) *Gene* 54:113-123), and pYES2 (invitrogen Corporation, San Diego, Calif.).

The adenylate cyclase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow et al. (1989) *Virology* 170:31-39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187-195).

The expression vectors listed herein are provided by way of example only of the well-known vectors available to those of ordinary skill in the art that would be useful to express the adenylate cyclase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual* 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described-herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as, mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the adenylate cyclase polynucleotides can be introduced either alone or with other polynucleotides that are not related to the adenylate cyclase polynucleotides such as those providing trans-acting factors for expression vectors. When more than one vector is introduced into a cell, the vectors can be introduced independently, co-introduced or joined to the adenylate cyclase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the adenylate cyclase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Pharmaceutical Compositions

The invention encompasses use of the polypeptides, nucleic acids, and other agents in pharmaceutical compositions to administer to the cells in which expression of the adenylate cyclase is relevant and in disorders as disclosed herein. Uses are both diagnostic and therapeutic. The adenylate cyclase nucleic acid molecules, protein, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier. It is understood however, that administration can also be to cells in vitro as well as to in vivo model systems such as non-human transgenic animals.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a adenylate cyclase protein or anti-adenylate cyclase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

CHAPTER 6

Novel Human GTPase Activator Proteins

BACKGROUND OF THE INVENTION

The Ras Superfamily of GTPases

Proteins regulating Ras and its relatives have been reviewed in Boguski et al. (*Nature* 366:643-654 (1993)), summarized below. Ras proteins and their relatives are key in the control of normal and transformed cell growth. Small GTPases related to Ras control a wide variety of cellular processes which include aspects of growth and differentiation, control of the cytoskeleton and regulation of cellular traffic between membrane bound compartments. These proteins cycle between active and inactive states bound to GTP and GDP. This cycling is influenced by three classes of proteins that switch the GTPase on, switch it off, and prevent it from switching. Further, the intracellular location of the GTPase can be controlled by another class of regulatory protein. The GTP-bound form of the GTPase is converted to the GDP-bound form by an intrinsic capacity to hydrolyze GTP. This process is accelerated by a GTPase-activating protein (GAP). Activation involves the replacement of GDP with GTP. This event is mediated by proteins designated guanine nucleotide exchange factors (GEF) or guanine nucleotide releasing protein (GNRP) and guanine nucleotide dissociation stimulator (GDS). The process is inhibited by guanine nucleotide dissociation inhibitors (GDI). Further, membrane anchoring of the GTPase is critical for proper function and is regulated, among other enzymes, by prenyl-transferases.

The Ras superfamily of GTPases can be roughly divided into three main families. The first family is the "true" Ras protein, each of which has the ability to function as an oncogene following mutational activation. These proteins transmit signals from tyrosine kinases at the plasma membrane to a cascade of serine/threonine kinases, which deliver signals to the cell nucleus. Constitutive activation of the pathway contributes to malignant transformation. The second group is the Rho/Rac protein subgroup, involved in organizing the cytoskeleton. Rac is required for membrane ruffling induced by growth factors and the formation of actin stress fibers requires Rho. In yeast, the CDC42 product controls cell polarity, another process in which actin is involved. In addition, Rac proteins are components of the NADPH oxidase system that generates superoxide in phagocytes. A third family is the Rab protein family. Members of this group regulate membrane trafficking, i.e., transport of vesicles between different intracellular compartments.

In addition to the three major families, further subgroups exist, exemplified by Ran and Arf. Ran proteins are nuclear GTPases involved in mitosis. Arf (ADP-ribosylation factor) proteins are necessary for ADP-ribosylation of $G_{sa}$ (the GTPase subunit of s-type heterotrimeric G-proteins) by cholera toxin and are thought to be involved in membrane vesicle fusion and transport.

Ras GEFs are proteins that activate Ras proteins by exchanging bound GDP for free GTP. These include Ras GRF, MmSosI, DnSoS, Ste6, Cdc25, Scd25, Lte1, and BUD5. The loss of GEF function can be complemented by mutations that constitutively activate the Ras proteins or, in some cases, by a loss of GAP activity. GEFs first associate with the GDP-bound form of the GTPase. GDP dissociates from this complex at an increased rate leaving the GEF bound to the empty GTPase. GTP then binds immediately, effecting GEF dissociation and leaving the GTPase in active form. Accordingly, a stable complex can exist between GEF and GTPase in the absence of nucleotide. Thus, GEFs recognize both GDP and GTP-bound forms of Ras in vitro and in vivo.

Dominant negative Ras mutants exist that block normal Ras activation. These have reduced affinity for GTP and may be defective in the final step of the exchange process, i.e. displacement of GEF by GTP. Accordingly, these mutants sequester GEF into a dead-end complex and are useful to remove GEF activity from cells so that activation of endogenous Ras proteins cannot occur. However, Ras may also be activated by inhibiting GAP activity without the need for GEF.

GEFs also include rap GEF. It is 20-fold more active on Ral A and Ral B than on members of the Ras, Rho/Rac and Rab GTPase families.

GEFs also include rap GEF. Cell polarity and budding in yeast involve GTPases of the Rap and Rho subgroup. A GEF specific for mammalian Rap proteins remains to be identified. Rap has the ability to interfere with Ras signaling by blocking activation of RAF and the serine/threonine kinase cascade.

GEFs also include Rho/Rac GEFs. GEFs specific for Rac and Rho proteins include, but are not limited to, Cdc24, Dbl, Vav, Bcr, Ras GRF, and ect 2. The human Dbl has been shown to act as a GEF for CDC42Hs (the human homolog of CDC42 is known as G25K) and on Rho. Further, Dbl binds several Rac/Rho-like proteins in vitro.

smg GDS (small GTP-binding protein) was originally described as a GEF for mammalian Rap proteins. It also promotes nucleotide exchange on Rho and Rac proteins. The protein works efficiently only on isoprenylated proteins. Ras and Rho/Rac proteins are modified by different isoprenoid moieties. Rho/Rac proteins receive 20-carbon geranylgeranyl groups.

Guanine nucleotide dissociation inhibitors (GDIs) include rab GDI. The protein affects the rate of GDP dissociation from Rab proteins. It inhibits GDP/GTP exchange and prevents the GDP-bound form from binding to membranes. These activities depend on the C-terminal geranylgeranyl group, at least of Rab3A.

Rho GDI was first identified as a factor capable of inhibiting dissociation of GDP from post-translationally modified Rho proteins. It has the ability to remove Rho proteins from cellular membranes in cell-free systems. This indicates that it could regulate the available Rho proteins associated with membranes or facilitate movement of Rho from one membrane compartment to another. Rac proteins bound to Rho GDI have also been identified as components of the NADPH oxidase system that generates oxygen radicals in activated phagocytes. Rac and Rho GDI form a heterodimer required for oxidase stimulation in vitro. Along with two other cytosolic factors, the components assemble into a membrane-bound complex which uses electrons from NADPH to generate superoxide anions. Recombinant Rac proteins in their GDP-bound state can replace the requirement for Rac and Rho GDI in this system. This indicates that Rho GDI can recognize the GTP-bound form of Rac and protect it from Rac GAPs.

GTPase-activating proteins are disclosed in Table 1 in Boguski et al., above. These include Ras GAP proteins. These proteins have low intrinsic GTPase activity and their inactivation is dependent on GAP in vivo. Of the Ras GAPs, neurofibromin, p120 GAP, Ira1, and Ira2 also have specificity for Rac. Of the rap GAP family, Rap1GAP also has specificity for Rac. Rho/Rac GAPs with specificity for Rac include Bcr, N-chimerin, rotund, p190, GRB-1/p85a, and 3BP-1.

Ras-like GTPases are targeted to membranes where they act by the post-translational attachment of isoprenoid lipids (or prenyl groups). Prenylation involves the covalent thioether linkage of farnesyl (15-carbon) or geranylgeranyl (20-carbon) groups to cysteine residues near the C-terminus. These reactions are catalyzed by prenyltransferases that differ in their isoprenoid substrates and protein targets. Type 1 geranylgeranyl transferase recognizes a CAAX motif but prefers a leucine residue in the X-position. Substrates include members of Rho/Rac families.

p21-activated protein kinases (PAKs) are activated through direct interaction with the GTPases Rac and Cdc42Hs. These GTPases are implicated in the control of mitogen-activated protein kinase (MAP) kinase c-Jun N-terminal kinase (JNK) and the reorganization of the actin cytoskeleton. Recently, Aronheim et al. (*Current Biology* 8:1125-1128 (1998)) reported on the biological role of PAK2 and identified its molecular targets. A two-hybrid system, "the Ras recruitment system" was used to detect protein-protein interactions at the inner surface of the plasma membranes. The PAK2 regulatory domain was fused at the carboxy terminus of a Ras mutant protein and screened against a cDNA library. Four clones were identified that interacted specifically with PAK regulatory region and were shown to encode a homolog of the GTPase Cdc42Hs. This protein, designated Chp, showed an overall sequence identity to Cdc42Hs of approximately 52%. Results from microinjection of this protein into cells implicated it in the induction of lamellipodia and showed that it activates the JNK MAP kinase cascade.

Proteins regulating Ras and its relatives have been reviewed in Boguski et al., *Nature* 366: 643-654 (1993), summarized below. As indicated above, GTPases cycle between inactive and active states bound to GDP and GTP respectively. As indicated above, cycling can be influenced by three different classes of proteins that switch the GTPase on, switch it off, and protect it from switching. Classes of regulatory proteins of Ras-like GTPases include GEF, GDI, and GAP. GEFs catalyze exchange of GDP for GTP. GAPs catalyze conversion of GTP-bound forms back to their inactive GDP states. GDI proteins for Rab and Rho affect nucleotide dissociation and GAP attack and may also be involved in membrane localization and solubility. The intracellular location of the GTPase can be controlled by a fourth class of regulatory protein affecting the regulators with which the GTPase can interact.

Table 1 of Boguski et al. lists various GAPs, the organisms from which they are derived, substrate specificity, and other characterization. These include (in the Table) the following GAPs: RasGAP; Neurofibromin (NF1) with a positive specificity for H-ras, N-ras, K-ras, RAS1 and RAS2 and a negative specificity for Rho, Rac, and Rab; p120GAP with a positive specificity for H-ras, N-ras, K-ras, R-ras, RAS1 and RAS2 and a negative specificity for Rho, Rac and Rab; Gap1 with a positive specificity for Ras1; Ira1 with a positive specificity for RAS and RAS2 and a negative specificity for Rho, Rac and Rab and potentially H-ras; Ira2 with a positive specificity for RAS and RAS2 and a negative specificity Rho, Rac and Rab and potentially H-ras; Sar1/gap1 with a positive specificity for Ras1, RAS1 and Ras2; Bud2 with a positive specificity for Bud1; RapGAP and Rap1GAP with a positive specificity for Rap1A and Rap2 and a negative specificity for Ras, Rho and Rac; Rho/racGAP and Bar with a positive specificity for Ras and CDC42Hs and a negative specificity for Rho and Ras; n-Chimaerin with a positive specificity for Rac and a negative specificity for Rho, CDC42Hs and Ras; rotund locus and p 190 with a positive specificity for Rac, Rho and CDC42Hs and a negative specificity for Ras, GRB-1/p85a and 3BP-1.

RasGAP is one class of GAP. Ras proteins have a very low intrinsic GTPase activity and their inactivation is dependent on GAPs in vivo. For example, some oncogenic mutants of Ras proteins are resistant to GAP-mediated GTPase stimulation and are constitutively blocked in their active GTP-bound states. Yeast contains two RasGAP proteins, IRA1 and IRA2 which contain domains homologous to the human and other mammalian p120-GAPs. In the absence of IRA gene product, yeast RAS proteins accumulate in their GTP-bound state, becoming hyperactive and leading to overproduction of cAMP. In yeast, therefore, RasGAPs are not effectors but serve as negative regulators. NF1 is a human protein defective in von Recklinghausen neurofibromatosis. This protein contains a domain homologous to the catalytic domains of p120-GAP IRA1 and IRA2. It may, in fact, be the mammalian homolog of IRA1 and IRA2. Mutant NF1 alleles are associated with sporadic cancers unrelated to neurofibromatosis or to neural crest tissues. *Drosophila* contains a protein, 70% identical to neurofibromin. It also contains a distinct RasGAP (referred to as GAP1) that is a component of the Sos tyrosine kinase/Ras1 signalling pathway. Loss of GAP1 stimulates Ras1 function, indicating that it is a negative regulator.

RapGAP is another GAP class. Rap1A is around 50% identical to Ras and, like Ras, binds to p120-GAP and to raf1 by its effector binding domain. Rap1A binds p120-GAP but its GTPase activity is not enhanced by this interaction. Another protein, rap1GAP, is responsible for the Rap1A GTPase activation. Rap1GAP is unrelated to rap1GAP but contains several sites for phosphorylation by Cdc2 and cAMP-dependent kinases. Ras proteins, and most GTPases, depend on a glutamine residue at position 61 (or equivalent) for intrinsic or GAP-mediated GTP hydrolysis. Rap1, however, has a threonine at this position.

Rho/Rac GAP is another class of GAP. A mammalian GAP specific for Rho has been purified and shown to contain a region related to the C-terminal domain of Bcr and to a human brain protein, n-chimaerin. Bcr is a putative RhoGEF. Bcr and n-chimaerin stimulate GTP hydrolysis by the Rho-like proteins Rac1 and Rac2, but not by Rho proteins themselves. This activity is mediated by the C-terminal 401 amino acids of Bcr. This domain does not resemble RasGAP or Rap1GAP. Chimaerin also contains an N-terminal DAG binding motif. Further, a multidomain protein, p90, that binds to p120-GAP and regulates its activity contains a central domain related to a putative DNA binding transcriptional repressor. At the C-terminus, there is a 145 residue region that is related to RhoGAPs.

GTPase activators (GAPs) are a major target for drug action and development. Accordingly, it is valuable to the field of pharmaceutical development to identify and characterize previously unknown GAPs. The present invention advances the state of the art by providing previously unidentified human GAPs.

SUMMARY OF THE INVENTION

It is an object of the invention to identify novel GAPs.

It is a further object of the invention to provide novel GAP polypeptides that are useful as reagents or targets in assays applicable to treatment and diagnosis of GAP-mediated disorders.

It is a further object of the invention to provide polynucleotides corresponding to the novel polypeptides that are useful as targets and reagents in assays applicable to treatment and diagnosis of GAP-mediated disorders and useful for producing novel GAP polypeptides by recombinant methods.

A specific object of the invention is to identify compounds that act as agonists and antagonists and modulate the expression or activity of the novel GAP.

A further specific object of the invention is to provide compounds that modulate expression of the GAP for treatment and diagnosis of GAP-related disorders.

The invention is thus based on the identification of two novel GAPs, designated herein 26651 and 26138.

The invention provides isolated GAP polypeptides including a polypeptide having an amino acid sequence shown in SEQ ID NO:22, SEQ ID NO:25, or an amino acid sequence encoded by the cDNA deposited with the ATCC as PTA-1918 on May 25, 2000 ("the deposited cDNA").

The invention also provides isolated GAP nucleic acid molecules having a sequence shown in SEQ ID NO:21, 23, 24, or 26, or in the deposited cDNA.

The invention also provides variant polypeptides having an amino acid sequence that is substantially homologous to an amino acid sequence shown in SEQ ID NO:22, SEQ ID NO:25, or encoded by the deposited cDNA.

The invention also provides variant nucleic acid sequences that are substantially homologous to a nucleotide sequence shown in SEQ ID NO:21, 23, 24, or 26, or in the deposited cDNA.

The invention also provides fragments of polypeptides shown in SEQ ID NO:22 or SEQ ID NO:25 and polynucleotides shown in SEQ ID NO:21, 23, 24, or 26, as well as substantially homologous fragments of the polypeptide or nucleic acid.

The invention further provides nucleic acid constructs comprising the nucleic acid molecules described above. In a preferred embodiment, the nucleic acid molecules of the invention are operatively linked to a regulatory sequence.

The invention also provides vectors and host cells for expressing the GAP nucleic acid molecules and polypeptides and particularly recombinant vectors and host cells.

The invention also provides methods of making the vectors and host cells and methods for using them to produce the GAP nucleic acid molecules and polypeptides.

The invention also provides antibodies or antigen-binding fragments thereof that selectively bind the GAP polypeptides and fragments.

The invention also provides methods of screening for compounds that modulate expression or activity of the GAP polypeptides or nucleic acid (RNA or DNA).

The invention also provides a process for modulating the GAP polypeptide or nucleic acid expression or activity, especially using the screened compounds. Modulation may be used to treat conditions related to aberrant activity or expression of the GAP polypeptides or nucleic acids.

The invention also provides assays for determining the presence or absence of and level of the GAP polypeptides or nucleic acid molecules in a biological sample, including for disease diagnosis.

The invention also provides assays for determining the presence of a mutation in the GAP polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Receptor Function/Signal Pathway

As used herein, a "signaling pathway" refers to the modulation (e.g., stimulation or inhibition) of a cellular function/activity upon the binding of a ligand to a GPCR. Examples of such functions include mobilization of intracellular molecules that participate in a signal transduction pathway, e.g., phosphatidylinositol 4,5-bisphosphate ($PIP_2$), inositol 1,4,5-triphosphate ($IP_3$) and adenylate cyclase; polarization of the plasma membrane; production or secretion of molecules; alteration in the structure of a cellular component; cell proliferation, e.g., synthesis of DNA; cell migration; cell differentiation; and cell survival.

Since the 22651 GAP is expressed in tissues that include, but are not limited to, adrenal gland, pituitary, skin and spinal cord, cells participating in a receptor protein signaling pathway in which this protein is involved may include, but are not limited to cells derived from these tissues.

Figure 64A:
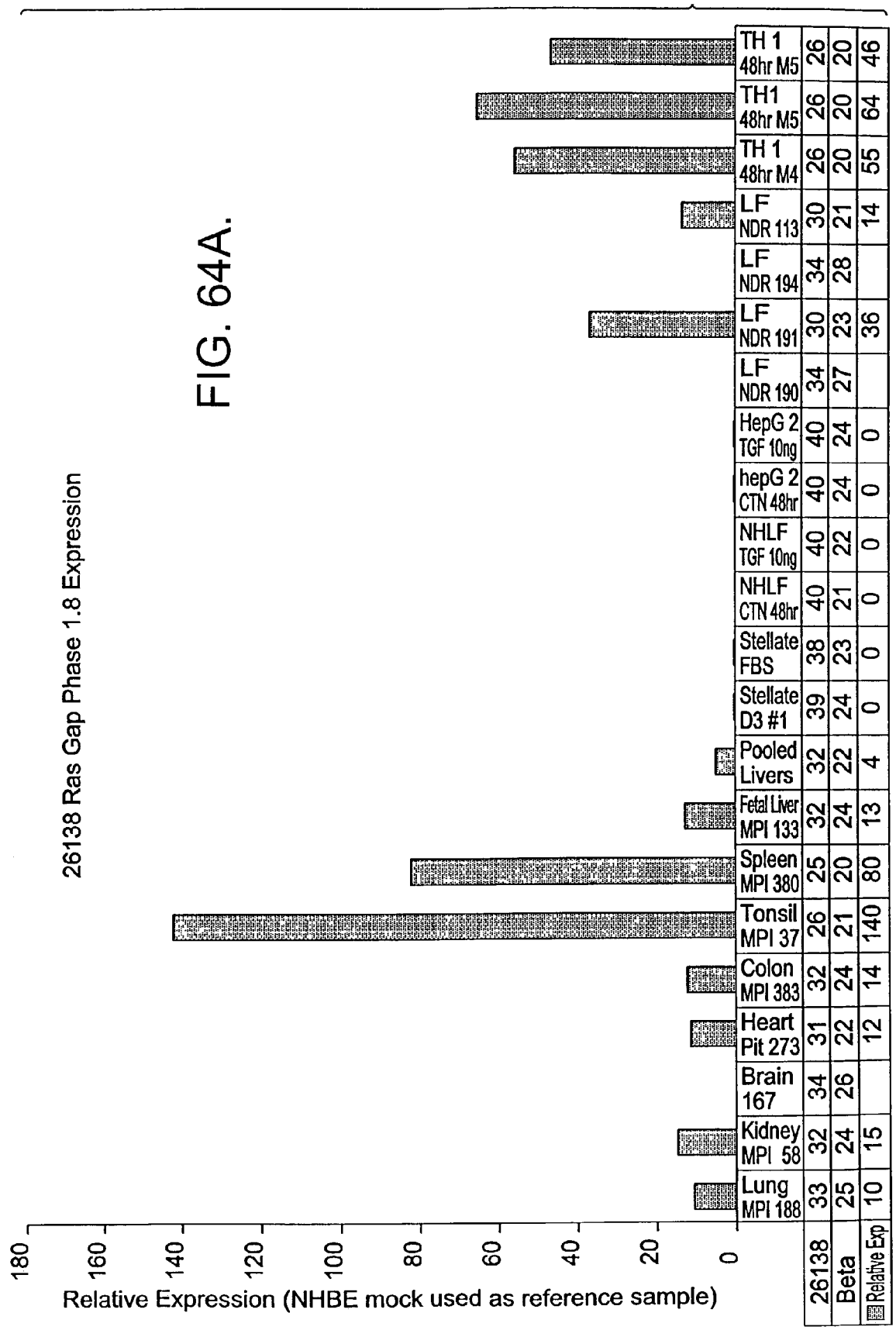
FIGS. 64A-64B depict expression of 26138 in various human tissues and cell types: lung (column 1); kidney (column 2); brain (column 3); heart (column 4); colon (column 5); tonsil (column 6); spleen (column 7); fetal liver (column 8); pooled liver samples (column 9); stellate cells treated with 1,25-dihydroxyvitamin D3 (column 10); serum reactivated stellate cells (column 11); NHLF-CTN (column 12); NHLF-TGF, normal human lung fibroblasts treated with TGF-β (column 13); hepG2 CTN (column 14); hepG2 TGF, hepG2 cells treated with TGF-β (column 15); LF NDR 190, fibrotic liver (column 16); LF NDR 191, fibrotic liver (column 17); LF NDR 194, fibrotic liver (column 18); LF NDR 113 (column 19); Th1 48 hr M4 (column 20); Th1 48 hr M5 (column 21); Th2 48 hr M5 (column 22); granulocytes (column 23); CD19+ cells (column 24); CD14+ cells (column 25); PBMC mock, peripheral blood mononuclear cells (column 26); PBMC PHA, PBMC treated with phytohaemagglutinin (column 27); PBMC IL10, PBMC producing IL10 (column 28); PBMC 1113 (column 29); NHBE mock, normal human bronchial epithelial cells (column 30); NHBE IL13-1 (column 31); BM-MNC, bone marrow mononuclear cells (column 32); mPB CD34, CD34+ cells from mobilized peripheral blood (column 33); ABM CD34+, CD34+ cells from adult bone marrow (column 34); erythroid cells (column 35); megakaryocytes (column 36); neutrophils (column 37); mBM CD11 b+, CD11b+ cells from human mobilized bone marrow (column 38); mBM CD15+, CD15+ mobilized human bone marrow (column 39); mBM CD11b-, CD11b-cells from human mobilized bone marrow (column 40); BM/GPA, GPA+cells from human bone marrow (column 41); BM CD71, CD71 positive bone marrow cells (column 42); HepG2A (column 43); HepG2 2.21-a (column 44); and no template control (column 45). Expression levels were determined by quantitative RT-PCR (Taqman® brand quantitative PCR kit, Applied Biosystems). The quantitative RT-PCR reactions were performed according to the kit manufacturer's instructions.
Figure 64B:
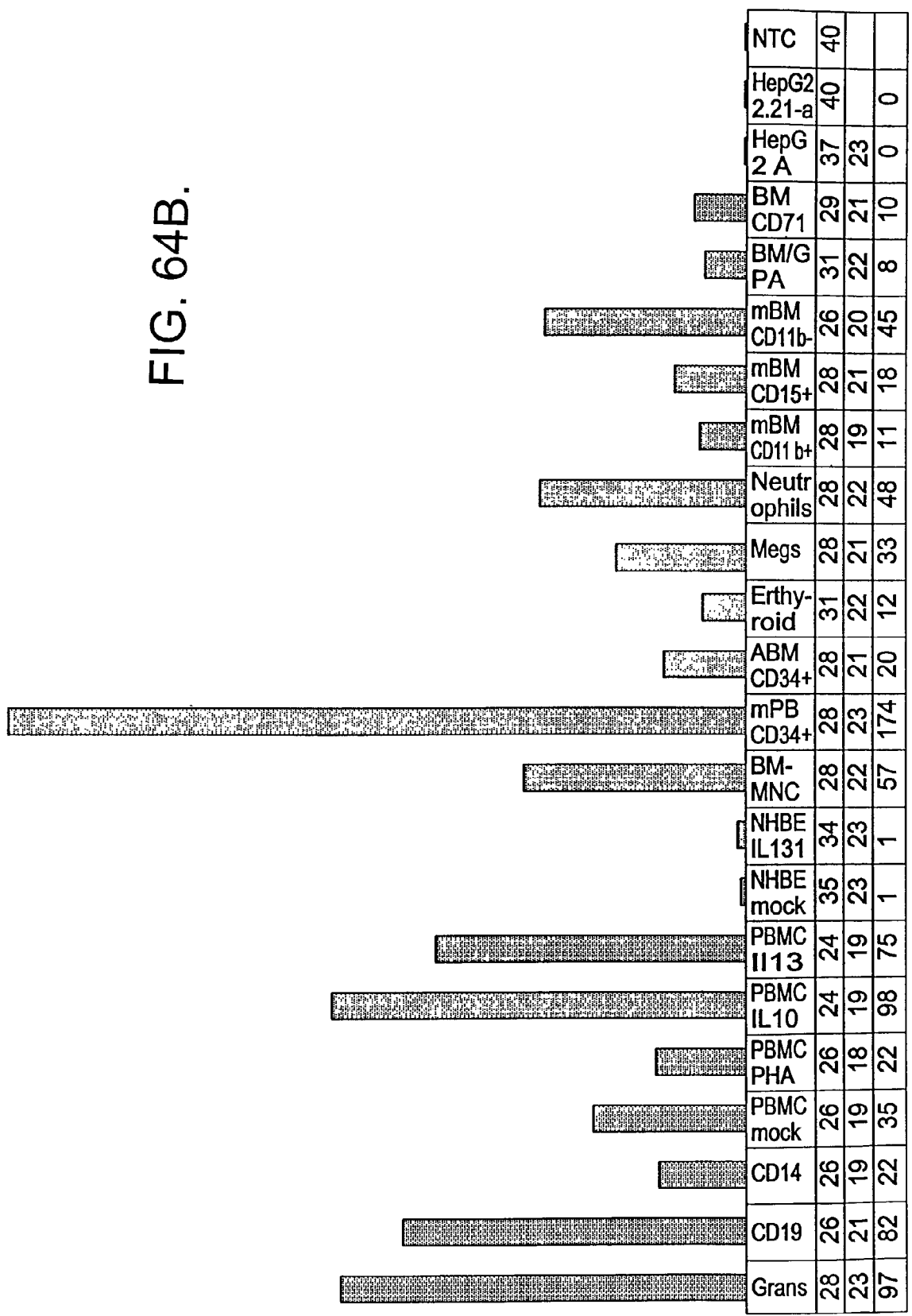

Since the 26138 GAP is expressed in tonsil, spleen, fetal liver, adult liver, fibrotic liver, granulocytes, neutrophils, erythroid cells, adipose tissue, bone marrow, colon, lung, kidney, heart, lymphocyte, megakaryocytes and T-cells, among others, cells participating in a receptor protein signaling pathway in which this protein is involved may include, but are not limited to cells derived from these tissues as well as those tissues and cell lines shown in FIGS. 64A-64B.

The response mediated by a receptor protein depends on the type of cell. For example, in some cells, binding of a ligand to the receptor protein may stimulate an activity such as release of compounds, gating of a channel, cellular adhesion, migration, differentiation, etc., through phosphatidylinositol or cyclic AMP metabolism and turnover while in other cells, the binding of the ligand will produce a different result. Regardless of the cellular activity/response modulated by the receptor protein, the protein, as a GPCR, would interact with G proteins to produce one or more secondary signals, in a variety of intracellular signal transduction pathways, e.g., through phosphatidylinositol or cyclic AMP metabolism and turnover, in a cell.

As used herein, "phosphatidylinositol turnover and metabolism" refers to the molecules involved in the turnover and metabolism of phosphatidylinositol 4,5-bisphosphate ($PIP_2$) as well as to the activities of these molecules. $PIP_2$ is a phospholipid found in the cytosolic leaflet of the plasma membrane. Binding of ligand to the receptor activates, in some cells, the plasma-membrane enzyme phospholipase C that in turn can hydrolyze $PIP_2$ to produce 1,2-diacylglycerol (DAG) and inositol 1,4,5-triphosphate ($IP_3$). Once formed $IP_3$ can diffuse to the endoplasmic reticulum surface where it can bind an $IP_3$ receptor, e.g., a calcium channel protein containing an $IP_3$ binding site. $IP_3$ binding can induce opening of the channel, allowing calcium ions to be released into the cytoplasm. $IP_3$ can also be phosphorylated by a specific kinase to form inositol 1,3,4,5-tetraphosphate ($IP_4$), a molecule which can cause calcium entry into the cytoplasm from the extracellular medium. $IP_3$ and $IP_4$ can subsequently be hydrolyzed very rapidly to the inactive products inositol 1,4-biphosphate ($IP_2$) and inositol 1,3,4-triphosphate, respectively. These inactive products can be recycled by the cell to synthesize $PIP_2$. The other second messenger produced by the hydrolysis of $PIP_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-kB. The language "phosphatidylinositol activity", as used herein, refers to an activity of $PIP_2$ or one of its metabolites.

Another signaling pathway in which a receptor may participate is the cAMP turnover pathway. As used herein, "cyclic AMP turnover and metabolism" refers to the molecules involved in the turnover and metabolism of cyclic AMP (cAMP) as well as to the activities of these molecules. Cyclic AMP is a second messenger produced in response to ligand-induced stimulation of certain G protein coupled receptors. In the cAMP signaling pathway, binding of a ligand to a GPCR can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

Polypeptides

The invention is based on the identification of novel human GAPs. Specifically, an expressed sequence tag (EST) was selected based on homology to GAP sequences. This EST was used to design primers based on primary sequences that it contains and used to identify a cDNA from human cDNA libraries. Positive clones were sequenced and the overlapping fragments were assembled. Analysis of the assembled sequence revealed that the cloned cDNA molecule encodes a GAP.

The invention thus relates to novel GAPs having the deduced amino acid sequence shown in FIGS. 52A-52B and 57A-57C (SEQ ID NO:22 and SEQ ID NO:25) or having the amino acid sequence encoded by the deposited cDNA, ATCC Patent Deposit No. PTA-1918.

Plasmids containing the 26651 sequences of the invention were deposited with the Patent Depository of the American Type Culture Collection (ATCC), Manassas, Va., on May 25, 2000 and assigned Patent Deposit No. PTA-1918. The deposit will be maintained under the terms of the Budapest Treaty on the International Recognition of the Deposit of Microorganisms. The deposit is provided as a convenience to those of skill in the art and is not an admission that a deposit is required under 35 U.S.C. § 112. The deposited sequence, as well as the polypeptide encoded by the sequence, is incorporated herein by reference and controls in the event of any conflict, such as a sequencing error, with description in this application.

"GAP", "GAP polypeptide" or "GAP protein" refer to a polypeptide set forth in SEQ ID NO:22, SEQ ID NO:25, or encoded by the deposited cDNA. The terms, however, further include the numerous variants described herein, as well as fragments derived from the full-length GAP polypeptide and variants.

The present invention thus provides an isolated or purified GAP polypeptide and variants and fragments thereof. By "variants" is intended proteins or polypeptides having an amino acid sequence that is at least about 60%, 65%, or 70%, preferably about 75%, 85%, 95%, or 98% identical to the amino acid sequence of SEQ ID NO:22 or SEQ ID NO:25. Variants also include polypeptides encoded by the cDNA insert of the plasmid deposited with ATCC as Patent Deposit No. PTA-1918, or polypeptides encoded by a nucleic acid molecule that hybridizes to the nucleic acid molecule of SEQ ID NO:21, 23, 24 or 26, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:22 or SEQ ID NO:25. If alignment is needed for this comparison the sequences should be aligned for maximum identity. "Looped" out sequences from deletions or insertions, or mismatches, are considered differences. Such variants retain the functional activity of the polypeptide set forth in SEQ ID NO:22 or SEQ ID NO:25. Variants include polypeptides that differ in amino acid sequence due to natural allelic variation or mutagenesis.

Based on a BLAST search of the 26651 sequence, homology was shown to human and other mammalian Rho-GTPase activators. A search for complete domains in PFAM showed a classification in the RhoGAP family. PRODOM analysis also shows a relationship with Rho-type GTPase activating proteins.

A search for complete domains in PFAM with the 26138 sequence showed classification in the rasGAP family, GTPase-activator protein for Ras-like GTPase.

26651 nucleic acid is expressed in tissues that include, but are not limited to, adrenal gland, pituitary, skin and spinal cord. Chromosome mapping with STS using WI-13730 shows that the gene is located on the X chromosome between DXS 994 and DXS 1062 (143.2-145 cM).

The 26138 nucleic acid is expressed in tissues that include, but are not limited to, tonsil, spleen, fetal liver, adult liver, fibrotic liver, granulocytes, neutrophils, erythroid cells, adipose tissue, bone marrow, colon, lung, kidney, heart, lymphocyte, megakaryocytes and T-cells, as well as the tissues and cell lines shown in FIGS. 64A-64B. Chromosome mapping information for this gene is shown in FIG. 63.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The GAP polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the GAP polypeptide having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A polypeptide is also considered to be isolated when it is part of a membrane preparation or is purified and then reconstituted with membrane vesicles or liposomes.

The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the polypeptide comprises an amino acid sequence shown in SEQ ID NO:22 or SEQ ID NO:25. However, the invention also encompasses sequence variants. Variants include a substantially homologous protein encoded by the same genetic locus in an organism, i.e., an allelic variant. Variants also encompass proteins derived from other genetic loci in an organism, but having substantial homology to a GAP of SEQ ID NO:22 or SEQ ID NO:25. Variants also include proteins substantially homologous to the GAP but derived from another organism, i.e., an ortholog. Variants also include proteins that are substantially homologous to GAP polypeptides of the invention that are produced by chemical synthesis. Variants also include proteins that are substantially homologous to the GAP that are produced by recombinant methods. Variants retain the GAP activity of the polypeptides set forth in SEQ ID NO:22 or SEQ ID NO:25. It is understood, however, that variants exclude any amino acid sequences disclosed prior to the invention.

As used herein, two amino acid or nucleotide sequences are substantially homologous when the sequences have at least about 60%, 65%, 70%, 75%, 80%, 85%, 90%, 91%, 92%, 93%, 94%, 95%, 96%, 97%, 98%, or 99% identity. A substantially homologous amino acid sequence, according to the present invention, will be encoded by a nucleic acid sequence hybridizing to the nucleic acid sequence, or portion thereof, of the sequence shown in SEQ ID NO:21, 23, 24, or 26 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444-453 algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) *CABIOS* 4:11-17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to the 26651 or 26138 nucleic acid molecules of the invention. BLAST protein searches can be performed with the XBLAST program, score=50, wordlength=3 to obtain amino acid sequences homologous to the 26651 or 26138 protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

The invention also encompasses polypeptides having a lower degree of identity but having sufficient similarity so as to perform one or more of the same functions performed by a polypeptide of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306-1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more regions corresponding to, membrane association, GTPase binding, interaction with regulatory proteins such as those in the background above.

Fully functional variants typically contain only conservative variation or variation in non-critical residues or in non-critical regions. Functional variants can also contain substitution of similar amino acids which result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for a polypeptide of the invention. This includes preventing immunogenicity from pharmaceutical formulations by preventing protein aggregation.

Useful variations further include alteration of binding characteristics. For example, one embodiment involves a variation at the binding site that results in binding but not release, or slower release of a binding molecule. A further useful variation at the same sites can result in a higher affinity. Useful variations also include changes that provide for affinity for another binding molecule. Another useful variation includes one that allows binding but which prevents activation by an effector. A useful variation affects binding to the GTPase, e.g., Ras or Rho. Binding can be with greater affinity, with less tendency to dissociate or lesser affinity with a higher tendency to dissociate. Alternatively, a variation can affect interaction with any of the regulatory proteins which in turn affects association with the GTPase. A further useful variation affects interaction with the regulatory protein responsible for subcellular localization of the GAP.

Another useful variation provides a fusion protein in which one or more domains or subregions is operationally fused to one or more domains or subregions from another GAP, including, but not limited to, subfamilies discussed above in the background in the families of GTPase activators.

Amino acids that are essential for function can be identified by methods known in the art, such as site-directed mutagenesis or alanine-scanning mutagenesis (Cunningham et al., *Science* 244:1081-1085 (1989)). The latter procedure introduces single alanine mutations at every residue in the molecule. The resulting mutant molecules are then tested for biological activity such as receptor binding or in vitro, or in vivo proliferative activity. Sites that are critical for substrate or effector binding can also be determined by structural analysis such as crystallization, nuclear magnetic resonance or photoaffinity labeling (Smith et al., *J. Mol. Biol.* 224:899-904 (1992); de Vos et al. *Science* 255:306-312 (1992)).

Substantial homology can be to the entire nucleic acid or amino acid sequence or to fragments of these sequences.

The invention thus also includes polypeptide fragments of the GAPs. Fragments can be derived from an amino acid sequence shown in SEQ ID NO:22 or SEQ ID NO:25. However, the invention also encompasses fragments of the variants of the proteins of the invention as described herein.

The fragments to which the invention pertains, however, are not to be construed as encompassing fragments that may be disclosed prior to the present invention.

As used herein, a fragment comprises at least 5 contiguous amino acids. Fragments can retain one or more of the biological activities of the protein, for example the ability to bind to a GTPase, as well as fragments that can be used as an immunogen to generate antibodies.

Biologically active fragments (peptides which are about, for example, 5-10, 10-15, 15-20, 25-30, 35-40, 40-50, 50-60, 60-70, 70-80, 80-90, 90-100, 100-110, 110-120, 120-130, 130-150, 150-200, 200-250, 250-300, 300-350, 350-400, 400-450, 450-500, 500-547 or up to the number of amino acids in the full length sequence) can comprise a domain or motif, e.g., a GTPase binding site, a regulatory site for interaction with any of the regulatory proteins affecting GAP activity, membrane anchoring site, or glycosylation sites, phosphorylation sites, and myristoylation sites. Such domains or motifs can be identified by means of routine computerized homology searching procedures. Domains/motifs include, but are not limited to, those shown in the figures.

Fragments also include combinations of domains or motifs including, but not limited to, those mentioned above. Fragments, for example, can extend in one or both directions from the functional site to encompass 5, 10, 15, 20, 30, 40, 50, 100, 150, 200, 250, 300, 350, 400, 450, 500, 547, or up to the number of amino acids disclosed in SEQ ID NO:22 and SEQ ID NO:25. Further, fragments can include sub-fragments of the specific domains mentioned above, which sub-fragments retain the function of the domain from which they are derived.

These regions can be identified by well-known methods involving computerized homology analysis.

Figure 54:
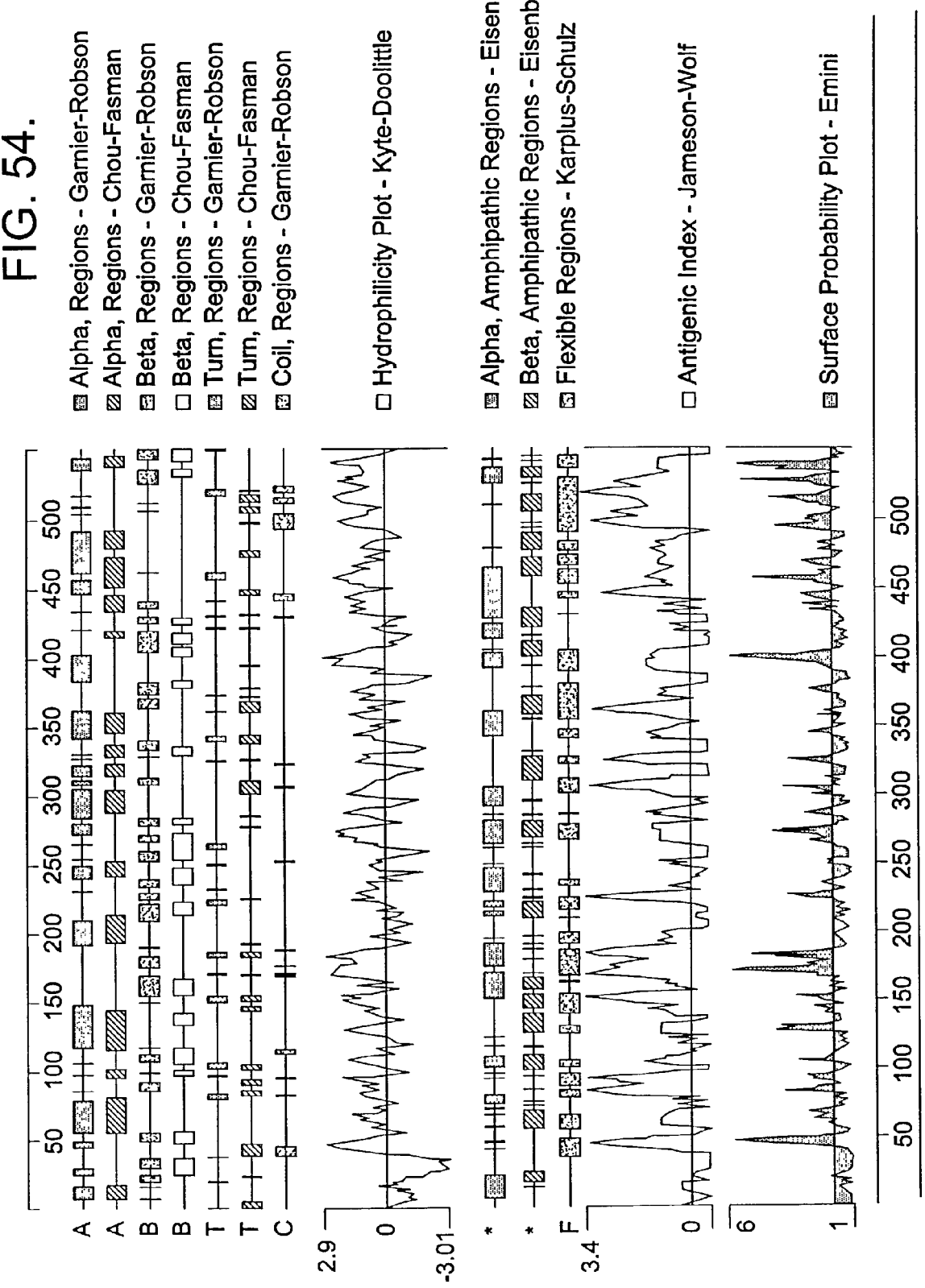
FIG. 54 shows an analysis of the 26651 amino acid sequence: αβturn and coil regions; hydrophilicity; amphipathic regions; flexible regions; antigenic index; and surface probability plot.
Figure 58:
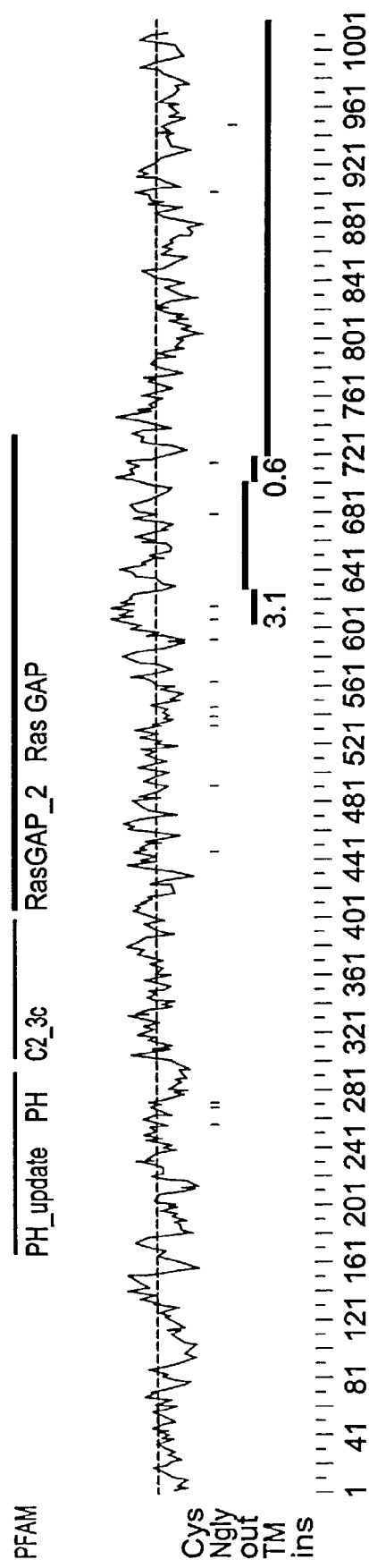
FIG. 58 shows a 26138 protein hydrophobicity plot. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:25) of human 26138 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 59:
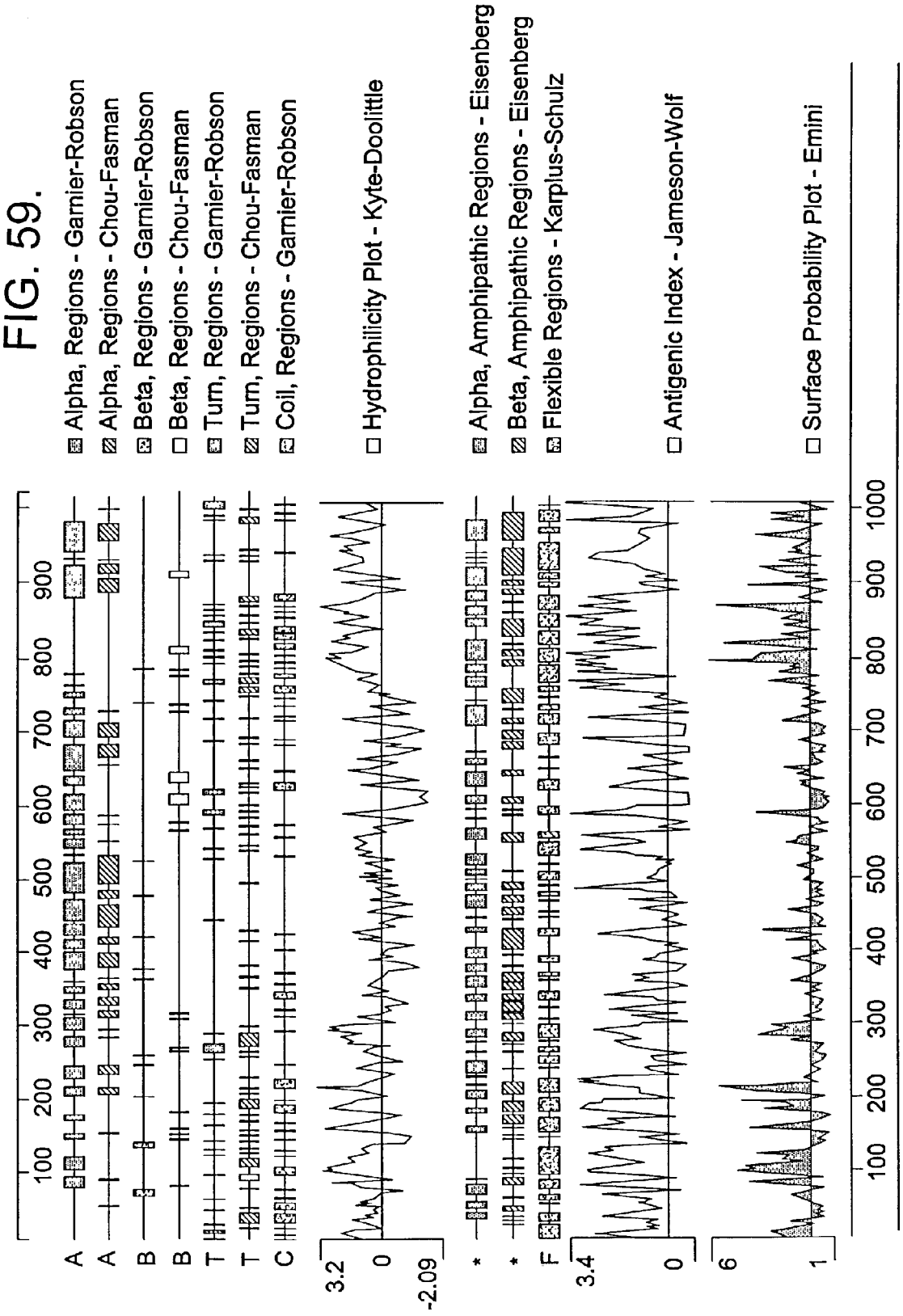
FIG. 59 shows an analysis of the 26138 amino acid sequence: αβturn and coil regions; hydrophilicity; amphipathic regions; flexible regions; antigenic index; and surface probability plot.

Fragments also include antigenic fragments and specifically those shown to have a high antigenic index in FIGS. 54 and 58.

Further possible fragments include but are not limited to fragments defining a GTPase binding site, regulatory protein binding, or membrane association. By this is intended a discrete fragment that provides the relevant function or allows the relevant function to be identified. In a preferred embodiment, the fragment contains a GTPase-binding site.

The invention also provides fragments with immunogenic properties. These contain an epitope-bearing portion of a protein of the invention and variants. These epitope-bearing peptides are useful to raise antibodies that bind specifically to a polypeptide of the invention or region or fragment. These peptides can contain at least 6, 10, 12, at least 14, or between at least about 15 to about 30 amino acids.

A polypeptide of the invention (including variants and fragments which may have been disclosed prior to the present invention) are useful for biological assays related to GAPs, especially of the RasGAP or RhoGAP family. Such assays involve any of the known GAP functions or activities or properties useful for diagnosis and treatment of GAP-related conditions. They include, especially, diseases involving the tissues in which a protein of the invention is expressed as disclosed herein. For GAP activity, assays include but are not limited to those disclosed herein, including those in references cited in the background herein, which are incorporated herein by reference for teaching these assays. Such assays include but are not limited to GTPase binding or activation, binding to GAP regulatory proteins, complex formation with any of the regulatory proteins, and biological effects such as those disclosed in the Background above. These include but are not limited to reorganization the actin cytoskeleton, transformation, growth, effects on differentiation, membrane ruffling induced by growth factors, formation of actin stress fibers, and generation of superoxide in phagocytes.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute non-specific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myelocytic series (polymorphoneuclear cells) make up approximately 60% of the cellular elements, and the erythrocytic series, 20-30%. Lymphocytes, monocytes, reticular cells, plasma cells and megakaryocytes together constitute 10-20%. Lymphocytes make up 5-15% of normal adult marrow. In the bone marrow, cell types are add mixed so that precursors of red blood cells (erythroblasts), macrophages (monoblasts), platelets (megakaryocytes), polymorphoneuclear leukocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2-8) of *Immunology, Immunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, cosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadenoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, mycloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyangiitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angioimmunoblastic T-cell lymphoma, angiocentric lymphoma (NK/T-cell lymphoma[4a]), intestinal T-cell lymphoma, adult T-cell leukemia/lymphoma, and anaplastic large cell lymphoma.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matrix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyclitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Disorders involving the tonsils include, but are not limited to, tonsillitis, Peritonsillar abscess, squamous cell carcinoma, dyspnea, hyperplasia, follicular hyperplasia, reactive lymphoid hyperplasia, non-Hodgkin's lymphoma and B-cell lymphoma.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

The epitope-bearing polypeptides may be produced by any conventional means (Houghten, R. A., *Proc. Natl. Acad. Sci. USA* 82:5131-5135 (1985)). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention thus provides chimeric or fusion proteins. These comprise a protein of the invention operatively linked to a heterologous protein having an amino acid sequence not substantially homologous to the protein of the invention. In the case where an expression cassette contains two protein coding regions joined in a contiguous manner in the same reading frame, the encoded polypeptide is herein defined as a "heterologous polypeptide" or a "chimeric polypeptide" or a "fusion polypeptide". As used herein, a GAP "heterologous protein" or "chimeric protein" or "fusion protein" comprises a GAP polypeptide operably linked to a non-GAP polypeptide. The heterologous protein can be fused to the N-terminus or C-terminus of the protein of the invention. "Operatively linked" indicates that the protein of the invention and the heterologous protein are fused in-frame.

In one embodiment the fusion protein does not affect GAP function per se. For example, the fusion protein can be a GST-fusion protein in which the sequences of the invention are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of a recombinant protein of the invention. In certain host cells (e.g., mammalian host cells), expression and/or secretion of a protein can be increased by using a heterologous signal sequence. Therefore, in another embodiment, the fusion protein contains a heterologous signal sequence at its C- or N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al. (*J. Mol. Recog.* 8:52-58 (1995)) and Johanson et al. (*J. Biol. Chem.* 270, 16:9459-9471 (1995)). Thus, this invention also encompasses soluble fusion proteins containing a polypeptide of the invention and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A GAP-encoding nucleic acid of the invention can be cloned into such an expression vector such that the fusion moiety is linked in-frame to the GAP.

Another form of fusion protein is one that directly affects the GAP functions. Accordingly, a polypeptide is encompassed by the present invention in which one or more of the domains (or parts thereof) has been replaced by homologous domains (or parts thereof) from another GAP. Various permutations are possible. Thus, chimeric proteins can be formed in which one or more of the native domains, subregions, or motifs has been replaced. A form of fusion protein is that in which GAP activator or regulatory domains are derived from a different GAP family, including but not limited to those described in the background herein above, such as RabGAP.

The isolated protein of the invention can be purified from cells that naturally express it, including but not limited to, those described herein above, purified from cells that have been altered to express it (recombinant), or synthesized using known protein synthesis methods.

In one embodiment, the protein is produced by recombinant DNA techniques. For example, a nucleic acid molecule encoding a polypeptide of the invention is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cysteine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W.H. Freeman and Company, New York (1993). Many detailed reviews are available on this subject, such as by Wold, F., *Posttranslational Covalent Modification of Proteins*, B. C. Johnson, Ed., Academic Press, New York 1-12 (1983); Seifter et al. (*Meth. Enzymol.* 182: 626-646 (1990)) and Rattan et al. (*Ann. N.Y. Acad. Sci.* 663:48-62 (1992)).

As is also well known, polypeptides are not always entirely linear. For instance, polypeptides may be branched as a result of ubiquitination, and they may be circular, with or without branching, generally as a result of post-translation events, including natural processing event and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the amino terminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The polypeptides of the invention are useful for producing antibodies specific for the protein, regions, or fragments. Regions having a high antigenicity index score are shown in FIGS. 54 and 58.

The polypeptides (including variants and fragments which may have been disclosed prior to the present invention) are useful for biological assays related to GAPs. Such assays involve any of the known GAP functions or activities such as those described herein, such functions or activities or properties being useful for diagnosis and treatment of GAP-related conditions. Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. "Subject", as used herein, can refer to a mammal, e.g. a human, or to an experimental or animal or disease model. The subject can also be a non-human animal, e.g. a horse, cow, goat, or other domestic animal. A therapeutic agent includes, but is not limited to, small molecules, peptides, antibodies, ribozymes and antisense oligonucleotides.

The polypeptides of the invention are also useful in drug screening assays, in cell-based or cell-free systems. Cell-based systems can be native, i.e., cells that normally express the protein, as a biopsy or expanded in cell culture. For the various biological assays described herein, these cells included but are not limited to, those disclosed above. In one embodiment, however, cell-based assays involve recombinant host cells expressing the protein.

Determining the ability of the test compound to interact with the polypeptide can also comprise determining the ability of the test compound to preferentially bind to the polypeptide as compared to the ability of the substrate (i.e., GTPase) or effector (i.e., regulatory molecule), or a biologically active portion thereof, to bind to the polypeptide.

The polypeptides can be used to identify compounds that modulate peptide, e.g., GAP activity. Such compounds, for example, can increase or decrease affinity or rate of binding to a known substrate or effector, compete with substrate or effector for binding, or displace bound substrate or effector. Both a protein of the invention and appropriate variants and fragments can be used in high-throughput screens to assay candidate compounds for the ability to bind to a protein of the invention (i.e., 26651 GAP or 26138 GAP). These compounds can be further screened against a functional polypeptide of the invention to determine the effect of the compound on the protein activity. Compounds can be identified that activate (agonist) or inactivate (antagonist) the protein to a desired degree. Modulatory methods can be performed in vitro (e.g., by culturing the cell with the agent) or, alternatively, in vivo (e.g., by administering the agent to a subject).

The polypeptides can be used to screen a compound for the ability to stimulate or inhibit interaction between the protein and a target molecule that normally interacts with the GAP. The target can be a GTPase, regulatory protein, or other regulatory molecule or a component of the signal pathway with which the GAP normally interacts. The assay includes the steps of combining the protein of the invention with a candidate compound under conditions that allow the protein or fragment to interact with the target molecule, and to detect the formation of a complex between the protein and the target or to detect the biochemical consequence of the interaction with the protein and the target. When a protein of the invention is involved in a specific signal pathway, the biological consequence can include any of the associated effects of signal transduction such as G-protein phosphorylation, cyclic AMP or phosphatidylinositol turnover, and adenylate cyclase or phospholipase C activation, or any of the associated effects of GTPase activity including, but not limited to, programmed cell death (apoptosis), membrane trafficking, organization of the actin cytoskeleton, activation of protein kinases activated by direct interaction with GTPases, and in particular, with Rho and Ras, membrane ruffling, formation of actin stress fibers, or generalized cellular effects such as transformation, and effects on growth and differentiation.

Determining the ability of the protein to bind to a target molecule can also be accomplished using a technology such as real-time Bimolecular Interaction Analysis (BIA). Sjolander, S., and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 97:6378-6382); (Felici (1991) *J. Mol. Biol.* 222:301-310); (Ladner supra).

Candidate compounds include, for example, 1) peptides such as soluble peptides, including Ig-tailed fusion peptides and members of random peptide libraries (see, e.g., Lam et al., *Nature* 354:82-84 (1991); Houghten et al., *Nature* 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767-778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length protein of the invention or fragment that competes for substrate or effector binding. Other candidate compounds include mutant proteins of the invention or appropriate fragments containing mutations that affect protein function and thus compete for substrate or effector. Accordingly, a fragment that competes for substrate or effector, for example with a higher affinity, or a fragment that binds but does not allow release, is encompassed by the invention. A candidate compound includes, but is not limited to, a GTPase analog that competes for native GTPase binding.

The invention provides other end points to identify compounds that modulate (stimulate or inhibit) protein activity. When the function of a protein of the invention is related to a signal transduction pathway, the assays typically involve an assay of events in the signal transduction pathway that indicate GAP activity. Thus, the expression of genes that are up- or down-regulated in response to the receptor protein dependent signal cascade can be assayed. For GAP function, assays typically involve an assay of events in the pathway for example, GTPase activation or inhibition, GTP or GDP binding to a GTPase, and end points such as membrane ruffling and effects on cytoskeletal organization, actin organization, and the like. In one embodiment, the regulatory region of such genes can be operably linked to a marker that is easily detectable, such as luciferase. Alternatively, phosphorylation of a protein of the invention, or a G-protein target, could also be measured.

Any of the biological or biochemical functions mediated by a protein of the invention can be used as an endpoint assay. These include all of the biochemical or biochemical/biological events described herein, in the references cited herein, incorporated by reference for these endpoint assay targets, and other functions known to those of ordinary skill in the art.

Binding and/or activating regions, or domains, such as compounds can also be screened by using chimeric proteins of the invention in which regions or domains, such as the GTPase binding regions, catalytic (i.e., activation or inhibition) regions, regions interacting with regulatory proteins of GAP, or parts thereof, can be replaced by heterologous domains or regions. Activation can also be detected by a reporter gene containing an easily detectable coding region operably linked to a transcriptional regulatory sequence that is part of a signal transduction pathway in which a GAP of the invention is involved.

The polypeptides of the invention are also useful in competition binding assays in methods designed to discover compounds that interact with the polypeptide. Thus, a compound is exposed to the polypeptide under conditions that allow the compound to bind or to otherwise interact with the polypeptide. Soluble polypeptide of the invention is also added to the mixture. If the test compound interacts with the soluble polypeptide, it decreases the amount of complex formed or activity from the target. This type of assay is particularly useful in cases in which compounds are sought that interact with specific regions of the polypeptide. Thus, the soluble polypeptide that competes with the target region is designed to contain peptide sequences corresponding to the region of interest.

To perform cell free drug screening assays, it is desirable to immobilize either the protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/GAP fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of GAP-binding protein found in the bead fraction quantified from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a GAP binding protein and a candidate compound are incubated in the GAP presenting wells and the amount of complex trapped in the well can be quantified. Methods for detecting such complexes, in addition to those described above for the GST-immobilized complexes, include immunodetection of complexes using antibodies reactive with the GAP target molecule, or which are reactive with GAP and compete with the target molecule; as well as enzyme-linked assays which rely on detecting an enzymatic activity associated with the target molecule.

Modulators of GAP activity identified according to these drug screening assays can be used to treat a subject with a disorder mediated by a protein of the invention, by treating cells that express a protein of the invention, such as those disclosed herein.

These methods of treatment include the steps of administering the modulators of protein activity in a pharmaceutical composition as described herein, to a subject in need of such treatment.

The polypeptides of the invention are thus useful for treating a GAP-associated disorder characterized by aberrant expression or activity of a GAP. In one embodiment, the method involves administering an agent (e.g., an agent identified by a screening assay described herein), or combination of agents that modulates (e.g., upregulates or downregulates) expression or activity of the protein. In another embodiment, the method involves administering a protein as therapy to compensate for reduced or aberrant expression or activity of the protein.

Stimulation of protein activity is desirable in situations in which the protein is abnormally downregulated and/or in which increased protein activity is likely to have a beneficial effect. Likewise, inhibition of protein activity is desirable in situations in which the protein is abnormally upregulated and/or in which decreased protein activity is likely to have a beneficial effect. An example of such a situation occurs when the GAP is inactivating a protein and inhibition of the GAP allows activation of the protein (Chen et al. (1998) *Neuron* 20:895-904). In one example of such a situation, a subject has a disorder characterized by aberrant development or cellular differentiation. In another example of such a situation, the subject has a proliferative disease (e.g., cancer) or a disorder characterized by an aberrant hematopoietic response. In another example of such a situation, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO 94/10300), to identify other proteins (captured proteins) which bind to or interact with the proteins of the invention and modulate their activity.

The polypeptides of the invention also are useful to provide a target for diagnosing a disease or predisposition to disease mediated by a GAP, especially in diseases involving the tissues in which a protein of the invention is expressed such as are disclosed herein. Accordingly, methods are provided for detecting the presence, or levels of, a protein of the invention in a cell, tissue, or organism. The method involves contacting a biological sample with a compound capable of interacting with the protein such that the interaction can be detected.

One agent for detecting the protein is an antibody capable of selectively binding to the protein. A biological sample includes tissues, cells and biological fluids isolated from a subject, as well as tissues, cells and fluids present within a subject.

The protein of the invention also provides a target for diagnosing active disease, or predisposition to disease, in a patient having a variant protein of the invention. Thus, the protein can be isolated from a biological sample, assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered GAP activity in cell-based or cell-free assays, altered antibody-binding pattern, altered isoelectric point, direct amino acid sequencing, and any other of the known assay techniques useful for detecting mutations in a protein.

In vitro techniques for detection of protein of the invention include enzyme linked immunosorbent assays (ELISAs), Western blots, immunoprecipitations and immunofluorescence. Alternatively, the protein can be detected in vivo in a subject by introducing into the subject a labeled anti-GAP antibody. For example, the antibody can be labeled with a radioactive marker whose presence and location in a subject can be detected by standard imaging techniques. Particularly useful are methods which detect the allelic variant of the protein expressed in a subject and methods which detect fragments of the protein in a sample.

The polypeptides are also useful in pharmacogenomic analysis. Pharmacogenomics deal with clinically significant hereditary variations in the response to drugs due to altered drug disposition and abnormal action in affected persons. See, e.g., Eichelbaum, M., *Clin. Exp. Pharmacol. Physiol.* 23(10-11):983-985 (1996), and Linder, M. W., *Clin. Chem.* 43(2):254-266 (1997). The clinical outcomes of these variations result in severe toxicity of therapeutic drugs in certain individuals or therapeutic failure of drugs in certain individuals as a result of individual variation in metabolism.

Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants in which one or more functions in one population are different from those in another population. The polypeptides thus allow a target to ascertain a genetic predisposition that can affect treatment modality. Thus, in a substrate or effector-based treatment, polymorphism may give rise to domains and/or other binding regions that are more or less active in binding and/or activation. Accordingly, dosage would necessarily be modified to maximize the therapeutic effect within a given population containing a polymorphism. As an alternative to genotyping, specific polymorphic polypeptides could be identified.

The polypeptides are also useful for monitoring therapeutic effects during clinical trials and other treatment. Thus, the therapeutic effectiveness of an agent that is designed to increase or decrease gene expression, protein levels or activity can be monitored over the course of treatment using the polypeptides as an end-point target. The monitoring can be, for example, as follows: (i) obtaining a pre-administration sample from a subject prior to administration of the agent; (ii) detecting the level of expression or activity of a specified protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

The polypeptides are also useful for treating a GAP-associated disorder. Accordingly, methods for treatment include the use of soluble protein or fragments of the protein that compete for GTPase binding. These proteins or fragments can have a higher affinity for the GTPase so as to provide effective competition.

Antibodies

The invention also provides antibodies that selectively bind to a protein of the invention and its variants and fragments. An antibody is considered to selectively bind, even if it also binds to other proteins that are not substantially homologous with the protein. These other proteins share homology with a fragment or domain of the protein. This conservation in specific regions gives rise to antibodies that bind to both proteins by virtue of the homologous sequence. In this case, it would be understood that antibody binding to the protein is still selective.

To generate antibodies, an isolated polypeptide is used as an immunogen to generate antibodies using standard techniques for polyclonal and monoclonal antibody preparation.

Either the full-length protein or antigenic peptide fragment can be used. Regions having a high antigenicity index are shown in FIGS. 54 and 58.

Antibodies are preferably prepared from these regions or from discrete fragments in these regions. However, antibodies can be prepared from any region of the peptide as described herein. A preferred fragment produces an antibody that diminishes or completely prevents GTPase binding. Antibodies can be developed against the entire protein or portions of the protein. Antibodies may also be developed against specific functional sites, such as the site of GTPase binding, or sites that are phosphorylated, myristoylated, or glycosylated.

An antigenic fragment will typically comprise at least 6 contiguous amino acid residues. The antigenic peptide can comprise a contiguous sequence of at least 12, at least 14 amino acid residues, at least 15 amino acid residues, at least 20 amino acid residues, or at least 30 amino acid residues. In one embodiment, fragments correspond to regions that are located on the surface of the protein, e.g., hydrophilic regions. These fragments are not to be construed, however, as encompassing any fragments which may be disclosed prior to the invention.

Antibodies can be polyclonal or monoclonal. An intact antibody, or a fragment thereof (e.g., Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An appropriate immunogenic preparation can be derived from native, recombinantly expressed, protein or chemically synthesized peptides.

Antibody Uses

The antibodies can be used to isolate a protein by standard techniques, such as affinity chromatography or immunoprecipitation. The antibodies can facilitate the purification of the natural protein from cells and recombinantly produced protein expressed in host cells.

The antibodies are useful to detect the presence of the protein in cells or tissues to determine the pattern of expression among various tissues in an organism and over the course of normal development.

The antibodies can be used to detect the protein in situ, in vitro, or in a cell lysate or supernatant in order to evaluate the abundance and pattern of expression.

The antibodies can be used to assess abnormal tissue distribution or abnormal expression during development.

Antibody detection of circulating fragments of a full-length protein of the invention can be used to identify protein turnover.

Further, the antibodies can be used to assess the GAP expression in disease states such as in active stages of the disease or in an individual with a predisposition toward disease related to the GAP function. When a disorder is caused by an inappropriate tissue distribution, developmental expression, or level of expression of the protein, the antibody can be prepared against the normal protein. If a disorder is characterized by a specific mutation in the protein, antibodies specific for this mutant protein can be used to assay for the presence of the specific mutant protein. However, intracellularly-made antibodies ("intrabodies") are also encompassed, which would recognize intracellular peptide regions.

The antibodies can also be used to assess normal and aberrant subcellular localization of cells in the various tissues in an organism. Antibodies can be developed against the whole protein or portions, such as those discussed herein.

The diagnostic uses can be applied, not only in genetic testing, but also in monitoring a treatment modality. Accordingly, where treatment is ultimately aimed at correcting the expression level or the presence of an aberrant protein of the invention and aberrant tissue distribution or developmental expression, antibodies directed against the protein or relevant fragments can be used to monitor therapeutic efficacy. Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic proteins of the invention can be used to identify individuals that require modified treatment modalities.

The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Thus, where a specific GAP of the invention has been correlated with expression in a specific tissue, antibodies that are specific for this protein can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting protein function, for example, blocking GTPase or regulatory molecule, e.g., protein, binding.

These uses can also be applied in a therapeutic context in which treatment involves inhibiting a function. An antibody can be used, for example, to block GTPase binding. Antibodies can be prepared against specific fragments containing sites required for function or against an intact protein of the invention associated with a cell.

Completely human antibodies are particularly desirable for therapeutic treatment of human patients. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a protein of the invention in a biological sample. The kit can comprise antibodies such as a labeled or labelable antibody and a compound or agent for detecting the protein in a biological sample; means for determining the amount of the protein in the sample; and means for comparing the amount of the protein in the sample with a standard. The compound or agent can be packaged in a suitable container. The kit can further comprise instructions for using the kit to detect the protein.

Polynucleotides

The nucleotide sequences in SEQ ID NO:21, 23, 24, and 26 were obtained by sequencing the deposited human full length cDNAs. Accordingly, the sequence of the deposited clone is controlling as to any discrepancies between the two and any reference to a sequence of SEQ ID NO:21, 23, 24, or 26 includes reference to a sequence of the deposited cDNA.

The specifically disclosed cDNAs comprise the coding region and 5' and 3' untranslated sequences (SEQ ID NO:21 or SEQ ID NO:24).

The invention provides isolated polynucleotides encoding a protein of the invention. The term "GAP polynucleotide," "GAP nucleic acid," "polynucleotide of the invention" or "nucleic acid of the invention" refers to a sequence shown in SEQ ID NO:21, 23, 24, 26, or in the deposited cDNA. The terms further include variants and fragments of a polynucleotide of the invention.

An "isolated" nucleic acid is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the nucleic acid is isolated from flanking sequences such that it can be subjected to the specific manipulations described herein such as recombinant expression, preparation of probes and primers, and other uses specific to GAP nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The GAP polynucleotides can encode the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The GAP polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Polynucleotides can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

One nucleic acid comprises a nucleotide sequence shown in SEQ ID NO:21, 23, 24, or 26, corresponding to human cDNA.

In one embodiment, the nucleic acid comprises the coding regions set forth in SEQ ID NO:23 or 26.

The invention further provides variant polynucleotides, and fragments thereof, that differ from a nucleotide sequence shown in SEQ ID NO:21, 23, 24, or 26 due to degeneracy of the genetic code and thus encode the same polypeptides as those set forth in SEQ ID NO:22 or 25.

The invention also provides nucleic acid molecules encoding the variant polypeptides described herein. Generally, nucleotide sequence variants of the invention will have at least 60%, 65%, 70%, 75%, 80%, 85%, 90%, 91%, 92%, 93%, 94%, 95%, 96%, 97%, 98%, or 99% identity to the nucleotide sequences disclosed herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Variation can occur in either or both the coding and non-coding regions. The variations can produce both conservative and non-conservative amino acid substitutions.

Typically, variants have a substantial identity with a nucleic acid molecule of SEQ ID NO:21, 23, 24, or 26, or the complements thereof.

Orthologs, homologs, and allelic variants can be identified using methods well known in the art. These variants comprise a nucleotide sequence encoding a protein that is at least about 60%, 65%, 70%, 75%, 80%, 85%, 90%, 91%, 92%, 93%, 94%, 95%, 96%, 97%, 98%, 99% or more homologous to a nucleotide sequence shown in SEQ ID NO:21, 23, 24, 26, or a fragment of this sequence. Such nucleic acid molecules can readily be identified as being able to hybridize under stringent conditions, to a nucleotide sequence shown in SEQ ID NO:21, 23, 24, 26, or a fragment of the sequence. It is understood that stringent hybridization does not indicate substantial homology where it is due to general homology, such as poly A sequences, or sequences common to all or most proteins, all or most GAPs, or all or most RasGAPs or RhoGAPs. Moreover, it is understood that variants do not include any of the nucleic acid sequences that may have been disclosed prior to the invention.

As used herein, the term "hybridizes under stringent conditions" describes conditions for hybridization and washing. Stringent conditions are known to those skilled in the art and can be found in *Current Protocols in Molecular Biology* John Wiley & Sons, N.Y. (1989), 6.3.1-6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:21, 23, 24, or 26, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to a nucleotide sequence of SEQ ID NO:21, 23, 24, 26, or the complements thereof. In one embodiment, the nucleic acid consists of a portion of a nucleotide sequence of SEQ ID NO:21, 23, 24, 26 or complements thereof. The nucleic acid fragments of the invention are at least about 10, 15, preferably at least about 20 or 25 nucleotides, and can be 30, 38, 40, 50, 68, 75, 100, 150, 200, 250, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, or 2847 nucleotides for SEQ ID NO:21. Alternatively, a nucleic acid molecule that is a fragment of a 26651-like nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2600, 2600-2700, 2700-2800, 2800-2847 of SEQ ID NO:21. The nucleic acid fragments of the invention are at least about 10, 15, 20, 25, 30, 38, 40, 50, 68, 75, 100, 150, 200, 250, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, or 3391 nucleotides for SEQ ID NO:24. Alternatively, a nucleic acid molecule that is a fragment of a 26138-like nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2600, 2600-2700, 2700-2800, 2800-2900, 2900-3000, 3000-3100, 3100-3200, 3200-3300, 3300-3391 of SEQ ID NO:24. Longer fragments, for example, 30 or more nucleotides in length, which encode antigenic proteins or polypeptides described herein are useful.

Furthermore, the invention provides polynucleotides that comprise a fragment of the full-length GAP polynucleotides. The fragment can be single or double stranded and can comprise DNA or RNA. The fragment can be derived from either the coding or the non-coding sequence.

In another embodiment an isolated nucleic acid encodes the entire coding region. Other fragments include nucleotide sequences encoding the amino acid fragments described herein. Further fragments can include subfragments of the specific domains or sites described herein. Fragments also include nucleic acid sequences corresponding to specific amino acid sequences described above or fragments thereof. Nucleic acid fragments, according to the present invention, are not to be construed as encompassing those fragments that may have been disclosed prior to the invention.

Nucleic acid fragments further include sequences corresponding to the domains described herein, subregions also described, and specific functional sites. Nucleic acid fragments also include combinations of the domains, segments, loops, and other functional sites described above. A person of ordinary skill in the art would be aware of the many permutations that are possible.

Where the location of the domains or sites have been predicted by computer analysis, one of ordinary skill would appreciate that the amino acid residues constituting these domains can vary depending on the criteria used to define the domains.

However, it is understood that a fragment includes any nucleic acid sequence that does not include the entire gene.

The invention also provides nucleic acid fragments that encode epitope bearing regions of the proteins described herein.

The isolated polynucleotide sequences, and especially fragments, are useful as DNA probes and primers.

For example, the coding region of a gene of the invention can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of these genes.

A probe/primer typically comprises substantially purified oligonucleotide. The oligonucleotide typically comprises a region of nucleotide sequence that hybridizes under stringent conditions to at least about 5, 10, 12, typically about 25, more typically about 40, 50 or 75 consecutive nucleotides of the sense or antisense strand of SEQ ID NO:21, 23, 24, 26, or other GAP polynucleotides. A probe further comprises a label, e.g., radioisotope, fluorescent compound, enzyme, or enzyme co-factor.

Polynucleotide Uses

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497-1500. Typically, a probe comprises a region of nucleotide sequence that hybridizes under highly stringent conditions to at least about 15, typically about 20-25, and more typically about 40, 50 or 75 consecutive nucleotides of a nucleic acid of SEQ ID NO:21, 23, 24, 26, or the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The polynucleotides are useful for probes, primers, and in biological assays, including, but not limited to, methods using the cells and tissues in which the gene is expressed, particularly in which the gene is significantly expressed, and involving disorders including, but not limited to, those also discussed herein above with respect to biological methods and assays involving the GAP polypeptides of the invention.

Where the polynucleotides are used to assess or GAP properties or functions, such as in the assays described herein, all or less than all of the entire cDNA can be useful. In this case, even fragments that may have been known prior to the invention are encompassed. Thus, for example, assays specifically directed to GAPs, and especially RasGAP or RhoGAP functions, such as assessing agonist or antagonist activity, encompass the use of known fragments. Further, diagnostic methods for assessing function can also be practiced with any fragment, including those fragments that may have been known prior to the invention. Similarly, in methods involving modulation or treatment of GAP-related dysfunction, all fragments are encompassed including those which may have been known in the art.

The polynucleotides are useful as a hybridization probe for cDNA and genomic DNA to isolate a full-length cDNA and genomic clones encoding a polypeptide described in SEQ ID NO:22 or SEQ ID NO:25 and to isolate cDNA and genomic clones that correspond to variants producing one of the same polypeptides shown in SEQ ID NO:22, SEQ ID NO:25, or the other variants described herein. Variants can be isolated from the same tissue and organism from which a polypeptide shown in SEQ ID NO:22 or SEQ ID NO:25 was isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding a protein of the invention. Accordingly, it could be derived from 5' noncoding regions, the coding region, and 3' noncoding regions. It is understood, however, as discussed herein, that fragments corresponding to the probe do not include those fragments that may have been disclosed prior to the present invention.

The nucleic acid probe can be, for example, a full-length cDNA that encodes a polypeptide set forth in SEQ ID NO:22 or a fragment thereof, such as an oligonucleotide of at least 5, 10, 12, 15, 30, 38, 50, 68, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2847 nucleotides in length for SEQ ID NO:21 and sufficient to specifically hybridize under stringent conditions to mRNA or DNA. The nucleic acid probe can be, for example, a full-length cDNA that encodes a polypeptide set forth in SEQ ID NO:25 or a fragment thereof, such as an oligonucleotide of at least 5, 10, 12, 15, 30, 38, 50, 68, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, or 3391 nucleotides in length for SEQ ID NO:24 and sufficient to specifically hybridize under stringent conditions to mRNA or DNA.

Fragments of the polynucleotides' described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using a nucleotide sequence of SEQ ID NO:21, 23, 24 or 26, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357-63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell 26651 or 26138 proteins in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958-976) or intercalating agents (see, e.g., Zon (1988) *Pharm Res.* 5:539-549).

The polynucleotides are also useful as primers for PCR to amplify any given region of a polynucleotide of the invention.

The polynucleotides are also useful for constructing recombinant vectors. Such vectors include expression vectors that express a portion of, or all of, the GAP polypeptides of the invention. Vectors also include insertion vectors, used to integrate into another polynucleotide sequence, such as into the cellular genome, to alter in situ expression of genes and gene products of the invention. For example, an endogenous coding sequence can be replaced via homologous recombination with all or part of the coding region containing one or more specifically introduced mutations.

The polynucleotides are also useful for expressing antigenic portions of the proteins of the invention.

The polynucleotides are also useful as probes for determining the chromosomal positions of the polynucleotides of the invention by means of in situ hybridization methods, such as FISH (For a review of this technique, see Verma et al. (1988) *Human Chromosomes: A Manual of Basic Techniques* (Pergamon Press, New York)), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in *Mendelian Inheritance in Man*, V. McKusick, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) *Nature* 325:783-787. The chromosomal location of 26138 on human chromosome 19 is indicated in FIG. 63.

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible form chromosome spreads or detectable using PCR based on that DNA sequence. Ultimately, complete sequencing of genes from several individuals can be performed to confirm the presence of a mutation and to distinguish mutations from polymorphisms.

The polynucleotide probes are also useful to determine patterns of the presence of the gene encoding the proteins and their variants with respect to tissue distribution, for example, whether gene duplication has occurred and whether the duplication occurs in all or only a subset of tissues. The genes can be naturally occurring or can have been introduced into a cell, tissue, or organism exogenously.

The polynucleotides are also useful for designing ribozymes corresponding to all, or a part, of the mRNA produced from genes encoding the polynucleotides described herein.

The polynucleotides are also useful for constructing host cells expressing a part, or all, of the polynucleotides and polypeptides.

The polynucleotides are also useful for constructing transgenic animals expressing all, or a part, of the polynucleotides and polypeptides.

The polynucleotides are also useful for making vectors that express part, or all, of the polypeptides.

The polynucleotides are also useful as hybridization probes for determining the level of nucleic acid expression of a sequence of the invention. Accordingly, the probes can be used to detect the presence of, or to determine levels of, a nucleic acid molecule of the invention in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of a gene of the invention.

Alternatively, the probe can be used in an in situ hybridization context to assess the position of extra copies of a gene of the invention, as on extrachromosomal elements or as integrated into chromosomes in which the gene is not normally found, for example as a homogeneously staining region.

These uses are relevant for diagnosis of disorders involving an increase or decrease in expression relative to normal, such as a proliferative disorder, a differentiative or developmental disorder, a hematopoietic disorder or a viral disorder, especially as disclosed herein.

Thus, the present invention provides a method for identifying a disease or disorder associated with aberrant expression or activity of a nucleic acid of the invention, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid. "Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protein of the invention, such as by measuring the level of a nucleic acid encoding the protein in a sample of cells from a subject e.g., mRNA or genomic DNA, or determining if the gene has been mutated.

Nucleic acid expression assays are useful for drug screening to identify compounds that modulate expression of a nucleic acid of the invention (e.g., antisense, polypeptides, peptidomimetics, small molecules or other drugs). A cell is contacted with a candidate compound and the expression of mRNA determined. The level of expression of an mRNA of the invention in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the agent to a subject) in patients or in transgenic animals.

The invention thus provides a method for identifying a compound that can be used to treat a disorder associated with nucleic acid expression of a gene of the invention. The method typically includes assaying the ability of the compound to modulate the expression of a nucleic acid of the invention and thus identifying a compound that can be used to treat a disorder characterized by undesired expression of a nucleic acid of the invention.

The assays can be performed in cell-based and cell-free systems. Cell-based assays include cells naturally expressing a nucleic acid of the invention, such as discussed herein above, or recombinant cells genetically engineered to express specific nucleic acid sequences.

Alternatively, candidate compounds can be assayed in vivo in patients or in transgenic animals.

The assay for expression of a nucleic acid of the invention can involve direct assay of nucleic acid levels, such as mRNA levels, or on collateral compounds involved in GAP function. Further, the expression of genes that are up- or down-regulated in response to GAP activity, as in a signal pathway (such as cyclic AMP or phosphatidylinositol turnover) can also be assayed. In this embodiment the regulatory regions of these genes can be operably linked to a reporter gene such as luciferase.

Thus, modulators of gene expression can be identified in a method wherein a cell is contacted with a candidate compound and the expression of mRNA determined. The level of expression of mRNA in the presence of the candidate compound is compared to the level of expression of mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate nucleic acid expression. Modulation includes both up-regulation (i.e. activation or agonization) or down-regulation (suppression or antagonization) or effects on nucleic acid activity (e.g. when nucleic acid is mutated or improperly modified) Treatment is of disorders characterized by aberrant expression or activity of the nucleic acid.

Alternatively, a modulator for nucleic acid expression can be a small molecule or drug identified using the screening assays described herein as long as the drug or small molecule inhibits the nucleic acid expression.

The polynucleotides are also useful for monitoring the effectiveness of modulating compounds on the expression or activity of the gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The polynucleotides are also useful in diagnostic assays for qualitative changes in a nucleic acid of the invention, and particularly in qualitative changes that lead to pathology. The polynucleotides can be used to detect mutations in genes of the invention and gene expression products such as mRNA. The polynucleotides can be used as hybridization probes to detect naturally-occurring genetic mutations in a gene of the invention and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the gene associated with a dysfunction provides a diagnostic tool for an active disease or susceptibility to disease when the disease results from overexpression, underexpression, or altered expression of a protein of the invention.

Mutations in the gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or Race PCR, or, alternatively, in a ligation chain reaction (LCR) (see, e.g., Landegran et al., *Science* 241:1077-1080 (1988); and Nakazawa et al., *PNAS* 91:360-364 (1994)), the latter of which can be particularly useful for detecting point mutations in the gene (see Abravaya et al., *Nucleic Acids Res.* 23:675-682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a gene of the invention can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant gene of the invention and the wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al., *Adv. Chromatogr.* 36:127-162 (1996); and Griffin et al., *Appl. Biochem. Biotechnol.* 38:147-159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286-295 (1992)), electrophoretic mobility of mutant and wild type nucleic acid is compared (Orita et al., *PNAS* 86:2766 (1989); Cotton et al., *Mutat. Res.* 285:125-144 (1993); and Hayashi et al, *Genet. Anal. Tech. Appl.* 9:73-79 (1992)), and movement of mutant or wild-type fragments in polyacrylamide gels containing a gradient of denaturant is assayed using denaturing gradient gel electrophoresis (Myers et al., *Nature* 313:495 (1985)). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244-255; Kozal et al. (1996) *Nature Medicine* 2:753-759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the gene that results in altered affinity for a GTPase or an effector molecule (or analog) could result in an excessive or decreased drug effect with standard concentrations of GTPase, or effector (or analog). Accordingly, the polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control-sample with the presence of mRNA or genomic DNA in the test sample.

The polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the sequence can be used to provide an alternative technique which determines the actual DNA sequence of selected fragments in the genome of an individual. Thus, the sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of probes can be used to identify tissue by species and/or by organ type.

In a similar fashion, these primers and probes can be used to screen tissue culture for contamination (i.e. screen for the presence of a mixture of different types of cells in a culture).

Alternatively, the polynucleotides can be used directly to block transcription or translation of nucleic acid sequences of the invention by means of antisense or ribozyme constructs. Thus, in a disorder characterized by abnormally high or undesirable expression of a gene of the invention, nucleic acids can be directly used for treatment.

The polynucleotides are thus useful as antisense constructs to control expression of a gene of the invention in cells, tissues, and organisms. A DNA antisense polynucleotide is designed to be complementary to a region of the gene involved in transcription, preventing transcription and hence production of protein. An antisense RNA or DNA polynucleotide would hybridize to the mRNA and thus block translation of mRNA into protein.

Examples of antisense molecules useful to inhibit nucleic acid expression include antisense molecules complementary to a fragment of the 5' untranslated region of a sequence of SEQ ID NO:21 or SEQ ID NO:24 which also includes the start codon and antisense molecules which are complementary to a fragment of the 3' untranslated region of the sequence.

Alternatively, a class of antisense molecules can be used to inactivate mRNA in order to decrease expression of a nucleic acid of the invention. Accordingly, these molecules can treat a disorder characterized by abnormal or undesired expression of a nucleic acid of the invention. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protein, such as GTPase binding. It is understood that these regions include any of those specific domains, sites, segments, motifs, and the like that are disclosed as specific regions or sites herein.

The polynucleotides also provide vectors for gene therapy in patients containing cells that are aberrant in expression of a gene of the invention. Thus, recombinant cells, which include the patient's cells that have been engineered ex vivo and returned to the patient, are introduced into an individual where the cells produce the desired protein to treat the individual.

The invention also encompasses kits for detecting the presence of a nucleic acid of the invention in a biological sample. For example, the kit can comprise reagents such as a labeled or labelable nucleic acid or agent capable of detecting the nucleic acid in a biological sample; means for determining the amount of the nucleic acid in the sample; and means for comparing the amount of the nucleic acid in the sample with a standard. The compound or agent can be packaged in a suitable container. The kit can further comprise instructions for using the kit to detect a mRNA or DNA of the invention.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBIA).

For example, software which implements the BLAST (Altschul et al. (1990) J. Mol. Biol. 215:403-410) and BLAZE (Brutlag et al. (1993) Comp. Chem. 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/host cells

The invention also provides vectors containing the polynucleotides of the invention. The term "vector" refers to a vehicle, preferably a nucleic acid molecule, that can transport the polynucleotides. When the vector is a nucleic acid molecule, the polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the polynucleotides. Alternatively, the vector may integrate into the host cell genome and produce additional copies of the polynucleotides when the host cell replicates.

The invention provides vectors for the maintenance (cloning vectors) or vectors for expression (expression vectors) of the polynucleotides. The vectors can function in prokaryotic or eukaryotic cells or in both (shuttle vectors).

Expression vectors contain cis-acting regulatory regions that are operably linked in the vector to the polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the polynucleotides from the vector. Alternatively, a trans-acting factor may be supplied by the host cell. Finally, a trans-acting factor can be produced from the vector itself.

It is understood, however, that in some embodiments, transcription and/or translation of the polynucleotides can occur in a cell-free system.

The regulatory sequences to which the polynucleotides described herein can be operably linked include promoters for directing mRNA transcription. These include, but are not limited to, the left promoter from bacteriophage λ, the lac, TRP, and TAC promoters from *E. Coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a polynucleotide of the invention. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g., cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e., tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al., *Gene* 67:31-40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301-315 (1988)) and pET 11d (Studier et al., *Gene Expression Technology: Methods in Enzymology* 185:60-89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119-128). Alternatively, the sequence of the polynucleotide of interest can be altered to provide preferential codon usage for a specific host cell, for example *E. coli*. (Wada et al., *Nucleic Acids Res.* 20:2111-2118 (1992)).

The polynucleotides can also be expressed by expression vectors that are operative in yeast. Examples of vectors for expression in yeast e.g., *S. cerevisiae* include pYepSec1 (Baldari, et al., *EMBO J.* 6:229-234 (1987)), pMFa (Kurjan et al., *Cell* 30:933-943(1982)), pJRY88 (Schultz et al., *Gene* 54:113-123 (1987)), and pYES2 (Invitrogen Corporation, San Diego, Calif.).

The polynucleotides can also be expressed in insect cells using, for example, baculovirus expression vectors. Baculovirus vectors available for expression of proteins in cultured insect cells (e.g., Sf 9 cells) include the pAc series (Smith et al., *Mol. Cell. Biol.* 3:2156-2165 (1983)) and the pVL series (Lucklow et al., *Virology* 170:31-39 (1989)).

In certain embodiments of the invention, the polynucleotides described herein are expressed in mammalian cells using mammalian expression vectors. Examples of mammalian expression vectors include pCDM8 (Seed, B. *Nature* 329:840 (1987)) and pMT2PC (Kaufman et al., *EMBO J.* 6:187-195 (1987)).

The expression vectors listed herein are provided by way of example only of the well-known vectors available to those of ordinary skill in the art that would be useful to express the 26651 or 26138 polynucleotides. The person of ordinary skill in the art would be aware of other vectors suitable for maintenance propagation or expression of the polynucleotides described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the polynucleotides can be introduced either alone or with other polynucleotides that are not related to the polynucleotides such as those providing trans-acting factors for expression vectors. When more than one vector is introduced into a cell, the vectors can be introduced independently, co-introduced or joined to the polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Host cells of particular interest include those derived from the tissues in which the 26651 polypeptides of the invention are expressed, including tonsil, spleen, fetal liver, adult liver, fibrotic liver, granulocytes, neutrophils, erythroid cells, adipose tissue, bone marrow, colon, lung, kidney, heart, lymphocyte, megakaryocytes, T-cells, and the tissues and cell lines shown in FIGS. 64A-64B.

Host cells of particular interest include those derived from the tissues in which the 26138 polypeptides of the invention are expressed, including tonsil, spleen, fetal liver, adult liver, fibrotic liver, granulocytes, neutrophils, erythroid cells, adipose tissue, bone marrow, colon, lung, kidney, heart, lymphocyte, megakaryocytes, T-cells, and the tissues and cell lines shown in FIGS. 64A-64B.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

The host cells expressing the polypeptides described herein, and particularly recombinant host cells, have a variety of uses. First, the cells are useful for producing proteins or polypeptides of the invention that can be further purified to produce desired amounts of the proteins or polypeptides, including fusion proteins or polypeptides, encoded by nucleic acids as described herein (e.g. 26651-like or 26138-like polypeptides, mutant forms of 26651-like or 26138-like polypeptides, fusion proteins, etc.). It is further recognized that the nucleic acid sequences of the invention can be altered to contain codons, which are preferred, or non-preferred, for a particular expression system. For example, the nucleic acid can be one in which at least one altered codon, and preferably at least 10% or 20% of the codons have been altered such that the sequence is optimized for expression in *E. coli*, yeast, human, insect, or CHO cells. Methods for determining codon usage are well known in the art. Thus, host cells containing expression vectors are useful for polypeptide production.

Host cells are also useful for conducting cell-based assays involving the protein of the invention or fragments. Thus, a recombinant host cell expressing the native protein is useful to assay for compounds that stimulate or inhibit protein function. This can include GTPase binding, gene expression at the level of transcription or translation, effector interaction, and components of a signal transduction or other pathway.

Cells of particular relevance are those in which the protein is expressed as disclosed herein.

Host cells are also useful for identifying mutants in which these functions are affected. If the mutants naturally occur and give rise to a pathology, host cells containing the mutations are useful to assay compounds that have a desired effect on the mutant protein (for example, stimulating or inhibiting function) which may not be indicated by their effect on the native protein.

Recombinant host cells are also useful for expressing the chimeric polypeptides described herein to assess compounds that activate or suppress activation by means of heterologous sites or domains, for example, a binding region, on any given host cell.

Further, mutant proteins of the invention can be designed in which one or more of the various functions is engineered to be increased or decreased (e.g., GTPase binding) and used to augment or replace proteins of the invention in an individual. Thus, host cells can provide a therapeutic benefit by replacing an aberrant protein or providing an aberrant protein that provides a therapeutic result. In one embodiment, the cells provide proteins that are abnormally active.

In another embodiment, the cells provide proteins that are abnormally inactive. These can compete with the endogenous protein in the individual.

In another embodiment, cells expressing the proteins that cannot be activated, are introduced into an individual in order to compete with the endogenous protein for GTPase. For example, in the case in which excessive GTPase (or analog) is part of a treatment modality, it may be necessary to inactivate the compound at a specific point in treatment. Providing cells that compete for the compound, but which cannot be affected by protein activation would be beneficial.

Homologously recombinant host cells can also be produced that allow the in situ alteration of the endogenous polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the GAP polynucleotides or sequences proximal or distal to a GAP gene are allowed to integrate into a host cell genome by homologous recombination where expression of the gene can be affected. In one embodiment, regulatory sequences are introduced that either increase or decrease expression of an endogenous sequence. Accordingly, a GAP protein can be produced in a cell not normally producing it. Alternatively, increased expression of GAP protein can be effected in a cell normally producing the protein at a specific level. Further, expression can be decreased or eliminated by introducing a specific regulatory sequence. The regulatory sequence can be heterologous to the protein sequence or can be a homologous sequence with a desired mutation that affects expression. Alternatively, the entire-gene can be deleted. The regulatory sequence can be specific to the host cell or capable of functioning in more than one cell type. Still further, specific mutations can be introduced into any desired region of the gene to produce mutant GAP proteins. Such mutations could be introduced, for example, into the specific functional regions such as the ligand-binding site.

In one embodiment, the host cell can be a fertilized oocyte or embryonic stem cell that can be used to produce a transgenic animal containing the altered gene of the invention. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous gene is selected (see e.g., Li, E. et al., *Cell* 69:915 (1992)). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinions in Biotechnology* 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protein of the invention and identifying and evaluating modulators of the protein activity. Other examples of transgenic animals include non-human primates, sheep, dogs, cows, goats, chickens, and amphibians.

In one embodiment, a host cell is a fertilized oocyte or an embryonic stem cell into which polynucleotide sequences of the invention have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the nucleotide sequences of the invention can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232-6236 (1992). Another example of a recombinase system is the FLP recombinase system of *S. cerevisiae* (O'Gorman et al. *Science* 251:1351-1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810-813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect GTPase binding or activation, and signal transduction, may not be evident from in vitro cell-free or cell-based assays. Accordingly, it is useful to provide non-human transgenic animals to assay in vivo GAP function, including GTPase interaction, the effect of specific mutant proteins on GAP function and GTPase interaction, and the effect of chimeric proteins. It is also possible to assess the effect of null mutations, that is mutations that substantially or completely eliminate one or more protein functions.

In general, methods for producing transgenic animals include introducing a nucleic acid sequence according to the present invention, the nucleic acid sequence capable of expressing the protein in a transgenic animal, into a cell in culture or in vivo. When introduced in vivo, the nucleic acid is introduced into an intact organism such that one or more cell types and, accordingly, one or more tissue types, express the nucleic acid encoding the protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The nucleic acid molecules, proteins, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetctraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a protein of the invention or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al., *PNAS* 91:3054-3057 (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

OTHER EMBODIMENTS

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 26651 or 26138, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 26651 or 26138 nucleic acid, polypeptide, or antibody.

The capture probes can be a set of nucleic acids from a selected sample, e.g., a sample of nucleic acids derived from a control or non-stimulated tissue or cell.

The method can include contacting the 26651 or 26138 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 26651 or 26138. Such methods can be used to diagnose a subject, e.g., to evaluate risk for a disease or disorder, to evaluate suitability of a selected treatment for a subject, to evaluate whether a subject has a disease or disorder. 26651 or 26138 is associated with GAP activity, thus it is useful for disorders associated with abnormal GTPase signaling, GTPase release of substrates, GTPase activation, or other GAP regulated processes.

The method can be used to detect SNPs.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or mis express 26651 or 26138 or from a cell or subject in which a 26651 or 26138 mediated response has been elicited, e.g., by contact of the cell with 26651 or 26138 nucleic acid or protein, or administration to the cell or subject 26651 or 26138 nucleic acid or protein; contacting the array with one or more inquiry probe, wherein an inquiry probe can be a nucleic acid, polypeptide, or antibody (which is preferably other than 26651 or 26138 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 26651 or 26138 (or does not express as highly as in the case of the 26651 or 26138 positive plurality of capture probes) or from a cell or subject which in which a 26651 or 26138 mediated response has not been elicited (or has been elicited to a lesser extent than in the first sample); contacting the array with one or more inquiry probes (which is preferably other than a 26651 or 26138 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 26651 or 26138, e.g., analyzing structure, function, or relatedness to other nucleic acid or amino acid sequences. The method includes: providing a 26651 or 26138 nucleic acid or amino acid sequence; comparing the 26651 or 26138 sequence with one or more preferably a plurality of sequences from a collection of sequences, e.g., a nucleic acid or protein sequence database; to thereby analyze 26651 or 26138.

Preferred databases include GenBank™. The method can include evaluating the sequence identity between a 26651 or 26138 sequence and a database sequence. The method can be performed by accessing the database at a second site, e.g., over the internet.

In another aspect, the invention features, a set of oligonucleotides, useful, e.g., for identifying SNP's, or identifying specific alleles of 26651 or 26138. The set includes a plurality of oligonucleotides, each of which has a different nucleotide at an interrogation position, e.g., an SNP or the site of a mutation. In a preferred embodiment, the oligonucleotides of the plurality are identical in sequence with one another (except for differences in length). The oligonucleotides can be provided with different labels, such that an oligonucleotide that hybridizes to one allele provides a signal that is distinguishable from an oligonucleotide which hybridizes to a second allele.

This invention is further illustrated by the following examples which should not be construed as limiting. The contents of all references, patents and published patent applications cited throughout this application are incorporated herein by reference.

EXPERIMENTAL

Example 1

Identification and Characterization of Human 26651 GAP

The human 26651 GAP sequence (FIGS. 52A-52B), which is approximately 2847 nucleotides long including untranslated regions, contains a predicted methionine-initiated coding sequence of about 547 amino acids (nucleotides 60-1703 of SEQ ID NO:21; SEQ ID NO:23). The coding sequence encodes a 547 amino acid protein (SEQ ID NO:22).

PFAM analysis indicates that the 26651 polypeptide shares a high degree of sequence similarity with GAPs. Further, PFAM analysis indicates that the 26651 shares a high degree of sequence similarity with the Rho-GAP subclass. For general information regarding PFAM identifiers, PS prefix and PF prefix domain identification numbers, refer to Sonnhammer et al. (1997) *Protein* 28:405-420.

As used herein, the term "Rho-GAP domain" includes an amino acid sequence of about 80-300 amino acid residues in length and having a bit score for the alignment of the sequence to the Rho-GAP domain (HMM) of at least 8. Preferably, a Rho-GAP domain includes at least about 100-250 amino acids, more preferably about 120-200 amino acid residues, or about 120-180 amino acids and has a bit score for the alignment of the sequence to the Rho-GAP domain (HMM) of at least 16 or greater. The Rho-GAP domain (HMM) has been assigned the PFAM Accession PF00620 (pfam.wustl.edu/). An alignment of the Rho-GAP domain (amino acids 236 to 397 of SEQ ID NO:22) of human 26651-like polypeptides with a consensus amino acid sequence derived from a hidden Markov model (SEQ ID NO:27) is depicted in FIGS. 56A-B.

In a preferred embodiment a 26651-like polypeptide or protein has a "Rho-GAP domain" or a region which includes at least about 100-250, more preferably about 120-200, or 120-180 amino acid residues and has at least about 60%, 70%, 80%, 90%, 95%, 99%, or 100% sequence identity with an "Rho-GAP domain," e.g., the Rho-GAP domain of human 26651 (e.g., amino acid residues 236-397 of SEQ ID NO:22).

PFAM analysis indicates that the 26651 polypeptide shares a high degree of sequence similarity with dockerin. The dockerin domain (HMM) has been assigned the PFAM Accession PF00404 (pfam.wustl.edu/). The dockerin domain of 26651 falls between amino acids 278 to 298 of SEQ ID NO:22.

To identify the presence of a "Rho-GAP domain" in a 26651-like protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405-420 and a detailed description of HMMs can be found, for example, in Gribskov et al. (1990) *Meth. Enzymol.* 183:146-159; Gribskov et al. (1987) *Proc. Natl. Acad. Sci. USA* 84:43554358; Krogh et al. (1994) *J. Mol. Biol.* 235: 1501-1531; and Stultz et al. (1993) *Protein Sci.* 2:305-314, the contents of which are incorporated herein by reference.

ProDom analysis of 26651 revealed 35% identity to a protein GTPase domain (p99.2 (80) P85A(4) P85B(4)CHIN (2)//PROTEIN GTPASE DOMAIN SH2 ACTIVATION ZINC 3-KINASE SH3 PHOSPHATIDYLINOSITOL REGULATORY). ProDom analysis further revealed regions having 27% and 37% identity with the long isoform of RhoGapX-1 (P99.2 (2) O43182(1) O43437(1)//RHO-TYPE GTPASE ACTIVATING PROTEIN RhoGapX-1 LONG ISOFORM). A region having 28% identity to a trithorax transcription regulation protein (p99.2 (3) Q24742(1) Q27255(1) TRX(1)//TRITHORAX PROTEIN PREDICTED TRX TRANSCRIPTION REGULATION ZINC-FINGER METAL-BINDING DNA-BINDING NUCLEAR) was identified by ProDom analysis. The ProDom analysis also identified regions of 26651 with 29%, 26%, and 23% identity to the T-DNA region of a TI plasmid (p99.2 (1) Q44390-AGRTU//TI PLASMID PT11 5955 T-DNA REGION PLASMID), cosmid (p99.2 (1) Q20299_CAELL// COSMID F41H10), and a hypothetical protein (p99.2 (1) O26888-METTH//HYPOTHETICAL 21.6 KD PROTEIN HYPOTHETICAL PROTEIN), respectively.

Example 2

Identification and Characterization of Human 26138 GAP

The human 26138 GAP sequence (FIGS. 57A-57C), which is approximately 3391 nucleotides long including untranslated regions, contains a predicted methionine-initiated coding sequence of about 3018 nucleotides (nucleotides 78-3095 of SEQ ID NO:24: SEQ ID NO:26). The coding sequence encodes a 1005 amino acid protein (SEQ ID NO:25).

PFAM analysis indicates that the 26138 polypeptide shares a high degree of sequence similarity with GAPs. Further, PFAM analysis indicates that the 26138 polypeptide shares a high degree of sequence similarity with the Ras-GAP subclass. For general information regarding PFAM identifiers, PS prefix and PF prefix domain identification numbers, refer to Sonnhammer et al. (1997) *Protein* 28:405-420.

As used herein, the term "Ras-GAP domain" includes an amino acid sequence of about 80-300 amino acid residues in length and having a bit score for the alignment of the sequence to the Ras-GAP domain (HMM) of at least 8. Preferably, a Ras-GAP domain includes at least about 100-250 amino acids, more preferably about 130-200 amino acid residues, or about 160-200 amino acids and has a bit score for the alignment of the sequence to the Ras-GAP domain (HMM) of at least 16 or greater. Ras-GAP domain (HMM) has been assigned the PFAM Accession PF 00616 (pfam-.wustl.edu/). An alignment of the Ras-GAP domain (amino acids 473 to 645 of SEQ ID NO:25) of human 26138 with a consensus amino acid sequence derived from a hidden Markov model (SEQ ID NO:29) is depicted in FIGS. 61A-61B.

In a preferred embodiment a 26138-like polypeptide or protein has a "Ras-GAP domain" or a region which includes at least about 100-250 more preferably about 130-200 or 160-200 amino acid residues and has at least about 60%, 70%, 80%, 90%, 95%, 99%, or 100% sequence identity with an "Ras-GAP domain," e.g., the Ras-GAP domain of human 26138 (e.g., amino acid residues 473 to 645 of SEQ ID NO:25).

PFAM analysis indicates that the 26138 polypeptide shares a high degree of sequence similarity with the gntR family of bacterial regulatory proteins. The gntR domain (HMM) has been assigned the PFAM Accession Number PF00392 (pfam.wustl.edu/). The gntR domain of 26138 falls between amino acids 405 to 433 of SEQ ID NO:25. PFAM analysis indicates that the 26138 polypeptide shares a region (amino acids 253 to 287 of SEQ ID NO:25) with similarity to the pleckstrin homology domain. The pleckstrin homology domain has been assigned the PFAM Accession Number PF00169.

To identify the presence of a "Ras-GAP domain" in a 26138-like protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235: 1501-1531; and Stultz et al. (1993) *Protein Sci.* 2:305-314, the contents of which are incorporated herein by reference.

ProDom analysis of 2613 revealed 25% identity to p99.2 (1) O44242_CAEEL//GAP 2-4. Further analysis revealed 38% identity to a ras-GAP inhibitory regulator (p99.2 (29) GTPA(3) NF1(2) GAP 1(2)//PROTEIN GTPASE ACTIVATION GTPASE-ACTIVATING RAS NEUROFIBROMIN P21 ACTIVATOR INHIBITORY REGULATOR). A region having 31% identity to a filament intermediate repeat heptad (p99.2 (314) LAMA (10) DESM (8) LAM1(8)//FILAMENT INTERMEDIATE REPEAT HEPTAD PATTERN COILED COIL KERATIN PROTEIN TYPE) was identified by ProDom analysis. 26138 is 26%, 30%, and 26% identical to several hypothetical proteins: p99.2 (1) YWKC_BACSU// HYPOTHETICAL 21.1 KD PROTEIN IN TDK-PRFA INTERGENIC REGION; p99.2 (1) YBY0_YEAST//HYPOTHETICAL 47.4 KD PROTEIN IN OPY1-AGP2 INTERGENIC REGION; and p99.2 (1) YFHG_ECOLI// HYPOTHETICAL 27.3 KD PROTEIN IN GLNB-PURL INTERGENIC REGION ORF-1 F239, respectively. 26138 also shares 23% identity to GAG GAG-POL polypeptides (p99.2 (2) Q88284 (1) Q88285 (1)//POLYPROTEIN GAG GAG-POL).

Example 3

Tissue Distribution of 26138 mRNA

Expression levels of 26138 in various tissue and cell types were determined by quantitative RT-PCR (Reverse Transcriptase Polymerase Chain Reaction; Taqman® brand PCR kit, Applied Biosystems). The quantitative RT-PCR reactions were performed according to the kit manufacturer's instructions. The results of the Taqman® analysis are shown in FIGS. 64A-64B.

26138 was expressed in a variety of human tissues including tonsil, spleen, fetal liver, adult liver, fibrotic liver, granulocytes, neutrophils, erythroid cells, adipose tissue, bone marrow, colon, lung, kidney, heart, lymphocyte, megakaryocytes and T-cells.

Example 4

Tissue Distribution of 26651 or 26138 mRNA

Northern blot hybridizations with various RNA samples are performed under standard conditions and washed under stringent conditions, i.e., 0.2×SSC at 65° C. A DNA probe corresponding to all or a portion of the 26651 or 26138 cDNA (SEQ ID NO:21 or 24) can be used. The DNA is radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) are probed in ExpressHyb hybridization solution (Clontech) and washed at high stringency according to manufacturer's recommendations.

Example 5

Recombinant Expression of 26651 or 26138 in Bacterial Cells

In this example, 26651 or 26138 is expressed as a recombinant glutathione-S-transferase (GST) fusion polypeptide in *E. coli* and the fusion polypeptide is isolated and characterized. Specifically, 26651 or 26138 is fused to GST and this fusion polypeptide is expressed in *E. coli*, e.g., strain PEB199. Expression of the GST-26651 or 26138 fusion protein in PEB 199 is induced with FPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 6

Expression of Recombinant 26651 or 26138 Protein in COS Cells

To express the 26651 or 26138 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 26651 or 26138 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 26651 or 26138 DNA sequence is amplified by PCR using two primers. The 5' primer contains the restriction site of interest followed by approximately twenty nucleotides of the 26651 or 26138 coding sequence starting from the initiation codon; the 3' end sequence contains complementary sequences to the other restriction site of interest, a translation stop codon, the HA tag or FLAG tag and the last 20 nucleotides of the 26651 or 26138 coding sequence. The PCR amplified fragment and the pcDNA/Amp vector are digested with the appropriate restriction enzymes and the vector is dephosphorylated using the CLAP enzyme (New England Biolabs, Beverly, Mass.). Preferably the two restriction sites chosen are different so that the 26651 or 26138 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 26651 or 26138-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the 26651 or 26138 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 26651 or 26138 coding sequence is cloned directly into the polylinker of the pcDNA/Amp vector using the appropriate restriction sites. The resulting plasmid is transfected into COS cells in the manner described above, and the expression of the 26651 or 26138 polypeptide is detected by radiolabelling and immunoprecipitation using a 26651 or 26138 specific monoclonal antibody.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

SEQUENCE LISTING

<160> NUMBER OF SEQ ID NOS: 30

<210> SEQ ID NO 1
<211> LENGTH: 1434
<212> TYPE: DNA
<213> ORGANISM: Homo sapiens
<220> FEATURE:
<221> NAME/KEY: CDS
<222> LOCATION: (200)...(886)

<400> SEQUENCE: 1

```
cgtgggcgga cgcgtgggtg cgtgtgtggc cttttttatt tgagagagca agaggcgccg      60
cggacgcctg ggcagccacg gcggcggggc gcggtgggc gccggctcag cccgcccctt     120
tctcccgccg cctccccgcc ccgccccgcg ccgcgccggc cgctgtcagc tccctcagcg     180
tccggccgag gcgcggtgt atg ctg agc cgc tgc cgc agc cgg ctg ctc cac      232
                       Met Leu Ser Arg Cys Arg Ser Arg Leu Leu His
                        1               5                  10 gtc ctg ggc ctt agc ttc ctg ctg cag acc cgc cgg ccg att ctc ctc      280
Val Leu Gly Leu Ser Phe Leu Leu Gln Thr Arg Arg Pro Ile Leu Leu
             15                  20                  25 tgc tct cca cgt ctc atg aag ccg ctg gtc gtg ttc gtc ctc ggc ggc      328
Cys Ser Pro Arg Leu Met Lys Pro Leu Val Val Phe Val Leu Gly Gly
         30                  35                  40 ccc ggc gcc ggc aag ggg acc cag tgc gcc cgc atc gtc gag aaa tat      376
Pro Gly Ala Gly Lys Gly Thr Gln Cys Ala Arg Ile Val Glu Lys Tyr
     45                  50                  55 ggc tac aca cac ctt tct gca gga gag ctg ctt cgt gat gaa agg aag      424
Gly Tyr Thr His Leu Ser Ala Gly Glu Leu Leu Arg Asp Glu Arg Lys
 60                  65                  70                  75 aac cca gat tca cag tat ggt gaa ctt att gaa aag tac att aaa gaa      472
Asn Pro Asp Ser Gln Tyr Gly Glu Leu Ile Glu Lys Tyr Ile Lys Glu
                 80                  85                  90 gga aag att gta cca gtt gag ata acc atc agt tta tta aag agg gaa      520
Gly Lys Ile Val Pro Val Glu Ile Thr Ile Ser Leu Leu Lys Arg Glu
             95                 100                 105 atg gat cag aca atg gct gcc aat gct cag aag aat aaa ttc ttg att      568
Met Asp Gln Thr Met Ala Ala Asn Ala Gln Lys Asn Lys Phe Leu Ile
        110                 115                 120 gat ggg ttt cca aga aat caa gac aac ctt caa gga tgg aac aag acc      616
Asp Gly Phe Pro Arg Asn Gln Asp Asn Leu Gln Gly Trp Asn Lys Thr
    125                 130                 135 atg gat ggg aag gca gat gta tct ttc gtt ctc ttt ttt gac tgt aat      664
Met Asp Gly Lys Ala Asp Val Ser Phe Val Leu Phe Phe Asp Cys Asn
140                 145                 150                 155 aat gag att tgt att gaa cga tgt ctt gag agg gga aag agt agt ggt      712
Asn Glu Ile Cys Ile Glu Arg Cys Leu Glu Arg Gly Lys Ser Ser Gly
                160                 165                 170 agg agt gat gac aac aga gag agc ttg gaa aag aga att cag acc tac      760
Arg Ser Asp Asp Asn Arg Glu Ser Leu Glu Lys Arg Ile Gln Thr Tyr
            175                 180                 185 ctt cag tca aca aag cca att att gac tta tat gaa gaa atg ggg aaa      808
Leu Gln Ser Thr Lys Pro Ile Ile Asp Leu Tyr Glu Glu Met Gly Lys
        190                 195                 200 gtc aag aaa ata gat gct tct aaa tct gtt gat gaa gtt ttt gat gaa      856
Val Lys Lys Ile Asp Ala Ser Lys Ser Val Asp Glu Val Phe Asp Glu
    205                 210                 215 gtt gtg cag att ttt gac aag gaa ggc taa ttctaaacct gaaagcatcc        906
Val Val Gln Ile Phe Asp Lys Glu Gly  *
```

```
                220          225
ttgaaatcat gcttgaatat tgctttgata gctgctatca tgaccccttt ttaaggcaat        966
tctaatcttt cataactaca tctcaattag tggctggaaa gtacatggta aaacaaagta       1026
aattttttta tgttcttttt tttggtcaca ggagtagaca gtgaattcag gtttaacttc       1086
accttagtta tggtgctcac caaacgaagg gtatcagcta tttttttta aattcaaaaa        1146 gaatatccct tttatagttt gtgccttctg tgagcaaaac tttttagtac gcgtatatat       1206
ccctctagta atcacaacat tttaggattt agggatcccg cttcctcttt ttcttgcaag       1266
ttttaaattt ccaaccttaa gtgaatttgt ggaccaaatt tcaaaggaac tttttgtgta       1326
gtcagttctt gcacatgtgt ttggtaaaca aactcaaaat ggattcttag gagcatttaa       1386
gtggttatta aatactgacc atttgctgta aaagatgaa aaaactta                     1434
```

<210> SEQ ID NO 2
<211> LENGTH: 228
<212> TYPE: PRT
<213> ORGANISM: Homo sapiens

<400> SEQUENCE: 2

```
Met Leu Ser Arg Cys Arg Ser Arg Leu Leu His Val Leu Gly Leu Ser
 1               5                  10                  15

Phe Leu Leu Gln Thr Arg Arg Pro Ile Leu Leu Cys Ser Pro Arg Leu
            20                  25                  30

Met Lys Pro Leu Val Val Phe Val Leu Gly Gly Pro Gly Ala Gly Lys
        35                  40                  45

Gly Thr Gln Cys Ala Arg Ile Val Glu Lys Tyr Gly Tyr Thr His Leu
    50                  55                  60

Ser Ala Gly Glu Leu Leu Arg Asp Glu Arg Lys Asn Pro Asp Ser Gln
65                  70                  75                  80

Tyr Gly Glu Leu Ile Glu Lys Tyr Ile Lys Glu Gly Lys Ile Val Pro
                85                  90                  95

Val Glu Ile Thr Ile Ser Leu Leu Lys Arg Glu Met Asp Gln Thr Met
            100                 105                 110

Ala Ala Asn Ala Gln Lys Asn Lys Phe Leu Ile Asp Gly Phe Pro Arg
        115                 120                 125

Asn Gln Asp Asn Leu Gln Gly Trp Asn Lys Thr Met Asp Gly Lys Ala
    130                 135                 140

Asp Val Ser Phe Val Leu Phe Phe Asp Cys Asn Asn Glu Ile Cys Ile
145                 150                 155                 160

Glu Arg Cys Leu Glu Arg Gly Lys Ser Ser Gly Arg Ser Asp Asp Asn
                165                 170                 175

Arg Glu Ser Leu Glu Lys Arg Ile Gln Thr Tyr Leu Gln Ser Thr Lys
            180                 185                 190

Pro Ile Ile Asp Leu Tyr Glu Glu Met Gly Lys Val Lys Lys Ile Asp
        195                 200                 205

Ala Ser Lys Ser Val Asp Glu Val Phe Asp Glu Val Val Gln Ile Phe
    210                 215                 220

Asp Lys Glu Gly
225
```

<210> SEQ ID NO 3
<211> LENGTH: 196
<212> TYPE: PRT
<213> ORGANISM: Sus scrofa

```
<400> SEQUENCE: 3

Met Arg Pro Lys Val Val Phe Val Leu Gly Gly Pro Gly Ala Gly Lys
 1               5                   10                  15

Gly Thr Gln Cys Ala Arg Ile Val Glu Lys Tyr Gly Tyr Thr His Leu
                20                  25                  30

Ser Ala Gly Glu Leu Leu Arg Asp Glu Arg Lys Asn Pro Asp Ser Gln
            35                  40                  45

Tyr Gly Glu Leu Ile Glu Lys Tyr Ile Lys Asp Gly Lys Ile Val Pro
        50                  55                  60

Val Glu Ile Thr Ile Ser Leu Leu Arg Arg Glu Met Asp Gln Thr Met
65                  70                  75                  80

Ala Ala Asn Ala Gln Lys Asn Lys Phe Leu Ile Asp Gly Phe Pro Arg
                85                  90                  95

Asn Gln Asp Asn Leu Gln Gly Trp Asn Lys Thr Met Asp Gly Lys Ala
            100                 105                 110

Asp Val Ser Phe Val Leu Phe Phe Asp Cys Asn Asn Glu Ile Cys Ile
        115                 120                 125

Glu Arg Cys Leu Glu Arg Gly Lys Ser Ser Gly Arg Ser Asp Asp Asn
130                 135                 140

Arg Glu Ser Leu Glu Lys Arg Ile Gln Thr Tyr Leu Gln Ser Thr Lys
145                 150                 155                 160

Pro Ile Ile Asp Leu Tyr Glu Glu Met Gly Lys Val Lys Lys Ile Asp
                165                 170                 175

Ala Ser Lys Ser Val Asp Glu Val Phe Asp Glu Val Lys Ile Phe
            180                 185                 190

Asp Lys Glu Gly
        195

<210> SEQ ID NO 4
<211> LENGTH: 190
<212> TYPE: PRT
<213> ORGANISM: Artificial Sequence
<220> FEATURE:
<223> OTHER INFORMATION: Consensus sequence for adenylate kinase

<400> SEQUENCE: 4

Leu Leu Gly Pro Pro Gly Ala Gly Lys Gly Thr Gln Ala Glu Arg Ile
 1               5                  10                  15

Val Lys Lys Tyr Gly Ile Pro His Leu Ser Thr Gly Asp Leu Leu Arg
                20                  25                  30

Ala Glu Val Lys Ser Gly Thr Glu Leu Gly Lys Glu Ala Lys Glu Tyr
            35                  40                  45

Met Asp Lys Gly Glu Leu Val Pro Asp Glu Val Ile Gly Leu Val
        50                  55                  60

Lys Glu Arg Leu Glu Gln Asn Val Asp Ala Lys Lys Asn Gly Phe Leu
65                  70                  75                  80

Leu Asp Gly Phe Pro Arg Thr Val Pro Gln Ala Glu Ala Leu Glu Glu
                85                  90                  95

Met Leu Glu Glu Ala Gly Ile Lys Leu Asp Ala Val Ile Glu Leu Asp
            100                 105                 110

Val Pro Asp Glu Val Leu Val Glu Arg Leu Thr Gly Arg Arg Ile His
        115                 120                 125

Pro Thr Ser Gly Arg Ser Tyr His Leu Glu Phe Asn Pro Pro Lys Val
130                 135                 140

Glu Gly Lys Asp Asp Val Thr Gly Glu Pro Leu Leu Gln Arg Arg Ala
```

```
                145                 150                 155                 160
Asp Asp Asn Glu Glu Thr Val Lys Lys Arg Leu Glu Thr Tyr His Lys
                    165                 170                 175
Gln Thr Glu Pro Val Ile Asp Tyr Tyr Lys Lys Gly Lys
                180                 185                 190

<210> SEQ ID NO 5
<211> LENGTH: 260
<212> TYPE: PRT
<213> ORGANISM: Homo sapiens

<400> SEQUENCE: 5

Met Ala Arg Pro Gly Met Glu Arg Trp Arg Asp Arg Leu Ala Leu Val
 1               5                  10                  15
Thr Gly Ala Ser Gly Gly Ile Gly Ala Ala Val Ala Arg Ala Leu Val
                20                  25                  30
Gln Gln Gly Leu Lys Val Val Gly Cys Ala Arg Thr Val Gly Asn Ile
            35                  40                  45
Glu Glu Leu Ala Ala Glu Cys Lys Ser Ala Gly Tyr Pro Gly Thr Leu
        50                  55                  60
Ile Pro Tyr Arg Cys Asp Leu Ser Asn Glu Glu Asp Ile Leu Ser Met
65                  70                  75                  80
Phe Ser Ala Ile Arg Ser Gln His Ser Gly Val Asp Ile Cys Ile Asn
                85                  90                  95
Asn Ala Gly Leu Ala Arg Pro Asp Thr Leu Leu Ser Gly Ser Thr Ser
            100                 105                 110
Gly Trp Lys Asp Met Phe Asn Val Asn Val Leu Ala Leu Ser Ile Cys
        115                 120                 125
Thr Arg Glu Ala Tyr Gln Ser Met Lys Glu Arg Asn Val Asp Asp Gly
130                 135                 140
His Ile Ile Asn Ile Asn Ser Met Ser Gly His Arg Val Leu Pro Leu
145                 150                 155                 160
Ser Val Thr His Phe Tyr Ser Ala Thr Lys Tyr Ala Val Thr Ala Leu
                165                 170                 175
Thr Glu Gly Leu Arg Gln Glu Leu Arg Glu Ala Gln Thr His Ile Arg
            180                 185                 190
Ala Thr Cys Ile Ser Pro Gly Val Val Glu Thr Gln Phe Ala Phe Lys
        195                 200                 205
Leu His Asp Lys Asp Pro Glu Lys Ala Ala Thr Tyr Glu Gln Met
210                 215                 220
Lys Cys Leu Lys Pro Glu Asp Val Ala Glu Ala Val Ile Tyr Val Leu
225                 230                 235                 240
Ser Thr Pro Ala His Ile Gln Ile Gly Asp Ile Gln Met Arg Pro Thr
                245                 250                 255
Glu Gln Val Thr
        260

<210> SEQ ID NO 6
<211> LENGTH: 1909
<212> TYPE: DNA
<213> ORGANISM: Homo sapiens
<220> FEATURE:
<221> NAME/KEY: CDS
<222> LOCATION: (421)...(1203)
<220> FEATURE:
<221> NAME/KEY: misc_feature
<222> LOCATION: 1552, 1883, 1888, 1890
<223> OTHER INFORMATION: n = A,T,C or G
```

-continued

```
<400> SEQUENCE: 6
tacttagact cagccggctt ttccacgctt tgcctgaccc tgctttgctc aactgtacgt      60
cttgtttcgt tttctgttct gcgccgttac agatccaagc tctgaaaaac cagaaagtta     120
actggtaagt ttagtctttt tgtctttat ttcaggtccc ggatccggtg atccaaatct      180
aagaactgct cctcagtgag tgttgccttt acttctaggc ctgtacggaa gtgttacttc     240
tgctctaaaa gctgcggaat tctaatacga ctcactatag ggagtcgacc cacgcgtccg     300
gggtctaggc gcggatcgga cccaagcagg tcggcggcgg cggcaggaga gcggccgggc    360
gtcagctcct cgaccccgt gtcgggctag tccagcgagg cggacgggcg gcgtgggccc     420
```

| | | | | | | | | | | | | | | | | |
|---|---|---|---|---|---|---|---|---|---|---|---|---|---|---|---|---|
| atg | gcc | agg | ccc | ggc | atg | gag | cgg | tgg | cgc | gac | cgg | ctg | gcg | ctg | gtg | 468 |
| Met | Ala | Arg | Pro | Gly | Met | Glu | Arg | Trp | Arg | Asp | Arg | Leu | Ala | Leu | Val | |
| 1 | | | | 5 | | | | | 10 | | | | | 15 | | |

| acg | ggg | gcc | tcg | ggg | ggc | atc | ggc | gcg | gcc | gtg | gcc | cgg | gcc | ctg | gtc | 516 |
|---|---|---|---|---|---|---|---|---|---|---|---|---|---|---|---|---|
| Thr | Gly | Ala | Ser | Gly | Gly | Ile | Gly | Ala | Ala | Val | Ala | Arg | Ala | Leu | Val | |
| | | | 20 | | | | | 25 | | | | | 30 | | | |

| cag | cag | gga | ctg | aag | gtg | gtg | ggc | tgc | gcc | cgc | act | gtg | ggc | aac | atc | 564 |
|---|---|---|---|---|---|---|---|---|---|---|---|---|---|---|---|---|
| Gln | Gln | Gly | Leu | Lys | Val | Val | Gly | Cys | Ala | Arg | Thr | Val | Gly | Asn | Ile | |
| | 35 | | | | | 40 | | | | | 45 | | | | | |

| gag | gag | ctg | gct | gct | gaa | tgt | aag | agt | gca | ggc | tac | ccc | ggg | act | ttg | 612 |
|---|---|---|---|---|---|---|---|---|---|---|---|---|---|---|---|---|
| Glu | Glu | Leu | Ala | Ala | Glu | Cys | Lys | Ser | Ala | Gly | Tyr | Pro | Gly | Thr | Leu | |
| 50 | | | | | 55 | | | | | 60 | | | | | | |

| atc | ccc | tac | aga | tgt | gac | cta | tca | aat | gaa | gag | gac | atc | ctc | tcc | atg | 660 |
|---|---|---|---|---|---|---|---|---|---|---|---|---|---|---|---|---|
| Ile | Pro | Tyr | Arg | Cys | Asp | Leu | Ser | Asn | Glu | Glu | Asp | Ile | Leu | Ser | Met | |
| 65 | | | | 70 | | | | | 75 | | | | | 80 | | |

| ttc | tca | gct | atc | cgt | tct | cag | cac | agc | ggt | gta | gac | atc | tgc | atc | aac | 708 |
|---|---|---|---|---|---|---|---|---|---|---|---|---|---|---|---|---|
| Phe | Ser | Ala | Ile | Arg | Ser | Gln | His | Ser | Gly | Val | Asp | Ile | Cys | Ile | Asn | |
| | | | 85 | | | | | 90 | | | | | 95 | | | |

| aat | gct | ggc | ttg | gcc | cgg | cct | gac | acc | ctg | ctc | tca | ggc | agc | acc | agt | 756 |
|---|---|---|---|---|---|---|---|---|---|---|---|---|---|---|---|---|
| Asn | Ala | Gly | Leu | Ala | Arg | Pro | Asp | Thr | Leu | Leu | Ser | Gly | Ser | Thr | Ser | |
| | 100 | | | | | 105 | | | | | 110 | | | | | |

| ggt | tgg | aag | gac | atg | ttc | aat | gtg | aac | gtg | ctg | gcc | ctc | agc | atc | tgc | 804 |
|---|---|---|---|---|---|---|---|---|---|---|---|---|---|---|---|---|
| Gly | Trp | Lys | Asp | Met | Phe | Asn | Val | Asn | Val | Leu | Ala | Leu | Ser | Ile | Cys | |
| | | 115 | | | | | 120 | | | | | 125 | | | | |

| aca | cgg | gaa | gcc | tac | cag | tcc | atg | aag | gag | cgg | aat | gtg | gac | gat | ggg | 852 |
|---|---|---|---|---|---|---|---|---|---|---|---|---|---|---|---|---|
| Thr | Arg | Glu | Ala | Tyr | Gln | Ser | Met | Lys | Glu | Arg | Asn | Val | Asp | Asp | Gly | |
| 130 | | | | | 135 | | | | | 140 | | | | | | |

| cac | atc | att | aac | atc | aat | agc | atg | tct | ggc | cac | cga | gtg | tta | ccc | ctg | 900 |
|---|---|---|---|---|---|---|---|---|---|---|---|---|---|---|---|---|
| His | Ile | Ile | Asn | Ile | Asn | Ser | Met | Ser | Gly | His | Arg | Val | Leu | Pro | Leu | |
| 145 | | | | 150 | | | | | 155 | | | | | 160 | | |

| tct | gtg | acc | cac | ttc | tat | agt | gcc | acc | aag | tat | gcc | gtc | act | gcg | ctg | 948 |
|---|---|---|---|---|---|---|---|---|---|---|---|---|---|---|---|---|
| Ser | Val | Thr | His | Phe | Tyr | Ser | Ala | Thr | Lys | Tyr | Ala | Val | Thr | Ala | Leu | |
| | | | 165 | | | | | 170 | | | | | 175 | | | |

| aca | gag | gga | ctg | agg | caa | gag | ctt | cgg | gag | gcc | cag | acc | cac | atc | cga | 996 |
|---|---|---|---|---|---|---|---|---|---|---|---|---|---|---|---|---|
| Thr | Glu | Gly | Leu | Arg | Gln | Glu | Leu | Arg | Glu | Ala | Gln | Thr | His | Ile | Arg | |
| | | 180 | | | | | 185 | | | | | 190 | | | | |

| gcc | acg | tgc | atc | tct | cca | ggt | gtg | gtg | gag | aca | caa | ttc | gcc | ttc | aaa | 1044 |
|---|---|---|---|---|---|---|---|---|---|---|---|---|---|---|---|---|
| Ala | Thr | Cys | Ile | Ser | Pro | Gly | Val | Val | Glu | Thr | Gln | Phe | Ala | Phe | Lys | |
| | 195 | | | | | 200 | | | | | 205 | | | | | |

| ctc | cac | gac | aag | gac | cct | gag | aag | gca | gct | gcc | acc | tat | gag | caa | atg | 1092 |
|---|---|---|---|---|---|---|---|---|---|---|---|---|---|---|---|---|
| Leu | His | Asp | Lys | Asp | Pro | Glu | Lys | Ala | Ala | Ala | Thr | Tyr | Glu | Gln | Met | |
| 210 | | | | | 215 | | | | | 220 | | | | | | |

| aag | tgt | ctc | aaa | ccc | gag | gat | gtg | gcc | gag | gct | gtt | atc | tac | gtc | ctc | 1140 |
|---|---|---|---|---|---|---|---|---|---|---|---|---|---|---|---|---|
| Lys | Cys | Leu | Lys | Pro | Glu | Asp | Val | Ala | Glu | Ala | Val | Ile | Tyr | Val | Leu | |
| 225 | | | | 230 | | | | | 235 | | | | | 240 | | |

| agc | act | ccc | gca | cac | atc | cag | att | gga | gac | atc | cag | atg | agg | ccc | acg | 1188 |
|---|---|---|---|---|---|---|---|---|---|---|---|---|---|---|---|---|
| Ser | Thr | Pro | Ala | His | Ile | Gln | Ile | Gly | Asp | Ile | Gln | Met | Arg | Pro | Thr | |

-continued

```
                245                 250                 255
gag cag gtg acc tag tgactgtggg agctcctcct tccctcccca cccttcatgg   1243
Glu Gln Val Thr *
            260 cttgcctcct gcctctggat tttaggtgtt gatttctgga tcacgggata ccacttcctg   1303 tccacacccc gaccagggc tagaaaattt gtttgagatt tttatatcat cttgtcaaat   1363 tgcttcagtt gtaaatgtga aaatgggct ggggaaagga ggtggtgtcc ctaattgttt   1423 tacttgttaa cttgttcttg tgccctggg cacttggcct ttgtctgctc tcagtgtctt   1483 cccttgaca tgggaaagga gttgtggcca aatccccat cttcttgcac ctcaacgtct   1543 gtggctyang ggctggggtg gcagagggag gccttcacct tatatctgtg ttgttatcca   1603 gggctccaga cttcctcctc tgcctgcccc actgcacccc ctcccccta tctatctcct   1663 tctcggctcc ccagcccagt cttggcttct tgtcccctcc tggggtcatc cctccactct   1723 gactctgact atggcagcag aacaccaggg cctggcccag tggatttcat ggtgatcatt   1783 aaaaaagaaa aatcgcaacc aaaaaaaaaa aaaaagggc gggccgctag actagtytag   1843 agaaaaaacc tcccacacct ccccybdamm ytkacgccgn acgcnanggg ggcaatcaag   1903 gacgct                                                             1909
```

<210> SEQ ID NO 7
<211> LENGTH: 260
<212> TYPE: PRT
<213> ORGANISM: Homo sapiens

<400> SEQUENCE: 7

```
Met Glu Lys Cys Glu Ala Ala Lys Asp Ile Arg Gly Glu Thr Leu
 1               5                  10                  15

Asn His His Val Asn Ala Arg His Leu Asp Leu Ala Ser Leu Lys Ser
                20                  25                  30

Ile Arg Glu Phe Ala Ala Lys Ile Glu Glu Glu Arg Val Asp
            35                  40                  45

Ile Leu Ile Asn Asn Ala Gly Val Met Arg Cys Pro His Trp Thr Thr
        50                  55                  60

Glu Asp Gly Phe Glu Met Gln Phe Gly Val Asn His Leu Gly His Phe
65                  70                  75                  80

Leu Leu Thr Asn Leu Leu Asp Lys Leu Lys Ala Ser Ala Pro Ser
                85                  90                  95

Arg Ile Ile Asn Leu Ser Ser Leu Ala His Val Ala Gly His Ile Asp
            100                 105                 110

Phe Asp Asp Leu Asn Trp Gln Thr Arg Lys Tyr Asn Thr Lys Ala Ala
        115                 120                 125

Tyr Cys Gln Ser Lys Leu Ala Ile Val Leu Phe Thr Lys Glu Leu Ser
    130                 135                 140

Arg Arg Leu Gln Gly Ser Gly Val Thr Val Asn Ala Leu His Pro Gly
145                 150                 155                 160

Val Ala Arg Thr Glu Leu Gly Arg His Thr Gly Ile His Gly Ser Thr
                165                 170                 175

Phe Ser Ser Thr Thr Leu Gly Pro Ile Phe Trp Leu Val Lys Ser
            180                 185                 190

Pro Glu Leu Ala Ala Gln Pro Ser Thr Tyr Leu Ala Val Ala Glu Glu
        195                 200                 205

Leu Ala Asp Val Ser Gly Lys Tyr Phe Asp Gly Leu Lys Gln Lys Ala
    210                 215                 220
```

```
Pro Ala Pro Glu Ala Glu Asp Glu Val Ala Arg Arg Leu Trp Ala
225                 230                 235                 240

Glu Ser Ala Arg Leu Val Gly Leu Glu Ala Pro Ser Val Arg Glu Gln
            245                 250                 255

Pro Leu Pro Arg
        260

<210> SEQ ID NO 8
<211> LENGTH: 1153
<212> TYPE: DNA
<213> ORGANISM: Homo sapiens
<220> FEATURE:
<221> NAME/KEY: CDS
<222> LOCATION: (265)...(1047)
<220> FEATURE:
<221> NAME/KEY: misc_feature
<222> LOCATION: 24, 25, 27, 77, 78
<223> OTHER INFORMATION: n = A,T,C or G

<400> SEQUENCE: 8 ccgcgcccg ccctcgcagc ccanntncgg acgcgggccc agccgcgcct gcgcttccgc      60
tcgcctgtgg ctgcaannag cgcgctcttc ctcggagcta cccaggcggc tggtgtagca    120
gcaagctccg cgccgacccc tgacgcctga cgcctgtccc cggccggca tgagccgcta    180 cctgctgccg ctgtcggcgc tgggcacggt agcaggcgct cgccgtgctg ctcaagaggc    240
aacatcatcc tggcctgccg agac atg gag aag tgt gag gcg gca gca aag      291
                          Met Glu Lys Cys Glu Ala Ala Ala Lys
                          1               5 gac atc cgc ggg gag acc ctc aat cac cat gtc aac gcc cgg cac ctg      339
Asp Ile Arg Gly Glu Thr Leu Asn His His Val Asn Ala Arg His Leu
 10              15                  20                  25 gac ttg gct tcc ctc aag tct atc cga gag ttt gca gca aag atc att      387
Asp Leu Ala Ser Leu Lys Ser Ile Arg Glu Phe Ala Ala Lys Ile Ile
            30                  35                  40 gaa gag gag gag cga gtg gac att cta atc aac aac gcg ggt gtg atg      435
Glu Glu Glu Glu Arg Val Asp Ile Leu Ile Asn Asn Ala Gly Val Met
        45                  50                  55 cgg tgc ccc cac tgg acc acc gag gac ggc ttc gag atg cag ttt ggc      483
Arg Cys Pro His Trp Thr Thr Glu Asp Gly Phe Glu Met Gln Phe Gly
    60                  65                  70 gtt aac cac ctg ggt cac ttt ctc ttg aca aac ttg ctg ctg gac aag      531
Val Asn His Leu Gly His Phe Leu Leu Thr Asn Leu Leu Leu Asp Lys
75                  80                  85 ctg aaa gcc tca gcc cct tcg cgg atc atc aac ctc tcg tcc ctg gcc      579
Leu Lys Ala Ser Ala Pro Ser Arg Ile Ile Asn Leu Ser Ser Leu Ala
 90                  95                 100                 105 cat gtt gct ggg cac ata gac ttt gac gac ttg aac tgg cag acg agg      627
His Val Ala Gly His Ile Asp Phe Asp Asp Leu Asn Trp Gln Thr Arg
            110                 115                 120 aag tat aac acc aaa gcc gcc tac tgc cag agc aag ctc gcc atc gtc      675
Lys Tyr Asn Thr Lys Ala Ala Tyr Cys Gln Ser Lys Leu Ala Ile Val
        125                 130                 135 ctc ttc acc aag gag ttg agc cgg cgg ctg caa ggc tct ggt gtg act      723
Leu Phe Thr Lys Glu Leu Ser Arg Arg Leu Gln Gly Ser Gly Val Thr
    140                 145                 150 gtc aac gcc ctg cac ccc ggc gtg gcc agg aca gag ctg ggc aga cac      771
Val Asn Ala Leu His Pro Gly Val Ala Arg Thr Glu Leu Gly Arg His
155                 160                 165 acg ggc atc cat ggc tcc acc ttc tcc agc acc aca ctc ggg ccc atc      819
Thr Gly Ile His Gly Ser Thr Phe Ser Ser Thr Thr Leu Gly Pro Ile
```

```
                170               175               180               185
ttc tgg ctg ctg gtc aag agc ccc gag ctg gcc gcc cag ccc agc aca       867
Phe Trp Leu Leu Val Lys Ser Pro Glu Leu Ala Ala Gln Pro Ser Thr
            190                   195                   200 tac ctg gcc gtg gcg gag gaa ctg gcg gat gtt tcc gga aag tac ttc       915
Tyr Leu Ala Val Ala Glu Glu Leu Ala Asp Val Ser Gly Lys Tyr Phe
            205                   210                   215 gat gga ctc aaa cag aag gcc ccg gcc ccc gag gct gag gat gag gag       963
Asp Gly Leu Lys Gln Lys Ala Pro Ala Pro Glu Ala Glu Asp Glu Glu
            220                   225                   230 gtg gcc cgg agg ctt tgg gct gaa agt gcc cgc ctg gtg ggc tta gag      1011
Val Ala Arg Arg Leu Trp Ala Glu Ser Ala Arg Leu Val Gly Leu Glu
235                   240                   245 gct ccc tct gtg agg gag cag ccc ctc ccc aga taa cctctggagc           1057
Ala Pro Ser Val Arg Glu Gln Pro Leu Pro Arg *
250                   255                   260 agatttgaaa gccaggatgg cgcctccaga ccgaggacag ctgtccgcca tgcccgcagc    1117
ttcctggcac tacctgagcc gggagaccca ggactg                              1153

<210> SEQ ID NO 9
<211> LENGTH: 331
<212> TYPE: PRT
<213> ORGANISM: Homo sapiens

<400> SEQUENCE: 9

Met Ser Arg Tyr Leu Leu Pro Leu Ser Ala Leu Gly Thr Val Ala Gly
1               5                   10                  15

Ala Ala Val Leu Leu Lys Asp Tyr Val Thr Gly Gly Ala Cys Pro Ser
                20                  25                  30

Lys Ala Thr Ile Pro Gly Lys Thr Val Ile Val Thr Gly Ala Asn Thr
            35                  40                  45

Gly Ile Gly Lys Gln Thr Ala Leu Glu Leu Ala Arg Arg Gly Gly Asn
        50                  55                  60

Ile Ile Leu Ala Cys Arg Asp Met Glu Lys Cys Glu Ala Ala Ala Lys
65                  70                  75                  80

Asp Ile Arg Gly Glu Thr Leu Asn His His Val Asn Ala Arg His Leu
                85                  90                  95

Asp Leu Ala Ser Leu Lys Ser Ile Arg Glu Phe Ala Ala Lys Ile Ile
            100                 105                 110

Glu Glu Glu Glu Arg Val Asp Ile Leu Ile Asn Asn Ala Gly Val Met
        115                 120                 125

Arg Cys Pro His Trp Thr Thr Glu Asp Gly Phe Glu Met Gln Phe Gly
    130                 135                 140

Val Asn His Leu Gly His Phe Leu Leu Thr Asn Leu Leu Leu Asp Lys
145                 150                 155                 160

Leu Lys Ala Ser Ala Pro Ser Arg Ile Ile Asn Leu Ser Ser Leu Ala
                165                 170                 175

His Val Ala Gly His Ile Asp Phe Asp Asp Leu Asn Trp Gln Thr Arg
            180                 185                 190

Lys Tyr Asn Thr Lys Ala Ala Tyr Cys Gln Ser Lys Leu Ala Ile Val
        195                 200                 205

Leu Phe Thr Lys Glu Leu Ser Arg Arg Leu Gln Gly Ser Gly Val Thr
    210                 215                 220

Val Asn Ala Leu His Pro Gly Val Ala Arg Thr Glu Leu Gly Arg His
225                 230                 235                 240
```

```
Thr Gly Ile His Gly Ser Thr Phe Ser Ser Thr Thr Leu Gly Pro Ile
                245                 250                 255

Phe Trp Leu Leu Val Lys Ser Pro Glu Leu Val Ala Gln Pro Ser Thr
            260                 265                 270

Tyr Leu Ala Val Ala Glu Glu Leu Ala Asp Val Ser Gly Lys Tyr Phe
        275                 280                 285

Asp Gly Leu Lys Gln Lys Ala Pro Ala Glu Ala Glu Asp Glu Glu
    290                 295                 300

Val Ala Arg Arg Leu Trp Ala Glu Ser Ala Arg Leu Val Gly Leu Glu
305                 310                 315                 320

Ala Pro Ser Val Arg Glu Gln Pro Leu Pro Arg
                325                 330

<210> SEQ ID NO 10
<211> LENGTH: 1699
<212> TYPE: DNA
<213> ORGANISM: Homo sapiens
<220> FEATURE:
<221> NAME/KEY: CDS
<222> LOCATION: (538)...(1533)
<220> FEATURE:
<221> NAME/KEY: misc_feature
<222> LOCATION: 3, 19, 71, 74, 111, 138, 160
<223> OTHER INFORMATION: n = A,T,C or G

<400> SEQUENCE: 10
gcntgtgggt cccttcttna aattgggtcc ccccgtttta ggtaagttta aaagctcaag      60
gttcaaagac nggnccttt gtcgggggct ccttgaagcc tactagatca ncggctctca     120 gcttttttt ttgggggncc cccccttg ggaaccccn tggctttgct tcaaacttct        180
aaggtctttt gtttcgtttt ctgttcctgc gccgttacag atccaagytc tgaaaaacca    240
gaaagttaac tggtaagttt agtcttttg tcttttattt caggtcccgg atccggtggt     300
ggtgcaaatc aaagaactgc tcctcagtgg atgttgcctt tacttctagg cctgtacgaa    360
gtgttacttc tgctctaaaa gctgcggaat tctaatacga ctcactatag ggagtcgacc    420
cacgcgtccg cggacgcgtg gcggacgcg tgggcggagc tacccaggcg ctggtgtgc      480 agcaagctcc gcgccgactc cggacgcctg acgcctgacg cctgtccccg gccggc atg   540
                                                                Met
                                                                 1 agc cgc tac ctg ctg ccg ctg tcg gcg ctg ggc acg gta gca ggc gcc     588
Ser Arg Tyr Leu Leu Pro Leu Ser Ala Leu Gly Thr Val Ala Gly Ala
        5                  10                  15 gcc gtg ctg ctc aag gac tat gtc acc ggt ggg gct tgc ccc agc aag     636
Ala Val Leu Leu Lys Asp Tyr Val Thr Gly Gly Ala Cys Pro Ser Lys
     20                  25                  30 gcc acc atc cct ggg aag acg gtc atc gtg acg ggc gcc aac aca ggc     684
Ala Thr Ile Pro Gly Lys Thr Val Ile Val Thr Gly Ala Asn Thr Gly
 35                  40                  45 atc ggg aag cag acc gcc ttg gaa ctg gcc agg aga gga ggc aac atc     732
Ile Gly Lys Gln Thr Ala Leu Glu Leu Ala Arg Arg Gly Gly Asn Ile
 50                  55                  60                  65 atc ctg gcc tgc cga gac atg gag aag tgt gag gcg gca gca aag gac     780
Ile Leu Ala Cys Arg Asp Met Glu Lys Cys Glu Ala Ala Ala Lys Asp
             70                  75                  80 atc cgc ggg gag acc ctc aat cac cat gtc aac gcc cgg cac ctg gac     828
Ile Arg Gly Glu Thr Leu Asn His His Val Asn Ala Arg His Leu Asp
         85                  90                  95 ttg gct tcc ctc aag tct atc cga gag ttt gca gca aag atc att gaa     876
Leu Ala Ser Leu Lys Ser Ile Arg Glu Phe Ala Ala Lys Ile Ile Glu
```

```
                    100                 105                 110
gag gag gag cga gtg gac att cta atc aac aac gcg ggt gtg atg cgg    924
Glu Glu Glu Arg Val Asp Ile Leu Ile Asn Asn Ala Gly Val Met Arg
        115                 120                 125 tgc ccc cac tgg acc acc gag gac ggc ttc gag atg cag ttt ggc gtt    972
Cys Pro His Trp Thr Thr Glu Asp Gly Phe Glu Met Gln Phe Gly Val
130                 135                 140                 145 aac cac ctg ggt cac ttt ctc ttg aca aac ttg ctg ctg gac aag ctg   1020
Asn His Leu Gly His Phe Leu Leu Thr Asn Leu Leu Leu Asp Lys Leu
                150                 155                 160 aaa gcc tca gcc cct tcg cgg atc atc aac ctc tcg tcc ctg gcc cat   1068
Lys Ala Ser Ala Pro Ser Arg Ile Ile Asn Leu Ser Ser Leu Ala His
        165                 170                 175 gtt gct ggg cac ata gac ttt gac gac ttg aac tgg cag acg agg aag   1116
Val Ala Gly His Ile Asp Phe Asp Asp Leu Asn Trp Gln Thr Arg Lys
                180                 185                 190 tat aac acc aaa gcc gcc tac tgc cag agc aag ctc gcc atc gtc ctc   1164
Tyr Asn Thr Lys Ala Ala Tyr Cys Gln Ser Lys Leu Ala Ile Val Leu
195                 200                 205 ttc acc aag gag ctg agc cgg cgg ctg caa ggc tct ggt gtg act gtc   1212
Phe Thr Lys Glu Leu Ser Arg Arg Leu Gln Gly Ser Gly Val Thr Val
210                 215                 220                 225 aac gcc ctg cac ccc ggc gtg gcc agg aca gag ctg ggc aga cac acg   1260
Asn Ala Leu His Pro Gly Val Ala Arg Thr Glu Leu Gly Arg His Thr
        230                 235                 240 ggc atc cat ggc tcc acc ttc tcc agc acc aca ctc ggg ccc atc ttc   1308
Gly Ile His Gly Ser Thr Phe Ser Ser Thr Thr Leu Gly Pro Ile Phe
                245                 250                 255 tgg ctg ctg gtc aag agc ccc gag ctg gtc gcc cag ccc agc aca tac   1356
Trp Leu Leu Val Lys Ser Pro Glu Leu Val Ala Gln Pro Ser Thr Tyr
        260                 265                 270 ctg gcc gtg gcg gag gaa ctg gcg gat gtt tcc gga aag tac ttc gat   1404
Leu Ala Val Ala Glu Glu Leu Ala Asp Val Ser Gly Lys Tyr Phe Asp
275                 280                 285 gga ctc aaa cag aag gcc ccg gcc ccc gag gct gag gat gag gag gtg   1452
Gly Leu Lys Gln Lys Ala Pro Ala Pro Glu Ala Glu Asp Glu Glu Val
290                 295                 300                 305 gcc cgg agg ctt tgg gct gaa agt gcc cgc ctg gtg ggc tta gag gct   1500
Ala Arg Arg Leu Trp Ala Glu Ser Ala Arg Leu Val Gly Leu Glu Ala
        310                 315                 320 ccc tct gtg agg gag cag ccc ctc ccc aga taa cctctggagc agatttgaaa  1553
Pro Ser Val Arg Glu Gln Pro Leu Pro Arg  *
                325                 330 gccaggatgg cgcctccaga ccgaggacag ctgtccgcca tgcccgcagc ttcctggcac   1613
tacctgagcc gggagaccca ggactggcgg ccgctagact agtctagaga aaaacctcc   1673 cacacctccc cctgaacctg aaacat                                       1699

<210> SEQ ID NO 11
<211> LENGTH: 418
<212> TYPE: PRT
<213> ORGANISM: Homo sapiens

<400> SEQUENCE: 11

Met Leu Pro Asn Thr Gly Arg Leu Ala Gly Cys Thr Val Phe Ile Thr
1               5                   10                  15

Gly Ala Ser Arg Gly Ile Gly Lys Ala Ile Ala Leu Lys Ala Ala Lys
            20                  25                  30

Asp Gly Ala Asn Ile Val Ile Ala Ala Lys Thr Ala Gln Pro His Pro
```

```
                 35                  40                  45
Lys Leu Leu Gly Thr Ile Tyr Thr Ala Ala Glu Glu Ile Glu Ala Val
 50                  55                  60
Gly Gly Lys Ala Leu Pro Cys Ile Val Asp Val Arg Asp Glu Gln Gln
 65                  70                  75                  80
Ile Ser Ala Ala Val Glu Lys Ala Ile Lys Lys Phe Gly Gly Ile Asp
                 85                  90                  95
Ile Leu Val Asn Asn Ala Ser Ala Ile Ser Leu Thr Asn Thr Leu Asp
                100                 105                 110
Thr Pro Thr Lys Arg Leu Asp Leu Met Met Asn Val Asn Thr Arg Gly
                115                 120                 125
Thr Tyr Leu Ala Ser Lys Ala Cys Ile Pro Tyr Leu Lys Lys Ser Lys
                130                 135                 140
Val Ala His Ile Leu Asn Ile Ser Pro Pro Leu Asn Leu Asn Pro Val
145                 150                 155                 160
Trp Phe Lys Gln His Cys Ala Tyr Thr Ile Ala Lys Tyr Gly Met Ser
                165                 170                 175
Met Tyr Val Leu Gly Met Ala Glu Glu Phe Lys Gly Glu Ile Ala Val
                180                 185                 190
Asn Ala Leu Trp Pro Lys Thr Ala Ile His Thr Ala Ala Met Asp Met
                195                 200                 205
Leu Gly Gly Pro Gly Ile Glu Ser Gln Cys Arg Lys Val Asp Ile Ile
                210                 215                 220
Ala Asp Ala Ala Tyr Ser Ile Phe Gln Lys Pro Lys Ser Phe Thr Gly
225                 230                 235                 240
Asn Phe Val Ile Asp Glu Asn Ile Leu Lys Glu Glu Gly Ile Glu Asn
                245                 250                 255
Phe Asp Val Tyr Ala Ile Lys Pro Gly His Pro Leu Gln Pro Asp Phe
                260                 265                 270
Phe Leu Asp Glu Tyr Pro Glu Ala Val Ser Lys Lys Val Glu Ser Thr
                275                 280                 285
Gly Ala Val Pro Glu Phe Lys Glu Glu Lys Leu Gln Leu Gln Pro Lys
                290                 295                 300
Pro Arg Ser Gly Ala Val Glu Glu Thr Phe Arg Ile Val Lys Asp Ser
305                 310                 315                 320
Leu Ser Asp Asp Val Val Lys Ala Thr Gln Ala Ile Tyr Leu Phe Glu
                325                 330                 335
Leu Ser Gly Glu Asp Gly Gly Thr Trp Phe Leu Asp Leu Lys Ser Lys
                340                 345                 350
Gly Gly Asn Val Gly Tyr Gly Glu Pro Ser Asp Gln Ala Asp Val Val
                355                 360                 365
Met Ser Met Thr Thr Asp Asp Phe Val Lys Met Phe Ser Gly Lys Leu
                370                 375                 380
Lys Pro Thr Met Ala Phe Met Ser Gly Lys Leu Lys Ile Lys Gly Asn
385                 390                 395                 400
Met Ala Leu Ala Ile Lys Leu Glu Lys Leu Met Asn Gln Met Asn Ala
                405                 410                 415
Arg Leu

<210> SEQ ID NO 12
<211> LENGTH: 2535
<212> TYPE: DNA
<213> ORGANISM: Homo sapiens
<220> FEATURE:
```

-continued

```
<221> NAME/KEY: CDS
<222> LOCATION: (762)...(2018)
<220> FEATURE:
<221> NAME/KEY: misc_feature
<222> LOCATION: 89
<223> OTHER INFORMATION: n = A,T,C or G

<400> SEQUENCE: 12
aggcagaagt atgcaaagca tgcatctcaa attagtcagc aaaccatagt cccggcccct      60
aactccgccc atcccgcccc taactccgnc ccagttccgg cccattctcc gcccatggc     120 tgactaattt ttttattta tgcagagccg aggccgcctc ggcctctgag ctattccaga     180
agtagtgagg aggcttttt ggaggcctag cttttgcaa aaagctcctc gatcgagggg      240
ctcgcatctc tccttcacgc gcccgccgcc ctacctgagg ccgccatcca cgccggttga     300
gtcgcgttct gccgcctccc gcctgtggtg cctcctgaac tgcgtccgcc gtctaggtaa     360
gtttaaagct caggtcgaga ccgggccttt gtccggcgct cccttggagc ctacctagac     420
tcagccggct ctccacgctt tgcctgaccc tgcttgctca actctacgtc tttgtttcag     480
ttttctgttc tgcgccgtta cagatccaag ctctgaaaaa ccagaaagtt aactggtaag     540
tttagtcttt ttgtcttta tttcaggtcc cggatccggt ggtggtgcaa atcaaagaac      600
tgctcctcag tggatgttgc ctttacttct aggcctgtac ggaagtgtta cttctgctct     660
aaaagctgcg gaattctaat acgactcact ataggwgtc gacccacgcg tccgctcgcc     720
gccgccgctg tcgccgccac ctcctctgat ctacgaaagt c atg tta ccc aac acc     776
                                             Met Leu Pro Asn Thr
                                               1               5 ggg agg ctg gca gga tgt aca gtt ttt atc aca ggt gca agc cgt ggc       824
Gly Arg Leu Ala Gly Cys Thr Val Phe Ile Thr Gly Ala Ser Arg Gly
         10                  15                  20 att ggc aaa gct att gca ttg aaa gca gca aag gat gga gca aat att       872
Ile Gly Lys Ala Ile Ala Leu Lys Ala Ala Lys Asp Gly Ala Asn Ile
     25                  30                  35 gtt att gct gca aag acc gcc cag cca cat cca aaa ctt cta ggc aca       920
Val Ile Ala Ala Lys Thr Ala Gln Pro His Pro Lys Leu Leu Gly Thr
 40                  45                  50 atc tat act gct gct gaa gaa att gaa gca gtt gga gga aag gcc ttg       968
Ile Tyr Thr Ala Ala Glu Glu Ile Glu Ala Val Gly Gly Lys Ala Leu
             55                  60                  65 cca tgt att gtt gat gtg aga gat gaa cag cag atc agt gct gca gtg      1016
Pro Cys Ile Val Asp Val Arg Asp Glu Gln Gln Ile Ser Ala Ala Val
 70                  75                  80                  85 gag aaa gcc atc aag aaa ttt gga gga att gat att ctg gta aat aat      1064
Glu Lys Ala Ile Lys Lys Phe Gly Gly Ile Asp Ile Leu Val Asn Asn
                 90                  95                 100 gcc agt gcc att agt ttg acc aat aca ttg gac aca cct acc aag aga      1112
Ala Ser Ala Ile Ser Leu Thr Asn Thr Leu Asp Thr Pro Thr Lys Arg
            105                 110                 115 ttg gat ctg atg atg aac gtg aac acc aga ggc acc tac ctt gca tct      1160
Leu Asp Leu Met Met Asn Val Asn Thr Arg Gly Thr Tyr Leu Ala Ser
        120                 125                 130 aaa gca tgt att cct tat ttg aaa aag agc aaa gtt gct cat atc ctc      1208
Lys Ala Cys Ile Pro Tyr Leu Lys Lys Ser Lys Val Ala His Ile Leu
    135                 140                 145 aat atc agt cca cca ctg aac cta aat cca gtt tgg ttc aaa cag cac      1256
Asn Ile Ser Pro Pro Leu Asn Leu Asn Pro Val Trp Phe Lys Gln His
150                 155                 160                 165 tgt gct tat acc att gct aag tat ggt atg tct atg tat gtg ctt gga      1304
Cys Ala Tyr Thr Ile Ala Lys Tyr Gly Met Ser Met Tyr Val Leu Gly
```

```
                    170               175               180
atg gca gaa gaa ttt aaa ggt gaa att gca gtc aat gca tta tgg cct    1352
Met Ala Glu Glu Phe Lys Gly Glu Ile Ala Val Asn Ala Leu Trp Pro
            185               190               195 aaa aca gcc ata cac act gct gct atg gat atg ctg gga gga cct ggt    1400
Lys Thr Ala Ile His Thr Ala Ala Met Asp Met Leu Gly Gly Pro Gly
            200               205               210 atc gaa agc cag tgt aga aaa gtt gat atc att gca gat gca gca tat    1448
Ile Glu Ser Gln Cys Arg Lys Val Asp Ile Ile Ala Asp Ala Ala Tyr
            215               220               225 tcc att ttc caa aag cca aaa agt ttt act ggc aac ttt gtc att gat    1496
Ser Ile Phe Gln Lys Pro Lys Ser Phe Thr Gly Asn Phe Val Ile Asp
230               235               240               245 gaa aat atc tta aaa gaa gaa gga ata gaa aat ttt gac gtt tat gca    1544
Glu Asn Ile Leu Lys Glu Glu Gly Ile Glu Asn Phe Asp Val Tyr Ala
            250               255               260 att aaa cca ggt cat cct ttg caa cca gat ttc ttc tta gat gaa tac    1592
Ile Lys Pro Gly His Pro Leu Gln Pro Asp Phe Phe Leu Asp Glu Tyr
            265               270               275 cca gaa gca gtt agc aag aaa gtg gaa tca act ggt gct gtt cca gaa    1640
Pro Glu Ala Val Ser Lys Lys Val Glu Ser Thr Gly Ala Val Pro Glu
            280               285               290 ttc aaa gaa gag aaa ctg cag ctg caa cca aaa cca cgt tct gga gct    1688
Phe Lys Glu Glu Lys Leu Gln Leu Gln Pro Lys Pro Arg Ser Gly Ala
295               300               305 gtg gaa gaa aca ttt aga att gtt aag gac tct ctc agt gat gat gtt    1736
Val Glu Glu Thr Phe Arg Ile Val Lys Asp Ser Leu Ser Asp Asp Val
310               315               320               325 gtt aaa gcc act caa gca atc tat ctg ttt gaa ctc tcc ggt gaa gat    1784
Val Lys Ala Thr Gln Ala Ile Tyr Leu Phe Glu Leu Ser Gly Glu Asp
            330               335               340 ggt ggc acg tgg ttt ctt gat ctg aaa agc aag ggt ggg aat gtc gga    1832
Gly Gly Thr Trp Phe Leu Asp Leu Lys Ser Lys Gly Gly Asn Val Gly
            345               350               355 tat gga gag cct tct gat cag gca gat gtg gtg atg agt atg act act    1880
Tyr Gly Glu Pro Ser Asp Gln Ala Asp Val Val Met Ser Met Thr Thr
            360               365               370 gat gac ttt gta aaa atg ttt tca ggg aaa cta aaa cca aca atg gca    1928
Asp Asp Phe Val Lys Met Phe Ser Gly Lys Leu Lys Pro Thr Met Ala
375               380               385 ttc atg tca ggg aaa ttg aag att aaa ggt aac atg gcc cta gca atc    1976
Phe Met Ser Gly Lys Leu Lys Ile Lys Gly Asn Met Ala Leu Ala Ile
390               395               400               405 aaa ttg gag aag cta atg aat cag atg aat gcc aga ctg tga             2018
Lys Leu Glu Lys Leu Met Asn Gln Met Asn Ala Arg Leu  *
            410               415 aggaaaatat aaaaaaaaag tcgactgcta tgctcaaaaa gtaaaaaaag ctcaacagtt   2078
aaaatctaat gtttgttttc tttcctgtta tattataagg atatgcacgt ttgttctgga   2138
aaagatagaa tttgtctcta aaagacttga aattgtaatt aaaatggcaa gctaatcaaa   2198
cataagcttc attaagtggg attctaagac agtctgtgtt tttatatttc aagggtttaa   2258 cccttttgagc cttacatctc attcactgtc tttctccaag aaaagtattt tgggcggaca   2318
gtcagatcaa gcagtaaaat tagctctttc aaatcttctt gtcatgtaaa atgaagctag   2378
tctgttttaa aatttttagt tttggattgt atactaatga aaatcttaat gatgttttkr   2438
wtttttatat acytawtttw aarraaawyy twwwwwrkwc mtttttwmcaa aaawtwttaa   2498 aaawkrrwww kwrytskgsg mgraswmwaw rwrammc                             2535
```

<210> SEQ ID NO 13
<211> LENGTH: 245
<212> TYPE: PRT
<213> ORGANISM: Homo sapiens

<400> SEQUENCE: 13

```
Met Gly Arg Leu Asp Gly Lys Val Ile Ile Leu Thr Ala Ala Ala Gln
 1               5                  10                  15

Gly Ile Gly Gln Ala Ala Ala Leu Ala Phe Ala Arg Glu Gly Ala Lys
            20                  25                  30

Val Ile Ala Thr Asp Ile Asn Glu Ser Lys Leu Gln Glu Leu Glu Lys
        35                  40                  45

Tyr Pro Gly Ile Gln Thr Arg Val Leu Asp Val Thr Lys Lys Lys Gln
    50                  55                  60

Ile Asp Gln Phe Ala Asn Glu Val Glu Arg Leu Asp Val Leu Phe Asn
65                  70                  75                  80

Val Ala Gly Phe Val His His Gly Thr Val Leu Asp Cys Glu Glu Lys
                85                  90                  95

Asp Trp Asp Phe Ser Met Asn Leu Asn Val Arg Ser Met Tyr Leu Met
            100                 105                 110

Ile Lys Ala Phe Leu Pro Lys Met Leu Ala Gln Lys Ser Gly Asn Ile
        115                 120                 125

Ile Asn Met Ser Ser Val Ala Ser Ser Val Lys Gly Val Val Asn Arg
    130                 135                 140

Cys Val Tyr Ser Thr Thr Lys Ala Ala Val Ile Gly Leu Thr Lys Ser
145                 150                 155                 160

Val Ala Ala Asp Phe Ile Gln Gln Gly Ile Arg Cys Asn Cys Val Cys
                165                 170                 175

Pro Gly Thr Val Asp Thr Pro Ser Leu Gln Glu Arg Ile Gln Ala Arg
            180                 185                 190

Gly Asn Pro Glu Glu Ala Arg Asn Asp Phe Leu Lys Arg Gln Lys Thr
        195                 200                 205

Gly Arg Phe Ala Thr Ala Glu Ile Ala Met Leu Cys Val Tyr Leu
    210                 215                 220

Ala Ser Asp Glu Ser Ala Tyr Val Thr Gly Asn Pro Val Ile Ile Asp
225                 230                 235                 240

Gly Gly Trp Ser Leu
                245
```

<210> SEQ ID NO 14
<211> LENGTH: 1716
<212> TYPE: DNA
<213> ORGANISM: Homo sapiens
<220> FEATURE:
<221> NAME/KEY: CDS
<222> LOCATION: (637)...(1374)
<220> FEATURE:
<221> NAME/KEY: misc_feature
<222> LOCATION: 15
<223> OTHER INFORMATION: n = A,T,C or G

<400> SEQUENCE: 14

| | | | |
|---|---|---|---|
| atgcaaaagc cgagnccgcc tcggcctcta agctattcca gaagtagtaa gaaggctttt | 60 |
| ttgaaggcct aggcttttgc aaaaagctcc tcgatcgagg ggctcgcatc tctccttcac | 120 |
| ggggccgccg ccctacctga ggccgccatc cacgccggtt gagtcgcgtt ctgccgcctc | 180 |
| ccgcctgtgg tgcctcctga actgcgtccg ccgtytaggt aagtttaaag ctcaggtcga | 240 |

```
gaccgggcct ttgtccggcg ctcccttgga gcctacctag actcagccgg ctctccacgc    300
tttgcctgac cctgcttgct caactctacg tctttgtttc gttttctgtt ctgcgccgtt    360
acagatccaa gctctgaaaa accagaaagt taactggtaa gtttagtctt tttgtctttt    420
atttcaggtc ccggatccgg tggtggtgca aatcaaagaa ctgctcctca gtggatgttg    480
cctttacttc taggcctgta cggaagtgtt acttctgctc taaaagctgc ggaattctaa    540
tacgactcac tatagggagt cgacccacgc gtccgcaaac cgagttctgg agaacgccat    600
cagctcgctg cttaaaatta aaccacaggt tccatt atg ggt cga ctt gat ggg     654
                                         Met Gly Arg Leu Asp Gly
                                          1               5 aaa gtc atc atc ctg acg gcc gct gct cag ggg att ggc caa gca gct     702
Lys Val Ile Ile Leu Thr Ala Ala Ala Gln Gly Ile Gly Gln Ala Ala
                10                  15                  20 gcc tta gct ttt gca aga gaa ggt gcc aaa gtc ata gcc aca gac att     750
Ala Leu Ala Phe Ala Arg Glu Gly Ala Lys Val Ile Ala Thr Asp Ile
         25                  30                  35 aat gag tcc aaa ctt cag gaa ctg gaa aag tac ccg ggt att caa act     798
Asn Glu Ser Lys Leu Gln Glu Leu Glu Lys Tyr Pro Gly Ile Gln Thr
 40                  45                  50 cgt gtc ctt gat gtc aca aag aag aaa caa att gat cag ttt gcc aat     846
Arg Val Leu Asp Val Thr Lys Lys Lys Gln Ile Asp Gln Phe Ala Asn
 55                  60                  65                  70 gaa gtt gag aga ctt gat gtt ctc ttt aat gtt gct ggt ttt gtc cat     894
Glu Val Glu Arg Leu Asp Val Leu Phe Asn Val Ala Gly Phe Val His
                 75                  80                  85 cat gga act gtc ctg gat tgt gag gag aaa gac tgg gac ttc tcg atg     942
His Gly Thr Val Leu Asp Cys Glu Glu Lys Asp Trp Asp Phe Ser Met
         90                  95                 100 aat ctc aat gtg cgc agc atg tac ctg atg atc aag gca ttc ctt cct     990
Asn Leu Asn Val Arg Ser Met Tyr Leu Met Ile Lys Ala Phe Leu Pro
             105                 110                 115 aaa atg ctt gct cag aaa tct ggc aat att atc aac atg tct tct gtg    1038
Lys Met Leu Ala Gln Lys Ser Gly Asn Ile Ile Asn Met Ser Ser Val
120                 125                 130 gct tcc agc gtc aaa gga gtt gtg aac aga tgt gta tac agc aca acc    1086
Ala Ser Ser Val Lys Gly Val Val Asn Arg Cys Val Tyr Ser Thr Thr
135                 140                 145                 150 aag gca gcc gtg att ggc ctc aca aaa tct gtg gct gca gat ttc atc    1134
Lys Ala Ala Val Ile Gly Leu Thr Lys Ser Val Ala Ala Asp Phe Ile
                155                 160                 165 cag cag ggc atc agg tgc aac tgt gtg tgc cca gga aca gtt gat acg    1182
Gln Gln Gly Ile Arg Cys Asn Cys Val Cys Pro Gly Thr Val Asp Thr
            170                 175                 180 cca tct cta caa gaa aga ata caa gcc aga gga aat cct gaa gag gca    1230
Pro Ser Leu Gln Glu Arg Ile Gln Ala Arg Gly Asn Pro Glu Glu Ala
                185                 190                 195 cgg aat gat ttc ctg aag aga caa aag acg gga aga ttc gca act gca    1278
Arg Asn Asp Phe Leu Lys Arg Gln Lys Thr Gly Arg Phe Ala Thr Ala
200                 205                 210 gaa gaa ata gcc atg ctc tgc gtg tat ttg gct tct gat gaa tct gct    1326
Glu Glu Ile Ala Met Leu Cys Val Tyr Leu Ala Ser Asp Glu Ser Ala
215                 220                 225                 230 tat gta act ggt aac cct gtc atc att gat gga ggc tgg agc ttg tga    1374
Tyr Val Thr Gly Asn Pro Val Ile Ile Asp Gly Gly Trp Ser Leu  *
                235                 240                 245 ttttaggatc ccatggtgg gaaggaaggc aggcccttcc tatccacagt gaacctggtt    1434
```

-continued

```
acgaagaaaa ctcaccaatc atctccttcc tgttaatcac atgttaatga aaataagctc    1494
tttttaatga tgtcactgtt tgcaagagtc tgattcttta agtatattaa tctctttgta    1554
atctcttctg aaatcattgt aaagaaataa aaatattgaa ctcaaaaaaa aaaaaaaaaa    1614
aagggcggcc gctagactag tctagagaaa aaacctccca cacctccccc tgaacctgaa    1674
acataaaatg aatgcmattg ttgktggtaa cttgttattg ca                       1716
```

<210> SEQ ID NO 15
<211> LENGTH: 1123
<212> TYPE: PRT
<213> ORGANISM: Homo sapiens

<400> SEQUENCE: 15

```
Met Pro Ile Val Asp Lys Leu Lys Glu Ala Leu Lys Pro Gly Arg Lys
 1               5                   10                  15

Asp Ser Ala Asp Asp Gly Glu Leu Gly Lys Leu Leu Ala Ser Ser Ala
                20                  25                  30

Lys Lys Val Leu Leu Gln Lys Ile Glu Phe Glu Pro Ala Ser Lys Ser
            35                  40                  45

Phe Ser Tyr Gln Leu Glu Ala Leu Lys Ser Lys Tyr Val Leu Leu Asn
        50                  55                  60

Pro Lys Thr Glu Gly Ala Ser Arg His Lys Ser Gly Asp Asp Pro Pro
    65                  70                  75                  80

Ala Arg Arg Gln Gly Ser Glu His Thr Tyr Glu Ser Cys Gly Asp Gly
                85                  90                  95

Val Pro Ala Pro Gln Lys Val Leu Phe Pro Thr Glu Arg Leu Ser Leu
            100                 105                 110

Arg Trp Glu Arg Val Phe Arg Val Gly Ala Gly Leu His Asn Leu Gly
        115                 120                 125

Asn Thr Cys Phe Leu Asn Ala Thr Ile Gln Cys Leu Thr Tyr Thr Pro
    130                 135                 140

Pro Leu Ala Asn Tyr Leu Leu Ser Lys Glu His Ala Arg Ser Cys His
145                 150                 155                 160

Gln Gly Ser Phe Cys Met Leu Cys Val Met Gln Asn His Ile Val Gln
                165                 170                 175

Ala Phe Ala Asn Ser Gly Asn Ala Ile Lys Pro Val Ser Phe Ile Arg
            180                 185                 190

Asp Leu Lys Lys Ile Ala Arg His Phe Arg Phe Gly Asn Gln Glu Asp
        195                 200                 205

Ala His Glu Phe Leu Arg Tyr Thr Ile Asp Ala Met Gln Lys Ala Cys
    210                 215                 220

Leu Asn Gly Cys Ala Lys Leu Asp Arg Gln Thr Gln Ala Thr Thr Leu
225                 230                 235                 240

Val His Gln Ile Phe Gly Gly Tyr Leu Arg Ser Arg Val Lys Cys Ser
                245                 250                 255

Val Cys Lys Ser Val Ser Asp Thr Tyr Asp Pro Tyr Leu Asp Val Ala
            260                 265                 270

Leu Glu Ile Arg Gln Ala Ala Asn Ile Val Arg Ala Leu Glu Leu Phe
        275                 280                 285

Val Lys Ala Asp Val Leu Ser Gly Glu Asn Ala Tyr Met Cys Ala Lys
    290                 295                 300

Cys Lys Lys Lys Val Pro Ala Ser Lys Arg Phe Thr Ile His Arg Thr
305                 310                 315                 320

Ser Asn Val Leu Thr Leu Ser Leu Lys Arg Phe Ala Asn Phe Ser Gly
```

-continued

```
                325                 330                 335
Gly Lys Ile Thr Lys Asp Val Gly Tyr Pro Glu Phe Leu Asn Ile Arg
            340                 345                 350

Pro Tyr Met Ser Gln Asn Asn Gly Asp Pro Val Met Tyr Gly Leu Tyr
            355                 360                 365

Ala Val Leu Val His Ser Gly Tyr Ser Cys His Ala Gly His Tyr Tyr
            370                 375                 380

Cys Tyr Val Lys Ala Ser Asn Gly Gln Trp Tyr Gln Met Asn Asp Ser
385                 390                 395                 400

Leu Val His Ser Ser Asn Val Lys Val Leu Asn Gln Gln Ala Tyr
                405                 410                 415

Val Leu Phe Tyr Leu Arg Ile Pro Gly Ser Lys Lys Ser Pro Glu Gly
            420                 425                 430

Leu Ile Ser Arg Thr Gly Ser Ser Leu Pro Gly Arg Pro Ser Val
                435                 440                 445

Ile Pro Asp His Ser Lys Lys Asn Ile Gly Asn Gly Ile Ile Ser Ser
            450                 455                 460

Pro Leu Thr Gly Lys Arg Gln Asp Ser Gly Thr Met Lys Lys Pro His
465                 470                 475                 480

Thr Thr Glu Glu Ile Gly Val Pro Ile Ser Arg Asn Gly Ser Thr Leu
                485                 490                 495

Gly Leu Lys Ser Gln Asn Gly Cys Ile Pro Pro Lys Leu Pro Ser Gly
            500                 505                 510

Ser Pro Ser Pro Lys Leu Ser Gln Thr Pro Thr His Met Pro Thr Ile
            515                 520                 525

Leu Asp Asp Pro Gly Lys Lys Val Lys Lys Pro Ala Pro Pro Gln His
            530                 535                 540

Phe Ser Pro Arg Thr Ala Gln Gly Leu Pro Gly Thr Ser Asn Ser Asn
545                 550                 555                 560

Ser Ser Arg Ser Gly Ser Gln Arg Gln Gly Ser Trp Asp Ser Arg Asp
                565                 570                 575

Val Val Leu Ser Thr Ser Pro Lys Leu Leu Ala Thr Ala Thr Ala Asn
                580                 585                 590

Gly His Gly Leu Lys Gly Asn Asp Glu Ser Ala Gly Leu Asp Arg Arg
            595                 600                 605

Gly Ser Ser Ser Ser Pro Glu His Ser Ala Ser Ser Asp Ser Thr
            610                 615                 620

Lys Ala Pro Gln Thr Pro Arg Ser Gly Ala Ala His Leu Cys Asp Ser
625                 630                 635                 640

Gln Glu Thr Asn Cys Ser Thr Ala Gly His Ser Lys Thr Pro Pro Ser
                645                 650                 655

Gly Ala Asp Ser Lys Thr Val Lys Leu Lys Ser Pro Val Leu Ser Asn
            660                 665                 670

Thr Thr Thr Glu Pro Ala Ser Thr Met Ser Pro Pro Ala Lys Lys
                675                 680                 685

Leu Ala Leu Ser Ala Lys Lys Ala Ser Thr Leu Trp Arg Ala Thr Gly
            690                 695                 700

Asn Asp Leu Arg Pro Pro Pro Ser Pro Ser Ser Asp Leu Thr His
705                 710                 715                 720

Pro Met Lys Thr Ser His Pro Val Val Ala Ser Thr Trp Pro Val His
                725                 730                 735

Arg Ala Arg Ala Val Ser Pro Ala Pro Gln Ser Ser Arg Leu Gln
                740                 745                 750
```

Pro Pro Phe Ser Pro His Pro Thr Leu Leu Ser Ser Thr Pro Lys Pro
        755                 760                 765

Pro Gly Thr Ser Glu Pro Arg Ser Cys Ser Ser Ile Ser Thr Ala Leu
        770                 775                 780

Pro Gln Val Asn Glu Asp Leu Val Ser Leu Pro His Gln Leu Pro Glu
785                 790                 795                 800

Ala Ser Glu Pro Pro Gln Ser Pro Ser Glu Lys Arg Lys Lys Thr Phe
                805                 810                 815

Val Gly Glu Pro Gln Arg Leu Gly Ser Glu Thr Arg Leu Pro Gln His
        820                 825                 830

Ile Arg Glu Ala Thr Ala Ala Pro His Gly Lys Arg Lys Arg Lys Lys
        835                 840                 845

Lys Lys Arg Pro Glu Asp Thr Ala Ala Ser Ala Leu Gln Glu Gly Gln
        850                 855                 860

Thr Gln Arg Gln Pro Gly Ser Pro Met Tyr Arg Arg Glu Gly Gln Ala
865                 870                 875                 880

Gln Leu Pro Ala Val Arg Arg Gln Glu Asp Gly Thr Gln Pro Gln Val
                885                 890                 895

Asn Gly Gln Gln Val Gly Cys Val Thr Asp Gly His His Ala Ser Ser
        900                 905                 910

Arg Lys Arg Arg Lys Gly Ala Glu Gly Leu Gly Glu Glu Gly Gly
        915                 920                 925

Leu His Gln Asp Pro Leu Arg His Ser Cys Ser Pro Met Gly Asp Gly
        930                 935                 940

Asp Pro Glu Ala Met Glu Glu Ser Pro Arg Lys Lys Lys Lys Lys
945                 950                 955                 960

Arg Lys Gln Glu Thr Gln Arg Ala Val Glu Glu Asp Gly His Leu Lys
                965                 970                 975

Cys Pro Arg Ser Ala Lys Pro Gln Asp Ala Val Val Pro Glu Ser Ser
        980                 985                 990

Ser Cys Ala Pro Ser Ala Asn Gly Trp Cys Pro Gly Asp Arg Met Gly
        995                 1000                1005

Leu Ser Gln Ala Pro Pro Val Ser Trp Asn Gly Glu Arg Glu Ser Asp
        1010                1015                1020

Val Val Gln Glu Leu Leu Lys Tyr Ser Ser Asp Lys Ala Tyr Gly Arg
1025                1030                1035                1040

Lys Val Leu Thr Trp Asp Gly Lys Met Ser Ala Val Ser Gln Asp Ala
                1045                1050                1055

Ile Glu Asp Ser Arg Gln Ala Arg Thr Glu Thr Val Val Asp Asp Trp
        1060                1065                1070

Asp Glu Glu Phe Asp Arg Gly Lys Glu Lys Lys Ile Lys Lys Phe Lys
        1075                1080                1085

Arg Glu Lys Arg Arg Asn Phe Asn Ala Phe Gln Lys Leu Gln Thr Arg
        1090                1095                1100

Arg Asn Phe Trp Ser Val Thr His Pro Ala Lys Ala Ala Ser Leu Ser
1105                1110                1115                1120

Tyr Arg Arg

<210> SEQ ID NO 16
<211> LENGTH: 3941
<212> TYPE: DNA
<213> ORGANISM: Homo sapiens
<220> FEATURE:
<221> NAME/KEY: CDS -continued

```
<222> LOCATION: (279)...(3650)

<400> SEQUENCE: 16
cacgcgtccg ggcgccggag gcccggatgg tgcgcgtgct gggccgcggg ccgaaggagt      60
cgccagggct gcgtaggctt gtggcgcgcc cgcggagagg ccggggctct gacgcccgct     120
ctgcggcttc ggtgtttgaa caggccacag tccaggagcg cttacattca ggagctccgc     180
gtagcacctg cccaaccaaa ctcagccctc cgttaagatc ctggttccat gccgcagtag     240
gacagcaggc ccaagtctgc acatcccagt gatgcacc atg cca ata gtg gat aag    296
                                         Met Pro Ile Val Asp Lys
                                           1               5 ttg aag gag gcc ctg aaa ccc ggc cgc aag gac tcg gct gat gat gga      344
Leu Lys Glu Ala Leu Lys Pro Gly Arg Lys Asp Ser Ala Asp Asp Gly
         10                  15                  20 gaa ctg ggg aag ctt ctt gcc tcc tct gcc aag aag gtc ctt tta cag      392
Glu Leu Gly Lys Leu Leu Ala Ser Ser Ala Lys Lys Val Leu Leu Gln
     25                  30                  35 aaa atc gag ttc gag cca gcc agc aag agc ttc tcc tac cag ctg gag      440
Lys Ile Glu Phe Glu Pro Ala Ser Lys Ser Phe Ser Tyr Gln Leu Glu
 40                  45                  50 gcc tta aag agc aaa tat gtg ttg ctc aac ccc aaa aca gag gga gct      488
Ala Leu Lys Ser Lys Tyr Val Leu Leu Asn Pro Lys Thr Glu Gly Ala
 55                  60                  65                  70 agt cgc cac aag agt gga gat gac cca ccg gcc agg aga cag ggc agt      536
Ser Arg His Lys Ser Gly Asp Asp Pro Pro Ala Arg Arg Gln Gly Ser
             75                  80                  85 gag cac acg tat gag agc tgt ggt gac gga gtc cca gcc ccg cag aaa      584
Glu His Thr Tyr Glu Ser Cys Gly Asp Gly Val Pro Ala Pro Gln Lys
         90                  95                 100 gtg ctt ttc ccc acg gag cga ctg tct ctg agg tgg gag cgg gtc ttc      632
Val Leu Phe Pro Thr Glu Arg Leu Ser Leu Arg Trp Glu Arg Val Phe
     105                 110                 115 cgc gtg ggc gca gga ctc cac aac ctt ggc aac acc tgc ttt ctc aat      680
Arg Val Gly Ala Gly Leu His Asn Leu Gly Asn Thr Cys Phe Leu Asn
 120                 125                 130 gcc acc atc cag tgc ttg acc tac aca cca cct cta gcc aac tac ctg      728
Ala Thr Ile Gln Cys Leu Thr Tyr Thr Pro Pro Leu Ala Asn Tyr Leu
135                 140                 145                 150 ctc tcc aag gag cat gct cgc agc tgc cac cag gga agc ttc tgc atg      776
Leu Ser Lys Glu His Ala Arg Ser Cys His Gln Gly Ser Phe Cys Met
             155                 160                 165 ctg tgt gtc atg cag aac cac att gtc cag gcc ttc gcc aac agc ggc      824
Leu Cys Val Met Gln Asn His Ile Val Gln Ala Phe Ala Asn Ser Gly
         170                 175                 180 aac gcc atc aag ccc gtc tcc ttc atc cga gac ctg aaa aag atc gcc      872
Asn Ala Ile Lys Pro Val Ser Phe Ile Arg Asp Leu Lys Lys Ile Ala
     185                 190                 195 cga cac ttc cgc ttt ggg aac cag gag gac gcg cat gag ttc ctg cgg      920
Arg His Phe Arg Phe Gly Asn Gln Glu Asp Ala His Glu Phe Leu Arg
 200                 205                 210 tac acc atc gac gcc atg cag aaa gcc tgc ctg aat ggc tgt gcc aag      968
Tyr Thr Ile Asp Ala Met Gln Lys Ala Cys Leu Asn Gly Cys Ala Lys
215                 220                 225                 230 ttg gat cgt caa acg cag gct act acc ttg gtc cat caa att ttt gga     1016
Leu Asp Arg Gln Thr Gln Ala Thr Thr Leu Val His Gln Ile Phe Gly
             235                 240                 245 ggg tat ctc aga tca cgc gtg aag tgc tcc gtg tgc aag agc gtc tcg     1064
Gly Tyr Leu Arg Ser Arg Val Lys Cys Ser Val Cys Lys Ser Val Ser
         250                 255                 260
```

-continued

| | |
|---|---|
| gac acc tac gac ccc tac ttg gac gtc gcg ctg gag atc cgg caa gct<br>Asp Thr Tyr Asp Pro Tyr Leu Asp Val Ala Leu Glu Ile Arg Gln Ala<br>265                        270                      275 | 1112 |
| gcg aat att gtg cgt gct ctg gaa ctt ttt gtg aaa gca gat gtc ctg<br>Ala Asn Ile Val Arg Ala Leu Glu Leu Phe Val Lys Ala Asp Val Leu<br>280                        285                      290 | 1160 |
| agt gga gag aat gcc tac atg tgt gct aaa tgc aag aag aag gtt cca<br>Ser Gly Glu Asn Ala Tyr Met Cys Ala Lys Cys Lys Lys Lys Val Pro<br>295                        300                      305                      310 | 1208 |
| gcc agc aag cgc ttc acc atc cac aga aca tcc aac gtc tta acc ctt<br>Ala Ser Lys Arg Phe Thr Ile His Arg Thr Ser Asn Val Leu Thr Leu<br>                      315                      320                      325 | 1256 |
| tcc ctc aag cgc ttt gcc aac ttc agc ggg ggg aag atc acc aag gat<br>Ser Leu Lys Arg Phe Ala Asn Phe Ser Gly Gly Lys Ile Thr Lys Asp<br>                      330                      335                      340 | 1304 |
| gta ggc tat ccg gaa ttc ctc aac ata cgt ccg tat atg tcc cag aat<br>Val Gly Tyr Pro Glu Phe Leu Asn Ile Arg Pro Tyr Met Ser Gln Asn<br>            345                      350                      355 | 1352 |
| aat ggt gat cct gtc atg tat gga ctc tat gct gtc ctg gtg cac tcg<br>Asn Gly Asp Pro Val Met Tyr Gly Leu Tyr Ala Val Leu Val His Ser<br>360                        365                      370 | 1400 |
| ggc tac agc tgc cat gcc ggg cac tat tac tgc tac gtg aag gca agc<br>Gly Tyr Ser Cys His Ala Gly His Tyr Tyr Cys Tyr Val Lys Ala Ser<br>375                        380                      385                      390 | 1448 |
| aat gga cag tgg tac cag atg aat gat tcc ttg gtc cat tcc agc aac<br>Asn Gly Gln Trp Tyr Gln Met Asn Asp Ser Leu Val His Ser Ser Asn<br>                      395                      400                      405 | 1496 |
| gtc aag gtg gtt ctg aac cag cag gcc tac gtg ctg ttc tat ctg cga<br>Val Lys Val Val Leu Asn Gln Gln Ala Tyr Val Leu Phe Tyr Leu Arg<br>            410                      415                      420 | 1544 |
| att cca ggc tct aag aaa agt ccc gag ggc ctc atc tcc agg aca ggc<br>Ile Pro Gly Ser Lys Lys Ser Pro Glu Gly Leu Ile Ser Arg Thr Gly<br>            425                      430                      435 | 1592 |
| tcc tcc tcc ctt ccc ggc cgc ccg agt gtg att cca gat cac tcc aag<br>Ser Ser Ser Leu Pro Gly Arg Pro Ser Val Ile Pro Asp His Ser Lys<br>440                        445                      450 | 1640 |
| aag aac atc ggc aat ggg att att tcc tcc cca ctg act gga aag cga<br>Lys Asn Ile Gly Asn Gly Ile Ile Ser Ser Pro Leu Thr Gly Lys Arg<br>455                        460                      465                      470 | 1688 |
| caa gac tct ggg acg atg aag aag ccg cac acc act gaa gag att ggt<br>Gln Asp Ser Gly Thr Met Lys Lys Pro His Thr Thr Glu Glu Ile Gly<br>                      475                      480                      485 | 1736 |
| gtg ccc ata tcc agg aat ggc tcc acc ctg ggc ctg aag tcc cag aac<br>Val Pro Ile Ser Arg Asn Gly Ser Thr Leu Gly Leu Lys Ser Gln Asn<br>            490                      495                      500 | 1784 |
| ggc tgc att cct cca aag ctg ccc tcg ggg tcc cct tcc ccc aaa ctc<br>Gly Cys Ile Pro Pro Lys Leu Pro Ser Gly Ser Pro Ser Pro Lys Leu<br>505                        510                      515 | 1832 |
| tcc cag aca ccc aca cac atg cca acc atc cta gac gac cct gga aag<br>Ser Gln Thr Pro Thr His Met Pro Thr Ile Leu Asp Asp Pro Gly Lys<br>520                        525                      530 | 1880 |
| aag gtg aag aag cca gct cct cca cag cac ttt tcc ccc aga act gct<br>Lys Val Lys Lys Pro Ala Pro Pro Gln His Phe Ser Pro Arg Thr Ala<br>535                        540                      545                      550 | 1928 |
| cag ggg ctg cct ggg acc agc aac tcg aat agc agc aga tct ggg agc<br>Gln Gly Leu Pro Gly Thr Ser Asn Ser Asn Ser Ser Arg Ser Gly Ser<br>                      555                      560                      565 | 1976 |
| caa agg cag ggc tcc tgg gac agc agg gat gtt gtc ctc tct acc tca<br>Gln Arg Gln Gly Ser Trp Asp Ser Arg Asp Val Val Leu Ser Thr Ser | 2024 |

-continued

```
              570                 575                 580
cct aag ctc ctg gct aca gcc act gcc aac ggg cat ggg ctg aag ggg      2072
Pro Lys Leu Leu Ala Thr Ala Thr Ala Asn Gly His Gly Leu Lys Gly
        585                 590                 595 aac gac gag agc gct ggc ctc gac agg agg ggc tcc agc agc tcc agc      2120
Asn Asp Glu Ser Ala Gly Leu Asp Arg Arg Gly Ser Ser Ser Ser Ser
600                 605                 610 cca gag cac tcg gcc agc agc gac tcc acc aag gcc ccc cag acc ccc      2168
Pro Glu His Ser Ala Ser Ser Asp Ser Thr Lys Ala Pro Gln Thr Pro
615                 620                 625                 630 agg agt gga gcg gcc cat ctc tgc gat tct cag gaa acg aac tgt tcc      2216
Arg Ser Gly Ala Ala His Leu Cys Asp Ser Gln Glu Thr Asn Cys Ser
            635                 640                 645 acc gct ggc cac tcc aaa acg ccg cca agt gga gca gat tct aag acg      2264
Thr Ala Gly His Ser Lys Thr Pro Pro Ser Gly Ala Asp Ser Lys Thr
        650                 655                 660 gtg aag ctg aag tcc cct gtc ctg agc aac acc acc act gag cct gca      2312
Val Lys Leu Lys Ser Pro Val Leu Ser Asn Thr Thr Thr Glu Pro Ala
    665                 670                 675 agc acc atg tct cct cca cca gcc aaa aaa ctg gcc ctt tct gcc aag      2360
Ser Thr Met Ser Pro Pro Ala Lys Lys Leu Ala Leu Ser Ala Lys
680                 685                 690 aag gcc agc acc ctg tgg agg gcg acc ggc aat gac ctc cgt cca cct      2408
Lys Ala Ser Thr Leu Trp Arg Ala Thr Gly Asn Asp Leu Arg Pro Pro
695                 700                 705                 710 ccc ccc tca cca tcc tcc gac ctc acc cac ccc atg aaa acc tct cac      2456
Pro Pro Ser Pro Ser Ser Asp Leu Thr His Pro Met Lys Thr Ser His
            715                 720                 725 ccc gtc gtt gcc tcc act tgg ccc gtc cat aga gcc agg gct gtg tca      2504
Pro Val Val Ala Ser Thr Trp Pro Val His Arg Ala Arg Ala Val Ser
        730                 735                 740 cct gct ccc caa tca tcc agc cgc ctg caa ccc ccc ttc agc ccc cac      2552
Pro Ala Pro Gln Ser Ser Ser Arg Leu Gln Pro Pro Phe Ser Pro His
    745                 750                 755 ccc aca ttg ctg tcc agt acc ccc aag ccc cca ggg acg tca gaa cca      2600
Pro Thr Leu Leu Ser Ser Thr Pro Lys Pro Pro Gly Thr Ser Glu Pro
760                 765                 770 cgg agc tgc tcc tcc atc tcg acg gcg ctg cct cag gtc aac gag gac      2648
Arg Ser Cys Ser Ser Ile Ser Thr Ala Leu Pro Gln Val Asn Glu Asp
775                 780                 785                 790 ctt gtg tct ctt cca cac cag ttg cca gag gcc agt gag ccc ccc cag      2696
Leu Val Ser Leu Pro His Gln Leu Pro Glu Ala Ser Glu Pro Pro Gln
            795                 800                 805 agc ccc tct gag aag agg aaa aag acc ttt gtg gga gag ccg cag agg      2744
Ser Pro Ser Glu Lys Arg Lys Lys Thr Phe Val Gly Glu Pro Gln Arg
        810                 815                 820 ctg ggc tca gag acg cgc ctc cca cag cac atc agg gag gcc act gcg      2792
Leu Gly Ser Glu Thr Arg Leu Pro Gln His Ile Arg Glu Ala Thr Ala
    825                 830                 835 gct ccc cac ggg aag agg aag agg aag aag aag cgc ccg gag gac           2840
Ala Pro His Gly Lys Arg Lys Arg Lys Lys Lys Arg Pro Glu Asp
840                 845                 850 aca gct gcc agc gcc ctg cag gag ggg cag aca cag aga cag cct ggg      2888
Thr Ala Ala Ser Ala Leu Gln Glu Gly Gln Thr Gln Arg Gln Pro Gly
855                 860                 865                 870 agc ccc atg tac agg agg gag ggc cag gca cag ctg ccc gct gtc aga      2936
Ser Pro Met Tyr Arg Arg Glu Gly Gln Ala Gln Leu Pro Ala Val Arg
            875                 880                 885 cgg cag gaa gat ggc aca cag cca cag gtg aat ggc cag cag gtg gga      2984
```

-continued

| | | | | | | | | | | | | |
|---|---|---|---|---|---|---|---|---|---|---|---|---|
|Arg|Gln|Glu|Asp|Gly|Thr|Gln|Pro|Gln|Val|Asn|Gly|Gln|Gln|Val|Gly|
| | |890| | | |895| | | |900| | |

```
tgt gtt acg gac ggc cac cac gcg agc agc agg aag cgg agg agg aaa      3032
Cys Val Thr Asp Gly His His Ala Ser Ser Arg Lys Arg Arg Arg Lys
        905                 910                 915 gga gca gaa ggt ctt ggt gaa gaa ggc ggc ctg cac cag gac cca ctt      3080
Gly Ala Glu Gly Leu Gly Glu Glu Gly Gly Leu His Gln Asp Pro Leu
    920                 925                 930 cgg cac agc tgc tct ccc atg ggt gat ggt gat cca gag gcc atg gaa      3128
Arg His Ser Cys Ser Pro Met Gly Asp Gly Asp Pro Glu Ala Met Glu
935                 940                 945                 950 gag tct cca agg aaa aag aaa aag aaa aaa aga aag cag gag aca cag      3176
Glu Ser Pro Arg Lys Lys Lys Lys Lys Lys Arg Lys Gln Glu Thr Gln
                955                 960                 965 cgg gca gta gaa gag gat ggg cat ctc aaa tgc cca agg agt gcc aag      3224
Arg Ala Val Glu Glu Asp Gly His Leu Lys Cys Pro Arg Ser Ala Lys
            970                 975                 980 ccc caa gat gct gtt gtc ccc gag tcc agc agc tgc gca cca tcc gcg      3272
Pro Gln Asp Ala Val Val Pro Glu Ser Ser Ser Cys Ala Pro Ser Ala
        985                 990                 995 aat ggc tgg tgt cct ggg gac cgc atg ggg ctg agc cag gcc cct cct      3320
Asn Gly Trp Cys Pro Gly Asp Arg Met Gly Leu Ser Gln Ala Pro Pro
    1000                1005                1010 gtg tct tgg aat gga gag cgg gag tct gat gtg gtc cag gaa ctg ctc      3368
Val Ser Trp Asn Gly Glu Arg Glu Ser Asp Val Val Gln Glu Leu Leu
1015                1020                1025                1030 aaa tac tca tct gat aaa gct tac ggg aga aaa gtt ctg acc tgg gat      3416
Lys Tyr Ser Ser Asp Lys Ala Tyr Gly Arg Lys Val Leu Thr Trp Asp
                1035                1040                1045 ggc aag atg tcg gcg gtc agt cag gat gct att gaa gac agc aga cag      3464
Gly Lys Met Ser Ala Val Ser Gln Asp Ala Ile Glu Asp Ser Arg Gln
            1050                1055                1060 gcc cgg act gag acc gtg gtt gat gac tgg gac gaa gag ttt gac cga      3512
Ala Arg Thr Glu Thr Val Val Asp Asp Trp Asp Glu Glu Phe Asp Arg
        1065                1070                1075 ggg aag gaa aag aaa att aaa aaa ttt aag aga gag aag agg aga aac      3560
Gly Lys Glu Lys Lys Ile Lys Lys Phe Lys Arg Glu Lys Arg Arg Asn
    1080                1085                1090 ttc aac gcc ttc cag aaa ctt cag act cga cgg aac ttc tgg tct gtg      3608
Phe Asn Ala Phe Gln Lys Leu Gln Thr Arg Arg Asn Phe Trp Ser Val
1095                1100                1105                1110 act cac cca gca aag gct gcc agc ctc agc tat cgc cgc tga              3650
Thr His Pro Ala Lys Ala Ala Ser Leu Ser Tyr Arg Arg *
                1115                1120 ctgtgcccct gtggaaggag atgatcaagc ggtgctgatt cacgagagtg gaagcctcca   3710
gagcttgggg ctttctggct gctcttcatt gacctgtgtg ttcccagcac acgaacagcg   3770
cccctaacgg agatttgttc agcgactgaa tatacacctg taaacgagta gcatgtatac   3830
attgattttg attacaaatg gttctgtatt atataccacc gttctgactg cttttttcac   3890
ttatagcttg gaaattgtct tctgttggta atacagaaat ctgtttcagt c           3941

<210> SEQ ID NO 17
<211> LENGTH: 337
<212> TYPE: PRT
<213> ORGANISM: Homo sapiens

<400> SEQUENCE: 17

Met Asp Leu Asp Val Val Asn Met Phe Val Ile Ala Gly Gly Thr Leu
1               5                   10                  15
```

```
Ala Ile Pro Ile Leu Ala Phe Val Ala Ser Phe Leu Leu Trp Pro Ser
            20                  25                  30

Ala Leu Ile Arg Ile Tyr Tyr Trp Tyr Trp Arg Arg Thr Leu Gly Met
        35                  40                  45

Gln Val Arg Tyr Val His His Glu Asp Tyr Gln Phe Cys Tyr Ser Phe
    50                  55                  60

Arg Gly Arg Pro Gly His Lys Pro Ser Ile Leu Met Leu His Gly Phe
65                  70                  75                  80

Ser Ala His Lys Asp Met Trp Leu Ser Val Val Lys Phe Leu Pro Lys
                85                  90                  95

Asn Leu His Leu Val Cys Val Asp Met Pro Gly His Glu Gly Thr Thr
            100                 105                 110

Arg Ser Ser Leu Asp Asp Leu Ser Ile Asp Gly Gln Val Lys Arg Ile
        115                 120                 125

His Gln Phe Val Glu Cys Leu Lys Leu Asn Lys Lys Pro Phe His Leu
    130                 135                 140

Val Gly Thr Ser Met Gly Gly Gln Val Ala Gly Val Tyr Ala Ala Tyr
145                 150                 155                 160

Tyr Pro Ser Asp Val Ser Ser Leu Cys Leu Val Cys Pro Ala Gly Leu
                165                 170                 175

Gln Tyr Ser Thr Asp Asn Gln Phe Val Gln Arg Leu Lys Glu Leu Gln
            180                 185                 190

Gly Ser Ala Ala Val Glu Lys Ile Pro Leu Ile Pro Ser Thr Pro Glu
        195                 200                 205

Glu Met Ser Glu Met Leu Gln Leu Cys Ser Tyr Val Arg Phe Lys Val
    210                 215                 220

Pro Gln Gln Ile Leu Gln Gly Leu Val Asp Val Arg Ile Pro His Asn
225                 230                 235                 240

Asn Phe Tyr Arg Lys Leu Phe Leu Glu Ile Val Ser Glu Lys Ser Arg
                245                 250                 255

Tyr Ser Leu His Gln Asn Met Asp Lys Ile Lys Val Pro Thr Gln Ile
            260                 265                 270

Ile Trp Gly Lys Gln Asp Gln Val Leu Asp Val Ser Gly Ala Asp Met
        275                 280                 285

Leu Ala Lys Ser Ile Ala Asn Cys Gln Val Glu Leu Leu Glu Asn Cys
    290                 295                 300

Gly His Ser Val Val Met Glu Arg Pro Arg Lys Thr Ala Lys Leu Ile
305                 310                 315                 320

Ile Asp Phe Leu Ala Ser Val His Asn Thr Asp Asn Asn Lys Lys Leu
                325                 330                 335

Asp

<210> SEQ ID NO 18
<211> LENGTH: 1964
<212> TYPE: DNA
<213> ORGANISM: Homo sapiens
<220> FEATURE:
<221> NAME/KEY: CDS
<222> LOCATION: (164)...(1174)

<400> SEQUENCE: 18
cacgcgtccg gctgggctgg gcgccggagc tgggagcggc gcgggtagga gcccggcggc      60
aggtcccagc ccggggctag agaccgaggg ccggggtccg ggcccggcgg cgggacccag     120
gcggttgagg ctggtcagga gtcagccagc ctgaaagagc agg atg gat ctt gat      175
```

-continued

```
                                              Met Asp Leu Asp
                                               1
gtg gtt aac atg ttt gtg att gcg ggc ggc acg ctg gcc atc cca atc      223
Val Val Asn Met Phe Val Ile Ala Gly Gly Thr Leu Ala Ile Pro Ile
 5              10                  15                  20 ctg gca ttt gtg gct tca ttt ctt ctg tgg cct tca gca ctg ata aga      271
Leu Ala Phe Val Ala Ser Phe Leu Leu Trp Pro Ser Ala Leu Ile Arg
                25                  30                  35 atc tat tat tgg tac tgg cgg agg aca ttg ggc atg caa gtc cgc tat      319
Ile Tyr Tyr Trp Tyr Trp Arg Arg Thr Leu Gly Met Gln Val Arg Tyr
            40                  45                  50 gtt cac cat gaa gac tat cag ttc tgt tat tcc ttc cgg ggc agg cct      367
Val His His Glu Asp Tyr Gln Phe Cys Tyr Ser Phe Arg Gly Arg Pro
        55                  60                  65 ggg cac aaa ccc tcc atc ctc atg ctc cac gga ttc tct gcc cac aag      415
Gly His Lys Pro Ser Ile Leu Met Leu His Gly Phe Ser Ala His Lys
    70                  75                  80 gat atg tgg ctc agt gtg gtc aag ttc ctt cca aag aac ctg cac ttg      463
Asp Met Trp Leu Ser Val Val Lys Phe Leu Pro Lys Asn Leu His Leu
85                  90                  95                 100 gtc tgc gtg gac atg cca gga cat gag ggc acc acc cgc tcc tcc ctg      511
Val Cys Val Asp Met Pro Gly His Glu Gly Thr Thr Arg Ser Ser Leu
                105                 110                 115 gat gac ctg tcc ata gat ggg caa gtt aag agg ata cac cag ttt gta      559
Asp Asp Leu Ser Ile Asp Gly Gln Val Lys Arg Ile His Gln Phe Val
            120                 125                 130 gaa tgc ctg aag ctg aac aaa aaa cct ttc cac ctg gta ggc acc tcc      607
Glu Cys Leu Lys Leu Asn Lys Lys Pro Phe His Leu Val Gly Thr Ser
        135                 140                 145 atg ggt ggc cag gtg gct ggg gtg tat gct gct tac tac cca tcg gat      655
Met Gly Gly Gln Val Ala Gly Val Tyr Ala Ala Tyr Tyr Pro Ser Asp
    150                 155                 160 gtc tcc agc ctg tgt ctc gtg tgt cct gct ggc ctg cag tac tca act      703
Val Ser Ser Leu Cys Leu Val Cys Pro Ala Gly Leu Gln Tyr Ser Thr
165                 170                 175                 180 gac aat caa ttt gta caa cgg ctc aaa gaa ctg cag ggc tct gcc gcc      751
Asp Asn Gln Phe Val Gln Arg Leu Lys Glu Leu Gln Gly Ser Ala Ala
                185                 190                 195 gtg gag aag att ccc ttg atc ccg tct acc cca gaa gag atg agt gaa      799
Val Glu Lys Ile Pro Leu Ile Pro Ser Thr Pro Glu Glu Met Ser Glu
            200                 205                 210 atg ctt cag ctc tgc tcc tat gtc cgc ttc aag gtg ccc cag cag atc      847
Met Leu Gln Leu Cys Ser Tyr Val Arg Phe Lys Val Pro Gln Gln Ile
        215                 220                 225 ctg caa ggc ctt gtc gat gtc cgc atc cct cat aac aac ttc tac cga      895
Leu Gln Gly Leu Val Asp Val Arg Ile Pro His Asn Asn Phe Tyr Arg
    230                 235                 240 aag ttg ttt ttg gaa atc gtc agt gag aag tcc aga tac tct ctc cat      943
Lys Leu Phe Leu Glu Ile Val Ser Glu Lys Ser Arg Tyr Ser Leu His
245                 250                 255                 260 cag aac atg gac aag atc aag gtt ccg acg cag atc atc tgg ggg aaa      991
Gln Asn Met Asp Lys Ile Lys Val Pro Thr Gln Ile Ile Trp Gly Lys
                265                 270                 275 caa gac cag gtg ctg gat gtg tct ggg gca gac atg ttg gcc aag tca     1039
Gln Asp Gln Val Leu Asp Val Ser Gly Ala Asp Met Leu Ala Lys Ser
            280                 285                 290 att gcc aac tgc cag gtg gag ctt ctg gaa aac tgt ggg cac tca gta     1087
Ile Ala Asn Cys Gln Val Glu Leu Leu Glu Asn Cys Gly His Ser Val
        295                 300                 305
```

-continued

```
gtg atg gaa aga ccc agg aag aca gcc aag ctc ata atc gac ttt tta    1135
Val Met Glu Arg Pro Arg Lys Thr Ala Lys Leu Ile Ile Asp Phe Leu
    310             315                 320 gct tct gtg cac aac aca gac aac aac aag aag ctg gac tgaggccccg    1184
Ala Ser Val His Asn Thr Asp Asn Asn Lys Lys Leu Asp
325             330                 335 actgcagcct gcattctgca cacagcatct gctcccatcc cccaagtctg acgcagccac    1244
cactctcagg gatcctgccc caaatgcggt cggagcgcca gtgaccctga ggaagcccgt    1304
cccttatccc tggtatccac ggttccccag agctttgggg accacgcgaa aacctccaag    1364
atatttttca caaatagaa actcatatgg aacaaaataa gaaacccag ccatgaaatc    1424 taccatgaag tcttcaagtt catgtcactg agaagcttgt gcaaagcagc caccttggac    1484
cataattaaa tcaaggacat tttctttgag acattcctta tagttggaga ctcaagatat    1544
ttttgttgca tcaggtgtat tcccttgcat gggcagtggc ttttatagga gcattagtcc    1604
tcattcgctg aaccctgttg tttaggtcta atttaagttt tacatagaga cccatgtatg    1664
actgcagccc attggctgca agaccaggga ggaaagtggc aagctgtaga aatgtttac    1724 acgcatggag gggcattgct ctagccctca gagcgtccgg agcagcaggg tacatgggtg    1784
ggaggttcat tcagcaccca ccagtcaggt atgttctgag tgaacccaca gcagtcgcag    1844
aatgagcacc tggcagggtg ggtttcctag gaataattta ttattttttaa aaataggcct    1904 aataaagcaa taatgttcta gaaaaaaaaa aaaaaaaaaa aaaaaaaaa aaaaaaaaa    1964
```

<210> SEQ ID NO 19
<211> LENGTH: 1086
<212> TYPE: PRT
<213> ORGANISM: Homo sapiens

<400> SEQUENCE: 19

```
Met Arg Arg Arg Tyr Leu Arg Asp Arg Ser Glu Glu Ala Ala Gly
1               5                   10                  15

Gly Gly Asp Gly Leu Pro Arg Ser Arg Asp Trp Leu Tyr Glu Ser Tyr
            20                  25                  30

Tyr Cys Met Ser Gln Gln His Pro Leu Ile Val Phe Leu Leu Ile
        35                  40                  45

Val Met Gly Ser Cys Leu Ala Leu Leu Ala Val Phe Ala Leu Gly
    50                  55                  60

Leu Glu Val Glu Asp His Val Ala Phe Leu Ile Thr Val Pro Thr Ala
65                  70                  75                  80

Leu Ala Ile Phe Phe Ala Ile Phe Ile Leu Val Cys Ile Glu Ser Val
                85                  90                  95

Phe Lys Lys Leu Leu Arg Leu Phe Ser Leu Val Ile Trp Ile Cys Leu
            100                 105                 110

Val Ala Met Gly Tyr Leu Phe Met Cys Phe Gly Gly Thr Val Ser Pro
        115                 120                 125

Trp Asp Gln Val Ser Phe Phe Leu Phe Ile Ile Phe Val Val Tyr Thr
    130                 135                 140

Met Leu Pro Phe Asn Met Arg Asp Ala Ile Ile Ala Ser Val Leu Thr
145                 150                 155                 160

Ser Ser Ser His Thr Ile Val Leu Ser Val Cys Leu Ser Ala Thr Pro
                165                 170                 175

Gly Gly Lys Glu His Leu Val Trp Gln Ile Leu Ala Asn Val Ile Ile
            180                 185                 190

Phe Ile Cys Gly Asn Leu Ala Gly Ala Tyr His Lys His Leu Met Glu
```

```
            195                 200                 205
Leu Ala Leu Gln Gln Thr Tyr Gln Asp Thr Cys Asn Cys Ile Lys Ser
    210                 215                 220

Arg Ile Lys Leu Glu Phe Glu Lys Arg Gln Gln Glu Arg Leu Leu Leu
225                 230                 235                 240

Ser Leu Leu Pro Ala His Ile Ala Met Glu Met Lys Ala Glu Ile Ile
                245                 250                 255

Gln Arg Leu Gln Gly Pro Lys Ala Gly Gln Met Glu Asn Thr Asn Asn
            260                 265                 270

Phe His Asn Leu Tyr Val Lys Arg His Thr Asn Val Ser Ile Leu Tyr
        275                 280                 285

Ala Asp Ile Val Gly Phe Thr Arg Leu Ala Ser Asp Cys Ser Pro Gly
290                 295                 300

Glu Leu Val His Met Leu Asn Glu Leu Phe Gly Lys Phe Asp Gln Ile
305                 310                 315                 320

Ala Lys Glu Asn Glu Cys Met Arg Ile Lys Ile Leu Gly Asp Cys Tyr
                325                 330                 335

Tyr Cys Val Ser Gly Leu Pro Ile Ser Leu Pro Asn His Ala Lys Asn
            340                 345                 350

Cys Val Lys Met Gly Leu Asp Met Cys Glu Ala Ile Lys Lys Val Arg
        355                 360                 365

Asp Ala Thr Gly Val Asp Ile Asn Met Arg Val Gly Val His Ser Gly
    370                 375                 380

Asn Val Leu Cys Gly Val Ile Gly Leu Gln Lys Trp Gln Tyr Asp Val
385                 390                 395                 400

Trp Ser His Asp Val Thr Leu Ala Asn His Met Glu Ala Gly Gly Val
                405                 410                 415

Pro Gly Arg Val His Ile Ser Ser Val Thr Leu Glu His Leu Asn Gly
            420                 425                 430

Ala Tyr Lys Val Glu Glu Gly Asp Gly Asp Ile Arg Asp Pro Tyr Leu
        435                 440                 445

Lys Gln His Leu Val Lys Thr Tyr Phe Val Ile Asn Pro Lys Gly Glu
    450                 455                 460

Arg Arg Ser Pro Gln His Leu Phe Arg Pro Arg His Thr Leu Asp Gly
465                 470                 475                 480

Ala Lys Met Arg Ala Ser Val Arg Met Thr Arg Tyr Leu Glu Ser Trp
                485                 490                 495

Gly Ala Ala Lys Pro Phe Ala His Leu His His Arg Asp Ser Met Thr
            500                 505                 510

Thr Glu Asn Gly Lys Ile Ser Thr Thr Asp Val Pro Met Gly Gln His
        515                 520                 525

Asn Phe Gln Asn Arg Thr Leu Arg Thr Lys Ser Gln Lys Lys Arg Phe
    530                 535                 540

Glu Glu Glu Leu Asn Glu Arg Met Ile Gln Ala Ile Asp Gly Ile Asn
545                 550                 555                 560

Ala Gln Lys Gln Trp Leu Lys Ser Glu Asp Ile Gln Arg Ile Ser Leu
                565                 570                 575

Leu Phe Tyr Asn Lys Val Leu Glu Lys Glu Tyr Arg Ala Thr Ala Leu
            580                 585                 590

Pro Ala Phe Lys Tyr Tyr Val Thr Cys Ala Cys Leu Ile Phe Phe Cys
        595                 600                 605

Ile Phe Ile Val Gln Ile Leu Val Leu Pro Lys Thr Ser Val Leu Gly
    610                 615                 620
```

```
Ile Ser Phe Gly Ala Ala Phe Leu Leu Ala Phe Ile Leu Phe Val
625                 630                 635                 640

Cys Phe Ala Gly Gln Leu Leu Gln Cys Ser Lys Lys Ala Ser Pro Leu
            645                 650                 655

Leu Met Trp Leu Leu Lys Ser Ser Gly Ile Ile Ala Asn Arg Pro Trp
            660                 665                 670

Pro Arg Ile Ser Leu Thr Ile Ile Thr Thr Ala Ile Ile Leu Met Met
            675                 680                 685

Ala Val Phe Asn Met Phe Phe Leu Ser Asp Ser Glu Glu Thr Ile Pro
690                 695                 700

Pro Thr Ala Asn Thr Thr Asn Thr Ser Phe Ser Ala Ser Asn Asn Gln
705                 710                 715                 720

Val Ala Ile Leu Arg Ala Gln Asn Leu Phe Leu Pro Tyr Phe Ile
                725                 730                 735

Tyr Ser Cys Ile Leu Gly Leu Ile Ser Cys Ser Val Phe Leu Arg Val
            740                 745                 750

Asn Tyr Glu Leu Lys Met Leu Ile Met Met Val Ala Leu Val Gly Tyr
            755                 760                 765

Asn Thr Ile Leu Leu His Thr His Ala His Val Leu Gly Asp Tyr Ser
770                 775                 780

Gln Val Leu Phe Glu Arg Pro Gly Ile Trp Lys Asp Leu Lys Thr Met
785                 790                 795                 800

Gly Ser Val Ser Leu Ser Ile Phe Phe Ile Thr Leu Leu Val Leu Gly
                805                 810                 815

Arg Gln Asn Glu Tyr Tyr Cys Arg Leu Asp Phe Leu Trp Lys Asn Lys
            820                 825                 830

Phe Lys Lys Glu Arg Glu Ile Glu Thr Met Glu Asn Leu Asn Arg
            835                 840                 845

Val Leu Leu Glu Asn Val Leu Pro Ala His Val Ala Glu His Phe Leu
850                 855                 860

Ala Arg Ser Leu Lys Asn Glu Glu Leu Tyr His Gln Ser Tyr Asp Cys
865                 870                 875                 880

Val Cys Val Met Phe Ala Ser Ile Pro Asp Phe Lys Glu Phe Tyr Thr
                885                 890                 895

Glu Ser Asp Val Asn Lys Glu Gly Leu Glu Cys Leu Arg Leu Leu Asn
            900                 905                 910

Glu Ile Ile Ala Asp Phe Asp Asp Leu Leu Ser Lys Pro Lys Phe Ser
            915                 920                 925

Gly Val Glu Lys Ile Lys Thr Ile Gly Ser Thr Tyr Met Ala Ala Thr
930                 935                 940

Gly Leu Ser Ala Val Pro Ser Gln Glu His Ser Gln Glu Pro Glu Arg
945                 950                 955                 960

Gln Tyr Met His Ile Gly Thr Met Val Glu Phe Ala Phe Ala Leu Val
                965                 970                 975

Gly Lys Leu Asp Ala Ile Asn Lys His Ser Phe Asn Asp Phe Lys Leu
            980                 985                 990

Arg Val Gly Ile Asn His Gly Pro Val Ile Ala Gly Val Ile Gly Ala
            995                 1000                1005

Gln Lys Pro Gln Tyr Asp Ile Trp Gly Asn Thr Val Asn Val Ala Ser
        1010                1015                1020

Arg Met Asp Ser Thr Gly Val Leu Asp Lys Ile Gln Val Thr Glu Glu
1025                1030                1035                1040
```

```
Thr Ser Leu Val Leu Gln Thr Leu Gly Tyr Thr Cys Thr Cys Arg Gly
            1045                1050                1055

Ile Ile Asn Val Lys Gly Lys Gly Asp Leu Lys Thr Tyr Phe Val Asn
            1060                1065                1070

Thr Glu Met Ser Arg Ser Leu Ser Gln Ser Asn Val Ala Ser
            1075                1080                1085

<210> SEQ ID NO 20
<211> LENGTH: 4011
<212> TYPE: DNA
<213> ORGANISM: Homo sapiens
<220> FEATURE:
<221> NAME/KEY: CDS
<222> LOCATION: (71)...(3331)

<400> SEQUENCE: 20
cacgcgtccg cccggccccc gcccgcgcac ggcgggcgcc ctgtgagcgg ccccgatgtg      60
gcaggaggcg atg cgg cgc cgc cgc tac ctg cgg gac cgc tcc gag gag        109
            Met Arg Arg Arg Arg Tyr Leu Arg Asp Arg Ser Glu Glu
             1               5                  10 gcg gcg ggc ggc gga gac ggg ctg ccg cgg tcc cgg gac tgg ctc tac      157
Ala Ala Gly Gly Gly Asp Gly Leu Pro Arg Ser Arg Asp Trp Leu Tyr
 15                  20                  25 gag tcc tac tac tgc atg agc cag cag cac ccg ctc atc gtc ttc ctg      205
Glu Ser Tyr Tyr Cys Met Ser Gln Gln His Pro Leu Ile Val Phe Leu
 30                  35                  40                  45 ctc ctc atc gtc atg ggc tcc tgc ctc gcc ctc gtc gcc gtc ttc ttc      253
Leu Leu Ile Val Met Gly Ser Cys Leu Ala Leu Val Ala Val Phe Phe
                 50                  55                  60 gcg ctc ggg ctg gaa gtt gaa gac cat gtg gcg ttt cta ata aca gtt      301
Ala Leu Gly Leu Glu Val Glu Asp His Val Ala Phe Leu Ile Thr Val
             65                  70                  75 cca act gcc ctg gcg att ttc ttt gcg ata ttt atc ctg gtc tgc atc      349
Pro Thr Ala Leu Ala Ile Phe Phe Ala Ile Phe Ile Leu Val Cys Ile
         80                  85                  90 gag tct gtg ttt aag aag ctg ctg cgc ctc ttc tcg ttg gtg ata tgg      397
Glu Ser Val Phe Lys Lys Leu Leu Arg Leu Phe Ser Leu Val Ile Trp
     95                 100                 105 ata tgc ctt gtt gcc atg gga tac ctg ttc atg tgt ttt gga ggc acc      445
Ile Cys Leu Val Ala Met Gly Tyr Leu Phe Met Cys Phe Gly Gly Thr
110                 115                 120                 125 gtc tct ccc tgg gac cag gta tcg ttc ttc ctc ttc atc atc ttc gtg      493
Val Ser Pro Trp Asp Gln Val Ser Phe Phe Leu Phe Ile Ile Phe Val
                130                 135                 140 gtg tac acc atg ctg ccc ttc aac atg cga gac gcc atc att gcc agc      541
Val Tyr Thr Met Leu Pro Phe Asn Met Arg Asp Ala Ile Ile Ala Ser
            145                 150                 155 gtc ctc acc tcc tcc tcc cac acc atc gtg ctt agc gtc tgc ctg tct      589
Val Leu Thr Ser Ser Ser His Thr Ile Val Leu Ser Val Cys Leu Ser
        160                 165                 170 gca aca ccg gga ggc aag gag cac ctg gtc tgg cag atc ctg gcc aat      637
Ala Thr Pro Gly Gly Lys Glu His Leu Val Trp Gln Ile Leu Ala Asn
    175                 180                 185 gtg atc att ttc atc tgt ggg aac ctg gcg gga gcc tac cat aag cac      685
Val Ile Ile Phe Ile Cys Gly Asn Leu Ala Gly Ala Tyr His Lys His
190                 195                 200                 205 ctc atg gaa ctc gct ctt cag caa aca tat cag gac acc tgt aat tgc      733
Leu Met Glu Leu Ala Leu Gln Gln Thr Tyr Gln Asp Thr Cys Asn Cys
                210                 215                 220 atc aag tcg cgg atc aag ttg gaa ttt gaa aaa cgt caa cag gag cgg      781
```

-continued

| | | | | | | | | | | | | |
|---|---|---|---|---|---|---|---|---|---|---|---|---|
| Ile | Lys | Ser | Arg | Ile | Lys | Leu | Glu | Phe | Glu | Lys | Arg | Gln | Gln | Glu | Arg |
| | | | 225 | | | | 230 | | | | 235 | | | | |

```
ctt ctg ctc tcc ctg ctg ccg gcc cac atc gcc atg gag atg aaa gcg     829
Leu Leu Leu Ser Leu Leu Pro Ala His Ile Ala Met Glu Met Lys Ala
        240                 245                 250 gag atc atc cag agg ctg cag ggc ccc aag gcg ggc cag atg gag aac     877
Glu Ile Ile Gln Arg Leu Gln Gly Pro Lys Ala Gly Gln Met Glu Asn
    255                 260                 265 aca aat aac ttc cac aac ctg tat gtg aag cgg cat aca aac gtg agc     925
Thr Asn Asn Phe His Asn Leu Tyr Val Lys Arg His Thr Asn Val Ser
270                 275                 280                 285 atc tta tac gct gac atc gtt ggc ttt acc cgg ctg gca agt gac tgc     973
Ile Leu Tyr Ala Asp Ile Val Gly Phe Thr Arg Leu Ala Ser Asp Cys
                290                 295                 300 tcc ccg gga gaa cta gtc cac atg ctg aat gag ctc ttt gga aag ttt    1021
Ser Pro Gly Glu Leu Val His Met Leu Asn Glu Leu Phe Gly Lys Phe
            305                 310                 315 gat caa att gca aag gag aat gaa tgc atg aga att aaa att tta gga    1069
Asp Gln Ile Ala Lys Glu Asn Glu Cys Met Arg Ile Lys Ile Leu Gly
        320                 325                 330 gac tgc tac tac tgt gta tct gga ctc cct ata tct ctc cct aac cat    1117
Asp Cys Tyr Tyr Cys Val Ser Gly Leu Pro Ile Ser Leu Pro Asn His
    335                 340                 345 gcc aag aac tgt gtg aaa atg ggg ctg gac atg tgt gaa gcc ata aag    1165
Ala Lys Asn Cys Val Lys Met Gly Leu Asp Met Cys Glu Ala Ile Lys
350                 355                 360                 365 aaa gtg agg gat gct act gga gtt gat atc aac atg cgc gtg ggc gtg    1213
Lys Val Arg Asp Ala Thr Gly Val Asp Ile Asn Met Arg Val Gly Val
                370                 375                 380 cat tct ggg aat gtc ctg tgt ggc gtg att ggt ctg cag aag tgg caa    1261
His Ser Gly Asn Val Leu Cys Gly Val Ile Gly Leu Gln Lys Trp Gln
            385                 390                 395 tat gat gtg tgg tca cat gat gtg acc ttg gcc aac cac atg gaa gct    1309
Tyr Asp Val Trp Ser His Asp Val Thr Leu Ala Asn His Met Glu Ala
        400                 405                 410 gga ggg gtc cct gga cgt gtt cac att tct tct gtc acc ctg gag cac    1357
Gly Gly Val Pro Gly Arg Val His Ile Ser Ser Val Thr Leu Glu His
    415                 420                 425 ttg aat ggc gct tat aaa gtg gag gag gga gat ggt gac att agg gac    1405
Leu Asn Gly Ala Tyr Lys Val Glu Glu Gly Asp Gly Asp Ile Arg Asp
430                 435                 440                 445 cca tat tta aaa cag cac ctg gtg aaa acc tac ttt gtg atc aac ccc    1453
Pro Tyr Leu Lys Gln His Leu Val Lys Thr Tyr Phe Val Ile Asn Pro
                450                 455                 460 aag gga gaa cga cgg agc ccc cag cat ctc ttc aga cct cgc cac acc    1501
Lys Gly Glu Arg Arg Ser Pro Gln His Leu Phe Arg Pro Arg His Thr
            465                 470                 475 ctt gat gga gcc aaa atg agg gcc tcg gtc cgc atg acc cgg tac ttg    1549
Leu Asp Gly Ala Lys Met Arg Ala Ser Val Arg Met Thr Arg Tyr Leu
        480                 485                 490 gag tcc tgg ggg gca gcc aag ccc ttt gca cac cta cat cac agg gac    1597
Glu Ser Trp Gly Ala Ala Lys Pro Phe Ala His Leu His His Arg Asp
    495                 500                 505 agc atg acc aca gag aac ggc aag atc agc acc acg gat gta ccc atg    1645
Ser Met Thr Thr Glu Asn Gly Lys Ile Ser Thr Thr Asp Val Pro Met
510                 515                 520                 525 ggt cag cat aat ttt caa aat cgc acc tta aga acc aag tca caa aag    1693
Gly Gln His Asn Phe Gln Asn Arg Thr Leu Arg Thr Lys Ser Gln Lys
                530                 535                 540
```

```
aag aga ttt gaa gaa gaa ttg aat gaa agg atg att caa gca att gat      1741
Lys Arg Phe Glu Glu Glu Leu Asn Glu Arg Met Ile Gln Ala Ile Asp
            545                 550                 555 ggg att aat gca cag aag caa tgg ctc aag tct gaa gac att cag aga      1789
Gly Ile Asn Ala Gln Lys Gln Trp Leu Lys Ser Glu Asp Ile Gln Arg
        560                 565                 570 atc tca ctg ctt ttc tat aac aaa gta cta gaa aaa gag tac cgg gcc      1837
Ile Ser Leu Leu Phe Tyr Asn Lys Val Leu Glu Lys Glu Tyr Arg Ala
575                 580                 585 acg gca ctg cca gcg ttc aag tat tat gtg act tgt gcc tgt ctc ata      1885
Thr Ala Leu Pro Ala Phe Lys Tyr Tyr Val Thr Cys Ala Cys Leu Ile
590                 595                 600                 605 ttc ttc tgc atc ttc att gtg cag att ctc gtg ctg cca aaa acg tct      1933
Phe Phe Cys Ile Phe Ile Val Gln Ile Leu Val Leu Pro Lys Thr Ser
                610                 615                 620 gtc ctg ggc atc tcc ttt ggg gct gcg ttt ctc ttg ctg gcc ttc atc      1981
Val Leu Gly Ile Ser Phe Gly Ala Ala Phe Leu Leu Leu Ala Phe Ile
                625                 630                 635 ctc ttc gtc tgc ttt gct gga cag ctt ctg caa tgc agc aaa aaa gcc      2029
Leu Phe Val Cys Phe Ala Gly Gln Leu Leu Gln Cys Ser Lys Lys Ala
            640                 645                 650 tct ccc ctg ctc atg tgg ctt ttg aag tcc tcg ggc atc att gcc aac      2077
Ser Pro Leu Leu Met Trp Leu Leu Lys Ser Ser Gly Ile Ile Ala Asn
655                 660                 665 cgc ccc tgg cca cgg atc tct ctc acg atc atc acc aca gcc atc ata      2125
Arg Pro Trp Pro Arg Ile Ser Leu Thr Ile Ile Thr Thr Ala Ile Ile
670                 675                 680                 685 tta atg atg gcc gtg ttc aac atg ttt ttc ctg agt gac tca gag gaa      2173
Leu Met Met Ala Val Phe Asn Met Phe Phe Leu Ser Asp Ser Glu Glu
                690                 695                 700 aca atc cct cca act gcc aac aca aca aac aca agc ttt tca gcc tca      2221
Thr Ile Pro Pro Thr Ala Asn Thr Thr Asn Thr Ser Phe Ser Ala Ser
                705                 710                 715 aat aat cag gtg gcg att ctg cgt gcg cag aat tta ttt ttc ctc ccg      2269
Asn Asn Gln Val Ala Ile Leu Arg Ala Gln Asn Leu Phe Phe Leu Pro
            720                 725                 730 tac ttt atc tac agc tgc att ctg gga ctg ata tcc tgt tcc gtg ttc      2317
Tyr Phe Ile Tyr Ser Cys Ile Leu Gly Leu Ile Ser Cys Ser Val Phe
735                 740                 745 ctg cgg gta aac tat gag ctg aag atg ttg atc atg atg gtg gcc ttg      2365
Leu Arg Val Asn Tyr Glu Leu Lys Met Leu Ile Met Met Val Ala Leu
750                 755                 760                 765 gtg ggc tac aac acc atc cta ctc cac acc cac gcc cac gtc ctg ggc      2413
Val Gly Tyr Asn Thr Ile Leu Leu His Thr His Ala His Val Leu Gly
                770                 775                 780 gac tac agc cag gtc tta ttt gag aga cca ggc att tgg aaa gac ctg      2461
Asp Tyr Ser Gln Val Leu Phe Glu Arg Pro Gly Ile Trp Lys Asp Leu
            785                 790                 795 aag acc atg ggc tct gtg tct ctc tct ata ttc ttc atc aca ctg ctt      2509
Lys Thr Met Gly Ser Val Ser Leu Ser Ile Phe Phe Ile Thr Leu Leu
        800                 805                 810 gtt ctg ggt aga cag aat gaa tat tac tgt agg tta gac ttc tta tgg      2557
Val Leu Gly Arg Gln Asn Glu Tyr Tyr Cys Arg Leu Asp Phe Leu Trp
815                 820                 825 aag aac aaa ttc aaa aaa gag cgg gag gag ata gag acc atg gag aac      2605
Lys Asn Lys Phe Lys Lys Glu Arg Glu Glu Ile Glu Thr Met Glu Asn
830                 835                 840                 845 ctg aac cgc gtg ctg ctg gag aac gtg ctt ccc gcg cac gtg gct gag      2653
Leu Asn Arg Val Leu Leu Glu Asn Val Leu Pro Ala His Val Ala Glu
            850                 855                 860
```

```
cac ttc ctg gcc agg agc ctg aag aat gag gag cta tac cac cag tcc    2701
His Phe Leu Ala Arg Ser Leu Lys Asn Glu Glu Leu Tyr His Gln Ser
            865                 870                 875 tat gac tgc gtc tgc gtc atg ttt gcc tcc att ccg gat ttc aaa gaa    2749
Tyr Asp Cys Val Cys Val Met Phe Ala Ser Ile Pro Asp Phe Lys Glu
        880                 885                 890 ttt tat aca gaa tcc gac gtg aac aag gag ggc ttg gaa tgc ctt cgg    2797
Phe Tyr Thr Glu Ser Asp Val Asn Lys Glu Gly Leu Glu Cys Leu Arg
    895                 900                 905 ctc ctg aac gag atc atc gct gac ttt gat gat ctt ctt tcc aag cca    2845
Leu Leu Asn Glu Ile Ile Ala Asp Phe Asp Asp Leu Leu Ser Lys Pro
910                 915                 920                 925 aaa ttc agt gga gtt gaa aag att aag acc att ggc agc aca tac atg    2893
Lys Phe Ser Gly Val Glu Lys Ile Lys Thr Ile Gly Ser Thr Tyr Met
                930                 935                 940 gca gca aca ggt ctg agc gct gtg ccc agc cag gag cac tcc cag gag    2941
Ala Ala Thr Gly Leu Ser Ala Val Pro Ser Gln Glu His Ser Gln Glu
            945                 950                 955 ccc gag cgg cag tac atg cac att ggc acc atg gtg gag ttt gct ttt    2989
Pro Glu Arg Gln Tyr Met His Ile Gly Thr Met Val Glu Phe Ala Phe
        960                 965                 970 gcc ctg gta ggg aag ctg gat gcc atc aac aag cac tcc ttc aac gac    3037
Ala Leu Val Gly Lys Leu Asp Ala Ile Asn Lys His Ser Phe Asn Asp
    975                 980                 985 ttc aaa ttg cga gtg ggt att aac cat gga cct gtg ata gct ggt gtg    3085
Phe Lys Leu Arg Val Gly Ile Asn His Gly Pro Val Ile Ala Gly Val
990                 995                 1000                1005 att gga gct cag aag cca caa tat gat atc tgg ggc aac act gtc aat    3133
Ile Gly Ala Gln Lys Pro Gln Tyr Asp Ile Trp Gly Asn Thr Val Asn
                1010                1015                1020 gtg gcc agt agg atg gac agc acc gga gtc ctg gac aaa ata cag gtt    3181
Val Ala Ser Arg Met Asp Ser Thr Gly Val Leu Asp Lys Ile Gln Val
            1025                1030                1035 acc gag gag acg agc ctc gtc ctg cag acc ctc gga tac acg tgc acc    3229
Thr Glu Glu Thr Ser Leu Val Leu Gln Thr Leu Gly Tyr Thr Cys Thr
        1040                1045                1050 tgt cga gga ata atc aac gtg aaa gga aag ggg gac ctg aag acg tac    3277
Cys Arg Gly Ile Ile Asn Val Lys Gly Lys Gly Asp Leu Lys Thr Tyr
    1055                1060                1065 ttt gta aac aca gaa atg tca agg tcc ctt tcc cag agc aac gtg gca    3325
Phe Val Asn Thr Glu Met Ser Arg Ser Leu Ser Gln Ser Asn Val Ala
1070                1075                1080                1085 tcc tga agagtcacct tcattttggc aagaagactg tattttcagg aagtatcac    3381
Ser * acactttctg actgcaactt ctgtcccttg tttttgatgt gcgtgctgtc tgtcctatgg    3441
agcctctgca gactcgttct cgtgacccag tggcataccg tttggtgtct gatgtgtgcc    3501
cagatcgttc tgccacttgc actgtgcttg ctcctaagca aaagggaaaa ggagcgcgcg    3561
tgatagaaga aaagcactgg gagaactaac agaggagaaa ggtgaaacac acacacattc    3621
ttaaggcaat aaaactaggg ggtgtatatt atcttctggg gcatgttctt ttctggaaaa    3681
tatggtagct cgccaaccgc atctgctcat ctgatattca aacacacagt attcgtgaat    3741
aagttgattc tgtcccccac gtggactctg tgctcaccca ttgtctcatt gccagtggtg    3801
tccaagggcc ccgttgggac ccacggctc tcgtccctct gctccgtgtg tctcatgcca    3861
gcagcacgtc gccatccgtc accagaatta gtcctcacag cctaggacca gttttgtatc    3921
aaactcgtct gatgttttga tgccatttgt cttttgtaaa gttaattcat taaaagtttt    3981
```

-continued

```
atgtactttg aaaaaaaaaa aaaaagagcg                                        4011
```

<210> SEQ ID NO 21
<211> LENGTH: 2847
<212> TYPE: DNA
<213> ORGANISM: Homo sapiens
<220> FEATURE:
<221> NAME/KEY: CDS
<222> LOCATION: (60)...(1703)

<400> SEQUENCE: 21

```
tcactatagg gagtcgaccc acgcgtccga tgcagccttg ataatcatcc gattccaga         59 atg ggt ggc tgc att cct ttt ctg aag gca gca agg gca ctg tgc ccc        107
Met Gly Gly Cys Ile Pro Phe Leu Lys Ala Ala Arg Ala Leu Cys Pro
 1               5                  10                  15 aga atc atg ccc cct ttg ctg ttg ttg tcc gcc ttc att ttt tta gtg        155
Arg Ile Met Pro Pro Leu Leu Leu Leu Ser Ala Phe Ile Phe Leu Val
             20                  25                  30 agt gtc ttg gga gga gcc cca gga cac aac ccc gac cgc agg acg aag        203
Ser Val Leu Gly Gly Ala Pro Gly His Asn Pro Asp Arg Arg Thr Lys
         35                  40                  45 atg gta tcg ata cac agc ctc tct gag ctg gag cgt ctg aag ctg caa        251
Met Val Ser Ile His Ser Leu Ser Glu Leu Glu Arg Leu Lys Leu Gln
     50                  55                  60 gag act gct tac cac gaa ctc gtg gcc aga cat ttc ctc tcc gaa ttc        299
Glu Thr Ala Tyr His Glu Leu Val Ala Arg His Phe Leu Ser Glu Phe
 65                  70                  75                  80 aaa cct gac aga gct ctg cct att gac cgt ccg aac acc ttg gat aag        347
Lys Pro Asp Arg Ala Leu Pro Ile Asp Arg Pro Asn Thr Leu Asp Lys
                 85                  90                  95 tgg ttt ctg att ttg aga gga cag cag agg gct gta tca cac aag aca        395
Trp Phe Leu Ile Leu Arg Gly Gln Gln Arg Ala Val Ser His Lys Thr
            100                 105                 110 ttt ggc att agc ctg gaa gag gtc ctg gtg aac gag ttt acc cgc cgc        443
Phe Gly Ile Ser Leu Glu Glu Val Leu Val Asn Glu Phe Thr Arg Arg
        115                 120                 125 aag cat ctt gaa ctg aca gcc acg atg cag gtt gaa gaa gcc acc ggt        491
Lys His Leu Glu Leu Thr Ala Thr Met Gln Val Glu Glu Ala Thr Gly
    130                 135                 140 cag gct gcg ggc cgt cgt cgg gga aac gtg gtc cga agg gtg ttt ggc        539
Gln Ala Ala Gly Arg Arg Arg Gly Asn Val Val Arg Arg Val Phe Gly
145                 150                 155                 160 cgc atc cgg cgc ttt ttc agt cgc agg cgg aat gag ccc acc ttg ccc        587
Arg Ile Arg Arg Phe Phe Ser Arg Arg Arg Asn Glu Pro Thr Leu Pro
                165                 170                 175 cgg gag ttc act cgc cgt ggg cgt cga ggt gca gtg tct gtg gat agt        635
Arg Glu Phe Thr Arg Arg Gly Arg Arg Gly Ala Val Ser Val Asp Ser
            180                 185                 190 ctg gct gag ctg gaa gac gga gcc ctg ctg cag acc ctg cag ctt            683
Leu Ala Glu Leu Glu Asp Gly Ala Leu Leu Gln Thr Leu Gln Leu
        195                 200                 205 tca aaa att tcc ttt cca att ggc caa cga ctt ctg gga tcc aaa agg        731
Ser Lys Ile Ser Phe Pro Ile Gly Gln Arg Leu Leu Gly Ser Lys Arg
    210                 215                 220 aag atg agt ctc aat ccg att gcg aaa caa atc ccc cag gtt gtt gag        779
Lys Met Ser Leu Asn Pro Ile Ala Lys Gln Ile Pro Gln Val Val Glu
225                 230                 235                 240 gct tgc tgc caa ttc att gaa aaa cat ggc tta agc gca gtg ggg att        827
Ala Cys Cys Gln Phe Ile Glu Lys His Gly Leu Ser Ala Val Gly Ile
                245                 250                 255
```

```
ttt acc ctt gaa tac tcc gtg cag cga gtg cgt cag ctc cgt gaa gaa      875
Phe Thr Leu Glu Tyr Ser Val Gln Arg Val Arg Gln Leu Arg Glu Glu
        260                 265                 270 ttt gat caa ggt ctg gat gta gtg ctg gat gac aat cag aat gtg cat      923
Phe Asp Gln Gly Leu Asp Val Val Leu Asp Asp Asn Gln Asn Val His
            275                 280                 285 gat gtg gct gca ctc ctc aag gag ttt ttc cgt gac atg aag gat tct      971
Asp Val Ala Ala Leu Leu Lys Glu Phe Phe Arg Asp Met Lys Asp Ser
    290                 295                 300 ctg ctg cca gat gat ctg tac atg tca ttc ctc ctg aca gca act tta     1019
Leu Leu Pro Asp Asp Leu Tyr Met Ser Phe Leu Leu Thr Ala Thr Leu
305                 310                 315                 320 aag ccc cag gat cag ctt tct gcc ctg cag ttg ctg gtc tac ctg atg     1067
Lys Pro Gln Asp Gln Leu Ser Ala Leu Gln Leu Leu Val Tyr Leu Met
                325                 330                 335 cca ccc tgc cac agt gat acc ctg gag cgt ctg ctg aag gcc ctg cat     1115
Pro Pro Cys His Ser Asp Thr Leu Glu Arg Leu Leu Lys Ala Leu His
            340                 345                 350 aaa atc act gag aac tgc gag gac tca att ggc att gat gga cag ttg     1163
Lys Ile Thr Glu Asn Cys Glu Asp Ser Ile Gly Ile Asp Gly Gln Leu
    355                 360                 365 gtc cca ggc aac cgt atg act tcc act aac ttg gcc ttg gtg ttt gga     1211
Val Pro Gly Asn Arg Met Thr Ser Thr Asn Leu Ala Leu Val Phe Gly
370                 375                 380 tct gct ctc ctg aaa aaa gga aag ttt ggc aag aga gag tcc agg aaa     1259
Ser Ala Leu Leu Lys Lys Gly Lys Phe Gly Lys Arg Glu Ser Arg Lys
385                 390                 395                 400 aca aag ctg ggg att gat cac tat gtt gct tct gtc aat gtg gtc cgt     1307
Thr Lys Leu Gly Ile Asp His Tyr Val Ala Ser Val Asn Val Val Arg
                405                 410                 415 gcc atg att gat aac tgg gat gtc ctc ttc cag gtg cct ccc cat att     1355
Ala Met Ile Asp Asn Trp Asp Val Leu Phe Gln Val Pro Pro His Ile
            420                 425                 430 cag agg cag gtt gct aag cgc gtg tgg aag tcc agc ccg gaa gca ctt     1403
Gln Arg Gln Val Ala Lys Arg Val Trp Lys Ser Ser Pro Glu Ala Leu
    435                 440                 445 gat ttt atc aga cgc agg aac ttg agg aag atc cag agt gca cgc ata     1451
Asp Phe Ile Arg Arg Arg Asn Leu Arg Lys Ile Gln Ser Ala Arg Ile
450                 455                 460 aag atg gaa gag gat gca cta ctt tct gat cca gtg gaa acc tct gct     1499
Lys Met Glu Glu Asp Ala Leu Leu Ser Asp Pro Val Glu Thr Ser Ala
465                 470                 475                 480 gaa gcc cgg gct gct gtc ctt gct caa agc aag cct tct gat gaa ggt     1547
Glu Ala Arg Ala Ala Val Leu Ala Gln Ser Lys Pro Ser Asp Glu Gly
                485                 490                 495 tcc tct gag gag cca gct gtg cct tcc ggc act gcc cgt tcc cat gac     1595
Ser Ser Glu Glu Pro Ala Val Pro Ser Gly Thr Ala Arg Ser His Asp
            500                 505                 510 gat gag gaa gga gcg ggt aac cct ccc att ccg gag caa gac cgc cca     1643
Asp Glu Glu Gly Ala Gly Asn Pro Pro Ile Pro Glu Gln Asp Arg Pro
    515                 520                 525 ttg ctc cgt gtg ccc cgg gag aag gag gcc aaa act ggc gtc agc tac     1691
Leu Leu Arg Val Pro Arg Glu Lys Glu Ala Lys Thr Gly Val Ser Tyr
530                 535                 540 ttc ttt cct tag atgtttttcc ttctataagg tgccagacag gggaaaggg          1743
Phe Phe Pro *
545 tgggggtaca tctgggatgt cacaggaaac attaaggaga gagttgaagg taaagatctg   1803
```

-continued

```
aaggtaagaa ggagttccac ctgatgctcg ggtcaggatg agaattccaa acacactgcc    1863
agccccttca ctggggatgc ttggkctctt ctgctggtaa aagcagagat gttttctgtg    1923
tcatgcccaa gctccccggt gctaccttgc cttctctctt tacccctgat cttggctttc    1983
tctctctctc tgcagacttt cctttaattg atgtgacatt tgtggtaaac accttcccca    2043
gggaacctca caaatcttga gatgctttcc cttccccaaa tgggattgca tgatttccct    2103
gactttccta ccctcctcca gagagctcag ttggaaaggc cctcaagagg catgctagaa    2163
cgttaggtca gcctactgac agctgacaaa caattaatgc gaaatcatgt cacaccaacc    2223
catagccgtg tccacgcagc aactccacca ccttaggatt tcccctcca aattattcag     2283 accaatggct tgccaaatgg cctctcccaa aattctgtac agttttgctc aggtcacgcc    2343
aacagggaaa cctcaagtgt aggtctaatt agtgtttctg ggatccaaag ttagaggaaa    2403
atttagattt tattgcctgg atctgcttta aagacaattg gtgtttacac cctcttgtca    2463
gcaaaacagc tagttaggta aggacatata gttccaagta ggtaaagtca cttgattaca    2523
aatgttctta actatcgtct ctgtaattcc tttatacagg acagtacaaa attgtgggac    2583
atgctctggt aacacacaga tatgggttgc atatgatcca gaattacagc tgatatttatg   2643 gatgacaact gctaaggtcc ataaaatgaa gactgtattg tattgaggga tagaaattga    2703
tcatttaatg ggtaacaact gctgagctca aagatttgtg attgttaaaa cttctctggc    2763
atttaatcat taataaacat ctgtattgtg ccaccagcat aaaaaaaaaa aaaaaaaaa     2823 aaaaaaaaaa aaaaaaaaaa aagg                                           2847
```

<210> SEQ ID NO 22
<211> LENGTH: 547
<212> TYPE: PRT
<213> ORGANISM: Homo sapiens

<400> SEQUENCE: 22

```
Met Gly Gly Cys Ile Pro Phe Leu Lys Ala Ala Arg Ala Leu Cys Pro
1               5                   10                  15

Arg Ile Met Pro Pro Leu Leu Leu Leu Ser Ala Phe Ile Phe Leu Val
            20                  25                  30

Ser Val Leu Gly Gly Ala Pro Gly His Asn Pro Asp Arg Arg Thr Lys
        35                  40                  45

Met Val Ser Ile His Ser Leu Ser Glu Leu Glu Arg Leu Lys Leu Gln
    50                  55                  60

Glu Thr Ala Tyr His Glu Leu Val Ala Arg His Phe Leu Ser Glu Phe
65                  70                  75                  80

Lys Pro Asp Arg Ala Leu Pro Ile Asp Arg Pro Asn Thr Leu Asp Lys
                85                  90                  95

Trp Phe Leu Ile Leu Arg Gly Gln Gln Arg Ala Val Ser His Lys Thr
            100                 105                 110

Phe Gly Ile Ser Leu Glu Glu Val Leu Val Asn Glu Phe Thr Arg Arg
        115                 120                 125

Lys His Leu Glu Leu Thr Ala Thr Met Gln Val Glu Ala Thr Gly
    130                 135                 140

Gln Ala Ala Gly Arg Arg Gly Asn Val Val Arg Val Phe Gly
145                 150                 155                 160

Arg Ile Arg Arg Phe Phe Ser Arg Arg Asn Glu Pro Thr Leu Pro
                165                 170                 175

Arg Glu Phe Thr Arg Arg Gly Arg Arg Gly Ala Val Ser Val Asp Ser
            180                 185                 190
```

```
Leu Ala Glu Leu Glu Asp Gly Ala Leu Leu Gln Thr Leu Gln Leu
            195                 200                 205

Ser Lys Ile Ser Phe Pro Ile Gly Gln Arg Leu Leu Gly Ser Lys Arg
    210                 215                 220

Lys Met Ser Leu Asn Pro Ile Ala Lys Gln Ile Pro Gln Val Val Glu
225                 230                 235                 240

Ala Cys Cys Gln Phe Ile Glu Lys His Gly Leu Ser Ala Val Gly Ile
            245                 250                 255

Phe Thr Leu Glu Tyr Ser Val Gln Arg Val Arg Gln Leu Arg Glu Glu
            260                 265                 270

Phe Asp Gln Gly Leu Asp Val Leu Asp Asp Gln Asn Val His
            275                 280                 285

Asp Val Ala Ala Leu Leu Lys Glu Phe Phe Arg Asp Met Lys Asp Ser
            290                 295                 300

Leu Leu Pro Asp Asp Leu Tyr Met Ser Phe Leu Leu Thr Ala Thr Leu
305                 310                 315                 320

Lys Pro Gln Asp Gln Leu Ser Ala Leu Gln Leu Val Tyr Leu Met
            325                 330                 335

Pro Pro Cys His Ser Asp Thr Leu Glu Arg Leu Leu Lys Ala Leu His
            340                 345                 350

Lys Ile Thr Glu Asn Cys Glu Asp Ser Ile Gly Ile Asp Gly Gln Leu
            355                 360                 365

Val Pro Gly Asn Arg Met Thr Ser Thr Asn Leu Ala Leu Val Phe Gly
            370                 375                 380

Ser Ala Leu Leu Lys Lys Gly Lys Phe Gly Lys Arg Glu Ser Arg Lys
385                 390                 395                 400

Thr Lys Leu Gly Ile Asp His Tyr Val Ala Ser Val Asn Val Val Arg
            405                 410                 415

Ala Met Ile Asp Asn Trp Asp Val Leu Phe Gln Val Pro Pro His Ile
            420                 425                 430

Gln Arg Gln Val Ala Lys Arg Val Trp Lys Ser Ser Pro Glu Ala Leu
            435                 440                 445

Asp Phe Ile Arg Arg Arg Asn Leu Arg Lys Ile Gln Ser Ala Arg Ile
            450                 455                 460

Lys Met Glu Glu Asp Ala Leu Leu Ser Asp Pro Val Glu Thr Ser Ala
465                 470                 475                 480

Glu Ala Arg Ala Ala Val Leu Ala Gln Ser Lys Pro Ser Asp Glu Gly
            485                 490                 495

Ser Ser Glu Glu Pro Ala Val Pro Ser Gly Thr Ala Arg Ser His Asp
            500                 505                 510

Asp Glu Glu Gly Ala Gly Asn Pro Ile Pro Glu Gln Asp Arg Pro
            515                 520                 525

Leu Leu Arg Val Pro Arg Glu Lys Glu Ala Lys Thr Gly Val Ser Tyr
            530                 535                 540

Phe Phe Pro
545

<210> SEQ ID NO 23
<211> LENGTH: 1644
<212> TYPE: DNA
<213> ORGANISM: Homo sapiens

<400> SEQUENCE: 23
atgggtggct gcattccttt tctgaaggca gcaagggcac tgtgcccag aatcatgccc    60
```

-continued

```
cctttgctgt tgttgtccgc cttcattttt ttagtgagtg tcttgggagg agccccagga      120
cacaaccccg accgcaggac gaagatggta tcgatacaca gcctctctga gctggagcgt      180
ctgaagctgc aagagactgc ttaccacgaa ctcgtggcca gacatttcct ctccgaattc      240
aaacctgaca gagctctgcc tattgaccgt ccgaacacct tggataagtg gtttctgatt      300
ttgagaggac agcagagggc tgtatcacac aagacatttg gcattagcct ggaagaggtc      360
ctggtgaacg agtttacccg ccgcaagcat cttgaactga cagccacgat gcaggttgaa      420
gaagccaccg gtcaggctgc gggccgtcgt cggggaaacg tggtgcgaag ggtgttttggc     480 cgcatccggc gcttttttcag tcgcaggcgg aatgagccca ccttgccccg ggagttcact     540
cgccgtgggc gtcgaggtgc agtgtctgtg gatagtctgg ctgagctgga agacggagcc      600
ctgctgctgc agaccctgca gctttcaaaa atttcctttc caattggcca acgacttctg      660
ggatccaaaa ggaagatgag tctcaatccg attgcgaaac aaatccccca ggttgttgag      720
gcttgctgcc aattcattga aaaacatggc ttaagcgcag tggggatttt tacccttgaa      780
tactccgtgc agcgagtgcg tcagctccgt gaagaatttg atcaaggtct ggatgtagtg      840
ctggatgaca atcagaatgt gcatgatgtg gctgcactcc tcaaggagtt tttccgtgac      900
atgaaggatt ctctgctgcc agatgatctg tacatgtcat tcctcctgac agcaactta      960 aagccccagg atcagctttc tgccctgcag ttgctggtct acctgatgcc accctgccac     1020
agtgataccc tggagcgtct gctgaaggcc ctgcataaaa tcactgagaa ctgcgaggac     1080
tcaattggca ttgatggaca gttggtccca ggcaaccgta tgacttccac taacttggcc     1140
ttggtgtttg gatctgctct cctgaaaaaa ggaaagtttg gcaagagaga gtccaggaaa     1200
acaaagctgg ggattgatca ctatgttgct tctgtcaatg tggtccgtgc catgattgat     1260
aactgggatg tcctcttcca ggtgcctccc catattcaga ggcaggttgc taagcgcgtg     1320
tggaagtcca gcccggaagc acttgatttt atcagacgca ggaacttgag gaagatccag     1380
agtgcacgca taaagatgga agaggatgca ctactttctg atccagtgga aacctctgct     1440
gaagcccggg ctgctgtcct tgctcaaagc aagccttctg atgaaggttc ctctgaggag     1500
ccagctgtgc cttccggcac tgcccgttcc catgacgatg aggaaggagc gggtaaccct     1560
cccattccgg agcaagaccg cccattgctc cgtgtgcccc gggagaagga ggccaaaact     1620
ggcgtcagct acttctttcc ttag                                            1644
```

<210> SEQ ID NO 24
<211> LENGTH: 3391
<212> TYPE: DNA
<213> ORGANISM: Homo sapiens
<220> FEATURE:
<221> NAME/KEY: CDS
<222> LOCATION: (78)...(3095)

<400> SEQUENCE: 24

```
gaggaagcca ggcggggtgc agacggctgc tgattctggg gctggtcagg aaaccaagga      60
gacccccccc cccaacc atg gac cca ccg tcg cca agc cgg acc tcc caa        110
                Met Asp Pro Pro Ser Pro Ser Arg Thr Ser Gln
                  1               5                  10 acc cag ccc aca gcc acc tct ccg ctg act tcc tac cgc tgg cac aca       158
Thr Gln Pro Thr Ala Thr Ser Pro Leu Thr Ser Tyr Arg Trp His Thr
            15                  20                  25 ggg ggc ggt ggg gag aag gcg gct gga ggg ttc cgc tgg ggc cgc ttt       206
Gly Gly Gly Gly Glu Lys Ala Ala Gly Gly Phe Arg Trp Gly Arg Phe
        30                  35                  40
```

-continued

| | |
|---|---|
| gct ggc tgg ggc agg gcc ctg agc cac cag gag ccc atg gtc agc acc<br>Ala Gly Trp Gly Arg Ala Leu Ser His Gln Glu Pro Met Val Ser Thr<br>    45                              50                            55 | 254 |
| cag cca gcc cct cgc tcg ata ttc cgt cgg gtc cta tct gcg cct ccc<br>Gln Pro Ala Pro Arg Ser Ile Phe Arg Arg Val Leu Ser Ala Pro Pro<br> 60                               65                            70                       75 | 302 |
| aag gag tca cgg acc agt cgc ctt cga ctc tcc aag gcc ctc tgg ggg<br>Lys Glu Ser Arg Thr Ser Arg Leu Arg Leu Ser Lys Ala Leu Trp Gly<br>                    80                            85                           90 | 350 |
| agg cat aag aac cca ccg ccg gag cca gac ccg gag ccg gag cag gag<br>Arg His Lys Asn Pro Pro Pro Glu Pro Asp Pro Glu Pro Glu Gln Glu<br>                95                            100                         105 | 398 |
| gcc cca gag ctg gag ccg gag cca gag ctg gag ccc cct acc cca cag<br>Ala Pro Glu Leu Glu Pro Glu Pro Glu Leu Glu Pro Pro Thr Pro Gln<br>          110                           115                         120 | 446 |
| atc cct gag gcc ccc aca ccc aac gtg cct gtc tgg gac att ggg ggc<br>Ile Pro Glu Ala Pro Thr Pro Asn Val Pro Val Trp Asp Ile Gly Gly<br>     125                            130                         135 | 494 |
| ttc acc ctg ctt gat ggg aag ctg gtg ctg ctt gga gga gag gag gag<br>Phe Thr Leu Leu Asp Gly Lys Leu Val Leu Leu Gly Gly Glu Glu Glu<br>140                       145                         150                       155 | 542 |
| ggt cct cga agg ccc cgg gtg gga agt gct agc tcc gag ggc agc atc<br>Gly Pro Arg Arg Pro Arg Val Gly Ser Ala Ser Ser Glu Gly Ser Ile<br>                    160                           165                       170 | 590 |
| cac gtg gcc atg ggg aac ttc agg gat cca gat cgg atg cct gga aaa<br>His Val Ala Met Gly Asn Phe Arg Asp Pro Asp Arg Met Pro Gly Lys<br>               175                           180                         185 | 638 |
| aca gaa ccg gag act gct ggt ccc aac cag gtc cac aac gtt cgg ggg<br>Thr Glu Pro Glu Thr Ala Gly Pro Asn Gln Val His Asn Val Arg Gly<br>          190                           195                         200 | 686 |
| ttg ctc aag agg ctg aaa gag aag aaa aag gcc aga ccc ccc agt gct<br>Leu Leu Lys Arg Leu Lys Glu Lys Lys Lys Ala Arg Pro Pro Ser Ala<br>     205                            210                         215 | 734 |
| ctg ggc tct agg gag tcg ctg gcc aca ctc tct gaa ctg gac ctg ggt<br>Leu Gly Ser Arg Glu Ser Leu Ala Thr Leu Ser Glu Leu Asp Leu Gly<br>220                       225                         230                       235 | 782 |
| gcc gag cgg gat gtg cgg atc tgg cca ctg cac ccc agc ctc ctg ggg<br>Ala Glu Arg Asp Val Arg Ile Trp Pro Leu His Pro Ser Leu Leu Gly<br>               240                           245                         250 | 830 |
| gag ccc cac tgc ttt cag gta acc tgg acg ggt gga agc cgc tgc ttc<br>Glu Pro His Cys Phe Gln Val Thr Trp Thr Gly Gly Ser Arg Cys Phe<br>          255                           260                         265 | 878 |
| tct tgt cgc tcg gcc gct gag aga gac cgc tgg atc gag gac ctt cgt<br>Ser Cys Arg Ser Ala Ala Glu Arg Asp Arg Trp Ile Glu Asp Leu Arg<br>               270                           275                         280 | 926 |
| cgc caa ttc cag ccc acc cag gac aac gtg gag cgg gaa gag aca tgg<br>Arg Gln Phe Gln Pro Thr Gln Asp Asn Val Glu Arg Glu Glu Thr Trp<br>     285                            290                         295 | 974 |
| ctg agc gtg tgg gtg cac gaa gcg aag ggg ctt ccc cga gca gcg gcg<br>Leu Ser Val Trp Val His Glu Ala Lys Gly Leu Pro Arg Ala Ala Ala<br>300                       305                         310                       315 | 1022 |
| ggg gca ccc ggc gtg cgc gcc gag ctg tgg ctg gat ggc gcg ctg ctg<br>Gly Ala Pro Gly Val Arg Ala Glu Leu Trp Leu Asp Gly Ala Leu Leu<br>                    320                           325                       330 | 1070 |
| gca cgc acg gcg cct cgg gcc ggc cca ggc cag ctc ttc tgg gcc gag<br>Ala Arg Thr Ala Pro Arg Ala Gly Pro Gly Gln Leu Phe Trp Ala Glu<br>               335                           340                         345 | 1118 |
| cgc ttc cac ttc gag gcg ctg cca ccg gca cgt cgc ctg tcg ctg cgg<br>Arg Phe His Phe Glu Ala Leu Pro Pro Ala Arg Arg Leu Ser Leu Arg | 1166 |

-continued

```
              350                 355                 360
ctg cgc ggc ttg ggc ccg gga agc gcg gtg ctg ggc cgc gtg gcc ctg      1214
Leu Arg Gly Leu Gly Pro Gly Ser Ala Val Leu Gly Arg Val Ala Leu
    365                 370                 375 gcg ctg gag gag ctg gac gcc cca cgc gcg cct gcc gcc ggt ctg gag      1262
Ala Leu Glu Glu Leu Asp Ala Pro Arg Ala Pro Ala Ala Gly Leu Glu
380                 385                 390                 395 cgc tgg ttc ccg ctg ctc ggg gcg ccg gcg ggc gca gcg ctg cgg gcg      1310
Arg Trp Phe Pro Leu Leu Gly Ala Pro Ala Gly Ala Ala Leu Arg Ala
                    400                 405                 410 cgg att cgg gcg cgt cgc ctg cgc gtg ctg ccg tcc gag cgc tac aag      1358
Arg Ile Arg Ala Arg Arg Leu Arg Val Leu Pro Ser Glu Arg Tyr Lys
            415                 420                 425 gag ctg gcg gag ttc ctc acc ttc cac tat gcg cgc ctc tgc ggg gcc      1406
Glu Leu Ala Glu Phe Leu Thr Phe His Tyr Ala Arg Leu Cys Gly Ala
        430                 435                 440 ctg gag ccc gcg ctg cct gcg cag gcc aag gag gag ctg gcg gca gcc      1454
Leu Glu Pro Ala Leu Pro Ala Gln Ala Lys Glu Glu Leu Ala Ala Ala
    445                 450                 455 atg gtg cgc gtg ctg cgg gcc acc ggc cgg gcg cag gcg ctg gtg act      1502
Met Val Arg Val Leu Arg Ala Thr Gly Arg Ala Gln Ala Leu Val Thr
460                 465                 470                 475 gac ctg ggc act gcg gag ctg gcg cgc tgt gga ggc cgt gag gcg ctg      1550
Asp Leu Gly Thr Ala Glu Leu Ala Arg Cys Gly Gly Arg Glu Ala Leu
                    480                 485                 490 ctg ttc cgg gaa aac aca ttg gcc acc aag gct atc gat gag tac atg      1598
Leu Phe Arg Glu Asn Thr Leu Ala Thr Lys Ala Ile Asp Glu Tyr Met
            495                 500                 505 aag ctc gtg gca cag gat tac ctc cag gag acc ctg gga cag gtt gtg      1646
Lys Leu Val Ala Gln Asp Tyr Leu Gln Glu Thr Leu Gly Gln Val Val
        510                 515                 520 cgg cgt ctc tgt gct tct act gag gac tgt gaa gtg gac ccc agc aaa      1694
Arg Arg Leu Cys Ala Ser Thr Glu Asp Cys Glu Val Asp Pro Ser Lys
    525                 530                 535 tgt cca gcc tcg gag ctg cca gag cac cag gcc aga ctt cgg aac agc      1742
Cys Pro Ala Ser Glu Leu Pro Glu His Gln Ala Arg Leu Arg Asn Ser
540                 545                 550                 555 tgc gag gag gtc ttc gaa acc att atc cat tcc tac gac tgg ttc cct      1790
Cys Glu Glu Val Phe Glu Thr Ile Ile His Ser Tyr Asp Trp Phe Pro
                    560                 565                 570 gcg gag ctg ggc atc gtg ttc tca agc tgg cga gaa gca tgt aaa gaa      1838
Ala Glu Leu Gly Ile Val Phe Ser Ser Trp Arg Glu Ala Cys Lys Glu
            575                 580                 585 cgt ggc tct gag gtg ctg ggc ccc cga ctg gtg tgc gcc tcc ctc ttc      1886
Arg Gly Ser Glu Val Leu Gly Pro Arg Leu Val Cys Ala Ser Leu Phe
        590                 595                 600 ctg cgg ctc ctg tgc cct gcc atc ctg gca ccc agc ctc ttt ggt ttg      1934
Leu Arg Leu Leu Cys Pro Ala Ile Leu Ala Pro Ser Leu Phe Gly Leu
    605                 610                 615 gca cca gac cat cca gca ccc ggc cca gcc cgc acc ctc aca ctg att      1982
Ala Pro Asp His Pro Ala Pro Gly Pro Ala Arg Thr Leu Thr Leu Ile
620                 625                 630                 635 gcc aag gtc atc cag aac ctc gcc aac cgt gcc ccg ttc ggt gag aag      2030
Ala Lys Val Ile Gln Asn Leu Ala Asn Arg Ala Pro Phe Gly Glu Lys
                    640                 645                 650 gag gcc tac atg ggc ttc atg aat agc ttc ctg gag gaa cat gga cca      2078
Glu Ala Tyr Met Gly Phe Met Asn Ser Phe Leu Glu Glu His Gly Pro
            655                 660                 665 gcc atg caa tgc ttc ctg gac cag gta gcc atg gtg gat gtg gat gct      2126
```

-continued

| | | |
|---|---|---|
| Ala Met Gln Cys Phe Leu Asp Gln Val Ala Met Val Asp Val Asp Ala<br>670     675     680 | | |
| gcc ccc agt ggt tac cag ggc agt ggt gat ctg gcc ctc cag tta gct<br>Ala Pro Ser Gly Tyr Gln Gly Ser Gly Asp Leu Ala Leu Gln Leu Ala<br>685     690     695 | | 2174 |
| gtc ctg cat gcc cag ctc tgt aca att ttt gct gag ctt gac cag aca<br>Val Leu His Ala Gln Leu Cys Thr Ile Phe Ala Glu Leu Asp Gln Thr<br>700     705     710     715 | | 2222 |
| acc cga gac acc ctg gaa cca ctg ccc acc atc ctg cga gcc att gag<br>Thr Arg Asp Thr Leu Glu Pro Leu Pro Thr Ile Leu Arg Ala Ile Glu<br>     720     725     730 | | 2270 |
| gag ggc cag cct gtg ctt gtg tca gtg cca atg cgt ctc cca ctg ccc<br>Glu Gly Gln Pro Val Leu Val Ser Val Pro Met Arg Leu Pro Leu Pro<br>     735     740     745 | | 2318 |
| ccg gcc cag gtc cac tcc agc ctc tcc gca ggg gag aag ccc ggc ttc<br>Pro Ala Gln Val His Ser Ser Leu Ser Ala Gly Glu Lys Pro Gly Phe<br>750     755     760 | | 2366 |
| ctg gcc ccc cgg gac ctc ccc aag cac acc cct ctc atc tcc aag agc<br>Leu Ala Pro Arg Asp Leu Pro Lys His Thr Pro Leu Ile Ser Lys Ser<br>765     770     775 | | 2414 |
| cag tct ctg cgc agc gtt cgc cgc tca gag agt tgg gcc cgg cca cgg<br>Gln Ser Leu Arg Ser Val Arg Arg Ser Glu Ser Trp Ala Arg Pro Arg<br>780     785     790     795 | | 2462 |
| ccg gac gaa gag cgg ccc ctg cgg cgg ccc cgg ccg gtg cag cgc acg<br>Pro Asp Glu Glu Arg Pro Leu Arg Arg Pro Arg Pro Val Gln Arg Thr<br>     800     805     810 | | 2510 |
| cag agt gtc ccg gtc cgg cgt cct gcc cgc cgc cgc caa tct gcg ggg<br>Gln Ser Val Pro Val Arg Arg Pro Ala Arg Arg Arg Gln Ser Ala Gly<br>   815     820     825 | | 2558 |
| ccc tgg ccg cga ccc aaa ggc tcc ctg agc atg gga cca gcg ccc cgc<br>Pro Trp Pro Arg Pro Lys Gly Ser Leu Ser Met Gly Pro Ala Pro Arg<br>830     835     840 | | 2606 |
| gcc cgg cct tgg acc cgg gac tcc gcc tcg ctg cct cgg aag ccg tcg<br>Ala Arg Pro Trp Thr Arg Asp Ser Ala Ser Leu Pro Arg Lys Pro Ser<br>845     850     855 | | 2654 |
| gta ccc tgg cag cgc caa atg gac cag ccg caa gac cga aac cag gca<br>Val Pro Trp Gln Arg Gln Met Asp Gln Pro Gln Asp Arg Asn Gln Ala<br>860     865     870     875 | | 2702 |
| ctg ggc acg cac cga cct gtg aac aag ttg gca gag ctg cag tgc gag<br>Leu Gly Thr His Arg Pro Val Asn Lys Leu Ala Glu Leu Gln Cys Glu<br>     880     885     890 | | 2750 |
| gtg gcc gct ctg cgt gag gag cag aaa gtg ctg tcc cgc ctc gtg gag<br>Val Ala Ala Leu Arg Glu Glu Gln Lys Val Leu Ser Arg Leu Val Glu<br>   895     900     905 | | 2798 |
| tcg ctg agc acc caa atc cgg gcc ttg acg gag cag cag gag cag ctg<br>Ser Leu Ser Thr Gln Ile Arg Ala Leu Thr Glu Gln Gln Glu Gln Leu<br>910     915     920 | | 2846 |
| cgg ggc cag ctg cag gat ctg gac tcc agg ctc cgt gct ggg agc tca<br>Arg Gly Gln Leu Gln Asp Leu Asp Ser Arg Leu Arg Ala Gly Ser Ser<br>925     930     935 | | 2894 |
| gag ttt gat tca gag cac aac cta aca agc aat gaa ggg cac agt ctg<br>Glu Phe Asp Ser Glu His Asn Leu Thr Ser Asn Glu Gly His Ser Leu<br>940     945     950     955 | | 2942 |
| aaa aac ctg gag cac cgc cta aat gag atg gag aga act cag gct cag<br>Lys Asn Leu Glu His Arg Leu Asn Glu Met Glu Arg Thr Gln Ala Gln<br>     960     965     970 | | 2990 |
| ctg agg gat gct gtc cag agc ctg cag ctt tct cca agg acg cgg ggg<br>Leu Arg Asp Ala Val Gln Ser Leu Gln Leu Ser Pro Arg Thr Arg Gly<br>975     980     985 | | 3038 |

-continued

```
tct tgg agt caa ccc cag ccc ctc aaa gca ccc tgc ctc aat gga gac    3086
Ser Trp Ser Gln Pro Gln Pro Leu Lys Ala Pro Cys Leu Asn Gly Asp
        990                 995                 1000 acc acc tga gctgcccatc ctgcctcatc acacgtggtc tgggagcaga            3135
Thr Thr *
    1005 gagatagcca tcttaggggg ggtgtctgac tttgccttag ccctacttgg cctacagtgg  3195 ggagtggagc tgctggtccc aaccactctg gcagtatgaa gttgcccagt aaaatcttga  3255 tttcagtgaa aaaaaaaaaa aaagggcgg rccgctagac twagtctaga gaaaaaacct   3315 cccacacctc cccctgaacc traaacathc cammacctcc ccctsawsmw smwrmawmaw  3375 araawksaaw gcaatg                                                  3391
```

<210> SEQ ID NO 25
<211> LENGTH: 1005
<212> TYPE: PRT
<213> ORGANISM: Homo sapiens

<400> SEQUENCE: 25

```
Met Asp Pro Pro Ser Pro Ser Arg Thr Ser Gln Thr Gln Pro Thr Ala
 1               5                  10                  15

Thr Ser Pro Leu Thr Ser Tyr Arg Trp His Thr Gly Gly Gly Gly Glu
             20                  25                  30

Lys Ala Ala Gly Gly Phe Arg Trp Gly Arg Phe Ala Gly Trp Gly Arg
         35                  40                  45

Ala Leu Ser His Gln Glu Pro Met Val Ser Thr Gln Pro Ala Pro Arg
     50                  55                  60

Ser Ile Phe Arg Arg Val Leu Ser Ala Pro Pro Lys Glu Ser Arg Thr
 65                  70                  75                  80

Ser Arg Leu Arg Leu Ser Lys Ala Leu Trp Gly Arg His Lys Asn Pro
                 85                  90                  95

Pro Pro Glu Pro Asp Pro Glu Pro Gln Glu Ala Pro Glu Leu Glu
            100                 105                 110

Pro Glu Pro Glu Leu Glu Pro Pro Thr Pro Gln Ile Pro Glu Ala Pro
        115                 120                 125

Thr Pro Asn Val Pro Val Trp Asp Ile Gly Gly Phe Thr Leu Leu Asp
    130                 135                 140

Gly Lys Leu Val Leu Leu Gly Gly Glu Glu Glu Gly Pro Arg Arg Pro
145                 150                 155                 160

Arg Val Gly Ser Ala Ser Ser Glu Gly Ser Ile His Val Ala Met Gly
                165                 170                 175

Asn Phe Arg Asp Pro Asp Arg Met Pro Gly Lys Thr Glu Pro Glu Thr
            180                 185                 190

Ala Gly Pro Asn Gln Val His Asn Val Arg Gly Leu Leu Lys Arg Leu
        195                 200                 205

Lys Glu Lys Lys Lys Ala Arg Pro Pro Ser Ala Leu Gly Ser Arg Glu
    210                 215                 220

Ser Leu Ala Thr Leu Ser Glu Leu Asp Leu Gly Ala Glu Arg Asp Val
225                 230                 235                 240

Arg Ile Trp Pro Leu His Pro Ser Leu Leu Gly Glu Pro His Cys Phe
                245                 250                 255

Gln Val Thr Trp Thr Gly Gly Ser Arg Cys Phe Ser Cys Arg Ser Ala
            260                 265                 270

Ala Glu Arg Asp Arg Trp Ile Glu Asp Leu Arg Arg Gln Phe Gln Pro
        275                 280                 285
```

-continued

```
Thr Gln Asp Asn Val Glu Arg Glu Thr Trp Leu Ser Val Trp Val
    290                 295                 300
His Glu Ala Lys Gly Leu Pro Arg Ala Ala Gly Ala Pro Gly Val
305                 310                 315                 320
Arg Ala Glu Leu Trp Leu Asp Gly Ala Leu Leu Ala Arg Thr Ala Pro
                325                 330                 335
Arg Ala Gly Pro Gly Gln Leu Phe Trp Ala Glu Arg Phe His Phe Glu
                340                 345                 350
Ala Leu Pro Pro Ala Arg Arg Leu Ser Leu Arg Leu Arg Gly Leu Gly
                355                 360                 365
Pro Gly Ser Ala Val Leu Gly Arg Val Ala Leu Ala Leu Glu Glu Leu
370                 375                 380
Asp Ala Pro Arg Ala Pro Ala Ala Gly Leu Glu Arg Trp Phe Pro Leu
385                 390                 395                 400
Leu Gly Ala Pro Ala Gly Ala Ala Leu Arg Ala Arg Ile Arg Ala Arg
                405                 410                 415
Arg Leu Arg Val Leu Pro Ser Glu Arg Tyr Lys Glu Leu Ala Glu Phe
                420                 425                 430
Leu Thr Phe His Tyr Ala Arg Leu Cys Gly Ala Leu Glu Pro Ala Leu
                435                 440                 445
Pro Ala Gln Ala Lys Glu Glu Leu Ala Ala Ala Met Val Arg Val Leu
450                 455                 460
Arg Ala Thr Gly Arg Ala Gln Ala Leu Val Thr Asp Leu Gly Thr Ala
465                 470                 475                 480
Glu Leu Ala Arg Cys Gly Gly Arg Glu Ala Leu Leu Phe Arg Glu Asn
                485                 490                 495
Thr Leu Ala Thr Lys Ala Ile Asp Glu Tyr Met Lys Leu Val Ala Gln
                500                 505                 510
Asp Tyr Leu Gln Glu Thr Leu Gly Gln Val Val Arg Arg Leu Cys Ala
                515                 520                 525
Ser Thr Glu Asp Cys Glu Val Asp Pro Ser Lys Cys Pro Ala Ser Glu
530                 535                 540
Leu Pro Glu His Gln Ala Arg Leu Arg Asn Ser Cys Glu Glu Val Phe
545                 550                 555                 560
Glu Thr Ile Ile His Ser Tyr Asp Trp Phe Pro Ala Glu Leu Gly Ile
                565                 570                 575
Val Phe Ser Ser Trp Arg Glu Ala Cys Lys Glu Arg Gly Ser Glu Val
                580                 585                 590
Leu Gly Pro Arg Leu Val Cys Ala Ser Leu Phe Leu Arg Leu Leu Cys
                595                 600                 605
Pro Ala Ile Leu Ala Pro Ser Leu Phe Gly Leu Ala Pro Asp His Pro
610                 615                 620
Ala Pro Gly Pro Ala Arg Thr Leu Thr Leu Ile Ala Lys Val Ile Gln
625                 630                 635                 640
Asn Leu Ala Asn Arg Ala Pro Phe Gly Glu Lys Glu Ala Tyr Met Gly
                645                 650                 655
Phe Met Asn Ser Phe Leu Glu Glu His Gly Pro Ala Met Gln Cys Phe
                660                 665                 670
Leu Asp Gln Val Ala Met Val Asp Val Asp Ala Ala Pro Ser Gly Tyr
                675                 680                 685
Gln Gly Ser Gly Asp Leu Ala Leu Gln Leu Ala Val Leu His Ala Gln
690                 695                 700
```

Leu Cys Thr Ile Phe Ala Glu Leu Asp Gln Thr Thr Arg Asp Thr Leu
705                 710                 715                 720

Glu Pro Leu Pro Thr Ile Leu Arg Ala Ile Glu Gly Gln Pro Val
            725                 730                 735

Leu Val Ser Val Pro Met Arg Leu Pro Leu Pro Ala Gln Val His
            740                 745                 750

Ser Ser Leu Ser Ala Gly Glu Lys Pro Gly Phe Leu Ala Pro Arg Asp
        755                 760                 765

Leu Pro Lys His Thr Pro Leu Ile Ser Lys Ser Gln Ser Leu Arg Ser
    770                 775                 780

Val Arg Arg Ser Glu Ser Trp Ala Arg Pro Pro Asp Glu Glu Arg
785                 790                 795                 800

Pro Leu Arg Arg Pro Arg Pro Val Gln Arg Thr Gln Ser Val Pro Val
                805                 810                 815

Arg Arg Pro Ala Arg Arg Gln Ser Ala Gly Pro Trp Pro Arg Pro
            820                 825                 830

Lys Gly Ser Leu Ser Met Gly Pro Ala Pro Arg Ala Arg Pro Trp Thr
        835                 840                 845

Arg Asp Ser Ala Ser Leu Pro Arg Lys Pro Ser Val Pro Trp Gln Arg
    850                 855                 860

Gln Met Asp Gln Pro Gln Asp Arg Asn Gln Ala Leu Gly Thr His Arg
865                 870                 875                 880

Pro Val Asn Lys Leu Ala Glu Leu Gln Cys Glu Val Ala Ala Leu Arg
                885                 890                 895

Glu Glu Gln Lys Val Leu Ser Arg Leu Val Glu Ser Leu Ser Thr Gln
            900                 905                 910

Ile Arg Ala Leu Thr Glu Gln Gln Glu Gln Leu Arg Gly Gln Leu Gln
        915                 920                 925

Asp Leu Asp Ser Arg Leu Arg Ala Gly Ser Ser Glu Phe Asp Ser Glu
    930                 935                 940

His Asn Leu Thr Ser Asn Glu Gly His Ser Leu Lys Asn Leu Glu His
945                 950                 955                 960

Arg Leu Asn Glu Met Glu Arg Thr Gln Ala Gln Leu Arg Asp Ala Val
                965                 970                 975

Gln Ser Leu Gln Leu Ser Pro Arg Thr Arg Gly Ser Trp Ser Gln Pro
            980                 985                 990

Gln Pro Leu Lys Ala Pro Cys Leu Asn Gly Asp Thr Thr
        995                 1000                1005

<210> SEQ ID NO 26
<211> LENGTH: 3018
<212> TYPE: DNA
<213> ORGANISM: Homo sapiens

<400> SEQUENCE: 26
atggacccac cgtcgccaag ccggacctcc caaacccagc ccacagccac ctctccgctg     60
acttcctacc gctggcacac agggggcggt ggggagaagg cggctggagg gttccgctgg    120
ggccgctttg ctggctgggg cagggccctg agccaccagg agcccatggt cagcacccag    180
ccagcccctc gctcgatatt ccgtcgggtc ctatctgcgc ctcccaagga gtcacggacc    240
agtcgccttc gactctccaa ggccctctgg gggaggcata agaacccacc gccggagcca    300
gacccggagc cggagcagga ggccccagag ctggagccgg agccagagct ggagcccct    360 accccacaga tccctgaggc ccccacaccc aacgtgcctg tctgggacat tgggggcttc    420

-continued

| | |
|---|---|
| accctgcttg atgggaagct ggtgctgctt ggaggagagg aggagggtcc tcgaaggccc | 480 |
| cgggtgggaa gtgctagctc cgagggcagc atccacgtgg ccatgggaaa cttcagggat | 540 |
| ccagatcgga tgcctggaaa aacagaaccg gagactgctg gtcccaacca ggtccacaac | 600 |
| gttcggggt tgctcaagag gctgaaagag aagaaaaagg ccagacccccc cagtgctctg | 660 |
| ggctctaggg agtcgctggc cacactctct gaactggacc tgggtgccga gcgggatgtg | 720 |
| cggatctggc cactgcaccc cagcctcctg ggggagcccc actgctttca ggtaacctgg | 780 |
| acgggtggaa gccgctgctt ctcttgtcgc tcggccgctg agagagaccg ctggatcgag | 840 |
| gaccttcgtc gccaattcca gcccacccag gacaacgtgg agcgggaaga gacatggctg | 900 |
| agcgtgtggg tgcacgaagc gaagggggctt ccccgagcag cggcggggggc acccggcgtg | 960 |
| cgcgccgagc tgtggctgga tggcgcgctg ctggcacgca cggcgcctcg ggccggccca | 1020 |
| ggccagctct tctgggccga gcgcttccac ttcgaggcgc tgccaccggc acgtcgcctg | 1080 |
| tcgctgcggc tgcgcggctt gggcccggga agcgcggtgc tggccgcgt ggccctggcg | 1140 |
| ctggaggagc tggacgcccc acgcgcgcct gccgccggtc tggagcgctg gttcccgctg | 1200 |
| ctcggggcgc cggcgggcgc agcgctgcgg gcgcggattc gggcgcgtcg cctgcgcgtg | 1260 |
| ctgccgtccg agcgctacaa ggagctggcg gagttcctca ccttccacta tgcgcgcctc | 1320 |
| tgcggggccc tggagcccgc gctgcctgcg caggccaagg aggagctggc ggcagccatg | 1380 |
| gtgcgcgtgc tgcgggccac cggccgggcg caggcgctgg tgactgacct gggcactgcg | 1440 |
| gagctggcgc gctgtggagg ccgtgaggcg ctgctgttcc gggaaaacac attggccacc | 1500 |
| aaggctatcg atgagtacat gaagctcgtg gcacaggatt acctccagga gaccctggga | 1560 |
| caggttgtgc ggcgtctctg tgcttctact gaggactgtg aagtggaccc cagcaaatgt | 1620 |
| ccagcctcgg agctgccaga gcaccaggcc agacttcgga acagctgcga ggaggtcttc | 1680 |
| gaaaccatta tccattccta cgactggttc cctgcggagc tgggcatcgt gttctcaagc | 1740 |
| tggcgagaag catgtaaaga acgtggctct gaggtgctgg gccccgact ggtgtgcgcc | 1800 |
| tccctcttcc tgcggctcct gtgccctgcc atcctggcac ccagcctctt tggtttggca | 1860 |
| ccagaccatc cagcacccgg cccagcccgc accctcacac tgattgccaa ggtcatccag | 1920 |
| aacctcgcca accgtgcccc gttcggtgag aaggaggcct acatgggctt catgaatagc | 1980 |
| ttcctggagg aacatggacc agccatgcaa tgcttcctgg accaggtagc catggtggat | 2040 |
| gtggatgctg cccccagtgg ttaccagggc agtggtgatc tggcccctcca gttagctgtc | 2100 |
| ctgcatgccc agctctgtac aattttttgct gagcttgacc agacaacccg agacaccctg | 2160 |
| gaaccactgc ccaccatcct gcgagccatt gaggagggcc agcctgtgct tgtgtcagtg | 2220 |
| ccaatgcgtc tcccactgcc cccggcccag gtccactcca gcctctccgc aggggagaag | 2280 |
| cccggcttcc tggcccccccg ggacctcccc aagcacaccc ctctcatctc caagagccag | 2340 |
| tctctgcgca gcgttcgccg ctcagagagt tgggcccggc cacggccgga cgaagagcgg | 2400 |
| cccctgcggc ggccccggcc ggtgcagcgc acgcagagtg tcccggtccg gcgtcctgcc | 2460 |
| cgccgccgcc aatctgcggg gccctggccg cgacccaaag ctccctgag catgggacca | 2520 |
| gcgccccgcg cccggccttg gacccgggac tccgcctcgc tgcctcggaa gccgtcggta | 2580 |
| ccctggcagc gccaaatgga ccagccgcaa gaccgaaacc aggcactggg cacgcaccga | 2640 |
| cctgtgaaca agttggcaga gctgcagtgc gaggtggccg ctctgcgtga ggagcagaaa | 2700 |
| gtgctgtccc gcctcgtgga gtcgctgagc acccaaatcc gggccttgac ggagcagcag | 2760 |
| gagcagctgc ggggccagct gcaggatctg gactccaggc tccgtgctgg gagctcagag | 2820 |

```
tttgattcag agcacaacct aacaagcaat gaagggcaca gtctgaaaaa cctggagcac    2880
cgcctaaatg agatggagag aactcaggct cagctgaggg atgctgtcca gagcctgcag    2940
ctttctccaa ggacgcgggg gtcttggagt caaccccagc ccctcaaagc accctgcctc    3000
aatggagaca ccacctga                                                  3018
```

<210> SEQ ID NO 27
<211> LENGTH: 170
<212> TYPE: PRT
<213> ORGANISM: Artificial Sequence
<220> FEATURE:
<223> OTHER INFORMATION: Rho-Gap Consensus sequence

<400> SEQUENCE: 27

```
Pro Ile Ile Val Glu Lys Cys Val Glu Tyr Ile Glu Lys Leu Tyr Pro
 1               5                  10                  15

Leu Ala Glu Arg Gly Leu Gln Glu Gly Ile Tyr Arg Val Ser Gly
            20                  25                  30

Ser Ala Ser Arg Val Lys Glu Leu Arg Glu Ala Phe Asp Lys Asp Gly
        35                  40                  45

Ala Pro Asp Ser Leu Glu Leu Ser Glu Lys Glu Trp Phe Asp Val His
    50                  55                  60

Val Val Ala Gly Leu Leu Lys Leu Tyr Leu Arg Glu Leu Pro Glu Pro
65                  70                  75                  80

Leu Ile Pro Tyr Asp Leu Tyr Glu Glu Phe Ile Arg Ala Ala Lys Glu
                85                  90                  95

Gln Ile Glu Asp Pro Asp Glu Arg Leu Arg Ala Leu Lys Glu Leu Leu
            100                 105                 110

Ser Ser Lys Leu Pro Arg Ala His Tyr Asn Thr Leu Arg Tyr Leu Leu
        115                 120                 125

Thr His Leu Asn Arg Val Ala Glu Ile Tyr Ile Glu Asn Ser Ala Val
    130                 135                 140

Asn Lys Met Asn Ala Arg Asn Leu Ala Ile Val Phe Gly Pro Thr Leu
145                 150                 155                 160

Leu Arg Pro Pro Asp Lys Glu Ser Asn Asp
                165                 170
```

<210> SEQ ID NO 28
<211> LENGTH: 193
<212> TYPE: PRT
<213> ORGANISM: Artificial Sequence
<220> FEATURE:
<223> OTHER INFORMATION: Rho-Gap3 Consensus sequence

<400> SEQUENCE: 28

```
Ser Pro Ile Pro Ile Ile Val Glu Lys Cys Ile Glu Tyr Leu Glu Lys
 1               5                  10                  15

Arg Gly Leu Asp Thr Glu Gly Ile Tyr Arg Val Ser Gly Ser Lys Ser
            20                  25                  30

Arg Val Lys Glu Leu Arg Glu Ala Phe Asp Ser Gly Glu Asp Asp Leu
        35                  40                  45

Asp Ser Leu Asp Glu Ser Ile Thr Glu Glu Ser Glu Asp Leu Glu Glu
    50                  55                  60

Tyr Asp Val His Asp Val Ala Gly Leu Leu Lys Leu Tyr Leu Arg Glu
65                  70                  75                  80

Leu Pro Glu Pro Leu Leu Thr Phe Glu Leu Tyr Glu Glu Phe Ile Glu
                85                  90                  95
```

-continued

```
Ala Ala Lys Leu Tyr Gln Ile Glu Ala Thr Ser Arg Lys Gln Ser Glu
            100                 105                 110

Lys Ser Glu Asp Glu Glu Arg Leu Arg Ala Leu Arg Glu Leu Leu
            115                 120                 125

Ser Leu Leu Pro Pro Ala Asn Arg Ala Thr Leu Arg Tyr Leu Leu His
130                 135                 140

Leu Asn Arg Val Ala Glu His Ser Glu Val Asn Lys Met Thr Ala Arg
145                 150                 155                 160

Asn Leu Ala Ile Val Phe Gly Pro Thr Leu Leu Arg Pro Pro Leu Thr
                165                 170                 175

Asp Ile Lys His Gln Asn Lys Val Val Glu Thr Leu Ile Glu Asn Ala
            180                 185                 190

Asp

<210> SEQ ID NO 29
<211> LENGTH: 231
<212> TYPE: PRT
<213> ORGANISM: Artificial Sequence
<220> FEATURE:
<223> OTHER INFORMATION: Ras-Gap Consensus sequence

<400> SEQUENCE: 29

Leu Val Lys Thr Leu Leu Gln Lys Glu Ile Glu Ser Lys Ala Asp Asp
 1               5                  10                  15

Pro Thr Thr Leu Phe Arg Gly Asn Ser Leu Ala Ser Lys Met Leu Glu
            20                  25                  30

Gln Tyr Phe Arg Arg Ala Arg Gly Asn Glu Tyr Leu Arg Lys Thr Leu
            35                  40                  45

Arg Pro Val Leu Lys Glu Ile Ile Glu Ser Lys Asp Trp Gln His Leu
        50                  55                  60

Ser Cys Glu Ile Asp Pro Leu Lys Val Tyr Lys Lys Leu Val Asn Gln
65                  70                  75                  80

Gly Glu Leu Ser Thr Ser Glu Leu Asp Tyr Asp Leu Thr Asn Glu Glu
                85                  90                  95

Val Leu Asp Glu Glu Glu Lys Ser Glu Ala Ile Glu Glu Asn Leu Arg
            100                 105                 110

Asn Leu Leu Lys Tyr Thr Glu Lys Leu Leu Glu Ala Ile Thr Ser Ser
            115                 120                 125

Ser Asp Glu Phe Pro Pro Glu Leu Arg Tyr Ile Cys Lys Cys Leu Arg
        130                 135                 140

Gln Ser Ala Cys Glu Lys Phe Pro Asp Asn Ala Thr Val Lys Glu Lys
145                 150                 155                 160

Lys Glu Asn Lys Lys Ser Val Val Ser Gln Arg Phe Glu Gln Val Ile
                165                 170                 175

Leu Ser Ala Val Gly Gly Phe Val Phe Leu Arg Phe Ile Asn Pro Ala
            180                 185                 190

Ile Val Ser Pro Asp Leu Phe Asn Ile Ile Asp Lys Ser Pro Ser Ala
        195                 200                 205

Gln Ala Thr Thr Asp Gln Arg Arg Thr Leu Thr Leu Ile Ala Lys Val
    210                 215                 220

Ile Gln Ser Leu Ala Asn Gly
225                 230

<210> SEQ ID NO 30
<211> LENGTH: 390
```

```
<212> TYPE: PRT
<213> ORGANISM: Artificial Sequence
<220> FEATURE:
<223> OTHER INFORMATION: Ras-Gap2 Consensus sequence

<400> SEQUENCE: 30

Leu Lys Gln Gly Glu Leu Gly Ser Leu Arg Leu Lys Thr Val Tyr Thr
1               5                   10                  15

Thr Asp Phe Ile Leu Pro Ser Glu Ala Tyr Glu Glu Leu Leu Glu Leu
            20                  25                  30

Leu Leu Glu Ser Val Asp Val Glu Pro Leu Thr Ala Ser Leu Ala Ser
        35                  40                  45

Ala Leu Glu Glu Val Cys Ser Val Leu Asp Lys Asp Glu Leu Ala Thr
    50                  55                  60

Lys Leu Val Arg Leu Phe Leu Arg Arg Gly Arg Gly Lys Pro Phe Leu
65                  70                  75                  80

Arg Ala Leu Ile Asp Lys Glu Val Glu Arg Thr Asp Asp Pro Val Asn
                85                  90                  95

Thr Leu Phe Arg Gly Asn Ser Leu Ala Thr Lys Ser Met Glu Val Tyr
            100                 105                 110

Met Lys Leu Val Gly Asn Gln Tyr Leu His Thr Thr Leu Lys Pro Val
        115                 120                 125

Leu Lys Lys Ile Val Glu Glu Lys Lys Glu Ser Cys Glu Val Asp Pro
    130                 135                 140

Ser Lys Leu Glu Val Asn Asp Val Ile Ser Phe Gly Asp Pro Val Glu
145                 150                 155                 160

Gly Glu Asp Leu Glu Thr Asn Leu Glu Asn Leu Leu Gln Tyr Val Glu
                165                 170                 175

Arg Leu Phe Asp Ala Ile Ile Asn Ser Ser Asp Arg Leu Pro Tyr Gly
            180                 185                 190

Leu Arg Asp Ile Cys Lys Gln Leu Arg Gln Ala Ala Glu Lys Arg Phe
        195                 200                 205

Pro Ser Ala Thr Gln Asp Val Arg Tyr Lys Ala Val Ser Ser Phe Val
    210                 215                 220

Phe Leu Arg Phe Phe Cys Pro Ala Ile Leu Ser Pro Lys Leu Phe Asn
225                 230                 235                 240

Leu Val Asp Glu His Pro Asp Pro Thr Thr Arg Arg Thr Leu Thr Leu
                245                 250                 255

Ile Ala Lys Val Leu Gln Asn Leu Ala Asn Leu Ser Glu Ser Lys Ser
            260                 265                 270

Lys Leu Phe Gly Ser Lys Glu Pro Trp Met Glu Pro Leu Phe Lys Asn
        275                 280                 285

Asp Phe Leu Lys Gln His Lys Asp Arg Val Lys Asp Phe Leu Asp Glu
    290                 295                 300

Leu Ser Ser Val Asp Glu Pro Ser Glu Ser Leu Val Asp Lys Val Glu
305                 310                 315                 320

Glu Leu Pro Thr Lys Ser Lys Pro Val Ser Thr Ile Ser Gly Arg Glu
                325                 330                 335

Leu Ser Leu Leu His Ser Leu Leu Glu Asn Gly Asp Ala Leu Lys
            340                 345                 350

Arg Lys Lys Asn Asn Asn Arg Asp His Lys Ala Leu Gly Glu Asp Pro
        355                 360                 365

Leu Asp Lys Leu Leu Phe Lys Leu Arg Tyr Phe Arg Leu Thr Thr His
    370                 375                 380
```

```
-continued
Lys Leu Thr Asn Gly Lys
385                 390
```

The invention claimed is:

1. An isolated polypeptide selected from the group consisting of:
   a) a polypeptide which is encoded by a nucleic acid molecule comprising the nucleotide sequence set forth in SEQ ID NO:16;
   b) a polypeptide comprising the amino acid sequence of SEQ ID NO:15; and
   c) a polypeptide encoded by the nucleotide sequence of the cDNA insert of the plasmid deposited with ATCC as Patent Deposit Number PTA-1849.

2. The isolated polypeptide of claim 1 comprising the amino acid sequence of SEQ ID NO:15.

3. The polypeptide of claim 1 further comprising heterologous amino acid sequences.

4. A method for identifying a compound that binds to the polypeptide of claim 1 comprising the steps of:
   (a) contacting the polypeptide, or a cell expressing the polypeptide of claim 1 with a test compound; and
   (b) determining whether the polypeptide binds to the test compound.

5. The method of claim 4, wherein the binding of the test compound to the polypeptide is detected by a method selected from the group consisting of:
   a) detection of binding by direct detecting of test compound/polypeptide binding;
   b) detection of binding using a competition binding assay; and
   c) detection of binding using an assay for ubiquitin protease activity.

6. A method for identifying a compound which modulates the ubiquitin protease activity of the polypeptide of claim 1, comprising:
   (a) contacting the polypeptide of claim 1 with a test compound; and
   (b) determining the effect of the test compound on the ubiquitin protease activity of the polypeptide to thereby identify a compound that modulates the ubiquitin protease activity of the polypeptide.

7. The polypeptide of claim 1, which is encoded by a nucleic acid molecule comprising the nucleotide sequence of SEQ ID NO:16.

8. The polypeptide of claim 1, which is encoded by the nucleotide sequence of the cDNA insert of the plasmid deposited with ATCC as Patent Deposit Number PTA-1849.

* * * * *